(12) United States Patent  
Park et al.

(10) Patent No.: US 8,440,881 B2  
(45) Date of Patent: May 14, 2013

(54) PLANTS HAVING ENHANCED YIELD-RELATED TRAITS AND A METHOD FOR MAKING THE SAME

(75) Inventors: Youn-Il Park, Daejeon (KR); Yang Do Choi, Seoul (KR); Seok Won Jeong, Daejeon (KR); In Gyu Hwang, Seoul (KR); Jonghee Oh, Seoul (KR)

(73) Assignees: CropDesign N.V., Zwijnaarde (BE); Crop Functional Genomics Center, Seoul (KR)

( * ) Notice: Subject to any disclaimer, the term of this patent is extended or adjusted under 35 U.S.C. 154(b) by 373 days.

(21) Appl. No.: 12/528,809

(22) PCT Filed: Feb. 28, 2008

(86) PCT No.: PCT/EP2008/052450  
§ 371 (c)(1), (2), (4) Date: Nov. 10, 2009

(87) PCT Pub. No.: WO2008/104598  
PCT Pub. Date: Sep. 4, 2008

(65) Prior Publication Data  
US 2010/0064386 A1      Mar. 11, 2010

Related U.S. Application Data

(60) Provisional application No. 60/896,050, filed on Mar. 21, 2007, provisional application No. 60/909,510, filed on Apr. 2, 2007.

(30) Foreign Application Priority Data

Feb. 28, 2007   (EP) .................................... 07103271  
Mar. 15, 2007  (EP) .................................... 07104197

(51) Int. Cl.  
*A01H 5/00* (2006.01)  
*C12N 15/82* (2006.01)

(52) U.S. Cl.  
USPC ............ 800/290; 800/298; 435/468; 435/419

(58) Field of Classification Search .................... None  
See application file for complete search history.

(56) References Cited

U.S. PATENT DOCUMENTS

2003/0233670 A1 * 12/2003 Edgerton et al. .............. 800/278  
2005/0108791 A1 *  5/2005 Edgerton ...................... 800/284

FOREIGN PATENT DOCUMENTS

| CN | 1300547 A | 6/2001 |
| CN | 1219059 C | 9/2005 |
| CN | 1225559 C | 11/2005 |
| KR | 2003-0068302 | * 8/2003 |
| KR | 20030068302 A | 8/2003 |
| WO | WO 2004/070039 A2 | * 8/2004 |

OTHER PUBLICATIONS

Ren et al (J.Biosci 31(5) Dec. 2006, 617-627).*  
Kim, J.-G., et al., "Mutational Analysis of *Xanthomonas* Harpin HpaG Identifies a Key Functional Region That Elicits the Hypersensitive Response in Nonhost Plants", Journal of Bacteriology, vol. 186, No. 18, (2004), pp. 6239-6247.  
Liu, F., et al., "The Internal Glycine-Rich Motif and Cysteine Suppress Several Effects of the $HpaG_{Xooc}$ Protein in Plants", Phytopathology, vol. 96, No. 10, (2006), pp. 1052-1059.  
Peng, J.-L., et al., "Expression of $Harpin_{Xoo}$ in Transgenic Tobacco Induces Pathogen Defense in the Absence of Hypersensitive Cell Death", Phytopathology, vol. 94, No. 10, (2004), pp. 1048-1055.  
Ren, H., et al., "Combinative Effects of a Bacterial Type-III Effector and a Biocontrol Bacterium on Rice Growth and Disease Resistance", J. Biosci., vol. 31, No. 5, (2006), pp. 617-627.

* cited by examiner

*Primary Examiner* — Brent T Page  
*Assistant Examiner* — Lee A Visone  
(74) *Attorney, Agent, or Firm* — Novak Druce Connolly Bove + Quigg LLP

(57) ABSTRACT

The present invention relates generally to the field of molecular biology and concerns a method for enhancing various economically important yield-related traits in plants. More specifically, the present invention concerns a method for enhancing yield-related traits in plants by modulating expression in a plant of a nucleic acid encoding a Harpin-associated Factor G polypeptide (hereinafter termed HpaG"). The present invention also concerns plants having modulated expression of a nucleic acid encoding an HpaG polypeptide, which plants have enhanced yield-related traits relative to control plants. The invention also provides constructs comprising HpaG-encoding nucleic acids, useful in performing the methods of the invention. The present invention also provides a method for enhancing yield-related traits in plants relative to control plants, by modulating (preferably increasing) expression in a plant of a nucleic acid sequence encoding a SWITCH 2/SUCROSE NON-FERMENTING 2 (SWI2/SNF2) polypeptide. The present invention also concerns plants having modulated expression of a nucleic acid sequence encoding a SWI2/SNF2 polypeptide, which plants have enhanced yield-related traits relative to control plants. The invention also provides constructs useful in performing the methods of the invention.

17 Claims, 96 Drawing Sheets

CLUSTAL W (1.83) multiple sequence alignment

```
ABJ97680   MNSLNTQFGGSTSNLQVGPSQ--DTTFGSNQG--GNQGISEKQLDQLLCQLISALLQSSK
AAC95121   MNSLNTQFGGSTSNLQVGPSQ--DTTFGSNQG--GNQGISEKQLDQLLCQLISALLQSSK
BAD29979   MNSLNTQFGGSTSNLQVGPSQ--DTTFGSNQG--GNQGISEKQLDQLLCQLISALLQSSK
ABB72197   MNSLNTQFGGSASNFQVDQSQ--NAQSDSSQGSNGSQGISEKQLDQLLCQLIQALLQPNK
SEQID2     MNSLNTQLGANSSFFQVDPGQ--NTQSS-----PNQGNQGISEKQLDQLLTQLIMALLQQSN
ABK51590   MNSLNTQLGANSSFFQVDPGQ--NTQSS-----PNQGN-------TQLIMALLQQSN
ABK51589   MNSLNTQLGANSSFFQVDPGQ--NTQSS-----PNQGNQGISEKQLDQLLCQLIMALLQQSN
ABK51587   MNSLNTQLGANSSFFQVDPGQ--NTQSS-----PNQGNQGISEKQLDQLLTQLIMALLQQSN
ABK51588   MNSLNTQLGANSSFFQVDPGQ--NTQSS-----PNQGNQGISEKQLDQLLTQLIMALLQQSN
AAM35307   MNSLNTQLGANSSFFQVDPSQ--NTQSG----SNQGNQGISEKQLDQLLTQLIMALLQQSN
ABG36696   MNSLNTQIGANSSFLQVDPSQ--NTQFG---PNQGNQGISEKQLDQLLTQLIMALLQQSN
AAM40538   ---MDSSIGNKFSNFINLQTMGIGPQQTQNSSQRSPSADSEQQLDQLLAMFIMMLQQSQ
                 :  *    * ..               .        . :  *      . :**
```

| ID | Sequence |
|---|---|
| ABJ97680 | GGFGGDFS------GDLGLGTNLSSDSASMQ |
| AAC95121 | GGFGGDFS------GDLGLGTNLSSDSASMQ |
| BAD29979 | GGFGGDFS------GDLGLGTNLSSDSASMQ |
| ABB72197 | GSFASSFS------NDSGSMQ---------- |
| SEQID2 | GFGGILVT----SLASDTGSMQ---------- |
| ABK51590 | GFGGILVT----SLASDTGSMQ---------- |
| ABK51589 | GFGGILVT----SLASDTGSMQ---------- |
| ABK51587 | GFGGILVT----SLASDTGSMQ---------- |
| ABK51588 | --GFILVT----SLASDTGSMQ---------- |
| AAM35307 | GFGGGLGTSLGTSLASDTGSMQ---------- |
| ABG36696 | GFGGGLGTSLGSSLASDTGSMQ---------- |
| AAM40538 | GGFNANLS------SITGQA----------- |

FIGURE 1 (continued)

SEQ ID NO: 1, EF050509.1, Xanthomonas axonopodis elicitor of hypersensitive response HpaG (hpaG) gene, complete cds
ATGAATTCTTTGAACACACAGCTCGGCGCCAACTCGTCCTTCTTTCAGGTTGACCCCGGCCAGAAC
ACGCAATCTAGTCCGAACCAGGGCAACCAGGGCATCTCGGAAAAGCAACTGGACCAGCTGCTGACC
CAGCTCATCATGGCCCTGCTTCAGCAGAGCAACAATGCCGAGCAGGGTCAGGGTCAAGGCCAGGGT
GGTGACTCTGGCGGTCAGGGCGGCAATCCGCGGCAGGCCGGGCAGTCCAACGGCTCCCCCTCGCAA
TACACCCAGGCGCTGATGAATATCGTCGGAGACATTCTCCAGGCGCAGAATGGTGGCGGCTTCGGC
GGCGGCTTTGGTGGTGGCTTCGGTGGCATCCTCGTCACCAGCCTTGCGAGCGACACCGGATCGATG
CAGTAA

SEQ ID NO: 2, ABK51582.1, elicitor of hypersensitive response HpaG [Xanthomonas axonopodis]

MNSLNTQLGANSSFFQVDPGQNTQSSPNQGNQGISEKQLDQLLTQLIMALLQQSNNAEQGQGQGQG
GDSGGQGGNPRQAGQSNGSPSQYTQALMNIVGDILQAQNGGGFGGGFGGGFGGILVTSLASDTGSM
Q

SEQ ID NO: 3, conserved motif 1

G(G/E/D)(N/E)X(Q/R/P)Q(A/S)GX(N/D)G

SEQ ID NO: 4, conserved motif 2

(P/A/V)S(P/Q/A)(F/L/Y)TQ(M/A)LM(H/N/Q)IV(G/M)(E/D/Q)

SEQ ID NO: 5, constitutive promoter GOS2

AATCCGAAAAGTTTCTGCACCGTTTTCACCCCCTAACTAACAATATAGGGAACGTGTGCTAAATAT
AAAATGAGACCTTATATATGTAGCGCTGATAACTAGAACTATGCAAGAAAAACTCATCCACCTACT
TTAGTGGCAATCGGGCTAAATAAAAAAGAGTCGCTACACTAGTTTCGTTTTCCTTAGTAATTAAGT
GGGAAAATGAAATCATTATTGCTTAGAATATACGTTCACATCTCTGTCATGAAGTTAAATTATTCG
AGGTAGCCATAATTGTCATCAAACTCTTCTTGAATAAAAAAATCTTTCTAGCTGAACTCAATGGGT
AAAGAGAGAGATTTTTTTTAAAAAAATAGAATGAAGATATTCTGAACGTATTGGCAAAGATTTAAA
CATATAATTATATAATTTTATAGTTTGTGCATTCGTCATATCGCACATCATTAAGGACATGTCTTA
CTCCATCCCAATTTTTATTTAGTAATTAAAGACAATTGACTTATTTTTATTATTTATCTTTTTTCG
ATTAGATGCAAGGTACTTACGCACACACTTTGTGCTCATGTGCATGTGTGAGTGCACCTCCTCAAT
ACACGTTCAACTAGCAACACATCTCTAATATCACTCGCCTATTTAATACATTTAGGTAGCAATATC
TGAATTCAAGCACTCCACCATCACCAGACCACTTTTAATAATATCTAAAATACAAAAAATAATTTT
ACAGAATAGCATGAAAAGTATGAAACGAACTATTTAGGTTTTTCACATACAAAAAAAAAAAGAATT
TTGCTCGTGCGCGAGCGCCAATCTCCCATATTGGGCACACAGGCAACAACAGAGTGGCTGCCCACA
GAACAACCCACAAAAAACGATGATCTAACGGAGGACAGCAAGTCCGCAACAACCTTTTAACAGCAG
GCTTTGCGGCCAGGAGAGAGGAGGAGAGGCAAAGAAAACCAAGCATCCTCCTTCTCCCATCTATAA
ATTCCTCCCCCCTTTTCCCCTCTCTATATAGGAGGCATCCAAGCCAAGAAGAGGGAGAGCACCAAG
GACACGCGACTAGCAGAAGCCGAGCGACCGCCTTCTCGATCCATATCTTCCGGTCGAGTTCTTGGT
CGATCTCTTCCCTCCTCCACCTCCTCCTCACAGGGTATGTGCCTCCCTTCGGTTGTTCTTGGATTT
ATTGTTCTAGGTTGTGTAGTACGGGCGTTGATGTTAGGAAAGGGGATCTGTATCTGTGATGATTCC
TGTTCTTGGATTTGGGATAGAGGGGTTCTTGATGTTGCATGTTATCGGTTCGGTTTGATTAGTAGT
ATGGTTTTCAATCGTCTGGAGAGCTCTATGGAAATGAAATGGTTTAGGGATCGGAATCTTGCGATT
TTGTGAGTACCTTTTGTTTGAGGTAAAATCAGAGCACCGGTGATTTTGCTTGGTGTAATAAAGTAC
GGTTGTTTGGTCCTCGATTCTGGTAGTGATGCTTCTCGATTTGACGAAGCTATCCTTTGTTTATTC
CCTATTGAACAAAAATAATCCAACTTTGAAGACGGTCCCGTTGATGAGATTGAATGATTGATTCTT
AAGCCTGTCCAAAATTTCGCAGCTGGCTTGTTTAGATACAGTAGTCCCCATCACGAAATTCATGGA

FIGURE 4

```
AACAGTTATAATCCTCAGGAACAGGGGATTCCCTGTTCTTCCGATTTGCTTTAGTCCCAGAATTTT
TTTTCCCAAATATCTTAAAAAGTCACTTTCTGGTTCAGTTCAATGAATTGATTGCTACAAATAATG
CTTTTATAGCGTTATCCTAGCTGTAGTTCAGTTAATAGGTAATACCCCTATAGTTTAGTCAGGAGA
AGAACTTATCCGATTTCTGATCTCCATTTTTAATTATATGAAATGAACTGTAGCATAAGCAGTATT
CATTTGGATTATTTTTTTATTAGCTCTCACCCCTTCATTATTCTGAGCTGAAAGTCTGGCATGAA
CTGTCCTCAATTTTGTTTTCAAATTCACATCGATTATCTATGCATTATCCTCTTGTATCTACCTGT
AGAAGTTTCTTTTTGGTTATTCCTTGACTGCTTGATTACAGAAAGAAATTTATGAAGCTGTAATCG
GGATAGTTATACTGCTTGTTCTTATGATTCATTTCCTTTGTGCAGTTCTTGGTGTAGCTTGCCACT
TTCACCAGCAAAGTTC
```

SEQ ID NO: 6, green tissue specific promoter PCR
```
TTGCAGTTGTGACCAAGTAAGCTGAGCATGCCCTTAACTTCACCTAGAAAAAAGTATACTTGGCTT
AACTGCTAGTAAGACATTTCAGAACTGAGACTGGTGTACGCATTTCATGCAAGCCATTACCACTTT
ACCTGACATTTTGGACAGAGATTAGAAATAGTTTCGTACTACCTGCAAGTTGCAACTTGAAAAGTG
AAATTTGTTCCTTGCTAATATATTGGCGTGTAATTCTTTTATGCGTTAGCGTAAAAAGTTGAAATT
TGGGTCAAGTTACTGGTCAGATTAACCAGTAACTGGTTAAAGTTGAAAGATGGTCTTTTAGTAATG
GAGGGAGTACTACACTATCCTCAGCTGATTTAAATCTTATTCCGTCGGTGGTGATTTCGTCAATCT
CCCAACTTAGTTTTTCAATATATTCATAGGATAGAGTGTGCATATGTGTGTTTATAGGGATGAGTC
TACGCGCCTTATGAACACCTACTTTTGTACTGTATTTGTCAATGAAAAGAAATCTTACCAATGCT
GCGATGCTGACACCAAGAAGAGGCGATGAAAAGTGCAACGGATATCGTGCCACGTCGGTTGCCAAG
TCAGCACAGACCCAATGGGCCTTTCCTACGTGTCTCGGCCACAGCCAGTCGTTTACCGCACGTTCA
CATGGGCACGAACTCGCGTCATCTTCCCACGCAAAACGACAGATCTGCCCTATCTGGTCCCACCCA
TCAGTGGCCCACACCTCCCATGCTGCATTATTTGCGACTCCCATCCCGTCCTCCACGCCCAAACAC
CGCACACGGGTCGCGATAGCCACGACCCAATCACACAACGCCACGTCACCATATGTTACGGGCAGC
CATGCGCAGAAGATCCCGCGACGTCGCTGTCCCCCGTGTCGGTTACGAAAAAATATCCCACCACGT
GTCGCTTTCACAGGACAATATCTCGAAGGAAAAAAATCGTAGCGGAAAATCCGAGGCACGAGCTGC
GATTGGCTGGGAGGCGTCCAGCGTGGTGGGGGGCCCACCCCCTTATCCTTAGCCCGTGGCGCTCCT
CGCTCCTCGGGTCCGTGTATAAATACCCTCCGGAACTCACTCTTGCTGGTCACCAACACGAAGCAA
AAGGACACCAGAAACATAGTACACTTGAGCTCACTCCAAACTCAAACACTCACACCA
```

SEQ ID NO: 7, EF042294, Synthetic construct mutant elicitor of hypersensitive response HpaG_T44C gene, complete cds
```
ATGAATTCTTTGAACACACAGCTCGGCGCCAACTCGTCCTTCTTTCAGGTTGACCCCGGCCAGAA SEQ ID NO: 9, EF042292, Synthetic construct mutant elicitor of hypersensitive response HpaG-T gene, complete cds
ATGAATTCTTTGAACACACAGCTCGGCGCCAACTCGTCCTTCTTTCAGGTTGACCCCGGCCAGAAC
ACGCAATCTAGTCCGAACCAGGGCAACCAGGGCATCTCGGAAAAGCAACTGGACCAGCTGCTGACC
CAGCTCATCATGGCCCTGCTTCAGCAGAGCAACAATGCCGAGCAGGGTCAGGGTCAAGGCCAGGGT
GGTGACTCTGGCGGTCAGGGCGGCAATCCGCGGCAGGCCGGGCAGTCCAACGGCTCCCCCTCGCAA
TACACCCAGGCGCTGATGAATATCGTCGGAGACGGCTTCGGCGGCGGCTTTGGTGGTGGCTTCGGT
GGCATCCTCGTCACCAGCCTTGCGAGCGACACCGGATCGATGCAGTAA SEQ ID NO: 10, ABK51587, mutant elicitor of hypersensitive response HpaG-T [synthetic construct]
MNSLNTQLGANSSFFQVDPGQNTQSSPNQGNQGISEKQLDQLLTQLIMALLQQSNNAEQGQGQGQG
GDSGGQGGNPRQAGQSNGSPSQYTQALMNIVGDGFGGGFGGGFGGILVTSLASDTGSMQ SEQ ID NO: 11, 21106495:2613-3026 Xanthomonas axonopodis pv. citri str. 306, section 45 of 469 of the complete genome
TTACTGCATCGATCCGGTGTCGCTCGCAAGGCTGGTGCCGAGGCTGGTGCCGAGGCCGCCGCCGAA
GCCACCACCAAAGCCGCCGCCGAAGCCACCACCATTCTGCGCCTGGAGAATGTCTCCGACGATATT
CATCAGCATCTGGGTGTATTGCGAGGGGAGCCGTTGGACTGACCGGCCTGCTGCCGATTGCCGCC
CTGACCACCAGAGTCACCACCCTGGCCTTGACCCTGACCCTGCTCGGCATTGTTGCTCTGCTGAAG
CAGGGCCATGATGAGCTGGGTCAGCAGCTGGTCCAGTTGCTTTTCCGAGATGCCCTGGTTGCCCTG
GTTCGAACCAGATTGCGTGTTCTGGCTGGGGTCAACCTGAAAGAAGGACGAGTTGGCGCCGAGCTG
TGTGTTCAAAGAATTCAT SEQ ID NO: 12, AAM35307, Hpa1 protein [Xanthomonas axonopodis pv. citri str. 306]
MNSLNTQLGANSSFFQVDPSQNTQSGSNQGNQGISEKQLDQLLTQLIMALLQQSNNAEQGQGQGQG
GDSGGQGGNRQQAGQSNGSPSQYTQMLMNIVGDILQAQNGGGFGGGFGGGFGGGLGTSLGTSLASD
TGSMQ

SEQ ID NO: 13, EF042295, Synthetic construct mutant elicitor of hypersensitive response HpaG-N gene, complete cds
ATGAATTCTTTGAACACACAGCTCGGCGCCAACTCGTCCTTCTTTCAGGTTGACCCCGGCCAGAAC
ACGCAATCTAGTCCGAACCAGGGCAACACCCAGCTCATCATGGCCCTGCTTCAGCAGAGCAACAAT
GCCGAGCAGGGTCAGGGTCAAGGCCAGGGTGGTGACTCTGGCGGTCAGGGCGGCAATCCGCGGCAG
GCCGGGCAGTCCAACGGCTCCCCCTCGCAATACACCCAGGCGCTGATGAATATCGTCGGAGACATT
CTCCAGGCGCAGAATGGTGGCGGCTTCGGCGGCGGCTTTGGTGGTGGCTTCGGTGGCATCCTCGTC
ACCAGCCTTGCGAGCGACACCGGATCGATGCAGTAA

SEQ ID NO: 14, ABK51590, mutant elicitor of hypersensitive response HpaG-N [synthetic construct]
MNSLNTQLGANSSFFQVDPGQNTQSSPNQGNTQLIMALLQQSNNAEQGQGQGQGGDSGGQGGNPRQ
AGQSNGSPSQYTQALMNIVGDILQAQNGGGFGGGFGGGFGGILVTSLASDTGSMQ

SEQ ID NO: 15, EF042293, Xanthomonas axonopodis HpaG_G gene, complete cds
ATGAATTCTTTGAACACACAGCTCGGCGCCAACTCGTCCTTCTTTCAGGTTGACCCCGGCCAGAAC
ACGCAATCTAGTCCGAACCAGGGCAACCAGGGCATCTCGGAAAAGCAACTGGACCAGCTGCTGACC

FIGURE 4 (continued)

CAGCTCATCATGGCCCTGCTTCAGCAGAGCAACAATGCCGAGCAGGGTCAGGGTCAAGGCCAGGGT
GGTGACTCTGGCGGTCAGGGCGGCAATCCGCGGCAGGCCGGGCAGTCCAACGGCTCCCCTCGCAA
TACACCCAGGCGCTGATGAATATCGTCGGAGACATTCTCCAGGCGCAGAATGGCTTTATCCTCGTC
ACCAGCCTTGCGAGCGACACCGGATCGATGCAGTAA

SEQ ID NO: 16, ABK51588, HpaG_G [Xanthomonas axonopodis]
MNSLNTQLGANSSFFQVDPGQNTQSSPNQGNQGISEKQLDQLLTQLIMALLQQSNNAEQGQGQGQG
GDSGGQGGNPRQAGQSNGSPSQYTQALMNIVGDILQAQNGFILVTSLASDTGSMQ

SEQ ID NO: 17, DQ643828, Xanthomonas smithii subsp. smithii Hrp gene, complete cds
ATGAATTCTTTGAACACACAGATCGGCGCCAACTCGTCCTTCTTGCAGGTCGACCCGAGCCAGAAC
ACGCAATTCGGTCCGAACCAGGGCAATCAAGGCATCTCGGAAAAGCAGCTGGACCAGCTGCTGACC
CAGCTCATCATGGCCCTGCTTCAGCAGAGCAACAATGCCGACCAGGGTCAGGGTGGTGACTCTGGT
GGTCAAGGCGGCAATTCGCGGCAGGCCGGGCAGCCCAATGGTTCCCCCTCGGCATACACCCAGATG
CTGATGAATATCGTCGGAGACATTCTCCAGGCGCAGAATGGTGGTGGCTTCGGCGGCGGGTTCGGC
GGTGGCTTTGGTGGCGGGCTCGGCACCAGCCTCGGCAGCAGCCTTGCGAGCGACACCGGATCGATG
CAGTAA

SEQ ID NO: 18, ABG36696, Hrp [Xanthomonas smithii subsp. smithii]
MNSLNTQIGANSSFLQVDPSQNTQFGPNQGNQGISEKQLDQLLTQLIMALLQQSNNADQGQGGDSG
GQGGNSRQAGQPNGSPSAYTQMLMNIVGDILQAQNGGGFGGGFGGGFGGGLGTSLGSSLASDTGSM
Q

SEQ ID NO: 19, gi|116292746:1016-1435 Xanthomonas oryzae pv. oryzae strain JXOIII hrp gene cluster, partial sequence
ATGAACTCTTTGAACACACAATTCGGCGGCAGCACGTCCAACCTTCAGGTTGGCCCAAGCCAGGAC
ACAACGTTCGGTTCGAACCAGGGCGGCAACCAGGGCATCTCGGAAAAGCAACTGGACCAGTTGCTG
TGCCAGCTCATCTCGGCCCTGCTTCAGTCGAGCAAAAATGCTGAGGAGGGTAAGGGTCAGGGTGGC
GATAATGGCGGTGGCCAGGGCGGCAATTCGCAGCAGGCCGGGCAGCAGAATGGCCCCTCGCCATTC
ACCCAGATGCTGATGCATATCGTCGGAGAGATTCTCCAGGCGCAGAATGGTGGTGGTGCTGGTGGC
GGCGGTTTCGGCGGCGGGTTCGGCGGCGACTTTAGTGGCGACCTCGGCCTCGGCACCAACCTCTCG
AGCGACAGCGCATCAATGCAGTAA

SEQ ID NO: 20, ABJ97680, hypersensitive response-functioning factor A [Xanthomonas oryzae pv. oryzae]
MNSLNTQFGGSTSNLQVGPSQDTTFGSNQGGNQGISEKQLDQLLCQLISALLQSSKNAEEGKGQGG
DNGGGQGGNSQQAGQQNGPSPFTQMLMHIVGEILQAQNGGGAGGGGFGGGFGGDFSGDLGLGTNLS
SDSASMQ

SEQ ID NO: 21, gi|42717988:1136-1555 Xanthomonas oryzae pv. oryzae hrp gene cluster, partial sequence
ATGAATTCTTTGAACACACAATTCGGCGGCAGCACGTCCAACCTTCAGGTTGGCCCAAGCCAGGAC
ACAACGTTCGGTTCGAACCAGGGCGGCAACCAGGGCATCTCGGAAAAGCAACTGGACCAGTTGCTG
TGCCAGCTCATCTCGGCCCTGCTTCAGTCGAGCAAAAATGCTGAGGAGGGTAAGGGTCAGGGTGGC
GATAATGGCGGTGGCCAGGGCGGCAATTCGCAGCAGGCTGGGCAGCAGAATGGCCCCTCGCCATTC
ACCCAGATGCTGATGCATATCGTCGGAGAGATTCTCCAGGCGCAGAATGGTGGTGGTGCTGGTGGC
GGCGGGTTCGGCGGCGGGTTCGGCGGTGACTTTAGTGGCGACCTCGGCCTCGGCACCAACCTCTCG
AGCGACAGCGCATCGATGCAGTAA

FIGURE 4 (continued)

SEQ ID NO: 22, AAC95121.2| Hpa1 [Xanthomonas oryzae pv. oryzae]
MNSLNTQFGGSTSNLQVGPSQDTTFGSNQGGNQGISEKQLDQLLCQLISALLQSSKNAEEGKGQGG
DNGGGQGGNSQQAGQQNGPSPFTQMLMHIVGEILQAQNGGGAGGGGFGGGFGGDFSGDLGLGTNLS
SDSASMQ

SEQ ID NO: 23, gi|50428340:1138-1557 Xanthomonas oryzae pv. oryzae hrp gene cluster, complete cds
ATGAATTCTTTGAACACACAATTCGGCGGCAGCACGTCCAACCTTCAGGTTGGCCCAAGCCAGGAC
ACAACGTTCGGTTCGAACCAGGGCGGCAACCAGGGCATCTCGGAAAAGCAACTGGACCAGTTGCTG
TGCCAGCTCATCTCGGCCCTGCTTCAGTCGAGCAAAAATGCTGAGGAGGGTAAGGGTCAGGGTGGC
GATAATGGCGGTGGCCAGGGCGGCAATTCGCAGCAGGCCGGGCAGCAGAATGGCCCCTCGCCATTC
ACCCAGATGCTGATGCATATCGTCGGAGAGATTCTCCAGGCGCAGAATGGTGGTGGTGCTGGTGGC
GGCGGGTTCGGCGGCGGGTTCGGCGGTGACTTTAGTGGCGACCTCGGCCTCGGCACCAACCTCTCG
AGCGACAGCGCATCGATGCAGTAA

SEQ ID NO: 24, BAD29979, Hpa1 [Xanthomonas oryzae pv. oryzae]
MNSLNTQFGGSTSNLQVGPSQDTTFGSNQGGNQGISEKQLDQLLCQLISALLQSSKNAEEGKGQGG
DNGGGQGGNSQQAGQQNGPSPFTQMLMHIVGEILQAQNGGGAGGGGFGGGFGGDFSGDLGLGTNLS
SDSASMQ

SEQ ID NO: 25, gi|82393799:1-378 Xanthomonas oryzae pv. oryzicola hpaGXooc gene, complete cds
ATGAATTCTTTGAACACACAATTCGGCGGCAGCGCGTCCAACTTCCAGGTTGACCAAAGCCAGAAC
GCGCAATCCGATTCGAGCCAGGGCAGCAATGGCAGCCAGGGTATCTCGGAAAAGCAACTGGACCAG
TTGCTGTGCCAGCTCATCCAGGCCCTGCTTCAGCCGAACAAAAATGCTGAGGAAGGTAAGGGTCAG
CAGGGTGGCGAGAATAATCAGCAGGCCGGGAAGGAGAATGGCGCCTCGCCACTCACCCAGATGCTG
ATGAATATCGTCGGAGAGATTCTCCAGGCGCAGAATGCCGGCGGCAGCAGCGGCGGCGACTTTGGT
GGCAGTTTCGCCAGCAGCTTCTCGAACGACAGCGGATCGATGCAGTAA

SEQ ID NO: 26, ABB72197, hpaGXooc [Xanthomonas oryzae pv. oryzicola]
MNSLNTQFGGSASNFQVDQSQNAQSDSSQGSNGSQGISEKQLDQLLCQLIQALLQPNKNAEEGKGQ
QGGENNQQAGKENGASPLTQMLMNIVGEILQAQNAGGSSGGDFGGSFASSFSNDSGSMQ

SEQ ID NO: 27, gi|21112286:70-435 Xanthomonas campestris pv. campestris str. ATCC 33913, section 131 of 460 of the complete genome
TCAGGCTTGGCCGGTGATGCTCGACAGGTTGGCATTGAAGCCGCCACCCAAGCTGGTGCCGCCCAT
GCCGGCGCCGCCTTGGTTCTGCATCAGCTGCATCACGATCTGCATCAGCATCTGCGTCAACGGACT
CACACCGTCCTGTTGACCGCTCTGCGGTTGTTCGTCTCCGCACTCCTGATCGGCATCGCTGCCCTG
GCTCTGTTGGAGCATCATCATGATGAACATGGCGAGCAGCTGATCCAGCTGCTGCTCGGAGTCAGC
CGAAGGCGAGCGCTGACTGGAGTTCTGGGTTTGCTGGGGCCCGATGCCCATCGTCTGCAGGTTGAT
GAAGTTGGAAAATTTGTTTCCGATAGATGAGTCCAT

SEQ ID NO: 28, AAM40538, Hpa1 protein [Xanthomonas campestris pv. campestris str. ATCC 33913]
MDSSIGNKFSNFINLQTMGIGPQQTQNSSQRSPSADSEQQLDQLLAMFIMMMLQQSQGSDADQECG
DEQPQSGQQDGVSPLTQMLMQIVMQLMQNQGGAGMGGTSLGGGFNANLSSITGQA

FIGURE 4 (continued)

CLUSTAL W (1.83) multiple sequence alignment

```
Synco_SNF2                  ------------------------------------MATIHGNWQPSHGEN---  15
Anava_SNF2                  ------------------------------------MAILHGSWILSEQDS---  15
Nostoc_SNF2                 ------------------------------------MAILHGSWILNEQES---  15
Nodsp_SNF2                  ------------------------------------MAILHGNWLVRNQNG---  15
Lyn_sp_SNF2                 ------------------------------------MAILHGSWLQHPKN----  14
Crowa_SNF2                  ------------------------------------MTILHGTWIENTSEK---  15
Synel_PCC6301_SNF2          ------------------------------------MAVLHGGWLGD------  11
Synel_PCC7942_SNF2          ------------------------------------MAVLHGGWLGD------  11
Theel_BP-1_SNF2             ------------------------------------MAIFHGTWLPEPAP---  14
Glovi_SNF2                  ------------------------------------MAILHGIWVHQPPRA---  15
Proma_CCMP1375_SNF2         ------------------------------------MTLLHATWISTNWHPSNL  18
Proma_MIT\9211_SNF2         ------------------------------------MSLLHATWLPAMRTGSSH  18
Proma_MIT\9303_SNF2         MIGCGTPAWMVAVDRQCTPAPRNPTHTFCVAAMSLLHATWLPAIRTPTSS      50
Proma_MIT9313_SNF2          MIGCGTPAWMVAVDRQCTPAPRNPTHTFCVAAMSLLHATWLPAIRTPTSS      50
Syn_sp_CC9311_SNF2          ------------------------------------MSLLHATWLPAIRTPTSS  18
Syn_sp_WH\7805_SNF2         ------------------------------------MSLLHATWLPAIRTPSSS  18
Syn_sp_RS9916_SNF2          ------------------------------------MSLLHATWLPAIRTPTSS  18
Syn_sp_CC9605_SNF2          ------------------------------------MSLLHATWLPAIRTSSSS  18
Syn_sp_WH\8102_SNF2         ------------------------------------MSLLHATWLPAIRTSGSS  18
Syn_sp_CC9902_SNF2          ------------------------------------MSLLHATWLPAIRTSSSS  18
Syn_sp_\WH\5701_SNF2        ------------------------------------MSLLHATWLSADTAAVPA  18
Myctu_SNF2                  ------------------------------------MLVLHGFWSNSG------  12
Mycbo_SNF2                  ------------------------------------MLVLHGFWSNSG------  12
Nocfa_IFM\10152_SNF2        -------------------------------------MVGAGGPPGVG-----  11
Myxxa_DK_SNF2               --------------------VRAWRGVLRWAAAGLSLSAARSPTGHLPVFS    31
Symth_IAM14863_SNF2         ------------------------------------MITVHGSFVPSG-----  12
Metac_C2A_SNF2              ------------------------------------MIILH-----AGRVG--  10
Metma_Go1_SNF2              ------------------------------------MIILH-----AGRVG--  10
Pelph_BU-1_SNF2             ------------------------------------MIALH-----ISIID--  10
Archaeon\RC-I_SNF2          ------------------------------------MITLHGTWTTVDPLN--  15
Nos_sp_PCC7120_SNF2\II      ------------------------------------MKVLHGSWIPNQYSDFVQ 18
Bacce_ATCC10987_SNF2        ------------------------------------------------------
Methu_JF-1_SNF2             --------------------VTAKRPAPIHDKEEETIPDTSLPVFHALIYP    31
```

FIGURE 8

```
Synco_SNF2              ----------------GGKLFLWADTWGHPLPETIG-------DRHPFALDLPDLLQAWSN  53
Anava_SNF2              ----------------YLFIWGETWRSPQVNFSF-------EEIALNPLALSASELSEWLQS  54
Nostoc_SNF2             ----------------CLFIWGETWRSPQVDFNF-----AEISLNPLALSALELSEWLQS    54
Nodsp_SNF2              ----------------CLFIWGETWRSSRVDFALNVSQDIPLHPLVMSPIDLSELLSY     57
Lyn_sp_SNF2             ----------------YLFIWGETWRR-ITPNEFNPADGVLGYPFALSPVELEKWCSE     55
Crowa_SNF2              ----------------HFFIWGETWRSLSSDISSD--DSILMYPFSVDKQGIIEQLNS     55
Synel_PCC6301_SNF2      ----------------RFCVWAEAWQAGEPQSAAEIAIH----PYAIAATDLNDWCQK     49
Synel_PCC7942_SNF2      ----------------RFCVWAEAWQAGEPQSAAEIAIH----PYAIAATDLNDWCQK     49
Theel_BP-1_SNF2         ----------------QFFIWAEEWRS-------LAQAIT---PWAPPAIPVYPYATQ     46
Glovi_SNF2              ---------------G--LFLWGETWRQVAKRRKRS----EAPAPHPYVQQPAELSPRLAA  55
Proma_CCMP1375_SNF2     ---------------G----QSELFLWADQWRVVTPKQIIQ---TPSPHPFSLSSDELKEWLNS  60
Proma_MIT\9211_SNF2     ---------------N----PG-LLIWADSWRVAKPSIVSN---QPVIHPFALSAADLRIWLLQ  59
Proma_MIT\9303_SNF2     ---------------G----RPALLVWADTWRVATPAGPAA---TPALHPFTLNPDDLRAWLIE  92
Proma_MIT9313_SNF2      ---------------G----RPALLVWADTWRVATPAGPAA---TPALHPFTLSPDDLRAWLIE  92
Syn_sp_CC9311_SNF2      ---------------G----RAALLVWADTWRVAEPAGPST---TPALHPFTLSPDDLRALLTE  60
Syn_sp_WH\7805_SNF2     ---------------G----RAALLVWADTWRVADPLGPGA---TPALHPFTLSAEDLRAWLTE  60
Syn_sp_RS9916_SNF2      ---------------G----RAALLVWADTWRVAEPAGPGV---TPATHPFTLSADDLRAWLSE  60
Syn_sp_CC9605_SNF2      ---------------G----QPALLIWADTWRVATPEGPGL---TPALHPFTLSHEDLRAWLSE  60
Syn_sp_WH\8102_SNF2     ---------------G----QPALLIWADTWRVATPEGPGL---TPALHPFTLEPDDLKAWLQE  60
Syn_sp_CC9902_SNF2      ---------------G----QPALLIWADTWRVASPEGPGL---TPALHPFTLGSDDLKAWLTE  60
Syn_sp_\WH\5701_SNF2    LGGG-YRPGLLIWADTWRVAEPQTPAS----EAPQHPLSLDQDDLGAWLEE             64
Myctu_SNF2              ---------------------GMRLWAEDSD-LLVKSPSQA----LRSARPHPFAAPAD     45
Mycbo_SNF2              ---------------------GMRLWAEDSD-LLVKSPSQA----LRSARPHPFAAPAD     45
Nocfa_IFM\10152_SNF2    ---------------------ATCLDGRMLHGLSVRALVHQGPGGG----LWTEGEVPPALP-- 43
Myxxa_DK_SNF2           GFSVATDGVGLFAGLSVRALVHQGPGGG----PLRAPHGQPGRPAA                  73
Symth_IAM14863_SNF2     ---------------------ASGFFFLWGLDGVAARDAAPPG----RRRRGVPRHPCA     46
Metac_C2A_SNF2          ---------------------KQFFLWGESPAENETPPVRRGRKPKKPVAKPYPYDSGVENLSS  53
Metma_Gol_SNF2          ---------------------KQFFLWGESPAENETPVVRRGRKPKTPIVKPYPYDSGFENLSS  53
Pelph_BU-1_SNF2         ---------------------GVPLLWSEGKKIGMLKELRLAT----------AGIGMFS-   39
Archaeon\RC-I_SNF2      ---------------------GTFFLWGESD--PATQHKRRGRPRKSAGEKQHPFHAGIKELEA  56
Nos_sp_PCC7120_SNF2\II  ---------------S-----GAFYLWVETPINNKKRTHTQVHPGHLSSLELLNFLTQTLGIKE  62
Bacce_ATCC10987_SNF2    ---------------------MINQTEVTIRLQHVSHG-----                     17
Methu_JF-1_SNF2         AVEG---VAICAEYITDKPAPVRKKGYAKDKPGEYPYSLDHTALKTLIEN              78
```

```
Synco_SNF2              LPLAFPKADGVT------------------EAALTLHLPSHRQQK-  80
Anava_SNF2              QHQAIAQILPQQ------LAKKTSKAASSPTTNLPIHSQIIVLPTEISQPR  99
Nostoc_SNF2             QHQAIAKLLPQQ------LEKRTSKAASSVKINLLTHSQIIALPTEISQPR  99
Nodsp_SNF2              HNIKIPSLIQQSQVALSGTGRTRKSTSTTKFSWTTHSLIIDLPTHISENN  107
Lyn_sp_SNF2             KQLSIESKVVVT------------------ETLALPTKLSP--  78
Crowa_SNF2              NKIKIEKNKNIES-----------------VSQIFYLPSKFIAK-  82
Synel_PCC6301_SNF2      YRLGS-LTGTPT------------------EVLLSIPSDLKKE-  73
Synel_PCC7942_SNF2      YRLGS-LTGTPT------------------EVLLSIPSDLKKE-  73
Theel_BP-1_SNF2         RKTPLRKTARPS------------------ATYVALPAQIQGH-  71
Glovi_SNF2              QFPQIPLSLLVP------------------ETLALQLPATVEN-  80
Proma_CCMP1375_SNF2     KKLLPNESINTS------------------ACLTLPSKPIH--  83
Proma_MIT\9211_SNF2     KKLLPKESIECT------------------ALLTLPSKSIKNS  84
Proma_MIT\9303_SNF2     RDLLPDEIIDAT------------------ACLTLPSRTVKPR 117
Proma_MIT9313_SNF2      RDLLPDEIIDAT------------------ACLTLPSRTVKPR 117
Syn_sp_CC9311_SNF2      RDLLPDGIIDAT------------------ACLTLPSRSVKPR  85
Syn_sp_WH\7805_SNF2     RDLLPDGIIDAT------------------ACLTLPSRSVKPR  85
Syn_sp_RS9916_SNF2      RELLPDGIIDAT------------------ACLTLPSRTVKPK  85
Syn_sp_CC9605_SNF2      RDLLPGGCIDAT------------------ACLTLPSRTVKLR  85
Syn_sp_WH\8102_SNF2     RDLLPGGSIDAT------------------ACLTLPSRTVKPR  85
Syn_sp_CC9902_SNF2      RDLMPGGSIDAT------------------ACLTLPSRSVKPR  85
Syn_sp_\WH\5701_SNF2    ADLWTEDFRPAG------------------ATLCLPSRRQGAR  89
Myctu_SNF2              LIAGIHPGKPAT------------------AVLLLPSLRSAPL  70
Mycbo_SNF2              LIAGIHPGKPAT------------------AVLLLPSLRSAPL  70
Nocfa_IFM\10152_SNF2    ------DPAG--------------------ALLRASRFRHR--  58
Myxxa_DK_SNF2           HGAGNPVQGRSQ------------------ACLRVPLARTEFT  98
Symth_IAM14863_SNF2     TEP---------------------------EALYPALRGLPYL  62
Metac_C2A_SNF2          ALELLLGSTG--------RKKAEEINVWIPTAG---  78
Metma_Go1_SNF2          ALELLLGSTD--------RKKAEKINVWTPTIG---  78
Pelph_BU-1_SNF2         ----LLDNT---------TKEFCVWLPCRE-----  56
Archaeon\RC-I_SNF2      GAGAINSSCIRHI-----ADAGARAEQVLIPSATDRPL  90
Nos_sp_PCC7120_SNF2\II  TEAQLKQRICSK------YFALPTANNEP-  85
Bacce_ATCC10987_SNF2    ------------------WFLWGEDDSGTP-  29
Methu_JF-1_SNF2         CFGAYDDLKATR------WIIYLPAEETVP- 102
```

```
Synco_SNF2              QTLTLLQSIPLGG----QALAN-------------------LGSEFYFYGQL 143
Anava_SNF2              AAVKFLTSLPLNI----TSTENAF-----------------LGGDLRFWSQI 168
Nostoc_SNF2             AAIKLLTSLPLNI----TSGENAF-----------------LGGDLRFWSQI 168
Nodsp_SNF2              EAIKFLAAVPLNA----AREEDTL-----------------FGGDLRFWSQI 176
Lyn_sp_SNF2             EAFDFLQSLPLGN----LTTENSF-----------------IGSDLQFWSHL 146
Crowa_SNF2              DTINILSQLPLGL----TNNDENY-----------------IGDNLKFWTHI 150
Synel_PCC6301_SNF2      IAGQWLATLPLG-----SAEDHPW-----------------LGPDLRFWSHI 133
Synel_PCC7942_SNF2      IAGQWLATLPLG-----SAEDHPW-----------------LGPDLRFWSHI 133
Theel_BP-1_SNF2         EVLEQLHQLSL------HGQDSGS-----------------IGDDLRYWLHV 128
Glovi_SNF2              QAFELLLGVPLG-----GGDAS-------------------IGDDLRFWSQC 137
Proma_CCMP1375_SNF2     EATEWLTKLPLS-----KKDSD-------------------LSEELLWWAHL 159
Proma_MIT\9211_SNF2     EAASWLANLPLT-----KKDPE-------------------LSEEILWWSHL 162
Proma_MIT\9303_SNF2     AATAWLSKLPLS-----GDHPD-------------------LADELRWWSHL 195
Proma_MIT9313_SNF2      AATAWLSKLPLS-----GNHPD-------------------LADELRWWSHL 195
Syn_sp_CC9311_SNF2      AATAWLSKLPLS-----GRHPD-------------------LADELRWWSHM 158
Syn_sp_WH\7805_SNF2     AATAWLAKLPLS-----GHHPD-------------------LADELRWWSHM 161
Syn_sp_RS9916_SNF2      AATAWLARLPLS-----GRHPD-------------------LADELRWWSHM 156
Syn_sp_CC9605_SNF2      AATEWLSRLPLS-----GTNPD-------------------LADELRWWSHL 159
Syn_sp_WH\8102_SNF2     AATEWLSRLPLS-----GRNPD-------------------LADELRWWSHL 159
Syn_sp_CC9902_SNF2      AATEWLARLPLS-----GRHPD-------------------LGDELRWWSHL 159
Syn_sp_\WH\5701_SNF2    AATLWLGRLPLS-----GDHPD-------------------LADDLRWWSHL 157
Myctu_SNF2              AALAAFDQP--------APDVR-------------------YGASVDYLAEL 128
Mycbo_SNF2              AALAAFDQP--------APDVR-------------------YGASVDYLAEL 128
Nocfa_IFM\10152_SNF2    AAVDVLRQR--------LPVES-------------------VAGDLRFLAHV 107
Myxxa_DK_SNF2           RASALLVTPEGLRECEGHGLPLAATVERLAVVQTSEAESFPGSIALWTLA 183
Symth_IAM14863_SNF2     AVQWLLDLPDHFR----GTPLRP------------------GHSIQLMCVA 120
Metac_C2A_SNF2          EAIVLLCACMGKK----VLAPG-------------------IISGNDLLWWADA 144
Metma_Go1_SNF2          EAIVLLCTCMEKK----VLAPG-------------------IISGNDLLWWADA 144
Pelph_BU-1_SNF2         ALFELSLLTEKGN----IPGSG-------------------IIFGSSLHWARQV 122
Archaeon\RC-I_SNF2      NALVLLSSIAESQ----KRIGD-------------------MAIGPDLLYWSKV 156
Nos_sp_PCC7120_SNF2\II  VKAVIAINIIKLLKDIHFLALYNAS----------------EFQLGSDLLFWYHY 158
Bacce_ATCC10987_SNF2    TFLKEASFEGRQG--------------------------------VMLTNAQAFEYI 74
Methu_JF-1_SNF2         TFFQIWKAAQNTD--------------------------------KNYIAGDSFQYI 160
```

FIGURE 8 (continued)

| Name | Sequence | # |
|---|---|---|
| Synco_SNF2 | HRWCLDLVLRGKFVPGLEQRGED-GNYYAQWIPILDSIQDQTHLAQFSQR | 192 |
| Anava_SNF2 | ARWSLDLISRSKFLPIIQRQPN--NSVSAKWQVLLDSAVDGTRLEKFAAK | 216 |
| Nostoc_SNF2 | ARWSLDLISRSKFLPIIQRQPN--NSVSAKWQVLLDSAVDGTRLEKFAAK | 216 |
| Nodsp_SNF2 | ARWSLDLISRCKFLPTIQRQFD--SSIVARMQVLLDSAIDGTRLEKFSAK | 224 |
| Lyn_sp_SNF2 | SRWSLDLLARSKFLPSLTFNPSK-DHFIAEWKPLLDSATDQARLIRFSKQ | 195 |
| Crowa_SNF2 | YRWMAQSLLARGRFYPALESSDR---NCYGQWEPLLDSLVDQQRFSKFIQT | 197 |
| Synel_PCC6301_SNF2 | YRWAQSLLARGRFYPALESSDR---GLTAVWLPLFNQAGDRQRFDRYSQQ | 180 |
| Synel_PCC7942_SNF2 | YRWAQSLLARGRFYPALESSDR---GLTAVWLPLFNQAGDRQRFDRYSQQ | 180 |
| Theel_BP-1_SNF2 | SRWLLDLIVRGQYLPTPEG--------WRILLTHGGDRDRLRHFSQL | 167 |
| Glovi_SNF2 | ARWVLDLLVRAKYLPDLESGDGQ-EIPTARWVPLLDSAVDQARLKEFAAR | 186 |
| Proma_CCMP1375_SNF2 | ERWSLNLIASGLWLPQVKLHKKEGNEYRASWIPLLNQENERNRLEEFAKN | 209 |
| Proma_MIT\9211_SNF2 | ERWSLSLIARGLWLPQVELNTIDNIGARARWSPLLNNENERKRLEEFSIR | 212 |
| Proma_MIT\9303_SNF2 | QRWALSMIARGRWLPQVELSKGEGYPHRARWTPLLNREDDRRRLEDLAAQ | 245 |
| Proma_MIT9313_SNF2 | QRWALSMIARGRWLPQVELSKGEGYPHRARWTPLLNREDDRRRLEDLAAQ | 245 |
| Syn_sp_CC9311_SNF2 | QRWSLSLVARSRWLPQVELSKGEGYPHRARWVPLLNREEDRRRLEDLAAG | 208 |
| Syn_sp_WH\7805_SNF2 | QRWALSLVARGRWLPQVELSRGEGYPHRARWVPLLNREEDRRRLEDLAAR | 211 |
| Syn_sp_RS9916_SNF2 | QRWALSLIARSRWIPQVELSKGEGYPHRARWVPLLNREDDRRRLEDMAAR | 206 |
| Syn_sp_CC9605_SNF2 | QRWALSLVARGRWIPQMEFSKGEGYPHRARWVPLLNREEDRRRLEDLAAS | 209 |
| Syn_sp_WH\8102_SNF2 | QRWALSLVARGRWIPQMELSKGEGYPHRARWVPLLNREEDRRRLEDLAAS | 209 |
| Syn_sp_CC9902_SNF2 | QRWSLSLVARGRWIPQMELSKGEGYPHRARWVPLLNREEDRRRLEDLAAT | 209 |
| Syn_sp_\WH\5701_SNF2 | QRWSLSLLARGRLLPQVEGG-------RARWLPLINREDDRRRLEDLASR | 200 |
| Myctu_SNF2 | AVFARELVERGRVLPQLRRDTH---GAAACWRPVLQG-RDVVAMTSLVSA | 174 |
| Mycbo_SNF2 | AVFARELVERGRVLPQLRRDTH---GAAACWRPVLQG-RDVVAMTSLVSA | 174 |
| Nocfa_IFM\10152_SNF2 | ADGIDRWVRAGRVVPDLHRADG---QWWARWRLVGGA-RQRAWLAELAVA | 153 |
| Myxxa_DK_SNF2 | SKLALELVARERVVPTLLRRGE---RIEARWAAALSATEDAGRVAALARS | 230 |
| Symth_IAM14863_SNF2 | SKLLLEFLGRGLMLPVLQAEAG---VLSAGWALHLTDADDVRRLTRLAAG | 167 |
| Metac_C2A_SNF2 | LKFAGSLVAGQKYLPGVRGGEG----EYKAFWEPVFSGEDAGELARLAKQ | 190 |
| Metma_Go1_SNF2 | LKFAGSLVAGQKYLPGVRGGEG----EYRAFWEPVFSGEDAGKLAKLAKQ | 190 |
| Pelph_BU-1_SNF2 | VKIALNIVRTQSLLPSIIKNDT----FWEALWLPLPDSATSLAVEQLADA | 168 |
| Archaeon\RC-I_SNF2 | AKFTLKLLISQQFRPEVVEVMSG--KAYSRWRFALTDETDRKHYASLENS | 204 |
| Nos_sp_PCC7120_SNF2\II | TQSFRQIITKDQYIPSLKYRAN-AATTKKKPKQPPPGFEIYAGWEIISEQ | 207 |
| Bacce_ATCC10987_SNF2 | ANKPMNSFARIQMNGPITALTEDANELWDAFTSGSFVPDMERWPKQPSWK | 124 |
| Methu_JF-1_SNF2 | S-ILMESTVRLIQNGRFKPSLERTFAGYHAVWVPALSPQDMEWVSDFSSR | 209 |

FIGURE 8 (continued)

| Sequence | Alignment | Position |
|---|---|---|
| Synco_SNF2 | VPACALANLT------------------------------------DSQEPQMLVVD | 213 |
| Anava_SNF2 | MPLVCRTYQR-LGNEEL---------SPSP--------IYIDFPSQPQELILG | 251 |
| Nostoc_SNF2 | MPLVCRTYQE-IGS------------GESP--------IYIDFSQPQDLILG | 248 |
| Nodsp_SNF2 | MPLACRTYRKGMGSGEWGVGSGEESSPSI---------MYVDFPTEPQELLLG | 268 |
| Lyn_sp_SNF2 | IPSACRIYQLWSKEAQN---------QFEN--------LALDLPQNPQNLIDD | 231 |
| Crowa_SNF2 | MPNSSLAYHNLMEG------------------------ELSSSLLKQTTILD | 225 |
| Synel_PCC6301_SNF2 | LPFSQFCYQAIETA------------------------AACPWQPQPQDLLLR | 209 |
| Synel_PCC7942_SNF2 | LPFSQFCYQAIETA------------------------AACPWQPQPQDLLLR | 209 |
| Theel_BP-1_SNF2 | MPDLCRCYQADGTA------------------------LQLP--PHAADLLAD | 194 |
| Glovi_SNF2 | LPGACRAATP----------------------------ELSPHQILKS | 206 |
| Proma_CCMP1375_SNF2 | IPLVAICAVPWIEAKG---------QIVNTEQVSNSNNNTLSLYRPRHNRVEVMD | 255 |
| Proma_MIT\9211_SNF2 | LPLVATCAIKREETSEENQNHILKTTPRETLDEYGLAVCRPINSRLQVAY | 262 |
| Proma_MIT\9303_SNF2 | LPLVATCALPWREPTGRRSNRMTRLRPEAMRAANPVASCRPRSGRLRVAS | 295 |
| Proma_MIT9313_SNF2 | LPLVATCALPWREPTGRRSNRMTRLRPEAMRAANPVASCRPRSGRLRVAS | 295 |
| Syn_sp_CC9311_SNF2 | LPLVATCALPWREPTGKRSNRITRLRPEAMRAANPVACCRPRSGRLRVAT | 258 |
| Syn_sp_WH\7805_SNF2 | LPLVATCALPWREPTGKRSNRITRLRPEAMRAANPVACCRPRSGRLRVAT | 261 |
| Syn_sp_RS9916_SNF2 | LPLVATCALPWREPTGKRSNRTTRLRPEAMRAANPVACCRPRSGRLRVAT | 256 |
| Syn_sp_CC9605_SNF2 | LPLVATCALPWREPLGRRSNRTTRLRPEAMRAANPVASCRPRSGRLRVAT | 259 |
| Syn_sp_WH\8102_SNF2 | LPLVATCALPWREPMGRRSNRMTRLRPEAMRAANPVACCRPRSGRLRVAT | 259 |
| Syn_sp_CC9902_SNF2 | LPLVATCALPWREPLGRRSNRTTRLRPEAMRAANPVACCRPRSGRLRVAT | 259 |
| Syn_sp_\WH\5701_SNF2 | LPQVAVAAL-----------------EPGQGEAGVAMACWRPGSGRRRLAS | 234 |
| Myctu_SNF2 | MPPVCRAEVGG-----------------------------HDPHELATSALDA | 198 |
| Mycbo_SNF2 | MPPVCRAEVGG-----------------------------HDPHELATSALDA | 198 |
| Nocfa_IFM\10152_SNF2 | MPAALRVAG-------------------------------QPAAVLDDLVTE | 174 |
| Myxxa_DK_SNF2 | MPPGAHAVPAGARPG-------------------------RAVWAPDALLRA | 257 |
| Symth_IAM14863_SNF2 | LPEACRALVPPDRTPN-------------------------TYPLPVADGLVHQ | 196 |
| Metac_C2A_SNF2 | MPPAAKALALETSSVQP------------------------EILAAVAARQ | 217 |
| Metma_Go1_SNF2 | MPPAARALAPEASMPP-------------------------EMPAALAAKQ | 217 |
| Pelph_BU-1_SNF2 | MPAVCRSLG-RTDTQPP-------------------------ETPKKLLLKG | 194 |
| Archaeon\RC-I_SNF2 | MPLACIAVSGKAGIYN--------------------------RKEALDL | 227 |
| Nos_sp_PCC7120_SNF2\II | YEANIQKYIEYMPLICVAG-----------------------NSTQTDKLEFFAPET | 241 |
| Bacce_ATCC10987_SNF2 | VQNTP----------------------------------IEDETLAS | 137 |
| Methu_JF-1_SNF2 | MPTVCKYAIPRVAKDPY-----------------------IYKPETRLEK | 236 |

FIGURE 8 (continued)

| | |
|---|---|
| Synco_SNF2 | LLQKLLQAQIGAVSPS------------LANVKEVWLNDWLRGLTHGGQTSLGT 255 |
| Anava_SNF2 | FLNSAIDTQLREMVGNQPVV-ETRLMASLPSAVRQWLQGLSGASNSVDAD 300 |
| Nostoc_SNF2 | FLNSAIDTQLREMVGNQPVV-ETRLMASLPSAVRQWLQALIAASNSIDAD 297 |
| Nodsp_SNF2 | FLNSTIDAQVREMLASQPLL-ETRVMASLPSAVRQWLQGLTSASHTVNAD 317 |
| Lyn_sp_SNF2 | FLTAIIDSQVKKVAEESEKK-AITNLTAIQPIVQSWLHALASESNLAKSK 280 |
| Crowa_SNF2 | FLSTIINQQVRQFID------VAITPSSFIQKWLYSLTQDLSKFEAS 266 |
| Synel_PCC6301_SNF2 | VLQTWLTARLQPAIAA-------GTLVSADLLAAWQQSLAN-GKPLKLE 250 |
| Synel_PCC7942_SNF2 | VLQTWLTARLQPAIAA-------GTLVSADLLAAWQQSLAN-GKPLKLE 250 |
| Theel_BP-1_SNF2 | FLQHTLQGYLHTALAD-------LELPKVGLAKEHGHWIAF-LKTGQTP 235 |
| Glovi_SNF2 | FLSAMLDARVRTLLACEP----PDPRTLPAGAVRPWLLALAHAQPQLKSP 252 |
| Proma_CCMP1375_SNF2 | LLEELIDAQLRKDFQP------RTKNLDPLLKAWQEALGTKDGIINLS 297 |
| Proma_MIT\9211_SNF2 | LLEELVDGQLRKDFEE------SSEDLDPLLKAWQEALGSHNGVIRLP 304 |
| Proma_MIT\9303_SNF2 | LLEELLDAQLRTGFEA------SEQGLDPLLTAWQEALGSDSGVINLP 337 |
| Proma_MIT9313_SNF2 | LLEELLDAQLRTGFEA------SEQGLDPLLTAWQEALGSDSGVINLP 337 |
| Syn_sp_CC9311_SNF2 | LLADLMDAQLRKGFTP------DPDGLDPLLRAWEEALSSDTGEIQLS 300 |
| Syn_sp_WH\7805_SNF2 | LLEDLVDAQLRKGFHP------DDEGLDPLLCAWENALSSETGVIDLN 303 |
| Syn_sp_RS9916_SNF2 | LLEDLVDAQLRTGFTA------QTDGLDPLLAAWEEALGSDTGVIHLG 298 |
| Syn_sp_CC9605_SNF2 | LLEDLVDAQLRKDFEP------STDGLDPLITIWQEALGSETGVIEIG 301 |
| Syn_sp_WH\8102_SNF2 | LLEDLVDAQIRKDFEP------STDGLDPLITIWQDALGSETGVIEIG 301 |
| Syn_sp_CC9902_SNF2 | LLEDLVDAELRKGFEP------TTEGLDPLLTIWQEALASETGVVEVG 301 |
| Syn_sp_\WH\5701_SNF2 | ILTHLVDARMRAGFTP------SEEGLDPLLAAWQRALGPGDGRLDLG 276 |
| Myctu_SNF2 | MVDAAVRAALSPMDLLPPR---RGRS-KRHRAVEAMLTALTCPDGRFDAE 244 |
| Mycbo_SNF2 | MVDAAVRAALSPMDLLPPR---RGRS-KRHRAVEAMLTALTCPDGRFDAE 244 |
| Nocfa_IFM\10152_SNF2 | LTDPIVRTRLADAPVTHPL---VRAL-VRDQPLETGSHQLAEVLRRWRES 220 |
| Myxxa_DK_SNF2 | FLDATVDAFVRAARGAPSL---PARR--AASWDERWREALTGAR-RDFAP 301 |
| Symth_IAM14863_SNF2 | FMRTAAAGVIRLLLEEEPL---PEAQSLQDTALRHWLAALTGAEARDLPP 243 |
| Metac_C2A_SNF2 | FIEEALDWIVRSEIGEKELAKEARKRKSFDSVHDAWVSALKSPD-GLIHG 266 |
| Metma_Gol_SNF2 | FIEDSLDWIVRSEIGEKKLAKETRKRKSFDSVHDAWVSALRSPE-GLIYG 266 |
| Pelph_BU-1_SNF2 | LLSFLVNTLSRTFERAG-----VPKISDFFESIHDAWLHALSNSDPRLKWK 239 |
| Archaeon\RC-I_SNF2 | FINTALDTFIRDQIALP-------ADSRMTNLLSQAMLDSLGTGE--SIRL 269 |
| Nos_sp_PCC7120_SNF2\II | LLRHFSEYLLNNLVSKTP-------LTAAFEKQIDDSLIHYCLYPQKHNPL 285 |
| Bacce_ATCC10987_SNF2 | LFSAAVNESILQDNRSND------GWEDAKRLYEHYDFTKRQLDAALHEE 181 |
| Methu_JF-1_SNF2 | FIVEMMRVIIRTALGYT-------LKEETDPFYEPSENEMQFMTDLLGVT 280 |

FIGURE 8 (continued)

```
Synco_SNF2              S--KALQRLIATSLDHWYLPVQNYLGQKNNQALAQRQWRGALRLQPPADDG  303
Anava_SNF2              A---VGLERLEAALKAWTMPLQYQLASK------NQFRTCFELRSPEPG-  340
Nostoc_SNF2             A---VGLERLEAALKAWTMPLQYQLASK------NQFRTCFELRSPEPD-  337
Nodsp_SNF2              A---MEVERLEAALKSWTMPLQYQLVGK------PSFRACFQLLPPASG-  357
Lyn_sp_SNF2             K--SESKTLEKILSNWTAPLQQTLAEH------NLFRTGFRLSPPENN-  320
Crowa_SNF2              E--VERKGLKNAINNWKSSLSEYIIKSDNQPLGINQFRVCFKLENPAKSG  314
Synel_PCC6301_SNF2      D--SEASRLQTAIDRWLLP--VQNGAA------QAWRMVLRLVPPTEQ-  288
Synel_PCC7942_SNF2      D--SEASRLQTAIDRWLLP--VQNGAA------QAWRMVLRLVPPTEQ-  288
Theel_BP-1_SNF2         E--LPPP-LIERLHRWQEPYREQLHLR------PQWRLALQLVPPDTA-  274
Glovi_SNF2              D--PETPALAEALATWRAPLSYQVRSR------TCFRLQPPEES-  288
Proma_CCMP1375_SNF2     N--ENAKRLEKASKNWKRGLSSNVQPA------KTCLELIAPIDD-  334
Proma_MIT\9211_SNF2     L--EDCERLAKASKNWKENLSGNVKGA------RACLELFAPLEG-  341
Proma_MIT\9303_SNF2     D--EEAERLATASNHWREGVAGNVAPA------RACLELFTPGEG-  374
Proma_MIT9313_SNF2      D--EEAERLATASNHWREGVAGNVAPA------RACLELFTPGEG-  374
Syn_sp_CC9311_SNF2      D--EETERLATASNHWREGVAGNVAAA------RACLELATPADD-  337
Syn_sp_WH\7805_SNF2     D--EDAERLATASHHWREGVAGNVAAA------RACLELATPNEG-  340
Syn_sp_RS9916_SNF2      D--EDAERLATASHHWREGVAGTVAAA------RACLELETPDDG-  335
Syn_sp_CC9605_SNF2      D--EEAERLATASHHWREGIAGDFAAA------RTCLELHTPPDG-  338
Syn_sp_WH\8102_SNF2     D--EQAERLASASFHWREGIAGDFAAA------RTCLELQTPAEG-  338
Syn_sp_CC9902_SNF2      N--EDAERLTAASLHWREGIAGGFAAA------RTCLELNTPNEG-  338
Syn_sp_WH\5701_SNF2     D--DDCERLQVATHHWREAVAGRVEPA------RACLELDTPDEG-  313
Myctu_SNF2              P--DELDALAEALRPWDDVGIGTVGPAR-----ATFRLSEVETENEETPA  287
Mycbo_SNF2              P--DELDALAEALRPWDDVGIGTVGPAR-----ATFRLSEVETENEETPA  287
Nocfa_IFM\10152_SNF2    LTVDEPELVLRLLEPDGETGIDGDG--------GDDRDDTVA  254
Myxxa_DK_SNF2           EGFAERSVVDELTR-WSEPALGAR---------DKLRACFRLEPPTEER  340
Symth_IAM14863_SNF2     GLPGAQELYAALDR-WSAPATGVLS--------HASLRTGVRLHLPGPET  284
Metac_C2A_SNF2          EE-KELLQLAFRTREWQRPLTVLTSP-------FRFCFRLEEPAAEE  306
Metma_Gol_SNF2          DE-NELLQLAARTREWQRPLTILTTSP------FRFCFRLEEPALEE  306
Pelph_BU-1_SNF2         NE-QEIEQFACQLNAWRRPIDLHERSP------FRFCLQLTEP----  275
Archaeon\RC-I_SNF2      SA-PEMKKLKDSAGRWTSRMKTESKQA------LKTCFILEPPAP--  307
Nos_sp_PCC7120_SNF2\II  KTHTALQEYQQWLGWKNRIIRTQAESP------FHLCFQLHSPDAEQ  326
Bacce_ATCC10987_SNF2    DWLRKIGYIEDDL--------------------PFTIGLRLQEPQE--  207
Methu_JF-1_SNF2         DPIRNKGFERTFLRAMQDWLTFSSSGRF-----APFEFCMIKDPPEG-  323
```

FIGURE 8 (continued)

| | | |
|---|---|---|
| Synco_SNF2 | ----------------------------------GGTWQLDYGLQALDDG | 319 |
| Anava_SNF2 | ----------------------------------ETEWTLAYFLQAADNP | 356 |
| Nostoc_SNF2 | ----------------------------------ETEWTLAYFLQAADDP | 353 |
| Nodsp_SNF2 | ----------------------------------ETEWTLAYFLQAADDP | 373 |
| Lyn_sp_SNF2 | ----------------------------------ATDWILAYFLQAADDE | 336 |
| Crowa_SNF2 | ----------------------------------QKNWTLDYCLQAIDEP | 334 |
| Synel_PCC6301_SNF2 | KK--------------------------------LEQSNWQLHYYLQALDDP | 304 |
| Synel_PCC7942_SNF2 | ----------------------------------EQPWQLEFGLQAATDP | 304 |
| Theel_BP-1_SNF2 | ----------------------------------EQPWQLEFGLQAATDP | 290 |
| Glovi_SNF2 | ----------------------------------DGDWHLAFGLQTEGET | 304 |
| Proma_CCMP1375_SNF2 | ----------------------------------QGEWKLHFLLQTGDDP | 350 |
| Proma_MIT\9211_SNF2 | ----------------------------------LDLWDLNFSLQSESDP | 357 |
| Proma_MIT\9303_SNF2 | ----------------------------------EDLWDLQFSLQAEADP | 390 |
| Proma_MIT9313_SNF2 | ----------------------------------EDLWELRFALQAEADP | 390 |
| Syn_sp_CC9311_SNF2 | ----------------------------------EDLWELRFSLQAEADP | 353 |
| Syn_sp_WH\7805_SNF2 | ----------------------------------EELWPLRFFLQAEADP | 356 |
| Syn_sp_RS9916_SNF2 | ----------------------------------EELWDLRFYLQAEADP | 351 |
| Syn_sp_CC9605_SNF2 | ----------------------------------DDLWTLRFALQAEADP | 354 |
| Syn_sp_WH\8102_SNF2 | ----------------------------------EDLWELRFGLQAEADP | 354 |
| Syn_sp_CC9902_SNF2 | ----------------------------------EELWELRFGLQAESDP | 354 |
| Syn_sp_\WH\5701_SNF2 | ----------------------------------EELWDLKFGLQAEADP | 329 |
| Myctu_SNF2 | G---------------------------------EDLWPLRFSLQAEADP | 303 |
| Mycbo_SNF2 | G---------------------------------SLWRLEFLLQSTQDP | 303 |
| Nocfa_IFM\10152_SNF2 | ----------------------------------SLWRLEFLLQSTQDP | 268 |
| Myxxa_DK_SNF2 | E---------------------------------LWRLEVCLRTEGEA | 355 |
| Symth_IAM14863_SNF2 | D---------------------------------PFVLSFHLQSPDDP | 300 |
| Metac_C2A_SNF2 | ELEETEE------SEAGKMDTKKGRKGIADIEVPEELWYVRYMLQSYEDP | 350 |
| Metma_Gol_SNF2 | EIEETEETEEIEENEAGKRDTKKGREGIADIEVPEGLWYVRYMLQSYEDP | 356 |
| Pelph_BU-1_SNF2 | ----------------------------PLKGRK-------KERWHVAYQLQLKADP | 297 |
| Archaeon\RC-I_SNF2 | ----------------------------------DTEYPEAPWNLRYCLQASDDP | 328 |
| Nos_sp_PCC7120_SNF2\II | ----------------------------------IDNWQMQFLVSSKKDP | 342 |
| Bacce_ATCC10987_SNF2 | ----------------------------------EFEMWKLETIVTPKRGA | 224 |
| Methu_JF-1_SNF2 | ----------------------------------QTEPWDFTLAVRSEAEP | 340 |

FIGURE 8 (continued)

```
Synco_SNF2            EFWLPAASLWAMAGDRLVWQGRRV-DQGAESLLRGLGVAAQIYEPIAASL 368
Anava_SNF2            EFLVDAGTIWQHPVEQLIYQQRSI-QEPQETFLRGLGLASRLYPVIAPTL 405
Nostoc_SNF2           EFLVDAATIWQNPVEQLIYQQRTI-EEPQETFLRGLGLASRLYPVIAPTL 402
Nodsp_SNF2            NLLVDAATIWHHPVEQLVYQNRTI-DQPQETLLRGLGLASRLYPVLTPSL 422
Lyn_sp_SNF2           EFLVDAQTIWTHPVEAFVHNGRMI-KRPQETLLKGLGLASRLYPLLEPSL 385
Crowa_SNF2            NFLISAKVIWENPVTRLICNNRTI-NHPQETLLKGLGLASRLYYLIEESL 383
Synel_PCC6301_SNF2    DRFRPASLLWQDPLPPGLPD-----QSQELLLRGLGLGQACRLYPQLQTSL 348
Synel_PCC7942_SNF2    DRFWPASLLWQDPLPPGLPD-----QSQELLLRGLGLGQACRLYPQLQTSL 348
Theel_BP-1_SNF2       DTMLRAAEIWQCTQEALLYQGQVL-WQPQETLLRGLGLASRIYRPLDRSL 339
Glovi_SNF2            DSLMAAQQVWSSAG----------ELQEVFLAGLGLASRIFVPVERGL 342
Proma_CCMP1375_SNF2   SIRLAADQIWEAGVEVTKVGGITI-DNPSEILLEGLGRSLEIFPPIEKGL 399
Proma_MIT\9211_SNF2   SLKVAAEAVWNADSAVLQIGDIQI-AQPGEILLEGLGRALNIFQPIERGL 406
Proma_MIT\9303_SNF2   TIKVPAAAAWAAGPKVLQLGEIRV-EHPGEVLLEGMGRALTVFAPIERGL 439
Proma_MIT9313_SNF2    TIKVPAAAAWAAGPKVLQLGEIRV-EHPGEVLLEGMGRALTVFAPIERGL 439
Syn_sp_CC9311_SNF2    TLKLPAGAAWAAGPSGLQLGEIKV-EHPSEVLLEGMGRALTVFQPIERGL 402
Syn_sp_WH\7805_SNF2   TLKVPAGAAWAAGPEGLQLGEIPV-EHPGEVLLEGMGRALTVFEPIERGL 405
Syn_sp_RS9916_SNF2    TLKVPAALAWAAGPKGLQLGEIAV-EHPGELLLEGMGRALSVFPPIERGL 400
Syn_sp_CC9605_SNF2    SLKLPAAAAWAAGAEPLQLGEIRV-DQPGEVLLEGMGRALSVFPAIERGL 403
Syn_sp_CC9902_SNF2    SLKLPAAAAWASGADQLQLGEVTV-EQPGEVLLEGLGRALTVFPPIERGL 403
Syn_sp_WH\8102_SNF2   SLKLPAAAAWASGAETLQLGEIKV-DQAGEVLLEGLGRALTVFPPIERGL 403
Syn_sp_\WH\5701_SNF2  SLLLPAAGVWAAGAGCLQLGETEL-QQPGELLLEGLGRALQVFEPIERGL 378
Myctu_SNF2            SLLVPAEQAWNDDGS----LRRWL-DRPQELLLTELGRASRIFPELVPAL 348
Mycbo_SNF2            SLLVPAEQAWNDDGS----LRRWL-DRPQELLLTELGRASRIFPELVPAL 348
Nocfa_IFM10152_SNF2   PAPVPATADPN--------LLR----IAVEQLGRAQRAYPRLRDLP 302
Myxxa_DK_SNF2         SLLVPAADVWKTRGRSLEKLGRAF-RDPQESLLEALGRAARLFPPLALVL 404
Symth_IAM14863_SNF2   ALPVTADAVWASLGAEVEIGGQRY-QGAEQRLLADLPAMARLFPLAPLL 349
Metac_C2A_SNF2        SLLIPVKEAWKPK-KGSPLKRYDV-KNIRQFLLSSLGQAAGISAGIASSL 398
Metma_Gol_SNF2        SLLIPVKEAWKPK-KGSPLKKYDV-KNIRQFLLSSLGQASSISAGIASSL 404
Pelph_BU-1_SNF2       SLILDAGDLWNPESEASQHALTYT-SDCTEFLLTSLGQASGLCPAVTQSL 346
Archaeon\RC-I_SNF2    SLVIPAETVWKELKKTLKYLNKRY-DNPQEQLLQDLGKAMQMFPEIEPSL 377
Nos_sp_PCC7120_SNF2\II SLKLALADYWIMNSKTKAGVHKEFGKDFDTNLLLNLGYAARMYPKLWQGL 392
Bacce_ATCC10987_SNF2  HRIYVYESIDSLPKRWH--------DYEERILET----QESFSKLVPWL 261
Methu_JF-1_SNF2       SLLIPAEIIWELPDHQSGLFPQA--AYLKHILLAGIGLLTSSSSALWRPL 388
```

FIGURE 8 (continued)

```
Synco_SNF2            TERCPTGCGLDAIQAYEFILAIAHQLRDRGLGVILPPGLERG-GTAKRLG 417
Anava_SNF2            DTESPQFCHLNPMQAYEFIKAVAWRFEDSGLGVILPPSLANREGWANRLG 455
Nostoc_SNF2           DTESPQFCHLKPMQAYEFIKAVAWRFEDSGLGVILPPSLANREGWANRLG 452
Nodsp_SNF2            ETEYPQCCRLNPLQAYEFIKSVAWRFEDSGLGVILPPSLTNREGWANRLG 472
Lyn_sp_SNF2           QEARPQTCLLTPLQAYEFIKSINWRFTDSGLGVILPPSLVSQNGWANRLG 435
Crowa_SNF2            QDNKPSFSELDPIQVYEFLRSIANILKDNGLGVILPASLEQG-VEEKRLG 432
Synel_PCC6301_SNF2    ATACPEFHPLTTAEVYQLLKQVIPQWQEQGIEVQLPPGLR-GQQRHR-LG 396
Synel_PCC7942_SNF2    ATACPEFHPLTTAEVYQLLKQVIPQWQEQGIEVQLPPGLR-GQQRHR-LG 396
Theel_BP-1_SNF2       QERSPVALTLHTTEVYAFLQSAIAPLEQQGVAIILPPSLRRNSAQHR-LG 388
Glovi_SNF2            LVPQPTCCTMSTVEAFQFLKAATWRLRDSGFGVLLPESLADAGSLRNRLG 392
Proma_CCMP1375_SNF2   ESPTPHTMKLSASEAFVLIRTAAAKLRDMGIGVILPNSLSKG--FASRLG 447
Proma_MIT\9211_SNF2   ENATPNNMQLTPAEAFVLVRTASKQLRDIGIGVILPRSLSGG--LASRLG 454
Proma_MIT\9303_SNF2   DSATPEAMQLTPAEAFVLVRTAAAQLRDVGVGVELPASLSGG--LASRLG 487
Proma_MIT9313_SNF2    DSATPEAMQLTPAEAFVLVRTAATQLRDVGVGVELPASLSGG--LASRLG 487
Syn_sp_CC9311_SNF2    DSATPESMQLTPAEAFVLVRTAVRQLRDVGVGVDLPPSLSGG--LASRLG 450
Syn_sp_WH\7805_SNF2   DSATPEAMQLTPAEAFVLVRTAARQLRDVGVGVDLPPSLSGG--LASRLG 453
Syn_sp_RS9916_SNF2    DSATPEGMQLTPAEAFVLVRTAARELRDVGVGVELPASLSGG--LASRLG 448
Syn_sp_CC9605_SNF2    ESATPETMQLTPAEAFVLVRTAARQLRDAGVGVELPPSLSGG--LASRLG 451
Syn_sp_WH\8102_SNF2   ETATPDTMQLTPAEAFVLVRTAARQLRDAGVGVDLPPSLSGG--LASRLG 451
Syn_sp_CC9902_SNF2    ESATPETMQLTPAEAFVLVRTATHQLRNAGIGVELPPSLSGG--LASRLG 451
Syn_sp_\WH\5701_SNF2  DTATPERMALTPAEAFVLVRTAALKLRDVGVGVVLPPSLSGG--LASRLG 426
Myctu_SNF2            RTACPSGLELDADGAYRFLSGTAAVLDEAGFGVLLPSWW---DRRR-KLG 394
Mycbo_SNF2            RTACPSGLELDADGAYRFLSGTAAVLDEAGFGVRLLLPRAW---TIAEPTLR 394
Nocfa_IFM\10152_SNF2  GDPHSIDLLLPTEVVADLVAHGAQALREAGVRLLLPRAW---TIAEPTLR 349
Myxxa_DK_SNF2         ESPRPQALLLEPDTAWTFLSEGARVLSDAGFGVIVPGELTTSGRRRLRLR 454
Symth_IAM14863_SNF2   RDPAPSRMRIPADDVLALIQEGAMLLQQAGHPVLLPAALAKP--AALRVG 397
Metac_C2A_SNF2        EAPNPSGYSLDTKEAYRFLTESAADLSQAGFGLLLPGWWTRK-GTKTHLK 417
Metma_Gol_SNF2        EAPNPSGYSLDTKEAYRFLTESAANLSQAGFGVLLPGWWTRK-GTKTHLK 453
Pelph_BU-1_SNF2       KKKQPGGFDLDTEGAYRFLLEYAELLRSAGFVVKLPSWWIGR-RGVNRIG 395
Archaeon\RC-I_SNF2    NTSKPLSATLSTSEAYKFLTEAAPLLQDSGYSIILPEWWRNS-TGRLKLG 426
Nos_sp_PCC7120_SNF2\II ETDSPTGMQLSLDEAFDFLKDSAWVLEDSGFKVIVPAWYTPAGRRRAXIR 442
Bacce_ATCC10987_SNF2  KDGDTFRSELFETEAWNFLTEASNELLAAGITILLPSWWQNLKATKPXLR 311
Methu_JF-1_SNF2       SGSKPTGGSMTLKEAATFLGSDLARARRKGVTVLLPDWWTDTTYTPRVEI 438
                                                    .   :      :    *
```

```
Synco_SNF2              VKVVGEVQRQ------RGQR-LTLQSLINYDLQLMMGSDNARLLTAKDFEA  462
Anava_SNF2              LKISAETPKK------KPGR-LGLQSLLNFQWHLAIG-----GQTISKGEFDR  496
Nostoc_SNF2             LKISAETPKK------KPGR-LGLQSLLNFQWHLAIG-----GQTISKAEFDR  493
Nodsp_SNF2              LKISAETQKK------KQGR-LGLQSLLNFQWQLAIG-----GQTISKTEFNK  513
Lyn_sp_SNF2             LSVQAATSKS------KQNVSLGLDSLLNFKWELSIG-----GQTLSKTEFNR  477
Crowa_SNF2              ISLTAEVKSK------KGQR-LSLQSLLSYKLNLAIG-----DKTISKKDFEK  473
Synel_PCC6301_SNF2      VEVSATLPSD------RPS--VGLEALLQFRWELSLG-----GQRLTKAEVER  436
Synel_PCC7942_SNF2      VEVSATLPSD------RPS--VGLEALLQFRWELSLG-----GQRLTKAEVER  436
Theel_BP-1_SNF2         LKIIATLPPP------ATNG-LTIDSLMQFQWQLQLG-----QHPLSEADFDQ  429
Glovi_SNF2              LKLEANAPGR------NGSG-LGMQSLLAFKWELSLA-----GKTLSRAEFDR  433
Proma_CCMP1375_SNF2     LAIQAELPES------SLG--VMLGESLNWDWELMIG-----GINLSMKELEM  487
Proma_MIT\9211_SNF2     IAIKAELATS------ARG--LTLRENLEWSWELMIG-----GSILSLKDLEQ  494
Proma_MIT\9303_SNF2     LAIKAELSER------SRG--FTLGETLDWSWELMIG-----GVTLTLRELER  527
Proma_MIT9313_SNF2      LAIKAELSER------SRG--FTLGETLDWSWELMIG-----GVTLTLRELER  527
Syn_sp_CC9311_SNF2      LAIKAELSER------SRG--FTLGENLDWSWELMIG-----GVTLTLRELER  490
Syn_sp_WH\7805_SNF2     LAIKAELPKR------SRG--FTLGENLDWNWELMIG-----GVTLTLRELER  493
Syn_sp_RS9916_SNF2      LAIKAELPEK------SRG--FTLGETLDWSWELMIG-----GVTLTLRELER  488
Syn_sp_CC9605_SNF2      LAIQAELPER------SSG--FTLGECLAWEWDLMIG-----GVTLTLRELER  491
Syn_sp_WH\8102_SNF2     LSIKAELPER------SSG--FSLGESLDWSWDLMIG-----GVTLTLRELER  491
Syn_sp_CC9902_SNF2      LAIKAELPER------SSG--FTLGESLDWSWDLMIG-----GVTLTLRELER  491
Syn_sp_\WH\5701_SNF2    LAIKADLPDR------SRG--FSLGESLQWSWELMIG-----GVTLTLRDLER  466
Myctu_SNF2              LSIEADLPER------SRG--FSLGESLQWSWELMIG-----DDPLSEEEIAA  439
Mycbo_SNF2              LVLSAYTPVDGVV-GKASKFGREQLVEFRWELAVG-----DDPLSEEEIAA   439
Nocfa_IFM\10152_SNF2    LVLSAYTPVDGVV-GKASKFGREQLVEFRWELAVG-----DKVLTRAEMER   389
Myxxa_DK_SNF2           LAVSSAAPAA------ESTVGMQGLLSYRWELAVG-----DQPLSAQELAL   499
Symth_IAM14863_SNF2     MRVGASTKAAGAV-GGTAGLGLDALLRVDWDAVLG-----GTPLTLDELRH   436
Metac_C2A_SNF2          MRLSP------AG-GSPSMFGLHQIVNVRWDVALG-----DRALTVRELQA   489
Metma_Go1_SNF2          AQANVRGKK-LKA-GYG--LTLDKIVSFDWEIALG-----DRVLTVRELQA   496
Pelph_BU-1_SNF2         AQANVRGKKKLQA-GYG--LTLDEIVSFDWEIALG-----NEELDLQELKT   438
Archaeon\RC-I_SNF2      IKTKVKLPSMKGS-GSG--LTLDRMVACDYAAALG-----DQEITETEFRK   470
Nos_sp_PCC7120_SNF2\II  ARLRFKPKAEGKA-GKSQ-FTMDTLVSYDWRLALG-----EQTLTPQEWEQ   488
Bacce_ATCC10987_SNF2    LKASSGRKVAATVGESKSYFGLDSLVQYQYELAIG-----GIDLSESEFFE   351
Methu_JF-1_SNF2         VQLKQNATQT------QSFFGMNTLVNFDWRISTN-----DESFSPDEFWE   478
HARRRDPTHT------QTRIGLQELLSFDYRIAIG-----                 ..
```

```
Synco_SNF2              LLAQKSPLVVLDGEWITLQPADVRAAKVILQQQQS-APPLTVEDALRLSI  511
Anava_SNF2              LVALKSPLVEINGEWVELRPQDIKTAEAFFAARKD-QMALSLEDALRLSS  545
Nostoc_SNF2             LVALKSPLVEINGEWVELRPQDIKTAEAFFTARKD-QMALSLEDALRLSS  542
Nodsp_SNF2              LVALNSPLVEINGEWVELRPQDIKTAQTFFASRKD-EMTLSLEDALRLSS  562
Lyn_sp_SNF2             LVAQESPLVEINGEWVELRPTDIKAAKAFFSSRKD-QLSLTLEDALRLST  526
Crowa_SNF2              LLAQKSPLVEVKGEWIALQPADVKAAQQILNKSYD-PLELSVEDALRFST  522
Synel_PCC6301_SNF2      LAALETPLVEINGDWIEVRPQDIESAREFFRKRD-QPNLTLADAIAIAS   485
Synel_PCC7942_SNF2      LAALETPLVEINGDWIEVRPQDIESAREFFRKRD-QPNLTLADAIAIAS   485
Theel_BP-1_SNF2         LRRQGTPLVYLNGEWVLLRPQEVKAAQEFLQS-PP-KTQLSLAETLRIAT  477
Glovi_SNF2              LAASSEPLVKVNDNWVELRPQDVRAAHSFLQSRKD-QVGLSLEDVLRLNF  482
Proma_CCMP1375_SNF2     LAKKNSPLLNHKGTWIELRPNDLKNASKFFAN----TPELNLDKALRLSA  533
Proma_MIT\9211_SNF2     LASKRSPLVRYKDSWLELRPNDLKIAEKFCSN----NPELSLDDALRLTA  540
Proma_MIT\9303_SNF2     LASKRSPLVNHKGAWIELRPNDLKNAEHFCSV----NPGISLDDALRLTA  573
Proma_MIT9313_SNF2      LASKRSPLVNHKGAWIELRPNDLKHAEHFCSV----NPGISLDDALRLTA  573
Syn_sp_CC9311_SNF2      LAGKRSPLVRHKGAWIELRPNDLKNAERFCAA----NPDLSLDDALRLTA  536
Syn_sp_WH\7805_SNF2     LAGKRSPLVRHKGAWIELRPNDLKNAERFCAA----NPDLSLDDALRLTA  539
Syn_sp_RS9916_SNF2      LAGKRSPLVRHKGTWIELRPNDLKNAERFFAA----KPDLSLDDALRLTA  534
Syn_sp_CC9605_SNF2      LSGKRSPLVRHKGAWIELRPNDLRNAERFCGA----KPELSLDDALRLTG  537
Syn_sp_WH\8102_SNF2     LSGKRSPLVRHKGAWIELRPNDLRNAERFCGA----NPELSLDDALRITA  537
Syn_sp_CC9902_SNF2      LSGKRSPLVRHKGAWIELRPNDLRNAERFCGA----NPELSLDDALRLTA  537
Syn_sp_\WH\5701_SNF2    LAGKRSPLVQHKGAWIELRPGDLRNAEKFCAL----DPVLSLDDALRLTG  512
Myctu_SNF2              LTETKSPLIRLRGQWVALDTEQMRRGLEFLERKP--TGRKTTAEIL-ALA  486
Mycbo_SNF2              LTETKSPLIRLRGQWVALDTEQLRRGLEFLERKP--TGRKTTAEIL-ALA  486
Nocfa_IFM\10152_SNF2    LVRAKSDLVQLRGEWVQADHKVLAAAARYVAAHLD-TSPVTLADLIGEIA  438
Myxxa_DK_SNF2           LAQRKAPLVRFRGEWVAVDPLELDAIQRHLAQGPG-RMALSEAVRVSLLG  548
Symth_IAM14863_SNF2     LARQKRPLVQMQGRWVRVDERTLAAVLRRIEQHGG-QMELGTALRLAPEA  485
Metac_C2A_SNF2          LAKLKAPLVKFRGQWVEVNDAEIRAALEFWKKNP--HGEASLREVLKLAV  537
Metma_Gol_SNF2          LAKLKAPLVKFRGQWVEVNDAEIRAALEFWKKNP--NGEASLREVLKLAV  544
Pelph_BU-1_SNF2         LANLKVPLVRVRGQWTQIDHKELANALHFLEKHP--TGELSARELLSTAL  486
Archaeon\RC-I_SNF2      LAALKEPLLQIGGKWFALKKEDIDSIMKAFRAKK--TGEMALSEALRLNG  518
Nos_sp_PCC7120_SNF2\II  LINTKAPLVHFRGQWMELDRDKMQQLLEFWQSHGDEQPQMSLLEFMQRSA  538
Bacce_ATCC10987_SNF2    LVEQNKRLFNINGQWMRLDPAFIEEVRKLMNRAD-KYG-LEMKDVLQQHL  399
Methu_JF-1_SNF2         KVKEKAPFIWLGNRWISFHPDAIQHALDSFSRHQ-SKGGDTIGDLLRLSL  527
                                    *       :                            :.
```

FIGURE 8 (continued)

| | | |
|---|---|---|
| Synco_SNF2 | GDLQTVSKLP------VTQFAARGILQELIDTLRNPEGVKAIADPPGFQG | 555 |
| Anava_SNF2 | GDTQVIEKLP------VVSFEASGALQELIGALTNNQAVAPLPTPKNFQG | 589 |
| Nostoc_SNF2 | GDTQVIEKLP------VVSFEASGALQELIGALTNNQAVAPLPTPKNFQG | 586 |
| Nodsp_SNF2 | GDTQAIEKLP------VVSFEASGTLQELIGALTNNQAISPLPTPANFQG | 606 |
| Lyn_sp_SNF2 | GDSQMVEKLP------IVNFEAGGKLEELLNTLTNNRSLDEIKTPSNFQG | 570 |
| Crowa_SNF2 | GDISTVAKLP------ITNFEAKGELANLINAINNNESIPMIENPRGFKG | 566 |
| Synel_PCC6301_SNF2 | GESPNVGRLP------VVNFEAAGLLEEALAVFQGQRSPAALPAPPTFQG | 529 |
| Synel_PCC7942_SNF2 | GESPNVGRLP------VVNFEAAGLLEEALAVFQGQRSPAALPAPPTFQG | 529 |
| Theel_BP-1_SNF2 | GDTVTVAKLP------ILGLDTNDALQTLLDGLTGKQSLDPVPTPQEFCG | 521 |
| Glovi_SNF2 | GDTPKIDGLP------IVNFDSSGPIQQLLETLTDQRKLTPIDEPPGFKG | 526 |
| Proma_CCMP1375_SNF2 | NKGNTFMKLP------VHHFESGPRLQSVLEQYHHQKAPEPLPAPNGFHG | 577 |
| Proma_MIT\9211_SNF2 | TKGETLMKLP------VHQFNAGPKLQGVLEQYHQHTSPEPLAAPDGFYG | 584 |
| Proma_MIT\9303_SNF2 | TDGDTLMRLP------VHRFEAGPRLQAVLEQYHQQKAPDPLPAPEGFCG | 617 |
| Proma_MIT9313_SNF2 | TDGDTLMRLP------VHRFEAGPRLQAVLEQYHQQKAPDPLPAPEGFCG | 617 |
| Syn_sp_CC9311_SNF2 | TEGDTMMRLP------VHQFDAGPRLQAVLEQYHQQKAPDPLPAPEGFSG | 580 |
| Syn_sp_WH\7805_SNF2 | SEGDTLMRLP------VHAFDAGPRLQGVLEQYHQQKAPDPLPAPEGFCG | 583 |
| Syn_sp_RS9916_SNF2 | SEGDTLMRMP------VHRLEAGPRLQAVLEQYHQQKAPDPLPAPEGFCG | 578 |
| Syn_sp_CC9605_SNF2 | TEGELLMRMP------VHRFDAGPRLQSVLQQYHQQKAPDPLPAPEGFSG | 581 |
| Syn_sp_WH\8102_SNF2 | TEGDLLMRLP------VHRFDAGPRLQAVLEQYHQQKAPDPLPAPEGFCG | 581 |
| Syn_sp_CC9902_SNF2 | TEGELMMRLP------VHRFDAGPRLQGVLEQYHQQKAPDPLPAPEGFSG | 581 |
| Syn_sp_\WH\5701_SNF2 | NEGETLQRLP------VHRFTAGPRLKAVLEQYHQQKAPDPLPAPEGFAG | 556 |
| Myctu_SNF2 | ASHPDDVDTPLE------VTAVRADGWLGDLLAGAAA-ASLQPLDPPDGFTA | 531 |
| Mycbo_SNF2 | ASHPDDVDTPLE------VTAVRADGWLGDLLAGAAA-ASLQPLDPPDGFTA | 531 |
| Nocfa_IFM\10152_SNF2 | ATRVDKVP------LTEVTGWAGELFDGGR------EPVATPGGLKA | 475 |
| Myxxa_DK_SNF2 | ETRHGQLP------VTVLATGALEERLRLLRE-GGATAQDAPRALRA | 588 |
| Symth_IAM14863_SNF2 | DEAT------ATGWIAELLERLQEPARMEPVPTPGGFAG | 518 |
| Metac_C2A_SNF2 | GVSEKADGVD------VEGLNAAGWIEELIRRLKDKTGFEELPAPDGFSG | 581 |
| Metma_Go1_SNF2 | GVSEKADGVN------VEGLNATGWIGELISRLKDKTGFEELPAPNGFSG | 588 |
| Pelph_BU-1_SNF2 | GAQKKEDALF------LRSVEIEGWLQELLEKLSSGQFELLPPEHFEG | 530 |
| Archaeon\RC-I_SNF2 | GLEDFN-GIP------VSGMKSSGWLAELFDRLAAGEKITSLAPPDGFNG | 561 |
| Nos_sp_PCC7120_SNF2\II | QGEDD------WEIEYDAALSEIMAKLQDKSQLEPISEDLNLQG | 576 |
| Bacce_ATCC10987_SNF2 | SNTAETEIVEEDSPFTDIEIELDGYYEDLFQKLLHIGDIPKVDVPSSLNA | 449 |
| Methu_JF-1_SNF2 | KKMEDSAVP------VSIHAKDDWVADLLDFFRTETNQAVPVPKKFKG | 569 |

| | | | |
|---|---|---|---|
| Synco_SNF2 | VK------- | ----------PVLIVCPTSVLSNWGHEINKFAPQL | 632 |
| Anava_SNF2 | EK------- | ----------PTLLVCPTSVLGNWEREVKKFAPTL | 666 |
| Nostoc_SNF2 | EK------- | ----------PTLLVCPTSVLGNWEREVRKFAPTL | 663 |
| Nodsp_SNF2 | EN------- | ----------PTLLVCPTSILGNWEREIKKFAPTL | 683 |
| Lyn_sp_SNF2 | DA------- | ----------PVLLVCPTSVLGNWEREVKRFSPSL | 647 |
| Crowa_SNF2 | DQ------- | ----------PTLVICPTSVLNNWEREVQKFAPTL | 643 |
| Synel_PCC6301_SNF2 | TR------- | ----------PVLLVCPTSVLGNWEREVQKFAPEL | 606 |
| Synel_PCC7942_SNF2 | TR------- | ----------PVLLVCPTSVLGNWEREVQKFAPEL | 606 |
| Theel_BP-1_SNF2 | YR------- | ----------PTLLICPTSVLGNWLRECQKFAPTL | 598 |
| Glovi_SNF2 | DG------- | ----------PILLICPTSVMGNWEREIKKFSPSL | 603 |
| Proma_CCMP1375_SNF2 | TK------- | ----------PVLLIAPTSVLTNWKREAATFTPEL | 654 |
| Proma_MIT\9211_SNF2 | KK------- | ----------PVLLIAPTSVLTNWKREAYSFTPEL | 661 |
| Proma_MIT\9303_SNF2 | KR------- | ----------PVLLIAPTSVLTNWKREALAFTPEL | 694 |
| Proma_MIT9313_SNF2 | KR------- | ----------PVLLIAPTSVLTNWKREALAFTPEL | 694 |
| Syn_sp_CC9311_SNF2 | KR------- | ----------SVLLIAPTSVLTNWKREATAFTPEL | 657 |
| Syn_sp_WH\7805_SNF2 | KR------- | ----------PVLLVAPTSVLTNWKREAAAFTPEL | 660 |
| Syn_sp_RS9916_SNF2 | KR------- | ----------PVLLVAPTSVLTNWKREAAAFTPEL | 655 |
| Syn_sp_CC9605_SNF2 | KR------- | ----------PVLLVAPTSVLTNWRREAESFTPEL | 658 |
| Syn_sp_WH\8102_SNF2 | KR------- | ----------PVLLVAPTSVLTNWRREAEAFTPEL | 658 |
| Syn_sp_CC9902_SNF2 | KR------- | ----------PVLLVAPTSVLTNWRREAEAFTPEL | 658 |
| Syn_sp_\WH\5701_SNF2 | KR------- | ----------PVLLVAPTSVLTNWLREAKAFTPEL | 633 |
| Myctu_SNF2 | DRGV----- | ----------GPTLLLCPMSLVGNWPQEAARFAPNL | 611 |
| Mycbo_SNF2 | DRGV----- | ----------GPTLLLCPMSLVGNWQQEAARFAPNL | 611 |
| Nocfa_IFM\10152_SNF2 | PP------- | ----------GPTLLVCPMSVVGNWQREAQRFAPGL | 553 |
| Myxxa_DK_SNF2 | EAR------ | ----------PTLLVAPTSVVGNWERELARFAPTL | 666 |
| Symth_IAM14863_SNF2 | AAG------ | ----------PTLLVCPVSVLGNWCRELARFAPGL | 595 |
| Metac_C2A_SNF2 | QVEEKVIENAEEKVEG--- | ---LKAAKPVLLVCPTSVINNWXXEAARFTPEL | 677 |
| Metma_Go1_SNF2 | KAEEXIEEPAEEKIEEKVDGRKAPKPVLLVCPTSVINNWXXEASRFTPEL | 688 |
| Pelph_BU-1_SNF2 | -------- | -------LGEKRAVLLICPTSVVNNWREAERFTPDL | 606 |
| Archaeon\RC-I_SNF2 | -------- | -------RGTKGPTLLICPTSILGNWQREAKKFAPAL | 637 |
| Nos_sp_PCC7120_SNF2\II | PL------- | ----------PTLLIAPTSVVGNWQREIAKFAPHL | 653 |
| Bacce_ATCC10987_SNF2 | TG------- | ----------PALIVAPTSVLGNWQKEFERFAPNL | 526 |
| Methu_JF-1_SNF2 | TT------- | ----------PSLLICPMSVVGNWEREIQRFAPSL | 646 |
| | . | *::.* **:: * *: * :.* *| |
| | | Motif Ia | |

FIGURE 8 (continued)

| Sequence | Alignment | Position |
|---|---|---|
| Synco_SNF2 | KTLLHHGDRRK-KGQPLVKQVKDQQIVILTSYALLQRDFSSLKLVDWQGIV | 681 |
| Anava_SNF2 | KVLQYHGDKRP-KGKAFPEAVKNHDLVITSYSLIHRDIKSLQGLSWQIIV | 715 |
| Nostoc_SNF2 | KVLQYHGDKRP-KGKAFQEAVKKHDLVITSYSLIHRDIKSLQGIPWQIIV | 712 |
| Nodsp_SNF2 | KVLQHHGDKRL-KGKAFVEAVKKHDVITSYSLVHRDIKSLQSVDWQTVV | 732 |
| Lyn_sp_SNF2 | KVTVHHGDKRQ-KGKNFAQFAQKYNLIITSYPLTFRDEKELKTVNWKGLV | 696 |
| Crowa_SNF2 | STLIHHGDKRS-KGKAFVKAVSKKNVIITSYSLIYRDIKSFEQVEWQGIV | 692 |
| Synel_PCC6301_SNF2 | RWKLHYGPDRA-QGKALATALKDCDLVLTSYSLVARDQKAIAAIDWQGIV | 655 |
| Synel_PCC7942_SNF2 | RWKLHYGPDRA-QGKALATALKDCDLVLTSYSLVARDQKAIAAIDWQGIV | 655 |
| Theel_BP-1_SNF2 | RAYVHHGSDRP-KGKAFLKKVETHDLILITSYALLQRDRTTLQQVLMQHLV | 647 |
| Glovi_SNF2 | SVHVHHGARRP-KGRNFVETAQKKQIIVSSYALVQRDSKDLKRVEWLGLV | 652 |
| Proma_CCMP1375_SNF2 | CIHEHYGSKRHSSIPKLQNYLKKVDIMITSYGLLYRDGELLQEIDMQGIV | 704 |
| Proma_MIT\9211_SNF2 | SVLEHYGPNRSSTSTLLKKILKKVDILITSYGLLHRDKQLLKTIDWQGVI | 711 |
| Proma_MIT\9303_SNF2 | NVREHYGPRRPSTPAALKKALKGLDLVLTSYGLLQRDSELLETVDWQGVV | 744 |
| Proma_MIT9313_SNF2 | NVREHYGPRRPSTPAALKKALKGLDLVLTSYGLLQRDSELLETVDWQGVV | 744 |
| Syn_sp_CC9311_SNF2 | KVHEHYGPKRPSTPAALKKALKDVDLVLTSYGLLQRDSELLESHDWQGLV | 707 |
| Syn_sp_WH\7805_SNF2 | TVHEHYGPKRPSTPAALKKALKDVDLVLTSYGLLQRDSELLESFDWQGTV | 710 |
| Syn_sp_RS9916_SNF2 | EVKEHYGPRRPATPAALKKSLKDVDLVLTSYGLLQRDSELLESLDWQGVV | 705 |
| Syn_sp_CC9605_SNF2 | KVTEHYGPRRPSTPAELKKALKEVDLVLTSYGLLQRDSELLETQDWQGVV | 708 |
| Syn_sp_WH\8102_SNF2 | AVREHYGPRRPSTPAALKKALKDVDLVLTSYGLLQRDSELLESQDWQGVV | 708 |
| Syn_sp_CC9902_SNF2 | SVKEHYGPRRPSTPAALKKELKDVDLVLTSYGLMQRDSELLDSVDWQGVV | 708 |
| Syn_sp_\WH\5701_SNF2 | NVVEHYGPRRPSTPAALKKKLEGMDLVLTSYGLLQRDSELLSSLDWQGVV | 683 |
| Myctu_SNF2 | RVYAHHGGARLHGEALRDHLERT-DLVVSTYTTATRDIDELAEYEWNRVV | 660 |
| Mycbo_SNF2 | RVYAHHGGARLHGEALRDHLERT-DLVVSTYTTATRDIDELSEYEWNRVV | 660 |
| Nocfa_IFM\10152_SNF2 | RVLVHHGADRRRDAELDAAVADS-DLVLTTYAILARDAAELSRQSWDRVV | 602 |
| Myxxa_DK_SNF2 | RLTRHYGAERARAANRFPRAPGA--VVLTTYGLLRRDAALLARVDWGAVV | 714 |
| Symth_IAM14863_SNF2 | RVLVHHGPGRLGEPD-FARQAGAHDVLTTYSLLARDAALLGQVTWNGIV | 644 |
| Metac_C2A_SNF2 | SVMVHHGTSRK-KEEEFKKEATNHSIVVSSYGLLQRDLKFLKGVSWAGVV | 726 |
| Metma_Go1_SNF2 | SVMVHHGTSRK-KEEEFKKEAMNHAIVISSYGLVQRDLKFLKEVHWAGVV | 737 |
| Pelph_BU-1_SNF2 | AVLVHHGIDRM-KTADFRKAASASALVISSYGLLQRDLEFLSKVPWAGII | 655 |
| Archaeon\RC-I_SNF2 | KVHIHHGAGRA-DKEQFGKIVKAHDLILSTYAHAYRDEELLKEVNWKLVV | 686 |
| Nos_sp_PCC7120_SNF2\II | KTMVHHGSDRLQDAAEFKSACQQHDVVISSFTIARLDEKLLNSVTWQRLV | 703 |
| Bacce_ATCC10987_SNF2 | RVQLHYGSNRA-KGEPFKDFLQSADVVLTSYALAQLDEEELSTLCWDAVI | 575 |
| Methu_JF-1_SNF2 | RSWVHHGTDRC-KGDDFVRHVGSYDLVLTTYHLAARDVDHLKTVPWSAII | 695 |
| | :* : *: :.: * :: .: | |

| | | |
|---|---|---|
| Synco_SNF2 | ILEFLNPGFLGNQSFFQRRFANPIEKFGDRQSLLILRNLVRPFILRRLKT | 774 |
| Anava_SNF2 | ILDFLNPGYLGNKQFFQRRFAMPIEKYGDAASLNQLRALVQPFILRRLKT | 808 |
| Nostoc_SNF2 | ILDFLNPGYLGNKQFFQRRFAMPIEKYGDAASLNQLRALVQPFILRRLKT | 805 |
| Nodsp_SNF2 | ILDFLNPGYLGNRQFFQRRFAMPIEKYGDTASLNQLRGLVQPFILRRLKT | 825 |
| Lyn_sp_SNF2 | IMDFLNPGYLGQRQFFQRRFAIPIEKYGDTDSLKTLRSLVQPFILRRLKT | 789 |
| Crowa_SNF2 | ILDFLNPGFLGTQQFFRRRFATPIEKYGDKESLQIMRSLVRPFILRRLKT | 785 |
| Synel_PCC6301_SNF2 | IVEFLQPGHLGTKPFFQKRFVTPIERFGDADSLTALRQRVQPLILRRLKT | 754 |
| Synel_PCC7942_SNF2 | IVEFLQPGHLGTKPFFQKRFVTPIERFGDADSLTALRQRVQPLILRRLKT | 754 |
| Theel_BP-1_SNF2 | IMDFLHPGYLGHRTYFQHRYVRPIERYGDTTSLNALRTYVQPFILRRLKT | 740 |
| Glovi_SNF2 | ILDFLNPGYLGARNFFQRRFAVPIEKYGDRSSANALKALVQPFILRRLKS | 745 |
| Proma_CCMP1375_SNF2 | LMDFLNPFLNPXVLGEEDFFNQRYKLPIEHYGDISSLKDLKTQVSPFILRRLKT | 802 |
| Proma_MIT\9211_SNF2 | LMDFLNPSVLGEKEFFDQRYKLPIERYGDISSLTDLKARVSPFILRRLKS | 809 |
| Proma_MIT\9303_SNF2 | LMDFLNPRVLGEEDFFRQRYRLPIERYGDMSSLRDLKGRVGPFILRRLKT | 842 |
| Proma_MIT9313_SNF2 | LMDFLNPRVLGEEDFFRQRYRLPIERYGDMSSLRDLKGRVGPFILRRLKT | 842 |
| Syn_sp_CC9311_SNF2 | LMDFLNPRVLGEEEFFRHRYRMPIERYGDLSSLRDLKARVGPFILRRLKT | 805 |
| Syn_sp_WH\7805_SNF2 | LMDFLNPNVLGEEEFFRQRYRMPIERYGDMSSLRDLKSRVGPFILRRLKT | 808 |
| Syn_sp_RS9916_SNF2 | LMDFLNPRVLGEEDFFRQRYRMPIERYGDMSSLRDLKSRVGPFILRRLKT | 803 |
| Syn_sp_CC9605_SNF2 | LMDFLNPRVLGEEDFFRQRYRMPIERYGDMSSLRDLKGRVGPFILRRLKT | 808 |
| Syn_sp_WH\8102_SNF2 | LMDFLSPXVLGEEDFFRQRYRMPIERYGDMASLRDLKARVGPFILRRLKT | 806 |
| Syn_sp_CC9902_SNF2 | LMDFLNPKVLGEEDFFRQRYRMPIERYGDMSSLRDLKARVGPFILRRLKT | 806 |
| Syn_sp_\WH\5701_SNF2 | LMDFLNPKVLGEEEFFRQRYRLPIERYGDMASVRDLKARVGPFILRRLKT | 781 |
| Myctu_SNF2 | IMDFLNPGLLGSSERFRTRYAIPIERHGHTEPAERLRASTRPYILRRLKT | 753 |
| Mycbo_SNF2 | IMDFLNPGLLGSSERFRTRYAIPIERHGHTEPAERLRASTRPYILRRLKT | 753 |
| Nocfa_IFM\10152_SNF2 | IMDFAVPKLLGTAPTFRARFAVPIERGQDPNALSRIRFLTQPFVLRRVKA | 695 |
| Myxxa_DK_SNF2 | ILEFANPGLLGPLETFRRELALPIERHGNQEASARLRRLVSPFVLRRLKS | 807 |
| Symth_IAM14863_SNF2 | LFQFLNPGLLGSREEFERRYAVPIQRYQDEEAAARLRRQVGPFILRRQKN | 737 |
| Metac_C2A_SNF2 | IMEFLNPGLNQAGFKRNFFIPIQAERDQEAARRLKEITGPFILRRLKT | 819 |
| Metma_Gol_SNF2 | IMEFLNPGFLGSQAGFKRNFFIPIQAERDQEAARRLKEITGPFILRRLKT | 830 |
| Pelph_BU-1_SNF2 | LMDFLNPGFLGTQHFFKQNFYTPIQWYGDPEASARLKSLTGPFILRRMKS | 748 |
| Archaeon\RC-I_SNF2 | IVDFLNPGYLGKAETFRKQFAIPIERYDDAARSEKLKQAIKPLVLRRVKT | 779 |
| Nos_sp_PCC7120_SNF2\II | IFNFLNPGYLGKEAQFRKSFEIPIQKDNDKVKSTTLKKLVEPLILRRVKT | 796 |
| Bacce_ATCC10987_SNF2 | IFDFINHGYLGSLGQFQRRFVSPIEKDRDEGKIQQVQRFISPFLLRRTKK | 668 |
| Methu_JF-1_SNF2 | IMDFLNPGYLGSQSAFTNRYSRPIEQEKNTELIQELRSLIRPFLLRRMKT | 788 |

FIGURE 8 (continued)

```
Synco_SNF2         DQTIIQDLPEKQEMTVFCDLSQEQAGLYQQLVEESLQAIADSEG-IQRHG  823
Anava_SNF2         DRDIIQDLPDKQEMTVFCGLTGEQAALYQQLVEESLAEIESAEG-LQRRG  857
Nostoc_SNF2        DRDIIQDLPDKQEMTVFCGLTGEQAALYQKVVETSLAEIESAEG-LQRRG  854
Nodsp_SNF2         DRDIIQDLPDKQEMTVFCGLTGEQAALYQKAVETSLAEIESAEG-LQRRG  874
Lyn_sp_SNF2        DREIIQDLPEKQEMTVFCGLAAEQAALYQQVVEASLVEIESAAG-IQRRG  838
Crowa_SNF2         DKTIIQDLPEKQENTIFCSLSTEQATLYQKIVDQSLADIDSAAG-IERKG  834
Synel_PCC6301_SNF2 DRSIIADLPEKQEMTVFCGLSSEQGKLYQQLVDNSLVAIEEKTG-IERKG  803
Synel_PCC7942_SNF2 DRSIIADLPEKQEMTVFCPIVQEQADRYQVLVNEALANIEASEG-IQRRG  803
Theel_BP-1_SNF2    DRSIIQDLPEKQEMTVFCPLVQEQADRYQVLVNEALANIEASEG-IQRRG  789
Glovi_SNF2         DPQIIQDLPEKQETNVFCPLTPEQAALYERVVNESLAKIEQSTG-IQRRG  794
Proma_CCMP1375_SNF2 DQSIISDLPQKIELNEWVGLSQEQELLYKQTVEKSLDELASLPI-GQRQG 851
Proma_MIT\9211_SNF2 DKSIISDLPSKVELKEWITLSQEQRALYNKTVDNTLQEIARSPI-GQRHA 858
Proma_MIT\9303_SNF2 DKAIISDLPEKVELSEWVGLSKEQAALYRNTVDETLEAIARAPS-GQRHG 891
Proma_MIT9313_SNF2 DKAIISDLPEKVELSEWVGLSKEQAALYRNTVDETLEAIARAPR-GQRHG  891
Syn_sp_CC9311_SNF2 DKAIISDLPEKVELSEWVGLSKEQKSLYAKTVEDTLDAIARAPR-GKRHG  854
Syn_sp_WH\7805_SNF2 DKAIISDLPEKVELSEWVGLSKEQKSLYAKTVENTLDAIARAPR-GKRHG 857
Syn_sp_RS9916_SNF2 DKAIISDLPEKVELSEWVGLSREQKALYAKTVEDTLDAIARAPR-GQRHG  852
Syn_sp_CC9605_SNF2 DKTIISDLPEKVELSEWVGLSKEQKSLYSKTVEDTLDAIARAPR-GQRHG  857
Syn_sp_WH\8102_SNF2 DKTIISDLPEKVELSEWVGLSKEQKSLYSKTVEDTLDAIARAPR-GQRHG 855
Syn_sp_CC9902_SNF2 DKSIISDLPEKVELSEWVGLSKEQKSLYNKTVEDTLDAIATAPR-GQRHG  855
Syn_sp_\WH\5701_SNF2 DRSIISDLPEKVELKEWVGLSPEQVKLYRRTVEDTLDAIARAPV-GQKHG 830
Myctu_SNF2         DPAIIDDLPEKIEIKQYCQLTTEQASLYQAVVADMMEKIENTEG-IERRG  802
Mycoo_SNF2         DPAIIDDLPEKIEIKQYCQLTTEQASLYQAVVADMMEKIENTEG-IERRG  802
Nocfa_IFM\10152_SNF2 DPAVIGDLPDKLEMTVRANLTVEQAALYQAVVDDMLVKLRSAKG-MARKG 744
Myxxa_DK_SNF2      DPTIITDLPAKNEMKVVCTLTREQASLYKAVVDEELRRIEEADG-MERRG  856
Synth_IAM14863_SNF2 DPAIAPDLPDKLENTELVTLSVEQAALYEAIVQETLERAAQADG-IQRQA 786
Metac_C2A_SNF2     DTSIISDLPEKMEMKTYCTLTKEQASLYAAVLEDIEETMEEAEEGIQRKG  869
Metma_Go1_SNF2     DTSIISDLPEKMEMKTYCTLTKEQASLYAAVLEDIREAIEGAEEGIQRKG  880
Pelph_BU-1_SNF2    DKSIISDLPDKIEMKEYCSLTKEQASLYKEQASLYKAVVDELQEKIESAEG-IDRRG  797
Archaeon\RC-I_SNF2 DPAIIKDLPDKIEIKEPCNLTKEQATLYEAIVENMLKSIDKATA-MQRRG  828
Nos_sp_PCC7120_SNF2\II DQSIIKDLPDKVEQKLYTNLTKEQASLYEVVRDVEEKLQEAEG-IQRKG  845
Bacce_ATCC10987_SNF2 DQTVALNLPDKQEQKAYCPLTGEQASLYEQLVQDTLQNVEGLSG-IERRG 717
Methu_JF-1_SNF2    DKHVIDDLPEKMENRVYCTLTPEQATLYQAVVLDMAKNLDKVEG-IARKG  837
                   *     **  *  *       *                          :::
```

FIGURE 8 (continued)

```
Synco_SNF2              LVLTLTKLKQVCNHPDLL------------------LKKPAITHGH--QSGKLIRL  860
Anava_SNF2              MILALLIKLKQICNHPAQY------------------LKTNTLEQY----SSGKLQRL  893
Nostoc_SNF2             MILALLIKLKQICNHPAQY------------------LKINTLEQH----SSGKLQRL  890
Nodsp_SNF2              MILALIVKLKQICNHPAQY------------------LKAATLQEH----SSAKLQRL  910
Lyn_sp_SNF2             MILALIVKLKQVCNHPILLNGKATKTGKKKVETQGLSLQ--SSGKLQRF  885
Crowa_SNF2              LILSLLLKLKQICNHPAHF------------------LKQKSLKTAE--QSGKLLRL  871
Synel_PCC6301_SNF2      QILALLTRLKQLCNHPSLL------------------LEKPKLDPNFGDRSAKLQRL  842
Synel_PCC7942_SNF2      QILALLTRLKQLCNHPSLL------------------LEKPKLDPNFGDRSAKLQRL  842
Theel_BP-1_SNF2         NILATLTKLKQICNHPAQY------------------LKQEDYAP---DRSGKLQRL  825
Glovi_SNF2              TVLATIVKLKQICNHPSHY------------------LGDDGPLAN---RSGKLSRL  830
Proma_CCMP1375_SNF2     KTLGLLTRLKQICNHPAIA------------------LKETQVEKNFLLRSSKLQRL  890
Proma_MIT\9211_SNF2     KTLGLLTRLKQICNHPALA------------------LKEKNISDDFGIRSTKLQRL  897
Proma_MIT\9303_SNF2     KVLGLLTRLKQICNHPALA------------------LKEKTVAKGFMDRSAKLLRL  930
Proma_MIT9313_SNF2      KVLGLLTRLKQICNHPALA------------------LKEQTVAKGFMDRSAKLLRL  930
Syn_sp_CC9311_SNF2      QVLGLLTRLKQICNHPALA------------------LKEQGASEDFLKRSVKLQRL  893
Syn_sp_WH\7805_SNF2     QVIGLLTRLKQICNHPALA------------------LKEEVAGDDFLQRSVKLQRL  896
Syn_sp_RS9916_SNF2      QVIGLLTRLKQICNHPALA------------------LKEEAAGDEFLQRSMKLQRL  891
Syn_sp_CC9605_SNF2      QVLALLTRLKQICNHPALA------------------LSEGAVDDGFLGRSAKLQRL  896
Syn_sp_WH\8102_SNF2     QVIGLLTRLKQICNHPALA------------------LSENAVDDGFLGRSAKLQRL  894
Syn_sp_CC9902_SNF2      QVLALLTRLKQICNHPALA------------------QREGAVDSEFLGRSAKLMRL  894
Syn_sp_\WH\5701_SNF2    QVLGLLTKLKQVCNHPALM------------------LKEGEVGAGFSARSAKLQRL  869
Myctu_SNF2              NVLAAMAKLKQVCNHPAQL------------------LHDRSPVGRR---SGKVIRL  838
Mycbo_SNF2              NVIAAMAKLKQVCNHPAQI------------------LHDRSPVGRR---SGKVIRL  838
Nocfa_IFM\10152_SNF2    AVLGALTRLKQVCNHPAHF------------------LGDGSPVLHRGRHRSGKLALV  784
Myxxa_DK_SNF2           RVLALLYTKQIANHPAQY------------------LGESGPLPGR----SGKLARV  892
Symth_IAM14863_SNF2     AVLAGLTRLKQVCNHPAAA------------------TGD-GPLVGR----SGKIDRL  821
Metac_C2A_SNF2          IILSALTRLKQVCNHPAQFLK----------------DNSAVPG-----RSGKLARL  905
Metma_Go1_SNF2          IILSALSRLKQVCNHPAQFLK----------------DNSTIPG-----RSGKLARL  916
Pelph_BU-1_SNF2         LVLALLVKLKQVCNHPAHLLG----------------DNSAIAH-----RSGKIKRL  833
Archaeon\RC-I_SNF2      IVLASLMKLKQVCDHPSLYIK----------------TGAVTDDKTLIRSGKLKRL  868
Nos_sp_PCC7120_SNF2\II  LILSTLMKLKQICNHPRQFLQ----------------DNSEFLPE----RSHKLSRL  882
Bacce_ATCC10987_SNF2    FILMLNKLKQICNHPALYL------------------KETEPKDIIERSMKTSTL  755
Methu_JF-1_SNF2         AILAAITRLKQICNHPGRVG------------------RDKTIK---AERSGKVSRL  873
                         *   : * **..:**           *         *   .
```

FIGURE 8 (continued)

```
Synco_SNF2           AEMLEEIISEG-------DRVLIFTQFASWGHLLKPYLEKYFN---QEV 899
Anava_SNF2           EEMLEEVLAESNTYGVAGAGRALIFTQFAEWGKLLKPHLEKQLG---REV 940
Nostoc_SNF2          EEMLEEVLAESNTYGVAGAGRALIFTQFAEWGKLLKPHLEKQLG---REI 937
Nodsp_SNF2           DEMLTVALEEG-------DRALIFTQFAEWGKLLKAHLQQTLG---KEI 949
Lyn_sp_SNF2          KEMLEELLSEG-------DRAVFTQFAEWGKVLQPYLEQQLN---REV 924
Crowa_SNF2           EEMLEELIEEG-------DHALIFTQFSEWGKLLQPYLQKKFQ---QDV 910
Synel_PCC6301_SNF2   LEMLAELTDAG-------DRAVFTQFAGWGSLLQQFLQEQLG---REV 881
Synel_PCC7942_SNF2   LEMLAELTDAG-------DRAVFTQFAGWGSLLQQFLQEQLG---REV 881
Theel_BP-1_SNF2      IEMLQALQEVG-------DRAVFTQFAEFGTHLKTYLEKALQ---QEV 864
Glovi_SNF2           GEMLEEVLADE-------ERALIFTQFAEWGHLLQAHLSRQLG---SEV 869
Proma_CCMP1375_SNF2  EEILQEVKESH-------DRALLFTQFAEWGHLLQAYLQTKWE---SEV 929
Proma_MIT\9211_SNF2  EELLDVIFATE-------DRALLFTQFAEWGHLLQAYLEKKWG---HSI 936
Proma_MIT\9303_SNF2  EEILEEVIEAG-------DRALLFTQFAEWGHLLKAYLQQRWR---FEV 969
Proma_MIT9313_SNF2   EEILEEVIEAG-------DRALLFTQFAEWGHLLKAYLQQRWR---FEV 969
Syn_sp_CC9311_SNF2   EEILDEVVEAG-------DRALLFTQFAEWGKLLQDYLQRWR---SEV 932
Syn_sp_WH\7805_SNF2  EEILEEVIAAG-------DRALLFTQFAEWGHLLQGYLQRWR---SEV 935
Syn_sp_RS9916_SNF2   EEILEEVIDAG-------DRALLFTQFAEWGHLLQGYLQRWR---SEV 930
Syn_sp_CC9605_SNF2   EEILDEVIEAG-------DRALLFTQFAEWGHLLRAWMQQRWK---SEV 935
Syn_sp_WH\8102_SNF2  EEILDEVIEAG-------DRALLFTQFAEWGHLLQSWMQQRWK---ADV 933
Syn_sp_CC9902_SNF2   EEIVEEVIAAG-------DRALLFTQFAEWGHLLQAWMQQRWK---SEV 933
Syn_sp_\WH\5701_SNF2 EEILEEILAEG-------DRVLCFTQFTEFAELLVPHLQQRFH---QEV 908
Mycru_SNF2           EEILEEILAEG-------DRVLCFTQFTEFAELLVPHLAARFGRAARDI 880
Mycbo_SNF2           EDVLDTVVADG-------EKALFTQFREFGDLLAPYLSERFG---API 823
Nocfa_IFM10152_SNF2  VEMLEESLAAG-------DKALVFTQFREMGDKLVAHLSEYLG---HEV 931
Myxxa_DK_SNF2        VQLLQEVLAAG-------EQALLFTQFARFGGRLQAYLAETLG---CEV 860
Symth_IAM14863_SNF2  TEMLDVILENG-------EKALVFTQFAEMGKMLKEHLQASFG---CEV 944
Metac_C2A_SNF2       TEMLDVVLENG-------EKALVFTQFAEMGKMVKEHLQASFG---CEV 955
Metma_Go1_SNF2       TELLGDIREAG-------EKTLLFTQFTMMGTMLQHYLQELYG---EEV 872
Pelph_BU-1_SNF2      TELLEEALAEG-------DSVLIFTQFVEMGEMLKAYLQSTFD---EEA 907
Archaeon\RC-I_SNF2   VEMVDEAISEG-------ESLLIFSQFTEVCEQIEKYLKHNLH---CNT 921
Nos_sp_PCC7120_SNF2\II MELIENIKDQN-------ESCLIFTQYIGMGNMLKDVLEEHFG---QRV 794
Bacce_ATCC10987_SNF2 LEMIEEITSEG-------DSALIFSQYATFAEELAGMIEKQGD---TPV 912
Methu_JF-1_SNF2
                                              Motif IV
                     :::                    *::*  :           :           :
```

| | | |
|---|---|---|
| Synco_SNF2 | LYLHGTPAEQRQALVERFQ-QDPNSPYLFILSLKAGGTGLNLTRANHV | 948 |
| Anava_SNF2 | FFLYGSTSKKQREEMIDRFQ-HDPQGPPIMILSLKAGGVGLNLTRANHVF | 989 |
| Nostoc_SNF2 | FFLYGGTSKKQREEMIDRFQ-HDPQGPPIMILSLKAGGVGLNLTRANHVF | 986 |
| Nodsp_SNF2 | FFLYGGSSKKQREEMIDRFQ-HDPQGPPIMILSLKAGGVGLNLTRANHVF | 998 |
| Lyn_sp_SNF2 | LFLYGATRKNKREEMIDRFQ-QDPQGPPIFILSLKAGGVGLNLTRANHVF | 973 |
| Crowa_SNF2 | LFLYGATRRVQRQEMIDRFQ-QDPNGPRIFILSLKAGGVGLNLTRANHVF | 959 |
| Synel_PCC6301_SNF2 | LFLSGSTKKGDRQQMVDRFQ-NDPQAPAIFILSLKAGGVGLNLTKANHVF | 930 |
| Synel_PCC7942_SNF2 | LFLSGSTKKGDRQQMVDRFQ-NDPQAPAIFILSLKAGGVGLNLTKANHVF | 930 |
| Theel_BP-1_SNF2 | FFLSGRTPKAQRELMVERFQ-HDPEAPRVFILSLKAGGVGLNLTRANHVF | 913 |
| Glovi_SNF2 | FFLYGGTSKNQREAMIERFQ-SDPQGPRIFILSLKAGGVGLNLTRANHVF | 918 |
| Proma_CCMP1375_SNF2 | PFLHGGTPKGKRQEMIDRFQ-DDPRGPNIFILSLKAGGVGLNLTRANHVL | 978 |
| Proma_MIT\9211_SNF2 | LFLHGGTRKIDRQSMVDQFQ-EDPRGPKLFLLSLKAGGIGLNLTRASHVF | 985 |
| Proma_MIT\9303_SNF2 | PFLHGSTSKTERQAMVDRFQ-EDPRGPQLFLLSLKAGGVGLNLTRASHVF | 1018 |
| Proma_MIT9313_SNF2 | PFLHGSTSKTERQAMVDRFQ-EDPRGPQLFLLSLKAGGVGLNLTRASHVF | 1018 |
| Syn_sp_CC9311_SNF2 | PFLSGSTSKSERQAMVDRFQ-EDPRGPQLFLLSLKAGGVGLNLTRASHVF | 981 |
| Syn_sp_WH\7805_SNF2 | PFLSGSTSKSERQAMVDRFQ-EDPRGPQLFLLSLKAGGVGLNLTRASHVF | 984 |
| Syn_sp_RS9916_SNF2 | PFLNGSTSKSERQAMVDRFQ-EDPRGPQLFLLSLKAGGVGLNLTRASHVF | 979 |
| Syn_sp_CC9605_SNF2 | PFLHGGTRKNERQAMVDRFQ-EDPRGPQLFLLSLKAGGVGLNLTRASHVF | 984 |
| Syn_sp_WH\8102_SNF2 | PFLHGGTRKNERQAMVDRFQ-EDPRGPQLFLLSLKAGGVGLNLTRASHVF | 982 |
| Syn_sp_CC9902_SNF2 | PFLHGGTRKSDRQAMVDRFQ-EDPRGPQLFLLSLKAGGVGLNLTRASHVF | 982 |
| Syn_sp_\WH\5701_SNF2 | PFLHGGTRKSDRQAMVDRFQ-DDPRGPQLFLLSLKAGGVGLNLTRASHVF | 957 |
| Mycti_SNF2 | AYLHGGTPRKRRDEMVARFQ-SGDGPP-IFILSLKAGGTGLNLTAANHVV | 928 |
| Mycbo_SNF2 | AYLHGGTPRKRRDEMVARFQ-SGDGPP-IFLLSLKAGGTGLNLTAANHVV | 928 |
| Nocfa_IFM\10152_SNF2 | PFLHGGTPRKARDEMVRRFQ-SGDGPP-VMLLSLKAGGTGLTLTAANHVV | 871 |
| Myxxa_DK_SNF2 | LFLHGGTPRKARDENVRRFQ-EDVHGPRVFVLSVKAGGTGLNLTAATHVF | 980 |
| Symth_IAM14863_SNF2 | LFLHGGTPQPERDRLVARFQ-AGEAP--LFILSLKAGGLGLNLTAATHVF | 907 |
| Metac_C2A_SNF2 | LFLHGGVPRKQRDRMLERFQEGKEYLP-IFVLSLKAGGTGLNLTGANHVF | 993 |
| Metma_Gol_SNF2 | LFLHGGVPRKQRDRMLERFQEGKEYLP-IFVLSLKAGGTGLNLTGANHVF | 1004 |
| Pelph_BU-1_SNF2 | LFLHGGVTKKRRDEMVESFQKEEGSSPSIFILSLKAGGTGLNLTTANHVF | 922 |
| Archaeon\RC-I_SNF2 | LFLHGGVPQKARDKMVLRFGEKD--GPRIFIVSLKAGGVGLNLTKASHVF | 955 |
| Nos_sp_PCC7120_SNF2\II | YYLHGGTSRQRREQMISDFQ-NPDTEASVFVLSLKAGGVGITLTKANHVF | 970 |
| Bacce_ATCC10987_SNF2 | LFLNGSVPKKERDKMIEQFQ--NG-TYDIFILSLKAGGTGLNLTAANHVI | 841 |
| Methi_JF-1_SNF2 | LLLTGSTPRKKREQMIEEFQ--ASTTPIIFVISLKAGGTGLNLTKATHVF | 960 |
| | *     *   ::   *       :::    * : ***:   | |
| | MOTIF V | |

FIGURE 8 (continued)

| | Motif Va | Motif VI | |
|---|---|---|---|
| Synco_SNF2 | HVDRWWNPAVEN | QATDRAFRIGQ | TRNVQVHKFVCTGTLEEKINAMMADKQ 998 |
| Anava_SNF2 | HFDRWWNPAVEN | QATDRVFRIGQ | TRNVQVHKFVCNGTLEEKIHDMIESKK 1039 |
| Nostoc_SNF2 | HFDRWWNPAVEN | QATDRVFRIGQ | TRNVQVHKFVCNGTLEEKIHDMIESKK 1036 |
| Nodsp_SNF2 | HFDRWWNPAVEN | QATDRVFRIGQ | TRNVQVHKFVCTGTLEEKIHDMIESKK 1048 |
| Lyn_sp_SNF2 | HIDRWWNPAVEN | QATDRAFRLGQ | TRNVQVHKFVCTGTLEEKINEMLESKQ 1023 |
| Crowa_SNF2 | HIDRWWNPAVEN | QATDRAFRIGQ | KRNVQVHKFVCTGTLEEKINEMLESKQ 1009 |
| Synel_PCC6301_SNF2 | HYDRWWNPAVEN | QATDRAFRIGQ | RRNVQVHKFVCAGTLEEKIDQMIASKQ 980 |
| Synel_PCC7942_SNF2 | HYDRWWNPAVEN | QATDRAFRIGQ | RRNVQVHKFVCAGTLEEKIDQMIASKQ 980 |
| Theel_BP-1_SNF2 | HYDRWWNPAVEN | QASDRVFRIGQ | ARNVQIHKFICTGTLEEKIHEQIEQKK 963 |
| Glovi_SNF2 | HFDRWWNPAVEN | QATDRVFRIGQ | TKNVQVYKYVCTGTLEERINALIESKK 968 |
| Proma_CCMP1375_SNF2 | HIDRWWNPAVEN | QATDRAYRIGQ | KKSVIVHKFITTGTIEEKINQMILEKT 1028 |
| Proma_MIT\9211_SNF2 | HIDRWWNPAVEN | QATDRAYRIGQ | KNSVMVHKFIATGSVEEKIDQMITEKS 1035 |
| Proma_MIT\9303_SNF2 | HVDRWWNPAVEN | QATDRAYRIGQ | TNRVMVHKFITSGSVEEKIDRMIREKS 1068 |
| Proma_MIT9313_SNF2 | HVDRWWNPAVEN | QATDRAYRIGQ | TNRVMVHKFITSGSVEEKIDRMIREKS 1068 |
| Syn_sp_CC9311_SNF2 | HIDRWWNPAVEN | QATDRAYRIGQ | TNRVMVHKFITSGSVEEKIDRMIREKS 1031 |
| Syn_sp_WH\7805_SNF2 | HVDRWWNPAVEN | QATDRAYRIGQ | TNRVMVHKFITSGSVEEKIDRMIREKS 1034 |
| Syn_sp_RS9916_SNF2 | HVDRWWNPAVEN | QATDRAYRIGQ | TNRVMVHKFITSGSVEEKIDRMIREKS 1029 |
| Syn_sp_CC9605_SNF2 | HVDRWWNPAVEN | QATDRAYRIGQ | TNRVMVHKFITSGSVEEKIDRMIREKS 1034 |
| Syn_sp_WH\8102_SNF2 | HVDRWWNPAVEN | QATDRAYRIGQ | TNRVMVHKFVTRGSVEEKIDRMIREKS 1032 |
| Syn_sp_CC9902_SNF2 | HVDRWWNPAVEN | QATDRAYRIGQ | TNRVMVHKFITSGSVEEKIDQMIREKA 1032 |
| Syn_sp_\WH\5701_SNF2 | HIDRWWNPAVEN | QATDRAFRIGQ | RRTVQVRKFICTGTLEEKIDEMIEEKK 1007 |
| Myctu_SNF2 | HIDRWWNPAVEN | QATDRAFRIGQ | RRTVQVRKFICTGTLEEKIDEMIEEKK 978 |
| Mycbo_SNF2 | HIDRWWNPAVEN | QATDRAFRIGQ | RRDVQVRKLVCVDTIEERIDEMITGKS 978 |
| Nocfa_IFM\10152_SNF2 | HYDRWWNPAVEN | QATDRAFRIGQ | TRAVQVHKLVCAGTVEEKVDRLLEQKR 921 |
| Myxxa_DK_SNF2 | HVDRWWNPAVEN | QATDRAYRIGQ | TRRVLVHRLITAGTLEERIDRLLAEKR 1030 |
| Symth_IAM14863_SNF2 | HFDRWWNPAVEN | QATDRAYRIGQ | TKNVEVHKFICAGTLEEKIDEIIERKV 957 |
| Metac_C2A_SNF2 | HFDRWWNPAVEN | QATDRAFRIGQ | KKNVEVHKFICAGTLEEKIDEIIERKV 1043 |
| Metma_Go1_SNF2 | HFDRWWNPAVEN | QATDRAFRIGQ | HKNVEVHKFITTGTLEERIDEMIEKKT 1054 |
| Pelph_BU-1_SNF2 | HFDRWWNPAVEN | QATDRAFRIGQ | SKNVLVHKFVCAGTLEEKIDELIESKK 972 |
| Archaeon\RC-I_SNF2 | HFDRWWNPAVED | QATDRAYRIGQ | KKNVFVHKFVHKFVALGTLEERIDQMIEDKK 1005 |
| Nos_sp_PCC7120_SNF2\II | HFDRWWNPAVED | QATDRAYRIGK | KRFVHVHKLITTGTLEEKIDEMLERKQ 1020 |
| Bacce_ATCC10987_SNF2 | HYDRWWNPAVED | QATDRTYRIGQ | KRNVQVHLMITAGTLEERIDLINQEKR 891 |
| Methu_JF-1_SNF2 | HVDRWWNPAVED | QATDRTYRIGQ | KRNVQVHLMITAGTLEERIDLINQEKR 1010 |

FIGURE 8 (continued)

```
Synco_SNF2            QLAEQTVDAGENWLTRIDTDKLRQLLTLSATPVDYQAEASD----------  1039
Anava_SNF2            QLAEQVVGAGEEWLTELDTDQLRNLLILDRSAVIDEEAE-----------  1078
Nostoc_SNF2           QLAEQVVGAGEEWLTELDTDQLRNLLILDRSTVIDEEAD-----------  1075
Nodsp_SNF2            QLAEQVVGAGEEWLTEMNTDQLRDLLILDRSAIIDEDEV-----------  1087
Lyn_sp_SNF2           VLAEQVVGSGENWLTELDTDQLRNLLIIDRNAVIDEEE------------  1061
Crowa_SNF2            KLAEQTVDAGEQWLTELDTDQLRNLLLLDRDTIIDEQ-------------  1046
Synel_PCC6301_SNF2    ALAQQIVGSGEDWLTELDTNQLRQLLILDRSAWVEEEEP-----------  1019
Synel_PCC7942_SNF2    ALAQQIVGSGEDWLTELDTNQLRQLLILDRSAWVEEEEP-----------  1019
Theel_BP-1_SNF2       ALAEMIVGSGEHWLTELNLDQLRQLLTLDKERLITL--------------   999
Glovi_SNF2            ALAEQVVSAGENWLSDLNTDQLRQLLVLDRSEIIDTEDTA----------  1008
Proma_CCMP1375_SNF2   ELAENIVGSGESWLGQLSLEKLSELVALDSNPEF----------------  1062
Proma_MIT\9211_SNF2   KLAENIIGAGEDWLGKLGINELRELVSLEKES------------------  1067
Proma_MIT\9303_SNF2   RLAEDIIGSGEDWLGGLGVSQLRELVALEDS-------------------  1099
Proma_MIT9313_SNF2    RLAEDIIGSGEDWLGGLGVSQLRELVALEDS-------------------  1099
Syn_sp_CC9311_SNF2    RLAEDIIGSGEDWLGGLEMGQLKELVSLEDNQA-----------------  1064
Syn_sp_WH\7805_SNF2   RLAEDIVGSGEEWLGGFDMGQLKELVSLEDNETRNP--------------  1070
Syn_sp_WH\9916_SNF2   RLAEDIVGSGEDWLGGLDMGQLKELVSLDDNGSLSA--------------  1065
Syn_sp_CC9605_SNF2    RLAEDVIGSGEDWLGSLGGDQLRDLVSLEDT-------------------  1065
Syn_sp_WH\8102_SNF2   RLAEDVIGSGEDWLGCLAGDQLRNLVALEDT-------------------  1063
Syn_sp_CC9902_SNF2    RMAEDVIGSGEDWLGSLGGDQLRNLVALEDT-------------------  1063
Syn_sp_\WH\5701_SNF2  RLAEDIVGSGEEWLGGLDPGQLRDLVALEE--------------------  1037
Myctu_SNF2            ALADLVVTDGEGWLTELSTRDLREVFALSEGAVGE---------------  1013
Mycbo_SNF2            ALADLVVTDGEGWLTELSTRDLREVFALSEGAVGE---------------  1013
Nocfa_IFM\10152_SNF2  RLADLAVDAGENWITELGTEELRELFTLGAEAVGE---------------   956
Myxxa_DK_SNF2         QLAEKVVGAGEHWVTELDTTALRELFSLSEGAVADDGDAEGEDDARVRAP  1080
Symth_IAM14863_SNF2   ALAGQVIISGESWLGQLSTEELRALIALDREV------------------   989
Metac_C2A_SNF2        QVAENVVGTGEGWLTELSNEELKDILALREEAVGE---------------  1078
Metma_Go1_SNF2        QVAENVVGTGEDWLTELSNDELKDILALREEAVGE---------------  1089
Pelph_BU-1_SNF2       TVAGQVLGTGEQWLTELSNNDLRKLIMLGQEAMGE---------------  1007
Archaeon\RC-I_SNF2    ALSANILGTGEDWITELSTEQLRDMVMLRWDEVADDG-------------  1042
Nos_sp_PCC7120_SNF2\II KLSSAVVGSDESWLTELDNEAFKKLIALNKSTIME--------------  1055
Bacce_ATCC10987_SNF2  SLNNAVIT-SDSWMTELSTDELKELLGV----------------------   918
Methu_JF-1_SNF2       TLAKEVLAQSDEYLTNLSTKELLEIVSLRDSLFRGEDA------------  1048
                                 :.         :            ::
```

FIGURE 8 (continued)

SEQ ID NO: 29, Synechocystis sp. PCC 6803 BA000022 Synecho_PCC6803_SNF2 nucleic acid sequence

```
TGTTCGTTGCACAAATTGATGAGCAATGCTTTTTTATAATGCCAACTTTGTACAAAAAAGCAGGCT
TAAACAATGGCGACTATCCACGGTAATTGGCAACCCTCCCACGGGGAAAACGGCGGCAAACTGTTT
CTTTGGGCGGATACCTGGGGTCATCCTTTGCCAGAAACCATTGGCGATCGCCATCCCTTTGCGTTG
GATCTGCCGGATTTGCTACAGGCCTGGTCGAATTTGCCCCTGGCCTTCCCCAAGGCGGATGGGGTG
ACAGAGGCAGCCCTTACTCTGCATTTACCCAGCCATCGCCAGCAAAAAATTCCCCTACCCTTTGTC
ACAGGGCAAGATCCGGTGGCCATGGATGCGAAATATCTCCACTGGCGATCGTGGCAGGTAACCGGG
GTAAATCTGACCCCAAGCCAAACGTTAACGTTGCTCCAATCTATTCCCTGGGGGGCCAAGCCTTA
GCTAACTTAGGATCAGAGTTTTACTTTTACGGTCAACTGCACCGCTGGTGTTTAGATTTGGTGCTA
CGGGGTAAATTTGTGCCGGGACTGGAGCAAAGGGGGAAGACGGTAATTACTATGCCCAATGGATT
CCTATCCTCGATAGCATCCAAGACCAAACCCATTTAGCCCAATTTAGCCAGAGAGTACCTGCCTGC
GCCCTGGCCAACCTGACTGACTCCCAGGAGCCCCAAATGTTGGTGGTGGATTTACTACAAAAATTA
TTGCAAGCCCAAATTGGTGCCGTCAGTCCCAGCCTAGCCAACGTTAAAGAAGTCTGGTTGAATGAT
TGGCTCCGGGGATTAACCCATGGGGGGCAAACCTCCCTCGGCACAAGCAAAGCTCTACAACGATTA
GCCACATCCTTAGACCATTGGTATTTACCAGTCCAGAATTATTTGGGCCAAAAAAATAACCAAGCT
TTAGCCCAACGGCAATGGCGGGGGGCTCTGCGGTTACAACCTCCAGCGGACGATGGGGGGGGAACC
TGGCAACTGGATTATGGTTTACAAGCCCTGGATGACGGGGAATTTTGGCTCCCGGCGGCTTCCCTC
TGGGCCATGGCCGGCGATCGCCTGGTGTGGCAGGGAAGGAGGGTTGACCAGGGGCGGAAAGTTTA
CTGCGGGGCTTAGGGGTAGCTGCCCAAATTTACGAACCCATTGCTGCAAGTTTGACGGAAAGGTGT
CCCACGGGCTGTGGGCTAGATGCCATCCAAGCCTACGAATTTATCCTGGCAATCGCCCATCAATTG
CGGGATCGGGGGTTAGGGGTAATCCTCCCGCCGGGGTTAGAACGGGGCGGCACCGCCAAACGGTTA
GGGGTAAAAGTGGTGGGGAAGTGCAACGGCAAAGGGGCCAGCGGCTAACTCTGCAAAGTTTAATT
AATTACGACTTGCAACTAATGATGGGGAGCGGGGACAATGCCCGGTTATTGACGGCCAAGGACTTT
GAAGCGTTACTAGCCCAAAAATCTCCCCTGGTGGTGCTGGACGGAGAATGGATTACCCTGCAACCG
GCGGACGTGCGGGCGGCCAAGGTCATTTTACAGCAGCAACAATCTGCCCCGCCCCTCACAGTGGAG
GATGCTCTGCGCCTCAGCATTGGTGATTTACAAACCGTCTCTAAACTGCCGGTGACCCAGTTTGCT
GCTCGGGGCATATTACAGGAATTGATCGACACCCTCCGTAACCCGGAAGGAGTGAAAGCCATTGCT
GACCCACCGGGCTTTCAGGGTACTTTACGGCCCTACCAAGCTCGGGGAGTGGGCTGGTTAGCTTTT
CTGGAACGGTGGGGGCTGGGGGCCTGTTTGGCAGACGATATGGGTTTGGGAAAAACACCCCAGTTG
CTGGCTTTTCTGCTCCATTTAGCCGCGGAGGATATGTTAGTTAAGCCGGTGTTGATTGTTTGTCCT
ACGTCGGTGCTGAGCAATTGGGGTCATGAAATTAATAAGTTTGCGCCCCAACTTAAAACCCTATTG
CACCATGGCGATCGCCGGAAAAAGGGCAACCGTTGGTTAAACAGGTCAAAGACCAGCAAATTGTC
CTCACCAGTTACGCTTTACTGCAACGGGATTTTAGTAGTTTGAAATTGGTGGACTGGCAGGGGATC
GTGCTGGACGAAGCCCAAAATATCAAAAATCCCCAAGCTAAACAGTCCCAGGCGGCCCGGCAATTG
CCAGCGGGTTTTCGCATTGCCCTCACGGGGACTCCGGTGGAAAATCGCCTGACGGAATTGTGGTCA
ATTTTAGAATTTTTAAATCCCGGTTTCCTGGGTAATCAGAGCTTTTTCCAACGGCGCTTTGCCAAT
CCCATCGAAAAATTTGGCGATCGCCAGTCGTTGTTAATTTTGCGGAATTTAGTGCGGCCGTTTATT
TTGCGGCGGTTAAAAACCGACCAAACCATTATTCAAGATTTACCAGAAAAACAAGAAATGACCGTC
TTCTGTGACCTTTCCCAAGAGCAAGCTGGTTTATATCAACAATTGGTGGAGGAATCCCTCCAGGCG
ATCGCCGACAGCGAAGGCATTCAAGGCACGGTTTAGTTTTAACCCTATTAACCAAACTCAAACAG
GTTTGTAACCATCCCGATCTATTGCTGAAAAAGCCCGCCATCACCCACGGGCACCAGTCCGGCAAG
CTAATTCGTCTGGCGGAAATGCTGGAAGAAATCATCAGCGAAGGCGATCGGGTGTTAATTTTCACC
CAATTTGCCAGTTGGGGTCATTTACTCAAACCCTATCTGGAAAAATACTTTAACCAAGAGGTGCTC
TATCTCCACGGGGCACTCCAGCAGAGCAACGGCAAGCTCTGGTGGAACGATTCCAACAGGACCCC
AACAGTCCCTATTTATTTATCCTTTCTCTCAAGGCTGGCGGCACAGGGTTGAACCTCACGAGGGCT
AACCATGTGTTCCATGTGGACCGGTGGTGGAATCCGGCGGTGGAAAATCAGGCTACCGATCGTGCT
TTTCGCATTGGCCAAACTCGCAACGTCCAGGTGCACAAATTTGTCTGTACAGGCACCTTGGAAGAA
```

FIGURE 10

```
AAAATTAACGCCATGATGGCGGATAAACAACAATTGGCAGAACAAACCGTGGATGCCGGGGAAAAT
TGGCTCACCCGCCTAGACACCGATAAACTCCGTCAGTTGCTTACCCTCTCCGCCACCCCGGTGGAT
TACCAAGCCGAAGCGTCCGATTGAACCCAGCTTTCTTGTACAAAGTTGGCATGATAAGAAAGCATT
GCTTATCAATTTGTTGCAACGAACAGGTCACTATCAGTCAAATAAAT
```

SEQ ID NO: 30, Synechocystis sp. PCC 6803 BA000022 Synecho_PCC6803_SNF2 translated polypeptide
```
MATIHGNWQPSHGENGGKLFLWADTWGHPLPETIGDRHPFALDLPDLLQAWSNLPLAFPKADGVTE
AALTLHLPSHRQQKIPLPFVTGQDPVAMDAKYLHWRSWQVTGVNLTPSQTLTLLQSIPLGGQALAN
LGSEFYFYGQLHRWCLDLVLRGKFVPGLEQRGEDGNYYAQWIPILDSIQDQTHLAQFSQRVPACAL
ANLTDSQEPQMLVVDLLQKLLQAQIGAVSPSLANVKEVWLNDWLRGLTHGGQTSLGTSKALQRLAT
SLDHWYLPVQNYLGQKNNQALAQRQWRGALRLQPPADDGGGTWQLDYGLQALDDGEFWLPAASLWA
MAGDRLVWQGRRVDQGAESLLRGLGVAAQIYEPIAASLTERCPTGCGLDAIQAYEFILAIAHQLRD
RGLGVILPPGLERGGTAKRLGVKVVGEVQRQRGQRLTQSLINYDLQLMMGSGDNARLLTAKDFEA
LLAQKSPLVVLDGEWITLQPADVRAAKVILQQQQSAPPLTVEDALRLSIGDLQTVSKLPVTQFAAR
GILQELIDTLRNPEGVKAIADPPGFQGTLRPYQARGVGWLAFLERWGLGACLADDMGLGKTPQLLA
FLLHLAAEDMLVKPVLIVCPTSVLSNWGHEINKFAPQLKTLLHHGDRRKKGQPLVKQVKDQQIVLT
SYALLQRDFSSLKLVDWQGIVLDEAQNIKNPQAKQSQAARQLPAGFRIALTGTPVENRLTELWSIL
EFLNPGFLGNQSFFQRRFANPIEKFGDRQSLLILRNLVRPFILRRLKTDQTIIQDLPEKQEMTVFC
DLSQEQAGLYQQLVEESLQAIADSEGIQRHGLVLTLLTKLKQVCNHPDLLLKKPAITHGHQSGKLI
RLAEMLEEIISEGDRVLIFTQFASWGHLLKPYLEKYFNQEVLYLHGGTPAEQRQALVERFQQDPNS
PYLFILSLKAGGTGLNLTRANHVFHVDRWWNPAVENQATDRAFRIGQTRNVQVHKFVCTGTLEEKI
NAMMADKQQLAEQTVDAGENWLTRLDTDKLRQLLTLSATPVDYQAEASD
```

SEQ ID NO: 31, Anaebena variabilis ATCC 29413 Anava_SNF2 nucleic acid sequence
```
ATGGCAATTTTACACGGTAGTTGGATATTAAGTGAGCAGGATAGTTATTTATTTATTTGGGGGGAA
ACTTGGCGATCGCCACAAGTAAATTTTAGTTTTGAGGAAATAGCCCTCAATCCCTTGGCTCTGTCT
GCATCTGAATTAAGCGAGTGGTTGCAGTCTCAACATCAGGCGATCGCTCAGATTTTACCACAACAG
TTGGCAAAAAAAACCTCCAAAGCAGCAAGTTCCCCAACAACAAATTTACCAATTCACTCGCAAATA
ATTGTTCTGCCAACGGAAATTTCTCAACCTCGTAAGAAAGAAACAATTTTCATTTCTCCTGTGCAT
TCTGCCGCTTTAGAATCTGATGCAGACTCTGAAGTTTATTTACAACCTTGGCGTGTAGAAGGTTTT
TGTCTTCCTCCTAGTGCAGCAGTTAAATTTCTAACTTCTTTACCTTTAAATATCACTAGCACAGAG
AATGCTTTTTTAGGTGGAGATTTACGTTTTGGTCACAAATTGCCCGTTGGAGTTTAGATTTAATT
TCTAGGTCTAAGTTTCTCCCAATTATCCAACGACAACCTAATAATTCTGTAAGTGCCAAATGGCAA
GTACTGTTAGATAGTGCTGTAGATGGAACTCGTTTAGAAAAGTTCGCCGCGAAGATGCCTTTGGTT
TGTCGGACTTATCAGAGATTAGGGAACGAGGAATTATCTCCATCTCCTATATATATAGATTTTCCT
AGTCAGCCGCAGGAATTAATATTGGGTTTTCTCAATAGTGCAATAGATACGCAATTACGGGAAATG
GTGGGGAATCAGCCTGTGGTGGAAACTCGCTTGATGGCATCTTTACCGTCGGCGGTACGACAGTGG
CTGCAAGGGTTAAGTGGTGCATCTAATTCAGTTGATGCAGATGCAGTTGGTTTGGAAAGGCTGGAA
GCAGCGCTCAAGGCTTGGACGATGCCGCTACAATATCAACTAGCAAGTAAAAATCAATTTCGCACC
TGTTTTGAATTACGTTCTCCAGAACCAGGAGAAACTGAATGGACACTAGCCTATTTCCTGCAAGCA
GCCGATAATCCAGAATTTCTAGTAGATGCGGGCACTATTTGGCAACATCCTGTTGAACAGCTAATT
TATCAACAGCGATCGATTCAAGAACCCCAGGAAACATTTTACGAGGTTTGGGGTTAGCTTCTCGA
TTGTATCCGGTCATTGCCCCCACTTTAGATACAGAATCACCGCAATTTTGTCATCTCAACCCCATG
CAGGCTTATGAATTTATCAAGGCTGTGGCTTGGCGATTTGAAGATAGCGGTTTAGGGGTGATTTA
CCTCCTAGTTTGGCGAACCGGGAAGGCTGGGCAAACCGCTTGGGATTGAAAATCTCCGCCGAAACC
CCAAAGAAAAGCCAGGACGCTTGGGATTGCAGAGTTTGCTTAATTTTCAATGGCACTTAGCAATT
```

FIGURE 10 (continued)

```
GGTGGGCAAACTATTTCTAAAGGGGAATTTGACAGACTAGTAGCTTTAAAAAGCCCATTGGTAGAA
ATAAATGGCGAATGGGTGGAGTTGCGTCCCCAAGATATCAAGACAGCCGAAGCCTTTTTTGCTGCA
CGTAAAGACCAAATGGCCTTATCTTTAGAAGATGCTTTACGTCTGAGTAGTGGGGATACTCAAGTA
ATTGAGAAATTACCAGTAGTCAGCTTTGAAGCCTCTGGCGCATTACAAGAATTAATTGGGGCGCTG
ACAAATAATCAAGCAGTTGCACCATTACCTACGCCAAAGAACTTCCAAGGAAAGTTGCGTCCTTAT
CAAGAAGGGGTGCGGCTTGGTTGGCATTCCTCGAACGCTGGGGTTTAGGTGCTTGTCTCGCCGAC
GACATGGGACTGGGAAAAACGATACAGTTCATTGCTTTCCTTCTCCATCTTAAAGAACAGGATGTA
TTAGAAAAACCAACTTTACTAGTGTGTCCTACTTCTGTTTTAGGTAACTGGGAACGAGAAGTGAAA
AAATTTGCACCTACACTTAAAGTTCTCCAATATCATGGTGATAAACGTCCTAAAGGTAAAGCTTTT
CCAGAAGCAGTAAAAAATCATGATTTAGTTATCACCAGTTACTCACTAATTCATAGAGACATCAAA
TCATTGCAGGGTCTTTCTTGGCAGATAATTGTTTTAGATGAAGCCCAGAATGTGAAGAATGCGGAA
GCCAAACAATCACAAGCAGTCCGACAATTAGACACAACCTTTCGCATTGCTTTAACGGGGACACCA
GTCGAAATAGACTACAGGAACTTTGGTCAATTTTAGATTTCCTCAACCCTGGTTATTTAGGTAAT
AAGCAATTCTTCCAAAGACGCTTTGCCATGCCAATTGAAAAGTATGGTGATGCAGCATCTTTAAAT
CAATTGCGTGCCTTAGTACAACCATTTATTCTGCGTCGCCTGAAAACAGACCGTGATATTATTCAA
GACTTGCCAGATAAGCAAGAAATGACAGTATTTTGCGGTTTGACTGGAGAACAAGCTGCACTTTAT
CAAAAAGTGGTAGAAACATCTTTAGCAGAAATTGAATCGGCCGAAGGATTGCAACGCCAGGGATG
ATTTTAGCTTTATTAATTAAACTCAAACAAATCTGCAATCATCCAGCCCAATATCTGAAAACAAAT
ACCTTAGAACAATACAGTTCAGGAAAACTGCAACGATTAGAAGAAATGTTAGAAGAGGTGTTAGCG
GAGAGTAATACTTATGGTGTTGCTGGTGCGGGACGTGCTTTAATCTTCACCCAGTTTGCAGAATGG
GGTAAGTTACTCAAACCACATTTAGAAAAACAACTAGGGCGGGAAGTATTTTCTTATATGGTAGT
ACCAGTAAAAAGCAACGTGAAGAAATGATTGACCGTTTTCAACACGACCCTCAGGGGCCACCAATT
ATGATTCTCTCTCAAAGCAGGTGGTGTAGGGTTGAACTTAACCAGAGCAAATCATGTATTTCAC
TTTGATAGATGGTGGAATCCAGCCGTAGAGAACCAAGCCACAGACCGCGTATTTCGTATTGGTCAA
ACCCGCAATGTACAGGTGCATAAATTTGTTTGCAATGGTACCTTAGAAGAAAAAATCCACGACATG
ATTGAAAGTAAAAAACAACTAGCGGAACAGGTTGTTGGTGCAGGCGAAGAGTGGTTAACTGAATTA
GATACAGATCAACTCCGCAACTTACTGATACTTGATCGTAGTGCAGTAATTGATGAAGAAGCAGAG
TAA
```

SEQ ID NO: 32, Anaebena variabilis ATCC 29413 Anava_SNF2 translated polypeptide

```
MAILHGSWILSEQDSYLFIWGETWRSPQVNFSFEEIALNPLALSASELSEWLQSQHQAIAQILPQQ
LAKKTSKAASSPTTNLPIHSQIIVLPTEISQPRKKETIFISPVHSAALESDADSEVYLQPWRVEGF
CLPPSAAVKFLTSLPLNITSTENAFLGGDLRFWSQIARWSLDLISRSKFLPIIQRQPNNSVSAKWQ
VLLDSAVDGTRLEKFAAKMPLVCRTYQRLGNEELSPSPIYIDFPSQPQELILGFLNSAIDTQLREM
VGNQPVVETRLMASLPSAVRQWLQGLSGASNSVDADAVGLERLEAALKAWTMPLQYQLASKNQFRT
CFELRSPEPGETEWTLAYFLQAADNPEFLVDAGTIWQHPVEQLIYQQRSIQEPQETFLRGLGLASR
LYPVIAPTLDTESPQFCHLNPMQAYEFIKAVAWRFEDSGLGVILPPSLANREGWANRLGKISAET
PKKKPGRLGLQSLLNFQWHLAIGGQTISKGEFDRLVALKSPLVEINGEWVELRPQDIKTAEAFFAA
RKDQMALSLEDALRLSSGDTQVIEKLPVVSFEASGALQELIGALTNNQAVAPLPTPKNFQGKLRPY
QERGAAWLAFLERWGLGACLADDMGLGKTIQFIAFLLHLKEQDVLEKPTLLVCPTSVLGNWEREVK
KFAPTLKVLQYHGDKRPKGKAFPEAVKNHDLVITSYSLIHRDIKSLQGLSWQIIVLDEAQNVKNAE
AKQSQAVRQLDTTFRIALTGTPVENRLQELWSILDFLNPGYLGNKQFQRRFAMPIEKYGDAASLN
QLRALVQPFILRRLKTDRDIIQDLPDKQEMTVFCGLTGEQAALYQKVVETSLAEIESAEGLQRRGM
ILALLIKLKQICNHPAQYLKTNTLEQYSSGKLQRLEEMLEEVLAESNTYGVAGAGRALIFTQFAEW
GKLLKPHLEKQLGREVFFLYGSTSKKQREEMIDRFQHDPQGPPIMILSLKAGGVGLNLTRANHVFH
FDRWWNPAVENQATDRVFRIGQTRNVQVHKFVCNGTLEEKIHDMIESKKQLAEQVVGAGEEWLTEL
DTDQLRNLLILDRSAVIDEEAE
```

FIGURE 10 (continued)

SEQ ID NO: 33, uncultured methanogenic archaeon RC-I Archaeon_RC-I_SNF2 nucleic acid sequence
ATGATTACACTTCACGGAACCTGGACTACTGTCGATCCCCTGAATGGCACATTTTTCCTCTGGGGA
GAGAGTGATCCGGCCACGCAGCATAAAAGAAGAGGCAGGCCTCGGAAAAGTGCAGGGGAGAAACAG
CACCCGTTTCACGCCGGCATCAAAGAGCTGGAAGCTGGAGCGGGGGCTATCAATTCATCGTGTATA
AGACATATAGCAGATGCGGGAGCACGGGCGGAGCAGGTTTTAATTTTGCCGTCAGCTACGGACAGG
CCCCTGAGATCTGCGAGCCCTTCAGCACTGGAGTCAGGTGAAGAAACCAACCCTGACAGCAGTTTA
CAATTTCTTCCGTGGACGGTGACCGGCATCAACATTAAGCCCGGGAATGCTCTGGTACTTCTATCC
TCTATAGCCGAATCACAAAAGCGGATCGGAGATATGGCGATAGGCCCAGACCTGCTTTACTGGAGT
AAGGTAGCCAAGTTTACGCTTAAGCTCCTGATAAGCCAGCAGTTCAGGCCGGAGGTTGTCGAAGTA
ATGAGCGGAAAAGCATATAGCCGTTGGAGATTTGCGCTCACCGATGAAACTGACCGGAAACACTAT
GCCTCGCTCGAAAACTCCATGCCGCTGGCATGTATTGCGGTTTCAGGAAAGGCTGGCATTTATAAT
CGAAAAGAAGCCTTAGATTTGTTCATTAATACCGCCCTTGACACATTTATCCGGGACCAGATTGCC
CTGCCCGCTGACAGCAGGATGACGAACCTGCTATCGCAAGCATGGCTAGATTCGCTCGGCACCGGA
GAGAGTATCCGCCTGTCGGCTCCTGAGATGAAGAAACTCAAAGATTCGGCAGGCCGCTGGACATCC
CGCATGAAAACAGAGAGCAAACAAGCTTTAAAGACCTGCTTCATCCTGGAGCCGCCAGCCCCGGAT
ACAGAGTATCCTGAAGCGCCGTGGAACCTACGGTACTGCTTGCAGGCATCCGATGACCCCAGTCTG
GTAATTCCGGCTGAGACTGTGTGGAAAGAGTTGAAGAAGACGCTGAAGTACCTGAATAAGAGATAC
GATAACCCTCAGGAGCAATTGTTACAGGATCTCGGAAAAGCGATGCAGATGTTTCCCGAAATCGAG
CCCAGCCTCAACACGTCAAAACCTCTGTCCGCAACGCTGAGCACCAGTGAAGCCTACAAGTTCCTG
ACAGAAGCGGCGCCTCTGCTGCAGGACAGCGGGTATAGCATTATCCTACCGGAATGGTGGCGCAAC
AGCACTGGCAGGCTCAAGCTCGGCGCCAGGCTTCGCTTCAAGCCGAAAGCCGAAGGTAAAGCGGGT
AAAAGCCAGTTCACCATGGATACCCTCGTCAGCTACGACTGGCGCCTGGCGCTGGGCGATCAGGAG
ATCACCGAAACAGAGTTCAGGAAGCTGGCAGCCCTGAAAGAGCCGCTTCTGCAGATAGGCGGGAAA
TGGTTTGCGCTGAAAAAGGAAGACATAGACAGCATCATGAAAGCATTCAGGGCGAAGAAGACTGGA
GAGATGGCTTTATCGGAGGCACTGCGCCTCAACGGCGGGCTGGAAGACTTCAACGGCATCCCCGTC
AGCGGCATGAAATCGTCAGGATGGCTGGCAGAACTTTTCGACAGGCTGGCAGCCGGCGAAAAAATA
ACGAGCCTTGCCCCGCCGGACGGTTTCAACGGGGAGCTTAGAGATTACCAGGTTAAAGGCTACTCC
TGGCTGGCCTTCATGAAAAAGTATGGCCTGGGCTCCATTCTGGCTGACGACATGGGCCTGGGTAAG
ACGATACAGCTGCTGGCGTTGCTCCTGAAAGAGAAGGAAAGAGGCACTAAAGGCCCTACTCTGTTG
ATCTGCCCCACCTCGATTCTCGGAAACTGGCAGCGGGAGGCGAAGAAATTTGCCCCGGCCCTGAAA
GTCCACATACACCATGGGGCAGGAAGGGCTGATAAAGAGCAGTTCGGAAAAATCGTCAAGGCTCAC
GACCTGATCCTGAGCACTTACGCTCACGCCTACCGGGACGAGGAACTGCTTAAAGAGGTGAACTGG
AAGCTGGTAGTGCTCGACGAGGCTCAGAATATCAAGAATCATCATACCCGGCAGGCCAGAGCTATC
CGGGCTCTTAAGGCCGATCACCGAATAGCCATGACGGGAACGCCGATAGAGAACAGACTCTCGGAG
CTGTGGTCGATCGTGGACTTCCTGAACCCCGGCTACCTGGGCAAGGCGGAGACATTCAGGAAACAA
TTCGCCATACCTATCGAGAGATACGATGACGCTGCCCGGTCGGAAAAATTGAAGCAGGCCATCAAG
CCCCTGGTGCTGCGCAGAGTGAAGACGGATCCGGCCATCATCAAAGACCTGCCGGACAAGATCGAG
ATCAAGGAGCCCTGCAACCTCACCAAAGAACAGGCCACGCTCTACGAGGCCATCGTAGAGAACATG
CTGAAAAGTATAGATAAGGCCACGGCAATGCAGAGACGGGGAATCGTCTTAGCGTCCCTGATGAAG
CTCAAACAGGTCTGCGATCACCCGTCGCTGTACATCAAAACGGGCGCTGTGACCGACGATAAGACG
CTGATCAGGTCTGGCAAGCTGAAGCGCCTCACGGAGCTGCTCGAAGAAGCGCTGGCCGAAGGCGAC
AGCGTGCTGATCTTCACCCAGTTCGTGGAAATGGGGGAGATGCTGAAAGCCTACCTGCAGAGCACG
TTCGACGAAGAAGCCCTCTTTTTGCACGGCGGAGTACCGCAGAAGGCCAGAGACAAGATGGTCCTC
CGTTTCGGGGAAAAGGACGGGCCACGGATCTTTATCGTCTCGCTGAAAGCCGGCGGCGTCGGCCTC
AACCTGACGAAGGCAAGCCACGTGTTCCACTTCGATCGCTGGTGGAACCCGGCGGTCGAGAACCAG
GCGACAGATCGAGCTTACAGGATAGGCCAGAGCAAAAATGTACTGGTCCATAAATTCGTCTGCGCC
GGCACGCTGGAAGAAAGATCGACGAGCTGATCGAGAGCAAAAAGGCGCTGTCGGCGAACATCCTC
GGCACGGGAGAAGACTGGATCACGGAGTTGTCGACCGAACAGCTGAGGGACATGGTCATGCTGAGA
TGGGACGAGGTAGCCGATGATGGCTAA
```

SEQ ID NO: 34, uncultured methanogenic archaeon RC-I Archaeon_RC-I_SNF2 translated polypeptide
MITLHGTWTTVDPLNGTFFLWGESDPATQHKRRGRPRKSAGEKQHPFHAGIKELEAGAGAINSSCI
RHIADAGARAEQVLILPSATDRPLRSASPSALESGEETNPDSSLQFLPWTVTGINIKPGNALVLLS
SIAESQKRIGDMAIGPDLLYWSKVAKFTLKLLISQQFRPEVVEVMSGKAYSRWRFALTDETDRKHY
ASLENSMPLACIAVSGKAGIYNRKEALDLFINTALDTFIRDQIALPADSRMTNLLSQAWLDSLGTG
ESIRLSAPEMKKLKDSAGRWTSRMKTESKQALKTCFILEPPAPDTEYPEAPWNLRYCLQASDDPSL
VIPAETVWKELKKTLKYLNKRYDNPQEQLLQDLGKAMQMFPEIEPSLNTSKPLSATLSTSEAYKFL
TEAAPLLQDSGYSIILPEWWRNSTGRLKLGARLRFKPKAEGKAGKSQFTMDTLVSYDWRLALGDQE
ITETEFRKLAALKEPLLQIGGKWFALKKEDIDSIMKAFRAKKTGEMALSEALRLNGGLEDFNGIPV
SGMKSSGWLAELFDRLAAGEKITSLAPPDGFNGELRDYQVKGYSWLAFMKKYGLGSILADDMGLGK
TIQLLALLLKEKERGTKGPTLLICPTSILGNWQREAKKFAPALKVHIHHGAGRADKEQFGKIVKAH
DLILSTYAHAYRDEELLKEVNWKLVVLDEAQNIKNHHTRQARAIRALKADHRIAMTGTPIENRLSE
LWSIVDFLNPGYLGKAETFRKQFAIPIERYDDAARSEKLKQAIKPLVLRRVKTDPAIIKDLPDKIE
IKEPCNLTKEQATLYEAIVENMLKSIDKATAMQRRGIVLASLMKLKQVCDHPSLYIKTGAVTDDKT
LIRSGKLKRLTELLEEALAEGDSVLIFTQFVEMGEMLKAYLQSTFDEEALFLHGGVPQKARDKMVL
RFGEKDGPRIFIVSLKAGGVGLNLTKASHVFHDRWWNPAVENQATDRAYRIGQSKNVLVHKFVCA
GTLEEKIDELIESKKALSANILGTGEDWITELSTEQLRDMVMLRWDEVADDG SEQ ID NO: 35, Bacillus cereus ATCC 10987 Bacce_ATCC10987_SNF2 nucleic acid sequence
ATGATCAATCAAACTGAAGTAACAATTAGGCTCCAGCACGTTAGTCACGGTTGGTTCCTTTGGGGA
GAAGATGATAGCGGTACTCCATTATCCGTAACAAGTTGGAAACGAAATGCATTTACATGGCACTCC
ACTTCCTTCTACGGCACGTTTCTAAAAGAAGCAAGCTTTGAAGGAAGACAAGGTGTTATGCTAACA
AACGCACAAGCATTTGAATACATCGCGAATAAACCGATGAACTCCTTTGCCCGTATTCAAATGAAC
GGCCCTATTACAGCACTTACGGAAGATGCGAACGAATTGTGGGATGCCTTCACAAGCGGTAGCTTC
GTACCTGATATGGAGCGTTGGCCTAAACAACCATCTTGGAAAGTTCAAAATACTCCAATCGAAGAT
GAAACATTGGCATCTCTTTTCTCGGCTGCAGTAAATGAAAGCATATTACAAGATAACCGTTCAAAT
GACGGATGGGAAGATGCAAAGAGACTTTATGAACATTACGACTTTACGAAAAGACAATTAGACGCA
GCACTACATGAAGAAGATTGGCTTCGAAAAATTGGTTACATTGAAGATGACCTTCCCTTTACAATC
GGACTACGACTACAAGAGCCGCAAGAAGAATTTGAAATGTGGAAGCTTGAAACAATTGTTACGCCA
AAGCGCGGGGCACATCGCATATATGTATATGAGAGTATCGATTCTTTACCAAAACGATGGCACGAT
TATGAAGAACGTATTCTGGAAACACAAGAAAGCTTCAGTAAGCTCGTACCGTGGCTAAAAGATGGT
GATACATTCCGAAGTGAACTCTTTGAAACAGAAGCGTGGAACTTCTTAACAGAAGCAAGTAACGAA
TTACTCGCCGCAGGTATTACAATCTTATTACCATCGTGGTGGCAAAATTTAAAAGCGACAAAACCA
AAATTACGTGTGCAACTGAAGCAAAATGCTACACAAACGCAATCTTTCTTCGGCATGAATACACTC
GTTAATTTTGACTGGCGCATTTCAACGAACGGCATTGATTTATCAGAAAGCGAATTTTTTGAACTC
GTTGAACAAAACAAGCGGTTATTCAATATAAATGGTCAATGGATGCGACTAGATCCAGCCTTTATT
GAAGAAGTACGAAAGCTCATGAATCGTGCTGATAAGTATGGACTTGAAATGAAAGATGTCCTGCAG
CAACATTTATCAAACACGGCTGAAACAGAAATTGTAGAAGAGGATAGTCCGTTTACAGATATTGAA
ATTGAACTAGATGGATATTATGAAGACTTATTCCAAAAACTATTGCACATTGGAGATATTCCGAAA
GTAGATGTCCCTTCATCACTAAACGCCACACTCCGTCCGTATCAACAACATGGCATTGAGTGGTTA
TTATATTTAAGAAAGCTTGGATTCGGCGCATTGTTAGCTGACGACATGGGACTTGGAAAGAGTATT
CAAACGATCACTTACTTACTATATATAAAAGAAAACAATCTCCAAACAGGTCCTGCTTTAATCGTG
GCTCCGACATCTGTTCTTGGAAATTGGCAAAAAGAATTTGAGCGTTTCGCACCGAATTTACGTGTT
CAGTTACATTATGGAAGTAACCGAGCTAAAGGGGAACCCTTTAAAGATTTCCTTCAATCAGCAGAT
GTTGTATTAACATCTTATGCATTAGCTCAGCTTGATGAGGAAGAACTTAGTACGTTATGCTGGGAT
GCTGTTATTTTGGATGAAGCACAAAATATTAAAAACCCACATACGAAACAGTCTAAAGCAGTACGA

```
AACTTACAAGCAAATCACAAAATCGCATTAACTGGGACACCGATGGAAAACCGCCTTGCCGAGCTT
TGGTCTATTTTCGACTTCATTAATCATGGATATCTTGGCAGCTTAGGACAATTCCAGCGCCGCTTC
GTCTCACCAATTGAAAAGGACCGTGACGAAGGAAAAATCCAACAAGTTCAACGTTTTATCTCACCG
TTTTTACTGCGTCGTACGAAGAAAGATCAAACAGTCGCATTAAACTTACCAGATAAACAAGAACAG
AAAGCTTACTGTCCACTAACTGGTGAACAAGCTTCCTTATATGAACAACTTGTTCAAGATACGTTG
CAAAATGTAGAAGGATTAAGCGGAATTGAACGACGCGGATTTATATTACTCATGCTGAACAAACTT
AAACAAATTTGTAATCATCCCGCTCTTTATTTAAAAGAAACAGAACCGAAAGACATCATCGAGCGT
TCCATGAAAACGAGCACGCTCATGGAACTCATTGAAAATATAAAGATCAAAATGAAAGTTGCTTA
ATCTTCACGCAATACATCGGTATGGGAACATGCTAAAAGATGTGTTAGAAGAACATTTCGGTCAG
CGCGTCCTCTTCTTAAACGGTAGTGTACCGAAGAAAGAACGTGACAAAATGATCGAACAGTTCCAA
AACGGAACGTATGACATCTTCATTTTATCGTTAAAAGCAGGTGGTACAGGATTAAACTTAACAGCT
GCCAACCATGTCATTCACTACGATCGTTGGTGGAATCCAGCGGTAGAAAACCAAGCAACAGACCGT
GCATATCGCATTGGTCAAAAGCGCTTCGTTCACGTTCATAAACTGATTACAACGGGGACACTTGAA
GAGAAAATCGATGAAATGTTAGAAAGAAAACAATCATTAAACAACGCCGTCATTACAAGCGATAGT
TGGATGACAGAACTATCTACAGATGAACTAAAAGAATTACTTGGTGTATAA
```

SEQ ID NO: 36, Bacillus cereus ATCC 10987 Bacce_ATCC10987_SNF2 translated polypeptide
```
MINQTEVTIRLQHVSHGWFLWGEDDSGTPLSVTSWKRNAFTWHSTSFYGTFLKEASFEGRQGVMLT
NAQAFEYIANKPMNSFARIQMNGPITALTEDANELWDAFTSGSFVPDMERWPKQPSWKVQNTPIED
ETLASLFSAAVNESILQDNRSNDGWEDAKRLYEHYDFTKRQLDAALHEEDWLRKIGYIEDDLPFTI
GLRLQEPQEEFEMWKLETIVTPKRGAHRIYVYESIDSLPKRWHDYEERILETQESFSKLVPWLKDG
DTFRSELFETEAWNFLTEASNELLAAGITILLPSWWQNLKATKPKLRVQLKQNATQTQSFFGMNTL
VNFDWRISTNGIDLSESEFFELVEQNKRLFNINGQWMRLDPAFIEEVRKLMNRADKYGLEMKDVLQ
QHLSNTAETEIVEEDSPFTDIEIELDGYYEDLFQKLLHIGDIPKVDVPSSLNATLRPYQQHGIEWL
LYLRKLGFGALLADDMGLGKSIQTITYLLYIKENNLQTGPALIVAPTSVLGNWQKEFERFAPNLRV
QLHYGSNRAKGEPFKDFLQSADVVLTSYALAQLDEEELSTLCWDAVILDEAQNIKNPHTKQSKAVR
NLQANHKIALTGTPMENRLAELWSIFDFINHGYLGSLGQFQRRFVSPIEKDRDEGKIQQVQRFISP
FLLRRTKKDQTVALNLPDKQEQKAYCPLTGEQASLYEQLVQDTLQNVEGLSGIERRGFILLMLNKL
KQICNHPALYLKETEPKDIIERSMKTSTLMELIENIKDQNESCLIFTQYIGMGNMLKDVLEEHFGQ
RVLFLNGSVPKKERDKMIEQFQNGTYDIFILSLKAGGTGLNLTAANHVIHYDRWWNPAVENQATDR
AYRIGQKRFVHVHKLITTGTLEEKIDEMLERKQSLNNAVITSDSWMTELSTDELKELLGV
```

SEQ ID NO: 37, Crocosphaera watsonii WH 8501 ctg336 Crowa_SNF2 nucleic acid sequence
```
ATGACAATATTACATGGAACTTGGATTGAAAATACCTCTGAAAAACATTTTTTTATTTGGGGGGAA
ACTTGGCGTTCTTTATCCTCTGATATTTCCTCAGATGATTCTATTTTAATGTATCCATTTTCTGTA
GATAAACAGGGAATTATTGAACAATTAAACTCGAATAAGATTAAGATTGAAAAAACAAAAATATT
GAATCTGTTTCTCAAATATTTTATTTGCCTAGTAAATTTATTGCTAAATCGAAGCAAAGTATCCCT
TTACTATCAACAGAATTAAAAGATAAAGATTTTGAACAAGGGGATATTCAGTTAATTGCTTGGAAA
ATCGAAGGGATAAAATTAAATGTTGATGATACAATTAATATTTTAAGTCAGTTACCGTTGGGATTA
ACCAATAATGACGAAATTACATAGGCGATAATTTAAAATTTTGGACACATATTTATCGTTGGAGT
CTAGATTTATTAACTAGAGGTAAATATTTACCGCAAATGGAAGAACAAGATAATAACTGTTATGGA
CAATGGGAACCTTTACTAGATAGTTTAGTTGATCAGCAACGGTTCTCTAAATTTATACAAACTATG
CCAAATAGTTCTCTTGCTTATCATAATTTAATGGAGGGTGAATTATCCTCTTCTTTACTCAAACAA
ACTACTATTCTTGATTTTTATCTACTATCATTAATCAACAAGTACGTCAATTTATTGATGTTGCT
ATTACCCCTAGTTCATTTATCCAAAAGTGGTTATACTCTTTAACACAAGACTTATCTAAATTTGAA
GCATCAGAAGTTGAAAGAAAGGGATTAAAGAATGCTATTAATAATTGGAAATCTTCTTTAAGTGAA
```

```
TATATTATAAAGTCTGATAATCAACCATTAGGAATTAACCAGTTTCGTGTTTGTTTTAAACTAGAA
AATCCAGCTAAAAGTGGTAAGAAATTAGAACAAAGTAATTGGCAGTTACACTACTATCTCCAAGCT
TTAGATGATCCTAATTTTCTGATCTCTGCCAAGGTTATTTGGGAAAATCCTGTTACTAGATTAATC
TGCAATAATAGAACAATTAATCATCCTCAAGAAACCTTGCTAAAAGGACTAGGTTTAGCTTCACGT
CTATATTATCTAATTGAAGAAAGTTTACAAGACAATAAGCCTAGTTTTTCTGAGTTAGATCCCATA
CAAGTCTATGAATTTTTACGTTCAATTGCTAATATTCTTAAAGATAATGGCTTAGGGGTTATCTTA
CCAGCTAGTCTAGAGCAAGGAGTCGAAGAAAAACGCTTAGGAATTAGTCTAACCGCAGAAGTTAAG
TCGAAAAAAGGACAAAGACTTAGCTTACAAAGTTTGTTAAGTTATAAGCTAAATTTAGCAATTGGT
GATAAAACAATATCGAAAAAAGACTTTGAAAAACTATTAGCGCAAAAGTCACCTTTAGTTGAAGTA
AAAGGAGAATGGATAGCATTACAACCTGCTGATGTCAAGGCCGCACAACAAATTTTAAATAAGTCC
TATGATCCCCTAGAACTTTCTGTAGAAGATGCTTTACGCTTCAGCACAGGAGATATTTCAACTGTT
GCCAAACTGCCGATTACTAACTTTGAAGCAAAAGGGGAATTAGCCAATCTAATTAATGCTATAAAT
AATAATGAATCAATCCCTATGATCGAAAATCCCAGAGGATTTAAAGGTCAATTACGTCCCTATCAA
CAGCGAGGAGTCGGTTGGTTATCGTCTTAGAAAAATGGGGTTTAGGGGCTTGTCTTGCCGATGAT
ATGGGATTAGGAAAAACACCACAATTAATTGGGTTTCTCTTACATTTAAGAAGCGAAGGAATGTTA
GATCAACCTACCTTAGTTATTTGTCCTACATCTGTTTTAAATAACTGGGAAAGAGAAGTTCAAAAA
TTTGCCCCAACCCTTTCTACTTTGATTCATCATGGAGATAAACGTAGTAAAGGGAAAGCTTTTGTT
AAAGCAGTTAGTAAAAAAAATGTTATCATTACTAGCTATTCTTTAATTTATCGAGATATTAAAAGC
TTTGAACAGGTAGAATGGCAAGGTATTGTCTTAGATGAAGCACAAAATATAAAAAATCCCCAGGCA
AAACAATCCCAAGCAGTGCGTCAAATTTCCACACAGTTTCGTATTGCTTTAACAGGAACTCCTGTA
GAAAATCGCCTAACAGAATTATGGTCAATTCTTGACTTTCTTAACCCAGGATTTTTAGGGACACAG
CAGTTTTTCCGTCGTCGTTTTGCCACTCCTATCGAAAAATATGGGGATAAAGAATCACTGCAAATT
ATGCGTTCTTTGGTACGTCCTTTCATTCTCAGACGATTGAAAACAGATAAAACTATTATTCAAGAT
TTACCCGAAAAACAAGAAATGACCATTTTTTGTGGGTTATCCTCAGAACAAGGAAAACTTTATCAA
CAATTAGTAGATAATTCTCTGGTAGCAATAGAAGAGAAAACAGGAATTGAACGCAAAGGCTTAATT
TTAAGCTTACTGCTAAAACTCAAACAAATTTGTAACCATCCTGCTCATTTCTCAAGCAAAAGAGC
TTAAAAACAGCAGAACAATCTGGTAAATTATTAAGACTAGAAGAAATGCTAGAAGAATTAATCGAA
GAAGGAGATCATGCTTTAATCTTTACCCAATTTTCTGAATGGGTAAACTGCTGCAACCTTATTTA
CAGAAAAAATTTCAGCAAGACGTTCTCTTTTTGTATGGTGCTACTCGCAGAGTTCAAAGACAAGAA
ATGATCGATCGCTTTCAACAGGATCCCAACGGACCCAGAATTTTTATTCTCTCCTTAAAAGCAGGG
GGAACCGGATTAAATTTAACCCGCGCTAACCATGTATTTCATATTGATCGTTGGTGGAACCCAGCA
GTAGAAAATCAAGCAACCGATCGCGCGTTTCGTTTAGGACAAAAACGCAATGTTCAAGTACATAAA
TTTGTCTGTACAGGAACCCTAGAAGAAAAATTAACGAAATGTTAGAAAGTAAACAAAAATTAGCC
GAACAAACCGTTGACGCAGGGGAACAATGGTTGACAGAATTAGATACAGATCAACTGCGTAACCTC
TTATTATTGGATCGAGATACCATTATTGACGAACAATAA
```

SEQ ID NO: 38, Crocosphaera watsonii WH 8501 ctg336 Crowa_SNF2
translated polypeptide
```
MTILHGTWIENTSEKHFFIWGETWRSLSSDISSDDSILMYPFSVDKQGIIEQLNSNKIKIEKNKNI
ESVSQIFYLPSKFIAKSKQSIPLLSTELKDKDFEQGDIQLIAWKIEGIKLNVDDTINILSQLPLGL
TNNDENYIGDNLKFWTHIYRWSLDLLTRGKYLPQMEEQDNNCYGQWEPLLDSLVDQQRFSKFIQTM
PNSSLAYHNLMEGELSSSLLKQTTILDFLSTIINQQVRQFIDVAITPSSFIQKWLYSLTQDLSKFE
ASEVERKGLKNAINNWKSSLSEYIIKSDNQPLGINQFRVCFKLENPAKSGKKLEQSNWQLHYYLQA
LDDPNFLISAKVIWENPVTRLICNNRTINHPQETLLKGLGLASRLYYLIEESLQDNKPSFSELDPI
QVYEFLRSIANILKDNGLGVILPASLEQGVEEKRLGISLTAEVKSKKGQRLSLQSLLSYKLNLAIG
DKTISKKDFEKLLAQKSPLVEVKGEWIALQPADVKAAQQILNKSYDPLELSVEDALRFSTGDISTV
AKLPITNFEAKGELANLINAINNNESIPMIENPRGFKGQLRPYQQRGVGWLSFLEKWGLGACLADD
MGLGKTPQLIGFLLHLRSEGMLDQPTLVICPTSVLNNWEREVQKFAPTLSTLIHHGDKRSKGKAFV
```

FIGURE 10 (continued)

```
KAVSKKNVIITSYSLIYRDIKSFEQVEWQGIVLDEAQNIKNPQAKQSQAVRQISTQFRIALTGTPV
ENRLTELWSILDFLNPGFLGTQQFFRRRFATPIEKYGDKESLQIMRSLVRPFILRRLKTDKTIIQD
LPEKQEMTIFCGLSSEQGKLYQQLVDNSLVAIEEKTGIERKGLILSLLLKLKQICNHPAHFLKQKS
LKTAEQSGKLLRLEEMLEELIEEGDHALIFTQFSEWGKLLQPYLQKKFQQDVLFLYGATRRVQRQE
MIDRFQQDPNGPRIFILSLKAGGTGLNLTRANHVFHIDRWWNPAVENQATDRAFRLGQKRNVQVHK
FVCTGTLEEKINEMLESKQKLAEQTVDAGEQWLTELDTDQLRNLLLLDRDTIIDEQ
```

SEQ ID NO: 39, Gloeobacter violaceus PCC 7421 Glovi_SNF2 nucleic acid sequence

```
ATGGCTATCTTGCACGGTATCTGGGTTCACCAACCCCCCGGGCCGGGCTTTTCCTTTGGGGAGAA
ACCTGGAGGCAGGTCGCAAAGCGGCGCAAGCGCTCCGAAGCACCCGCTCCGCATCCCTATGTCCAG
CAACCGGCCGAGTTGTCCCCCCGCCTGGCTGCCCAGTTTCCCCAGATACCGCTCAGCTTGCTGGTA
CCCGAGACGCTTGCACTCCAGTTGCCCGCCACGGTCGAAAACGTGGTCTACTCCGCAAGCATTGCT
CCCGAGGGCAAGCTTTTGGAGTTGGAACCGTGGCTGGTGGAAGGTTTCTGGCTCGACGGTCACCAG
GCTTTTGAACTGTTGCTCGGGGTACCCCTGGGCGGCGGGGACGCATCGATTGGCGACGACCTGCGC
TTCTGGTCGCAGTGCGCCCGCTGGGTGCTTGACTTGCTGGTGCGCGCCAAGTACCTGCCCGACCTG
GAGAGCGGCGACGGCCAGGAAATCCCCACAGCCCGCTGGGTGCCCCTGCTCGACAGCGCCGTCGAT
CAAGCCCGCCTCAAAGAATTTGCCGCCCGTTTGCCGGGCGCCTGCCGCGCCGCTACCCCCGAACTA
TCTCCGCACCAGATTCTCAAGAGTTTCCTGAGCGCCATGCTCGACGCGCGGGTGCGCACGCTGCTC
GCTTGCGAGCCTCCCGATCCGCGCACGCTGCCTGCCGGAGCGGTGCGCCCCTGGCTTCTGGCCCTG
GCCCATGCCCAGCCCCAGCTCAAATCTCCGGACCCGGAGACGCCGGCTCTGGCGGAAGCCCTGGCC
ACCTGGCGCGCCCCCCTGAGCTATCAGGTTCGCTCGCGCACCTGCTTCCGTCTGCAGCCGCCCGAG
GAGAGCCAGGGCGAGTGGAAGCTGCACTTTCTATTGCAAACAGGCGACGATCCCGATTCGCTGATG
GCTGCCCAGCAAGTCTGGAGCAGCGCGGGTGAGCTGCAGGAGGTGTTTCTCGCGGGCTTGGGCCTC
GCCTCGCGTATCTTTGTGCCCGTCGAGCGGGGATTGCTCGTCCCCAGCCCACCTGCTGCACCATG
AGCACCGTCGAGGCGTTTCAGTTTCTCAAAGCCGCCACCTGGCGGTTGCGCGACAGCGGCTTCGGG
GTGTTGTTGCCCGAGAGCCTCGCGGACGCGGGCAGCCTGCGCAACCGCCTGGGCCTCAAACTCGAA
GCGAACGCGCCGGGGCGCAACGGTTCGGGCCTCGGCATGCAGAGCTTGCTCGCTTTTAAATGGGAG
CTGTCGCTCGCGGGCAAGACCCTGAGCCGCGCCGAGTTCGACCGCCTCGCCGCTAGTTCTGAACCC
CTGGTCAAAGTCAACGACAACTGGGTCGAATTGCGCCCCCAGGACGTGCGCGCCGCCCACAGCTTT
TTGCAGTCGCGCAAAGATCAGGTCGGACTCTCGTTGGAGGATGTGCTGCGCCTCAACTTCGGCGAC
ACCCCCAAAATCGACGGTCTCCCCATCGTCAACTTCGACAGCTCCGGCCCCATTCAGCAACTGCTG
GAGACCCTCACCGATCAGCGCAAACTCACCCCCATCGACGAACCGCCGGGGTTCAAGGGCACCCTG
CGGCCCTATCAAAAAATTGGCGTCGGCTGGCTCGCCTTTTTGCAGAAGTGGGGCCTGGGTGCTTGC
CTAGCCGACGACATGGGACTCGGGAAGACCGTAGAGTTGATAGCATTTCTTCTTTTTCTCAAATCC
AAAAATGAGCTGGACGGCCCTATATTGTTAATTTGTCCGACTTCAGTGATGGGAAACTGGAAAGA
GAAATAAAGAAATTTTCTCCTAGTTTATCTGTACATGTCCATCATGGGGCGCGGCGGCCGAAGGGG
CGCAATTTTGTCGAGACGGCCCAGAAAAAGCAAATCATCGTCAGCAGCTACGCCCTGGTACAGCGC
GACAGCAAAGATCTCAAGCGCGTCGAATGGTTGGGCCTGGTGCTCGACGAAGCCCAGAACATCAAA
AACCCCGACGCCAAGCAGACCCAGTCGATTCGGGAACTGACAGCGCGCTTTCGCATCGCCCTCACC
GGCACACCGGTCGAGAATCGCCTCGCGGAACTGTGGTCGATCCTCGATTTTCTCAATCCCGGCTAT
CTGGGGGCGCGCAACTTCTTTCAGCGCCGCTTCGCAGTTCCGATCGAAAAGTACGGGGATCGCTCC
TCGGCGAACGCCCTCAAAGCTCTGGTGCAGCCGTTTATCCTGCGGCGGCTCAAATCCGACCCGCAG
ATTATTCAAGATCTGCCCGAGAAGCAGGAGACGAATGTCTTCTGTCCGCTCACACCCGAGCAGGCG
GCCCTCTACGAGCGGGTGGTGAACGAATCGCTCGCCAAGATCGAGCAGAGCACCGGCATCCAGCGG
CGCGGGACGGTGCTGGCCACCTTGGTCAAACTCAAGCAGATCTGCAACCACCCGAGCCACTACCTG
GGTGACGACGGACCGCTCGCCAACCGCTCGGGCAAACTCAGCCGCCTGGGCGAGATGCTCGAAGAA
GTGCTCGCCGACGAGGAGCGGGCGCTGATTTTACCCAGTTCGCCGAGTGGGGCCACCTGCTGCAG
```

FIGURE 10 (continued)

```
GCGCACCTGAGCCGCCAGTTGGGTTCAGAAGTGTTTTTCCTCTACGGCGGCACCAGCAAAAACCAG
CGCGAGGCGATGATCGAGCGCTTCCAGAGCGATCCGCAGGGGCCGCGGATTTTTATTCTTTCGCTG
AAGGCAGGGGGTGTCGGCCTCAACCTCACCCGCGCCAACCACGTCTTCCACTTCGACCGCTGGTGG
AACCCGGCGGTCGAGAATCAGGCCACCGACCGCGTCTTCCGCATCGGCCAAACCAAGAACGTACAA
GTCTACAAGTACGTGTGCACCGGCACGCTCGAAGAGCGCATCAACGCCCTGATCGAAAGCAAAAAG
GCCCTGGCTGAGCAGGTGGTGAGCGCCGGTGAGAACTGGCTGTCGGATCTAAATACCGATCAACTG
CGGCAACTGTTGGTACTCGATCGCTCGGAGATTATCGACACGGAGGACACCGCGTGA
```

SEQ ID NO: 40, Gloeobacter violaceus PCC 7421 Glovi_SNF2 translated polypeptide

```
MAILHGIWVHQPPRAGLFLWGETWRQVAKRRKRSEAPAPHPYVQQPAELSPRLAAQFPQIPLSLLV
PETLALQLPATVENVVYSASIAPEGKLLELEPWLVEGFWLDGHQAFELLLGVPLGGGDASIGDDLR
FWSQCARWVLDLLVRAKYLPDLESGDGQEIPTARWVPLLDSAVDQARLKEFAARLPGACRAATPEL
SPHQILKSFLSAMLDARVRTLLACEPPDPRTLPAGAVRPWLLALAHAQPQLKSPDPETPALAEALA
TWRAPLSYQVRSRTCFRLQPPEESQGEWKLHFLLQTGDDPDSLMAAQQVWSSAGELQEVFLAGLGL
ASRIFVPVERGLLVPQPTCCTMSTVEAFQFLKAATWRLRDSGFGVLLPESLADAGSLRNRLGLKLE
ANAPGRNGSGLGMQSLLAFKWELSLAGKTLSRAEFDRLAASSEPLVKVNDNWVELRPQDVRAAHSF
LQSRKDQVGLSLEDVLRLNFGDTPKIDGLPIVNFDSSGPIQQLLETLTDQRKLTPIDEPPGFKGTL
RPYQKIGVGWLAFLQKWGLGACLADDMGLGKTVELIAFLLFLKSKNELDGPILLICPTSVMGNWER
EIKKFSPSLSVHVHHGARRPKGRNFVETAQKKQIIVSSYALVQRDSKDLKRVEWLGLVLDEAQNIK
NPDAKQTQSIRELTARFRIALTGTPVENRLAELWSILDFLNPGYLGARNFFQRRFAVPIEKYGDRS
SANALKALVQPFILRRLKSDPQIIQDLPEKQETNVFCPLTPEQAALYERVVNESLAKIEQSTGIQR
RGTVLATLVKLKQICNHPSHYLGDDGPLANRSGKLSRLGEMLEEVLADEERALIFTQFAEWGHLLQ
AHLSRQLGSEVFFLYGGTSKNQREAMIERFQSDPQGPRIFILSLKAGGVGLNLTRANHVFHFDRWW
NPAVENQATDRVFRIGQTKNVQVYKYVCTGTLEERINALIESKKALAEQVVSAGENWLSDLNTDQL
RQLLVLDRSEIIDTEDTA
```

SEQ ID NO: 41, Lyngbya sp. PCC 8106 Lyn_sp_SNF2 nucleic acid sequence

```
ATGGCAATTTTACACGGAAGTTGGCTCCAGCACCCCAAAAATTATTTGTTTATTTGGGGAGAAACC
TGGCGTCGCATTACACCCAATGAATTTAATCCGGCTGATGGTGTTTTGGGTTATCCTTTTGCTTTA
AGCCCTGTTGAATTGGAAAAGTGGTGCAGTGAAAAGCAGTTATCTATAGAGAGTAAAGTTGTCGTT
ACAGAAACTCTCGCCCTTCCCACTAAACTCTCCCCAAAAATAGGACTATATCCCCTTCAATCTACG
CCTCAAACTGATTCTGAAACTGATTCTGAGTCGATCTGTCTTTATCCCTGGAAAATTGAAGGTATT
TGTCTCAACAGTACAGAAGCCTTTGACTTTTTACAATCCCTTCCTCTGGGAAACCTGACCACAGAA
AACTCATTTATTGGCTCAGATTTACAGTTTTGGTCTCATCTTTCCCGTTGGAGTTTAGACTTACTC
GCCCGGAGTAAATTTTTACCCAGTCTCACTTTTAACCCCTCAAAAGATCACTTTATCGCTGAATGG
AAACCTTTACTCGATAGTGCGACAGATCAAGCCAGATTAATTCGTTTTTCTAAACAAATACCCTCT
GCTTGTCGGATCTATCAACTCTGGTCAAAAGAGGCTCAAAATCAATTTGAAAATTTAGCCCTAGAT
TTACCTCAAAATCCCCAAAACTTAATTGATGATTTTTAACGGCAATTATTGATAGTCAAGTCAAG
AAAGTTGCAGAAGAAAGTGAAAAAAAGCGATTACAAATCTAACCGCTATTCAACCGATTGTTCAG
AGTTGGTTACACGCTTTAGCCAGTGAATCTAATCTAGCAAAATCCAAAAAATCTGAATCAAAAACC
CTAGAAAAAATTCTTTCCAATTGGACGGCTCCTCTTCAACAAACTCTCGCTGAACATAATTTGTTT
AGAACGGGATTTCGACTCTCTCCTCCGGAAAATAATCAAAAAAATTGGACGCTAGATTATTGTTTA
CAAGCAATTGATGAACCCGAATTTTAGTGGATGCTCAAACTATTTGGACTCATCCAGTCGAAGCC
TTTGTTCACAATGGACGTATGATTAAACGTCCTCAAGAAACCCTCCTCAAAGGTTTAGGTTTAGCC
TCAAAACTATATCCTCTCCTAGAACCCAGTTTACAAGAAGCCCGTCCTCAAACTTGCTTATTAACG
CCCCTACAAGCCTATGAATTTATTAAAAGTATTAATTGGCGGTTTACAGATAGCGGTTTAGGAGTG
```

```
ATTTTACCCCCGAGTTTAGTCAGTCAAAATGGATGGGCGAACCGTTTAGGTTTAAGTGTTCAAGCG
GCGACATCAAAATCCAAACAAAATGTTAGCTTGGGATTAGATAGTCTGCTGAATTTTAAATGGGAA
TTGTCAATTGGGGGTCAAACCTTATCAAAAACAGAATTTAACCGTTTAGTCGCTCAAGAAAGTCCG
TTAGTTGAAATTAATGGCGAATGGGTGGAATTACGTCCTACTGATATTAAAGCCGCTAAAGCCTTC
TTTTCGAGTCGCAAAGATCAACTTTCACTTACCCTTGAAGATGCTTTACGTTTATCGACGGGTGAC
TCGCAAATGGTGGAAAAGTTACCGATTGTTAACTTTGAAGCGGGTGGAAAATTAGAAGAACTTCTC
AATACTTTAACGAATAACCGTTCGCTCGATGAGATCAAAACTCCTAGTAATTTTCAAGGAGAACTA
CGCCCCTATCAAGCCCGAGGGGTGAGTTGGTTAGCCTTTTTAGAAGAATGGGGTTTAGGGGCTTGT
TTAGCTGATGATATGGGGCTAGGAAAAACCATAGAATTAATTGCTTTTCTCTTGTATTTGCAGGAA
AAAGAAACCTTAGACGCTCCTGTTTTACTGGTTTGTCCGACATCAGTTTTAGGAAACTGGGAACGA
GAAGTTAAACGATTTAGTCCGAGTTTAAAAGTTACTGTTCATCACGGGGATAAACGCCAGAAAGGG
AAAAACTTTGCTCAATTTGCCCAGAAATATAATTTAATTATTACCAGTTATCCGTTAACTTTTCGA
GATGAGAAAGAACTCAAAACGGTAAATTGGAAAGGATTAGTTTTAGACGAAGCTCAAAATATTAAA
AATCCCGAGGCTAAACAATCAAAAACGGTGAGAAATCTACAGGCGAGTTTTAAAATTGCTCTGACT
GGAACACCTGTCGAAAACCGTCTGTCTGAATTATGGTCAATTATGGATTTTCTCAACCCAGGTTAT
TTAGGACAGCGACAATTTTTTCAGCGAAGATTTGCTATTCCGATTGAAAAATACGGCGATACAGAC
TCCTTAAAAACATTGCGATCTTTGGTTCAACCGTTTATTTTACGGCGCTTAAAAACAGATAGAGAG
ATTATCCAAGACTTACCCGAAAAACAGGAAAATACGATCTTTTGTTCTCTGTCTACAGAACAAGCA
ACGCTTTATCAAAAGATTGTTGATCAGTCTTTAGCTGACATAGACTCAGCCGCAGGAATTCAACGT
CGAGGGATGATTTTAGCGTTGTTAGTGAAATTAAAACAGGTTTGTAATCATCCCATTTTATTGAAT
GGAAAAGCGACAAAAACTGGAAAGAAAAAGGTCGAGACTCAGGGTTTAAGCCTGCAAAGTTCAGGG
AAGTTACAACGCTTCAAAGAAATGCTGGAAGAATTGTTGTCAGAAGGAGATCGCGCCATTGTATTT
ACCCAGTTTGCAGAATGGGGAAAAGTTTTACAACCTTATTTAGAACAGCAATTAAACCGAGAGGTA
TTATTTTTGTATGGCGCAACTCGTAAAAATAAACGAGAAGAAATGATTGATCGTTTTCAACAAGAT
CCTCAAGGGCCACCGATTTTTATTCTATCTTTAAAAGCGGGAGGTGTGGGTTTAAATTTGACTCGT
GCTAATCATGTTTTTCACTTTGATCGTTGGTGGAACCCTGCGGTTGAAAATCAAGCAACAGATCGG
GTGTTTAGAATTGGTCAAACGCGCAATGTTCAGGTTCATAAGTTTGTCTGTACCGGAACGTTGGAA
GAAAAAATCCATGATTTAATTGAAAGTAAAAAAGTGTTGGCTGAACAAGTTGTGGGTTCAGGAGAA
AATTGGTTAACTGAATTGGATACGGATCAACTCAGAAACTTACTCATTATTGACCGAAATGCGGTG
ATTGATGAAGAAGAATAA
```

SEQ ID NO: 42, Lyngbya sp. PCC 8106 Lyn_sp_SNF2 translated
polypeptide
```
MAILHGSWLQHPKNYLFIWGETWRRITPNEFNPADGVLGYPFALSPVELEKWCSEKQLSIESKVVV
TETLALPTKLSPKIGLYPLQSTPQTDSETDSESICLYPWKIEGICLNSTEAFDFLQSLPLGNLTTE
NSFIGSDLQFWSHLSRWSLDLLARSKFLPSLTFNPSKDHFIAEWKPLLDSATDQARLIRFSKQIPS
ACRIYQLWSKEAQNQFENLALDLPQNPQNLIDDFLTAIIDSQVKKVAEESEKKAITNLTAIQPIVQ
SWLHALASESNLAKSKKSESKTLEKILSNWTAPLQQTLAEHNLFRTGFRLSPPENNQKNWTLDYCL
QAIDEPEFLVDAQTIWTHPVEAFVHNGRMIKRPQETLLKGLGLASKLYPLLEPSLQEARPQTCLLT
PLQAYEFIKSINWRFTDSGLGVILPPSLVSQNGWANRLGLSVQAATSKSKQNVSLGLDSLLNFKWE
LSIGGQTLSKTEFNRLVAQESPLVEINGEWVELRPTDIKAAKAFFSSRKDQLSLTLEDALRLSTGD
SQMVEKLPIVNFEAGGKLEELLNTLTNNRSLDEIKTPSNFQGELRPYQARGVSWLAFLEEWGLGAC
LADDMGLGKTIELIAFLLYLQEKETLDAPVLLVCPTSVLGNWEREVKRFSPSLKVTVHHGDKRQKG
KNFAQFAQKYNLIITSYPLTFRDEKELKTVNWKGLVLDEAQNIKNPEAKQSKTVRNLQASFKIALT
GTPVENRLSELWSIMDFLNPGYLGQRQFFQRRFAIPIEKYGDTDSLKTLRSLVQPFILRRLKTDRE
IIQDLPEKQENTIFCSLSTEQATLYQKIVDQSLADIDSAAGIQRRGMILALLVKLKQVCNHPILLN
GKATKTGKKKVETQGLSLQSSGKLQRFKEMLEELLSEGDRAIVFTQFAEWGKVLQPYLEQQLNREV
LFLYGATRKNKREEMIDRFQQDPQGPPIFILSLKAGGVGLNLTRANHVFHFDRWWNPAVENQATDR
VFRIGQTRNVQVHKFVCTGTLEEKIHDLIESKKVLAEQVVGSGENWLTELDTDQLRNLLIIDRNAV
IDEEE
```

FIGURE 10 (continued)

SEQ ID NO: 43, Methanosarcina acetivorans C2A Metac_C2A_SNF2 nucleic acid sequence

ATGATAATTTTGCATGCAGGAAGAGTCGGAAAACAGTTCTTTCTGTGGGGCGAAAGCCCGGCTGAA
AATGAAACTCCGCCTGTCCGGCGCGGGAGAAAGCCTAAGAAGCCGGTTGCAAAACCTTATCCTTAC
GATTCGGGTGTTGAAAACCTGTCTTCTGCTCTTGAGCTGCTGCTGGGCAGTACTGGCCGGAAAAAG
GCAGAGGAAATCAATGTCTGGATCCCGACAGCAGGCTGGAATCCAATCCCCTCCAGTCCTCTCGTT
GCTGAAATTCCGGCTTCGAAAGCAGAACTTTCCCTAGCTCCCTGGACTGTTCACGCATATCCTCTG
GAAGCTGAAGAAGCTATTGTTCTCCTCTGCGCCTGTATGGGAAAAAAGGTTCTTGCTCCCGGCATA
ATCTCGGGAAATGATCTTCTCTGGTGGGCGGATGCCCTGAAATTTGCAGGCTCGCTGGTAGCAGGA
CAGAAATACCTGCCTGGCGTCAGGGCGGGGAAGGAGAGTACAAGGCTTTCTGGGAACCCGTATTT
TCCGGAGAAGATGCGGGGGAGCTGGCAAGACTTGCAAAGCAAATGCCTCCGGCTGCAAAGGCTCTT
GCTCTTGAAACCTCTTCCGTGCAGCCGGAAATACTTGCTGCTGTAGCGGCAAGGCAGTTTATCGAA
GAGGCTCTTGACTGGATAGTCCGGTCCGAGATCGGGGAAAAAGAGCTTGCAAAAGAGGCGCGTAAA
AGAAAATCCTTTGATAGCGTCCATGACGCCTGGGTTTCCGCTCTTAAAAGCCCTGACGGGTTGATC
CACGGAGAAGAAAAGAACTCCTGCAGCTTGCGTTCCGGACCCGTGAATGGCAGCGCCCCCTTACT
GTACTTACAACTTCTCCCTTCAGGTTCTGTTTCCGGCTTGAAGAGCCAGCTGCGGAAGAAGAACTC
GAAGAAACCGAGGAATCCGAAGCCGGAAAAATGGATACTAAAAAAGGCAGGAAAGGGATAGCTGAC
ATAGAAGTTCCCGAAGAACTCTGGTACGTCCGCTATATGCTTCAGTCCTACGAAGACCCAAGCCTT
CTGATTCCTGTAAAAGAGGCCTGGAAACCAAAGAAGGGCAGCCCGTTGAAAAGATATGATGTAAAA
AACATTCGCCAATTTCTGTTATCTTCCCTTGGACAGGCTGCTGGCATCAGTGCAGGAATTGCTTCC
AGCCTTGAAGCTCCCAACCCGTCCGGATATTCCCTTGATACGAAAGAAGCTTACCGCTTCCTGACT
GAAAGTGCAGCGGATTTAAGCCAGGCGGGCTTCGGGTTACTTCTCCCCGGCTGGTGGACCCGTAAA
GGTACAAAGACCCACTTAAAAGCCCAGGCTAATGTTAAGGGCAAGAAGTTGAAGGCCGGATACGGG
CTTACACTCGATAAAATCGTCAGCTTTGACTGGGAAATTGCCCTTGGAGACCGTGCACTCACAGTC
AGGGAACTGCAGGCTCTTGCAAAGCTCAAAGCTCCGCTTGTGAAATTCCGCGGGCAGTGGGTCGAG
GTCAACGATGCGGAAATCCGGGCTGCCCTTGAGTTCTGGAAGAAAAACCCCCACGGGGAAGCAAGT
CTGCGCGAAGTTCTAAAACTGGCTGTGGGAGTCTCCGAAAAAGCCGATGGTGTAGACGTTGAAGGG
CTTAATGCAGCCGGCTGGATCGAAGAATTAATCCGCCGCCTGAAGGACAAAACCGGGTTTGAAGAA
CTTCCGGCTCCTGACGGTTTTTCAGGCACCCTCAGGCCCTACCAGTTCAGAGGTTACTCCTGGCTG
GCTTTCCTGAGGCAGTGGGGCATAGGAGCCTGCCTTGCAGACGACATGGGGCTTGGTAAAACCATC
CAGACCCTTGCCCTTATCCAGCACGACCTGGAACAGGTTAAAGGGCAGGTTGAAGAAAAGGTTATA
GAAAATGCTGAAGAAAAGTTGAAGGACTTAAAGCTGCAAAACCGGTTCTTCTGGTCTGTCCGACC
TCTGTCATCAACAACTGGAAAAAAGAGGCGGCTCGCTTTACCCCGGAACTTTCGGTAATGGTCCAC
CACGGGACCAGCCGGAAAAAGGAAGAGGAATTCAAAAAGGAAGCCACGAATCATTCTATTGTCGTC
TCAAGCTACGGGCTTTTGCAGCGGGATCTTAAGTTTTTAAAAGGGGTTTCCTGGGCCGGAGTGGTA
CTTGACGAAGCCCAGAATATCAAAAACCCGGAAACCAAACAGGCAAAGGCAGCCAGAGCTCTTGAA
GCCGATTACCGCATAGCTCTTACGGGGACTCCGGTTGAAAACAACGTGGGAGACCTCTGGTCTATC
ATGGAGTTTTTAAACCCCGGCTTCCTAGGCAACCAGGCAGGTTTCAAGCGGAATTTCTTTATTCCC
ATTCAGGCCGAAAGGGATCAGGAAGCTGCAAGGAGGTTAAAAGAAATTACGGGCCCCTTTATCCTG
CGCCGTCTGAAGACCGATACTTCGATTATCTCCGACCTGCCGGAAAAGATGGAAATGAAAACCTAT
TGTACGCTGACAAAAGAACAGGCTTCCCTCTATGCCGCAGTCCTCGAAGACATCGAAGAGACGATG
GAAGAGGCTGAAGAAGGCATCCAGAGAAAAGGTATAATCCTGTCCGCCCTTACCAGGCTCAAACAG
GTCTGCAACCATCCGGCGCAGTTTTTGAAGGATAACTCTGCTGTACCCGGCAGGTCAGGAAAACTT
GCAAGGCTTACCGAAATGCTGGATGTAATCCTGGAAAATGGGGAAAAAGCCCTTGTGTTCACCCAG
TTTGCGGAGATGGGAAAAATGCTAAAAGAACACCTGCAGGCAAGTTTTGGCTGTGAAGTCCTTTTC
CTGCACGGCGGGGTCCCCAGAAAGCAGAGGGATCGGATGCTTGAGCGTTTCCAGGAGGGAAAAGAA
TACCTCCCTATCTTTGTCCTCTCCCTTAAAGCTGGAGGCACGGGGCTTAACCTTACAGGAGCGAAC
CACGTTTTCCATTTTGACCGCTGGTGGAACCCTGCTGTTGAAAACCAGGCTACGGACAGGGCTTTC

FIGURE 10 (continued)

CGTATAGGCCAGACGAAAAATGTAGAGGTGCATAAGTTCATCTGTGCGGGTACGCTTGAAGAAAAA
ATCGATGAGATTATCGAGCGCAAAGTGCAGGTTGCAGAGAACGTTGTCGGAACAGGTGAAGGTTGG
CTGACAGAACTTTCCAACGAGGAATTGAAGGATATTCTTGCTCTCCGAGAAGAAGCGGTAGGTGAA
TAA

SEQ ID NO: 44, Methanosarcina acetivorans C2A Metac_C2A_SNF2 translated polypeptide MIILHAGRVGKQFFLWGESPAENETPPVRRGRKPKKPVAKPYPYDSGVENLSSALELLLGSTGRKK
AEEINVWIPTAGWNPIPSSPLVAEIPASKAELSLAPWTVHAYPLEAEEAIVLLCACMGKKVLAPGI
ISGNDLLWWADALKFAGSLVAGQKYLPGVRGGEGEYKAFWEPVFSGEDAGELARLAKQMPPAAKAL
ALETSSVQPEILAAVAARQFIEEALDWIVRSEIGEKELAKEARKRKSFDSVHDAWVSALKSPDGLI
HGEEKELLQLAFRTREWQRPLTVLTTSPFRFCFRLEEPAAEEELEETEESEAGKMDTKKGRKGIAD
IEVPEELWYVRYMLQSYEDPSLLIPVKEAWKPKKGSPLKRYDVKNIRQFLLSSLGQAAGISAGIAS
SLEAPNPSGYSLDTKEAYRFLTESAADLSQAGFGLLLPGWWTRKGTKTHLKAQANVKGKKLKAGYG
LTLDKIVSFDWEIALGDRALTVRELQALAKLKAPLVKFRGQWVEVNDAEIRAALEFWKKNPHGEAS
LREVLKLAVGVSEKADGVDVEGLNAAGWIEELIRRLKDKTGFEELPAPDGFSGTLRPYQFRGYSWL
AFLRQWGIGACLADDMGLGKTIQTLALIQHDLEQVKGQVEEKVIENAEEKVEGLKAAKPVLLVCPT
SVINNWKKEAARFTPELSVMVHHGTSRKKEEEFKKEATNHSIVVSSYGLLQRDLKFLKGVSWAGVV
LDEAQNIKNPETKQAKAARALEADYRIALTGTPVENNVGDLWSIMEFLNPGFLGNQAGFKRNFFIP
IQAERDQEAARRLKEITGPFILRRLKTDTSIISDLPEKMEMKTYCTLTKEQASLYAAVLEDIEETM
EEAEEGIQRKGIILSALTRLKQVCNHPAQFLKDNSAVPGRSGKLARLTEMLDVILENGEKALVFTQ
FAEMGKMLKEHLQASFGCEVLFLHGGVPRKQRDRMLERFQEGKEYLPIFVLSLKAGGTGLNLTGAN
HVFHFDRWWNPAVENQATDRAFRIGQTKNVEVHKFICAGTLEEKIDEIIERKVQVAENVVGTGEGW
LTELSNEELKDILALREEAVGE SEQ ID NO: 45, Methanospirillum hungatei JF-1 Methu_JF-1_SNF2 nucleic acid sequence GTGACCGCGAAACGACCAGCACCAATCCACGATAAAGAAGAAGAGACCATACCCGATACTTCGCTT
CCGGTCTTTCATGCCCTGATTTACCCGGCCGTTGAAGGGGTAGCGATATGTGCCGAATATATAACT
GATAAACCTGCACCGGTCAGGAAAAAGGCTACGCAAAGGATAAACCTGGCGAATATCCATATTCC
CTGGATCATACCGCCCTTAAAACGCTCATAGAGAACTGTTTTGGAGCATATGATGACCTGAAGGCT
ACCAGATGGATTATCTATCTCCCCGCTGAAGAAACGGTTCCTCCTTCCTCTCAGTTCTCATCAAAA
AAGAAGCCATCACCAAAGGAGAAAAAACTCCCCCTTGTTCCGATGTATATCCCCGTTCTTCTCTGC
CCGTATGAAACCTTTTTTCAAATCTGGAAAGCCGCTCAGAATACAGATAAAAATTATATTGCTGGC
GATTCCTTCCAGTACATCTCCATTCTGATGGAGAGTACCGTCCGGCTCATACAAAACGGACGGTTC
AAACCATCTCTAGAACGGACCTTTGCCGGATATCATGCCGTATGGGTACCTGCCCTTTCTCCTCAG
GATATGGAATGGGTATCAGATTTTTCAAGCCGGATGCCAACGGTCTGCAAGTACGCTATCCCCCGG
GTCGCAAAAGATCCCTACATTTATAAACCTGAGACCAGATTAGAGAAATTCATCGTTGAGATGATG
CGGGTGATCATCCGTACTGCCCTTGGTGGTTATACACTGAAAGAAGAGACAGATCCCTTTTATGAA
CCCTCAGAAAACGAGATGCAGTTCATGACTGACCTTCTCGGGGTAACCGACCCAATAAGGAACAAA
GGATTTGAGAGAACTTTCTTACGGGCGATGCAGGACTGGCTGACCTTCTCAAGTTCAGGACGGTTT
GCTCCCTTTGAGTTCTGCATGATCATAAAAGATCCACCAGAAGGACAGACAGAACCATGGGATTTC
ACTCTCGCGGTCAGATCAGAGGCAGAACCATCTCTTCTCATCCCGGCAGAAATAATCTGGGAATTG
CCTGATCACCAGAGCGGGCTCTTCCCCCAGGCAGCCTATCTCAAACATATCCTCCTTGCTGGTATC
GGGCTCTTGACCTCATCATCATCGGCATTATGGCGTCCCCTGTCCGGATCGAAACCCACCGGGGGA
AGTATGACCCTGAAAGAGGCTGCAACGTTCTTGGGTTCAGACCTCGCAAGAGCCAGGAGGAAGGGA
GTAACGGTGCTCCTGCCAGACTGGTGGACTGATACGACCTATACACCACGGGTTGAAATCCATGCA
AGGCGGCGGGATCCCACCCATACGCAGACACGGATAGGACTGCAGGAACTCCTTTCTTTTGATTAC

FIGURE 10 (continued)

```
CGGATTGCAATCGGTGATGAGTCATTTTCACCGGATGAGTTCTGGGAAAAGGTAAAAGAAAAGGCT
CCCTTTATCTGGCTGGGGAACCGGTGGATATCCTTTCATCCGGATGCGATACAACATGCCCTGGAT
TCTTTCAGCAGGCATCAGAGCAAAGGAGGGGATACAATAGGAGATCTGCTCCGGCTCTCCCTGAAA
AAAATGGAGGATTCCGCGGTACCGGTATCGATTCATGCAAAAGATGACTGGGTTGCGGATCTTCTG
GATTTTTTCAGGACCGAAACAAATCAGGCAGTTCCAGTCCCAAAGAAATTTAAAGGGATACTCAGG
CCATACCAGGAAGAGGGGTTCTCCTTCCTTTGTCAATGTACCAGAAGGGGCTTTGGAGCCTGCCTT
GCAGATGACATGGGGCTTGGAAAAACTCCCCAGACACTTGCATGGCTGGTCTATCTCAAGGAGAAA
GAAAAACCCACGACTCCGTCCCTCCTTATATGCCCGATGTCGGTTGTTGGGAACTGGGAGCGGGAG
ATACAGCGGTTTGCGCCATCACTCCGTTCATGGGTGCATCATGGGACTGACCGATGCAAAGGCGAT
GATTTTGTGAGACATGTCGGTTCATATGACCTGGTCCTGACCACCTATCATCTGGCAGCACGGGAC
GTAGACCACCTCAAAACCGTTCCCTGGTCTGCAATCATTCTTGACGAGGCACAAAATATCAAGAAC
CTCCATGCAAACCAGACCGTAGCAGTCAAATCTCTCACCGGTGAGAGACGGGTTGCTCTGACCGGA
ACCCCGGTGGAGAACCGGTTACTCGAACTCTGGTCTATCATGGACTTTTTAAATCCAGGATACCTT
GGTTCACAGAGTGCATTTACAAACCGCTATTCCGCCCGATTGAGCAGGAAAAAAATACGGAACTG
ATACAGGAATTAAGGTCCCTCATCCGTCCGTTCCTGCTCAGGCGGATGAAAACAGACAAGCATGTT
ATCGATGATCTTCCGGAAAAGATGGAGAACCGGGTATATTGCACCCTCACACCCGAACAGGCAACC
TTATATCAGGCTGTTGTGCTTGATATGGCAAAGAACCTTGATAAAGTGGAGGGTATTGCCAGGAAA
GGGGCAATCCTTGCTGCGATCACACGACTGAAACAGATCTGTAACCATCCGGGACGTGTTGGCAGG
GATAAAACAATAAAGGCTGAGCGGTCCGGGAAGGTGAGCCGGCTGCTTGAGATGATTGAGGAGATC
ACTTCCGAAGGGGACTCAGCACTCATATTCAGTCAGTATGCAACATTTGCTGAGGAACTGGCAGGG
ATGATAGAGAAACAGGGAGATACGCCCGTTCTTCTCCTGACCGGGTCAACACCACGGAAAAAACGG
GAACAGATGATAGAGGAGTTTCAGGCCTCAACCACCCCGATAATCTTTGTTATTTCTCTGAAAGCC
GGGGGAACGGGTCTGAACCTGACGAAAGCGACTCATGTGTTTCATGTAGACCGGTGGTGGAATCCG
GCGGTTGAAGACCAGGCTACTGACCGGACGTACCGGATCGGACAAAAGAGAAATGTCCAAGTTCAC
CTGATGATAACCGCCGGAACCCTGGAGGAACGGATAGATCTGATAAACCAGGAGAAACGGACGCTT
GCAAAGGAAGTCCTTGCACAGAGTGATGAGTATCTGACAAATCTCTCAACAAAAGAACTTCTGGAG
ATTGTATCACTTCGTGACAGTCTCTTTCGCGGGGAGGATGCATGA
```

SEQ ID NO: 46, Methanospirillum hungatei JF-1 Methu_JF-1_SNF2 translated polypeptide

VTAKRPAPIHDKEEETIPDTSLPVFHALIYPAVEGVAICAEYITDKPAPVRKKGYAKDKPGEYPYS
LDHTALKTLIENCFGAYDDLKATRWIIYLPAEETVPPSSQFSSKKKPSPKEKKLPLVPMYIPVLLC
PYETFFQIWKAAQNTDKNYIAGDSFQYISILMESTVRLIQNGRFKPSLERTFAGYHAVWVPALSPQ
DMEWVSDFSSRMPTVCKYAIPRVAKDPYIYKPETRLEKFIVEMMRVIIRTALGGYTLKEETDPFYE
PSENEMQFMTDLLGVTDPIRNKGFERTFLRAMQDWLTFSSSGRFAPFEFCMIIKDPPEGQTEPWDF
TLAVRSEAEPSLLIPAEIIWELPDHQSGLFPQAAYLKHILLAGIGLLTSSSSALWRPLSGSKPTGG
SMTLKEAATFLGSDLARARRKGVTVLLPDWWTDTTYTPRVEIHARRRDPTHQTRIGLQELLSFDY
RIAIGDESFSPDEFWEKVKEKAPFIWLGNRWISFHPDAIQHALDSFSRHQSKGGDTIGDLLRLSLK
KMEDSAVPVSIHAKDDWVADLLDFFRTETNQAVPVPKKFKGILRPYQEEGFSFLCQCTRRGFGACL
ADDMGLGKTPQTLAWLVYLKEKEKPTTPSLLICPMSVVGNWEREIQRFAPSLRSWVHHGTDRCKGD
DFVRHVGSYDLVLTTYHLAARDVDHLKTVPWSAIILDEAQNIKNLHANQTVAVKSLTGERRVALTG
TPVENRLLELWSIMDFLNPGYLGSQSAFTNRYSRPIEQEKNTELIQELRSLIRPFLLRRMKTDKHV
IDDLPEKMENRVYCTLTPEQATLYQAVVLDMAKNLDKVEGIARKGAILAAITRLKQICNHPGRVGR
DKTIKAERSGKVSRLLEMIEEITSEGDSALIFSQYATFAEELAGMIEKQGDTPVLLLTGSTPRKKR
EQMIEEFQASTTPIIFVISLKAGGTGLNLTKATHVFHVDRWWNPAVEDQATDRTYRIGQKRNVQVH
LMITAGTLEERIDLINQEKRTLAKEVLAQSDEYLTNLSTKELLEIVSLRDSLFRGEDA

FIGURE 10 (continued)

SEQ ID NO: 47, Methanosarcina mazei Goe1 Metma_Go1_SNF2 nucleic acid sequence
ATGATAATTCTTCATGCAGGAAGAGTTGGAAAACAGTTCTTCTTATGGGGTGAAAGCCCGGCAGAA
AATGAAACTCCGGTTGTTCGGCGCGGGAGAAAGCCTAAAACCCCTATCGTAAAACCTTACCCTTAC
GATTCGGGCTTTGAAAACCTGTCTTCTGCCCTTGAGCTGCTGCTGGGCAGTACTGACCGGAAAAAG
GCGGAGAAAATCAACGTCTGGACCCCAACTATCGGAGGAATCCTGTCCCTTCCAGCCCTCTTGTT
GCTGAAATTTCGGATTCGAAAGCAGAACCTGCACTGGCTCCCTGTACTGTTCACGCATATCCTCTG
GAAGCTGAAGAAGCTATTGTTCTCCTCTGCACCTGTATGGAAAAAAGGTTCTGGCTCCCGGTATC
ATCTCGGGAAATGACCTTCTCTGGTGGGCAGATGCCCTGAAATTTGCAGGCTCGCTGGTAGCAGGG
CAGAAATATTTGCCTGGCGTCAGGGGCGGGGAAGGAGAGTACAGGGCTTTCTGGGAACCCGTATTT
TCCGGCGAAGATGCCGGAAAGCTGGCAAAACTTGCAAAGCAAATGCCTCCTGCTGCAAGGGCTCTT
GCTCCTGAAGCCTCTTCCATGCCGCCGGAAATGCCTGCTGCTTTAGCGGCAAAGCAGTTTATTGAA
GACTCTCTCGACTGGATAGTCCGGTCCAGATCGGGGAAAAAAAGCTTGCAAAAGAGACGCGCAAA
AGAAAATCCTTTGATAGCGTCCATGATGCCTGGGTTTCTGCTCTTAGAAGCCCTGAAGGGCTGATC
TATGGAGACGAAAACGAACTTCTGCAGCTTGCGGCCCGGACCCGCGAATGGCAGCGCCCACTCACC
ATCCTTACCACTTCTCCTTTCAGGTTCTGTTTCCGTCTTGAAGAACCGGCTTTAGAAGAAGAGATC
GAAGAAACTGAAGAAACCGAAGAAATAGAAGAAAATGAAGCCGGGAAAAGAGATACTAAAAAAGGC
AGGGAAGGGATAGCTGATATAGAAGTTCCCGAAGGGCTCTGGTACGTCCGTTATATGCTTCAGTCC
TACGAAGACCCGAGCCTTCTGATCCCTGTAAAAGAAGCCTGGAAGCCAAAAAAGGCAGCCCGTTG
AAAAAATACGATGTGAAAAACATTCGCCAATTCCTGTTATCTTCCCTTGGACAGGCTTCCAGTATA
AGTGCAGGAATTGCTTCGAGTCTTGAAGCTCCCAACCCATCTGGATATTCCCTTGATACTAAAGAG
GCTTACCGCTTTCTGACTGAAAGTGCAGCGAATTTAAGTCAGGCCGGTTTCGGGGTACTTCTCCCT
GGCTGGTGGACCCGTAAAGGTACAAAGACACACTTAAAAGCCCAGGCTAATGTTAAGGGCAAGAAG
AAGTTGCAGGCCGGATACGGGCTTACACTCGATGAAATCGTCAGCTTTGACTGGGAAATCGCCCTT
GGAGACAGGGTACTGACAGTCAGAGAACTGCAGGCTCTTGCAAAGCTTAAAGCTCCGCTTGTGAAA
TTCCGCGGGCAGTGGGTTGAGGTAAACGATGCGGAAATCAGGGCTGCCCTTGAGTTCTGGAAGAAA
AATCCCAACGGTGAAGCAAGTCTGCGTGAAGTTCTAAAACTGGCAGTGGGAGTTTCCGAAAAAGCC
GATGGTGTGAACGTTGAAGGGCTCAATGCAACCGGATGGATTGGAGAATTAATCAGCCGCTTAAAA
GACAAAACCGGGTTTGAAGAACTTCCTGCTCCCAACGGCTTTTCAGGCACCCTTCGGCCATATCAG
TTCAGAGGTTACTCCTGGCTGGCTTTTCTGAGGCAGTGGGGTATAGGAGCCTGCCTTGCAGACGAT
ATGGGGCTTGGTAAAACCGTCCAGACTCTTGCTCTTATTCAGCACGATCTGGAACAGGCTAAAGAG
AAAGCTGAAGAAAAGATTGAAGAACCGGCTGAAGAAAAGATTGAAGAAAAGTTGACGGACGTAAG
GCCCCAAAACCTGTTCTTCTGGTTTGTCCTACCTCTGTTATCAACAACTGGAAAAAAGAGGCTTCC
CGCTTTACGCCAGAACTTTCGGTAATGGTCCACCACGGGACCAGCCGGAAAAAGGAAGAGGAATTC
AAGAAGGAAGCCATGAATCATGCTATTGTCATCTCAAGCTATGGCCTTGTGCAGCGGGATCTTAAA
TTTTTAAAAGAGGTTCATTGGGCAGGAGTTGTACTTGACGAAGCCCAGAACATCAAAAACCCGGAA
ACCAAACAGGCAAAGGCAGCCAGGGCTCTTGAATCCGATTACCGCTTAGCTCTTACAGGGACTCCG
GTTGAAATAACGTGGGAGACCTCTGGTCCATAATGGAGTTTTTAAACCCCGGCTTCCTCGGAAGT
CAGGCGGGTTTCAAGCGGAATTTCTTTATCCCCATTCAGGCAGAAAGGGATCAGGAGGCTGCAAGG
AGGCTGAAAGAAATTACAGGTCCCTTCATCCTTCGCCGTTTGAAGACTGACACTTCGATTATCTCC
GACCTGCCGGAAAAAATGGAGATGAAGACCTATTGTACGCTGACAAAAGAACAGGCCTCCCTCTAT
GCTGCAGTCCTTGAAGACATCAGAGAAGCGATTGAAGGAGCCGAAGAAGGCATCCAGAGGAAGGT
ATAATCCTGTCTGCCCTTTCCAGGCTCAAGCAGGTCTGCAACCACCCTGCGCAGTTTTGAAGGAC
AACTCCACTATCCCCGGCAGGTCCGGAAAACTCGCAAGGCTTACCGAAATGCTGGATGTAGTCCTG
GAAAACGGGGAAAAGCCCTTGTTTTACCCAGTTTGCGGAGATGGGCAAAATGGTGAAAGAACAC
CTGCAAGCAAGCTTTGGCTGTGAAGTCCTTTTCCTGCACGGCGGGTCCCCAGGAAGCAGAGAGAC
CGGATGCTTGAGAGGTTCCAGGAAGGAAAAGAATACCTCCCTATTTTTGTCCTCTCCCTTAAAGCC
GGCGGCACGGGGCTTAACCCTCACAGGGGCAAACCACGTTTTCCACTTTGATCGCTGGTGGAACCCG

FIGURE 10 (continued)

```
GCTGTTGAAAACCAGGCTACAGACAGGGCATTCCGTATAGGCCAGAAGAAAAACGTTGAGGTCCAT
AAATTCATCTGCGCAGGTACGCTTGAAGAAAAATCGATGAGATTATCGAACGCAAAGTGCAGGTC
GCAGAGAACGTTGTTGGGACAGGTGAAGACTGGCTGACAGAGCTTTCCAACGATGAACTGAAGGAT
ATTCTTGCTCTTAGAGAAGAAGCGGTAGGTGAATAA
```

SEQ ID NO: 48, Methanosarcina mazei Goe1 Metma_Goe1_SNF2 translated polypeptide
```
MIILHAGRVGKQFFLWGESPAENETPVVRRGRKPKTPIVKPYPYDSGFENLSSALELLLGSTDRKK
AEKINVWTPTIGGNPVPSSPLVAEISDSKAEPALAPCTVHAYPLEAEEAIVLLCTCMEKKVLAPGI
ISGNDLLWWADALKFAGSLVAGQKYLPGVRGGEGEYRAFWEPVFSGEDAGKLAKLAKQMPPAARAL
APEASSMPPEMPAALAAKQFIEDSLDWIVRSEIGEKKLAKETRKRKSFDSVHDAWVSALRSPEGLI
YGDENELLQLAARTREWQRPLTILTTSPFRFCFRLEEPALEEEIEETEETEEIEENEAGKRDTKKG
REGIADIEVPEGLWYVRYMLQSYEDPSLLIPVKEAWKPKKGSPLKKYDVKNIRQFLLSSLGQASSI
SAGIASSLEAPNPSGYSLDTKEAYRFLTESAANLSQAGFGVLLPGWWTRKGTKTHLKAQANVKGKK
KLQAGYGLTLDEIVSFDWEIALGDRVLTVRELQALAKLKAPLVKFRGQWVEVNDAEIRAALEFWKK
NPNGEASLREVLKLAVGVSEKADGVNVEGLNATGWIGELISRLKDKTGFEELPAPNGFSGTLRPYQ
FRGYSWLAFLRQWGIGACLADDMGLGKTVQTLALIQHDLEQAKEKAEEKIEEPAEEKIEEKVDGRK
APKPVLLVCPTSVINNWKKEASRFTPELSVMVHHGTSRKKEEEFKKEAMNHAIVISSYGLVQRDLK
FLKEVHWAGVVLDEAQNIKNPETKQAKAARALESDYRLALTGTPVENNVGDLWSIMEFLNPGFLGS
QAGFKRNFFIPIQAERDQEAARRLKEITGPFILRRLKTDTSIISDLPEKMEMKTYCLTLTKEQASLY
AAVLEDIREAIEGAEEGIQRKGIILSALSRLKQVCNHPAQFLKDNSTIPGRSGKLARLTEMLDVVL
ENGEKALVFTQFAEMGKMVKEHLQASFGCEVLFLHGGVPRKQRDRMLERFQEGKEYLPIFVLSLKA
GGTGLNLTGANHVFHFDRWWNPAVENQATDRAFRIGQKKNVEVHKFICAGTLEEKIDEIIERKVQV
AENVVGTGEDWLTELSNDELKDILALREEAVGE
```

SEQ ID NO: 49, Mycobacterium bovis BCG Pasteur 1173P2 Mycbo_SNF2 nucleic acid sequence
```
ATGCTGGTTTTGCACGGCTTCTGGTCCAACTCCGGCGGGATGCGGCTGTGGGCGGAGGACTCCGAT
CTGCTGGTGAAGAGCCCGAGTCAGGCGCTGCGCTCCGCGCGGCCACACCCGTTCGCGGCGCCCGCT
GACCTGATCGCCGGCATACATCCGGGCAAACCCGCAACCGCCGTTTTGCTGTTGCCGTCGTTGCGA
TCGGCGCCGCTGGACTCGCCGGAGCTGATCCGGCTCGCCCCGCGCCCGGCCGCGCGAACCGATCCG
ATGCTGTTGGCGTGGACGGTACCGGTGGTGGACCTGGACCCCACCGCGGCGTTGGCCGCCTTCGAC
CAGCCCGCCCCGACGTCCGCTACGGCGCGTCCGTCGACTACCTGGCCGAGCTGGCCGTTTTCGCG
CGCGAGTTGGTCGAGCGTGGTCGCGTGCTGCCCCAGCTGCGCCGCGACACCCACGGCGCGGCCGCC
TGCTGGCGTCCGGTGTTGCAGGGACGCGACGTGGTCGCGATGACCTCGCTGGTCTCGGCGATGCCG
CCGGTCTGCCGCGCCGAAGTTGGTGGGCACGACCCGCACGAACTGGCAACCTCGGCTCTGGACGCG
ATGGTCGACGCCGCCGTGCGCGCGGCGCTGTCACCGATGGACCTGCTGCCCCGCGACGGGGTCGC
TCCAAACGGCATCGGGCCGTGGAGGCTTGGCTGACCGCGTTGACCTGCCCGGACGGCCGGTTCGAC
GCGGAGCCCGACGAACTCGACGCGCTGGCCGAGGCGTTGCGGCCATGGGACGACGTCGGTATCGGC
ACCGTCGGCCCGGCGCGGGCGACGTTTCGGCTGTCCGAAGTCGAGACCGAAAACGAGGAGACGCCC
GCGGGCTCGTTGTGGAGGCTGGAGTTCTTATTGCAGTCGACGCAGGACCCCAGCCTGCTGGTCCCC
GCCGAGCAGGCATGGAACGACGACGGCAGCCTGCGCCGCTGGCTGGACCGGCCGCAGGAGCTGCTG
CTGACCGAACTGGGCCGGGCCTCTCGGATTTTCCCCGAGCTCGTCCCGGCGCTGCGCACCGCGTGC
CCGTCCGGGCTTGAGCTCGACGCCGACGGCGCCTACCGATTCCTGTCGGGTACGGCCGCGGTGCTC
GACGAGGCTGGGTTTGGCGTGCTGCTGCCGTCCTGGTGGGACCGCCGCCGCAAGCTGGGCTTGGTC
CTGTCCGCATATACCCCGGTCGACGGCGTGGTGGGCAAGGCCAGCAAGTTCGGCCGCGAGCAGCTC
GTCGAGTTCCGCTGGGAGCTGGCCGTGGGCGACGATCCGCTCAGCGAGGAGGAGATCGCGGCGCTG
ACCGAAACCAAGTCCCCGCTGATCCGGCTGCGTGGCCAGTGGGTGGCGCTCGATACCGAACAGCTG
```

FIGURE 10 (continued)

CGCCGCGGGCTGGAGTTTTTGGAGCGTAAGCCAACCGGCCGCAAGACCACCGCCGAGATCCTCGCG
CTGGCCGCCAGCCACCCCGACGACGTGGACACCCCGCTCGAGGTCACCGCCGTACGCGCCGACGGC
TGGCTCGGGGACCTGCTCGCCGGGGCCGCCGCGGCGTCGCTGCAGCCGTTGGACCCGCCCGACGGA
TTCACCGCGACGCTGCGTCCCTACCAGCAGCGCGGTCTGGCGTGGCTGGCGTTTTTGTCCTCGCTC
GGTTTGGGCAGCTGCCTGGCCGACGACATGGGCCTGGGCAAGACGGTGCAGCTATTGGCCCTGGAA
ACCTTGGAATCCGTTCAGCGCCACCAGGATCGCGGCGTCGGACCCACACTGCTACTGTGCCCGATG
TCGTTGGTGGGCAACTGGCAGCAGGAAGCGGCCAGGTTTGCACCCAACCTGCGGGTGTACGCCCAC
CACGGGGGCGCCCGGCTGCACGGCGAGGCGTTGCGCGACCACCTCGAGCGCACCGACCTGGTCGTG
AGCACCTATACCACCGCCACCCGCGACATCGACGAGCTGTCGGAATACGAATGGAACCGGGTGGTG
CTGGACGAGGCCCAGGCGGTGAAGAACAGCCTGTCCCGGGCGGCCAAGGCGGTGCGACGGCTACGC
GCGGCGCACCGGGTCGCGCTGACCGGGACACCGATGGAGAACCGGCTCGCCGAGCTGTGGTCGATC
ATGGACTTCCTCAACCCGGGCCTGCTCGGATCCTCCGAACGCTTCCGCACCCGCTACGCGATCCCG
ATCGAGCGGCACGGGCACACCGAACCGGCCGAACGGCTGCGCGCATCGACGCGGCCCTACATCCTG
CGCCGGCTCAAGACCGACCCGGCGATCATCGACGATCTGCCGGAGAAGATCGAGATCAAGCAGTAC
TGCCAACTCACCACCGAGCAGGCGTCGCTGTATCAGGCCGTCGTCGCCGACATGATGGAAAAGATC
GAAAACACCGAAGGGATCGAGCGGCGCGGCAACGTGCTGGCCGCGATGGCCAAGCTCAAACAGGTG
TGCAACCACCCCGCCCAGCTGCTGCACGATCGCTCCCCGGTCGGTCGGCGGTCCGGGAAGGTGATC
CGGCTCGAGGAGATCCTGGAAGAGATCCTGGCCGAGGGCGACCGGGTGCTGTGTTTTACCCAGTTC
ACCGAGTTCGCCGAGCTGCTGGTGCCGCACCTGGCCGCACGCTTCGGCCGTGCCGCCCGAGACATT
GCCTACCTGCACGGTGGCACCCCGAGGAAGCGGCGTGACGAGATGGTGGCCCGGTTCCAGTCCGGT
GACGGCCCGCCCATTTTTCTGCTGTCGTTGAAGGCGGGCGGTACCGGGCTGAACCTCACCGCCGCC
AATCATGTTGTGCACCTGGACCGCTGGTGGAACCCGGCGGTCGAGAACCAGGCGACGGACCGGGCG
TTTCGGATCGGGCAGCGGCGCACGGTGCAGGTCCGCAAGTTCATCTGCACCGGCACCCTCGAGGAG
AAGATCGACGAAATGATCGAGGAGAAAAAGGCGCTGGCCGACTTGGTGGTCACCGACGGCGAAGGC
TGGCTGACCGAACTGTCCACCCGCGATCTGCGCGAGGTGTTCGCGCTGTCCGAAGGCGCCGTCGGT
GAGTAG

SEQ ID NO: 50, Mycobacterium bovis BCG Pasteur 1173P2 Mycbo_SNF2 translated polypeptide

MLVLHGFWSNSGGMRLWAEDSDLLVKSPSQALRSARPHPFAAPADLIAGIHPGKPATAVLLLPSLR
SAPLDSPELIRLAPRPAARTDPMLLAWTVPVVDLDPTAALAAFDQPAPDVRYGASVDYLAELAVFA
RELVERGRVLPQLRRDTHGAAACWRPVLQGRDVVAMTSLVSAMPPVCRAEVGGHDPHELATSALDA
MVDAAVRAALSPMDLLPPRRGRSKRHRAVEAWLTALTCPDGRFDAEPDELDALAEALRPWDDVGIG
TVGPARATFRLSEVETENEETPAGSLWRLEFLLQSTQDPSLLVPAEQAWNDDGSLRRWLDRPQELL
LTELGRASRIFPELVPALRTACPSGLELDADGAYRFLSGTAAVLDEAGFGVLLPSWWDRRRKLGLV
LSAYTPVDGVVGKASKFGREQLVEFRWELAVGDDPLSEEEIAALTETKSPLIRLRGQWVALDTEQL
RRGLEFLERKPTGRKTTAEILALAASHPDDVDTPLEVTAVRADGWLGDLLAGAAAASLQPLDPPDG
FTATLRPYQQRGLAWLAFLSSLGLGSCLADDMGLGKTVQLLALETLESVQRHQDRGVGPTLLLCPM
SLVGNWQQEAARFAPNLRVYAHHGGARLHGEALRDHLERTDLVVSTYTTATRDIDELSEYEWNRVV
LDEAQAVKNSLSRAAKAVRRLRAAHRVALTGTPMENRLAELWSIMDFLNPGLLGSSERFRTRYAIP
IERHGHTEPAERLRASTRPYILRRLKTDPAIIDDLPEKIEIKQYCQLTTEQASLYQAVVADMMEKI
ENTEGIERRGNVLAAMAKLKQVCNHPAQLLHDRSPVGRRSGKVIRLEEILEEILAEGDRVLCFTQF
TEFAELLVPHLAARFGRAARDIAYLHGGTPRKRRDEMVARFQSGDGPPIFLLSLKAGGTGLNLTAA
NHVVHLDRWWNPAVENQATDRAFRIGQRRTVQVRKFICTGTLEEKIDEMIEEKKALADLVVTDGEG
WLTELSTRDLREVFALSEGAVGE

FIGURE 10 (continued)

SEQ ID NO: 51, Mycobacterium tuberculosis H37Rv Myctu_SNF2 nucleic acid sequence
ATGCTGGTTTTGCACGGCTTCTGGTCCAACTCCGGCGGGATGCGGCTGTGGGCGGAGGACTCCGAT
CTGCTGGTGAAGAGCCCGAGTCAGGCGCTGCGCTCCGCGCGGCCACACCCGTTCGCGGCGCCCGCT
GACCTGATCGCCGGCATACATCCGGGCAAACCCGCAACCGCCGTTTTGCTGTTGCCGTCGTTGCGA
TCGGCGCCGCTGGACTCGCCGGAGCTGATCCGGCTCGCCCCGCGCCCGGCCGCGCGAACCGATCCG
ATGCTGTTGGCGTGGACGGTACCGGTGGTGGACCTGGACCCCACCGCGGCGTTGGCCGCCTTCGAC
CAGCCCGCCCCCGACGTCCGCTACGGCGCGTCCGTCGACTACCTGGCCGAGCTGGCCGTTTTCGCG
CGCGAGTTGGTCGAGCGTGGTCGCGTGCTGCCCCAGCTGCGCCGCGACACCCACGGCGCGGCCGCC
TGCTGGCGTCCGGTGTTGCAGGGACGCGACGTGGTCGCGATGACCTCGCTGGTCTCGGCGATGCCG
CCGGTCTGCCGCGCCGAAGTTGGTGGGCACGACCCGCACGAACTGGCAACCTCGGCTCTGGACGCG
ATGGTCGACGCCGCCGTGCGCGCGGCGCTGTCACCGATGGACCTGCTGCCCCCGCGACGGGGTCGC
TCCAAACGGCATCGGGCCGTGGAGGCTTGGCTGACCGCGTTGACCTGCCCGGACGGCCGGTTCGAC
GCGGAGCCCGACGAACTCGACGCGCTGGCCGAGGCGTTGCGGCCATGGGACGACGTCGGTATCGGC
ACCGTCGGCCCGGCGCGGGCGACGTTTCGGCTGTCCGAAGTCGAGACCGAAAACGAGGAGACGCCC
GCGGGCTCGTTGTGGAGGCTGGAGTTCTTATTGCAGTCGACGCAGGACCCCAGCCTGCTGGTCCCC
GCCGAGCAGGCATGGAACGACGACGGCAGCCTGCGCCGCTGGCTGGACCGGCCGCAGGAGCTGCTG
CTGACCGAACTGGGCCGGGCCTCTCGGATTTTCCCCGAGCTCGTCCCGGCGCTGCGCACCGCGTGC
CCGTCCGGGCTTGAGCTCGACGCCGACGGCGCCTACCGATTCCTGTCGGGTACGGCCGCGGTGCTC
GACGAGGCTGGGTTTGGCGTGCTGCTGCCGTCCTGGTGGGACCGCCGCCGCAAGCTGGGCTTGGTC
CTGTCCGCATATACCCCGGTCGACGGCGTGGTGGGCAAGGCCAGCAAGTTCGGCCGCGAGCAGCTC
GTCGAGTTCCGCTGGGAGCTGGCCGTGGGCGACGATCCGCTCAGCGAGGAGGAGATCGCGGCGCTG
ACCGAAACCAAGTCCCCGCTGATCCGGCTGCGTGGCCAGTGGGTCGCGCTCGATACCGAACAGATG
CGCCGCGGGCTGGAGTTTTTGGAGCGTAAGCCAACCGGCCGCAAGACCACCGCCGAGATCCTCGCG
CTGGCCGCCAGCCACCCCGACGACGTGGACACCCCGCTCGAGGTCACCGCCGTACGCGCCGACGGC
TGGCTCGGGGACCTGCTCGCCGGGGCCGCCGCGGCGTCGCTGCAGCCGTTGGACCCGCCCGACGGA
TTCACCGCGACGCTGCGTCCCTACCAGCAGCGCGGTCTGGCGTGGCTGGCGTTTTTGTCCTCGCTC
GGTTTGGGCAGCTGCCTGGCCGACGACATGGGCCTGGGCAAGACGGTGCAGCTATTGGCCCTGGAA
ACCTTGGAATCCGTTCAGCGCCACCAGGATCGCGGCGTCGGACCCACACTGCTACTGTGCCCGATG
TCGTTGGTGGGCAACTGGCCGCAGGAAGCGGCCAGGTTTGCACCCAACCTGCGGGTGTACGCCCAC
CACGGGGGCGCCCGGCTGCACGGCGAGGCGTTGCGCGACCACCTCGAGCGCACCGACCTGGTCGTG
AGCACCTATACCACCGCCACCCGCGACATCGACGAGCTGGCGGAATACGAATGGAACCGGGTGGTG
CTGGACGAGGCCCAGGCGGTGAAGAACAGCCTGTCCCGGGCGGCCAAGGCGGTGCGACGGCTACGC
GCGGCGCACCGGGTCGCGCTGACCGGGACACCGATGGAGAACCGGCTCGCCGAGCTGTGGTCGATC
ATGGACTTCCTCAACCCGGGCCTGCTCGGATCCTCCGAACGCTTCCGCACCCGCTACGCGATCCCG
ATCGAGCGGCACGGGCACACCGAACCGGCCGAACGGCTGCGCGCATCGACGCGGCCCTACATCCTG
CGCCGGCTCAAGACCGACCCGGCGATCATCGACGATCTGCCGGAGAAGATCGAGATCAAGCAGTAC
TGCCAACTCACCACCGAGCAGGCGTCGCTGTATCAGGCCGTCGTCGCCGACATGATGGAAAAGATC
GAAAACACCGAAGGGATCGAGCGGCGCGGCAACGTGCTGGCCGCGATGGCCAAGCTCAAACAGGTG
TGCAACCACCCCGCCAGCTGCTGCACGATCGCTCCCCGGTCGGTCGGCGGTCCGGGAAGGTGATC
CGGCTCGAGGAGATCCTGGAAGAGATCCTGGCCGAGGGCGACCGGGTGCTGTGTTTTACCCAGTTC
ACCGAGTTCGCCGAGCTGCTGGTGCCGCACCTGGCCGCACGCTTCGGCCGTGCCGCCCGAGACATT
GCCTACCTGCACGGTGGCACCCCGAGGAAGCGGCGTGACGAGATGGTGGCCCGGTTCCAGTCCGGT
GACGGCCCGCCCATTTTTCTGCTGTCGTTGAAGGCGGGCGGTACCGGGCTGAACCTCACCGCCGCC
AATCATGTTGTGCACCTGGACCGCTGGTGGAACCCGGCGGTCGAGAACCAGGCGACGGACCGGGCG
TTTCGGATCGGGCAGCGGCGCACGGTGCAGGTCCGCAAGTTCATCTGCACCGGCACCCTCGAGGAG
AAGATCGACGAAATGATCGAGGAGAAAAAGGCGCTGGCCGACTTGGTGGTCACCGACGGCGAAGGC
TGGCTGACCGAACTGTCCACCCGCGATCTGCGCGAGGTGTTCGCGCTGTCCAAGGCGCCGTCGGT
GAGTAG

SEQ ID NO: 52, Mycobacterium tuberculosis H37Rv Myctu_SNF2 translated polypeptide
MLVLHGFWSNSGGMRLWAEDSDLLVKSPSQALRSARPHPFAAPADLIAGIHPGKPATAVLLLPSLR
SAPLDSPELIRLAPRPAARTDPMLLAWTVPVVDLDPTAALAAFDQPAPDVRYGASVDYLAELAVFA
RELVERGRVLPQLRRDTHGAAACWRPVLQGRDVVAMTSLVSAMPPVCRAEVGGHDPHELATSALDA
MVDAAVRAALSPMDLLPPRRGRSKRHRAVEAWLTALTCPDGRFDAEPDELDALAEALRPWDDVGIG
TVGPARATFRLSEVETENEETPAGSLWRLEFLLQSTQDPSLLVPAEQAWNDDGSLRRWLDRPQELL
LTELGRASRIFPELVPALRTACPSGLELDADGAYRFLSGTAAVLDEAGFGVLLPSWWDRRRKLGLV
LSAYTPVDGVVGKASKFGREQLVEFRWELAVGDDPLSEEEIAALTETKSPLIRLRGQWVALDTEQM
RRGLEFLERKPTGRKTTAEILALAASHPDDVDTPLEVTAVRADGWLGDLLAGAAAASLQPLDPPDG
FTATLRPYQQRGLAWLAFLSSLGLGSCLADDMGLGKTVQLLALETLESVQRHQDRGVGPTLLLCPM
SLVGNWPQEAARFAPNLRVYAHHGGARLHGEALRDHLERTDLVVSTYTTATRDIDELAEYEWNRVV
LDEAQAVKNSLSRAAKAVRRLRAAHRVALTGTPMENRLAELWSIMDFLNPGLLGSSERFRTRYAIP
IERHGHTEPAERLRASTRPYILRRLKTDPAIIDDLPEKIEIKQYCQLTTEQASLYQAVVADMMEKI
ENTEGIERRGNVLAAMAKLKQVCNHPAQLLHDRSPVGRRSGKVIRLEEILEEILAEGDRVLCFTQF
TEFAELLVPHLAARFGRAARDIAYLHGGTPRKRRDEMVARFQSGDGPPIFLLSLKAGGTGLNLTAA
NHVVHLDRWWNPAVENQATDRAFRIGQRRTVQVRKFICTGTLEEKIDEMIEEKKALADLVVTDGEG
WLTELSTRDLREVFALSEGAVGE

SEQ ID NO: 53, Myxococcus xanthus DK 1622 Myxxa_DK_SNF2 nucleic acid sequence
GTGCGAGCCTGGAGGGCGTCCTCCGCTGGGCTGCCGCTGGCCTCTCCCTGTCCGCGGCTCGGAGT
CCGACCGGCCACCTCCCAGTGTTTTCAGGTTTTTCCGTGGCGACCGATGGCGTCGGGCTGTTCGCG
GGTCTGTCTGTTCGGGCCCTTGTCCATCAAGGGCCTGGAGGAGGACCGCTACGAGCGCCTCACGGA
CAACCCGGCAGGCCTGCGGCTCACGGAGCCGGCAATCCCGTGCAGGGCGCTCGCAGGCCTGCTTG
CGTGTGCCGCTTGCCCGGACGGAGTTTACATTCGCAGCGATGCCCTCGTGTTCCTGCCCGACGCC
GAGACGCTGTTCCTCTGGGGGCCCGACCGGCTGCCACGTGAGCTCGCCGGCCTGCCGGAGACGGGG
GACCGCGCCTCCGCGCTGCTCGTGACGCCCGAGGGATTGCGTGAATGCGAGGGGCACGGGCTGCCC
CTGGCCGCCACCGTCGAGCGGCTCGCGGTGGTGCAAACCTCCGAGGCCGAGTCCTTTCCTGGCTCC
ATCGCCCTGTGGACGCTGGCCAGCAAGCTCGCGCTGGAGTTGGTGGCGCGCGAGCGCGTGGTGCCC
ACGCTCCTGCGGCGGGGCGAGCGCATCGAGGCTCGCTGGGCGGCGGCCCTCTCCGCCACCGAGGAC
GCCGGCCGCGTCGCCGCGCTCGCCCGGAGCATGCCGCCCGGCGCGCACGCCGTCCCCGCAGGCGCC
AGGCCAGGCCGCGCCGTCTGGGCCCCGGACGCCTTGCTGCGCGCCTTCCTCGACGCCACCGTCGAC
GCCTTCGTGCGCGCCGCGCGCGGTGCGCCTTCGTTGCCGGCCCGGCGCGCGGCCTCGTGGGACGAG
CGCTGGCGCGAGGCGCTCACCGGCGCGCGACGCGACTTCGCGCCGGAGGGCTTCGCCGAGCGCTCC
GTCGTCGATGAGCTGACGCGCTGGAGCGAACCCGCGCTCGGCGCCCGGGACAAGCTGCGCGCCTGC
TTCCGGCTGGAGCCCCGACGGAGGAGCGCGAGCCCTTCGTGCTGAGCTTCCACCTCCAGTCCCCG
GACGACCCAAGCCTGCTCGTCCCGGCCGCGGACGTCTGGAAGACGCGCGGGCGCAGCCTGGAGAAG
CTCGGCCGCGCCTTCCGTGACCCGCAGGAGTCCCTGCTCGAGGCACTCGGCCGCGCCGCCCGGCTC
TTCCCCCCGCTGGCGCTCGTGCTGGAGAGCCCACGTCCCCAGGCGCTCCTGCTCGAGCCCGACACC
GCGTGGACGTTCCTCTCGGAGGGCGCCCGCGTGCTCTCAGACGCCGGCTTCGGCGTCATCGTCCCT
GGCGAGCTCACCACCTCGGGCCGACGCCGCCTGCGCCTGCGCATGCGCGTGGGCGCGAGCACGAAG
GCCGCGGGGGCCGTCGGTGGCACCGCGGGGCTCGGGCTCGACGCGCTGCTGCGCGTGGACTGGGAC
GCCGTGCTGGGCGACCAACCCCTCTCCGCCCAGGAGCTGGCGCTGCTGGCCCAGCGCAAGGCCCCG
CTCGTGCGATTCCGCGGCGAGTGGGTCGCGGTGGATCCCCTCGAACTCGACGCCATCCAGCGCCAC
CTCGCCCAGGGCCCCGGCCGCATGGCGCTGAGCGAGGCGGTGCGGGTGTCCCTGCTAGGCGAAACG
CGCCACGGACAGCTCCCCGTCACCGTTCTCGCCACCGGGGCGCTGGAGGAGCGCCTGCGCCTGCTT
CGGGAGGGCGGGGCCACCGCTCAGGACGCCCCCCGCGCGCTGCGCGCCACGCTGCGGCCCTACCAG FIGURE 10 (continued)

```
TCGCGCGGTCTGCACTGGCTGGACACGCTGGCCTCATTGGGGCTCGGCGCCTGCCTCGCGGACGAC
ATGGGCCTGGGCAAGACGGTGCAGGTGCTGGCCTTCCTGCTGCGGCGGCTCGAGCAGGCGCCTGAC
GAGGCGCGCCCCACGCTGCTGGTGGCCCCCACCTCCGTGGTGGGCAACTGGGAGCGTGAGCTCGCC
CGCTTCGCCCCCACCTTGCGCCTGACGCGGCACTACGGCGCCGAGCGCGCCCGCGCGGCGAACCGC
TTCCCCCGCGCGCCCGGCGCCGTCGTGCTCACCACCTACGGCTTGCTGCGCCGGGACGCCGCGCTG
CTCGCGCGCGTGGACTGGGGCGCGGTGGTGCTCGACGAGGCGCAGAACATCAAGAACGCGGCGTCG
GCTACCGCCCGCGCGGCCCGGGCGTTGCGCGCCAGCCAGCGCTTCGCGCTCACGGGCACGCCGGTG
GAGAACCGCCTGGCGGAGCTGTGGTCCATCCTCGAGTTCGCCAACCCGGGCCTGCTCGGGCCGCTG
GAGACGTTCCGGCGGGAGCTGGCGCTGCCCATTGAACGCCATGGCAATCAGGAGGCCTCGGCCCGG
CTGCGCCGGCTCGTGAGCCCCTTCGTCCTGCGCCGCCTCAAGAGCGACCCGACCATCATCACGGAC
CTGCCCGCGAAGAATGAGATGAAGGTCGTCTGCACGCTCACGCGCGAGCAGGCCTCGCTCTACAAG
GCGGTGGTGGACGAGGAGCTGCGGCGCATCGAGGAGGCCGACGGCATGGAGCGCCGGGGCCGCGTG
CTCGCGCTGCTGCTGTACACGAAGCAGATCGCCAACCACCCGGCGCAGTACCTCGGGGAGTCCGGG
CCCCTGCCGGGGCGCTCGGGGAAGCTGGCGCGCGTGGTGGAGATGCTCGAGGAGTCCCTGGCCGCT
GGCGACAAGGCGCTCGTCTTCACGCAGTTCCGGGAGATGGGCGACAAGCTGGTGGCGCACCTGTCG
GAGTACCTGGGCCACGAGGTGCTCTTCCTCCACGGCGGCACGCCCCGCAAGGCGCGCGACGAGATG
GTGCGGCGCTTCCAGGAGGACGTCCACGGTCCGCGTGTGTTCGTGCTGTCCGTCAAGGCGGGAGGC
ACGGGGCTCAACCTGACGGCGGCGAGCCATGTGTTCCATTACGACCGCTGGTGGAACCCGGCCGTC
GAGGACCAGGCCACCGACCGCGCGTACCGCATCGGGCAGACGCGCGCGGTGCAGGTCCACAAGCTG
GTGTGTGCGGGCACTGTCGAGGAGAAGGTGGACCGGCTGCTCGAACAGAAGCGCCAGCTCGCCGAG
AAGGTCGTGGGCGCGGGCGAGCACTGGGTGACCGAGCTGGACACGACGGCGCTGCGCGAGCTGTTC
TCGCTGTCCGAGGGCGCCGTGGCGGACGATGGCGACGCGGAAGGGGAAGACGACGCGCGGGTGCGC
GCCCCGCGACGGCGCGGCCGTGCGAGCGCGAAGGCGGTGTCGCGATGA
```

SEQ ID NO: 54, Myxococcus xanthus DK 1622 Myxxa_DK1622_SNF2 translated polypeptide
VRAWRGVLRWAAAGLSLSAARSPTGHLPVFSGFSVATDGVGLFAGLSVRALVHQGPGGGPLRAPHG
QPGRPAAHGAGNPVQGRSQACLRVPLARTEFTFAAMPLVFLPDAETLFLWGPDRLPRELAGLPETG
DRASALLVTPEGLRECEGHGLPLAATVERLAVVQTSEAESFPGSIALWTLASKLALELVARERVVP
TLLRRGERIEARWAAALSATEDAGRVAALARSMPPGAHAVPAGARPGRAVWAPDALLRAFLDATVD
AFVRAARGAPSLPARRAASWDERWREALTGARRDFAPEGFAERSVVDELTRWSEPALGARDKLRAC
FRLEPPTEEREPFVLSFHLQSPDDPSLLVPAADVWKTRGRSLEKLGRAFRDPQESLLEALGRAARL
FPPLALVLESPRPQALLLEPDTAWTFLSEGARVLSDAGFGVIVPGELTTSGRRRLRLRMRVGASTK
AAGAVGGTAGLGLDALLRVDWDAVLGDQPLSAQELALLAQRKAPLVRFRGEWVAVDPLELDAIQRH
LAQGPGRMALSEAVRVSLLGETRHGQLPVTVLATGALEERLRLLREGGATAQDAPRALRATLRPYQ
SRGLHWLDTLASLGLGACLADDMGLGKTVQVLAFLLRRLEQAPDEARPTLLVAPTSVVGNWERELA
RFAPTLRLTRHYGAERARAANRFPRAPGAVVLTTYGLLRRDAALLARVDWGAVVLDEAQNIKNAAS
ATARAARALRASQRFALTGTPVENRLAELWSILEFANPGLLGPLETFRRELALPIERHGNQEASAR
LRRLVSPFVLRRLKSDPTIITDLPAKNEMKVVCTLTREQASLYKAVVDEELRRIEEADGMERRGRV
LALLLYTKQIANHPAQYLGESGPLPGRSGKLARVVEMLEESLAAGDKALVFTQFREMGDKLVAHLS
EYLGHEVLFLHGGTPRKARDEMVRRFQEDVHGPRVFVLSVKAGGTGLNLTAASHVFHYDRWWNPAV
EDQATDRAYRIGQTRAVQVHKLVCAGTVEEKVDRLLEQKRQLAEKVVGAGEHWVTELDTTALRELF
SLSEGAVADDGDAEGEDDARVRAPRRRGRASAKAVSR FIGURE 10 (continued)

SEQ ID NO: 55, Nocardia farcinica IFM 10152 Nocfa_IFM\10152_SNF2 nucleic acid sequence
ATGGTGGGCGCCGGCGGCCCGCCGGGTGTCGGTGCCACCTGCTTGGATGGACGGATGCTGCACGGA
CTGTGGTCGCCGGGTTCCGGCCTGGTGCTGTGGACCGAGGGCGAGGTGCCGCCCGCGCTGCCCGAC
CCGGCCGGTGCGTTGCTGCGCGCATCGCGGTTCCGGCATCGGGCGCAGGTGCTGGTGCCGGGCCCC
GCCGGCCCACAGCTCACGCAGGTGCGCGCGCACGCCCTGGTGCCACAGGCCGCGGTCGACGTGCTG
CGGCAGCGGTTACCCGTCGAATCGGTGGCGGGTGACCTGCGCTTTCTCGCTCACGTCGCCGACGGG
ATCGATCGGTGGGTGCGGGCCGGTCGCGTGGTGCCCGACCTGCACCGGGCCGACGGACAGTGGTGG
GCGCGCTGGCGGCTGGTCGGCGGTGCCCGGCAGCGGGCCTGGCTGGCCGAACTCGCGGTGGCGATG
CCCGCGGCGCTGCGGGTGGCCGGGCAGCCCGCGGCGGTGCTCGACGATCTGGTCACCGAGCTGACC
GATCCGATCGTGCGCACCAGGCTCGCCGACGCGCCGGTGACGCACCCGCTGGTGCGCGCACTGGTG
CGGGACCAGCCGCTCGAGACGGGTAGCCACCAGCTGGCCGAGGTGCTGCGGCGCTGGCGCGAGAGC
CTCACCGTCGACGAGCCGGAGCTGGTGTTGCGGCTGCTGGAACCGGACGGGGAGACCGGTATCGAC
GGGGACGGCGGGGACGACCGGGACGACACCGTGGCGCTGTGGCGGCTGGAGGTCTGCCTCCGCACC
GAGGGCGAGGCCCCGGCCCCGGTGCCGGCGACCGCCGACCCGAACCTGCTGCGCATCGCCGTCGAG
CAGCTCGGCCGGGCGCAGCGGGCCTACCCCCGGCTGCGCGATCTGCCCGGCGATCCGCACAGCCTC
GACCTGCTGTTGCCCACCGAGGTGGTGGCCGATCTCGTCGCGCACGGTGCGCAGGCGTTGCGCGAG
GCGGGGGTGCGGCTGCTGCTGCCGCGCGCCTGGACCATCGCCGAACCCACCCTGCGGCTCGCGGTG
AGCAGCGCCGCGCCCGCCGCGGAGAGCACCGTGGGCATGCAGGGTCTGCTGTCCTATCGGTGGGAA
CTGGCGGTCGGCGACAAGGTGCTCACCCGCGCCGAGATGGAGCGCCTGGTCCGCGCCAAATCCGAC
CTGGTGCAGTTGCGCGGGGAATGGGTGCAGGCCGACCACAAGGTGCTCGCCGCCGCCGCCCGCTAC
GTCGCCGCGCATCTGGACACGTCGCCGGTCACCCTCGCCGACCTGCTCGGCGAGATCGCCGCCACC
CGCGTCGACAAGGTGCCGCTCACCGAGGTCACCGCCACCGGCTGGGCGGGCGAGTTGTTCGACGGC
GGCCGCGAGCCGGTGGCGACCCCGGGTGGGCTGAAGGCGCAGCTGCGCCCGTATCAGCTGCGCGGC
CTGAGCTGGCTGGCGACGATGAGCCGGATGGGCTGCGGCGGCATCCTCGCCGACGACATGGGTCTC
GGCAAGACGGTGCAGGTGCTGGCCCTGCTGGTGCACGAGCGCGAGACCAGCACGGCACCGCCCGGC
CCGACACTGCTGGTGTGCCCGATGTCGGTGGTCGGCAACTGGCAGCGCGAGGCGCAGCGGTTCGCC
CCCGGGCTGCGGGTGCTGGTGCACCACGGCGCCGACCGCCGTCGCGACGCCGAACTCGATGCCGCG
GTGGCGGATTCGGACCTGGTGCTCACCACCTACGCCATCCTGGCCAGGGATGCGGCCGAACTGTCG
CGCCAGTCGTGGGACCGGGTGGTGCTCGACGAGGCGCAGCACATCAAGAACGCCGCGACCAGGCAG
GCACGTGCCGCCCGTGCCCTGCCGGCCCGGCATCGCCTGGCGCTCACCGGAACCCCGGTGGAGAAC
CGGCTCGAAGAGTTGCGCTCGATCATGGATTTCGCGGTGCCCAAGCTGCTCGGTACCGCACCGACC
TTCCGCGCCCGGTTCGCCGTCCCCATCGAACGCGGGCAGGATCCCAACGCCCTGTCCCGCCTGCGC
TTCCTCACCCAACCGTTCGTGCTGCGCCGGGTCAAGGCCGATCCGGCGGTCATCGGCGATCTGCCC
GACAAGCTCGAGATGACGGTGCGGGCGAACCTGACCGTCGAGCAGGCCGCCCTGTACCAAGCCGTC
GTCGACGACATGCTGGTGAAACTGCGCAGTGCCAAGGGCATGGCCCGCAAGGGTGCGGTGCTCGGC
GCGCTCACCCGGCTCAAGCAGGTGTGCAACCATCCCGCGCACTTCCTCGGTGACGGTTCCCCGGTG
CTGCATCGCGGCAGGCACCGCTCCGGCAAGCTCGCCTTGGTCGAGGACGTGCTCGACACCGTCGTC
GCGGACGGGGAGAAGGCGTTGCTGTTCACCCAGTTCCGTGAGTTCGGCGACCTGCTCGCGCCCTAT
CTGTCCGAGCGGTTCGGCGCGCCGATCCCGTTCCTGCACGGCGGCGTGACCAAGAAGAACCGGGAC
ACGATGGTCGAGCGCTTCCAGTCCGGCGACGGCCCGCCGGTCATGCTGCTGTCCCTCAAGGCCGGC
GGCACCGGGCTCACCCTCACCGCCGCCAATCACGTGGTGCACCTGGATCGCTGGTGGAATCCGGCG
GTGGAGAACCAGGCCACCGATCGCGCCTTCCGCATCGGCCAGCGCCGCGACGTCCAGGTGCGCAAG
CTGGTCTGCGTCGACACCATCGAGGAACGGATCGACGAGATGATCACCGGCAAGAGCAGGCTCGCG
GACCTGGCCGTGGACGCGGGGGAGAACTGGATCACCGAGCTGGGCACCGAGGAGCTGCGCGAGTTG
TTCACCCTCGGCGCCGAGGCGGTGGGGGAGTGA

FIGURE 10 (continued)

SEQ ID NO: 56, Nocardia farcinica IFM 10152 Nocfa_IFM_10152_SNF2 translated polypeptide
MVGAGGPPGVGATCLDGRMLHGLWSPGSGLVLWTEGEVPPALPDPAGALLRASRFRHRAQVLVPGP
AGPQLTQVRAHALVPQAAVDVLRQRLPVESVAGDLRFLAHVADGIDRWVRAGRVVPDLHRADGQWW
ARWRLVGGARQRAWLAELAVAMPAALRVAGQPAAVLDDLVTELTDPIVRTRLADAPVTHPLVRALV
RDQPLETGSHQLAEVLRRWRESLTVDEPELVLRLLEPDGETGIDGDGGDDRDDTVALWRLEVCLRT
EGEAPAPVPATADPNLLRIAVEQLGRAQRAYPRLRDLPGDPHSLDLLLPTEVVADLVAHGAQALRE
AGVRLLLPRAWTIAEPTLRLAVSSAAPAAESTVGMQGLLSYRWELAVGDKVLTRAEMERLVRAKSD
LVQLRGEWVQADHKVLAAAARYVAAHLDTSPVTLADLLGEIAATRVDKVPLTEVTATGWAGELFDG
GREPVATPGGLKAQLRPYQLRGLSWLATMSRMGCGGILADDMGLGKTVQVLALLVHERETSTAPPG
PTLLVCPMSVVGNWQREAQRFAPGLRVLVHHGADRRRDAELDAAVADSDLVLTTYAILARDAAELS
RQSWDRVVLDEAQHIKNAATRQARAARALPARHRLALTGTPVENRLEELRSIMDFAVPKLLGTAPT
FRARFAVPIERGQDPNALSRLRFLTQPFVLRRVKADPAVIGDLPDKLEMTVRANLTVEQAALYQAV
VDDMLVKLRSAKGMARKGAVLGALTRLKQVCNHPAHFLGDGSPVLHRGRHRSGKLALVEDVLDTVV
ADGEKALLFTQFREFGDLLAPYLSERFGAPIPFLHGGVTKKNRDTMVERFQSGDGPPVMLLSLKAG
GTGLTLTAANHVVHLDRWWNPAVENQATDRAFRIGQRRDVQVRKLVCVDTIEERIDEMITGKSRLA
DLAVDAGENWITELGTEELRELFTLGAEAVGE

SEQ ID NO: 57, Nodularia spumigena Nodsp_SNF2 nucleic acid sequence
ATGGCAATTTTACACGGTAATTGGTTAGTAAGAAATCAAAATGGTTGTTTATTTATTTGGGGTGAA
ACTTGGCGTTCATCACGAGTCGATTTTGCTCTGAATGTATCTCAAGATATACCACTACATCCATTG
GTAATGTCACCAATTGATTTGAGTGAGTTGTTAAGTTATCATAATATCAAAATTCCTAGCTTAATA
CAGCAATCCCAAGTTGCTTTATCTGGCACTGGGCGAACTCGTAAAAGTACAAGTACTACTAAATTT
AGCTGGACAACTCACTCTCTAATCATTGATTTACCAACTCATATCTCAGAAAATAATCCCCAAGAA
ATAGAATTTATTTCCCCTTTGCATTCTGCTACTTTGGGTTCTGAAATAAATTCACCCCAATATCTC
CAACCGTGGCGAGTCGAGGGTTTTTGTCTCAACCCCACTGAAGCGATAAAATTTCTCGCTGCTGTT
CCTTTAAATGCTGCTAGAGAAGAAGATACTTTGTTCGGTGGAGATTTACGTTTTGGTCACAAATT
GCCCGTTGGAGTTTGGATTTAATCTCTCGGTGTAAGTTTTGCCAACTATTCAAAGACAGTTTGAT
AGTTCTATTGTTGCTAGGTGGCAAGTGCTTTTAGACAGTGCAATAGATGGAACACGCCTGGAAAAA
TTTTCTGCAAAAATGCCATTAGCTTGTCGTACTTATCGGAAGGGAATGGGGAGTGGGGAGTGGGGA
GTGGGGAGTGGGGAGGAATCTTCCCCATCCATAATGTATGTAGATTTTCCAACTGAACCCCAGGAA
CTATTATTAGGATTTCTCAACAGTACCATAGATGCCCAAGTGCGAGAAATGTTAGCTTCTCAACCT
CTACTAGAAACTAGAGTGATGGCATCTTTACCATCTGCGGTGCGACAGTGGTTGCAAGGTTTAACC
AGTGCATCTCACACAGTGAATGCAGATGCAATGGAAGTAGAAAGATTAGAAGCAGCCCTGAAATCT
TGGACTATGCCGTTGCAATATCAACTGGTAGGAAAACCCTCGTTTCGCGCCTGTTTTCAACTGCTT
CCCCCTGCTTCTGGGGCAACAGATTGGATATTGGCATATTTTCTCCAAGCTGCGGATGATGAAAAT
TTATTAGTGGATGCGGCAACTATTTGGCATCACCCAGTTGAACAATTAGTTTATCAAAATCGCACC
ATTGATCAACCCCAAGAAACTTTATTGCGGGGCTTGGGTTTAGCTTCGCGATTATATCCAGTTCTT
ACACCGAGTTTAGAAACAGAATATCCCCAATGTTGTCGCCTCAACCCATTACAAGCTTATGAATTT
ATCAAGTCTGTAGCTTGGCGATTTGAAGATAGTGGTTTGGGGGTAATTTTACCTCCTAGTTTGACT
AACCGCGAAGGATGGGCGAACCGTTTGGGGTTAAAAATTAGTGCTGAAACTCAAAAGAAAAAACAG
GGACGCTTGGGTTTACAAAGTTTACTGAATTTTCAATGGCAATTGGCAATTGGTGGACAAACAATT
TCTAAAACCGAGTTTAATAAACTGGTAGCTTTAAATAGCCCACTGGTAGAATTAACGGCGAATGG
GTGGAATTGCGACCCCAGGATATTAAAACAGCACAGACATTTTTTGCTTCTCGTAAAGACGAAATG
ACGCTTTCTTTGGAAGATGCTTTACGCCTCAGTTCTGGCGATACCCAAGCGATTGAAAAGTTACCT
GTGGTCAGTTTTGAAGCATCTGGGACATTGCAAGAGTTAATTGGGGCGTTAACCAATAATCAAGCC
ATTTCACCCCTCCCAACACCTGCAAATTTTCAAGGACAGTTACGACCTTATCAAGAAAGAGGGGCG

```
GCTTGGCTGGCTTTCTTAGAACGTTGGGGTTTAGGTGCTTGTTTGGCTGATGATATGGGGCTGGGA
AAAACAATTCAGTTAATTGCCTTTTTACTGCACCTCAAAGAACAAGACGCACTGGAAAATCCCACA
TTACTTGTTTGTCCGACTTCTATTTTAGGTAACTGGGAACGGGAAATTAAAAAATTTGCTCCTACT
CTCAAAGTTTTACAGCACCACGGCGATAAACGTCTCAAAGGTAAAGCGTTTGTAGAAGCAGTCAAA
AAACACGATGTAATTATTACCAGTTACTCACTCGTTCACCGGGATATTAAATCTTTGCAGAGTGTC
GATTGGCAAACAGTTGTATTAGATGAAGCCCAGAATGTGAAAAATCCTGAAGCTAAACAATCGCAG
GCTGTGAGGGGATTAAAAACTACATTTCGCATAGCTTTAACAGGGACACCAGTAGAAAACAAACTG
CAAGAATTGTGGTCTATTTTAGATTTTCTTAATCCTGGGTATTTGGGAAATCGTCAATTTTCCAG
AGACGGTTTGCTATGCCAATTGAAAAGTATGGTGATACAGCATCTTTAAATCAATTGCGGGGTTTA
GTTCAACCGTTTATTCTACGTCGTCTGAAAACAGATCGTGATATTATTCAAGATTTGCCAGAAAAG
CAAGAAATGACGGTTTTTTGTGGGCTTGCGGCTGAACAAGCTGCACTTTATCAACAAGTAGTTGAA
GCATCTTTAGTAGAAATTGAATCTGCTGAGGGTTTGCAACGTCGAGGGATGATTTTAGCTTTACTT
GTGAAACTTAAACAAATCTGTAATCATCCAGCCCAATATTTGAAAGCCGCGACATTACAAGAACAT
AGTTCTGCTAAACTGCAACGGCTAGATGAAATGTTAACGGTAGCTTTGGAGGAAGGAGATAGGGCT
TTAATTTTCACTCAATTTGCTGAATGGGGTAAGTTATTAAAAGCTCATTTACAACAAACACTTGGG
AAAGAAATATTCTTTTTATATGGTGGTAGCAGTAAAAAACAACGCGAGGAAATGATTGACCGTTTC
CAACATGACCCCCAAGGACCTCCGATTATGATTCTTTCTTTAAAAGCGGGTGGGGTAGGCTTGAAT
TTAACCAGGGCTAATCATGTATTTCACTTTGATAGATGGTGGAATCCCGCAGTGGAAAATCAAGCG
ACAGATAGAGTATTTCGTATTGGTCAAACCCGGAATGTGCAAGTGCATAAATTTGTCTGTACTGGC
ACATTAGAAGAAAAAATTCATGACATGATTGAAAGTAAAAAACAATTAGCGGAACAAGTAGTTGGT
GCTGGTGAGGAGTGGCTGACTGAAATGAATACTGACCAATTGCGTGATTTACTCATTCTTGATCGC
AGTGCCATAATTGATGAGGATGAAGTTTAA
```

SEQ ID NO: 58, Nodularia spumigena Nodsp_SNF2 translated polypeptide

```
MAILHGNWLVRNQNGCLFIWGETWRSSRVDFALNVSQDIPLHPLVMSPIDLSELLSYHNIKIPSLI
QQSQVALSGTGRTRKSTSTTKFSWTTHSLIIDLPTHISENNPQEIEFISPLHSATLGSEINSPQYL
QPWRVEGFCLNPTEAIKFLAAVPLNAAREEDTLFGGDLRFWSQIARWSLDLISRCKFLPTIQRQFD
SSIVARWQVLLDSAIDGTRLEKFSAKMPLACRTYRKGMSGEWGVGSGEESSPSIMYVDFPTEPQE
LLLGFLNSTIDAQVREMLASQPLLETRVMASLPSAVRQWLQGLTSASHTVNADAMEVERLEAALKS
WTMPLQYQLVGKPSFRACFQLLPPASGATDWILAYFLQAADDENLLVDAATIWHHPVEQLVYQNRT
IDQPQETLLRGLGLASRLYPVLTPSLETEYPQCCRLNPLQAYEFIKSVAWRFEDSGLGVILPPSLT
NREGWANRLGLKISAETQKKKQGRLGLQSLLNFWQLAIGGQTISKTEFNKLVALNSPLVEINGEW
VELRPQDIKTAQTFFASRKDEMTLSLEDALRLSSGDTQAIEKLPVVSFEASGTLQELIGALTNNQA
ISPLPTPANFQGQLRPYQERGAAWLAFLERWGLGACLADDMGLGKTIQLIAFLLHLKEQDALENPT
LLVCPTSILGNWEREIKKFAPTLKVLQHHGDKRLKGKAFVEAVKKHDVIITSYSLVHRDIKSLQSV
DWQTVVLDEAQNVKNPEAKQSQAVRGLKTTFRIALTGTPVENKLQELWSILDFLNPGYLGNRQFFQ
RRFAMPIEKYGDTASLNQLRGLVQPFILRRLKTDRDIIQDLPEKQEMTVFCGLAAEQAALYQQVVE
ASLVEIESAEGLQRRGMILALLVKLKQICNHPAQYLKAATLQEHSSAKLQRLDEMLTVALEEGDRA
LIFTQFAEWGKLLKAHLQQTLGKEIFFLYGGSSKKQREEMIDRFQHDPQGPPIMILSLKAGGVGLN
LTRANHVFHFDRWWNPAVENQATDRVFRIGQTRNVQHKFVCTGTLEEKIHDMIESKKQLAEQVVG
AGEEWLTEMNTDQLRDLLILDRSAIIDEDEV
```

FIGURE 10 (continued)

SEQ ID NO: 59, Nostoc sp. PCC7120 Nos_sp_PCC7120_SNF2 nucleic acid
sequence
ATGGCAATTCTACACGGTAGTTGGATATTAAATGAGCAGGAGAGTTGTTTATTTATTTGGGGGGAA
ACTTGGCGATCGCCACAAGTGGATTTTAATTTTGCGGAGATATCCCTCAATCCCTTGGCGCTGTCT
GCACTGGAATTAAGTGAGTGGTTGCAGTCTCAACATCAGGCGATCGCTAAGTTGTTACCGCAACAA
TTGGAAAAACGAACCTCCAAAGCAGCAAGTTCTGTAAAAATAAATTTATTAACTCATTCACAAATA
ATTGCCCTGCCAACGGAAATTTCCCAACCTCGTAAAAAAGAAACCATTTTAATTTCTCCTGTGCAT
TCTGCCGCTTTAGCATCTGAGTCAGACTCTGAAGTTTATTTACAAACTTGGCGTGTAGAAGGTTTT
TGTCTTCCTCCTAGTGCAGCAATTAAATTGCTAACTTCTTTACCTTTAAATATAACTAGTGGGGAG
AATGCTTTTTTAGGTGGAGATTTACGTTTCTGGTCACAAATTGCCCGTTGGAGTTTAGATTTAATT
TCTAGGTCTAAGTTTCTCCCAATTATCCAACGACAACCTAATAATTCTGTAAGTGCTAAATGGCAA
GTACTTTTAGATAGTGCCGTAGATGGAACTCGTTTAGAAAAGTTTGCTGCGAAGATGCCCTTGGTT
TGTCGGACTTATCAAGAAATTGGGAGTGGGGAATCTCCTATATATATAGATTTTCCTAGTCAGCCG
CAGGATTTAATCTTGGGTTTTCTCAATAGTGCGATAGATACGCAATTGCGGGAGATGGTGGGGAAT
CAGCCTGTGGTGGAAACTCGGTTGATGGCATCTTTACCATCGGCGGTGCGACAGTGGTTGCAAGCG
TTAATTGCTGCATCTAATTCAATTGATGCAGATGCTGTTGGTTTAGAAAGGCTGGAAGCGGCGCTC
AAGGCTTGGACGATGCCGCTACAATATCAACTAGCAAGTAAAAATCAATTTCGCACTTGTTTTGAA
TTACGTTCTCCAGAACCAGACGAAACTGAATGGACGCTGGCGTATTTCCTGCAAGCAGCCGATGAT
CCAGAATTTTTAGTAGATGCGGCGACTATTTGGCAAAATCCTGTTGAACAGCTAATTTATCAACAG
CGAACGATTGAAGAACCCCAGGAAACGTTTTTGCGAGGTTTGGGGTTAGCTTCTCGATTGTATCCG
GTCATTGCCCCCACTTTAGATACAGAATCACCCCAATTTTGTCATCTCAAGCCCATGCAGGCTTAT
GAATTTATCAAGGCTGTGGCTTGGCGATTTGAAGATAGCGGCTTAGGGGTGATTTTACCTCCTAGT
TTGGCGAATCGTGAAGGCTGGGCAAATCGCTTGGGTTTGAAAATCTCCGCCGAAACGCCGAAGAAA
AAACCAGGACGCTTAGGATTGCAGAGTTTGCTCAATTTCCAATGGCACTTAGCGATTGGTGGGCAA
ACTATTTCTAAAGCTGAATTTGACAGACTGGTAGCTTTAAAAAGCCCATTGGTAGAAATTAACGGC
GAGTGGGTGGAATTACGTCCCCAAGATATCAAAACAGCTGAAGCCTTTTTTACTGCGCGTAAAGAC
CAAATGGCCTTATCTTTAGAAGATGCCTTACGTCTAAGTAGTGGCGATACACAAGTAATTGAGAAA
TTACCAGTAGTCAGCTTTGAAGCCTCTGGCGCATTACAAGAATTGATTGGGGCGCTGACAAATAAT
CAAGCAGTTGCACCATTACCTACGCCGAAAAACTTCCAAGGACAGTTACGTCCTTATCAAGAAAGG
GGTGCGGCTTGGTTGGCGTTCCTCGAACGCTGGGGTTTAGGTGCTTGTCTCGCCGACGACATGGGA
CTGGGAAAAACGATACAGTTCATTGCTTTCCTTCTCCATCTTAAAGAACAGGATGTATTAGAAAAA
CCAACTTTACTAGTGTGTCCTACTTCTGTTTTAGGTAACTGGGAACGAGAGGTGAGAAAATTTGCA
CCTACACTTAAAGTTCTCCAGTATCATGGTGACAAACGTCCTAAAGGTAAAGCATTTCAAGAAGCA
GTAAAAAAACATGATTTAGTTATTACAAGTTACTCATTAATTCATAGAGATATCAAATCATTGCAG
GGTATTCCTTGGCAAATAATTGTTTTAGATGAAGCCCAAAATGTGAAGAATGCGGAAGCCAAACAA
TCACAAGCAGTCAGACAATTAGAAACAACATTTCGTATTGCTTTAACAGGTACACCAGTAGAAAAT
AGACTACAAGAACTTTGGTCAATTTTAGATTTTCTTAATCCTGGTTACTTAGGTAATAAGCAATTC
TTTCAAAGACGTTTTGCTATGCCAATTGAAAGTATGGTGATGCAGCATCTTTAAATCAATTGCGT
GCTTTAGTGCAACCATTTATTCTGCGTCGGCTGAAAACAGACCGTGATATTATTCAAGACTTGCCC
GATAAGCAAGAAATGACAGTATTTTGTGGTTTGACTGGAGAACAAGCTGCACTTTATCAAAAAGCG
GTAGAAACATCTTTAGCAGAAATTGAATCAGCCGAAGGATTGCAACGCCGAGGGATGATTTTAGCT
TTATTAATTAAACTCAAACAAATCTGCAATCATCCAGCCCAATATCTGAAAATAAATACATTAGAA
CAACACAGTTCTGGAAAACTGCAAAGATTAGAAGAAATGTTAGAAGAGGTGTTAGCAGAGAGTAAT
ACTTACGGTGTTGCCGGTGCGGGACGTGCTTTGATTTTACCCAATTTGCAGAATGGGGTAAGTTA
CTCAAACCACATTTAGAAAAACAACTAGGGCGGGAAATATTTTCTTATATGGTGGTACGAGTAAA
AAGCAACGAGAAGAAATGATTGACCGTTTTCAACACGACCCCAAGGGCCACCAATTATGATTCTC
TCCCTCAAAGCAGGTGGTGTAGGGTTGAACTTAACCAGGGCAAATCATGTATTTCACTTTGATAGA FIGURE 10 (continued)

TGGTGGAATCCAGCCGTAGAGAATCAAGCTACAGACCGCGTATTTCGCATTGGTCAAACTCGCAAT
GTACAGGTGCATAAATTTGTTTGTAATGGCACCTTAGAAGAGAAAATTCACGACATGATTGAAAGT
AAAAAACAACTAGCGGAACAGGTTGTTGGAGCAGGCGAAGAATGGTTAACTGAATTAGATACAGAT
CAACTCCGCAACTTACTGATACTTGATCGTAGTACAGTAATTGATGAAGAAGCAGATTGA

SEQ ID NO: 60, Nostoc sp. PCC7120 Nos_sp_PCC7120_SNF2 translated polypeptide
MAILHGSWILNEQESCLFIWGETWRSPQVDFNFAEISLNPLALSALELSEWLQSQHQAIAKLLPQQ
LEKRTSKAASSVKINLLTHSQIIALPTEISQPRKKETILISPVHSAALASESDSEVYLQTWRVEGF
CLPPSAAIKLLTSLPLNITSGENAFLGGDLRFWSQIARWSLDLISRSKFLPIIQRQPNNSVSAKWQ
VLLDSAVDGTRLEKFAAKMPLVCRTYQEIGSGESPIYIDFPSQPQDLILGFLNSAIDTQLREMVGN
QPVVETRLMASLPSAVRQWLQALIAASNSIDADAVGLERLEAALKAWTMPLQYQLASKNQFRTCFE
LRSPEPDETEWTLAYFLQAADDPEFLVDAATIWQNPVEQLIYQQRTIEEPQETFLRGLGLASRLYP
VIAPTLDTESPQFCHLKPMQAYEFIKAVAWRFEDSGLGVILPPSLANREGWANRLGLKISAETPKK
KPGRLGLQSLLNFQWHLAIGGQTISKAEFDRLVALKSPLVEINGEWVELRPQDIKTAEAFFTARKD
QMALSLEDALRLSSGDTQVIEKLPVVSFEASGALQELIGALTNNQAVAPLPTPKNFQGQLRPYQER
GAAWLAFLERWGLGACLADDMGLGKTIQFIAFLLHLKEQDVLEKPTLLVCPTSVLGNWEREVRKFA
PTLKVLQYHGDKRPKGKAFQEAVKKHDLVITSYSLIHRDIKSLQGIPWQIIVLDEAQNVKNAEAKQ
SQAVRQLETTFRIALTGTPVENRLQELWSILDFLNPGYLGNKQFFQRRFAMPIEKYGDAASLNQLR
ALVQPFILRRLKTDRDIIQDLPDKQEMTVFCGLTGEQAALYQKAVETSLAEIESAEGLQRRGMILA
LLIKLKQICNHPAQYLKINTLEQHSSGKLQRLEEMLEEVLAESNTYGVAGAGRALIFTQFAEWGKL
LKPHLEKQLGREIFFLYGGTSKKQREEMIDRFQHDPQGPPIMILSLKAGGVGLNLTRANHVFHFDR
WWNPAVENQATDRVFRIGQTRNVQVHKFVCNGTLEEKIHDMIESKKQLAEQVVGAGEEWLTELDTD
QLRNLLILDRSTVIDEEAD

SEQ ID NO: 61, Nostoc sp. PCC7120 Nos_sp_PCC7120_SNF2 II nucleic acid sequence
ATGAAAGTCCTTCATGGCTCGTGGATACCAAACCAATATAGCGATTTTGTGCAGTCTGGAGCATTT
TATCTATGGGTAGAAACTCCGATTAATAACAAAAAGCGTACTCATACACAAGTTCATCCCGGACAT
CTATCTTCTCTTGAATTACTCAATTTTCTGACTCAAACTTTGGGGATTAAAGAAACTGAAGCGCAA
TTAAAACAACGGATATGTTCTAAATATTTTGCCCTACCAACTGCTAATAATGAGCCATTACCTTCA
CCAGAGTTAGTCAAATATTTAGAAGTAGAAGTTCCTGAAGAGTATGAAAATTTTCAATATTGGCAG
GTAACTTGTTATGAAACTGTTACTTCTGTGAAAGCAGTGATAGCAATTAATATTATTAAATTACTC
AAAGATATTCATTTTTTAGCCCTGTACAATGCTAGTGAATTTCAATTAGGGTCAGATTTATTATTT
TGGTATCATTATACGCAATCATTTAGACAAATAATTACTAAGGATCAATATATTCCATCTTTAAAA
TATAGAGCGAACGCAGCGACTACAAAGAAAAAACCTAAACAACCACCCCCAGGATTTGAAATATAT
GCTGGTTGGGAAATAATTTCCGAGCAATACGAAGCCAATATTCAAAAATATATTGAATATATGCCA
TTGATTTGTGTAGCAGGTAACAGCACACAAACTGATAAATTAGAATTTTTGCTCCAGAAACTCTA
TTACGCCACTTCAGCGAGTATCTGCTTAATAATTTAGTGAGTAAGACACCATTGACCGCAGCATTT
GAAAAACAAATTGATGATTCTTTAATTCACTATTGTCTTTATCCCCAAAAACACAACCCACTCAAA
ACCCATACTGCTCTCCAAGAGTATCAGCAGTGGTTGGGATGGAAAAACAGGATTATCCGTACTCAA
GCTGAATCACCATTTCATCTTTGCTTCCAATTACATTCACCTGATGCTGAACAAATTGACAATTGG
CAGATGCAATTTTTAGTATCAAGTAAAAAGATCCGTCTCTAAAATTAGCTTTGGCAGATTACTGG
ATAATGAATTCCAAAACCAAAGCTGGTGTACATAAAGAGTTTGGCAAAGATTTCGATACTAATTTA
CTGCTGAATTTAGGCTATGCAGCAAGAATGTATCCCAAACTTTGGCAAGGTTTAGAAACGGACTCT
CCCACAGGAATGCAGCTAAGTTTAGATGAGGCGTTTGATTTTCTCAAAGATAGTGCTTGGGTGTTG
GAAGACTCAGGATTTAAGGTCATTGTCCCGGCTTGGTATACTCCGGCTGGTCGTCGTCGTGCGAAA
ATCCGCCTCAAAGCTTCTAGTGGTCGCAAGGTAGCTGCTACGGTAGGGAAAGCAAAAGTTATTTC

```
GGTTTAGATTCACTAGTGCAGTATCAGTATGAATTAGCAATTGGAGAGCAAACTCTCACACCTCAA
GAATGGGAACAATTGATTAATACTAAAGCACCACTAGTGCATTTTCGCGGTCAATGGATGGAATTA
GACCGGGATAAAATGCAGCAGTTATTAGAATTTTGGCAGTCCCACGGCGATGAACAGCCCCAAATG
AGCTTGTTAGAGTTCATGCAACGCAGCGCCCAAGGGGAAGATGACTGGGAAATTGAATATGATGCA
GCTTTATCAGAAATAATGGCAAAGTTACAAGATAAGAGTCAGCTAGAGCCAATTTCTGAAGACTTA
AATTTGCAAGGCAACCTGCGAGAATATCAAAAGCGGGGTGTAGCCTGGTTACAATATTTAGAAAAA
TTGGGATTAAATGGCTGTTTAGCCGATGATATGGGACTGGGTAAGTCCGTGCAGGTAATTGCGAGA
TTAGTACAGGAGAAAGATAGCCAAAGTTCCCCATTACCGACATTATTAATTGCGCCGACTTCGGTT
GTTGGTAACTGGCAAAGAGAAATTGCTAAGTTTGCACCCCATTTAAAAACTATGGTGCATCATGGT
AGCGATCGCCTGCAAGATGCTGCGGAGTTTAAGTCCGCCTGTCAACAGCATGATGTGGTGATAAGT
TCCTTTACTTTGGCTCGCTTAGATGAAAAACTCCTAAATAGTGTGACATGGCAACGGTTAGTTTTA
GATGAAGCACAAAACATTAAAAATCCCAAAGCAGCGCAGACTAAAGCTATACTCAAACTCAGTGCT
AAACACCGTCTAGCTTTAACTGGTACACCAGTTGAGAACCGCTTACTTGATTTGTGGTCAATTTTT
AATTTTCTCAATCCCGGTTATTTAGGGAAAGAAGCACAGTTTCGCAAATCCTTTGAAATTCCCATC
CAGAAGGACAACGATAAAGTAAAATCGACTACCTTAAAGAAACTGGTTGAACCGTTAATTTTACGA
CGGGTCAAAACAGACCAATCAATTATTAAAGACTTACCAGATAAAGTTGAACAAAAACTCTATACC
AACCTCACCAAAGAACAGGCTTCGCTATATGAAGTGGTAGTCAGAGATGTGGAAGAAAAATTGCAA
GAAGCTGAGGGAATACAACGCAAAGGTTTAATTCTCTCAACGCTGATGAAATTAAAACAGATTTGC
AATCATCCCAGACAGTTCCTCCAAGATAATAGCGAATTTTTACCGGAGCGCTCGCACAAACTTTCC
CGCTTAGTCGAAATGGTAGATGAAGCCATTTCTGAAGGAGAAAGTCTTTTAATATTTAGTCAATTT
ACAGAAGTCTGCGAACAAATAGAAAAATATCTCAAACACAACTTACATTGCAATACCTACTACCTA
CATGGGGGTACAAGTCGCCAACGTCGGGAACAAATGATTAGTGACTTTCAAAATCCTGATACGGAA
GCATCTGTATTTGTCCTTTCCCTAAAAGCTGGCGGCGTGGGGATTACTTTAACTAAAGCCAACCAC
GTCTTTCATTTTGACCGTTGGTGGAATCCAGCCGTTGAAGACCAAGCCACAGACCGCGCTTTTCGC
ATAGGTCAGAAAAAAAATGTGTTTGTACATAAATTTGTCGCCCTTGGGACTTTAGAAGAAAGAATC
GACCAAATGATTGAAGATAAGAAAAAACTTTCTTCCGCCGTAGTTGGTAGTGATGAATCGTGGCTA
ACCGAATTAGATAACGAAGCCTTTAAGAAACTAATTGCCTTGAATAAAAGCACAATTATGGAGTAG
```

SEQ ID NO: 62, Nostoc sp. PCC7120 Nos_sp_PCC7120_SNF2 translated polypeptide\II

```
MKVLHGSWIPNQYSDFVQSGAFYLWVETPINNKKRTHTQVHPGHLSSLELLNFLTQTLGIKETEAQ
LKQRICSKYFALPTANNEPLPSPELVKYLEVEVPEEYENFQYWQVTCYETVTSVKAVIAINIIKLL
KDIHFLALYNASEFQLGSDLLFWYHYTQSFRQIITKDQYIPSLKYRANAATTKKKPKQPPPGFEIY
AGWEIISEQYEANIQKYIEYMPLICVAGNSTQTDKLEFFAPETLLRHFSEYLLNNLVSKTPLTAAF
EKQIDDSLIHYCLYPQKHNPLKTHTALQEYQQWLGWKNRIIRTQAESPFHLCFQLHSPDAEQIDNW
QMQFLVSSKKDPSLKLALADYWIMNSKTKAGVHKEFGKDFDTNLLLNLGYAARMYPKLWQGLETDS
PTGMQLSLDEAFDFLKDSAWVLEDSGFKVIVPAWYTPAGRRRAKIRLKASSGRKVAATVGESKSYF
GLDSLVQYQYELAIGEQTLTPQEWEQLINTKAPLVHFRGQWMELDRDKMQQLLEFWQSHGDEQPQM
SLLEFMQRSAQGEDDWEIEYDAALSEIMAKLQDKSQLEPISEDLNLQGNLREYQKRGVAWLQYLEK
LGLNGCLADDMGLGKSVQVIARLVQEKDSQSSPLPTLLIAPTSVVGNWQREIAKFAPHLKTMVHHG
SDRLQDAAEFKSACQQHDVVISSFTLARLDEKLLNSVTWQRLVLDEAQNIKNPKAAQTKAILKLSA
KHRLALTGTPVENRLLDLWSIFNFLNPGYLGKEAQFRKSFEIPIQKDNDKVKSTTLKKLVEPLILR
RVKTDQSIIKDLPDKVEQKLYTNLTKEQASLYEVVVRDVEEKLQEAEGIQRKGLILSTLMKLKQIC
NHPRQFLQDNSEFLPERSHKLSRLVEMVDEAISEGESLLIFSQFTEVCEQIEKYLKHNLHCNTYYL
HGGTSRQRREQMISDFQNPDTEASVFVLSLKAGGVGITLTKANHVFHFDRWWNPAVEDQATDRAFR
IGQKKNVFVHKFVALGTLEERIDQMIEDKKKLSSAVVGSDESWLTELDNEAFKKLIALNKSTIME
```

FIGURE 10 (continued)

SEQ ID NO: 63, Nostoc punctiforme PCC 73102 Nospu_PCC\73102_SNF2
nucleic acid sequence
ATGGCGATTTTACACAGTAATTGGTTACTAAAAAGTCAAAAAGGTTGTTTATTTATTTGGGGAGAA
ACTTGGCGATCGCCACGAGTTAATTTCGAGTCTAATGGATCTGGAGATATCCCACTAAATCCATTG
GCAATGACATCACTAGAGTTGAGCGAGTGGTTGGTTTCCCAGAAGATGGCCATTACCAACTTTATC
CAGCAACCCCAAATTGCCATCGCTACTACTGGGCGAACACGTAAAGCAGCCACTGCCACTGAGATA
AACTTACCAACGCATTCACAAATAATTGCCTTACCAACTTATATTCCCGAAGAGAGTGCAGAAGGA
ACATCTGCAATTTTCCCTGTGCATTCTGCCAGCTTGAGACTAGAAACAGACTCTCCGCAATATTTG
CAACCGTGGCTAGTTGAGGGTTTTTGTCTTAACCCCAGCGAAGCAGTAAAATTTCTCGCTGCTGTT
CCCCTGAATGCTGCTAAAGGGGAAGATGCTTTTTTAGGAGGAGATTTACGTTTTTGGTCGCAAGTT
TCCCGATGGAGTTTAGATTTAATCTCGCGGTGTAAGTTTTTACCAAGAATTGAACGGCAATCAGAC
GGTGCATTTGCTGCTAAATGGCAAGTACTTCTAGACAGTGCTGTAGATGGAACTCGCCTAGAAAAG
TTTTCTGCGGATATGCCGTTGGTTTGCCGCACTTATCAGGAGGGAGTGGGGACTGGGGACTGGGGA
CTGAGGACTGGGGAGGAGTTTTCCCAATCCCTAATCCCTAATTCCCAATCCCTACTTTATGTAAAC
TTCCCTACTGAACCTCAAGAATTGTTGCTGGGATTTCTCAACAGTACGATAGATGCCCAAGTGCGA
GGGATGGTGGGTTCTCAGCCTCCAATGGAAGCTAAGGCAATGGCATCTTTACCATCTGGGGTGCGG
CAGTGGTTGCAAGGCTTGACTAGTACATCTGGTACAGTTAACGCAGATGCCATTGAAGTGGAACGA
CTGGAAGCGGCACTGAAGGCTTGGATGATGCCGCTACAATACCAATTAACTCTTAAAACTCTATTT
CGTACCTGTTTTCAACTGCGTTCTCCAGAAGCTGGCGAAACAGATTGGACATTGGCGTATTTTCTG
CAAGCGGCTGACGATCCTGATTTTTTGGTGGATGCGGCAACTATTTGGAACAATCCAGTTGAACGT
TTGGTTTATGAAAATCGAACAATTGAGCAACCACAGGAAACATTTTTGCGAGGTTTAGGGGTAGCT
TCCCGATTATATCCAGCGATCGCACCCAGTTTTGAAACCGAATATCCCCAATCTTCTCGGATCACA
CCCATGCAAGCTTATGAGTTTATCAAGGCTGTAGCTTGGAGGTTGGAAGACAGTGGTTTGGGGGTA
ATTTTGCCTCCTAGTTTAGCGAACCGCGAAGGATGGGCAAATCGTTTGGGTTTGAAAATTACTGCT
GAAACCCCAAAGAAAAAGCAGGGACGTTTAGGGTTGCAAAGTCTGCTGAATTTCCAATGGCAATTG
GCAATTGGCGGACAGACTATTTCCAAAGCTGAGTTTGATAAACTTGTGGCTTTAAATAGTCCACTA
GTGGAAATTAACGGTGAGTGGGTAGAATTGCGGCCCCAAGATATCAAGACAGCCCAAACATTTTTT
ACCACTCGCAAAGACCAAATGGCGCTTTCCTTGGAAGATGCCTTGCGTTTCAGTACAGGAGATACC
CAGGTAATTGAAAAATTACCAGTGGTCAGCTTTGAGGCATCTGGGGCATTGCAAGAGTTGATTGGG
GCGCTAAATAATAATCAAGCGATCGCACCTTTACCGACACCAGTAGGCTTTAAAGGACAGTTGCGA
CCTTATCAAGAACGTGGTGCTGCTTGGCTGTCCTTCTTGGAACGTTGGGGCTTAGGCGCGTGTCTC
GCCGACGATATGGGACTCGGTAAAACTATTCAGTTTATTGCTTTTTTGCTACATCTTAAAGAACAG
GATGCACTAGAAAATTCAACACTGCTAGTTTGTCCAACTTCTGTTTTAGGCAACTGGGAAAGGGAA
GTCAATAAATTTGCACCAAGCCTGAAAATTTTGCAATATCACGGTGACAAACGTCCAAAAGGGAAA
GCGTTTTTAGAAGCAGTGAAAAATCACGATTTAATCGTTACCAGCTACTCACTGCTTCATCGGGAT
ATCAAGTCATTGCAAAGTGTTCCTTGGCAGATAATTGTTTAGACGAAGCCCAGAATGTGAAAAAT
CCAGAGGCGAAGCAGTCAAAAGCTGTGCGGCAATTAGAAGCTACATTTCGCATTGCATTAACGGGG
ACACCAGTAGAAAATAGACTGCAAGAACTATGGTCTATTTTGGATTTTCTCAATCCAGGGTATTTA
GGTAATAAGCAATTTTTCCAGCGGCGGTTTGCCATGCCAATTGAAAAGTATGGTGATACGGCTTCT
TTGGGTCAATTACGTTCATTAGTTCAGCCATTTATACTGCGGCGATTAAAAAGCGATCGCGAAATT
ATTCAAGACTTGCCAGATAAGCAAGAGATGACCGTATTTTGCGGTTTAACTGCCGACCAAGCTGCA
CTTTATCAACAAGTTGTAGAACAATCTTTAGTAGAGATAGAATCTGCTGAAGGATTGCAACGTCGG
GGGATGATTTTGGCTTTGCTAATCAAACTGAAGCAAATCTGCAATCATCCAGCCCAATATTTGAAA
CAGGCGACATTAGAGCAACATAATTCAGCCAAACTTCTGCGGCTAGAAGAAATGTTAGAAGAAGTT
TTAGCAGAAAGTGACCGGGCTTTAATCTTTACACAATTTGCAGAGTGGGGTAAGTTACTTAAACCC
AAAAGTGTTGAATGTTAA FIGURE 10 (continued)

SEQ ID NO: 64, Nostoc punctiforme PCC 73102 Nospu_PCC\73102_SNF2 translated polypeptide
MAILHSNWLLKSQKGCLFIWGETWRSPRVNFESNGSGDIPLNPLAMTSLELSEWLVSQKMAITNFI
QQPQIAIATTGRTRKAATATEINLPTHSQIIALPTYIPEESAEGTSAIFPVHSASLRLETDSPQYL
QPWLVEGFCLNPSEAVKFLAAVPLNAAKGEDAFLGGDLRFWSQVSRWSLDLISRCKFLPRIERQSD
GAFAAKWQVLLDSAVDGTRLEKFSADMPLVCRTYQEGVGTGDWGLRTGEEFSQSLIPNSQSLLYVN
FPTEPQELLLGFLNSTIDAQVRGMVGSQPPMEAKAMASLPSGVRQWLQGLTSTSGTVNADAIEVER
LEAALKAWMMPLQYQLTLKTLFRTCFQLRSPEAGETDWTLAYFLQAADDPDFLVDAATIWNNPVER
LVYENRTIEQPQETFLRGLGVASRLYPAIAPSFETEYPQSSRITPMQAYEFIKAVAWRLEDSGLGV
ILPPSLANREGWANRLGLKITAETPKKKQGRLGLQSLLNFQWQLAIGGQTISKAEFDKLVALNSPL
VEINGEWVELRPQDIKTAQTFFTTRKDQMALSLEDALRFSTGDTQVIEKLPVVSFEASGALQELIG
ALNNNQAIAPLPTPVGFKGQLRPYQERGAAWLSFLERWGLGACLADDMGLGKTIQFIAFLLHLKEQ
DALENSTLLVCPTSVLGNWEREVNKFAPSLKILQYHGDKRPKGKAFLEAVKNHDLIVTSYSLLHRD
IKSLQSVPWQIIVLDEAQNVKNPEAKQSKAVRQLEATFRIALTGTPVENRLQELWSILDFLNPGYL
GNKQFFQRRFAMPIEKYGDTASLGQLRSLVQPFILRRLKSDREIIQDLPDKQEMTVFCGLTADQAA
LYQQVVEQSLVEIESAEGLQRRGMILALLIKLKQICNHPAQYLKQATLEQHNSAKLLRLEEMLEEV
LAESDRALIFTQFAEWGKLLKPKSVEC

SEQ ID NO: 65, Pelodictyon phaeoclathratiforme BU-1 Pelph_BU-1_SNF2 nucleic acid sequence
ATGATTGCGCTGCACATCTCCATCATTGACGGAGTCCCGCTACTCTGGAGTGAGGGAAAAAGATC
GGGATGCTGAAGGAGTTACGCCTCGCAACGGCTGGAATCGGCATGTTTTCCCTGCTCGACAACACC
ACAAAAGAGTTTTGTGTCTGGCTGCCCTGCCGCGAGAAAAAAGCTGTCCCATCATCTCCGCTTGTC
GGCGCCATGCCCGACCTGAGTGATGAAGAGCAACTCCATGCCTTTCCGATTACCGCGCTTCGGCTG
AATTTCAACGCTCTGTTCGAGCTTTCCCTGCTTACGGAAAAGGGCAACATCCCCGGCAGTGGCATC
ATCTTCGGAAGCTCTCTCCACTGGGCACGGCAGGTAGTAAAAATTGCACTGAACATTGTCAGAACC
CAGTCGCTGCTCCCTTCGATCATCAAAAACGATACATTCTGGGAGGCCTTGTGGTTGCCCCTCCCC
GACAGTGCCACATCCCTCGCAGTTGAACAGCTTGCCGATGCCATGCCTGCGGTCTGTCGCTCTCTC
GGCCGCACCGACACGCAACCGCCGGAAACACCAAAAAAGTTACTGCTCAAAGGACTTCTCTCTTTC
CTTGTCAATACACTGTCACGTACTTTTGAAAGAGCAGGGGTGCCAAAAATCAGTGACTTCGAGAGT
ATCCATGACGCGTGGCTTCATGCATTATCAAACAGTGATCCCCGGCTGAAATGGAAAAATGAGCAG
GAGATTGAGCAGTTTGCCTGTCAGCTCAACGCATGGCGGCGTCCCATTGACCTGCATGAGCGATCA
CCCTTCAGGTTTTGCCTGCAACTGACAGAGCCACCACTGAAAGGGCGGAAAAAGGAGCGCTGGCAT
GTTGCCTATCAACTGCAGTTGAAAGCGGATCCAAGCCTGATTCTTGACGCCGGGGATCTCTGGAAC
CCCGAAAGCGAGGCATCACAGCACGCTTTAACGTATACCTCCGATTGTACCGAATTCCTGCTTACT
TCCCTGGGACAAGCCTCCGGCCTCTGCCCCGCAGTCACCCAAAGCCTGAAAAAGAAGCAGCCGGGT
GGCTTTGATCTTGATACCGAAGGGGCTTACAGATTTTGCTGGAGTATGCGGAACTGTTGCGAAGC
GCAGGATTTGTGGTCAAGCTTCCCTCGTGGTGGATCGGTCGCAGAGGAGTCAACCGTATCGGGATC
AAGACAAAAGTGAAGCTTCCCTCTATGAAAGGAAGCGGGTCGGGTCTCACGCTGGATCGCATGGTT
GCCTGCGATTATGCTGCTGCACTTGGCAATGAGGAGCTTGACCTGCAGGAGCTGAAAACACTGGCA
AACCTGAAAGTTCCGCTGGTACGGGTGCGCGGACAGTGGACACAGATTGACCATAAGGAGCTTGCC
AATGCTCTCCATTTTCTTGAAAAACATCCAACTGGTGAACTTTCTGCCAGAGAACTCCTCTCAACA
GCTCTCGGAGCACAAAAAAGGAGGATGCTCTCTTTCTTCGATCGGTTGAAATCGAGGGGTGGCTT
CAGGAACTGCTTGAAAAACTTTCCTCTCAGGGACAATTTGAACTGCTTCCACCACCTGAGCATTTC
GAGGGAACGCTTCGCCTCTATCAGGAGCGAGGCTTTTCATGGCTCTCATTTCTCCGCAAGTGGGGA
CTGGGCGCCTGTCTTGCCGACGACATGGGCCTTGGCAAAACCATTCAGACGCTTGCACTGCTGCAG
CGGGAGCGTGAACTTGGAGAAAAAGGCGGTGCTCCTGATCTGCCCCACCTCTGTAGTCAACAAC
TGGCGAAAGGAGGCGGAGCGGTTCACTCCGGATTTAGCGGTGCTGGTGCATCATGGTATCGACCGG

```
ATGAAAACAGCAGATTTTCGCAAAGCTGCAAGCGCTTCAGCCCTTGTCATTTCAAGCTATGGATTG
TTACAGCGCGACCTTGAATTTCTGTCGAAGGTTCCCTGGGCAGGCATTATTCTCGATGAAGCGCAG
AACATCAAAAACCCTGAGACAAAACAGTCAAAAGCTGCCCGAACAATCCGGGCTGATTACCGTATT
GCCCTGACCGGCACTCCCGTTGAAAATCATGTCGGCGACCTTTGGGCACTCATGGATTTTCTCAAT
CCCGGTTTTCTTGGAACCCAGCACTTTTTCAAACAGAACTTCTACACGCCGATTCAGTGGTATGGC
GACCCTGAGGCTTCAGCACGACTGAAGTCGCTGACCGGCCCGTTTATTCTGCGCCGCATGAAAAGC
GACAAGTCGATTATTTCCGATCTGCCCGACAAGATCGAAATGAAAGAGTATTGCTCGCTGACCAAA
GAGCAGGCATCGCTCTACAAGGCTGTTGTCGATGAACTGCAGGAGAAAATTGAAAGCGCCGAAGGG
ATTGACCGGCGGGGCCTTGTACTTGCGCTGCTGGTCAAGCTCAAGCAGGTCTGCAACCATCCGGCA
CATTTGCTTGGCGACAACTCTGCCATTGCACATCGTTCAGGAAAAATAAAACGCCTGACCGAACTG
CTTGGCGACATCCGCGAAGCTGGCGAAAAAACGCTGCTCTTTACACAGTTTACCATGATGGGAACG
ATGCTCCAGCACTATCTTCAGGAGTTGTACGGTGAAGAGGTACTGTTTCTGCACGGTGGCGTAACC
AAAAAAAAGGCGGGATGAGATGGTAGAGAGCTTCCAGAAGGAAGAGGGCAGTTCACCCTCCATCTTT
ATTCTCTCACTGAAAGCCGGAGGAACGGGTCTTAACCTGACAACAGCGAACCACGTTGTTCACTTT
GACCGATGGTGGAACCCGGCAGTAGAGAATCAGGCAACTGACCGGGCTTTCCGTATCGGGCAGCAC
AAAAACGTTGAAGTTCATAAATTTATTACGACGGGCACGCTCGAAGAGCGCATTGATGAGATGATT
GAGAAAAAAACAACGGTCGCCGGCCAGGTTCTCGGAACGGGTGAGCAGTGGCTGACCGAACTGTCG
AACAATGATCTGCGCAAGCTCATTATGCTCGGACAGGAAGCAATGGGAGAATAA

SEQ ID NO: 66, Pelodictyon phaeoclathratiforme BU-1 Pelph_BU-1
SNF2 translated polypeptide
MIALHISIIDGVPLLWSEGKKIGMLKELRLATAGIGMFSLLDNTTKEFCVWLPCREKKAVPSSPLV
GAMPDLSDEEQLHAFPITALRLNFNALFELSLLTEKGNIPGSGIIFGSSLHWARQVVKIALNIVRT
QSLLPSIIKNDTFWEALWLPLPDSATSLAVEQLADAMPAVCRSLGRTDTQPPETPKKLLLKGLLSF
LVNTLSRTFERAGVPKISDFESIHDAWLHALSNSDPRLKWKNEQEIEQFACQLNAWRRPIDLHERS
PFRFCLQLTEPPLKGRKKERWHVAYQLQLKADPSLILDAGDLWNPESEASQHALTYTSDCTEFLLT
SLGQASGLCPAVTQSLKKKQPGGFDLDTEGAYRFLLEYAELLRSAGFVVKLPSWWIGRRGVNRIGI
KTKVKLPSMKGSGSGLTLDRMVACDYAAALGNEELDLQELKTLANLKVPLVRVRGQWTQIDHKELA
NALHFLEKHPTGELSARELLSTALGAQKKEDALFLRSVEIEGWLQELLEKLSSQGQFELLPPPEHF
EGTLRLYQERGFSWLSFLRKWGLGACLADDMGLGKTIQTLALLQRERELGEKRAVLLICPTSVVNN
WRKEAERFTPDLAVLVHHGIDRMKTADFRKAASASALVISSYGLLQRDLEFLSKVPWAGIILDEAQ
NIKNPETKQSKAARTIRADYRIALTGTPVENHVGDLWALMDFLNPGFLGTQHFFKQNFYTPIQWYG
DPEASARLKSLTGPFILRRMKSDKSIISDLPDKIEMKEYCSLTKEQASLYKAVVDELQEKIESAEG
IDRRGLVLALLVKLKQVCNHPAHLLGDNSAIAHRSGKIKRLTELLGDIREAGEKTLLFTQFTMMGT
MLQHYLQELYGEEVLFLHGGVTKKRRDEMVESFQKEEGSSPSIFILSLKAGGTGLNLTTANHVVHF
DRWWNPAVENQATDRAFRIGQHKNVEVHKFITTGTLEERIDEMIEKKTTVAGQVLGTGEQWLTELS
NNDLRKLIMLGQEAMGE SEQ ID NO: 67, Prochlorococcus marinus str. CCMP1375 Proma
CCMP1375 SNF2 nucleic acid sequence
ATGACTCTGCTGCACGCCACTTGGATTTCAACTAATTGGCATCCATCTAATTTAGGTCAATCAGAA
TTGTTCCTTTGGGCAGACCAATGGCGCGTAGTAACTCCAAAACAAATAATACAAACACCTTCACCT
CACCCGTTTAGCCTATCTTCAGATGAATTAAAAGAATGGCTCAATAGCAAAAATTATTGCCTAAT
GAGAGTATTAATACATCTGCATGTCTCACTCTTCCTAGTAAACCCATTCACAAAAAAAATAACCAA
AAATCTAAGAATCAAAAACTGGTATTGAATCTGAATGGAAGGGACTCCCTTTACAAGCTCATGAA
GAAATAGCAACACAATATGAATGTTGGCCATGGAAAGTAGATGGAATTTCACTCACTACTGTCGAA
GCAACAGAATGGCTTACAAAATTACCTTTATCAAAAAAGATTCTGATCTTAGTGAAGAATTACTT
TGGTGGGCTCATTTAGAGCGTTGGTCTCTTAATCTAATTGCGAGTGGACTATGGCTACCTCAAGTT
```

FIGURE 10 (continued)

```
AAATTACACAAGAAAGAAGGAAATGAATATCGTGCATCATGGATACCTCTGCTGAATCAAGAAAAT
GAAAGAAATCGCTTAGAAGAGTTTGCAAAAATATTCCCTTGGTCGCTATTTGTGCAGTCCCATGG
ATAGAAGCTAAAGGACAAATAGTCAATACTGAGCAAGTCTCAAATTCAAACAATAATACACTCTCT
TTATATAGGCCAAGACACAATCGCGTAGAAGTGATGGATCTTCTCGAAGAACTTATTGATGCACAA
CTTCGAAAAGATTTTCAACCAAGAACTAAAAACTTGGATCCATTGTTAAAGCGTGGCAAGAAGCA
CTTGGCACGAAAGATGGAATAATTAACCTATCGAATGAAAACGCTAAAAGATTAGAAAAAGCAAGT
AAGAATTGGAAAAGAGGGTTGTCTAGTAATGTTCAACCTGCGAAAACATGTCTAGAGCTAATTGCA
CCGATTGATGATCTAGATTTATGGGACTTAAACTTTTCATTGCAATCAGAATCAGATCCGAGTATC
AGACTAGCTGCAGATCAAATTTGGGAAGCAGGCGTAGAAGTAACCAAAGTTGGCGGAATAACAATT
GACAACCCAAGTGAAATTCTTTTAGAAGGCCTAGGAAGAAGTCTTGAAATTTTCCCTCCAATTGAA
AAAGGACTAGAAAGCCCAACTCCTCACACAATGAAACTGTCTGCATCAGAAGCATTTGTACTTATT
AGAACAGCAGCAGCAAAACTTCGTGACATGGGTATTGGTGTAATACTGCCTAATAGTTTGTCCAAA
GGATTTGCAAGTCGACTTGGTCTTGCTATTCAAGCCGAATTACCAGAGTCTTCACTAGGCGTAATG
CTAGGAGAAAGTTTGAACTGGGATTGGGAGTTAATGATCGGAGGTATAAATTTAAGCATGAAAGAA
CTAGAAATGCTTGCAAAAAAAATAGTCCTCTACTCAATCACAAAGGGACATGGATCGAATTACGT
CCTAATGATCTGAAAAATGCTTCAAAATTTTTGCTAATACTCCAGAATTAAACCTCGATAAAGCA
TTAAGGCTTAGTGCTAATAAAGGCAACACTTTTATGAAACTTCCAGTACATCATTTGAATCTGGA
CCAAGATTACAAAGTGTCTTAGAGCAATATCACCATCAGAAAGCGCCTGAACCTTTACCAGCACCT
AATGGATTCCATGGGCAATTAAGGCCTTACCAAGAAAGAGGTCTTGGGTGGCTTGCATTTCTTTAT
CGTTTTAAGCAAGGAGCATGCTTAGCAGATGACATGGGGCTTGGTAAAACTATTCAATTATTATGT
TTTATTCAGCACCTAAAAGTTCAAAACGAGCTTACTAAGCCTGTACTCCTAATTGCGCCTACATCT
GTGCTGACAAATTGGAAAAGAGAGGCTGCCACTTTTACTCCAGAACTATGTATACATGAACACTAT
GGTAGTAAGAGACATTCTTCAATACCAAAATTACAAAATTATCTAAAAAAGTTGACATTATGATC
ACAAGTTATGGGTTACTTTATCGAGATGGCGAGCTGCTACAAGAAATCGACTGGCAAGGAATAGTT
ATTGATGAAGCTCAAGCTATTAAAAATTCCAAATCAAAGCAAAGTATTATAACTAGAGCAATAAGC
AAAAATCTCATAAGTAATCCCTTTAGAATTGCTTTAACAGGAACGCCAGTAGAAAATCGTATTAGT
GAACTATGGGCACTAATGGATTTCCTTAATCCAAAAGTATTAGGTGAAGAAGATTTTTTTAATCAG
CGATACAAGTTACCGATTGAGCATTATGGCGACATCTCTTCATTAAAAGATCTCAAAACACAGGTC
AGTCCTTTTATTTTAAGAAGATTGAAAACCGATCAATCTATTATTTCTGATTTGCCTCAAAAGATT
GAATTAAATGAGTGGGTTGGACTAAGCCAAGAGCAAGAGCTTCTATATAAACAAACGGTAGAGAAA
AGCTTAGATGAACTCGCCTCATTACCCATTGGTCAACGCCAGGGTAAAACATTGGGTCTACTTACT
CGTCTTAAACAAATTTGTAATCATCCAGCAATTGCTTTAAAAGAAACTCAAGTCGAGAAGAATTTC
TTATTAAGATCTTCAAAATTACAAAGACTGGAAGAAATACTACAAGAAGTGAAAGAATCTCATGAT
AGAGCTCTGCTCTTTACTCAATTTGCTGAATGGGGGCATTTATTGCAAGCGTACTTACAAACAAAA
TGGGAATCAGAAGTACCTTTCCTACACGGAGGCACTCCTAAAGGGAAGCGACAAGAAATGATAGAT
CGTTTTCAAGATGATCCTAGAGGGCCAAATATCTTTTTACTTTCACTAAAAGCAGGAGGAGTGGGT
CTTAATCTAACTCGTGCGAATCATGTTTTTCATATTGATCGTTGGTGGAATCCAGCAGTAGAAAAT
CAAGCAACAGATCGTGCATACCGAATTGGTCAAAAAAAAGTGTTATCGTCCATAAGTTTATAACC
ACCGGCACAATCGAAGAAAAATCAATCAAATGATTCTCGAAAAGACTGAACTAGCAGAAAATATT
GTCGGATCAGGAGAAAGCTGGTTAGGGCAATTAAGTCTTGAAAAATTGAGTGAATTAGTTGCTTTA
GATAGCAATCCAGAATTCTAA
```

SEQ ID NO: 68, Prochlorococcus marinus str. CCMP1375 Proma
CCMP1375 SNF2 translated polypeptide
MTLLHATWISTNWHPSNLGQSELFLWADQWRVVTPKQIIQTPSPHPFSLSSDELKEWLNSKKLLPN
ESINTSACLTLPSKPIHKKNNQKSKNQKTGIESEWKGLPLQAHEEIATQYECWPWKVDGISLTTVE
ATEWLTKLPLSKKDSDLSEELLWWAHLERWSLNLIASGLWLPQVKLHKKEGNEYRASWIPLLNQEN
ERNRLEEFAKNIPLVAICAVPWIEAKGQIVNTEQVSNSNNNTLSLYRPRHNRVEVMDLLEELIDAQ LRKDFQPRTKNLDPLLKAWQEALGTKDGIINLSNENAKRLEKASKNWKRGLSSNVQPAKTCLELIA
PIDDLDLWDLNFSLQSESDPSIRLAADQIWEAGVEVTKVGGITIDNPSEILLEGLGRSLEIFPPIE
KGLESPTPHTMKLSASEAFVLIRTAAAKLRDMGIGVILPNSLSKGFASRLGLAIQAELPESSLGVM
LGESLNWDWELMIGGINLSMKELEMLAKKNSPLLNHKGTWIELRPNDLKNASKFFANTPELNLDKA
LRLSANKGNTFMKLPVHHFESGPRLQSVLEQYHHQKAPEPLPAPNGFHGQLRPYQERGLGWLAFLY
RFKQGACLADDMGLGKTIQLLCFIQHLKVQNELTKPVLLIAPTSVLTNWKREAATFTPELCIHEHY
GSKRHSSIPKLQNYLKKVDIMITSYGLLYRDGELLQEIDWQGIVIDEAQAIKNSKSKQSIITRAIS
KNLISNPFRIALTGTPVENRISELWALMDFLNPKVLGEEDFFNQRYKLPIEHYGDISSLKDLKTQV
SPFILRRLKTDQSIISDLPQKIELNEWVGLSQEQELLYKQTVEKSLDELASLPIGQRQGKTLGLLT
RLKQICNHPAIALKETQVEKNFLLRSSKLQRLEEILQEVKESHDRALLFTQFAEWGHLLQAYLQTK
WESEVPFLHGGTPKGKRQEMIDRFQDDPRGPNIFLLSLKAGGVGLNLTRANHVFHIDRWWNPAVEN
QATDRAYRIGQKKSVIVHKFITTGTIEEKINQMILEKTELAENIVGSGESWLGQLSLEKLSELVAL
DSNPEF

SEQ ID NO: 69, Prochlorococcus marinus str. MIT 9211 Proma MIT 9211 SNF2 nucleic acid sequence
ATGAGTCTGCTACACGCTACTTGGCTGCCAGCAATGCGAACCGGAAGTTCGCATAATCCAGGACTA
CTCATCTGGGCTGATTCATGGAGAGTTGCAAAACCAAGCATAGTCAGCAATCAGCCTGTAATACAT
CCATTTGCCTTATCAGCAGCAGATTTACGTATTTGGCTATTGCAAAAAAGCTTTTACCTAAAGAA
AGTATTGAATGTACAGCCTTATTAACTCTACCTAGTAAATCTATTAAAAACTCATTAGACAAAAAA
TTAAATGGAGTAACGGACTCACAAAATACTAGCGATCAACCTCAATGGAGTGGACTACCTTTACAA
GCAGGAGAGCCAGTAACTAAACAATGTGAATGGTGGCCCTGGCAAGTTGAAGGTATAGCAATCAAA
CCCAGTGAAGCTGCATCGTGGCTTGCAAACTTACCTCTCACGAAAAAAGATCCTGAGCTTAGTGAA
GAGATCCTATGGTGGAGTCATTTAGAACGTTGGTCTCTAAGTTTAATTGCTCGTGGCCTTTGGTTG
CCACAAGTTGAATTAAATACAATTGATAATATTGGAGCTAGAGCTAGGTGGAGTCCTTTACTTAAT
AACGAAAACGAGCGCAAAAGATTAGAAGAATTCTCTATCAGGCTTCCATTAGTAGCAACATGTGCC
ATAAAAAGAGAGGAAACTTCTGAAGAAAATCAAAACCATATATTAAAGACTACTCCTAGGGAAACA
CTCGATGAATACGGACTTGCAGTATGTCGACCAATCAATAGTCGACTTCAAGTGGCTTATCTCTTA
GAAGAACTCGTGGATGGACAGCTAAGAAAAGATTTTGAGGAAAGTTCTGAAGACCTTGATCCATTG
CTGAAAGCTTGGCAAGAGGCATTAGGATCACATAATGGAGTCATTCGTCTTCCGTTGGAAGATTGT
GAAAGATTAGCCAAGGCAAGTAAAAATTGGAAAGAAAATTTATCAGGCAATGTTAAAGGTGCAAGA
GCATGCCTTGAGCTTTTTGCACCACTTGAAGGAGAAGATTTATGGGACTTACAATTCTCTTTACAA
GCTGAAGCAGATCCATCACTAAAGGTAGCAGCAGAAGCAGTATGGAATGCAGACTCAGCAGTTCTA
CAGATTGGTGATATTCAAATAGCGCAGCCTGGAGAAATTCTACTAGAAGGTCTTGGCAGAGCACTC
AATATCTTTCAACCAATAGAAGGGGTCTGGAAAATGCTACTCCAAATAATATGCAACTCACACCT
GCAGAAGCTTTTGTTCTAGTACGTACAGCCTCAAAGCAATTACGTGATATTGGTATTGGTGTAATA
CTACCTAGAAGTTTATCAGGAGGATTAGCAAGTCGACTAGGTATAGCTATTAAAGCAGAGTTAGCG
ACTAGTGCCAGAGGATTAACACTTCGAGAGAATCTAGAATGGAGTTGGGAGCTAATGATAGGGGGA
AGCATATTAAGCCTTAAAGATCTAGAACAACTGGCAAGTAAACGCAGCCCTCTAGTTCGCTATAAG
GATTCATGGCTTGAATTACGTCCAAATGATCTTAAAATCGCCGAAAAATTCTGTAGCAATAATCCT
GAATTAAGCCTAGATGACGCATTAAGACTTACCGCAACTAAAGGGGAGACTCTAATGAAGCTTCCA
GTACATCAATTTAATGCTGGGCCAAAGCTCCAAGGCGTTTTAGAGCAATACCACCAACATACAAGT
CCTGAGCCTCTAGCTGCACCAGATGGCTTCTATGGACAACTGAGGCCTTATCAAGAACGTGGCATA
GGATGGTTGGCTTTCTTGCATCGTTTTAATCAAGGTGCATGTTTAGCAGATGACATGGGCCTGGGC
AAAACAATTCAAGTGCTTGCTTTTATTCAGCACTTAAAAAGTAACAAGGACCTCAAGAAACCTGTT
TTGCTAATTGCACCTACGTCAGTATTAACAAACTGGAAACGAGAAGCTTATTCATTTACACCAGAG
TTATCTGTATTAGAGCATTACGGTCCTAATCGTTCATCTACATCAACACTCTTGAAAAAGATTCTC
AAAAAAGTAGACATTCTTATTACTAGCTATGGCCTACTACATAGAGATAAACAGCTTCTGAAAACA

```
ATTGATTGGCAAGGTGTAATTATTGATGAAGCACAAGCTATAAAAAATCCAAATTCAAAACAAAGT
CAAACAACTCGTGAAATTGTTAAAGGCGGAAAAATAATCCCTTTTCGTATTGCATTAACTGGTACC
CCTATAGAAAATCGTGTAAGTGAGCTTTGGTCATTAATGGATTTTTAAATCCATCAGTACTTGGA
GAAAAAGAATTTTTTGATCAACGCTACAAATTACCGATTGAACGTTATGGTGATATTTCTTCGTTA
ACCGATCTCAAAGCTCGTGTCAGTCCCTTTATTCTTAGAAGGTTAAAAAGTGATAAATCAATTATC
TCGGATCTACCAAGCAAAGTCGAACTAAAAGAATGGATTACTCTTAGTCAAGAGCAAAGAGCTCTT
TATAACAAAACTGTAGACAATACCTTACAGGAAATCGCAAGAAGTCCTATTGGTCAGCGTCATGCG
AAAACCTTAGGTCTATTAACACGTCTCAAACAAATATGTAATCATCCTGCTCTTGCCCTCAAAGAA
AAAAACATTAGCGATGATTTTGGAATACGATCAACCAAACTTCAAAGGCTGGAAGAACTTCTTGAT
GTGATATTCGCAACAGAGGACAGAGCTCTTCTTTTTACCCAATTCGCTGAATGGGGTCACTTACTA
CAAGCTTATCTAGAAAAAAGTGGGGACATAGCATACTTTTTCTACATGGAGGAACTCGCAAAATA
GATAGACAATCAATGGTTGATCAATTTCAAGAAGATCCCAGAGGCCCAAAATTATTTTTACTTTCT
CTCAAAGCAGGTGGTATTGGTCTGAACCTGACTCGAGCTAACCACGTGTTGCATATTGATCGATGG
TGGAACCCTGCCGTAGAAAATCAGGCAACAGATCGTGCTTATAGAATTGGTCAAAAAAATAGCGTA
ATGGTTCACAAATTTATTGCTACAGGGTCAGTAGAAGAAAAAATTGATCAAATGATTACTGAAAAG
TCTAAGCTCGCAGAAAATATAATTGGTGCAGGTGAAGATTGGCTTGGCAAACTTGGCATCAATGAA
TTACGTGAATTAGTTTCCTTAGAAAAAGAGAGTTAA
```

SEQ ID NO: 70, Prochlorococcus marinus str. MIT 9211 Proma MIT 9211 SNF2 translated polypeptide
```
MSLLHATWLPAMRTGSSHNPGLLIWADSWRVAKPSIVSNQPVIHPFALSAADLRIWLLQKKLLPKE
SIECTALLTLPSKSIKNSLDKKLNGVTDSQNTSDQPQWSGLPLQAGEPVTKQCEWWPWQVEGIAIK
PSEAASWLANLPLTKKDPELSEEILWWSHLERWSLSLIARGLWLPQVELNTIDNIGARARWSPLLN
NENERKRLEEFSIRLPLVATCAIKREETSEENQNHILKTTPRETLDEYGLAVCRPINSRLQVAYLL
EELVDGQLRKDFEESSEDLDPLLKAWQEALGSHNGVIRLPLEDCERLAKASKNWKENLSGNVKGAR
ACLELFAPLEGEDLWDLQFSLQAEADPSLKVAAEAVWNADSAVLQIGDIQIAQPGEILLEGLGRAL
NIFQPIERGLENATPNNMQLTPAEAFVLVRTASKQLRDIGIGVILPRSLSGGLASRLGIAIKAELA
TSARGLTLRENLEWSWELMIGGSILSLKDLEQLASKRSPLVRYKDSWLELRPNDLKIAEKFCSNNP
ELSLDDALRLTATKGETLMKLPVHQFNAGPKLQGVLEQYHQHTSPEPLAAPDGFYGQLRPYQERGI
GWLAFLHRFNQGACLADDMGLGKTIQVLAFIQHLKSNKDLKKPVLLIAPTSVLTNWKREAYSFTPE
LSVLEHYGPNRSSTSTLLKKILKKVDILITSYGLLHRDKQLLKTIDWQGVIIDEAQAIKNPNSKQS
QTTREIVKGGKIIPFRIALTGTPIENRVSELWSLMDFLNPSVLGEKEFFDQRYKLPIERYGDISSL
TDLKARVSPFILRRLKSDKSIISDLPSKVELKEWITLSQEQRALYNKTVDNTLQEIARSPIGQRHA
KTLGLLTRLKQICNHPALALKEKNISDDFGIRSTKLQRLEELLDVIFATEDRALLFTQFAEWGHLL
QAYLEKKWGHSILFLHGGTRKIDRQSMVDQFQEDPRGPKLFLLSLKAGGIGLNLTRANHVLHIDRW
WNPAVENQATDRAYRIGQKNSVMVHKFIATGSVEEKIDQMITEKSKLAENIIGAGEDWLGKLGINE
LRELVSLEKES
```

SEQ ID NO: 71, Prochlorococcus marinus str. MIT 9303 Proma MIT 9303 SNF2 nucleic acid sequence
```
ATGATTGGTTGTGGAACTCCTGCGTGGATGGTTGCCGTTGATCGGCAGTGCACTCCTGCTCCAAGA
AACCCAACACATACTTTTTGCGTCGCGGCCATGAGCCTGCTGCACGCCACCTGGCTTCCAGCCATC
CGTACTCCGACCAGCTCCGGTCGCCCTGCGCTCCTTGTGTGGGCAGATACCTGGCGAGTCGCTACC
CCAGCAGGACCAGCAGCAACTCCCGCACTCCACCCCTTCACACTCAACCCAGACGATCTACGTGCC
TGGCTGATTGAGCGCGATCTACTGCCCGATGAAATCATCGACGCCACAGCATGTCTGACCCTGCCT
AGCCGAACAGTCAAACCGCGCAGCAAAGCCAAGAACGTATCCACTGAATCCGACGAAGACAAAGAC
CACAAAACAAGTTGGACAGGACTGCCCTTACAAGCAGGCGAACCCATTCCCAAACAGACTGAATGG
TGGCCCTGGCAGGTGCAAGGCCTGGCAGTGGAGCCTGCTGCTGCAACGGCCTGGCTTTCGAAACTG
```

CCTCTTTCAGGAGATCATCCTGATCTCGCCGATGAATTGCGCTGGTGGAGCCATCTACAGCGCTGG
GCCCTGAGCATGATTGCTCGCGGACGTTGGCTACCCCAGGTGGAACTCAGCAAGGGAGAGGGCTAT
CCCCACCGAGCACGCTGGACACCGCTACTCAACCGTGAAGATGATCGCCGCCGCCTCGAAGACCTT
GCCGCTCAGCTCCCCTTAGTGGCCACCTGCGCCCTCCCCTGGCGGGAGCCCACCGGAAGGCGTAGC
AACCGAATGACCCGCCTAAGACCAGAGGCGATGCGAGCCGCTAACCCTGTGGCTTCATGCCGACCC
CGCAGCGGTCGCCTTCGCGTAGCCAGCCTGCTGGAAGAACTCTTGGATGCCCAACTGCGCACCGGA
TTTGAAGCGAGTGAGCAAGGCCTAGACCCATTGCTCACAGCCTGGCAGGAAGCACTGGGGTCGGAC
AGCGGCGTGATCAACCTCCCCGATGAGGAAGCCGAACGTCTAGCGACAGCAAGCAACCATTGGCGA
GAAGGCGTGGCTGGCAACGTCGCACCAGCCAGGGCCTGCTTAGAACTCTTCACTCCCGGCGAAGGG
GAAGACCTCTGGGAGCTGCGCTTCGCCTTACAGGCTGAGGCTGATCCCACGATCAAAGTACCGGCC
GCAGCAGCCTGGGCAGCGGGTCCCAAGGTCCTGCAACTAGGCGAAATCCGTGTGGAACATCCAGGC
GAGGTGCTACTGGAAGGCATGGGGCGAGCCCTCACGGTGTTTGCACCGATCGAACGAGGCCTCGAC
AGCGCCACACCAGAAGCAATGCAGCTCACCCCTGCTGAAGCCTTTGTATTGGTGCGCACTGCAGCG
GCCCAACTGCGTGATGTTGGCGTTGGCGTGGAATTGCCTGCCAGCCTCTCGGGAGGGCTGGCCAGT
CGCCTAGGCCTAGCGATCAAGGCGGAGCTATCGGAGAGATCTAGAGGTTTCACTTTGGGCGAAACC
CTCGACTGGAGTTGGGAGCTCATGATCGGTGGCGTCACCCTGACGCTTCGCGAGCTGGAGCGACTA
GCAAGCAAGCGCAGCCCGCTTGTCAACCACAAGGGCGCCTGGATCGAATTACGCCCCAACGATCTC
AAAAATGCGGAACACTTCTGCAGCGTCAATCCAGGCATCAGCCTCGACGATGCCTTGCGCCTTACC
GCAACCGATGGCGACACGCTGATGAGACTGCCCGTTCACCGCTTTGAGGCCGGTCCACGACTACAG
GCGGTGTTGGAGCAGTACCACCAGCAAAAAGCTCCCGACCCCCTACCTGCTCCCGAAGGCTTCTGC
GGTCAGCTAAGGCCTTATCAGGAAAGGGGTCTGGGTTGGCTGGCCTTCCTGCATCGCTTCGATCAA
GGGGCATGCCTGGCCGACGACATGGGCCTGGGCAAAACGATCCAGCTACTGGCATTCCTGCAACAT
CTCAAGGCGGAACAGGAACTCAAACGGCCGGTATTGCTTATCGCTCCCACATCCGTACTTACCAAC
TGGAAGAGAGAGGCATTGGCCTTCACACCAGAGTTAAACGTCCGAGAACACTATGGGCCGCGTCGG
CCCTCTACCCCCGCCGCCTTAAAGAAAGCACTCAAAGGCTTAGACCTCGTTCTCACCAGTTACGGG
CTCCTGCAGCGAGATAGTGAGCTCCTGGAAACGGTCGACTGGCAAGGAGTGGTCATCGATGAAGCC
CAAGCCATTAAGAACCCCAACGCCAAACAGAGCCAAGCAGCACGCGATATGGGCCGCCCAGACAAA
AACAATCGCTTCAGGATTGCTCTTACCGGCACACCCGTCGAAAACCGAGTCAGTGAACTTTGGGCA
CTGATGGACTTCCTCAACCCAAGGGTTCTCGGTGAAGAAGACTTCTTCCGCCAGCGCTACCGGCTG
CCAATTGAACGCTATGGCGACATGTCTTCCCTGCGAGACCTCAAAGGCCGTGTTGGTCCCTTCATC
CTGAGACGACTAAAAACCGACAAGGCAATCATCTCCGACCTACCTGAAAAGGTAGAGCTGAGCGAA
TGGGTGGGTCTGAGCAAAGAACAGGCAGCCCTCTATCGCAACACAGTGGATGAAACACTGGAGGCC
ATTGCCCGCGCACCCAGTGGTCAACGTCATGGCAAGGTGCTCGGCTTGCTTACCCGACTGAAGCAA
ATCTGCAACCATCCCGCCCTAGCCCTCAAAGAAAAAACCGTTGCAAAAGGCTTCATGGACCGCTCC
GCCAAGCTGCTGCGTTTGGAAGAAATTCTCGAGGAAGTGATCGAGGCAGGAGATCGCGCTCTGTTA
TTCACCCAATTCGCAGAATGGGGTCATCTCCTTAAGGCCTACCTGCAACAACGCTGGCGCTTTGAA
GTTCCCTTCCTGCACGGCAGCACAAGCAAACTGAACGTCAGGCCATGGTTGATCGCTTCCAGGAG
GATCCACGTGGACCCCAACTGTTCCTGCTGTCACTCAAAGCCGGTGGCGTAGGCCTAAACCTCACG
CGGGCTAGCCATGTGTTTCATGTCGATCGCTGGTGGAATCCTGCCGTAGAAAACCAGGCCACTGAT
CGCGCTTACAGGATCGGACAAACCAATCGGGTGATGGTGCACAAATTCATCACCAGCGGCTCAGTT
GAAGAGAAAATTGATCGCATGATTCGCGAAAAATCTCGACTTGCCGAAGACATCATTGGCTCTGGA
GAAGACTGGTTAGGTGGCTTAGGCGTCAGTCAATTGCGCGAACTAGTGGCCCTAGAAGACAGCTGA

**SEQ ID NO: 72 Prochlorococcus marinus str. MIT 9303 Proma MIT 9303
SNF2 translated polypeptide**
MIGCGTPAWMVAVDRQCTPAPRNPTHTFCVAAMSLLHATWLPAIRTPTSSGRPALLVWADTWRVAT
PAGPAATPALHPFTLNPDDLRAWLIERDLLPDEIIDATACLTLPSRTVKPRSKAKNVSTESDEDKD
HKTSWTGLPLQAGEPIPKQTEWWPWQVQGLAVEPAAATAWLSKLPLSGDHPDLADELRWWSHLQRW

FIGURE 10 (continued)

ALSMIARGRWLPQVELSKGEGYPHRARWTPLLNREDDRRRLEDLAAQLPLVATCALPWREPTGRRS
NRMTRLRPEAMRAANPVASCRPRSGRLRVASLLEELLDAQLRTGFEASEQGLDPLLTAWQEALGSD
SGVINLPDEEAERLATASNHWREGVAGNVAPARACLELFTPGEGEDLWELRFALQAEADPTIKVPA
AAAWAAGPKVLQLGEIRVEHPGEVLLEGMGRALTVFAPIERGLDSATPEAMQLTPAEAFVLVRTAA
AQLRDVGVGVELPASLSGGLASRLGLAIKAELSERSRGFTLGETLDWSWELMIGGVTLTLRELERL
ASKRSPLVNHKGAWIELRPNDLKNAEHFCSVNPGISLDDALRLTATDGDTLMRLPVHRFEAGPRLQ
AVLEQYHQQKAPDPLPAPEGFCGQLRPYQERGLGWLAFLHRFDQGACLADDMGLGKTIQLLAFLQH
LKAEQELKRPVLLIAPTSVLTNWKREALAFTPELNVREHYGPRRPSTPAALKKALKGLDLVLTSYG
LLQRDSELLETVDWQGVVIDEAQAIKNPNAKQSQAARDMGRPDKNNRFRIALTGTPVENRVSELWA
LMDFLNPRVLGEEDFFRQRYRLPIERYGDMSSLRDLKGRVGPFILRRLKTDKAIISDLPEKVELSE
WVGLSKEQAALYRNTVDETLEAIARAPSGQRHGKVLGLLTRLKQICNHPALALKEKTVAKGFMDRS
AKLLRLEEILEEVIEAGDRALLFTQFAEWGHLLKAYLQQRWRFEVPFLHGSTSKTERQAMVDRFQE
DPRGPQLFLLSLKAGGVGLNLTRASHVFHVDRWWNPAVENQATDRAYRIGQTNRVMVHKFITSGSV
EEKIDRMIREKSRLAEDIIGSGEDWLGGLGVSQLRELVALEDS

SEQ ID NO: 73, Prochlorococcus marinus str. MIT 9313 Proma MIT 9313 SNF2 nucleic acid sequence
ATGATTGGTTGTGGAACTCCTGCGTGGATGGTTGCCGTTGATCGGCAGTGCACTCCTGCTCCAAGA
AACCCAACACATACTTTTTGCGTCGCGGCCATGAGCCTGCTGCACGCCACCTGGCTTCCAGCCATC
CGTACTCCGACCAGCTCCGGTCGCCCTGCGCTCCTTGTGTGGGCAGATACCTGGCGAGTCGCTACC
CCAGCAGGACCAGCAGCAACTCCCGCACTCCACCCCTTCACCCTCAGCCCAGACGATCTACGTGCC
TGGCTCATTGAGCGCGATCTACTGCCTGATGAAATCATCGACGCCACAGCATGTCTGACCCTGCCT
AGCCGAACAGTCAAACCGCGCAACAAAACCAAGAACGTATCCACTGAATCCGACGAAGCCAAAGAC
AACAAAACAAGTTGGACAGGACTGCCCTTACAAGCAGGCGAACCCATTCCCAAACAAACAGAATGG
TGGCCCTGGCAGGTGCAAGGCCTGGCAGTGGAACCTGCTGCCGCAACGGCCTGGCTTTCGAAACTG
CCTCTTTCAGGAAATCATCCTGATCTGGCCGATGAATTGCGCTGGTGGAGCCATCTACAGCGCTGG
GCCCTGAGCATGATTGCTCGCGGACGTTGGCTACCCCAGGTGGAACTCAGCAAGGGAGAGGCTAT
CCCCACCGAGCACGCTGGACACCGCTACTCAACCGTGAAGATGATCGCCGCCGCCTCGAAGACCTT
GCCGCTCAGCTTCCCTTAGTGGCCACCTGCGCCCTCCCCTGGCGGGAGCCCACCGGAAGGCGTAGC
AACCGAATGACCCGCCTAAGACCAGAGGCGATGCGAGCCGCTAACCCTGTGGCTTCATGCCGACCC
CGCAGCGGTCGCCTTCGCGTAGCCAGCTTGCTGGAAGAACTCTTGGATGCCCAACTGCGCACCGGA
TTTGAAGCGAGTGAGCAAGGCCTAGACCCATTGCTCACAGCCTGGCAGGAAGCACTGGGGTCCGAC
AGCGGCGTGATCAACCTCCCCGATGAGGAAGCCGAACGTCTAGCTACAGCAAGCAACCATTGGCGT
GAAGGCGTGGCTGGCAACGTCGCACCAGCCAGAGCCTGCTTAGAACTCTTCACTCCCGGAGAAGGG
GAAGACCTCTGGGAGCTGCGCTTCTCCTTACAGGCTGAGGCTGATCCCACAATCAAAGTACCGGCC
GCAGCAGCCTGGGCAGCTGGTCCCAAGGTGTTGCAACTAGGCGAAATCCGTGTGGAACATCCAGGC
GAGGTGCTACTGGAAGGCATGGGCGAGCCCTCACGGTGTTTGCACCGATCGAACGAGGCCTCGAC
AGCGCCACACCAGAAGCAATGCAGCTCACCCCTGCTGAAGCCTTTGTATTGGTGCGCACTGCAGCG
ACCCAACTGCGTGATGTTGGCGTTGGCGTGGAATTGCCTGCCAGCCTCTCGGGAGGGCTGGCCAGT
CGCCTAGGCCTAGCGATCAAGGCGGAGCTATCGGAGAGATCTAGAGGTTTCACTCTGGGCGAAACC
CTCGACTGGAGTTGGGAGCTCATGATCGGTGGCGTCACCCTGACGCTTCGCGAACTGGAGCGACTA
GCAAGCAAGCGCAGCCCGCTTGTCAACCACAAGGGCGCCTGGATCGAATTACGCCCCAACGATCTC
AAACATGCGGAACACTTCTGCAGCGTCAATCCAGGCATCAGCCTCGACGATGCCTTGCGCCTTACC
GCAACAGATGGCGACACGCTGATGAGACTGCCCGTTCACCGCTTTGAGGCCGGTCCACGACTACAG
GCGGTGTTGGAGCAGTACCACCAGCAAAAGCACCAGACCCCTACCTGCTCCCGAAGGCTTCTGC
GGTCAGCTAAGGCCTTATCAGGAAAGGGGTCTGGGTTGGCTGGCCTTCCTGCATCGCTTCGATCAA
GGGGCATGCCTGGCCGACGACATGGGCCTTGGCAAAACGATCCAGCTACTGGCATTCCTGCAACAT
CTCAAGGCGGAACAGGAACTCAAACGGCCGGTATTGCTTATCGCTCCCACGTCCGTACTCACCAAC FIGURE 10 (continued)

```
TGGAAGAGAGAGGCGTTGGCCTTCACACCAGAGTTAAACGTCCGCGAACACTATGGGCCGCGTCGG
CCCTCTACCCCCGCCGCCTTAAAGAAAGCACTCAAAGGCTTAGACCTCGTTCTCACCAGTTATGGG
CTCCTGCAGCGAGATAGTGAGCTCCTGGAAACGGTCGACTGGCAAGGCGTGGTCATCGATGAAGCC
CAAGCCATTAAGAACCCCAACGCCAAACAGAGCCAAGCAGCACGCGATATGGGCCGCCCAGACAAA
AACAATCGCTTCAGGATTGCTCTTACCGGCACACCCGTCGAAAACCGAGTAAGTGAACTTTGGGCA
CTAATGGACTTCCTTAACCCAAGGGTTCTCGGTGAAGAAGACTTCTTCCGCCAGCGCTACCGGCTG
CCGATTGAGCGCTATGGCGACATGTCTTCCCTGCGAGACCTCAAGGGCCGTGTTGGTCCCTTCATC
CTGAGACGACTCAAAACCGACAAGGCAATCATCTCCGACCTACCCGAAAAAGTAGAGCTGAGCGAA
TGGGTGGGGCTGAGCAAAGAACAGGCAGCCCTCTATCGCAACACAGTGGATGAAACACTGGAGGCC
ATTGCCCGCGCACCCAGGGGTCAACGCCATGGCAAGGTGCTCGGATTGCTTACCAGACTGAAGCAA
ATCTGCAACCATCCCGCCCTAGCCCTCAAAGAACAAACCGTTGCAAAAGGGTTCATGGACCGCTCC
GCCAAGCTGCTGCGTTTGGAAGAAATTCTCGAAGAAGTAATCGAGGCAGGAGATCGCGCTCTGTTA
TTCACCCAATTCGCAGAATGGGGTCATCTCCTTAAGGCCTACCTGCAACAACGCTGGCGCTTTGAA
GTTCCCTTCCTGCACGGCAGCACAAGCAAAACTGAACGTCAGGCCATGGTTGATCGCTTCCAGGAG
GATCCACGTGGACCCCAACTGTTCCTGCTGTCACTCAAAGCCGGTGGTGTAGGCCTCAACCTGACG
CGGGCTAGCCATGTGTTTCATGTTGATCGCTGGTGGAATCCTGCCGTAGAAAACCAGGCCACTGAT
CGCGCTTACAGGATCGGGCAAACCAGTCGGGTGATGGTGCACAAATTCATCACCAGCGGCTCAGTT
GAAGAGAAAATTGATCGCATGATTCGTGAAAAATCTCGACTTGCCGAAGACATCATTGGCTCTGGA
GAAGACTGGTTAGGTGGCTTAGGCGTCAGTCAATTGCGCGAACTAGTGGCCCTAGAAGACAGCTGA
```

SEQ ID NO: 74, Prochlorococcus marinus str. MIT 9313 Proma MIT
9313 SNF2 translated polypeptide
```
MIGCGTPAWMVAVDRQCTPAPRNPTHTFCVAAMSLLHATWLPAIRTPTSSGRPALLVWADTWRVAT
PAGPAATPALHPFTLSPDDLRAWLIERDLLPDEIIDATACLTLPSRTVKPRNKTKNVSTESDEAKD
NKTSWTGLPLQAGEPIPKQTEWWPWQVQGLAVEPAAATAWLSKLPLSGNHPDLADELRWWSHLQRW
ALSMIARGRWLPQVELSKGEGYPHRARWTPLLNREDDRRRLEDLAAQLPLVATCALPWREPTGRRS
NRMTRLRPEAMRAANPVASCRPRSGRLRVASLLEELLDAQLRTGFEASEQGLDPLLTAWQEALGSD
SGVINLPDEEAERLATASNHWREGVAGNVAPARACLELFTPGEGEDLWELRFSLQAEADPTIKVPA
AAAWAAGPKVLQLGEIRVEHPGEVLLEGMGRALTVFAPIERGLDSATPEAMQLTPAEAFVLVRTAA
TQLRDVGVGVELPASLSGGLASRLGLAIKAELSERSRGFTLGETLDWSWELMIGGVTLTLRELERL
ASKRSPLVNHKGAWIELRPNDLKHAEHFCSVNPGISLDDALRLTATDGDTLMRLPVHRFEAGPRLQ
AVLEQYHQQKAPDPLPAPEGFCGQLRPYQERGLGWLAFLHRFDQGACLADDMGLGKTIQLLAFLQH
LKAEQELKRPVLLIAPTSVLTNWKREALAFTPELNVREHYGPRRPSTPAALKKALKGLDLVLTSYG
LLQRDSELLETVDWQGVVIDEAQAIKNPNAKQSQAARDMGRPDKNNRFRIALTGTPVENRVSELWA
LMDFLNPRVLGEEDFFRQRYRLPIERYGDMSSLRDLKGRVGPFILRRLKTDKAIISDLPEKVELSE
WVGLSKEQAALYRNTVDETLEAIARAPRGQRHGKVLGLLTRLKQICNHPALALKEQTVAKGFMDRS
AKLLRLEEILEEVIEAGDRALLFTQFAEWGHLLKAYLQQRWRFEVPFLHGSTSKTERQAMVDRFQE
DPRGPQLFLLSLKAGGVGLNLTRASHVFHVDRWWNPAVENQATDRAYRIGQTSRVMVHKFITSGSV
EEKIDRMIREKSRLAEDIIGSGEDWLGGLGVSQLRELVALEDS
```

SEQ ID NO: 75, Rhodococcus sp. RHA1 Rho_sp_RHA1_SNF2 nucleic acid
sequence
```
ATGGCGCGAGCAGGGACTTCACGCGCTGTCGGTCGCACCTGCTTGGATGGGTGCATGCTGCACGGC
CTCTGGACACCGGGTTCGGGTCTCATGCTGTGGGTGGAGGATCGGAATCCGGCAGCTCCGGAGCCG
ACGGACGCGGTCGGCGGATGCTGGCGCGGAAGTTCCGGCATCACGTGAAGGTGCCGATGCCGACG
CCGTCGGGGCCGGAGATGCTCGAGTGGGCCGCGGTTGCGCTCGCACCACCGGATGCGACGGAGTTC
CTGCTGTCGGTGTCGTCCCGCGACCCCCGGATCGCCGGGGATCTGCGCTACCTCGCCCACGTCGCC
CGCGGTGTCGAGCGGTGGGCACGGGCCGGGCGGGTGGTGCCCGAGGTACACCGGGCGGAGGGCGGC
```

FIGURE 10 (continued)

```
TGGTGGCCGCGCTGGCGGCTGCTCGGCGGTGAACGGCAGCGTGCGTGGCTCACGGAGCTGGCCGTG
GCGATGCCGCCGGTCCAGCGTCACGGCACGACCCCCGGGCCGTGCTCGACGACATGGTCACCGAG
CTGACCGACCCCGTCGCCCGCCGTGTCCTCGAACGACGGCACCCGGACGATTCCGGCGGCGACGTG
GATCATCCGCTGATCGACGCGCTCGTGCGGGGTGACCAGTTCGCCGAGGGCACCGCCCAGCTGTCG
GGATCGCTGGACGGGTGGCGCGACAGCCTCAAGGTGGACGAGCCCGAACTGGTGCTGCGGCTCCTC
GAGCCGGAAGACGTGGACGTGGAGGGGATTGGGACCCGGACACGGTGCTGTGGCGACTGGAGGTC
TGCCTTCGACCGGAAGGCGAAGCCCCGGTGCCGATTCCGTTGCACCGCACGGAGGCGAGTCGTCTG
CAGATCGGGGTGCGCAAGCTGACGGAGGCCGTGGCCGCCTACCCGCGACTGCAGGACGTTCCCAGT
GACCCCGACAGCCTGGACCTGATGTTGCCCACCGCCGTGGTCATCGACCTTGTCGGGCACGGTGCG
GTGGCGTTGAAGGAGAAGGGCATCAGCCTGCTGCTGCCGCGGGCGTGGAGTGTGGCGTCGCCGTCG
ATGCGTCTGCGGGTGAGCTCGCCGAGCACTCCGGCGAGCGCGGAGAACCGGGCCGTCGGCAAAGAC
CAGTTGGTGCAATACAACTGGGAGCTGGCACTCGGCGACACGGTGCTCACCGCCGCGGAGATGAAT
CGACTGGTCAACTCCAAGAGCGATCTCGTGCGGTTGCGCGGTGAGTGGGTTCGGGCGGATCAGGAG
GTGCTCTCCCGCGCCGCGCGCTACGTGGCGGAGCGGCACGCCAGCGGCGACCGGGCCATCGTGGAC
CTGCTGAAGGACCTGATCGCGGACGATCTGTCCGATCTTCCCGTGGAGGAGGTCACGGCCACCGGC
TGGGCGGCCGCGTTGCTGGACGGCGACACGAAGCCGCAGGACGTGCCGACCCCGGACGGGTTGGAC
GCCACGCTGCGCCCGTACCAGAAGCGGGGGCTCGACTGGCTGGTGTTCATGAGCCGTCTCGGCCTC
GGGGCCGTCCTCGCCGACGACATGGGACTCGGCAAGACGCTGCAGTTGCTGGCGCTGCTGGCACAC
GAGAAGGCGCCCACGCCCACGCTGCTGGTGCCCGATGTCGGTGGTCGGCAACTGGCAGCGCGAG
GCAGCGCGCTTCGTCCCCTCGCTGCGGGTGCTCGTCCACCACGGTCCGCAGCGGCTGAGCGGCGCG
GAGTTCACCGCCGCCGTGACACAGAGCGATCTGGTGATCACCACGTATGCGCTGCTGGCCCGCGAC
GTCGCGCACCTGAAGGAGCAGGACTGGCGGCGTGTCGTGCTGGACGAGGCGCAGCACATCAAGAAC
GCGAAGACGTCGCAGGCGCGGGCGGCGCGGAGCATTCCGGCGGCGCACCGCGTCGCGCTGACCGGC
ACTCCGGTCGAGAACCGCCTCGACGAACTGCGCTCGATCCTCGACTTCGCGAACTCGGGCATCCTG
GGCTCGGAGGTGATGTTCCGCAAGCGCTTCGTGGTGCCGATCGAGCGGGAGCAGGACGAGACAGCC
GTCGCCCGGCTCCGCGCGGTCACGTCCCCGTTCGTGCTGCGCCGGGTCAAGACCGATCCCGCGGTC
ATCGCCGACCTCCCCGACAAGTTCGAGATGACGGTGCGCGCCAACCTCACCGCGGAGCAGGCCGCG
CTGTACCGGGCGGTGGTCGACGACATGATGGCGCAGATCAAGGACAAGAAGGGGATGAAGCGCAAG
GGCGCCGTCCTCGCCGCCCTGACGAAACTCAAGCAGGTGTGCAACCACCCGGCACACTTCCTGCGC
GACGGGTCGGCGGTGATGCGGCGCGGACAGCACCGCTCCGGCAAGCTGGGGCTCGTCGAGGACATC
CTGGATTCCGTGGTCGCGGACGGCGAGAAGGCGTTGCTGTTCACCCAGTTCCGGGAATTCGGCGAC
CTCGTCACCCCGTACCTCGCGGAGCGTTTCGGTACTCCCGTGCCGTTTCTGCACGGGGCGTGTCC
AAGCAGAAGCGCGACGACATGGTGGCCTCGTTCCAGGGCGACGACGGGCCGCCGATCATGATGCTC
TCGCTGAAGGCGGGCGGGACGGGTTTGAACCTCACCGCGGCCAATCACGTCGTCCACCTCGACCGG
TGGTGGAATCCGGCGGTCGAGAACCAGGCCACGGACAGGGCGTTCCGGATCGGCCAGCGGCGGGAC
GTGCAGGTGCGCAAGCTCGTGTGCGTCGGCACCCTGGAGGAGCGGATCGACGCGATGATCGCCACC
AAGCAGGAGCTGGCCGATCTCGCCGTCGGGACGGGCGAGAACTGGGTGACGGAGATGAGCACCGAA
CAACTGGGCGAACTGCTCCGCCTCGGTGACGAGGCGGTGGCGAATGA
```

SEQ ID NO: 76, Rhodococcus sp. RHA1 Rho_sp_RHA1_SNF2 translated polypeptide

```
MARAGTSRAVGRTCLDGCMLHGLWTPGSGLMLWVEDRNPAAPEPTDAVGRMLARKFRHHVKVPMPT
PSGPEMLEWAAVALAPPDATEFLLSVSSRDPRIAGDLRYLAHVARGVERWARAGRVVPEVHRAEGG
WWPRWRLLGGERQRAWLTELAVAMPPVQRHGTTPRAVLDDMVTELTDPVARRVLERRHPDDSGGDV
DHPLIDALVRGDQFAEGTAQLSGSLDGWRDSLKVDEPELVLRLLEPEDVDVEGDWDPDTVLWRLEV
CLRPEGEAPVPIPLHRTEASRLQIGVRKLTEAVAAYPRLQDVPSDPDSLDLMLPTAVVIDLVGHGA
VALKEKGISLLLPRAWSVASPSMRLRVSSPSTPASAENRAVGKDQLVQYNWELALGDTVLTAAEMN
RLVNSKSDLVRLRGEWVRADQEVLSRAARYVAERHASGDRAIVDLLKDLIADDLSDLPVEEVTATG
```

WAAALLDGDTKPQDVPTPDGLDATLRPYQKRGLDWLVFMSRLGLGAVLADDMGLGKTLQLLALLAH
EKAPTPTLLVCPMSVVGNWQREAARFVPSLRVLVHHGPQRLSGAEFTAAVTQSDLVITTYALLARD
VAHLKEQDWRRVVLDEAQHIKNAKTSQARAARSIPAAHRVALTGTPVENRLDELRSILDFANSGIL
GSEVMFRKRFVVPIEREQDETAVARLRAVTSPFVLRRVKTDPAVIADLPDKFEMTVRANLTAEQAA
LYRAVVDDMMAQIKDKKGMKRKGAVLAALTKLKQVCNHPAHFLRDGSAVMRRGQHRSGKLGLVEDI
LDSVVADGEKALLFTQFREFGDLVTPYLAERFGTPVPFLHGGVSKQKRDDMVASFQGDDGPPIMML
SLKAGGTGLNLTAANHVVHLDRWWNPAVENQATDRAFRIGQRRDVQVRKLVCVGTLEERIDAMIAT
KQELADLAVGTGENWVTEMSTEQLGELLRLGDEAVGE

SEQ ID NO: 77, Salinispora tropica CNB-440 Saltr_CNB-440_SNF2
nucleic acid sequence
GTGCTGGTTGTCCACGGGTCGTGGCGGCTCGGCATCGGGCTCGCCATCTGGGCCGAGGACAGCGCG
TCGCCGCCTCGGGCGCCGCGCCGGGCCGGGCGGGCGCCCCGCGAGCGACCCCACCCGTTCGCCGCC
GGTCACCCCGTGCTTGCGGCAGCTCTGGCCGAGGTCGCCGAGCCGACCGAGCCCGGCACGGCACTG
CTCACCCTGCCCACCCGAGCTGGTTCGCCGCTGGACTCGCCGGAGCTGGTCCGCACCGCGTCGGTC
GAGCCGCTCCGTGGGCCGGTCACGTTGGCCGGGTGGCGGGTGCCCGCCCTGGTTTACGCCCCGGAC
GCCGCCCTGTCGCTGCTCTCCCAGATCACCGCGGCCGGCGCTCTACCTGACGCCGTACCCGGTGCC
ACTCTGCGTCACCTCGCGGAGCTGGCGGCCTTCGCCGTGGACCTCGCCGCCCGTGGTCGGGTCCTG
CCCGGCGTCCGGCCACCGAAGGAACGTGCCAGCGCCGCCTGGGCGGTGTGGCAGCCCCTGCTCACC
GGCGTGGACGCTGGCTGGGCCCGGGCCCTCGCCCTCGCCCTGCCGCCCGCGGTCCGTGCCGCCGTC
GAGATCGATCCGGCTCCACTCGCCGTACCCGGCGGACCGGAAACGCCCGCCAACGGTGGTGTGCCG
CCGCAGGCTCGTACGAGGCGACCGACCGCAGCCGCCGGGGAACCAGGTGAACTGGTGGTCGAGGCG
CTCGACGCGCTCACCGACGCGGCCGTACGGGCTGCCCTCGCGGAGACCTCCCTTACCCGGGGAGCC
CGTCCGCGGGGCGCGGTCGCGGCCTGGCTCGCGGCGCTCACCGGCCCGCGTCGTGACTTCACCGCC
GACTCGGCGGAGCTCGACACCCTGCGCGGTGAGTTGGACGCCTGGCAGCGCGACGCTGTGGGAGGT
TCGGTCCGGGCCAGCTTCCGGCTGGTGGAGCCGCCGACGGACGGACTCTTTGAGGCGGCGGCCGGG
GGGCTGGCCGCGGCCGAGGGGTCGTGGCGGGTCGAGTTCGGCCTACAGCCGGCCGACCAGCCGGGT
CTGCATGTTGACGCCGTGCGGATCTGGCACGAGTCGGCGGCCCTACCGGGCCCGGCCGCTCCGCAG
GAGGCCCTGCTGACCGAGTTGGGGCGGGCCAGCCGACTCTGGCCGGAGCTGAACTCGGCCCTGCGC
ACCGCCACTCCAGAGGCGCTGGAGCTGGACGCCGCGGGCGCGCATCGCTTTCTACGCGACGGCGCG
CCGGTGCTGCACGCAGCCGGGTTCGCGGTGCTGTTGCCCTCGTGGTGGCAGCGTCCGTCGTCCCGG
CTCGGCGCTCGACTACAGGCCCAGAGCCGTACCGCCCCGGGCACCGTCGCCGGGGCTGGCGACGGG
GTGGGGTTGGATGCCCTGGTCGACTACCGCTGGGAGGTGTCCCTCGGCGACCAGCCGCTGACCGCC
GAGGAACTGGAGTCGCTGGCCGCGCTGAAATCTCCGTTGGTCCGCCTGCGTGGGCGCTGGGTGGAG
CTGGACCCGAAACGTCTCGCCGCCGGCCTGCGGCTGCTCCGTTCCGCCGGCGAGCTGACCGTCGGC
GACCTGCTGCGGCTCGGCCTCTCCGACCCTGCTACCGACGCGCTGCCGGTGCTCGAGGTGGCGGCC
GACGGTGCGTTGGGTGACTTGCTCGCCGGAGCTGTGGAGCGGCAACTCACCCCGGTGGACGCGGTT
CCGTCGTTCCAGGGCGTTCTCCGCCCCTACCAGCGGCGAGGGCTGGCCTGGCTGTCCTTTCTGCAG
TCCCTCGGCCTCGGCGGGGTGCTCGCTGACGACATGGGTCTCGGCAAGACGGTACAGCTACTCGCG
TTGCTCGCTGGTGACCCGCCGGGCGTCGGTCCGACCCTGTTGGTCTGTCCGATGTCACTGGTCGGT
AACTGGCAGCGGGAGGCGGCGACCTTCACCCCGGGCGTACGGGTCCATGTGCATCACGGCGCCGAG
CGGGCCCGCGGGCGGCGTTCACCGCGGCGGTGGAGGCAGCGGACCTGGTCCTCACCACCTACACG
GTGGCTGCCCGCGATGCGGGGGAGCTGGCCGGGGTCGACTGGCATCGGGTGGTGGTGGACGAGGCA
CAGGCCATCAAGAACGCCTCGACGCGGCAAGCCGAGGCGGTCCGGGCGTTGCCCGCCCGGCATCGG
ATCGCGGTCACCGGCACCCCGGTGGAGAATCGGCTCGCCGACCTCTGGTCGATCATGCAGTTCGCC
AATCCCGGTCTGCTCGGCCCGGCCGCCGAGTTCAAGAAGCGGTACGCCGAACCGATCGAGCGACAC
GGCGACGCGGAGGCGGCCGAGCGGCTGCGCCGGATCACCGGCCCGTTCGTGCTGCGTCGCCTCAAG

FIGURE 10 (continued)

```
ACCGACTCTTCGGTTATCTCCGACCTGCCAGAGAAGCTGGAGATGGAGGTGGTGTGCAACCTGACC
GCGGAACAGGCTGCCCTCTACCGTGCGGTGGTGGACGACATGATGGCCCAGATCGAGTCCAGCGAG
GGCATCGAGCGACGTGGGCTCGTGCTGGCCGCCATGACCCGGCTCAAGCAGGTCTGCAACCACCCG
GCGCACCTGCTGCGGGACAACTCGGCGCTGGTCGGCCGCTCCGGCAAGCTGGCCCGGCTGGAGGAG
ATCCTCGACGAGGTGCTTGTCGCGGGGAGAAGGCCCTGCTCTTCACCCAGTACGCCGAGTTCGGC
GGCATGCTGCGCGGCCACCTGTCGGCCCGGTTCGGACAGGAGACGCTGTTCCTGCACGGCGGCGTC
GGTAAGGCCGACCGGGACGCGATGGTGACGCGGTTCCAGTCCCCGGACGGCCCCGCGCTCTTCGTA
CTCTCGCTCAAGGCCGGTGGTACCGGTCTCACCCTGACCGCGGCCAACCATGTCGTGCACGTTGAC
CGCTGGTGGAATCCGGCGGTGGAGGACCAGGCCACGGACCGGGCGTTCCGCATCGGGCAGCGGCGG
CGCGTTCAGGTCCGCAAGTTTGTCTGCGCCGGCACGGTGGAGGAGAAGGTCGCCGCGCTCATCGCC
GACAAGCGTCGGCTCGCCTCGACGGTGGTGGGTGCCGGTGAGCAGTGGGTTACCGAGCTGTCCACG
GCGCAGCTGCGGGAGCTGTTCCAGCTGGAGTCCGGGGCGGTGGCCGAATGA
```

SEQ ID NO: 78, Salinispora tropica CNB-440 Saltr_CNB-440_SNF2 translated polypeptide
```
VLVVHGSWRLGIGLAIWAEDSASPPRAPRRAGRAPRERPHPFAAGHPVLAAALAEVAEPTEPGTAL
LTLPTRAGSPLDSPELVRTASVEPLRGPVTLAGWRVPALVYAPDAALSLLSQITAAGALPDAVPGA
TLRHLAELAAFAVDLAARGRVLPGVRPPKERASAAWAVWQPLLTGVDAGWARALALALPPAVRAAV
EIDPAPLAVPGGPETPANGGVPPQARTRRPTAAAGEPGELVVEALDALTDAAVRAALAETSLTRGA
RPRGAVAAWLAALTGPRRDFTADSAELDTLRGELDAWQRDAVGGSVRASFRLVEPPTDGLFEAAAG
GLAAAEGSWRVEFGLQPADQPGLHVDAVRIWHESAALPGPAAPQEALLTELGRASRLWPELNSALR
TATPEALELDAAGAHRFLRDGAPVLHAAGFAVLLPSWWQRPSSRLGARLQAQSRTAPGTVAGAGDG
VGLDALVDYRWEVSLGDQPLTAEELESLAALKSPLVRLRGRWVELDPKRLAAGLRLLRSAGELTVG
DLLRLGLSDPATDALPVLEVAADGALGDLLAGAVERQLTPVDAVPSFQGVLRPYQRRGLAWLSFLQ
SLGLGGVLADDMGLGKTVQLLALLAGDPPGVGPTLLVCPMSLVGNWQREAATFTPGVRVHVHHGAE
RARGAAFTAAVEAADLVLTTYTVAARDAGELAGVDWHRVVVDEAQAIKNASTRQAEAVRALPARHR
IAVTGTPVENRLADLWSIMQFANPGLLGPAAEFKKRYAEPIERHGDAEAAERLRRITGPFVLRRLK
TDSSVISDLPEKLEMEVVCNLTAEQAALYRAVVDDMMAQIESSEGIERRGLVLAAMTRLKQVCNHP
AHLLRDNSALVGRSGKLARLEEILDEVLVAGEKALLFTQYAEFGGMLRGHLSARFGQETLFLHGGV
GKADRDAMVTRFQSPDGPALFVLSLKAGGTGLTLTAANHVVHVDRWWNPAVEDQATDRAFRIGQRR
RVQVRKFVCAGTVEEKVAALIADKRRLASTVVGAGEQWVTELSTAQLRELFQLESGAVAE
```

SEQ ID NO: 79, Symbiobacterium thermophilum IAM 14863 Symth_IAM14863_SNF2 nucleic acid sequence
```
ATGATCACGGTTCACGGCAGTTTCGTCCCCTCCGGCGCGTCCGGCTTCTTCTTCCTGTGGGGCCTG
GACGGCGTGGCCGCCCGGGATGCCGCTCCTCCCGGCCGGCGCCGCCGCGGGGTTCCGCGCCACCCA
TGCGCAACCGAGCCGGAAGCGCTCTACCCCGCCCTGAGAGGATTGCCCTACCTGAACACCCTGTCC
CTGGTCCAGTGGCAGCCCGGACCGGACGGCGTCAGCCCGGCCCGGGTCCCGGGGATCGCCCTGTCC
GTGCCCAACGCCGTGCAGTGGCTGTTGGATCTGCCCGACCACTTCGCGGCACGCCCCTCCGGCCG
GGGCACAGCCTGCAGCTCTGGTGCGTCGCATCCAAGCTGCTTCTGGAGTTCCTGGGCGGGGCCTG
ATGCTGCCGGTGCTGCAGGCCGAGGCCGGGGTGCTGAGCGCGGGCTGGGCGCTCCACCTGACCGAC
GCCGACGACGTCCGCCGCCTGACCCGGCTGGCCGCTGGATTGCCGGAGGCCTGCCGCGCCCTTGTG
CCCCCCGACCGAACCCCCAACACCTACCCCCTGCCGGTCGCCGACGGCCTGGTCCACCAGTTCATG
CGTACGGCGGCCGCCGGCGTGATCCGGCTCCTCCTGGAGGAAGAGCCCCTGCCCGAGGCCCAGTCG
CTACAGGATACCGCCCTGCGCCACTGGCTGGCGGCGCTGACCGGGGCGGAGGCCCGGGACCTGCCG
CCGGGCCTGCCCGGCGCGCAGGAGCTGTACGCCGCCCTGGACCGCTGGAGCGCCCCGCCACCGGC
GTGCTGAGCCACGCCAGTCTGCGGACGGGGGTCCGCCTCCACCTGCCCGGCCCCGAGACCGACGGC
GAGTGGGAGCTGGAGCTCACGCTCCATGCGCCGGACGAGGGTGCGCTGCCCGTCACCGCCGATGCG
```

```
GTCTGGGCCAGCCTGGGCGCCGAGGTGGAGATCGGCGGGCAGCGGTACCAGGGCGCCGAGCAGCGG
CTGCTGGCCGACCTGCCGGCCATGGCCCGCCTCTTCCCGCCACTGGCGCCGCTGCTCCGGGACCCC
GCGCCCAGCCGCATGCGCATTCCGGCGGACGACGTGCTGGCCCTGATCCAGGAAGGGGCCATGCTG
CTCCAGCAGGCCGGCCACCCCGTGCTGCTGCCGGCCGCCCTTGCGAAGCCCGCCGCCCTCCGGGTC
GGAATGCGCCTCAGCCCCGCCGGGGGCAGCCCCTCCATGTTCGGGCTGCACCAGATCGTGAACGTG
CGCTGGGACGTGGCCCTGGGCGGCACCCCGCTCACGCTGGACGAGCTGCGCCACCTGGCGCGGCAG
AAGCGGCCCCTGGTACAGATGCAGGGCCGGTGGGTGCGGGTGGACGAACGCACCCTGGCTGCGGTC
CTCCGCCGGATCGAGCAGCACGGCGGGCAGATGGAGCTGGGCACGGCGCTGCGCCTGGCACCCGAG
GCGGACGAGGCCACCGCGACCGGCTGGATCGCCGAGCTGCTGGAGCGGCTGCAGGAGCCAGCCCGG
ATGGAGCCGGTGCCGACCCCCGGGGGCTTCGCCGGCACCCTGCGGCCGTACCAGCAGCGGGGCCTC
GCCTGGCTGGCGTTCCTGCGCCGCTGGGGCCTGGGCGCGTGCCTCGCCGACGACATGGGGCTGGGC
AAGACCGTGCAGCTCATCGCCCTTCTCCTGCACGAGCGGGAGGCCGGGTGGGCCGCGGGCCCGACC
CTGCTGGTCTGCCCCGTCTCGGTCCTGGGCAACTGGTGCCGGGAGCTGGCCCGCTTCGCCCCGGGC
CTGCGGGTCCTGGTGCACCATGGCCCCGGGAGGCTGGGCGAGCCGGACTTCGCCCGGCAGGCCGGG
GCCCACGACGTGGTGCTGACCACGTACTCCCTGCTGGCCCGGGATGCCGCGCTGCTGGGCCAGGTG
ACCTGGAACGGGATCGTCGCCGACGAGGCGCAGAACCTGAAAAACCCCGACACACAGCACGCCCGG
GCGCTGCGAAGCCTTTCCGGCGGCTACCGCATCGCCCTCACCGGTACGCCCGTCGAAAACCACCTG
GGCGACCTGTGGTCGCTCTTCCAGTTCCTCAACCCGGGGCTGCTGGGCAGCCGCGAGGAGTTCGAG
CGGCGCTACGCCGTGCCGATCCAGCGGTACCAGGACGAGGAGGCTGCGGCCCGGCTCCGCCGGCAG
GTGGGTCCCTTCATCCTGCGCCGGCAGAAGAACGACCCCGCCATCGCGCCGGACCTGCCCGACAAG
CTGGAGAACACCGAGCTGGTGACCCTCTCGGTGGAACAGGCGGCGCTGTACGAGGCCATCGTGCAG
GAGACGCTGGAGCGGGCCGCGCAGGCCGACGGCATCCAGCGGCAGGCGGCGGTCCTGGCAGGCCTC
ACGCGGCTGAAGCAGGTGTGCAACCATCCCGCAGCCGCCACCGGCGACGGCCCCCTGGTGGGGCGG
AGCGGCAAGATCGACCGGCTGGTGCAACTGCTGCAGGAGGTGCTGGCGGCGGGCGAGCAGGCCCTG
CTCTTCACCCAGTTCGCCCCGCTTCGGCGGGCGGCTGCAGGCCTACCTGGCGGAGACGCTGGGCTGC
GAGGTGCTCTTCCTGCACGGCGGCACGCCCCAGCCCGAGCGGGACCGGCTCGTCGCCCGGTTCCAG
GCCGGCGAGGCGCCCCTCTTCATCCTCTCGCTGAAAGCCGGCGGCCTTGGCCTCAACCTCACCGCC
GCGACCCACGTCTTTCACGTGGACCGGTGGTGGAATCCGGCGGTGGAGGATCAGGCCACAGACCGG
GCCTACCGCATCGGCCAGACGCGCAGGGTGCTGGTGCACCGGCTGATCACCGCCGGCACGCTGGAG
GAGCGCATCGACCGGCTGCTGGCCGAGAAGCGTGCCCTGGCGGGCCAGGTGATCATCAGCGGCGAG
TCGTGGCTCGGCCAGCTCTCCACCGAGGAGCTGCGGGCCCTGATCGCCCTGGACCGGGAGGTGTAG
```

SEQ ID NO: 80, Symbiobacterium thermophilum IAM 14863
Symth_IAM14863_SNF2 translated polypeptide
MITVHGSFVPSGASGFFFLWGLDGVAARDAAPPGRRRRGVPRHPCATEPEALYPALRGLPYLNTLS
LVQWQPGPDGVSPARVPGIALSVPNAVQWLLDLPDHFRGTPLRPGHSLQLWCVASKLLLEFLGRGL
MLPVLQAEAGVLSAGWALHLTDADDVRRLTRLAAGLPEACRALVPPDRTPNTYPLPVADGLVHQFM
RTAAAGVIRLLLEEEPLPEAQSLQDTALRHWLAALTGAEARDLPPGLPGAQELYAALDRWSAPATG
VLSHASLRTGVRLHLPGPETDGEWELELTLHAPDEGALPVTADAVWASLGAEVEIGGQRYQGAEQR
LLADLPAMARLFPPLAPLLRDPAPSRMRIPADDVLALIQEGAMLLQQAGHPVLLPAALAKPAALRV
GMRLSPAGGSPSMFGLHQIVNVRWDVALGGTPLTLDELRHLARQKRPLVQMQGRWVRVDERTLAAV
LRRIEQHGGQMELGTALRLAPEADEATATGWIAELLERLQEPARMEPVPTPGGFAGTLRPYQQRGL
AWLAFLRRWGLGACLADDMGLGKTVQLIALLLHEREAGWAAGPTLLVCPVSVLGNWCRELARFAPG
LRVLVHHGPGRLGEPDFARQAGAHDVVLTTYSLLARDAALLGQVTWNGIVADEAQNLKNPDTQHAR
ALRSLSGGYRIALTGTPVENHLGDLWSLFQFLNPGLLGSREEFERRYAVPIQRYQDEEAAARLRRQ
VGPFILRRQKNDPAIAPDLPDKLENTELVTLSVEQAALYEAIVQETLERAAQADGIQRQAAVLAGL
TRLKQVCNHPAAATGDGPLVGRSGKIDRLVQLLQEVLAAGEQALLFTQFARFGGRLQAYLAETLGC
EVLFLHGGTPQPERDRLVARFQAGEAPLFILSLKAGGLGLNLTAATHVFHVDRWWNPAVEDQATDR
AYRIGQTRRVLVHRLITAGTLEERIDRLLAEKRALAGQVIISGESWLGQLSTEELRALIALDREV FIGURE 10 (continued)

SEQ ID NO: 81, Synechococcus sp. WH 5701 Syn_sp_WH5701_SNF2 nucleic acid sequence

ATGAGCCTGCTGCACGCCACCTGGCTGTCGGCCGACACCGCCGCCGTGCCCGCCCTGGGAGGCGGC
TACCGGCCGGGCTTGCTGCTCTGGGCCGACACCTGGCGGGTGGCGGAACCCCAGACACCGGCCAGC
GAGGCGCCCCAGCACCCCCTCAGCCTCGACCAGGACGACCTCGGCGCCTGGCTTGAGGAGGCCGAC
CTCTGGACGGAGGATTTCCGCCCGGCCGGAGCCACCCTCTGCCTGCCCAGCCGCCGCCAGGGGGCC
AGGGGGAAAAAGAAAAGCGACACCAGCAGCTGGAGCGGCCTGCCCCTGCAGGCGGGCGAGCCGATC
CCGAAATCCGTGGAGTGGTGGCCCTGGCGGGTGGAGGGCTGGTGGCTGGAGCCCGGCGCCGCCACC
CTCTGGCTTGGGCGCCTGCCCCTCTCAGGCGACCATCCCGACCTGGCCGATGACCTGCGCTGGTGG
AGCCATCTGCAGCGCTGGTCGCTGAGCCTGCTGGCCCGGGGCCGGCTGCTGCCCCAGGTGGAGGGG
GGCCGCGCCCGCTGGCTGCCGTTGATCAACCGCGAAGACGACCGGCGCCGCCTGGAGGATCTGGCC
TCGCGTCTGCCCCAGGTGGCGGTGGCGGCCCTGGAGCCCGGCCAGGGGGAGGCCGGCGTCGCGATG
GCGTGCTGGCGGCCGGGATCCGGGCGTCGGCGGCTGGCCTCGATCCTCACGCACCTGGTGGATGCA
CGCATGCGTGCGGGCTTCACCCCCAGCGAAGAGGGGCTGGATCCGCTGCTGGCGGCCTGGCAGCGG
GCCCTCGGCCCCGGTGACGGCCGCCTCGATCTCGGGGACGACGACTGCGAACGCCTGCAGGTGGCC
ACTCACCACTGGCGCGAAGCGGTGGCTGGCCGGGTCGAGCCGGCCCGGGCCTGTCTTGAGCTCGAC
ACACCCGATGAGGGGGAAGATCTCTGGCCCCTGCGCTTCAGCCTCCAGGCCGAGGCCGATCCCAGT
CTGCTGCTGCCCGCAGCCGGGGTCTGGGCCGCCGGGGCCGGCTGCCTGCAGCTGGGTGAAACCGAA
CTCCAGCAACCCGGTGAACTGCTGCTGGAAGGCCTCGGGAGAGCCCTGCAGGTGTTCGAGCCGATC
GAGAGGGGTCTCGACACCGCCACACCGGAGCGGATGGCTCTCACCCCGGCCGAAGCCTTCGTGCTG
GTGCGCACCGCCGCGCTGAAGCTGCGTGATGTGGGCGTCGGCGTGGTCCTGCCCCCCAGCCTCAGC
GGTGGCCTGGCCAGCCGGCTCGGCCTCTCGATCGAGGCCGATCTGCCCGAGCGCTCCCGCGGCTTC
AGCCTCGGTGAAAGCCTGCAGTGGAGCTGGGAGCTGATGATCGGCGGCGTCACGCTCACCCTGCGG
GACCTGGAGCGGCTGGCGGGCAAGCGCAGCCCGCTGGTGCAGCACAAGGGGGCCTGGATCGAGCTG
CGTCCGGGTGATCTGCGCAATGCCGAGAAGTTCTGCGCCCTCGATCCGGTCCTCAGCCTCGATGAC
GCCCTGCGCCTGACCGGCAACGAGGGGGAGACCCTGCAGCGGCTGCCGGTGCACCGCTTCACAGCC
GGCCCGAGGCTGAAGGCGGTGCTGGAGCAGTACCACCAGCAGAAGGCCCCCGATCCCCTGCCGGCC
CCCGAGGGCTTCGCCGGCCAGCTGCGGCCCTACCAGGAGCGCGGCCTGGGCTGGCTGGCCTTCCTG
CACCGCTTCGATCAGGGGGCCTGCCTGGCCGACGACATGGGCCTGGGCAAGACAATCCAGCTGCTG
GCCTTCCTGCAGCACCTCAAGGCGGAGCAGGAACTGAAGCGTCCCGTACTGCTGGTGGCCCCCACC
TCGGTGCTCACCAACTGGCTGCGGGAAGCGAAGGCCTTCACGCCGGAACTGAACGTGGTGGAGCAC
TACGGCCCCCGGCGGCCCTCCACCCCCGCCGCCCTGAAGAAGAAGCTGGAGGGGATGGATCTGGTG
CTCACCAGCTACGGCCTGCTGCAGCGCGACAGCGAGTTACTGAGCAGCCTCGACTGGCAGGGGGTG
GTGATTGATGAGGCCCAGGCGATCAAGAATTCCTCAGCGCGCCAGTCGCAGGCAGCCCGCGATCTG
GCACGCCCGCTCAAGCAGAGCCGCTTCCGTATCGCACTCACCGGCACCCCGGTGGAGAACCGGGTC
AGTGAGCTCTGGGCCCTGATGGACTTCCTCAATCCGAAGGTGCTTGGGGAGGAGGAGTTCTTCCGC
CAGCGCTACCGCCTGCCGATCGAGCGCTATGGCGACATGGCCTCGGTGCGCGACCTCAAGGCCCGC
GTCGGCCCGTTCATCCTGCGGCGCCTCAAGACTGACCGCTCGATCATCTCCGACCTGCCCGAGAAG
GTGGAACTGAAGGAGTGGGTTGGACTCTCACCCGAGCAGGTCAAGCTCTACCGCCGCACCGTGGAG
GACACCCTCGATGCGATCGCGCGGGCACCCGTGGGCCAGAAGCACGGCCAGGTGCTGGGGCTGCTC
ACCAAGCTCAAGCAGGTCTGCAACCACCCGGCCCTGATGCTCAAGGAAGGGGAGGTGGGGGCCGGC
TTCAGCGCCCGCTCGGCCAAGTTGCAGCGGCTCGAGGAAATCGTCGAGGAGGTGATCGCGGCCGGC
GATCGGGCCCTCCTGTTTACCCAGTTCGCCGAATGGGGCCACCTGCTCCAGACCCACCTGCAGCAG
CGCTTCCACCAGGAGGTGCCCTTTCTCTATGGCAGTACCAGCAAGGGGGAGCGTCAGGCGATGGTG
GATCGCTTCCAGGACGACCCCGGGGACCACAGCTGTTCCTGCTCTCGCTCAAGGCAGGCGGCGTG
GGGCTCAACCTCACCCGGGCCAGTCATGTGTTCCACATCGACCGCTGGTGGAATCCGGCGGTGGAG
AACCAGGCCACCGACCGGGCCTACCGCATCGGCCAGACCAACCGGGTGATGGTGCACAAGTTCATC
ACCAGCGGCTCGGTGGAGGAGAAGATCGACCGCATGATCCGCGAAAAGGCCCGCCTGGCCGAAGAC
ATCGTCGGCAGCGGTGAGGAGTGGCTCGGAGGCCTCGATCCCGGCCAGCTGCGCGACCTGGTGGCC
CTGGAGGAGTGA

FIGURE 10 (continued)

SEQ ID NO: 82, Synechococcus sp. WH 5701 Syn_sp_WH5701_SNF2 translated polypeptide
MSLLHATWLSADTAAVPALGGGYRPGLLLWADTWRVAEPQTPASEAPQHPLSLDQDDLGAWLEEAD
LWTEDFRPAGATLCLPSRRQGARGKKKSDTSSWSGLPLQAGEPIPKSVEWWPWRVEGWWLEPGAAT
LWLGRLPLSGDHPDLADDLRWWSHLQRWSLSLLARGRLLPQVEGGRARWLPLINREDDRRRLEDLA
SRLPQVAVAALEPGQGEAGVAMACWRPGSGRRRLASILTHLVDARMRAGFTPSEEGLDPLLAAWQR
ALGPGDGRLDLGDDDCERLQVATHHWREAVAGRVEPARACLELDTPDEGEDLWPLRFSLQAEADPS
LLLPAAGVWAAGAGCLQLGETELQQPGELLLEGLGRALQVFEPIERGLDTATPERMALTPAEAFVL
VRTAALKLRDVGVGVVLPPSLSGGLASRLGLSIEADLPERSRGFSLGESLQWSWELMIGGVTLTLR
DLERLAGKRSPLVQHKGAWIELRPGDLRNAEKFCALDPVLSLDDALRLTGNEGETLQRLPVHRFTA
GPRLKAVLEQYHQQKAPDPLPAPEGFAGQLRPYQERGLGWLAFLHRFDQGACLADDMGLGKTIQLL
AFLQHLKAEQELKRPVLLVAPTSVLTNWLREAKAFTPELNVVEHYGPRRPSTPAALKKKLEGMDLV
LTSYGLLQRDSELLSSLDWQGVVIDEAQAIKNSSARQSQAARDLARPLKQSRFRIALTGTPVENRV
SELWALMDFLNPKVLGEEEFFRQRYRLPIERYGDMASVRDLKARVGPFILRRLKTDRSIISDLPEK
VELKEWVGLSPEQVKLYRRTVEDTLDAIARAPVGQKHGQVLGLLTKLKQVCNHPALMLKEGEVGAG
FSARSAKLQRLEEIVEEVIAAGDRALLFTQFAEWGHLLQTHLQQRFHQEVPFLYGSTSKGERQAMV
DRFQDDPRGPQLFLLSLKAGGVGLNLTRASHVFHIDRWWNPAVENQATDRAYRIGQTNRVMVHKFI
TSGSVEEKIDRMIREKARLAEDIVGSGEEWLGGLDPGQLRDLVALEE

SEQ ID NO: 83, Synechococcus sp. BL107 Syn_sp_BL107_SNF2 nucleic acid sequence
ATGAGCCTGCTGCACGCCACCTGGCTTCCCGCCATTCGTACTTCCAGCAGTTCCGGACAACCGGCA
CTGCTCGTTTGGGCTGACACCTGGCGTGTCGCCTCACCGGAGGGACCTGGACTCACACCCGCTCTG
CATCCCTTCACCCTTGGCTCGAACGATCTCAAGGCTTGGTTGACCGAACGGGACCTGATGCCTGGG
GGCAGCATCGATGCCACCGCCTGCCTCACCCTCCCAAGCCGCACCGTCAAACCCCGCAAAGTCGA
ACCCAATCGAGCGAACCAGATCCGGAGGGGCCAGCCTGGACCGGGTTGCCAATGCAAGCGGGAGAA
CCCATTCCAAAACAAATGGAATGGTGGCCATGGCAAGTGCAAGGCCTGGCGGTCGAGCCATCGGCC
GCCACGGAATGGCTGGCCCGTTTACCCCTATCGGGCCGACATCCAGACCTTGGGGATGAACTGCGC
TGGTGGAGTCACCTCCAACGTTGGTCCCTCAGCTTGGTGGCCCGTGGTCGCTGGATTCCCCAAATG
GAATTAAGCAAAGGCGAGGGGTACCCCCACCGAGCGCGCTGGGTTCCCCTGCTGAACCGTGAGGAG
GATCGACGCCGGCTCGAAGACCTCGCCGCGACGCTGCCCCTCGTAGCGACCTGTGCCCTCCCTTGG
CGTGAGCCACTCGGACGCCGCAGCAACCGCACCACCAGGCTTCGACCGGAAGCGATGCGAGCCGCC
AATCCGGTCGCCTGCTGTCGCCCACGAAGCGGTCGCCTCAGGGTGGCCACCTTGCTTGAAGACTTG
GTGGATGCGGAGCTGCGCAAGGGATTTGAACCAAGCACGGAAGGCCTCGACCCCTTACTCACCTTG
TGGCAAGAGGCCCTGGCCTCAGAAACCGGTGTTGTGGAGGTGGGCAACGAAGACGCAGAACGCCTC
ACCGCGGCAAGCCTGCACTGGCGCGAGGGAATTGCCGGAGGCTTCGCGGCCGCCCGCACCTGCCTC
GAACTCAACACCCCAAACGAAGGCGAAGAACTCTGGGACCTGAAGTTTGGATTGCAAGCGGAGGCC
GATCCCAGCCTCAAGCTGCCGGCCGCCGCGGCCTGGGCCTCAGGAGCGGAAACCCTTCAACTGGGG
GAAATCCAAGTTGACCAGGCGGGGGAAGTGCTGCTGGAGGGTCTTGGCCGAGCCCTCACGGTGTTC
CCTCCGATCGAACGCGGACTGGAAAGCGCAACACCGGAAACGATGCAGCTCACTCCAGCGGAGGCA
TTTGTGTTGGTGCGAACAGCAACGCACCAGCTCCGCAATGCCGGCATCGGCGTCGAACTGCCCCCC
AGTCTTTCAGGGGCCTCGCCAGCCGGCTTGCTTAGCGATTAAAGCGGATCTACCGGATCGATCC
AGCGGCTTCACCCTCGGCGAATCTCTTGACTGGAGCTGGGATCTCATGATCGGCGGCGTCACACTC
ACCCTCCGAGAGCTCGAACGTCTCAGCGGTAAGCGAAGTCCGCTGGTACGCCACAAGGGCGCCTGG
ATCGAACTACGGCCCAACGATCTCCGCAACGCCAACGCTTTTGTGGAGCCAATCCAGAACTGAGC
CTCGACGACGCACTACGGCTCACGGCCACAGAAGGGGAGCTCATGATGCGCCTGCCGGTGCATCGC
TTTGATGCAGGGCCTCGTCTTCAGGGAGTTCTCGAGCAATACCACCAGCAAAAAGCCCCCGATCCC
CTGCCAGCTCCAGAGGGATTTTCCGGACAACTCCGTCCCTATCAAGAACGTGGCTTGGGCTGGCTG

```
GCCTTCCTGCATCGCTTCGATCAGGGCGCCTGCCTGGCGGACGACATGGGCTTGGGCAAGACCATC
CAGTTATTGGCGTTCCTGCAGCACCTCAAAGCGGAAAACGAACTCAAACGCCCGGTGCTGTTGGTG
GCCCCAACCTCGGTGCTCACGAATTGGCGACGGGAAGCGGAAGCCTTCACCCCTGAGCTGTCGGTG
AGAGAGCACTACGGGCCACGCCGGCCTTCCACGCCGGCCGCCTTGAAAAAGAGCTCAAAGGTGTG
GATCTGGTGCTCACCAGTTACGGACTGATGCAACGCGACAGTGAGCTGCTGGACAACCTCGACTGG
CAAGGGGTTGTGATCGATGAAGCTCAGGCGATCAAGAACCCTGGGGCAAAGCAAAGCCAAGCGGCC
CGAGACCTAGCGCGAGCCGGGAAGAGCAGCAGGTTCGCATTGCACTCACGGGCACACCGGTGGAA
AACCGCGTCAGCGAGCTGTGGGCGCTGATGGATTTCCTCAACCCCAAAGTGTTGGGTGAGGAAGAC
TTTTTTCGTCAGCGCTACCGCATGCCAATTGAGCGCTACGGCGATATGTCGTCGTTACGCGATCTC
AAAGCACGGGTTGGTCCCTTCATCCTGCGCCGCCTCAAAACCGACAAGTCGATCATTTCCGACCTG
CCTGAAAAGGTGGAGCTCAGCGAATGGGTGGGGCTCAGCAAAGAACAGAAATCGCTGTACAACAAA
ACCGTTGAAGACACCCTCGATGCCATTGCCACCGCACCTCGAGGGCAACGCCATGGCCAGGTGCTG
GCGCTCTTGACCCGTTTAAAACAGATTTGCAATCACCCGGCCTTAGCCCAACGCGAAGGTGCCGTT
GACGCCGAATTCCTTAGCCGGTCCGCCAAGCTCATGCGGCTGGAAGAAATCCTTGAAGAGGTGATT
GAAGCCGGCGATCGCGCTTTGCTGTTCACCCAGTTCGCCGAATGGGGACACCTCTTGCAGGCCTGG
ATGCAACAACGCTGGAAGTCTGAGGTTCCCTTTCTGCACGGCGGAACCCGCAAAAGTGATCGGCAA
GCGATGGTGGATCGATTCCAAGAGGACCCCCGGGGACCTCAACTCTTCCTTCTCTCCCTCAAGGCC
GGTGGTGTTGGCCTAAACCTCACCCGGGCCAGCCACGTGTTCCACGTTGGATCGCTGGTGGAATCC
AGCGGTGGAAAACCAAGCCACCGACCGGGCCTATCGAATTGGTCAAACCAACCGGGTGATGGTGCA
CAAATTCGTCACCCGTGGCTCGGTGGAAGAAAAAATCGACCAAATGATTCGTGA
```

SEQ ID NO: 84, Synechococcus sp. BL107 Syn_sp_BL107_SNF2 translated polypeptide

```
MSLLHATWLPAIRTSSSSGQPALLVWADTWRVASPEGPGLTPALHPFTLGSNDLKAWLTERDLMPG
GSIDATACLTLPSRTVKPRKSRTQSSEPDPEGPAWTGLPMQAGEPIPKQMEWWPWQVQGLAVEPSA
ATEWLARLPLSGRHPDLGDELRWWSHLQRWSLSLVARGRWIPQMELSKGEGYPHRARWVPLLNREE
DRRRLEDLAATLPLVATCALPWREPLGRRSNRTTRLRPEAMRAANPVACCRPRSGRLRVATLLEDL
VDAELRKGFEPSTEGLDPLLTLWQEALASETGVVEVGNEDAERLTAASLHWREGIAGGFAAARTCL
ELNTPNEGEELWDLKFGLQAEADPSLKLPAAAAWASGAETLQLGEIQVDQAGEVLLEGLGRALTVF
PPIERGLESATPETMQLTPAEAFVLVRTATHQLRNAGIGVELPPSLSGGLASRLGLAIKADLPDRS
SGFTLGESLDWSWDLMIGGVTLTLRELERLSGKRSPLVRHKGAWIELRPNDLRNAERFCGANPELS
LDDALRLTATEGELMMRLPVHRFDAGPRLQGVLEQYHQQKAPDPLPAPEGFSGQLRPYQERGLGWL
AFLHRFDQGACLADDMGLGKTIQLLAFLQHLKAENELKRPVLLVAPTSVLTNWRREAEAFTPELSV
REHYGPRRPSTPAALKKELKGVDLVLTSYGLMQRDSELLDNLDWQGVVIDEAQAIKNPGAKQSQAA
RDLARAGKSSRFRIALTGTPVENRVSELWALMDFLNPKVLGEEDFFRQRYRMPIERYGDMSSLRDL
KARVGPFILRRLKTDKSIISDLPEKVELSEWVGLSKEQKSLYNKTVEDTLDAIATAPRGQRHGQVL
ALLTRLKQICNHPALAQREGAVDAEFLSRSAKLMRLEEILEEVIEAGDRALLFTQFAEWGHLLQAW
MQQRWKSEVPFLHGGTRKSDRQAMVDRFQEDPRGPQLFLLSLKAGGVGLNLTRASHVFHVGSLVES
SGGKPSHRPGLSNWSNQPGDGAQIRHPWLGGRKNRPNDS
```

SEQ ID NO: 85, Synechococcus sp. CC9311 Syn_sp_CC9311_SNF2 nucleic acid sequence

```
ATGAGCCTGCTGCACGCCACCTGGCTTCCGGCCATTCGTACTCCTACCAGCTCTGGACGAGCTGCC
CTTTTGGTGTGGGCCGACACCTGGCGCGTTGCCGAGCCTGCAGGCCCAAGTACAACCCCTGCGCTT
CACCCGTTCACCCTCAGCCCAGACGATCTCCGGGCCTTGCTCACGGAACGGGATCTTTTACCCGAC
GGCATCATTGATGCCACGGCATGCCTCACCCTGCCGAGCCGCAGCGTGAAGCCCCGAAAAAACGC
GAAACAGAGACCAGCAGCACTGAACAGCCCAGCTGGACAGGCCTTCCCTTACAGGCTGGAGAACCG
ATCCCCAAACAAACAGAGTGGTGGCCTTGGCAGGTTCAGGGGCTCGCAATTGACCCCATGGCGGCC
```

FIGURE 10 (continued)

```
ACCGCCTGGCTGTCCAAACTGCCTCTGTCAGGACGACATCCTGATTTGGCTGATGAGTTGCGCTGG
TGGAGTCACATGCAGCGTTGGTCCCTCAGCCTCGTAGCCCGAAGTCGCTGGCTCCCCCAAGTGGAG
CTGAGCAAGGGCGAGGGCTATCCCCATCGCGCCCGCTGGGTACCGCTTCTGAATCGGGAAGAAGAC
AGGCGCCGTCTAGAAGACTTGGCCGCAGGGCTCCCTCTCGTTGCCACCTGTGCCCTGCCTTGGCGA
GAACCAACGGGCAAACGCAGCAACCGAATCACCAGGCTCAGACCAGAAGCCATGCGCGCCGCGAAT
CCCGTGGCTTGCTGCAGGCCTCGCAGCGGACGACTAAGGGTTGCCACGTTATTGGCCGACCTGATG
GACGCGCAGCTGCGCAAGGGCTTTACTCCTGACCCTGACGGCTTGGACCCCCTGCTACGCGCCTGG
GAGGAGGCCTTGAGCTCGGATACAGGTGAAATCCAACTCAGCGATGAAGAAACCGAACGCCTAGCC
ACCGCCAGTAATCATTGGCGTGAAGGGGTCGCTGGAAATGTTGCTGCAGCCCGCGCCTGCCTGGAG
CTGGCAACACCAGCGGACGATGAGGACCTTTGGCCACTGCGCTTCTTTCTGCAGGCGGAAGCAGAT
CCAACCCTCAAGCTGCCCGCAGGAGCGGCATGGGCTGCAGGCCCCAGCGGCCTCCAACTTGGGGAA
ATCAAGGTGGAGCACCCCAGCGAGGTCTTGCTCGAGGGTATGGGCGAGCCCTGACCGTGTTCCAA
CCGATCGAGCGCGGACTGGACAGTGCCACGCCAGAGAGCATGCAGCTCACACCAGCTGAAGCGTTT
GTTTTGGTGCGCACAGCAGTCCGACAACTGCGGGATGTGGGCGTTGGCGTTGACCTGCCACCAAGC
CTGTCTGGAGGGCTGGCTAGCAGGCTTGGCCTCGCCATCAAGGCAGAACTCTCCGAGCGTTCGCGA
GGCTTCACGCTCGGTGAAAACCTTGACTGGAGCTGGGAGCTGATGATCGGCGGGGTGACGCTGACC
TTGCGAGAGCTTGAGCGATTGGCTGGTAAGCGCAGCCCTCTGGTGCGTCACAAAGGGGCTTGGATC
GAACTACGGCCCAATGACCTCAAAAATGCCGAGCGCTTTTGCGCCGCCAATCCAGACCTGAGCCTC
GACGACGCGCTTCGGCTCACCGCCACCGAAGGCGACACGATGATGCGCCTGCCCGTGCATCAATTT
GATGCCGGTCCGCGGCTGCAAGCCGTGCTGGAGCAGTACCACCAGCAGAAAGCGCCAGACCCACTC
CCCGCTCCCGAGGGCTTTTCGGGTCAACTCAGGCCCTATCAAGAGAGAGGACTCGGCTGGCTTGCC
TTCCTGCATCGCTTCGACCAAGGCGCCTGCTTGGCCGATGACATGGGCCTTGGCAAAACCATCCAG
CTGCTGGCTTTTCTGCAACACCTCAAGGCAGAAAACGAACTCAAGCGATCAGTGCTTTTAATTGCA
CCCACATCTGTCCTTACGAACTGGAAACGAGAGGCAACAGCGTTTACACCCGAGCTCAAGGTGCAT
GAGCACTACGGTCCAAAACGCCCGAGCACCCCAGCAGCACTGAAAAAGGCGCTGAAAGACGTGGAT
CTCGTGCTCACCAGCTATGGCCTGTTACAACGCGACAGTGAGCTCCTCGAAAGTCACGATTGGCAA
GGCCTCGTGATCGATGAAGCGCAGGCGATAAAAAACCCCTCCGCGAAGCAAAGCCAAGCCGCCCGT
GATCTGGCCCGCCCGAAAAAGAACAGCCGTTTTCGCATCGCACTCACCGGCACACCAGTTGAGAAC
CGCGTCAGCGAGCTCTGGGCCCTGATGGACTTCCTCAACCCTCGGGTACTGGGAGAGGAAGAATTT
TTCCGACATCGCTATCGCATGCCGATTGAGCGTTACGGAGACCTGTCCTCGCTGCGCGACCTCAAA
GCCCGAGTGGGACCTTTCATCCTCAGACGACTCAAAACAGACAAAGCGATCATCTCGGATCTACCC
GAGAAGGTGGAATTGAGCGAGTGGGTTGGGCTGAGCAAAGAGCAGAAGTCGCTGTATGCCAAAACC
GTTGAAGACACCTTGGATGCCATTGCCCGCGCGCCACGCGGCAAACGTCATGGTCAGGTGTTGGGT
CTGCTCACCAAGCTCAAGCAGATTTGCAACCACCCTGCGCTTGCCCTCAAGGAGCAGGGCGCCAGC
GAAGATTTCCTCAAACGGTCCGTGAAGCTGCAACGTCTCGAAGAAATTTTGGACGAGGTTGTAGAA
GCTGGGGATCGAGCCTTGCTGTTTACCCAGTTCGCGGAATGGGGCAAGTTGCTCCAGGATTATTTG
CAACGACGCTGGCGCAGCGAAGTTCCCTTCCTCAGCGGCAGCACCAGCAAAAGTGAACGGCAAGCC
ATGGTCGATCGCTTCCAGGAGGATCCGCGCGGGCCCCAGCTTTTCCTGTTATCACTCAAAGCTGGC
GGAGTCGGCCTCAACCTCACGCGCGCCAGTCATGTCTTTCACATCGACCGTTGGTGGAACCCCGCC
GTTGAAAATCAAGCCACGGACCGTGCCTATCGCATCGGCCAAACGAACCGGGTCATGGTGCATAAG
TTCATCACCAGCGGCTCCGTTGAGGAGAAAATTGACCGCATGATCCGCGAGAAGTCCAGACTGGCG
GAAGACATCATTGGCTCCGGCGAAGACTGGCTTGGAGGCCTGGAAATGGGACAACTCAAAGAGCTA
GTGAGCCTGGAGGACAACCAAGCATGA
```

FIGURE 10 (continued)

SEQ ID NO: 86, Synechococcus sp. CC9311 Syn_sp_CC9311_SNF2 translated polypeptide
MSLLHATWLPAIRTPTSSGRAALLVWADTWRVAEPAGPSTTPALHPFTLSPDDLRALLTERDLLPD
GIIDATACLTLPSRSVKPRKKRETETSSTEQPSWTGLPLQAGEPIPKQTEWWPWQVQGLAIDPMAA
TAWLSKLPLSGRHPDLADELRWWSHMQRWSLSLVARSRWLPQVELSKGEGYPHRARWVPLLNREED
RRRLEDLAAGLPLVATCALPWREPTGKRSNRITRLRPEAMRAANPVACCRPRSGRLRVATLLADLM
DAQLRKGFTPDPDGLDPLLRAWEEALSSDTGEIQLSDEETERLATASNHWREGVAGNVAAARACLE
LATPADDEDLWPLRFFLQAEADPTLKLPAGAAWAAGPSGLQLGEIKVEHPSEVLLEGMGRALTVFQ
PIERGLDSATPESMQLTPAEAFVLVRTAVRQLRDVGVGVDLPPSLSGGLASRLGLAIKAELSERSR
GFTLGENLDWSWELMIGGVTLTLRELERLAGKRSPLVRHKGAWIELRPNDLKNAERFCAANPDLSL
DDALRLTATEGDTMMRLPVHQFDAGPRLQAVLEQYHQQKAPDPLPAPEGFSGQLRPYQERGLGWLA
FLHRFDQGACLADDMGLGKTIQLLAFLQHLKAENELKRSVLLIAPTSVLTNWKREATAFTPELKVH
EHYGPKRPSTPAALKKALKDVDLVLTSYGLLQRDSELLESHDWQGLVIDEAQAIKNPSAKQSQAAR
DLARPKKNSRFRIALTGTPVENRVSELWALMDFLNPRVLGEEEFFRHRYRMPIERYGDLSSLRDLK
ARVGPFILRRLKTDKAIISDLPEKVELSEWVGLSKEQKSLYAKTVEDTLDAIARAPRGKRHGQVLG
LLTKLKQICNHPALALKEQGASEDFLKRSVKLQRLEEILDEVVEAGDRALLFTQFAEWGKLLQDYL
QRRWRSEVPFLSGSTSKSERQAMVDRFQEDPRGPQLFLLSLKAGGVGLNLTRASHVFHIDRWWNPA
VENQATDRAYRIGQTNRVMVHKFITSGSVEEKIDRMIREKSRLAEDIIGSGEDWLGGLEMGQLKEL
VSLEDNQA

SEQ ID NO: 87, Synechococcus sp. CC9605 Syn_sp_CC9605_SNF2 nucleic acid sequence
ATGAGCCTGCTGCACGCCACCTGGCTTCCCGCCATCCGCACCTCCAGCAGTTCCGGTCAACCGGCA
CTGCTCGTTTGGGCTGACACCTGGCGGGTGGCCACACCGGAAGGCCCGGGCCTTACCCCAGCGCTG
CACCCCTTCACCCTAAGCCATGAAGACCTCAGGGCCTGGCTGAGCGAACGCGACCTCTTGCCCGGC
GGCTGCATCGATGCCACGGCGTGCCTCACCCTGCCGAGCCGCACGGTGAAGCTGCGCAAAAGCCGC
AGCACAAAAGAGGAGCCAACACCGGAACCACCGGGTTGGACCGGGCTACCGATGCAGGCCGGCGAA
CCGATCCCCAAGCAAACCGAATGGTGGCCCTGGCAGGTGCAGGGGCTCGCGGTGGAACCGTCGGCA
GCCACGGAGTGGCTGTCCCGATTGCCGCTCTCCGGCACCAATCCAGACCTGGCTGATGAACTGCGC
TGGTGGAGCCATCTGCAGCGCTGGGCCTTGAGTCTGGTGGCCCGGGGCCGCTGGATTCCCCAGATG
GAGTTCAGCAAAGGGGAGGGCTATCCCCATCGGGCCCGTTGGGTGCCGCTTCTCAACCGGGAAGAA
GACCGGCGCCGGCTGGAGGATCTGGCGGCCAGCCTGCCGCTGGTGGCCACCTGCGCCTTGCCCTGG
CGGGAACCCCTGGGGCGCCGCAGCAACCGCACCACCCGGTTACGACCGGAGGCGATGCGAGCCGCC
AACCCTGTGGCCAGCTGCCGGCCCCGCAGCGGACGCCTGCGGGTGGCGACGCTGCTGGAAGATCTA
GTGGACGCGCAGCTGCGCAAGGACTTTGAACCCTCCACCGATGGGCTTGATCCCCTGCTGACCCTC
TGGCAGGAGGCCCTGGGGTCGGAGACCGGGGTGATCGAGATCGGCGATGAAGAGGCCGAACGCCTG
GCCACCGCCAGCCATCACTGGCGGGAGGGCATCGCCGGCGATTTTGCTGCGGCCCGCACCTGCCTT
GAACTGCACACCCCACCGGATGGGGAGGATCTCTGGGAGCTGCGCTTCGGGCTGCAGGCGGAAGCT
GACCCCAGCCTGAAGCTCCCGGCCGCCGCGGCCTGGGCGGCTGGTGCGGAACCGCTACAGCTTGGA
GAGATCCGGGTGGACCAACCGGGTGAAGTGCTGCTGGAAGGCATGGGCCGCGCCCTGAGCGTGTTT
CCGGCAATTGAGCGGGGTCTGGAGAGCGCCACACCTGAAACGATGCAGCTCACCCCGGCCGAGGCC
TTCGTGCTGGTGCGCACGGCCGCCCGGCAGCTGCGGGATGCCGGCGTGGGAGTGGAGCTGCCGCCC
AGCCTCTCCGGTGGCCTGGCCAGCCGACTGGGCCTGTCGATCAAAGCGGAACTGCCCGAACGCTCG
AGCGGTTTCACGTTGGGTGAGTGTCTGGCCTGGGAGTGGGATCTGATGATCGGCGGGGTGACGCTC
ACCCTGCGGGAATTGGAGCGCCTGAGCGGCAAGCGCAGCCCCCTGGTGCGCCACAAGGGGGCCTGG
ATCGAACTGCGGCCCAACGACCTCAAAAATGCCGAACGCTTCTGTGGGGCGAAACCTGAACTGAGC
CTCGACGACGCGCTGCGGCTGACGGGGACGGAAGGGGAACTGTTGATGCGGATGCCGGTGCACCGC
TTCGACGCCGGCCCACGGCTGCAATCGGTGTTGCAGCAATACCACCAGCAGAAGGCCCCCGACCCC

```
TTGCCGGCCCCGGAAGGATTCAGCGGGCAGCTGCGGCCTTATCAGGAGCGGGGCCTCGGCTGGCTC
GCCTTCCTGCACCGCTTCGATCAAGGGGCCTGTCTAGCTGACGACATGGGCTTGGGCAAAACCATT
CAGTTGCTAGCGTTCCTGCAGCACCTCAAAGCGGAGCAAGAACTGAAACGCCCGGTGCTGCTGGTG
GCCCCCACATCGGTGCTCACCAACTGGCGACGGGAGGCGGAATCGTTCACTCCAGAGTTGAAGGTC
ACCGAGCATTACGGGCCTCGCCGGCCCTCCACACCCGCCGAACTCAAAAAAGCGTTGAAGGAGGTG
GATCTGGTGCTCACCAGCTACGGGCTGCTGCAGCGTGACAGCGAACTGCTGGAAACCCAGGACTGG
CAGGGGGTGGTGATTGACGAAGCCCAGGCGATCAAGAACCCTGGCGCCAAACAGAGCCAAGCCGCC
CGGGATCTGGCCCGCACCGGCCGCATCAAGAGCAACCGCTTCCGCATCGCACTCACCGGCACCCCC
GTGGAAAACCGGGTGAGCGAACTGTGGGCCTTGATGGACTTCCTCAACCCAAAGGTGCTTGGGGAA
GAAGACTTCTTCCGCCAGCGCTATCGGATGCCGATTGAGCGCTACGGCGACATGTCGTCCCTGCGG
GACCTGAAAGGCCGCGTGGGTCCGTTCATCCTGCGCCGGCTGAAAACCGACAAGACGATCATTTCC
GACCTGCCTGAAAAGGTGGAGCTGAGCGAATGGGTGGGGCTGAGCAAGGAGCAGAAATCTCTGTAC
AGCAAGACCGTGGAAGACACCCTCGATGCCATTGCCCGGGCGCCGCGCGGGCAGCGCCACGGGCAG
GTGCTGGCCCTGCTCACCCGGCTGAAACAGATCTGCAACCATCCCGCCCTGGCCCTGAGCGAAGGG
GCCGTGGACGATGGCTTCCTGGGCCGTTCGGCCAAGCTGCAGCGGCTGGAGGAGATCCTCGATGAG
GTGATCGAAGCGGGCGATCGGGCCCTGCTGTTCACCCAGTTCGCCGAATGGGGGCATTTGCTAAGG
GCCTGGATGCAGCAGCGCTGGAAATCAGAAGTGCCCTTCCTGCACGGCGGCACCCGCAAGAACGAA
CGCCAGGCGATGGTGGATCGCTTCCAGGAGGATCCCCGCGGTCCACAGCTGTTCCTGCTCTCGCTC
AAGGCCGGTGGTGTGGGCCTCAACCTCACGCGGGCCAGCCATGTGTTCCACATCGATCGCTGGTGG
AACCCTGCCGTGGAAAACCAGGCCACCGACCGGGCCTATCGGATCGGCCAAACGAACCGAGTGATG
GTTCATAAATTCATCACCAGCGGTTCGGTGGAGGAAAAAATCGATCGCATGATCCGCGAGAAATCA
CGCCTGGCCGAAGATGTGATCGGCTCCGGCGAAGATTGGCTGGGAAGCCTCGGTGGCGATCAATTG
CGCGATCTCGTTTCTTTGGAGGACACCTGA
```

SEQ ID NO: 88, Synechococcus sp. CC9605 Syn_sp_CC9605_SNF2 translated polypeptide

```
MSLLHATWLPAIRTSSSSGQPALLVWADTWRVATPEGPGLTPALHPFTLSHEDLRAWLSERDLLPG
GCIDATACLTLPSRTVKLRKSRSTKEEPTPEPPGWTGLPMQAGEPIPKQTEWWPWQVQGLAVEPSA
ATEWLSRLPLSGTNPDLADELRWWSHLQRWALSLVARGRWIPQMEFSKGEGYPHRARWVPLLNREE
DRRRLEDLAASLPLVATCALPWREPLGRRSNRTTRLRPEAMRAANPVASCRPRSGRLRVATLLEDL
VDAQLRKDFEPSTDGLDPLLTLWQEALGSETGVIEIGDEEAERLATASHHWREGIAGDFAAARTCL
ELHTPPDGEDLWELRFGLQAEADPSLKLPAAAAWAAGAEPLQLGEIRVDQPGEVLLEGMGRALSVF
PAIERGLESATPETMQLTPAEAFVLVRTAARQLRDAGVGVELPPSLSGGLASRLGLSIKAELPERS
SGFTLGECLAWEWDLMIGGVTLTLRELERLSGKRSPLVRHKGAWIELRPNDLKNAERFCGAKPELS
LDDALRLTGTEGELLMRMPVHRFDAGPRLQSVLQQYHQQKAPDPLPAPEGFSGQLRPYQERGLGWL
AFLHRFDQGACLADDMGLGKTIQLLAFLQHLKAEQELKRPVLLVAPTSVLTNWRREAESFTPELKV
TEHYGPRRPSTPAELKKALKEVDLVLTSYGLLQRDSELLETQDWQGVVIDEAQAIKNPGAKQSQAA
RDLARTGRIKSNRFRIALTGTPVENRVSELWALMDFLNPKVLGEEDFFRQRYRMPIERYGDMSSLR
DLKGRVGPFILRRLKTDKTIISDLPEKVELSEWVGLSKEQKSLYSKTVEDTLDAIARAPRGQRHGQ
VLALLTRLKQICNHPALALSEGAVDDGFLGRSAKLQRLEEILDEVIEAGDRALLFTQFAEWGHLLR
AWMQQRWKSEVPFLHGGTRKNERQAMVDRFQEDPRGPQLFLLSLKAGGVGLNLTRASHVFHIDRWW
NPAVENQATDRAYRIGQTNRVMVHKFITSGSVEEKIDRMIREKSRLAEDVIGSGEDWLGSLGGDQL
RDLVSLEDT
```

FIGURE 10 (continued)

SEQ ID NO: 89, Synechococcus sp. CC9902 Syn_sp_CC9902_SNF2 nucleic acid sequence ATGAGCCTGCTGCACGCCACCTGGCTTCCCGCCATTCGTACTTCCAGCAGTTCCGGACAGCCGGCA
CTGCTCATTTGGGCTGACACCTGGCGTGTCGCCTCACCGGAGGGGCCCGGACTCACACCCGCTCTG
CATCCCTTCACCCTTGGCTCGGACGATCTCAAAGCTTGGTTGACCGAACGGGACCTGATGCCTGGG
GGCAGCATCGATGCCACCGCCTGCCTCACCCTCCCAAGCCGCAGCGTCAAACCCGCAAAGTCGA
ACCCAACCGAGCGAACCAGCCCCAGAGGGACCGGCCTGGACCGGATTGCCAATGCAAGCAGGAGAG
CCCATTCCGAAGCAAATGGAATGGTGGCCCTGGCAGGTACAAGGCCTCGCGGTGGAGCCATCGGCC
GCAACGGAATGGCTCGCCCGTTTACCCCTATCGGGCCGACATCCAGACCTCGGAGATGAATTGCGC
TGGTGGAGCCATCTCCAACGTTGGTCCCTCAGCTTGGTGGCCCGGGGCGCTGGATTCCCCAGATG
GAATTAAGCAAAGGCGAGGGTTACCCCCACCGAGCGCGCTGGGTTCCCTTGTTGAACCGTGAGGAA
GATCGACGACGGCTCGAAGACCTCGCGGCCACGCTGCCCTCGTGGCGACCTGTGCCCTCCCTTGG
CGTGAGCCACTTGGACGCCGTAGCAACCGCACCACCAGGCTTCGACCGGAAGCGATGCGAGCCGCC
AACCCGGTGGCTTGCTGCCGCCCCGGAGCGGTCGCCTCAGGGTGGCCACCTTGCTTGAAGACTTG
GTGGATGCAGAGCTGCGCAAGGGATTTGAACCCACCACAGAGGGGCTCGACCCCCTACTCACCCTG
TGGCAAGAGGCCCTGGCCTCAGAAACCGGTGTTGTGGAGGTGGGCAACGAGGATGCAGAACGCCTT
ACCGCGGCAAGCCTGCACTGGCGCGAAGGGATTGCCGGAGGCTTCGCTGCTGCCCGCACCTGCCTC
GAACTAAACACCCCAAACGAAGGCGAAGAACTCTGGGACCTGAAGTTTGGCTTGCAAGCGGAGGCC
GATCCCAGCCTCAAGCTGCCGGCCGCCGCGGCCTGGGCCTCAGGAGCCGAAACACTCCAGCTCGGG
GAGATCAAAGTTGACCAGGCGGGGGAAGTGCTGCTGGAGGGTCTTGGCCGAGCCCTCACGGTGTTC
CCTCCGATCGAACGCGGACTGGAAAGCGCAACGCCAGAAACGATGCAGCTCACGCCAGCGGAGGCG
TTTGTCTTGGTGCGAACAGCAACGCACCAGCTCCGCAATGCCGGCATCGGCGTCGAACTGCCCCCC
AGCCTTTCAGGGGGCCTCGCCAGCCGGCTTGGTTTAGCCATCAAGGCAGATTTACCAGATCGATCC
AGCGGCTTCACCCTCGGAGAATCTCTGGACTGGAGCTGGGATCTGATGATCGGCGGCGTCACACTC
ACCCTGCGAGAGCTCGAACGGCTCAGCGGTAAGCGCAGTCCGCTTGTGCGCCACAAGGGAGCCTGG
ATCGAACTGCGACCCAACGATCTCCGCAACGCCGAACGCTTCTGTGGAGCCAATCCAGAACTGAGC
CTCGACGATGCCCTAAGGCTCACGGCCACAGAAGGGGAGCTAATGATGCGCTTGCCGGTGCATCGC
TTTGATGCGGGGCCTCGGCTTCAGGGAGTTCTCGAGCAATATCACCAGCAAAAAGCCCCCGATCCC
CTTCCCGCTCCAGAGGGATTTTCCGGACAACTGCGTCCTTATCAAGAACGTGGCTTGGGCTGGCTG
GCCTTCTTACATCGCTTCGATCAAGGCGCCTGCCTGGCGGACGACATGGGCTTGGGCAAGACCATC
CAATTGTTGGCCTTCCTGCAGCACCTCAAAGCCGAGCACGAACTCAAACGCCCGGTGCTGTTGGTG
GCCCCAACCTCGGTGCTCACGAATTGGCGACGGGAGGCGGAAGCCTTCACCCCCGAGCTGTCGGTG
AAAGAGCACTACGGCCCACGCCGGCCTTCCACGCCGGCCGCCTTGAAAAAAGAACTCAAAGATGTG
GATCTGGTGCTCACCAGTTACGGCCTGATGCAACGCGACAGCGAGCTGCTGGACAGCGTCGACTGG
CAAGGGGTTGTGATCGACGAAGCGCAGGCGATCAAAAACCCTGGGGCGAAACAAAGCCAAGCAGCC
CGAGACCTGGCCCGAGCTGGAAAGAGCAGCAGGTTCCGCATCGCACTCACCGGCACACCGGTGGAA
AACCGCGTCAGCGAGCTGTGGGCGCTGATGGATTTCCTCAACCCAAAGGTGTTGGGAGAGGAAGAC
TTCTTTCGTCAGCGCTACCGCATGCCAATTGAGCGCTACGGCGATATGTCGTCGTTACGCGATCTC
AAAGCGCGGGTCGGCCCCTTCATCCTGCGCCGTCTCAAAACCGACAAGTCGATCATTTCCGACCTG
CCTGAAAAGGTGGAGCTCAGTGAATGGGTGGGTCTCAGCAAAGAACAGAAATCGCTGTACAACAAA
ACCGTTGAAGACACCCTCGACGCCATTGCCACCGCACCGCGGGGGCAACGCCATGGCCAGGTGCTA
GCCCTCTTGACCCGGTTAAAGCAGATTTGCAATCACCCGGCTTTAGCCCAACGCGAAGGGGCCGTT
GACAGCGAATTCCTTGGCCGTTCCGCCAAGCTGATGCGACTCGAAGAAATCCTCGAAGAGGTGATT
GAAGCCGGCGATCGCGCTTTGCTATTCACCCAATTCGCCGAATGGGGCATCTCCTGCAGGCCTGG
ATGCAACAACGCTGGAAGTCTGAGGTTCCCTTCCTGCACGGCGGAACCCGCAAGAGTGATCGGCAA
GCGATGGTGGATCGATTCCAAGAGGACCCCCGGGACCTCAACTCTTTCTTCTGTCCCTCAAGGCC
GGTGGTGTAGGCCTCAACCTCACCCGGGCCAGTCATGTGTTCCACGTCGATCGCTGGTGGAATCCA

FIGURE 10 (continued)

```
GCGGTGGAAAACCAAGCCACCGACCGGGCCTATCGAATTGGTCAAACCAACCGGGTAATGGTGCAC
AAATTCGTCACCCGTGGCTCGGTGGAAGAAAAAATCGACCAAATGATTCGTGAAAAAGCTCGAATG
GCTGAAGACGTGATCGGCTCCGGTGAAGACTGGCTCGGGAGCCTTGGCGGCGATCAGCTGCGCAAT
CTTGTTGCCCTCGAGGACACCTAA
```

SEQ ID NO: 90, Synechococcus sp. CC9902 Syn_sp_CC9902_SNF2 translated polypeptide
```
MSLLHATWLPAIRTSSSSGQPALLIWADTWRVASPEGPGLTPALHPFTLGSDDLKAWLTERDLMPG
GSIDATACLTLPSRSVKPRKSRTQPSEPAPEGPAWTGLPMQAGEPIPKQMEWWPWQVQGLAVEPSA
ATEWLARLPLSGRHPDLGDELRWWSHLQRWSLSLVARGRWIPQMELSKGEGYPHRARWVPLLNREE
DRRRLEDLAATLPLVATCALPWREPLGRRSNRTTRLRPEAMRAANPVACCRPRSGRLRVATLLEDL
VDAELRKGFEPTTEGLDPLLTLWQEALASETGVVEVGNEDAERLTAASLHWREGIAGGFAAARTCL
ELNTPNEGEELWDLKFGLQAEADPSLKLPAAAAWASGAETLQLGEIKVDQAGEVLLEGLGRALTVF
PPIERGLESATPETMQLTPAEAFVLVRTATHQLRNAGIGVELPPSLSGGLASRLGLAIKADLPDRS
SGFTLGESLDWSWDLMIGGVTLTLRELERLSGKRSPLVRHKGAWIELRPNDLRNAERFCGANPELS
LDDALRLTATEGELMMRLPVHRFDAGPRLQGVLEQYHQQKAPDPLPAPEGFSGQLRPYQERGLGWL
AFLHRFDQGACLADDMGLGKTIQLLAFLQHLKAEHELKRPVLLVAPTSVLTNWRREAEAFTPELSV
KEHYGPRRPSTPAALKKELKDVDLVLTSYGLMQRDSELLDSVDWQGVVIDEAQAIKNPGAKQSQAA
RDLARAGKSSRFRIALTGTPVENRVSELWALMDFLNPKVLGEEDFFRQRYRMPIERYGDMSSLRDL
KARVGPFILRRLKTDKSIISDLPEKVELSEWVGLSKEQKSLYNKTVEDTLDAIATAPRGQRHGQVL
ALLTRLKQICNHPALAQREGAVDSEFLGRSAKLMRLEEILEEVIEAGDRALLFTQFAEWGHLLQAW
MQQRWKSEVPFLHGGTRKSDRQAMVDRFQEDPRGPQLFLLSLKAGGVGLNLTRASHVFHVDRWWNP
AVENQATDRAYRIGQTNRVMVHKFVTRGSVEEKIDQMIREKARMAEDVIGSGEDWLGSLGGDQLRN
LVALEDT
```

SEQ ID NO: 91, Synechococcus sp. RS9916 Syn_sp_RS9916_SNF2 nucleic acid sequence
```
ATGAGCCTGCTGCACGCCACCTGGCTCCCGGCCATCCGTACACCCACCAGTTCCGGGCGTGCCGCC
CTGCTGGTGTGGGCGGACACCTGGCGTGTGGCGGAGCCGGCGGGCCCCGGCGTGACCCCGGCCACC
CATCCCTTCACCCTCAGCGCCGATGACCTGCGCGCCTGGCTGAGCGAACGGGAGCTGCTGCCCGAC
GGCATCATCGATGCCACCGCCTGCCTCACCCTGCCCAGCCGCACGGTGAAACCGAAGCGGAAGCGT
GGCGAGACCGCCCCTGTGGATGAGGGCTGGACGGGTCTGCCCCTGCAGGCGGGAGAACCGATTCCG
AAGCAGACCGAATGGTGGCCCTGGCAGGTACAGGGCCTGGCGGTCGAACCCGGTGCAGCCACCGCC
TGGCTGGCCCGCTTGCCCCTCTCCGGCCGCCACCCCGACCTCGCCGATGAGCTGCGCTGGTGGAGC
CACATGCAGCGCTGGGCCCTCAGCCTGATTGCTCGCAGTCGCTGGATTCCCCAGGTGGAGCTGAGC
AAAGGGGAGGGCTACCCCCACCGCGCCCGTTGGGTGCCTCTGCTCAATCGCGAAGACGATCGCCGC
CGCCTGGAAGACATGGCGGCCCGCCTGCCGCTGGTGGCCACCTGCGCTCTCCCTGGCGCGAACCC
ACCGGGAAGCGCAGCAACCGCACCACCCGGCTGCGGCCTGAGGCGATGCGGGCGGCCAATCCGGTG
GCCTGTTGTCGTCCCCGCAGCGGCCGACTGCGCGTCGCCACCCTGCTCGAAGACCTGGTGGATGCC
CAGCTGCGCACGGGTTTCACAGCCCAGACGGACGGGCTCGATCCCCTGCTTGCCGCCTGGGAGGAG
GCCCTCGGCAGCGACACCGGCGTGATCCACCTGGGCGATGAAGACGCAGAGCGTCTGGCCACCGCC
AGCCATCACTGGCGCGAAGGGGTGGCCGGCACTGTGGCGGCGGCGCGGGCCTGCCTGGAACTGGAG
ACCCCCGACGACGGCGATGACCTCTGGACCCTGCGGTTCGCACTGCAGGCCGAAGCGGATCCCACG
CTCAAGGTGCCGGCCGCCCTCGCCTGGGCGGCCGGTCCGAAGGGACTCCAGCTCGGCGAAATCGCC
GTGGAGCATCCGGGCGAACTGCTGCTGGAAGGCATGGGCCGGCGCTCACGGTGTTTCCACCGATC
GAACGCGGTCTCGACAGCGCCACGCCGGAAGGGATGCAACTCACCCCCGCCGAAGCCTTCGTGCTG
GTGCGCACCGCAGCCCGCGAACTCCGCGATGTGGGGGTGGGCGTGGAGCTTCCAGCCAGCCTCTCG
GGTGGCCTGGCGAGCAGGCTCGGCCTGGCGATTCAGGCGGAACTACCGGAGAAATCCCGCGGTTTC
```

```
ACGCTGGGCGAAACCCTCGACTGGAGCTGGGAGCTGATGATCGGCGGCGTCACCCTGACGCTGCGG
GAACTGGAGCGCCTGGCGGGCAAGCGCAGCCCCCTGGTGCGGCACAAGGGCACCTGGATCGAGCTG
CGCCCCAACGATCTCAAGAATGCGGAGCGGTTTTTCGCCGCGAAGCCCGATCTCAGCCTCGACGAT
GCCCTGCGCCTCACCGCCAGCGAAGGCGACACGCTGATGCGCATGCCGGTGCACCGCCTGGAAGCG
GGCCCACGGCTGCAGGCGGTGCTCGAGCAGTATCACCAACAGAAAGCTCCCGATCCCCTGCCGGCG
CCGGAGGGCTTCTGCGGCCAGCTGCGGCCTTACCAGGAGCGGGGCCTCGGCTGGCTGGCCTTTCTG
CACCGCTTTGATCAAGGCGCCTGCCTGGCCGACGACATGGGTCTGGGCAAGACCATCCAGCTGCTC
GCCTTTCTGCAGCACCTGAAGGCCGAGCAGGAGCTGAAGAGGCCGGTGTTGCTCGTGGCGCCCACC
TCGGTGCTCACCAACTGGAAGCGGGAGGCCGCCGCCTTCACGCCGGAGCTCGAGGTGAAGGAGCAC
TACGGGCCCAGGCGCCCTGCCACCCCTGCAGCACTCAAGAAGAGCCTCAAGGATGTGGATCTGGTG
CTCACCAGCTACGGCCTGCTCCAACGCGACAGCGAACTGCTCGAAAGTCTCGATTGGCAGGGGGTG
GTGATCGACGAAGCGCAGGCAATCAAGAATCCGAGCGCCAAACAGAGCATGGCGGCCCGAGACCTG
GCCCGCGCAGGACGCAGCAGCCGTTTCCGCATTGCCCTCACCGGCACGCCGGTGGAGAACCGGGTG
AGCGAGCTCTGGGCCTTGATGGATTTCCTCAACCCGCGGGTGCTCGGCGAAGAGGACTTCTTCCGC
CAGCGCTACCGCATGCCGATTGAGCGCTATGGCGACATGTCGTCGCTGCGGGATCTGAAATCCCGC
GTGGGACCTTTCATTCTTCGCCGGCTCAAAACCGACAAGCGATCATTTCCGACCTGCCCGAAAAG
GTGGAACTGAGCGAATGGGTGGGATTGAGCAGGGAGCAGAAAGCGCTCTATGCCAAAACCGTCGAG
GACACCCTCGATGCGATTGCCCGGGCGCCCCGCGGACAACGGCATGGCCAGGTGCTGGGGTTGCTC
ACCAAGCTGAAGCAGATCTGTAACCATCCCGCCCTGGCCCTGAAAGAGGAGGCGGCCGGCGACGAG
TTCCTGCAGCGCTCCATGAAACTGCAGCGCCTGGAGGAAATCCTCGAGGAGGTGATCGACGCCGGC
GACCGCGCCCTGCTCTTCACCCAGTTCGCCGAATGGGGCCATCTGCTGCAGGGTTACCTGCAACGG
CGCTGGCGCAGCGAAGTGCCGTTCCTGAACGGCAGCACCAGCAAGAGCGAACGCCAGGCGATGGTC
GATCGCTTCCAGGAAGACCCGCGGGGGCCTCAGCTGTTCCTGCTGTCACTGAAAGCCGGTGGTGTG
GGCCTCAACCTCACCCGCGCCAGCCATGTGTTTCACATCGATCGCTGGTGGAATCCGGCGGTGGAA
AACCAGGCCACCGACCGCGCCTACCGGATCGGCCAGACGAACCGGGTGATGGTGCACAAGTTCATC
ACCAGTGGATCGGTCGAAGAAAAAATCGACCGGATGATCCGCGAGAAATCACGCCTCGCCGAAGAC
ATCATCGGCTCAGGCGAAGATTGGCTCGGCGGGCTCGACATGGGCCAGCTGAAGGAACTGGTGAGC
CTCGACGACAACGGATCACTTTCAGCATGA
```

SEQ ID NO: 92, Synechococcus sp. RS9916 Syn_sp_RS9916_SNF2 translated polypeptide

```
MSLLHATWLPAIRTPTSSGRAALLVWADTWRVAEPAGPGVTPATHPFTLSADDLRAWLSERELLPD
GIIDATACLTLPSRTVKPKRKRGETAPVDEGWTGLPLQAGEPIPKQTEWWPWQVQGLAVEPGAATA
WLARLPLSGRHPDLADELRWWSHMQRWALSLIARSRWIPQVELSKGEGYPHRARWVPLLNREDDRR
RLEDMAARLPLVATCALPWREPTGKRSNRTTRLRPEAMRAANPVACCRPRSGRLRVATLLEDLVDA
QLRTGFTAQTDGLDPLLAAWEEALGSDTGVIHLGDEDAERLATASHHWREGVAGTVAAARACLELE
TPDDGDDLWTLRFALQAEADPTLKVPAALAWAAGPKGLQLGEIAVEHPGELLLEGMGRALTVFPPI
ERGLDSATPEGMQLTPAEAFVLVRTAARELRDVGVGVELPASLSGGLASRLGLAIQAELPEKSRGF
TLGETLDWSWELMIGGVTLTLRELERLAGKRSPLVRHKGTWIELRPNDLKNAERFFAAKPDLSLDD
ALRLTASEGDTLMRMPVHRLEAGPRLQAVLEQYHQQKAPDPLPAPEGFCGQLRPYQERGLGWLAFL
HRFDQGACLADDMGLGKTIQLLAFLQHLKAEQELKRPVLLVAPTSVLTNWKREAAAFTPELEVKEH
YGPRRPATPAALKKSLKDVDLVLTSYGLLQRDSELLESLDWQGVVIDEAQAIKNPSAKQSMAARDL
ARAGRSSRFRIALTGTPVENRVSELWALMDFLNPRVLGEEDFFRQRYRMPIERYGDMSSLRDLKSR
VGPFILRRLKTDKAIISDLPEKVELSEWVGLSREQKALYAKTVEDTLDAIARAPRGQRHGQVLGLL
TKLKQICNHPALALKEEAAGDEFLQRSMKLQRLEEILEEVIDAGDRALLFTQFAEWGHLLQGYLQR
RWRSEVPFLNGSTSKSERQAMVDRFQEDPRGPQLFLLSLKAGGVGLNLTRASHVFHIDRWWNPAVE
NQATDRAYRIGQTNRVMVHKFITSGSVEEKIDRMIREKSRLAEDIIGSGEDWLGGLDMGQLKELVS
LDDNGSLSA
```

FIGURE 10 (continued)

SEQ ID NO: 93, Synechococcus sp. WH 7805 Syn_sp_WH7805_SNF2 nucleic acid sequence
ATGAGCCTGCTGCACGCCACCTGGCTACCCGCCATCCGCACTCCCAGCAGCTCCGGAAGGGCTGCT
TTGCTGGTATGGGCTGACACCTGGCGTGTGGCCGACCCCTCGGCCCCGGGGCCACACCCGCCCTT
CATCCGTTCACCCTGAGCGCGGAGGATCTGCGCGCCTGGCTCACAGAGCGCGATTTGCTTCCGGAC
GGAATCATCGATGCGACCGCATGCCTCACCCTGCCGAGCCGCAGTGTGAAACCACGGCGGCCCCGT
GGCTCAGCTGCCGCCACCCCCTCATCAGAAGAGCAGCCCCCTTGGTGCGGGCTGCCGCTGCAAGCC
GGCGAACCGATCCCGAAAACCACCGAGTGGTGGCCATGGCAGGTGCAGGGGCTGGCGATCGAACCG
ATGGCCGCCACGGCATGGCTGGCCAAGCTTCCACTGTCAGGCCATCACCCTGATCTGGCCGATGAG
TTGCGCTGGTGGAGTCACATGCAGCGATGGGCCCTCAGTCTTGTGGCTAGGGGGCGCTGGCTGCCC
CAGGTGGAATTGAGCCGAGGTGAGGGTATCCACACCGGGCCCGCTGGGTCCCGCTTCTCAATCGA
GAGGAAGACCGGCGCCGCCTGGAGGACCTTGCCGCCCGTCTGCCCCTGGTTGCCACGTGTGCGTTG
CCCTGGAGAGAGCCCACAGGAAAGCGCAGCAATCGCATCACCAGGCTGCGCCCAGAGGCCATGCGC
GCTGCCAATCCCGTGGCCTGCTGTCGTCCCCGCAGCGGTCGATTGCGGGTGGCCACATTGCTGGAG
GATCTGGTAGATGCCCAGCTGCGCAAGGGCTTCCATCCCGATGACGAGGGGCTCGACCCCCTGCTC
TGCGCCTGGGAAAACGCCCTGAGTTCGGAGACCGGGGTGATCGATCTGAATGATGAAGATGCCGAA
CGCCTTGCCACGGCGAGCCACCACTGGCGCGAGGGAGTGGCTGGCAATGTGGCGGCTGCCAGGGCC
TGCCTTGAACTCGCCACACCGAACGAGGGGAAGAGCTCTGGGATCTGCGCTTCTATCTGCAGGCC
GAAGCCGATCCAACGCTGAAGGTACCGGCCGGAGCAGCCTGGGCCGCTGGACCCGAAGGCCTTCAA
CTCGGGGAGATTCCTGTGGAGCATCCCGGTGAGGTGCTGCTCGAAGGCATGGGGCGTGCTCTCACG
GTGTTCGAACCAATCGAACGGGGCCTGGATAGCGCCACGCCGGAAGCGATGCAGCTCACCCCGGCG
GAAGCCTTCGTGCTGGTGCGCACCGCCGCCCGTCAGCTCCGGGACGTGGGCGTTGGTGTGGATCTC
CCTCCCAGCCTCTCGGGAGGCCTGGCCAGCCGCCTCGGTCTGGCGATCAAGGCCGAACTACCCAAA
CGCTCGCGGGGGTTCACCCTTGGGGAAAATCTCGACTGGAACTGGGAGCTGATGATCGGGGCGTC
ACCCTGACGCTGCGGGAGCTGGAACGGCTGGCCGGCAAGCGCAGCCCCTTGGTGCGCCACAAGGGG
GCCTGGATCGAACTCAGGCCCAATGATCTCAAAAATGCAGAACGATTCTGTGCCGCCAATCCTGAT
CTGAGCCTGGACGATGCCCTTCGCCTGACGGCCAGCGAAGGGGACACGCTGATGCGCCTCCCCGTT
CATGCCTTTGATGCTGGCCCTCGCCTTCAAGGGGTGTTGGAGCAATACCACCAGCAGAAAGCACCG
GATCCACTTCCTGCGCCCGAGGGTTTCTGCGGTCAGCTTCGCCCTTACCAGGAACGAGGCCTGGGC
TGGCTGGCCTTCCTGCACCGCTTCGATCAGGGAGCCTGCCTCGCCGACGACATGGGCCTGGGCAAG
ACGATCCAGCTGCTGGCCTTCCTCCAGCACCTGAAGATGGAACAAGAACTGAAACGGCCGGTGCTG
CTGGTGGCTCCCACCTCCGTGCTCACCAACTGGAAACGGGAAGCCGCGGCCTTCACCCCCGAGCTC
ACAGTGCATGAGCACTACGGCCCCAAACGACCCTCCACCCCAGCAGCACTGAAAAAAGCCCTGAAA
GACGTTGACCTGGTGCTCACCAGCTACGGGCTTCTGCAAAGAGACAGTGAACTGCTTGAAAGTTTC
GACTGGCAGGGAACCGTGATCGATGAAGCTCAGGCGATCAAGAACCCTTCGGCCAAGCAAAGCCAG
GCAGCCCGTGATCTGGCTCGCACCCGCAAGGGCTCCAGGTTCCGCATTGCCCTCACTGGCACACCG
GTTGAAAACAGAGTGAGCGAGCTCTGGGCCCTGATGGATTTCCTCAATCCGAACGTGCTCGGCGAA
GAGGAATTTTTCCGGCAGCGCTACCGCATGCCGATCGAACGCTATGGCGATATGTCGTCGCTTCGC
GATCTCAAGTCGCGGGTGGGACCATTCATTCTGCGGCGCTTGAAAACCGACAAGGCGATCATCTCC
GACCTCCCCGAAAAGTGGAGCTGAGTGAATGGGTGGGGCTGAGCAAGGAACAGAAGTCCCTTTAC
GCGAAAACCGTGGAGAACACCCTCGATGCCATCGCCCGAGCTCCCCGAGGCAAGCGTCACGGCCAG
GTGCTGGGACTGCTGACGCGCCTCAAACAGATCTGCAATCACCCGGCTCTGGCCTTAAAGGAAGAG
GTGGCAGGCGACGACTTCCTGCAGCGATCGGTGAAGCTGCAGCGGCTCGAAGAGATTCTCGAAGAG
GTGATTGCAGCGGGGGATCGAGCCCTGCTGTTCACCCAGTTCGCGGAATGGGGGCATCTGCTGCAG
GGCTACCTGCAACGCCGCTGGCGCAGCGAGGTGCCGTTCCTGAGCGGCAGCACTAGCAAAGGAGAA
CGTCAGGCCATGGTGGATCGCTTCCAGGAAGACCCGCGCGGCCCCAGCTGTTCCTGTTGTCCCTC
AAAGCCGGCGGTGTGGGATTGAACCTGACCCGGGCCAGCCACGTGTTCCACATCGACCGCTGGTGG FIGURE 10 (continued)

```
AATCCTGCAGTTGAAAACCAGGCCACTGACCGTGCTTACCGGATTGGCCAGACCAATCGGGTGATG
GTGCATAAGTTCATCACCAGTGGCTCAGTGGAAGAGAAGATCGACCGGATGATCCGGGAGAAGTCC
AGACTGGCGGAAGACATCGTGGGCTCCGGCGAGGAGTGGCTCGGTGGCTTCGACATGGGCCAACTC
AAGGAGCTGGTGAGCCTCGAGGACAACGAAACACGCAACCCATGA
```

SEQ ID NO: 94, Synechococcus sp. WH 7805 Syn_sp_WH7805_SNF2 translated polypeptide

```
MSLLHATWLPAIRTPSSSGRAALLVWADTWRVADPLGPGATPALHPFTLSAEDLRAWLTERDLLPD
GIIDATACLTLPSRSVKPRRPRGSAAATPSSEEQPPWCGLPLQAGEPIPKTTEWWPWQVQGLAIEP
MAATAWLAKLPLSGHHPDLADELRWWSHMQRWALSLVARGRWLPQVELSRGEGYPHRARWVPLLNR
EEDRRRLEDLAARLPLVATCALPWREPTGKRSNRITRLRPEAMRAANPVACCRPRSGRLRVATLLE
DLVDAQLRKGFHPDDEGLDPLLCAWENALSSETGVIDLNDEDAERLATASHHWREGVAGNVAAARA
CLELATPNEGEELWDLRFYLQAEADPTLKVPAGAAWAAGPEGLQLGEIPVEHPGEVLLEGMGRALT
VFEPIERGLDSATPEAMQLTPAEAFVLVRTAARQLRDVGVGVDLPPSLSGGLASRLGLAIKAELPK
RSRGFTLGENLDWNWELMIGGVTLTLRELERLAGKRSPLVRHKGAWIELRPNDLKNAERFCAANPD
LSLDDALRLTASEGDTLMRLPVHAFDAGPRLQGVLEQYHQQKAPDPLPAPEGFCGQLRPYQERGLG
WLAFLHRFDQGACLADDMGLGKTIQLLAFLQHLKMEQELKRPVLLVAPTSVLTNWKREAAAFTPEL
TVHEHYGPKRPSTPAALKKALKDVDLVLTSYGLLQRDSELLESFDWQGTVIDEAQAIKNPSAKQSQ
AARDLARTRKGSRFRIALTGTPVENRVSELWALMDFLNPNVLGEEEFFRQRYRMPIERYGDMSSLR
DLKSRVGPFILRRLKTDKAIISDLPEKVELSEWVGLSKEQKSLYAKTVENTLDAIARAPRGKRHGQ
VLGLLTRLKQICNHPALALKEEVAGDDFLQRSVKLQRLEEILEEVIAAGDRALLFTQFAEWGHLLQ
GYLQRRWRSEVPFLSGSTSKGERQAMVDRFQEDPRGPQLFLLSLKAGGVGLNLTRASHVFHIDRWW
NPAVENQATDRAYRIGQTNRVMVHKFITSGSVEEKIDRMIREKSRLAEDIVGSGEEWLGGFDMGQL
KELVSLEDNETRNP
```

SEQ ID NO: 95, Synechococcus sp. WH 8102 Syn_sp_WH8102_SNF2 nucleic acid sequence

```
ATGAGCCTGCTGCACGCCACCTGGCTTCCCGCCATCCGTACCTCTGGCAGTTCCGGCCAACCGGCA
CTGCTCATTTGGGCTGACACCTGGCGGGTGGCGACACCAGAGGGCCCCGGGCTAACTCCGGCGCTG
CACCCGTTCACCCTGGAACCCGACGACCTCAAGGCCTGGCTTCAGGAACGCGACCTGTTGCCAGGC
GGCAGCATCGATGCCACCGCCTGCCTCACCCTGCCCAGTCGCACGGTAAAACCCCGCAAGAGCCGC
AGCAAAACGGCCGAACCAGCGCCCGAAGAGCCCATCTGGACCGGTCTGCCGATGCAGGCCGGAGAG
CCGATTCCGAAACAGACAGAATGGTGGCCGTGGCAAGTCCAGGGCCTCGCTGTCGAGCCCTCTGCC
GCCACGGAGTGGCTCTCACGCCTTCCCCTGTCAGGACGGAATCCAGACCTGGCCGATGAGCTGCGC
TGGTGGAGCCACCTGCAGCGCTGGGCCCTCAGCCTTGTGGCCCGGGGGCGCTGGATTCCCCAGATG
GAACTGAGCAAAGGCGAGGGATATCCCCACCGGGCCCGTTGGGTGCCTCTGCTCAACCGCGAGGAG
GACCGGCGACGTCTGGAGGATCTGGCCGCCAGCCTGCCGCTGGTGGCCACCTGCGCCCTGCCCTGG
CGGGAACCGATGGGTCGGCGCAGCAACCGCATGACACGGCTGCGTCCGGAGGCCATGCGTGCCGCC
AACCCGGTGGCCTGCTGCCGGCCCCGCAGTGGCCGCCTGCGGGTGGCCACGCTGCTGGAGGATCTG
GTCGACGCACAGCTGCGCAAGGACTTTGAACCATCCACCGACGGCCTCGATCCCCTGTTGACCCTG
TGGCAAGACGCCCTGGGCTCCGAAACAGGGGTGATTGAGATCGGTGATGAACAGGCCGAACGGCTG
GCCAGCGCCAGCTTCCATTGGCGCGAGGGCATCGCTGGAGATTTCGCCGCTGCACGCACCTGCCTG
GAACTGCAGACACCTGCAGAGGGAGAAGAGCTCTGGGAGCTGCGGTTTGGGCTGCAGGCGGAGTCG
GATCCGAGCCTCAAGCTGCCCGCCGCTGCGGCCTGGGCCTCCGGTGCCGACCAACTCCAGTTGGGA
GAAGTGACAGTCGAGCAGCCCGGTGAAGTGCTGCTGGAGGGTCTGGGACGCGCCCTCACCGTGTTC
CCACCGATCGAAAGGGGCCTGGAGACCGCTACGCCTGACACGATGCAGCTGACCCCCGCCGAAGCC
TTCGTGCTGGTGCGGACCGCAGCGCGGCAGCTGCGGGATGCCGGCGTCGGCGTCGACCTTCCCCCC
AGCCTGTCGGGGGGCCTGGCCAGCCGCCTGGGTCTGGCGATCAAGGCGGAGCTGCCAGAGCGCTCC
```

FIGURE 10 (continued)

```
AGCGGCTTCAGCCTCGGCGAATCCCTCGACTGGAGCTGGGATCTGATGATCGGCGGGGTGACGCTC
ACCCTGCGGGAACTGGAGCGGTTGAGCGGCAAACGCAGCCCCTCGTGCGCCACAAGGGGCCTGG
ATCGAATTGCGACCGAACGATCTGAGAAACGCCGAACGCTTCTGCGGTGCCAACCCGGAGCTCAGC
CTGGACGATGCCCTGCGGATCACCGCCACCGAAGGCGATCTGCTGATGCGTCTGCCGGTGCATCGC
TTTGAGGCCGGCCCCAGGCTGCAGGCGGTGCTGGAGCAGTACCACCAGCAGAAGGCCCCGGATCCG
TTGCCAGCGCCGGAGGGGTTCTGCGGCCAGCTGCGGCCTTACCAGGAGCGTGGCCTGGGCTGGCTG
GCCTTCCTCAACCGCTTCGACCAAGGCGCCTGCCTGGCGGACGACATGGGTCTGGGTAAGACCATC
CAGCTGCTGGCCTTCCTGCAGCACCTGAAAGCAGAGCAGGAACTGAAGCGCCCGGTGCTGCTGGTG
GCCCCCACATCGGTGCTCACAAACTGGCGACGGGAAGCGGAAGCCTTCACCCCCGAACTGGCGGTG
CGCGAGCACTACGGACCGCGGCGTCCCTCCACTCCGGCTGCGCTGAAGAAGGCGTTGAAGGATGTC
GACTTAGTCCTCACCAGCTACGGCCTACTGCAGAGGGACAGTGAATTGCTGGAGTCTCAGGATTGG
CAGGGGGTTGTGATCGATGAAGCCCAAGCGATCAAGAATCCCAGTGCCAAGCAGAGCCAGGCAGCC
CGAGACCTGGCCAGACCAGCCAAAGGCAACCGCTTCCGCATCGCCCTCACGGGCACACCGGTGGAG
AACAGGGTCAGCGAGCTCTGGGCTTTGATGGATTTCCTCAGTCCCAAGGTGCTGGGAGAAGAAGAC
TTCTTCCGTCAGCGCTACCGGATGCCGATCGAGCGCTATGGCGACATGGCATCCCTACGGGACTTA
AAAGCCAGGGTCGGCCCCTTCATCCTGCGCCGGCTGAAAACCGACAAGACGATCATTTCCGATCTG
CCCGAGAAGGTGGAACTCAGCGAATGGGTGGGGTTGAGCAAGGAGCAGAAATCGCTGTACAGCAAA
ACCGTTGAAGACACCCTGGATGCCATTGCCCGGGCGCCTCGTGGACAGCGCCATGGTCAGGTGCTG
GGACTGCTCACCCGCCTGAAGCAGATCTGCAACCATCCGGCCCTGGCATTGAGTGAAAACGCTGTT
GACGACGGCTTTCTGGGGCGCTCCGCCAAGTTGCAACGGCTTGAGGAAATCCTCGATGAGGTGATC
GAAGCAGGGGATCGGGCGCTGCTGTTCACCCAGTTCGCCGAGTGGGGCCATCTGCTGCAGTCCTGG
ATGCAACAACGTTGGAAGGCGGATGTGCCCTTCCTGCATGAGGGACGCGCAAAAACGAACGGCAG
GCCATGGTGGATCGTTTTCAGGAGGACCCCGCGGCCCGCAGCTGTTCCTGCTGTCGCTCAAAGCC
GGCGGGGTGGGTCTGAACCTGACCAGGGCCAGCCACGTGTTCCACATCGATCGCTGGTGGAACCCT
GCGGTAGAGAACCAGGCCACCGACCGTGCTTATCGGATCGGCCAGACCAACCGGGTGATGGTGCAC
AAATTCATCACAAGCGGATCCGTAGAAGAAAAAATTGACCGGATGATCCGAGAGAAGTCGCGCCTG
GCAGAGGATGTGATCGGTTCCGGTGAAGACTGGCTCGGGTGCCTGGCCGGTGATCAGCTGCGCAAT
CTCGTTGCCCTGGAGGACACCTGA
```

SEQ ID NO: 96, Synechococcus sp. WH 8102 yn_sp_WH8102_SNF2 translated polypeptide

```
MSLLHATWLPAIRTSGSSGQPALLIWADTWRVATPEGPGLTPALHPFTLEPDDLKAWLQERDLLPG
GSIDATACLTLPSRTVKPRKSRSKTAEPAPEEPIWTGLPMQAGEPIPKQTEWWPWQVQGLAVEPSA
ATEWLSRLPLSGRNPDLADELRWWSHLQRWALSLVARGRWIPQMELSKGEYPHRARWVPLLNREE
DRRRLEDLAASLPLVATCALPWREPMGRRSNRMTRLRPEAMRAANPVACCRPRSGRLRVATLLEDL
VDAQLRKDFEPSTDGLDPLLTLWQDALGSETGVIEIGDEQAERLASASFHWREGIAGDFAAARTCL
ELQTPAEGEELWELRFGLQAESDPSLKLPAAAAWASGADQLQLGEVTVEQPGEVLLEGLGRALTVF
PPIERGLETATPDTMQLTPAEAFVLVRTAARQLRDAGVGVDLPPSLSGGLASRLGLAIKAELPERS
SGFSLGESLDWSWDLMIGGVTLTLRELERLSGKRSPLVRHKGAWIELRPNDLRNAERFCGANPELS
LDDALRITATEGDLLMRLPVHRFEAGPRLQAVLEQYHQQKAPDPLPAPEGFCGQLRPYQERGLGWL
AFLNRFDQGACLADDMGLGKTIQLLAFLQHLKAEQELKRPVLLAPTSVLTNWRREAEAFTPELAV
REHYGPRRPSTPAALKKALKDVDLVLTSYGLLQRDSELLESQDWQGVVIDEAQAIKNPSAKQSQAA
RDLARPAKGNRFRIALTGPVENRVSELWALMDFLSPKVLGEEDFFRQRYRMPIERYGDMASLRDL
KARVGPFILRRLKTDKTIISDLPEKVELSEWVGLSKEQKSLYSKTVEDTLDAIARAPRGQRHGQVL
GLLTRLKQICNHPALALSENAVDDGFLGRSAKLQRLEEILDEVIEAGDRALLFTQFAEWGHLLQSW
MQQRWKADVPFLHGGTRKNERQAMVDRFQEDPRGPQLFLLSLKAGGVGLNLTRASHVFHIDRWWNP
AVENQATDRAYRIGQTNRVMVHKFITSGSVEEKIDRMIREKSRLAEDVIGSGEDWLGCLAGDQLRN
LVALEDT
```

FIGURE 10 (continued)

SEQ ID NO: 97, Synechococcus elongatus PCC 6301 Synel_PCC6301_SNF2 nucleic acid sequence

```
ATGGCAGTGCTGCACGGTGGCTGGCTCGGCGATCGCTTCTGCGTTTGGGCCGAGGCTTGGCAGGCT
GGTGAGCCTCAGTCGGCAGCAGAAATTGCGATTCATCCCTACGCGATCGCGGCCACTGACTTAAAT
GATTGGTGCCAGAAGTACCGTCTGGGATCCCTGACGGGGACGCCAACAGAAGTCCTGCTCTCTATT
CCCAGTGACCTGAAGAAAGAGGCGGTTCTACCGTTTCTGAGTGGTCAGGAAATTCCAGATGGGGCG
CTGCTTTGGTCTTGGCAGATCCCCGTGCTGTCGCTAGAAGCCGCGATCGCCGGTCAATGGCTGGCG
ACCTTGCCGCTGGGTTCGGCGGAGGATCATCCTTGGCTGGGGCCAGATCTACGCTTTTGGAGCCAC
ATCTACCGCTGGGCACAAAGTTTGCTGGCTCGGGGCGCTTTTATCCGGCGCTGGAGTCGAGCGAT
CGCGGTTTAACGGCAGTTTGGTTGCCACTGTTTAATCAAGCGGGCGATCGCCAGCGCTTCGATCGC
TATAGTCAGCAGCTGCCCTTTAGTCAGTTTTGCTATCAGGCAATCGAAACAGCGGCAGCTTGTCCT
TGGCAGCCTCAACCGCAGGATCTGTTGCTGCGAGTCCTACAGACTTGGTTGACAGCACGACTACAA
CCGGCGATCGCGGCGGGAACTCTCGTGTCTGCTGATCTGCTGGCGGCTTGGCAGCAATCGCTAGCG
AATGGAAAACCGCTAAAGCTAGAAGACAGTGAAGCCAGTCGCTTGCAAACGGCGATCGATCGCTGG
TTACTACCAGTGCAGAATGGCGCAGCTCAGGCTTGGCGGATGGTTTTGCGCCTTGTCCCGCCTACG
GAGCAAGAGCAGCCCTGGCAATTGGAGTTTGGCTTACAAGCAGCGACCGATCCCGATCGCTTTCGG
CCGGCCTCTCTCCTCTGGCAGGATCCGCTGCCACCTGGGCTACCAGATCAATCTCAGGAATTGCTG
TTACGCGGCTTGGGACAGGCTTGTCGGCTCTATCCCCAATTGCAAACCAGTCTGGCGACAGCCTGT
CCAGAATTCCATCCACTGACCACAGCGGAGGTCTATCAGCTGCTCAAGCAGGTGATTCCTCAGTGG
CAAGAGCAGGGCATTGAAGTGCAACTGCCGCCGGGCTTGCGTGGTCAAGGGCGACACCGGCTGGGA
GTGGAAGTCAGCGCCACGTTGCCGAGCGATCGCCCGAGTGTGGGCTGGAAGCACTACTGCAGTTT
CGTTGGGAGCTGAGTCTGGGCGGTCAGCGGCTGACCAAAGCAGAAGTGGAACGCTTGGCAGCCCTG
GAAACGCCCTTGGTGGAAATCAACGGCGACTGGATTGAGGTGCGGCCGCAGGATATTGAGTCGGCG
CGAGAGTTTTTCCGTAAGCGCAAGGATCAGCCAAATTTGACCTTGGCGGATGCGATCGCGATCGCC
AGTGGTGAGTCGCCGAATGTTGGTCGCCTGCCGGTGGTCAATTTTGAAGCGGCGGGCTTACTCGAA
GAAGCCTTGGCCGTGTTTCAGGGGCAGCGATCGCCTGCGGCTTTGCCCGCTCCGCCCACCTTTCAG
GGCGAGCTGCGACCCTATCAAGAGCGGGGGGTGGGCTGGCTCAGCTTTTTGCAGCGCTTCGGGATT
GGGGCTTGCCTCGCCGACGACATGGGCTTGGGTAAGACGATTCAGCTGCTGGCCTTTTTACTGCAT
CTCAAACACAGCAACGAGCTGACGCGGCCGGTGCTGCTAGTCTGTCCGACTTCGGTGCTGGGCAAC
TGGGAACGGGAGGTGCAGAAATTTGCACCGGAGCTTCGCTGGAAGCTGCACTATGGCCCCGATCGC
GCTCAGGGTAAGGCTTTGGCGACAGCGCTCAAGGACTGCGATTTGGTGCTGACCAGTTACTCCTTG
GTGGCGCGAGATCAGAAAGCGATCGCGGCGATCGACTGGCAAGGCATTGTGCTGGATGAAGCCCAG
AACATCAAGAATGACCAGGCGAAACAGACGCAGGCGGTGCGAGCGATCGCCCAAAGTCCGACGCAA
AAGCCCCGCTTTCGGATTGCCCTGACAGGGACGCCGGTTGAGAATCGCCTCAGTGAGTTGTGGTCG
ATTGTCGAGTTTTTGCAGCCGGGACATTTAGGCACCAAGCCATTCTTTCAAAAGCGCTTTGTCACG
CCGATCGAGCGTTTTGGCGATGCGGATTCGCTGACAGCATTGCGGCAGCGCGTGCAACCGTTAATC
CTACGGCGACTGAAAACCGATCGCAGCATTATTGCCGACTTGCCTGAGAAGCAAGAAATGACGGTC
TTTTGTCCGTTGGTACAGGAGCAGGCCGATCGCTATCAGGTGCTAGTCAATGAAGCGCTAGCCAAT
ATTGAAGCAAGTGAAGGCATTCAGCGGCGCGGCCAGATTTTGGCATTGCTAACGCGACTGAAGCAG
CTCTGTAATCATCCGTCGTTGTTGCTCGAAAAGCCGAAGCTCGATCCGAATTTTGGCGATCGCTCA
GCCAAGTTGCAGCGCTTACTAGAAATGTTGGCGGAGCTAACGGATGCGGGCGATCGCGCTTTGGTG
TTTACGCAGTTTGCGGGCTGGGGTAGTTTGCTGCAGCAATTTTTGCAGGAACAGCTAGGGCGAGAG
GTGCTGTTTTTGTCGGGCAGTACCAAGAAGGGCGATCGCCAACAGATGGTTGATCGCTTCCAAAAT
GATCCGCAGGCACCGGCAATTTTCATCCTGTCATTGAAGGCTGGCGGGTGGGCTCAACCTGACG
AAAGCCAATCATGTCTTTCATTACGATCGCTGGTGGAATCCGGCAGTTGAAAACCAAGCGACCGAT
CGCGCGTTTCGGATTGGGCAACGACGCAATGTACAGGTGCACAAGTTTGTCTGCGCTGGCACTCTA
GAAGAAAAAATTGATCAGATGATCGCTAGCAAGCAAGCATTAGCACAGCAGATTGTCGGTAGTGGT
GAGGATTGGCTAACGGAACTAGACACCAATCAACTCCGGCAACTCTTGATCCTCGATCGCTCAGCT
TGGGTAGAAGAGGAAGAGCCTTAG
```

FIGURE 10 (continued)

SEQ ID NO: 98, Synechococcus elongatus PCC 6301 Synel_PCC6301_SNF2 translated polypeptide
MAVLHGGWLGDRFCVWAEAWQAGEPQSAAEIAIHPYAIAATDLNDWCQKYRLGSLTGTPTEVLLSI
PSDLKKEAVLPFLSGQEIPDGALLWSWQIPVLSLEAAIAGQWLATLPLGSAEDHPWLGPDLRFWSH
IYRWAQSLLARGRFYPALESSDRGLTAVWLPLFNQAGDRQRFDRYSQQLPFSQFCYQAIETAAACP
WQPQPQDLLLRVLQTWLTARLQPAIAAGTLVSADLLAAWQQSLANGKPLKLEDSEASRLQTAIDRW
LLPVQNGAAQAWRMVLRLVPPTEQEQPWQLEFGLQAATDPDRFRPASLLWQDPLPPGLPDQSQELL
LRGLGQACRLYPQLQTSLATACPEFHPLTTAEVYQLLKQVIPQWQEQGIEVQLPPGLRGQGRHRLG
VEVSATLPSDRPSVGLEALLQFRWELSLGGQRLTKAEVERLAALETPLVEINGDWIEVRPQDIESA
REFFRKRKDQPNLTLADAIAIASGESPNVGRLPVVNFEAAGLLEEALAVFQGQRSPAALPAPPTFQ
GELRPYQERGVGWLSFLQRFGIGACLADDMGLGKTIQLLAFLLHLKHSNELTRPVLLVCPTSVLGN
WEREVQKFAPELRWKLHYGPDRAQGKALATALKDCDLVLTSYSLVARDQKAIAAIDWQGIVLDEAQ
NIKNDQAKQTQAVRAIAQSPTQKPRFRIALTGTPVENRLSELWSIVEFLQPGHLGTKPFFQKRFVT
PIERFGDADSLTALRQRVQPLILRRLKTDRSIIADLPEKQEMTVFCPLVQEQADRYQVLVNEALAN
IEASEGIQRRGQILALLTRLKQLCNHPSLLLEKPKLDPNFGDRSAKLQRLLEMLAELTDAGDRALV
FTQFAGWGSLLQQFLQEQLGREVLFLSGSTKKGDRQQMVDRFQNDPQAPAIFILSLKAGGVGLNLT
KANHVFHYDRWWNPAVENQATDRAFRIGQRRNVQVHKFVCAGTLEEKIDQMIASKQALAQQIVGSG
EDWLTELDTNQLRQLLILDRSAWVEEEEP

SEQ ID NO: 99, Synechococcus elongatus PCC 7942 Synel_PCC7942_SNF2 nucleic acid sequence
ATGGCAGTGCTGCACGGTGGCTGGCTCGGCGATCGCTTCTGCGTTTGGGCCGAGGCTTGGCAGGCT
GGTGAGCCTCAGTCGGCAGCAGAAATTGCGATTCATCCCTACGCGATCGCGGCCACTGACTTAAAT
GATTGGTGCCAGAAGTACCGTCTGGGATCCCTGACGGGGACGCCAACAGAAGTCCTGCTCTCTATT
CCCAGTGACCTGAAGAAAGAGGCGGTTCTACCGTTTCTGAGTGGTCAGGAAATTCCAGATGGGGCG
CTGCTTTGGTCTTGGCAGATCCCCGTGCTGTCACTAGAAGCCGCGATCGCCGGTCAATGGCTGGCG
ACCTTGCCGCTGGGTTCGGCGGAGGATCATCCTTGGCTGGGCCAGATCTACGCTTTTGGAGCCAC
ATCTACCGCTGGGCACAAAGTTTGCTGGCTCGGGGCGCTTTTATCCGGCGCTGGAGTCGAGCGAT
CGCGGTTTAACGGCAGTTTGGTTGCCACTGTTTAATCAAGCGGGCGATCGCCAGCGCTTCGATCGC
TATAGTCAGCAGCTGCCCTTTAGTCAGTTTTGCTATCAGGCAATCGAAACAGCGGCAGCTTGTCCT
TGGCAGCCTCAACCGCAGGATCTGTTGCTGCGAGTCCTACAGACTTGGTTGACAGCACGACTACAA
CCGGCGATCGCGGCGGGAACTCTCGTGTCTGCTGATCTGCTGGCGGCTTGGCAGCAATCGCTAGCG
AATGGAAAACCGCTAAAGCTAGAAGACAGTGAAGCCAGTCGCTTGCAAACGGCGATCGATCGCTGG
TTACTACCAGTGCAGAATGGCGCAGCTCAGGCTTGGCGGATGGTTTTGCGCCTTGTCCCGCCTACG
GAGCAAGAGCAGCCCTGGCAATTGGAGTTTGGCTTACAAGCAGCGACCGATCCCGATCGCTTTTGG
CCGGCCTCTCTCCTCTGGCAGGATCCGCTGCCACCTGGGCTACCAGATCAATCTCAGGAATTGCTG
TTACGCGGCTTGGGACAGGCTTGTCGGCTCTATCCCCAATTGCAAACCAGTCTGGCGACAGCCTGT
CCAGAATTCCATCCACTGACCACAGCGGAGGTCTATCAGCTGCTCAAGCAGGTGATTCCTCAGTGG
CAAGAGCAGGGCATTGAAGTGCAACTGCCGCCGGGCTTGCGTGGTCAAGGGCGACACCGGCTGGGA
GTGGAAGTCAGCGCCACGTTGCCGAGCGATCGCCCGAGTGTGGGCTGGAAGCACTACTGCAGTTT
CGTTGGGAGCTGAGTCTGGGCGGTCAGCGGCTGACCAAAGCAGAAGTGGAACGCTTGGCAGCCCTG
GAAACGCCCTTGGTGGAAATCAACGGCGACTGGATTGAGGTGCGGCCGCAGGATATTGAGTCGGCG
CGAGAGTTTTTCCGTAAGCGCAAGGATCAGCCAAATTTGACCTTGGCGGATGCGATCGCGATCGCC
AGTGGTGAGTCGCCGAATGTTGGTCGCCTGCCGGTGGTCAATTTTGAAGCGGCGGGCTTACTCGAA
GAAGCCTTGGCCGTGTTTCAGGGGCAGCGATCGCCTGCGGCTTTGCCCGCTCCGCCCACCTTTCAG
GGCGAGCTGCGACCCTATCAAGAGCGGGGGGTGGGCTGGCTCAGCTTTTTGCAGCGCTTCGGGATT
GGGGCTTGCCTCGCCGACGACATGGGCTTGGGTAAGACGATTCAGCTGCTGGCCTTTTTACTGCAT
CTCAAACACAGCAACGAGCTGACGCGGCCGGTGCTGCTAGTCTGTCCGACTTCGGTGCTGGGCAAC

```
TGGGAACGGGAGGTGCAGAAATTTGCACCGGAGCTTCGCTGGAAGCTGCACTATGGCCCCGATCGC
GCTCAGGGTAAGGCTTTGGCGACAGCGCTCAAGGACTGCGATTTGGTGCTGACCAGTTACTCCTTG
GTGGCGCGAGATCAGAAAGCGATCGCGGCGATCGACTGGCAAGGCATTGTGCTGGATGAAGCCCAG
AACATCAAGAATGACCAGGCGAAACAGACGCAGGCGGTGCGAGCGATCGCCCAAAGTCCGACGCAA
AAGCCCCGCTTTCGGATTGCCCTGACAGGGACGCCGGTTGAGAATCGCCTCAGTGAGTTGTGGTCG
ATTGTCGAGTTTTTGCAGCCGGGACATTTAGGCACCAAGCCATTCTTTCAAAAGCGCTTTGTCACG
CCGATCGAGCGTTTTGGCGATGCGGATTCGCTGACAGCATTGCGGCAGCGCGTGCAACCGTTAATC
CTACGGCGACTGAAAACCGATCGCAGCATTATTGCCGACTTGCCTGAGAAGCAAGAAATGACGGTC
TTTTGTCCGTTGGTACAGGAGCAGGCCGATCGCTATCAGGTGCTAGTCAATGAAGCGCTAGCCAAT
ATTGAAGCAAGTGAAGGCATTCAGCGGCGCGGCCAGATTTTGGCATTGCTAACGCGACTGAAGCAG
CTCTGTAATCATCCGTCGTTGTTGCTCGAAAAGCCGAAGCTCGATCCGAATTTTGGCGATCGCTCA
GCCAAGTTGCAGCGCTTACTAGAAATGTTGGCGGAGCTAACGGATGCGGGCGATCGCGCTTTGGTG
TTTACGCAGTTTGCGGGCTGGGGTAGTTTGCTGCAGCAATTTTTGCAGGAACAGCTAGGGCGAGAG
GTGCTGTTTTTGTCGGGCAGTACCAAGAAGGGCGATCGCCAACAGATGGTTGATCGCTTCCAAAAT
GATCCGCAGGCACCGGCAATTTTCATCCTGTCATTGAAGGCTGGCGGGGTGGGGCTCAACCTGACG
AAAGCCAATCATGTCTTTCATTACGATCGCTGGTGGAATCCGGCAGTTGAAAACCAAGCGACCGAT
CGCGCGTTTCGGATTGGGCAACGACGCAATGTACAGGTGCACAAGTTTGTCTGCGCTGGCACTCTA
GAAGAAAAATTGATCAGATGATCGCTAGCAAGCAAGCATTAGCACAGCAGATTGTCGGTAGTGGT
GAGGATTGGCTAACGGAACTAGACACCAATCAACTCCGGCAACTCTTGATCCTCGATCGCTCAGCT
TGGGTAGAAGAGGAAGAGCCTTAG
```

SEQ ID NO: 100, Synechococcus elongatus PCC 7942 Synel PCC7942 SNF2 translated polypeptide
```
MAVLHGGWLGDRFCVWAEAWQAGEPQSAAEIAIHPYAIAATDLNDWCQKYRLGSLTGTPTEVLLSI
PSDLKKEAVLPFLSGQEIPDGALLWSWQIPVLSLEAAIAGQWLATLPLGSAEDHPWLGPDLRFWSH
IYRWAQSLLARGRFYPALESSDRGLTAVWLPLFNQAGDRQRFDRYSQQLPFSQFCYQAIETAAACP
WQPQPQDLLLRVLQTWLTARLQPAIAAGTLVSADLLAAWQQSLANGKPLKLEDSEASRLQTAIDRW
LLPVQNGAAQAWRMVLRLVPPTEQEQPWQLEFGLQAATDPDRFWPASLLWQDPLPPGLPDQSQELL
LRGLGQACRLYPQLQTSLATACPEFHPLTTAEVYQLLKQVIPQWQEQGIEVQLPPGLRGQGRHRLG
VEVSATLPSDRPSVGLEALLQFRWELSLGGQRLTKAEVERLAALETPLVEINGDWIEVRPQDIESA
REFFRKRKDQPNLTLADAIAIASGESPNVGRLPVVNFEAAGLLEEALAVFQGQRSPAALPAPPTFQ
GELRPYQERGVGWLSFLQRFGIGACLADDMGLGKTIQLLAFLLHLKHSNELTRPVLLVCPTSVLGN
WEREVQKFAPELRWKLHYGPDRAQGKALATALKDCDLVLTSYSLVARDQKAIAAIDWQGIVLDEAQ
NIKNDQAKQTQAVRAIAQSPTQKPRFRIALTGTPVENRLSELWSIVEFLQPGHLGTKPFFQKRFVT
PIERFGDADSLTALRQRVQPLILRRLKTDRSIIADLPEKQEMTVFCPLVQEQADRYQVLVNEALAN
IEASEGIQRRGQILALLTRLKQLCNHPSLLLEKPKLDPNFGDRSAKLQRLLEMLAELTDAGDRALV
FTQFAGWGSLLQQFLQEQLGREVLFLSGSTKKGDRQQMVDRFQNDPQAPAIFILSLKAGGVGLNLT
KANHVFHYDRWWNPAVENQATDRAFRIGQRRNVQVHKFVCAGTLEEKIDQMIASKQALAQQIVGSG
EDWLTELDTNQLRQLLILDRSAWVEEEEP
```

SEQ ID NO: 101, Thermosynechococcus elongatus BP-1 Theel_BP-1_SNF2 nucleic acid sequence
```
ATGGCTATTTTCCATGGCACATGGCTCCCAGAGCCGGCGCCACAGTTTTTCATTTGGGCGGAAGAA
TGGCGATCGCTGGCTCAGGCAATCACGCCTTGGGCTCCCCCGGCGATTCCGGTTTATCCCTACGCC
ACCCAGAGAAAACACCTCTTAGGAAGACAGCCCGCCCAAGTGCCACCTACGTTGCTTTACCGGCC
CAGATTCAGGGGCATCAACTGTTACCACCACCGCTGGCGGAAGTGCAGGGGAACTCCTATTTTTG
TGGCAGGTGCCCGGCTGGTCAATTCCCGCTTCAGAAGTTTTAGAACAACTGCATCAACTGAGTCTT
CACGGCCAAGACAGTGGCAGTATTGGCGATGATTTGCGCTATTGGCTGCACGTGAGTCGCTGGTTG
```

```
CTGGATTTAATTGTGCGTGGCCAATACCTGCCAACACCAGAGGGCTGGCGGATTCTGCTGACCCAC
GGGGGCGATCGCGATCGCCTGCGCCACTTCAGCCAATTGATGCCGGATCTGTGTCGCTGTTATCAA
GCCGATGGCACAGCGTTGCAGTTGCCACCCCATGCTGCAGATCTCCTGGCGGATTTTCTACAGCAC
ACCCTACAGGGTTATCTCCACACTGCCCTTGCTGACCTCGAATTGCCCAAAGTAGGCTTAGCCAAA
GAACATGGCCACTGGCTAGCCTTCCTGAAAACGGGTCAAACCCCGGAACTGCCACCTCCCCTCATT
GAACGCCTGCACCGCTGGCAAGAACCCTACCGCGAGCAGTTGCATCTGCGTCCCCAATGGCGACTG
GCTCTGCAATTGGTTCCCCCAGATACTGCCGATGGTGACTGGCACTTGGCCTTTGGGCTGCAAACG
GAAGGGGAAACGGACACCATGCTAAGGGCCGCCGAGATTTGGCAATGCACCCAAGAGGCCCTCCTC
TATCAAGGGCAGGTGCTCTGGCAGCCCCAAGAAACCCTGTTGCGGGGACTGGGCTTGGCCTCCCGC
ATCTATCGTCCCCTCGATCGCAGTCTTCAAGAACGCTCCCCGTGGCTCTGACTTTGCACACCACG
GAAGTTTATGCCTTCTTGCAAAGTGCAATTGCGCCCTTGAGCAGCAGGGGGTTGCGATCATTTTG
CCACCGAGTCTGCGCCGCAATAGCGCCCAACATCGCTTGGGTCTGAAAATAATTGCCACATTGCCG
CCGCCGGCCACTAACGGCTTGACGATTGACAGCTTGATGCAGTTTCAGTGGCAGTTGCAGTTGGGG
CAGCATCCCCTCTCGGAGGCGGATTTTGATCAACTGCGCCGCCAAGGGACGCCCCTGGTTTATCTC
AATGGTGAGTGGGTCTTGCTGCGCCCCAAGAGGTCAAGGCCGCTCAAGAGTTTCTCCAGTCTCCC
CCAAAGACCCAACTCTCCCTTGCAGAGACACTGCGCATTGCTACGGGGGATACGGTAACGGTGGCC
AAGTTGCCGATTCTTGGCTTAGACACCAATGATGCACTCCAGACCCTCTTGGATGGCCTCACGGGC
AAACAAAGCCTTGATCCAGTGCCAACACCGCAGGAGTTTTGCGGTGAACTGCGCCCCTACCAGGCA
CGGGGGGTGGCGTGGCTGAGTTTCTTGGAACGCTGGCGGCTGGGGGCTTGCTTGGCGGACGATATG
GGCTTGGGGAAAACCATTCAACTGTTGGCCTTTTTGCTCCACCTCAAGGAAACGGGACGGGCCTAC
CGACCGACACTGTTGATCTGTCCTACCTCGGTGCTGGGGAACTGGCTGCGGGAGTGCCAAAAGTTT
GCCCCAACCTTGCGGGCCTATGTCCACCATGGGAGCGATCGCCCCAAGGGCAAGGCATTTCTGAAA
AAGGTTGAAACTCACGATCTAATTTTGACCAGTTATGCCCTCCTCCAGCGCGATCGCACCACCTTG
CAGCAGGTTCTGTGGCAGCATTTGGTACTGGATGAAGCCCAAAACATCAAGAATGCCAACACCCAG
CAGTCCCAAGCAGCGCGGGAACTTTCCGCCCAGTTTCGCATTGCCCTGACGGGAACCCCCCTAGAA
AACCGCCTCCTCGAACTTTGGTCCATTATGGACTTCCTCCATCCGGGGTACTTGGGCCATCGCACC
TACTTTCAACACCGCTATGTCCGTCCCATTGAACGCTATGGCGACACCACCTCCCTCAATGCTCTG
CGCACCTATGTCCAGCCCTTTATTCTGCGGCGCCTGAAAACCGACCGCAGTATTATTCAAGACCTG
CCGGAAAAACAGGAGATGCTGGTGTATTGTGGCCTCACCCTAGAGCAGATGCAGCTTTACACTGCT
GTGGTGGAAGACTCCCTTGCTGCTATCGAAAATAGTCAAGGCATTCAGCGGCGGGCAATATCTTG
GCCACCCTGACCAAGTTGAAGCAAATCTGTAACCATCCCGCCCAGTATCTCAAGCAAGAAGACTAT
GCCCCCGATCGCTCAGGTAAATTGCAACGGCTTATAGAAATGCTGCAAGCGCTTCAGGAAGTGGGC
GATCGCGCCCTTGTCTTTACCCAATTTGCCGAGTTTGGCACCCACCTGAAAACCTATCTGGAAAAG
GCGCTCCAGCAGGAGGTGTTTTTCCTCTCAGGACGCACCCCCAAAGCCCAGCGGGAACTCATGGTG
GAACGCTTTCAACACGATCCCGAGGCCCCCAGGGTCTTTATTCTTTCCCTCAAGGCAGGGGCGTC
GGTCTCAATTTGACTCGCGCTAACCATGTCTTTCACTACGATCGCTGGTGGAACCCAGCGGTAGAA
AATCAGGCCAGCGATCGCGTCTTCCGCATTGGTCAGGCCCGCAATGTCCAAATCCATAAATTTATC
TGCACGGGTACCCTCGAAGAAAAGATCCACGAGCAAATCGAACAGAAAAAGCCCTTGCGGAAATG
ATTGTGGGTAGTGGCGAACACTGGCTGACTGAACTCAACCTCGACCAGTTGCGGCAACTGCTCACC
TTAGACAAAGAGCGGCTGATCACCCTCTAG
```

SEQ ID NO: 102, Thermosynechococcus elongatus BP-1 Theel_BP-1_SNF2
translated polypeptide
```
MAIFHGTWLPEPAPQFFIWAEEWRSLAQAITPWAPPAIPVYPYATQRKTPLRKTARPSATYVALPA
QIQGHQLLPPPLAEVQGELLFLWQVPGWSIPASEVLEQLHQLSLHGQDSGSIGDDLRYWLHVSRWL
LDLIVRGQYLPTPEGWRILLTHGGDRDRLRHFSQLMPDLCRCYQADGTALQLPPHAADLLADFLQH
TLQGYLHTALADLELPKVGLAKEHGHWLAFLKTGQTPELPPPLIERLHRWQEPYREQLHLRPQWRL
ALQLVPPDTADGDWHLAFGLQTEGETDTMLRAAEIWQCTQEALLYQGQVLWQPQETLLRGLGLASR
```

FIGURE 10 (continued)

IYRPLDRSLQERSPVALTLHTTEVYAFLQSAIAPLEQQGVAIILPPSLRRNSAQHRLGLKIIATLP
PPATNGLTIDSLMQFQWQLQLGQHPLSEADFDQLRRQGTPLVYLNGEWVLLRPQEVKAAQEFLQSP
PKTQLSLAETLRIATGDTVTVAKLPILGLDTNDALQTLLDGLTGKQSLDPVPTPQEFCGELRPYQA
RGVAWLSFLERWRLGACLADDMGLGKTIQLLAFLLHLKETGRAYRPTLLICPTSVLGNWLRECQKF
APTLRAYVHHGSDRPKGKAFLKKVETHDLILTSYALLQRDRTTLQQVLWQHLVLDEAQNIKNANTQ
QSQAARELSAQFRIALTGTPLENRLLELWSIMDFLHPGYLGHRTYFQHRYVRPIERYGDTTSLNAL
RTYVQPFILRRLKTDRSIIQDLPEKQEMLVYCGLTLEQMQLYTAVVEDSLAAIENSQGIQRRGNIL
ATLTKLKQICNHPAQYLKQEDYAPDRSGKLQRLIEMLQALQEVGDRALVFTQFAEFGTHLKTYLEK
ALQQEVFFLSGRTPKAQRELMVERFQHDPEAPRVFILSLKAGGVGLNLTRANHVFHYDRWWNPAVE
NQASDRVFRIGQARNVQIHKFICTGTLEEKIHEQIEQKKALAEMIVGSGEHWLTELNLDQLRQLLT
LDKERLITL

SEQ ID NO: 103, Motif 1
LADDMGLGK(T/S)

SEQ ID NO: 104, Motif 1a
L(L/V/I)(V/I/L)(A/C)P(T/M/V)S(V/I/L)(V/I/L)XNW

SEQ ID NO: 105, Motif 2
DEAQ(N/A/H)(V/I/L)KN

SEQ ID NO: 106, Motif 3
A(L/M)TGTPXEN

SEQ ID NO: 107, Motif 4
(L/I)XF(T/S)Q(F/Y)

SEQ ID NO: 108, Motif 5
S(L/V)KAGG(V/T/L)G(L/I)(N/T)LTXA(N/S/T)HV

SEQ ID NO: 109, Motif 5a
DRWWNPAVE

SEQ ID NO: 110, Motif 6
QA(T/S)DR(A/T/V)(F/Y)R(I/L)GQ

SEQ ID NO: 111, ATPase domain of SEQ ID NO: 2
LADDMGLGKTPQLLAFLLHLAAEDMLVKPVLIVCPTSVLSNWGHEINKFAPQLKTLLHHGDRRKKG
QPLVKQVKDQQIVLTSYALLQRDFSSLKLVDWQGIVLDEAQNIKNPQAKQSQAARQLPAGFRIALT
GTPVENRLTELWSILEFLNPGFLGNQSFFQRRFANPIEKFGDRQSLLILRNLVRPFILRRLKTDQT
IIQDLPEKQEMTVFCDLSQEQAGLYQQLVEESLQAIADSEGIQRHGLVLTLLTKLKQVCNHPDLLL
KKPAITHGHQSGKLIRLAEMLEEIISEGDRVLIFTQFASWGHLLKPYLEKYFNQEVLYLHGGTPAE
QRQALVERFQQDPNSPYLFILSLKAGGTGLNLTRANHVFHVDRWWNPAVENQATDRAFRIGQTRNV
QVHKFVCTGTLEEKINAMMADKQQLAEQTVDAGENWLTRLDTDKLRQLLTLSATPVDYQAEASD FIGURE 10 (continued)

SEQ ID NO: 112, Oryza sativa beta-expansin promoter
AAAACCACCGAGGGACCTGATCTGCACCGGTTTTGATAGTTGAGGGACCCGTTGTGTCTGGTTTTC
CGATCGAGGGACGAAAATCGGATTCGGTGTAAAGTTAAGGGACCTCAGATGAACTTATTCCGGAGC
ATGATTGGGAAGGGAGGACATAAGGCCCATGTCGCATGTGTTTGGACGGTCCAGATCTCCAGATCA
CTCAGCAGGATCGGCCGCGTTCGCGTAGCACCCGCGGTTTGATTCGGCTTCCCGCAAGGCGGCGGC
CGGTGGCCGTGCCGCCGTAGCTTCCGCCGGAAGCGAGCACGCCGCCGCCGCCGACCCGGCTCTGCG
TTTGCACCGCCTTGCACGCGATACATCGGGATAGATAGCTACTACTCTCTCCGTTTCACAATGTAA
ATCATTCTACTATTTTCCACATTCATATTGATGTTAATGAATATAGACATATATATCTATTTAGAT
TCATTAACATCAATATGAATGTAGGAAATGCTAGAATGACTTACATTGTGAATTGTGAAATGGACG
AAGTACCTACGATGGATGGATGCAGGATCATGAAAGAATTAATGCAAGATCGTATCTGCCGCATGC
AAAATCTTACTAATTGCGCTGCATATATGCATGACAGCCTGCATGCGGGCGTGTAAGCGTGTTCAT
CCATTAGGAAGTAACCTTGTCATTACTTATACCAGTACTACATACTATATAGTATTGATTTCATGA
GCAAATCTACAAAACTGGAAAGCAATAAGAAATACGGGACTGGAAAAGACTCAACATTAATCACCA
AATATTTCGCCTTCTCCAGCAGAATATATATCTCTCCATCTTGATCACTGTACACACTGACAGTGT
ACGCATAAACGCAGCAGCCAGCTTAACTGTCGTCTCACCGTCGCACACTGGCCTTCCATCTCAGGC
TAGCTTTCTCAGCCACCCATCGTACATGTCAACTCGGCGCGCGCACAGGCACAAATTACGTACAAA
ACGCATGACCAAATCAAAACCACCGGAGAAGAATCGCTCCCGCGCGCGGCGGCGACGCGCACGTAC
GAACGCACGCACGCACGCCCAACCCCACGACACGATCGCGCGCGACGCCGGCGACACCGGCCGTCC
ACCCGCGCCCTCACCTCGCCGACTATAAATACGTAGGCATCTGCTTGATCTTGTCATCCATCTCAC
CACCAAAAAAAAAAGGAAAAAAAAACAAAACACACCAAGCCAAATAAAAGCGACAA

SEQ ID NO: 113, Prm 08774
GGGGACAAGTTTGTACAAAAAAGCAGGCTTAAACAATGGCGACTATCCACGGTAATTGG

SEQ ID NO: 114, Prm 08779
GGGGACCACTTTGTACAAGAAAGCTGGGTTCAATCGGACGCTTCGGCTT

FIGURE 10 (continued)

SEQUENCE LISTING

```
<160> NUMBER OF SEQ ID NOS: 114

<210> SEQ ID NO 1
<211> LENGTH: 402
<212> TYPE: DNA
<213> ORGANISM: Xanthomonas axonopodis

<400> SEQUENCE: 1
atgaattctt tgaacacaca gctcggcgcc aactcgtcct tctttcaggt tgaccccggc      60
cagaacacgc aatctagtcc gaaccagggc aaccagggca tctcggaaaa gcaactggac     120
cagctgctga cccagctcat catggccctg cttcagcaga gcaacaatgc cgagcagggt     180
cagggtcaag gccagggtgg tgactctggc ggtcagggcg gcaatccgcg gcaggccggg     240
cagtccaacg gctccccctc gcaatacacc caggcgctga tgaatatcgt cggagacatt     300
ctccaggcgc agaatggtgg cggcttcggc ggcggctttg gtggtggctt cggtggcatc     360
ctcgtcacca gccttgcgag cgacaccgga tcgatgcagt aa                        402

<210> SEQ ID NO 2
<211> LENGTH: 133
<212> TYPE: PRT
<213> ORGANISM: Xanthomonas axonopodis

<400> SEQUENCE: 2

Met Asn Ser Leu Asn Thr Gln Leu Gly Ala Asn Ser Ser Phe Phe Gln
1               5                   10                  15

Val Asp Pro Gly Gln Asn Thr Gln Ser Ser Pro Asn Gln Gly Asn Gln
            20                  25                  30

Gly Ile Ser Glu Lys Gln Leu Asp Gln Leu Leu Thr Gln Leu Ile Met
        35                  40                  45

Ala Leu Leu Gln Gln Ser Asn Asn Ala Glu Gln Gly Gln Gly Gln Gly
    50                  55                  60

Gln Gly Gly Asp Ser Gly Gly Gln Gly Gly Asn Pro Arg Gln Ala Gly
65                  70                  75                  80
```

```
Gln Ser Asn Gly Ser Pro Ser Gln Tyr Thr Gln Ala Leu Met Asn Ile
                85                  90                  95

Val Gly Asp Ile Leu Gln Ala Gln Asn Gly Gly Phe Gly Gly Gly
            100                 105                 110

Phe Gly Gly Gly Phe Gly Ile Leu Val Thr Ser Leu Ala Ser Asp
        115                 120                 125

Thr Gly Ser Met Gln
    130

<210> SEQ ID NO 3
<211> LENGTH: 11
<212> TYPE: PRT
<213> ORGANISM: Artificial sequence
<220> FEATURE:
<223> OTHER INFORMATION: conserved motif 1 of the HpaG protein
<220> FEATURE:
<221> NAME/KEY: VARIANT
<222> LOCATION: (2)..(2)
<223> OTHER INFORMATION: Xaa is Glu, Asp, or Gly
<220> FEATURE:
<221> NAME/KEY: VARIANT
<222> LOCATION: (3)..(3)
<223> OTHER INFORMATION: Xaa is Glu or Asn
<220> FEATURE:
<221> NAME/KEY: UNSURE
<222> LOCATION: (4)..(4)
<223> OTHER INFORMATION: Xaa can be any naturally occurring amino acid
<220> FEATURE:
<221> NAME/KEY: VARIANT
<222> LOCATION: (5)..(5)
<223> OTHER INFORMATION: Xaa is Arg, Pro or Gln
<220> FEATURE:
<221> NAME/KEY: VARIANT
<222> LOCATION: (7)..(7)
<223> OTHER INFORMATION: Xaa is Ser or Ala
<220> FEATURE:
<221> NAME/KEY: UNSURE
<222> LOCATION: (9)..(9)
<223> OTHER INFORMATION: Xaa can be any naturally occurring amino acid
<220> FEATURE:
<221> NAME/KEY: VARIANT
<222> LOCATION: (10)..(10)
<223> OTHER INFORMATION: Xaa is Asp or Asn

<400> SEQUENCE: 3

Gly Xaa Xaa Xaa Xaa Gln Xaa Gly Xaa Xaa Gly
1               5                   10

<210> SEQ ID NO 4
<211> LENGTH: 14
<212> TYPE: PRT
<213> ORGANISM: Artificial sequence
<220> FEATURE:
<223> OTHER INFORMATION: conserved motif 2 of the HpaG protein
<220> FEATURE:
<221> NAME/KEY: VARIANT
<222> LOCATION: (1)..(1)
<223> OTHER INFORMATION: Xaa is Ala, Val or Pro
<220> FEATURE:
<221> NAME/KEY: VARIANT
<222> LOCATION: (3)..(3)
<223> OTHER INFORMATION: Xaa is Gln, Ala or Pro
<220> FEATURE:
<221> NAME/KEY: VARIANT
<222> LOCATION: (4)..(4)
<223> OTHER INFORMATION: Xaa is Leu, Tyr or Phe
<220> FEATURE:
<221> NAME/KEY: VARIANT
<222> LOCATION: (7)..(7)
<223> OTHER INFORMATION: Xaa is Ala or Met
<220> FEATURE:
<221> NAME/KEY: VARIANT
<222> LOCATION: (10)..(10)
```

-continued

```
<223> OTHER INFORMATION: Xaa is Asn, Gln or His
<220> FEATURE:
<221> NAME/KEY: VARIANT
<222> LOCATION: (13)..(13)
<223> OTHER INFORMATION: Xaa is Met or Gly
<220> FEATURE:
<221> NAME/KEY: VARIANT
<222> LOCATION: (14)..(14)
<223> OTHER INFORMATION: Xaa is Asp, Gln or Glu

<400> SEQUENCE: 4

Xaa Ser Xaa Xaa Thr Gln Xaa Leu Met Xaa Ile Val Xaa Xaa
1               5                   10

<210> SEQ ID NO 5
<211> LENGTH: 2194
<212> TYPE: DNA
<213> ORGANISM: Oryza sativa

<400> SEQUENCE: 5
aatccgaaaa gtttctgcac cgttttcacc ccctaactaa caatataggg aacgtgtgct      60
aaatataaaa tgagacctta tatatgtagc gctgataact agaactatgc aagaaaaact     120
catccaccta ctttagtggc aatcgggcta ataaaaaag agtcgctaca ctagtttcgt      180
tttccttagt aattaagtgg gaaaatgaaa tcattattgc ttagaatata cgttcacatc     240
tctgtcatga agttaaatta ttcgaggtag ccataattgt catcaaactc ttcttgaata     300
aaaaaatctt tctagctgaa ctcaatgggt aagagagag attttttta aaaaaataga      360 atgaagatat tctgaacgta ttggcaaaga tttaaacata taattatata attttatagt     420
ttgtgcattc gtcatatcgc acatcattaa ggacatgtct tactccatcc caatttttat     480
ttagtaatta aagacaattg acttatttt attatttatc ttttttcgat tagatgcaag     540
gtacttacgc acacacttg tgctcatgtg catgtgtgag tgcacctcct caatacacgt     600
tcaactagca acacatctct aatatcactc gcctatttaa tacatttagg tagcaatatc    660
tgaattcaag cactccacca tcaccagacc acttttaata atatctaaaa tacaaaaaat    720
aattttacag aatagcatga aaagtatgaa acgaactatt taggttttc acatacaaaa     780 aaaaaagaa ttttgctcgt gcgcgagcgc caatctccca tattgggcac acaggcaaca     840
acagagtggc tgcccacaga acaacccaca aaaaacgatg atctaacgga ggacagcaag    900
tccgcaacaa ccttttaaca gcaggctttg cggccaggag agaggaggag aggcaaagaa    960
aaccaagcat cctccttctc ccatctataa attcctcccc ccttttcccc tctctatata   1020
ggaggcatcc aagccaagaa gagggagagc accaaggaca cgcgactagc agaagccgag   1080
cgaccgcctt ctcgatccat atcttccggt cgagttcttg gtcgatctct tccctcctcc   1140
acctcctcct cacagggtat gtgcctccct tcggttgttc ttggatttat tgttctaggt   1200
tgtgtagtac gggcgttgat gttaggaaag gggatctgta tctgtgatga ttcctgttct   1260
tggatttggg atagaggggt tcttgatgtt gcatgttatc ggttcggttt gattagtagt   1320
atggttttca atcgtctgga gagctctatg gaaatgaaat ggtttaggga tcggaatctt   1380
gcgattttgt gagtaccttt tgtttgaggt aaaatcagag caccggtgat tttgcttggt   1440
gtaataaagt acggttgttt ggtcctcgat tctggtagtg atgcttctcg atttgacgaa   1500
gctatccttt gtttattccc tattgaacaa aaataatcca actttgaaga cggtcccgtt   1560
gatgagattg aatgattgat tcttaagcct gtccaaaatt tcgcagctgg cttgtttaga   1620
tacagtagtc cccatcacga aattcatgga aacagttata atcctcagga acaggggatt   1680
ccctgttctt ccgatttgct ttagtcccag aattttttt cccaaatatc ttaaaaagtc   1740
```

-continued

```
actttctggt tcagttcaat gaattgattg ctacaaataa tgcttttata gcgttatcct   1800
agctgtagtt cagttaatag gtaatacccc tatagtttag tcaggagaag aacttatccg   1860
atttctgatc tccattttta attatatgaa atgaactgta gcataagcag tattcatttg   1920
gattattttt tttattagct ctcacccctt cattattctg agctgaaagt ctggcatgaa   1980
ctgtcctcaa ttttgttttc aaattcacat cgattatcta tgcattatcc tcttgtatct   2040
acctgtagaa gtttcttttt ggttattcct tgactgcttg attacagaaa gaaatttatg   2100
aagctgtaat cgggatagtt atactgcttg ttcttatgat tcatttcctt tgtgcagttc   2160
ttggtgtagc ttgccacttt caccagcaaa gttc                               2194
```

```
<210> SEQ ID NO 6
<211> LENGTH: 1179
<212> TYPE: DNA
<213> ORGANISM: Oryza sativa

<400> SEQUENCE: 6
ttgcagttgt gaccaagtaa gctgagcatg cccttaactt cacctagaaa aaagtatact     60
tggcttaact gctagtaaga catttcagaa ctgagactgg tgtacgcatt tcatgcaagc    120
cattaccact ttacctgaca ttttggacag agattagaaa tagtttcgta ctacctgcaa    180
gttgcaactt gaaaagtgaa atttgttcct tgctaatata ttggcgtgta attcttttat    240
gcgttagcgt aaaaagttga aatttgggtc aagttactgg tcagattaac cagtaactgg    300
ttaaagttga aagatggtct tttagtaatg gagggagtac tacactatcc tcagctgatt    360
taaatcttat tccgtcggtg gtgatttcgt caatctccca acttagtttt tcaatatatt    420
cataggatag agtgtgcata tgtgtgttta tagggatgag tctacgcgcc ttatgaacac    480
ctacttttgt actgtatttg tcaatgaaaa gaaaatctta ccaatgctgc gatgctgaca    540
ccaagaagag gcgatgaaaa gtgcaacgga tatcgtgcca cgtcggttgc caagtcagca    600
cagacccaat gggcctttcc tacgtgtctc ggccacagcc agtcgtttac cgcacgttca    660
catgggcacg aactcgcgtc atcttcccac gcaaaacgac agatctgccc tatctggtcc    720
cacccatcag tggcccacac ctcccatgct gcattatttg cgactcccat cccgtcctcc    780
acgcccaaac accgcacacg ggtcgcgata gccacgaccc aatcacacaa cgccacgtca    840
ccatatgtta cgggcagcca tgcgcagaag atcccgcgac gtcgctgtcc cccgtgtcgg    900
ttacgaaaaa atatcccacc acgtgtcgct ttcacaggac aatatctcga aggaaaaaaa    960
tcgtagcgga aaatccgagg cacgagctgc gattggctgg gaggcgtcca gcgtggtggg   1020
gggcccaccc ccttatcctt agcccgtggc gctcctcgct cctcgggtcc gtgtataaat   1080
accctccgga actcactctt gctggtcacc aacacgaagc aaaaggacac cagaaacata   1140
gtacacttga gctcactcca aactcaaaca ctcacacca                          1179
```

```
<210> SEQ ID NO 7
<211> LENGTH: 402
<212> TYPE: DNA
<213> ORGANISM: Artificial sequence
<220> FEATURE:
<223> OTHER INFORMATION: synthetic construct mutant elicitor of
      hypersensitive response HpaG_T44C gene

<400> SEQUENCE: 7
atgaattctt tgaacacaca gctcggcgcc aactcgtcct tctttcaggt tgaccccggc     60
cagaacacgc aatctagtcc gaaccagggc aaccagggca tctcggaaaa gcaactggac    120
```

-continued

```
cagctgctgt gccagctcat catggccctg cttcagcaga gcaacaatgc cgagcagggt        180
cagggtcaag gccagggtgg tgactctggc ggtcagggcg gcaatccgcg gcaggccggg        240
cagtccaacg gctccccctc gcaatacacc caggcgctga tgaatatcgt cggagacatt        300
ctccaggcgc agaatggtgg cggcttcggc ggcggctttg gtggtggctt cggtggcatc        360
ctcgtcacca gccttgcgag cgacaccgga tcgatgcagt aa                           402
```

<210> SEQ ID NO 8
<211> LENGTH: 133
<212> TYPE: PRT
<213> ORGANISM: Artificial sequence
<220> FEATURE:
<223> OTHER INFORMATION: mutant elicitor of hypersensitive response
      HpaG_T44C

<400> SEQUENCE: 8

```
Met Asn Ser Leu Asn Thr Gln Leu Gly Ala Asn Ser Ser Phe Phe Gln
1               5                   10                  15

Val Asp Pro Gly Gln Asn Thr Gln Ser Ser Pro Asn Gln Gly Asn Gln
            20                  25                  30

Gly Ile Ser Glu Lys Gln Leu Asp Gln Leu Leu Cys Gln Leu Ile Met
        35                  40                  45

Ala Leu Leu Gln Gln Ser Asn Asn Ala Glu Gln Gly Gln Gly Gln Gly
    50                  55                  60

Gln Gly Gly Asp Ser Gly Gly Gln Gly Gly Asn Pro Arg Gln Ala Gly
65                  70                  75                  80

Gln Ser Asn Gly Ser Pro Ser Gln Tyr Thr Gln Ala Leu Met Asn Ile
                85                  90                  95

Val Gly Asp Ile Leu Gln Ala Gln Asn Gly Gly Gly Phe Gly Gly Gly
            100                 105                 110

Phe Gly Gly Gly Phe Gly Gly Ile Leu Val Thr Ser Leu Ala Ser Asp
        115                 120                 125

Thr Gly Ser Met Gln
        130
```

<210> SEQ ID NO 9
<211> LENGTH: 378
<212> TYPE: DNA
<213> ORGANISM: Artificial sequence
<220> FEATURE:
<223> OTHER INFORMATION: synthetic construct mutant elicitor of
      hypersensitive response HpaG-T gene

<400> SEQUENCE: 9

```
atgaattctt tgaacacaca gctcggcgcc aactcgtcct tctttcaggt tgaccccggc         60
cagaacacgc aatctagtcc gaaccagggc aaccagggca tctcggaaaa gcaactggac        120
cagctgctga cccagctcat catggccctg cttcagcaga gcaacaatgc cgagcagggt        180
cagggtcaag gccagggtgg tgactctggc ggtcagggcg gcaatccgcg gcaggccggg        240
cagtccaacg gctccccctc gcaatacacc caggcgctga tgaatatcgt cggagacggc        300
ttcggcggcg gctttggtgg tggcttcggt ggcatcctcg tcaccagcct tgcgagcgac        360
accggatcga tgcagtaa                                                      378
```

<210> SEQ ID NO 10
<211> LENGTH: 125
<212> TYPE: PRT
<213> ORGANISM: Artificial sequence
<220> FEATURE:
<223> OTHER INFORMATION: mutant elicitor of hypersensitive response HpaG-T

<400> SEQUENCE: 10

Met Asn Ser Leu Asn Thr Gln Leu Gly Ala Asn Ser Ser Phe Phe Gln
1               5                   10                  15

Val Asp Pro Gly Gln Asn Thr Gln Ser Ser Pro Asn Gln Gly Asn Gln
            20                  25                  30

Gly Ile Ser Glu Lys Gln Leu Asp Gln Leu Leu Thr Gln Leu Ile Met
        35                  40                  45

Ala Leu Leu Gln Gln Ser Asn Asn Ala Glu Gln Gly Gln Gln Gln Gly
    50                  55                  60

Gln Gly Gly Asp Ser Gly Gln Gly Gly Asn Pro Arg Gln Ala Gly
65                  70                  75                  80

Gln Ser Asn Gly Ser Pro Ser Gln Tyr Thr Gln Ala Leu Met Asn Ile
                85                  90                  95

Val Gly Asp Gly Phe Gly Gly Phe Gly Gly Phe Gly Gly Ile
            100                 105                 110

Leu Val Thr Ser Leu Ala Ser Asp Thr Gly Ser Met Gln
        115                 120                 125

<210> SEQ ID NO 11
<211> LENGTH: 414
<212> TYPE: DNA
<213> ORGANISM: Xanthomonas axonopodis
<220> FEATURE:
<223> OTHER INFORMATION: Xanthomonas axonopodis pv. citri

<400> SEQUENCE: 11
ttactgcatc gatccggtgt cgctcgcaag gctggtgccg aggctggtgc cgaggccgcc 60
gccgaagcca ccaccaaagc cgccgccgaa gccaccacca ttctgcgcct ggagaatgtc 120
tccgacgata ttcatcagca tctgggtgta ttgcgagggg gagccgttgg actgaccggc 180
ctgctgccga ttgccgccct gaccaccaga gtcaccaccc tggccttgac cctgaccctg 240
ctcggcattg ttgctctgct gaagcagggc catgatgagc tgggtcagca gctggtccag 300
ttgcttttcc gagatgccct ggttgccctg gttcgaacca gattgcgtgt tctggctggg 360
gtcaacctga aagaaggacg agttggcgcc gagctgtgtg ttcaaagaat tcat 414

<210> SEQ ID NO 12
<211> LENGTH: 137
<212> TYPE: PRT
<213> ORGANISM: Xanthomonas axonopodis
<220> FEATURE:
<223> OTHER INFORMATION: Xanthomonas axonopodis pv. citri

<400> SEQUENCE: 12

Met Asn Ser Leu Asn Thr Gln Leu Gly Ala Asn Ser Ser Phe Phe Gln
1 5 10 15

Val Asp Pro Ser Gln Asn Thr Gln Ser Gly Ser Asn Gln Gly Asn Gln
20 25 30

Gly Ile Ser Glu Lys Gln Leu Asp Gln Leu Leu Thr Gln Leu Ile Met
35 40 45

Ala Leu Leu Gln Gln Ser Asn Asn Ala Glu Gln Gly Gln Gly Gln Gly
50 55 60

Gln Gly Gly Asp Ser Gly Gly Gln Gly Gly Asn Arg Gln Gln Ala Gly
65 70 75 80

Gln Ser Asn Gly Ser Pro Ser Gln Tyr Thr Gln Met Leu Met Asn Ile
85 90 95

```
Val Gly Asp Ile Leu Gln Ala Gln Asn Gly Gly Phe Gly Gly Gly
            100                 105                 110

Phe Gly Gly Gly Phe Gly Gly Gly Leu Gly Thr Ser Leu Gly Thr Ser
        115                 120                 125

Leu Ala Ser Asp Thr Gly Ser Met Gln
    130                 135

<210> SEQ ID NO 13
<211> LENGTH: 366
<212> TYPE: DNA
<213> ORGANISM: Artificial sequence
<220> FEATURE:
<223> OTHER INFORMATION: synthetic construct mutant elicitor of
      hypersensitive response HpaG-N gene

<400> SEQUENCE: 13
atgaattctt tgaacacaca gctcggcgcc aactcgtcct tctttcaggt tgaccccggc      60
cagaacacgc aatctagtcc gaaccagggc aacacccagc tcatcatggc cctgcttcag    120
cagagcaaca atgccgagca gggtcagggt caaggccagg gtggtgactc tggcggtcag    180
ggcggcaatc cgcggcaggc cgggcagtcc aacggctccc cctcgcaata cacccaggcg    240
ctgatgaata tcgtcggaga cattctccag gcgcagaatg gtggcggctt cggcggcggc    300
tttggtggtg gcttcggtgg catcctcgtc accagccttg cgagcgacac cggatcgatg    360
cagtaa                                                               366

<210> SEQ ID NO 14
<211> LENGTH: 121
<212> TYPE: PRT
<213> ORGANISM: Artificial sequence
<220> FEATURE:
<223> OTHER INFORMATION: mutant elicitor of hypersensitive response
      HpaG-N

<400> SEQUENCE: 14

Met Asn Ser Leu Asn Thr Gln Leu Gly Ala Asn Ser Ser Phe Phe Gln
1               5                   10                  15

Val Asp Pro Gly Gln Asn Thr Gln Ser Ser Pro Asn Gln Gly Asn Thr
            20                  25                  30

Gln Leu Ile Met Ala Leu Leu Gln Gln Ser Asn Asn Ala Glu Gln Gly
        35                  40                  45

Gln Gly Gln Gly Gln Gly Gly Asp Ser Gly Gly Gln Gly Gly Asn Pro
    50                  55                  60

Arg Gln Ala Gly Gln Ser Asn Gly Ser Pro Ser Gln Tyr Thr Gln Ala
65                  70                  75                  80

Leu Met Asn Ile Val Gly Asp Ile Leu Gln Ala Gln Asn Gly Gly
                85                  90                  95

Phe Gly Gly Gly Phe Gly Gly Gly Phe Gly Gly Ile Leu Val Thr Ser
            100                 105                 110

Leu Ala Ser Asp Thr Gly Ser Met Gln
        115                 120

<210> SEQ ID NO 15
<211> LENGTH: 366
<212> TYPE: DNA
<213> ORGANISM: Xanthomonas axonopodis

<400> SEQUENCE: 15
atgaattctt tgaacacaca gctcggcgcc aactcgtcct tctttcaggt tgaccccggc      60
cagaacacgc aatctagtcc gaaccagggc aaccagggca tctcggaaaa g

```
cagctgctga cccagctcat catggccctg cttcagcaga gcaacaatgc cgagcagggt    180
cagggtcaag gccagggtgg tgactctggc ggtcagggcg gcaatccgcg gcaggccggg    240
cagtccaacg gctcccccte gcaatacacc caggcgctga tgaatatcgt cggagacatt    300
ctccaggcgc agaatggctt tatcctcgtc accagccttg cgagcgacac cggatcgatg    360
cagtaa                                                              366
```

```
<210> SEQ ID NO 16
<211> LENGTH: 121
<212> TYPE: PRT
<213> ORGANISM: Xanthomonas axonopodis

<400> SEQUENCE: 16

Met Asn Ser Leu Asn Thr Gln Leu Gly Ala Asn Ser Ser Phe Phe Gln
1               5                   10                  15

Val Asp Pro Gly Gln Asn Thr Gln Ser Ser Pro Asn Gln Gly Asn Gln
            20                  25                  30

Gly Ile Ser Glu Lys Gln Leu Asp Gln Leu Leu Thr Gln Leu Ile Met
        35                  40                  45

Ala Leu Leu Gln Gln Ser Asn Asn Ala Glu Gln Gly Gln Gly Gln Gly
    50                  55                  60

Gln Gly Gly Asp Ser Gly Gly Gln Gly Gly Asn Pro Arg Gln Ala Gly
65                  70                  75                  80

Gln Ser Asn Gly Ser Pro Ser Gln Tyr Thr Gln Ala Leu Met Asn Ile
                85                  90                  95

Val Gly Asp Ile Leu Gln Ala Gln Asn Gly Phe Ile Leu Val Thr Ser
            100                 105                 110

Leu Ala Ser Asp Thr Gly Ser Met Gln
        115                 120
```

```
<210> SEQ ID NO 17
<211> LENGTH: 402
<212> TYPE: DNA
<213> ORGANISM: Xanthomonas smithii
<220> FEATURE:
<223> OTHER INFORMATION: Xanthomonas smithii subsp. smithii

<400> SEQUENCE: 17
atgaattctt tgaacacaca gatcggcgcc aactcgtcct tcttgcaggt cgacccgagc    60
cagaacacgc aattcggtcc gaaccagggc aatcaaggca tctcggaaaa gcagctggac    120
cagctgctga cccagctcat catggccctg cttcagcaga gcaacaatgc cgaccagggt    180
cagggtggtg actctggtgg tcaaggcggc aattcgcggc aggccgggca gcccaatggt    240
tccccctcgg catacaccca gatgctgatg aatatcgtcg gagacattct ccaggcgcag    300
aatggtggtg gcttcggcgg cgggttcggc ggtggctttg gtggcgggct cggcaccagc    360
ctcggcagca gccttgcgag cgacaccgga tcgatgcagt aa                      402
```

```
<210> SEQ ID NO 18
<211> LENGTH: 133
<212> TYPE: PRT
<213> ORGANISM: Xanthomonas smithii
<220> FEATURE:
<223> OTHER INFORMATION: Xanthomonas smithii subsp. smithii

<400> SEQUENCE: 18

Met Asn Ser Leu Asn Thr Gln Ile Gly Ala Asn Ser Ser Phe Leu Gln
1               5                   10                  15
```

```
Val Asp Pro Ser Gln Asn Thr Gln Phe Gly Pro Asn Gln Gly Asn Gln
            20                  25                  30

Gly Ile Ser Glu Lys Gln Leu Asp Gln Leu Leu Thr Gln Leu Ile Met
        35                  40                  45

Ala Leu Leu Gln Gln Ser Asn Asn Ala Asp Gln Gly Gln Gly Gly Asp
 50                  55                  60

Ser Gly Gly Gln Gly Gly Asn Ser Arg Gln Ala Gly Gln Pro Asn Gly
 65                  70                  75                  80

Ser Pro Ser Ala Tyr Thr Gln Met Leu Met Asn Ile Val Gly Asp Ile
                 85                  90                  95

Leu Gln Ala Gln Asn Gly Gly Phe Gly Gly Phe Gly Gly
            100                 105                 110

Phe Gly Gly Gly Leu Gly Thr Ser Leu Gly Ser Ser Leu Ala Ser Asp
        115                 120                 125

Thr Gly Ser Met Gln
        130
```

```
<210> SEQ ID NO 19
<211> LENGTH: 420
<212> TYPE: DNA
<213> ORGANISM: Xanthomonas oryzae
<220> FEATURE:
<223> OTHER INFORMATION: Xanthomonas oryzae pv. oryzae

<400> SEQUENCE: 19
atgaactctt tgaacacaca attcggcggc agcacgtcca accttcaggt tggcccaagc      60
caggacacaa cgttcggttc gaaccagggc ggcaaccagg gcatctcgga aaagcaactg     120
gaccagttgc tgtgccagct catctcggcc ctgcttcagt cgagcaaaaa tgctgaggag     180
ggtaagggtc agggtggcga taatggcggt ggccagggcg gcaattcgca gcaggccggg     240
cagcagaatg gcccctcgcc attcacccag atgctgatgc atatcgtcgg agagattctc     300
caggcgcaga tggtggtgg tgctggtggc ggcggtttcg gcggcgggtt cggcggcgac     360
tttagtggcg acctcggcct cggcaccaac ctctcgagcg acagcgcatc aatgcagtaa     420
```

```
<210> SEQ ID NO 20
<211> LENGTH: 139
<212> TYPE: PRT
<213> ORGANISM: Xanthomonas oryzae
<220> FEATURE:
<223> OTHER INFORMATION: Xanthomonas oryzae pv. oryzae

<400> SEQUENCE: 20

Met Asn Ser Leu Asn Thr Gln Phe Gly Gly Ser Thr Ser Asn Leu Gln
 1               5                  10                  15

Val Gly Pro Ser Gln Asp Thr Thr Phe Gly Ser Asn Gln Gly Gly Asn
            20                  25                  30

Gln Gly Ile Ser Glu Lys Gln Leu Asp Gln Leu Leu Cys Gln Leu Ile
        35                  40                  45

Ser Ala Leu Leu Gln Ser Ser Lys Asn Ala Glu Glu Gly Lys Gly Gln
 50                  55                  60

Gly Gly Asp Asn Gly Gly Gly Gln Gly Gly Asn Ser Gln Gln Ala Gly
 65                  70                  75                  80

Gln Gln Asn Gly Pro Ser Pro Phe Thr Gln Met Leu Met His Ile Val
                 85                  90                  95

Gly Glu Ile Leu Gln Ala Gln Asn Gly Gly Ala Gly Gly Gly
            100                 105                 110

Phe Gly Gly Gly Phe Gly Gly Asp Phe Ser Gly Asp Leu Gly Leu Gly
```

```
                115                 120                 125

Thr Asn Leu Ser Ser Asp Ser Ala Ser Met Gln
    130                 135

<210> SEQ ID NO 21
<211> LENGTH: 420
<212> TYPE: DNA
<213> ORGANISM: Xanthomonas oryzae
<220> FEATURE:
<223> OTHER INFORMATION: Xanthomonas oryzae pv. oryzae

<400> SEQUENCE: 21
atgaattctt tgaacacaca attcggcggc agcacgtcca accttcaggt tggcccaagc      60
caggacacaa cgttcggttc gaaccagggc ggcaaccagg gcatctcgga aaagcaactg     120
gaccagttgc tgtgccagct catctcggcc ctgcttcagt cgagcaaaaa tgctgaggag     180
ggtaagggtc agggtggcga taatggcggt ggccagggcg gcaattcgca gcaggctggg     240
cagcagaatg gcccctcgcc attcacccag atgctgatgc atatcgtcgg agagattctc     300
caggcgcaga atggtggtgg tgctggtggc ggcgggttcg gcggcgggtt cggcggtgac     360
tttagtggcg acctcggcct cggcaccaac ctctcgagcg acagcgcatc gatgcagtaa     420

<210> SEQ ID NO 22
<211> LENGTH: 139
<212> TYPE: PRT
<213> ORGANISM: Xanthomonas oryzae
<220> FEATURE:
<223> OTHER INFORMATION: Xanthomonas oryzae pv. oryzae

<400> SEQUENCE: 22

Met Asn Ser Leu Asn Thr Gln Phe Gly Gly Ser Thr Ser Asn Leu Gln
1               5                   10                  15

Val Gly Pro Ser Gln Asp Thr Thr Phe Gly Ser Asn Gln Gly Gly Asn
            20                  25                  30

Gln Gly Ile Ser Glu Lys Gln Leu Asp Gln Leu Leu Cys Gln Leu Ile
        35                  40                  45

Ser Ala Leu Leu Gln Ser Ser Lys Asn Ala Glu Glu Gly Lys Gly Gln
    50                  55                  60

Gly Gly Asp Asn Gly Gly Gln Gly Gly Asn Ser Gln Gln Ala Gly
65                  70                  75                  80

Gln Gln Asn Gly Pro Ser Pro Phe Thr Gln Met Leu Met His Ile Val
                85                  90                  95

Gly Glu Ile Leu Gln Ala Gln Asn Gly Gly Gly Ala Gly Gly Gly Gly
            100                 105                 110

Phe Gly Gly Gly Phe Gly Gly Asp Phe Ser Gly Asp Leu Gly Leu Gly
        115                 120                 125

Thr Asn Leu Ser Ser Asp Ser Ala Ser Met Gln
    130                 135

<210> SEQ ID NO 23
<211> LENGTH: 420
<212> TYPE: DNA
<213> ORGANISM: Xanthomonas oryzae
<220> FEATURE:
<223> OTHER INFORMATION: Xanthomonas oryzae pv. oryzae

<400> SEQUENCE: 23
atgaattctt tgaacacaca attcggcggc agcacgtcca accttcaggt tggcccaagc      60
caggacacaa cgttcggttc gaaccagggc ggcaaccagg gcatctcgga aaagcaactg     120
```

```
gaccagttgc tgtgccagct catctcggcc ctgcttcagt cgagcaaaaa tgctgaggag    180
ggtaagggtc agggtggcga taatggcggt ggccagggcg gcaattcgca gcaggccggg    240
cagcagaatg cccctcgcc attcacccag atgctgatgc atatcgtcgg agagattctc     300
caggcgcaga tggtggtgg tgctggtggc ggcgggttcg gcggcgggtt cggcggtgac     360
tttagtggcg acctcggcct cggcaccaac ctctcgagcg acagcgcatc gatgcagtaa    420
```

<210> SEQ ID NO 24
<211> LENGTH: 139
<212> TYPE: PRT
<213> ORGANISM: Xanthomonas oryzae
<220> FEATURE:
<223> OTHER INFORMATION: Xanthomonas oryzae pv. oryzae

<400> SEQUENCE: 24

```
Met Asn Ser Leu Asn Thr Gln Phe Gly Gly Ser Thr Ser Asn Leu Gln
1               5                   10                  15

Val Gly Pro Ser Gln Asp Thr Thr Phe Gly Ser Asn Gln Gly Gly Asn
            20                  25                  30

Gln Gly Ile Ser Glu Lys Gln Leu Asp Gln Leu Leu Cys Gln Leu Ile
        35                  40                  45

Ser Ala Leu Leu Gln Ser Ser Lys Asn Ala Glu Glu Gly Lys Gly Gln
    50                  55                  60

Gly Gly Asp Asn Gly Gly Gly Gln Gly Gly Asn Ser Gln Gln Ala Gly
65                  70                  75                  80

Gln Gln Asn Gly Pro Ser Pro Phe Thr Gln Met Leu Met His Ile Val
                85                  90                  95

Gly Glu Ile Leu Gln Ala Gln Asn Gly Gly Gly Ala Gly Gly Gly Gly
            100                 105                 110

Phe Gly Gly Gly Phe Gly Gly Asp Phe Ser Gly Asp Leu Gly Leu Gly
        115                 120                 125

Thr Asn Leu Ser Ser Asp Ser Ala Ser Met Gln
    130                 135
```

<210> SEQ ID NO 25
<211> LENGTH: 378
<212> TYPE: DNA
<213> ORGANISM: Xanthomonas oryzae pv.
<220> FEATURE:
<223> OTHER INFORMATION: Xanthomonas oryzae pv. oryzicola

<400> SEQUENCE: 25

```
atgaattctt tgaacacaca attcggcggc agcgcgtcca acttccaggt tgaccaaagc    60
cagaacgcgc aatccgattc gagccagggc agcaatggca gccagggtat ctcggaaaag   120
caactggacc agttgctgtg ccagctcatc caggccctgc ttcagccgaa caaaaatgct   180
gaggaaggta agggtcagca gggtggcgag aataatcagc aggccgggaa ggagaatggc   240
gcctcgccac tcacccagat gctgatgaat atcgtcggag agattctcca ggcgcagaat   300
gccggcggca gcagcggcgg cgactttggt ggcagtttcg ccagcagctt ctcgaacgac   360
agcggatcga tgcagtaa                                                 378
```

<210> SEQ ID NO 26
<211> LENGTH: 125
<212> TYPE: PRT
<213> ORGANISM: Xanthomonas oryzae
<220> FEATURE:
<223> OTHER INFORMATION: Xanthomonas oryzae pv. oryzicola

<400> SEQUENCE: 26

```
Met Asn Ser Leu Asn Thr Gln Phe Gly Gly Ser Ala Ser Asn Phe Gln
1               5                   10                  15

Val Asp Gln Ser Gln Asn Ala Gln Ser Asp Ser Ser Gln Gly Ser Asn
            20                  25                  30

Gly Ser Gln Gly Ile Ser Glu Lys Gln Leu Asp Gln Leu Leu Cys Gln
        35                  40                  45

Leu Ile Gln Ala Leu Leu Gln Pro Asn Lys Asn Ala Glu Glu Gly Lys
    50                  55                  60

Gly Gln Gln Gly Gly Glu Asn Asn Gln Gln Ala Gly Lys Glu Asn Gly
65                  70                  75                  80

Ala Ser Pro Leu Thr Gln Met Leu Met Asn Ile Val Gly Glu Ile Leu
                85                  90                  95

Gln Ala Gln Asn Ala Gly Gly Ser Ser Gly Gly Asp Phe Gly Gly Ser
            100                 105                 110

Phe Ala Ser Ser Phe Ser Asn Asp Ser Gly Ser Met Gln
        115                 120                 125

<210> SEQ ID NO 27
<211> LENGTH: 366
<212> TYPE: DNA
<213> ORGANISM: Xanthomonas campestris
<220> FEATURE:
<223> OTHER INFORMATION: Xanthomonas campestris pv. campestris

<400> SEQUENCE: 27
tcaggcttgg ccggtgatgc tcgacaggtt ggcattgaag ccgccaccca agctggtgcc      60
gcccatgccg gcgccgcctt ggttctgcat cagctgcatc acgatctgca tcagcatctg     120
cgtcaacgga ctcacaccgt cctgttgacc gctctgcggt tgttcgtctc cgcactcctg     180
atcggcatcg ctgccctggc tctgttggag catcatcatg atgaacatgg cgagcagctg     240
atccagctgc tgctcggagt cagccgaagg cgagcgctga ctggagttct gggtttgctg     300
gggcccgatg cccatcgtct gcaggttgat gaagttggaa aatttgtttc cgatagatga     360
gtccat                                                                366

<210> SEQ ID NO 28
<211> LENGTH: 121
<212> TYPE: PRT
<213> ORGANISM: Xanthomonas campestris
<220> FEATURE:
<223> OTHER INFORMATION: Xanthomonas campestris pv. campestris

<400> SEQUENCE: 28

Met Asp Ser Ser Ile Gly Asn Lys Phe Ser Asn Phe Ile Asn Leu Gln
1               5                   10                  15

Thr Met Gly Ile Gly Pro Gln Gln Thr Gln Asn Ser Ser Gln Arg Ser
            20                  25                  30

Pro Ser Ala Asp Ser Glu Gln Gln Leu Asp Gln Leu Leu Ala Met Phe
        35                  40                  45

Ile Met Met Met Leu Gln Gln Ser Gln Gly Ser Asp Ala Asp Gln Glu
    50                  55                  60

Cys Gly Asp Glu Gln Pro Gln Ser Gly Gln Gln Asp Gly Val Ser Pro
65                  70                  75                  80

Leu Thr Gln Met Leu Met Gln Ile Val Met Gln Leu Met Gln Asn Gln
                85                  90                  95

Gly Gly Ala Gly Met Gly Gly Thr Ser Leu Gly Gly Gly Phe Asn Ala
            100                 105                 110
```

Asn Leu Ser Ser Ile Thr Gly Gln Ala
    115                 120

<210> SEQ ID NO 29
<211> LENGTH: 3282
<212> TYPE: DNA
<213> ORGANISM: Synechocystis sp.

<400> SEQUENCE: 29

| | | | | | |
|---|---|---|---|---|---|
| tgttcgttgc | acaaattgat | gagcaatgct | tttttataat | gccaactttg | tacaaaaaag | 60 |
| caggcttaaa | caatggcgac | tatccacggt | aattggcaac | cctcccacgg | ggaaaacggc | 120 |
| ggcaaactgt | ttctttgggc | ggatacctgg | ggtcatcctt | gccagaaaac | cattggcgat | 180 |
| cgccatccct | ttgcgttgga | tctgccggat | ttgctacagg | cctggtcgaa | tttgcccctg | 240 |
| gccttcccca | aggcggatgg | ggtgacagag | gcagccctta | ctctgcattt | acccagccat | 300 |
| cgccagcaaa | aaattcccct | accctttgtc | acagggcaag | atccggtggc | catggatgcg | 360 |
| aaatatctcc | actggcgatc | gtggcaggta | accgggtaa | atctgacccc | aagccaaacg | 420 |
| ttaacgttgc | tccaatctat | tcccctgggg | ggccaagcct | tagctaactt | aggatcagag | 480 |
| ttttacttt | acggtcaact | gcaccgctgg | tgtttagatt | tggtgctacg | gggtaaattt | 540 |
| gtgccgggac | tggagcaaag | gggggaagac | ggtaattact | atgcccaatg | gattcctatc | 600 |
| ctcgatagca | tccaagacca | aacccattta | gcccaattta | gccagagagt | acctgcctgc | 660 |
| gccctggcca | acctgactga | ctcccaggag | ccccaaatgt | tggtggtgga | tttactacaa | 720 |
| aaattattgc | aagcccaaat | tggtgccgtc | agtcccagcc | tagccaacgt | taaagaagtc | 780 |
| tggttgaatg | attggctccg | gggattaacc | catggggggc | aaacctccct | cggcacaagc | 840 |
| aaagctctac | aacgattagc | cacatcctta | gaccattggt | atttaccagt | ccagaattat | 900 |
| ttgggccaaa | aaaataacca | agctttagcc | caacggcaat | ggcgggggc | tctgcggtta | 960 |
| caacctccag | cggacgatgg | ggggggaacc | tggcaactgg | attatggttt | acaagccctg | 1020 |
| gatgacgggg | aattttggct | cccggcggct | tccctctggg | ccatggccgg | cgatcgcctg | 1080 |
| gtgtggcagg | gaaggagggt | tgaccagggg | gcggaaagtt | tactgcgggg | cttagggta | 1140 |
| gctgcccaaa | tttacgaacc | cattgctgca | agtttgacgg | aaaggtgtcc | cacgggctgt | 1200 |
| gggctagatg | ccatccaagc | ctacgaattt | atcctggcaa | tcgcccatca | attgcgggat | 1260 |
| cgggggttag | gggtaatcct | cccgccgggg | ttagaacggg | gcggcaccgc | caaacggtta | 1320 |
| ggggtaaaag | tggtgggga | agtgcaacgg | caaggggcc | agcggctaac | tctgcaaagt | 1380 |
| ttaattaatt | acgacttgca | actaatgatg | gggagcgggg | acaatgcccg | gttattgacg | 1440 |
| gccaaggact | ttgaagcgtt | actagcccaa | aaatctcccc | tggtggtgct | ggacggagaa | 1500 |
| tggattaccc | tgcaaccggc | ggacgtgcgg | gcggccaagg | tcattttaca | gcagcaacaa | 1560 |
| tctgccccgc | ccctcacagt | ggaggatgct | ctgcgcctca | gcattggtga | tttacaaacc | 1620 |
| gtctctaaac | tgccggtgac | ccagtttgct | gctcgggca | tattacagga | attgatcgac | 1680 |
| accctccgta | acccgaagg | agtgaaagcc | attgctgacc | caccgggctt | tcagggtact | 1740 |
| ttacggcccct | accaagctcg | gggagtgggc | tggttagctt | ttctggaacg | gtgggggctg | 1800 |
| ggggcctgtt | tggcagacga | tatgggtttg | ggaaaaacac | cccagttgct | ggcttttctg | 1860 |
| ctccatttag | ccgcggagga | tatgttagtt | aagccggtgt | tgattgtttg | tcctacgtcg | 1920 |
| gtgctgagca | attggggtca | tgaaattaat | aagtttgcgc | cccaacttaa | aaccctattg | 1980 |
| caccatggcg | atcgccggaa | aaagggcaa | ccgttggtta | aacaggtcaa | agaccagcaa | 2040 |
| attgtcctca | ccagttacgc | tttactgcaa | cgggatttta | gtagtttgaa | attggtggac | 2100 |

```
tggcagggga tcgtgctgga cgaagcccaa aatatcaaaa atccccaagc taaacagtcc    2160
caggcggccc ggcaattgcc agcgggtttt cgcattgccc tcacggggac tccggtggaa    2220
aatcgcctga cggaattgtg gtcaatttta gaattttaa atcccggttt cctgggtaat    2280
cagagctttt tccaacggcg ctttgccaat cccatcgaaa aatttggcga tcgccagtcg    2340
ttgttaattt tgcggaattt agtgcggccg tttattttgc ggcggttaaa aaccgaccaa    2400
accattattc aagatttacc agaaaaacaa gaaatgaccg tcttctgtga cctttcccaa    2460
gagcaagctg gtttatatca acaattggtg gaggaatccc tccaggcgat cgccgacagc    2520
gaaggcattc aaaggcacgg tttagtttta accctattaa ccaaactcaa acaggtttgt    2580
aaccatcccg atctattgct gaaaaagccc gccatcaccc acgggcacca gtccggcaag    2640
ctaattcgtc tggcggaaat gctggaagaa atcatcagcg aaggcgatcg ggtgttaatt    2700
ttcacccaat ttgccagttg gggtcattta ctcaaaccct atctggaaaa atactttaac    2760
caagaggtgc tctatctcca cggggggcact ccagcagagc aacggcaagc tctggtggaa    2820
cgattccaac aggaccccaa cagtccctat ttatttatcc tttctctcaa ggctggcggc    2880
acagggttga acctcacgag ggctaaccat gtgttccatg tggaccggtg gtggaatccg    2940
gcggtggaaa atcaggctac cgatcgtgct tttcgcattg ccaaactcg caacgtccag    3000 gtgcacaaat ttgtctgtac aggcaccttg gaagaaaaaa ttaacgccat gatggcggat    3060
aaacaacaat tggcagaaca aaccgtggat gccggggaaa attggctcac ccgcctagac    3120
accgataaac tccgtcagtt gcttaccctc tccgccaccc cggtggatta ccaagccgaa    3180
gcgtccgatt gaacccagct ttcttgtaca aagttggcat gataagaaag cattgcttat    3240
caatttgttg caacgaacag gtcactatca gtcaaaataa at                      3282
```

<210> SEQ ID NO 30
<211> LENGTH: 1039
<212> TYPE: PRT
<213> ORGANISM: Synechocystis sp.

<400> SEQUENCE: 30

```
Met Ala Thr Ile His Gly Asn Trp Gln Pro Ser His Gly Glu Asn Gly
1               5                   10                  15

Gly Lys Leu Phe Leu Trp Ala Asp Thr Trp Gly His Pro Leu Pro Glu
            20                  25                  30

Thr Ile Gly Asp Arg His Pro Phe Ala Leu Asp Leu Pro Asp Leu Leu
        35                  40                  45

Gln Ala Trp Ser Asn Leu Pro Leu Ala Phe Pro Lys Ala Asp Gly Val
    50                  55                  60

Thr Glu Ala Ala Leu Thr Leu His Leu Pro Ser His Arg Gln Gln Lys
65                  70                  75                  80

Ile Pro Leu Pro Phe Val Thr Gly Gln Asp Pro Val Ala Met Asp Ala
                85                  90                  95

Lys Tyr Leu His Trp Arg Ser Trp Gln Val Thr Gly Val Asn Leu Thr
            100                 105                 110

Pro Ser Gln Thr Leu Thr Leu Leu Gln Ser Ile Pro Leu Gly Gly Gln
        115                 120                 125

Ala Leu Ala Asn Leu Gly Ser Glu Phe Tyr Tyr Gly Gln Leu His
    130                 135                 140

Arg Trp Cys Leu Asp Leu Val Leu Arg Gly Lys Phe Val Pro Gly Leu
145                 150                 155                 160

Glu Gln Arg Gly Glu Asp Gly Asn Tyr Tyr Ala Gln Trp Ile Pro Ile
```

```
                     165                 170                 175
Leu Asp Ser Ile Gln Asp Gln Thr His Leu Ala Gln Phe Ser Gln Arg
                180                 185                 190

Val Pro Ala Cys Ala Leu Ala Asn Leu Thr Asp Ser Gln Glu Pro Gln
            195                 200                 205

Met Leu Val Val Asp Leu Leu Gln Lys Leu Leu Gln Ala Gln Ile Gly
        210                 215                 220

Ala Val Ser Pro Ser Leu Ala Asn Val Lys Glu Val Trp Leu Asn Asp
225                 230                 235                 240

Trp Leu Arg Gly Leu Thr His Gly Gly Gln Thr Ser Leu Gly Thr Ser
                245                 250                 255

Lys Ala Leu Gln Arg Leu Ala Thr Ser Leu Asp His Trp Tyr Leu Pro
                260                 265                 270

Val Gln Asn Tyr Leu Gly Gln Lys Asn Asn Gln Ala Leu Ala Gln Arg
            275                 280                 285

Gln Trp Arg Gly Ala Leu Arg Leu Gln Pro Pro Ala Asp Asp Gly Gly
        290                 295                 300

Gly Thr Trp Gln Leu Asp Tyr Gly Leu Gln Ala Leu Asp Asp Gly Glu
305                 310                 315                 320

Phe Trp Leu Pro Ala Ala Ser Leu Trp Ala Met Ala Gly Asp Arg Leu
                325                 330                 335

Val Trp Gln Gly Arg Arg Val Asp Gln Gly Ala Glu Ser Leu Leu Arg
                340                 345                 350

Gly Leu Gly Val Ala Ala Gln Ile Tyr Glu Pro Ile Ala Ala Ser Leu
            355                 360                 365

Thr Glu Arg Cys Pro Thr Gly Cys Gly Leu Asp Ala Ile Gln Ala Tyr
        370                 375                 380

Glu Phe Ile Leu Ala Ile Ala His Gln Leu Arg Asp Arg Gly Leu Gly
385                 390                 395                 400

Val Ile Leu Pro Pro Gly Leu Glu Arg Gly Thr Ala Lys Arg Leu
                405                 410                 415

Gly Val Lys Val Val Gly Glu Val Gln Arg Gln Arg Gly Gln Arg Leu
                420                 425                 430

Thr Leu Gln Ser Leu Ile Asn Tyr Asp Leu Gln Leu Met Met Gly Ser
            435                 440                 445

Gly Asp Asn Ala Arg Leu Leu Thr Ala Lys Asp Phe Glu Ala Leu Leu
        450                 455                 460

Ala Gln Lys Ser Pro Leu Val Val Leu Asp Gly Glu Trp Ile Thr Leu
465                 470                 475                 480

Gln Pro Ala Asp Val Arg Ala Ala Lys Val Ile Leu Gln Gln Gln Gln
                485                 490                 495

Ser Ala Pro Pro Leu Thr Val Glu Asp Ala Leu Arg Leu Ser Ile Gly
            500                 505                 510

Asp Leu Gln Thr Val Ser Lys Leu Pro Val Thr Gln Phe Ala Ala Arg
        515                 520                 525

Gly Ile Leu Gln Glu Leu Ile Asp Thr Leu Arg Asn Pro Glu Gly Val
    530                 535                 540

Lys Ala Ile Ala Asp Pro Pro Gly Phe Gln Gly Thr Leu Arg Pro Tyr
545                 550                 555                 560

Gln Ala Arg Gly Val Gly Trp Leu Ala Phe Leu Glu Arg Trp Gly Leu
                565                 570                 575

Gly Ala Cys Leu Ala Asp Asp Met Gly Leu Gly Lys Thr Pro Gln Leu
                580                 585                 590
```

-continued

```
Leu Ala Phe Leu Leu His Leu Ala Glu Asp Met Leu Val Lys Pro
            595                 600                 605

Val Leu Ile Val Cys Pro Thr Ser Val Leu Ser Asn Trp Gly His Glu
    610                 615                 620

Ile Asn Lys Phe Ala Pro Gln Leu Lys Thr Leu Leu His His Gly Asp
625                 630                 635                 640

Arg Arg Lys Lys Gly Gln Pro Leu Val Lys Gln Val Lys Asp Gln Gln
                645                 650                 655

Ile Val Leu Thr Ser Tyr Ala Leu Leu Gln Arg Asp Phe Ser Ser Leu
            660                 665                 670

Lys Leu Val Asp Trp Gln Gly Ile Val Leu Asp Glu Ala Gln Asn Ile
        675                 680                 685

Lys Asn Pro Gln Ala Lys Gln Ser Gln Ala Ala Arg Gln Leu Pro Ala
690                 695                 700

Gly Phe Arg Ile Ala Leu Thr Gly Thr Pro Val Glu Asn Arg Leu Thr
705                 710                 715                 720

Glu Leu Trp Ser Ile Leu Glu Phe Leu Asn Pro Gly Phe Leu Gly Asn
                725                 730                 735

Gln Ser Phe Phe Gln Arg Arg Phe Ala Asn Pro Ile Glu Lys Phe Gly
            740                 745                 750

Asp Arg Gln Ser Leu Leu Ile Leu Arg Asn Leu Val Arg Pro Phe Ile
        755                 760                 765

Leu Arg Arg Leu Lys Thr Asp Gln Thr Ile Ile Gln Asp Leu Pro Glu
770                 775                 780

Lys Gln Glu Met Thr Val Phe Cys Asp Leu Ser Gln Glu Gln Ala Gly
785                 790                 795                 800

Leu Tyr Gln Gln Leu Val Glu Glu Ser Leu Gln Ala Ile Ala Asp Ser
                805                 810                 815

Glu Gly Ile Gln Arg His Gly Leu Val Leu Thr Leu Leu Thr Lys Leu
            820                 825                 830

Lys Gln Val Cys Asn His Pro Asp Leu Leu Leu Lys Lys Pro Ala Ile
        835                 840                 845

Thr His Gly His Gln Ser Gly Lys Leu Ile Arg Leu Ala Glu Met Leu
850                 855                 860

Glu Glu Ile Ile Ser Glu Gly Asp Arg Val Leu Ile Phe Thr Gln Phe
865                 870                 875                 880

Ala Ser Trp Gly His Leu Leu Lys Pro Tyr Leu Glu Lys Tyr Phe Asn
                885                 890                 895

Gln Glu Val Leu Tyr Leu His Gly Gly Thr Pro Ala Glu Gln Arg Gln
            900                 905                 910

Ala Leu Val Glu Arg Phe Gln Gln Asp Pro Asn Ser Pro Tyr Leu Phe
        915                 920                 925

Ile Leu Ser Leu Lys Ala Gly Gly Thr Gly Leu Asn Leu Thr Arg Ala
930                 935                 940

Asn His Val Phe His Val Asp Arg Trp Trp Asn Pro Ala Val Glu Asn
945                 950                 955                 960

Gln Ala Thr Asp Arg Ala Phe Arg Ile Gly Gln Thr Arg Asn Val Gln
                965                 970                 975

Val His Lys Phe Val Cys Thr Gly Thr Leu Glu Glu Lys Ile Asn Ala
            980                 985                 990

Met Met Ala Asp Lys Gln Gln Leu Ala Glu Gln Thr Val Asp Ala Gly
        995                1000                1005

Glu Asn Trp Leu Thr Arg Leu Asp Thr Asp Lys Leu Arg Gln Leu
       1010                1015                1020
```

Leu Thr Leu Ser Ala Thr Pro Val Asp Tyr Gln Ala Glu Ala Ser
    1025                1030                1035

Asp

<210> SEQ ID NO 31
<211> LENGTH: 3237
<212> TYPE: DNA
<213> ORGANISM: Anaebena variabilis

<400> SEQUENCE: 31

| | | | | | |
|---|---|---|---|---|---|
| atggcaattt | tacacggtag | ttggatatta | agtgagcagg | atagttattt | atttatttgg | 60 |
| ggggaaactt | ggcgatcgcc | acaagtaaat | tttagttttg | aggaaatagc | cctcaatccc | 120 |
| ttggctctgt | ctgcatctga | attaagcgag | tggttgcagt | ctcaacatca | ggcgatcgct | 180 |
| cagattttac | cacaacagtt | ggcaaaaaaa | acctccaaag | cagcaagttc | cccaacaaca | 240 |
| aatttaccaa | ttcactcgca | ataattgtt | ctgccaacgg | aaatttctca | acctcgtaag | 300 |
| aaagaaacaa | ttttcatttc | tcctgtgcat | tctgccgctt | tagaatctga | tgcagactct | 360 |
| gaagtttatt | tacaaccttg | gcgtgtagaa | ggttttttgtc | ttcctcctag | tgcagcagtt | 420 |
| aaatttctaa | cttctttacc | tttaaatatc | actagcacag | agaatgcttt | tttaggtgga | 480 |
| gatttacgtt | tttggtcaca | aattgcccgt | tggagtttag | atttaatttc | taggtctaag | 540 |
| tttctcccaa | ttatccaacg | acaacctaat | aattctgtaa | gtgccaaatg | gcaagtactg | 600 |
| ttagatagtg | ctgtagatgg | aactcgttta | gaaaagttcg | ccgcgaagat | gcctttggtt | 660 |
| tgtcggactt | atcagagatt | agggaacgag | gaattatctc | catctcctat | atatatagat | 720 |
| tttcctagtc | agccgcagga | attaatattg | ggttttctca | atagtgcaat | agatacgcaa | 780 |
| ttacgggaaa | tggtggggaa | tcagcctgtg | gtggaaactc | gcttgatggc | atctttaccg | 840 |
| tcggcggtac | gacagtggct | gcaagggtta | agtggtgcat | ctaattcagt | tgatgcagat | 900 |
| gcagttggtt | tggaaaggct | ggaagcagcg | ctcaaggctt | ggacgatgcc | gctacaatat | 960 |
| caactagcaa | gtaaaaatca | atttcgcacc | tgttttgaat | tacgttctcc | agaaccagga | 1020 |
| gaaactgaat | ggacactagc | ctatttcctg | caagcagccg | ataatccaga | atttctagta | 1080 |
| gatgcgggca | ctatttggca | acatcctgtt | gaacagctaa | tttatcaaca | gcgatcgatt | 1140 |
| caagaaccc | aggaaacatt | tttacgaggt | ttggggttag | cttctcgatt | gtatccggtc | 1200 |
| attgccccca | ctttagatac | agaatcaccg | caattttgtc | atctcaaccc | catgcaggct | 1260 |
| tatgaattta | tcaaggctgt | ggcttggcga | tttgaagata | gcggtttagg | ggtgattta | 1320 |
| cctcctagtt | tggcgaaccg | ggaaggctgg | gcaaaccgct | tgggattgaa | aatctccgcc | 1380 |
| gaaaccccaa | agaaaaagcc | aggacgcttg | ggattgcaga | gtttgcttaa | ttttcaatgg | 1440 |
| cacttagcaa | ttggtgggca | aactatttct | aaagggaat | ttgacagact | agtagcttta | 1500 |
| aaaagcccat | tggtagaaat | aaatggcgaa | tgggtggagt | tgcgtcccca | agatatcaag | 1560 |
| acagccgaag | cctttttgc | tgcacgtaaa | gaccaaatgg | ccttatcttt | agaagatgct | 1620 |
| ttacgtctga | gtagtgggga | tactcaagta | attgagaaat | taccagtagt | cagctttgaa | 1680 |
| gcctctggcg | cattacaaga | attaattggg | gcgctgacaa | ataatcaagc | agttgcacca | 1740 |
| ttacctacgc | caaagaactt | ccaaggaaag | ttgcgtcctt | atcaagaaag | gggtgcgcgt | 1800 |
| tggttggcat | tcctcgaacg | ctggggttta | ggtgcttgtc | tcgccgacga | catgggactg | 1860 |
| ggaaaaacga | tacagttcat | tgcttttcctt | ctccatctta | aagaacagga | tgtattagaa | 1920 |
| aaaccaactt | tactagtgtg | tcctacttct | gttttaggta | actgggaacg | agaagtgaaa | 1980 |

-continued

```
aaatttgcac ctacacttaa agttctccaa tatcatggtg ataaacgtcc taaaggtaaa    2040
gcttttccag aagcagtaaa aaatcatgat ttagttatca ccagttactc actaattcat    2100
agagacatca aatcattgca gggtctttct tggcagataa ttgttttaga tgaagcccag    2160
aatgtgaaga atgcggaagc caaacaatca caagcagtcc gacaattaga cacaaccttt    2220
cgcattgctt taacggggac accagtcgaa aatagactac aggaactttg gtcaatttta    2280
gatttcctca accctggtta tttaggtaat aagcaattct tccaaagacg ctttgccatg    2340
ccaattgaaa agtatggtga tgcagcatct ttaaatcaat tgcgtgcctt agtacaacca    2400
tttattctgc gtcgcctgaa aacagaccgt gatattattc aagacttgcc agataagcaa    2460
gaaatgacag tattttgcgg tttgactgga gaacaagctg cactttatca aaaagtggta    2520
gaaacatctt tagcagaaat tgaatcggcc gaaggattgc aacgccgagg gatgatttta    2580
gctttattaa ttaaactcaa acaaatctgc aatcatccag cccaatatct gaaaacaaat    2640
accttagaac aatacagttc aggaaaactg caacgattag aagaaatgtt agaagaggtg    2700
ttagcggaga gtaatactta tggtgttgct ggtgcgggac gtgctttaat cttcacccag    2760
tttgcagaat ggggtaagtt actcaaacca catttagaaa acaactagg gcgggaagta    2820 ttttcttat atggtagtac cagtaaaaag caacgtgaag aaatgattga ccgttttcaa    2880
cacgaccctc aggggccacc aattatgatt ctctctctca aagcaggtgg tgtagggttg    2940
aacttaacca gagcaaatca tgtatttcac tttgatagat ggtggaatcc agccgtagag    3000
aaccaagcca cagaccgcgt atttcgtatt ggtcaaaccc gcaatgtaca ggtgcataaa    3060 tttgttttgca atggtacctt agaagaaaaa atccacgaca tgattgaaag taaaaaacaa    3120
ctagcggaac aggttgttgg tgcaggcgaa gagtggttaa ctgaattaga tacagatcaa    3180
ctccgcaact tactgatact tgatcgtagt gcagtaattg atgaagaagc agagtaa       3237
```

<210> SEQ ID NO 32
<211> LENGTH: 1078
<212> TYPE: PRT
<213> ORGANISM: Anaebena variabilis

<400> SEQUENCE: 32

```
Met Ala Ile Leu His Gly Ser Trp Ile Leu Ser Glu Gln Asp Ser Tyr
1               5                   10                  15

Leu Phe Ile Trp Gly Glu Thr Trp Arg Ser Pro Gln Val Asn Phe Ser
                20                  25                  30

Phe Glu Glu Ile Ala Leu Asn Pro Leu Ala Leu Ser Ala Ser Glu Leu
            35                  40                  45

Ser Glu Trp Leu Gln Ser Gln His Gln Ala Ile Ala Gln Ile Leu Pro
        50                  55                  60

Gln Gln Leu Ala Lys Lys Thr Ser Lys Ala Ala Ser Ser Pro Thr Thr
65                  70                  75                  80

Asn Leu Pro Ile His Ser Gln Ile Ile Val Leu Pro Thr Glu Ile Ser
                85                  90                  95

Gln Pro Arg Lys Lys Glu Thr Ile Phe Ile Ser Pro Val His Ser Ala
            100                 105                 110

Ala Leu Glu Ser Asp Ala Asp Ser Glu Val Tyr Leu Gln Pro Trp Arg
        115                 120                 125

Val Glu Gly Phe Cys Leu Pro Pro Ser Ala Ala Val Lys Phe Leu Thr
    130                 135                 140

Ser Leu Pro Leu Asn Ile Thr Ser Thr Glu Asn Ala Phe Leu Gly Gly
145                 150                 155                 160
```

```
Asp Leu Arg Phe Trp Ser Gln Ile Ala Arg Trp Ser Leu Asp Leu Ile
            165                 170                 175

Ser Arg Ser Lys Phe Leu Pro Ile Ile Gln Arg Gln Pro Asn Asn Ser
        180                 185                 190

Val Ser Ala Lys Trp Gln Val Leu Leu Asp Ser Ala Val Asp Gly Thr
    195                 200                 205

Arg Leu Glu Lys Phe Ala Ala Lys Met Pro Leu Val Cys Arg Thr Tyr
210                 215                 220

Gln Arg Leu Gly Asn Glu Glu Leu Ser Pro Ser Pro Ile Tyr Ile Asp
225                 230                 235                 240

Phe Pro Ser Gln Pro Gln Glu Leu Ile Leu Gly Phe Leu Asn Ser Ala
                245                 250                 255

Ile Asp Thr Gln Leu Arg Glu Met Val Gly Asn Gln Pro Val Val Glu
            260                 265                 270

Thr Arg Leu Met Ala Ser Leu Pro Ser Ala Val Arg Gln Trp Leu Gln
        275                 280                 285

Gly Leu Ser Gly Ala Ser Asn Ser Val Asp Ala Asp Ala Val Gly Leu
    290                 295                 300

Glu Arg Leu Glu Ala Ala Leu Lys Ala Trp Thr Met Pro Leu Gln Tyr
305                 310                 315                 320

Gln Leu Ala Ser Lys Asn Gln Phe Arg Thr Cys Phe Glu Leu Arg Ser
                325                 330                 335

Pro Glu Pro Gly Glu Thr Glu Trp Thr Leu Ala Tyr Phe Leu Gln Ala
            340                 345                 350

Ala Asp Asn Pro Glu Phe Leu Val Asp Ala Gly Thr Ile Trp Gln His
        355                 360                 365

Pro Val Glu Gln Leu Ile Tyr Gln Gln Arg Ser Ile Gln Glu Pro Gln
    370                 375                 380

Glu Thr Phe Leu Arg Gly Leu Gly Leu Ala Ser Arg Leu Tyr Pro Val
385                 390                 395                 400

Ile Ala Pro Thr Leu Asp Thr Glu Ser Pro Gln Phe Cys His Leu Asn
                405                 410                 415

Pro Met Gln Ala Tyr Glu Phe Ile Lys Ala Val Ala Trp Arg Phe Glu
            420                 425                 430

Asp Ser Gly Leu Gly Val Ile Leu Pro Pro Ser Leu Ala Asn Arg Glu
        435                 440                 445

Gly Trp Ala Asn Arg Leu Gly Leu Lys Ile Ser Ala Glu Thr Pro Lys
    450                 455                 460

Lys Lys Pro Gly Arg Leu Gly Leu Gln Ser Leu Asn Phe Gln Trp
465                 470                 475                 480

His Leu Ala Ile Gly Gly Gln Thr Ile Ser Lys Gly Glu Phe Asp Arg
                485                 490                 495

Leu Val Ala Leu Lys Ser Pro Leu Val Glu Ile Asn Gly Glu Trp Val
            500                 505                 510

Glu Leu Arg Pro Gln Asp Ile Lys Thr Ala Glu Ala Phe Phe Ala Ala
        515                 520                 525

Arg Lys Asp Gln Met Ala Leu Ser Leu Glu Asp Ala Leu Arg Leu Ser
    530                 535                 540

Ser Gly Asp Thr Gln Val Ile Glu Lys Leu Pro Val Val Ser Phe Glu
545                 550                 555                 560

Ala Ser Gly Ala Leu Gln Glu Leu Ile Gly Ala Leu Thr Asn Asn Gln
                565                 570                 575

Ala Val Ala Pro Leu Pro Thr Pro Lys Asn Phe Gln Gly Lys Leu Arg
            580                 585                 590
```

```
Pro Tyr Gln Glu Arg Gly Ala Ala Trp Leu Ala Phe Leu Glu Arg Trp
    595                 600                 605

Gly Leu Gly Ala Cys Leu Ala Asp Asp Met Gly Leu Gly Lys Thr Ile
610                 615                 620

Gln Phe Ile Ala Phe Leu Leu His Leu Lys Glu Gln Asp Val Leu Glu
625                 630                 635                 640

Lys Pro Thr Leu Leu Val Cys Pro Thr Ser Val Leu Gly Asn Trp Glu
                645                 650                 655

Arg Glu Val Lys Lys Phe Ala Pro Thr Leu Lys Val Leu Gln Tyr His
            660                 665                 670

Gly Asp Lys Arg Pro Lys Gly Lys Ala Phe Pro Glu Ala Val Lys Asn
        675                 680                 685

His Asp Leu Val Ile Thr Ser Tyr Ser Leu Ile His Arg Asp Ile Lys
    690                 695                 700

Ser Leu Gln Gly Leu Ser Trp Gln Ile Ile Val Leu Asp Glu Ala Gln
705                 710                 715                 720

Asn Val Lys Asn Ala Glu Ala Lys Gln Ser Gln Ala Val Arg Gln Leu
                725                 730                 735

Asp Thr Thr Phe Arg Ile Ala Leu Thr Gly Thr Pro Val Glu Asn Arg
            740                 745                 750

Leu Gln Glu Leu Trp Ser Ile Leu Asp Phe Leu Asn Pro Gly Tyr Leu
        755                 760                 765

Gly Asn Lys Gln Phe Phe Gln Arg Arg Phe Ala Met Pro Ile Glu Lys
    770                 775                 780

Tyr Gly Asp Ala Ala Ser Leu Asn Gln Leu Arg Ala Leu Val Gln Pro
785                 790                 795                 800

Phe Ile Leu Arg Arg Leu Lys Thr Asp Arg Asp Ile Ile Gln Asp Leu
                805                 810                 815

Pro Asp Lys Gln Glu Met Thr Val Phe Cys Gly Leu Thr Gly Glu Gln
            820                 825                 830

Ala Ala Leu Tyr Gln Lys Val Val Glu Thr Ser Leu Ala Glu Ile Glu
        835                 840                 845

Ser Ala Glu Gly Leu Gln Arg Arg Gly Met Ile Leu Ala Leu Leu Ile
    850                 855                 860

Lys Leu Lys Gln Ile Cys Asn His Pro Ala Gln Tyr Leu Lys Thr Asn
865                 870                 875                 880

Thr Leu Glu Gln Tyr Ser Ser Gly Lys Leu Gln Arg Leu Glu Glu Met
                885                 890                 895

Leu Glu Glu Val Leu Ala Glu Ser Asn Thr Tyr Gly Val Ala Gly Ala
            900                 905                 910

Gly Arg Ala Leu Ile Phe Thr Gln Phe Ala Glu Trp Gly Lys Leu Leu
        915                 920                 925

Lys Pro His Leu Glu Lys Gln Leu Gly Arg Glu Val Phe Phe Leu Tyr
    930                 935                 940

Gly Ser Thr Ser Lys Lys Gln Arg Glu Glu Met Ile Asp Arg Phe Gln
945                 950                 955                 960

His Asp Pro Gln Gly Pro Pro Ile Met Ile Leu Ser Leu Lys Ala Gly
                965                 970                 975

Gly Val Gly Leu Asn Leu Thr Arg Ala Asn His Val Phe His Phe Asp
            980                 985                 990

Arg Trp Trp Asn Pro Ala Val Glu  Asn Gln Ala Thr Asp  Arg Val Phe
        995                 1000                1005

Arg Ile  Gly Gln Thr Arg Asn  Val Gln Val His Lys  Phe Val Cys
```

```
                    1010               1015                1020
Asn Gly Thr Leu Glu Glu Lys Ile His Asp Met Ile Glu Ser Lys
     1025                1030                1035

Lys Gln Leu Ala Glu Gln Val Val Gly Ala Gly Glu Glu Trp Leu
     1040                1045                1050

Thr Glu Leu Asp Thr Asp Gln Leu Arg Asn Leu Leu Ile Leu Asp
     1055                1060                1065

Arg Ser Ala Val Ile Asp Glu Glu Ala Glu
     1070                1075

<210> SEQ ID NO 33
<211> LENGTH: 3129
<212> TYPE: DNA
<213> ORGANISM: methanogenic archaeon
<220> FEATURE:
<223> OTHER INFORMATION: uncultured methanogenic archaeon

<400> SEQUENCE: 33
atgattacac ttcacggaac ctggactact gtcgatcccc tgaatggcac attttttcctc      60
tggggagaga gtgatccggc cacgcagcat aaaagaagag gcaggcctcg aaaagtgca     120
ggggagaaac agcacccgtt tcacgccggc atcaagagc tggaagctgg agcgggggct     180
atcaattcat cgtgtataag acatatagca gatgcgggag cacgggcgga gcaggtttta     240
attttgccgt cagctacgga caggcccctg agatctgcga gcccttcagc actggagtca     300
ggtgaagaaa ccaaccctga cagcagttta caatttcttc cgtggacggt gaccggcatc     360
aacattaagc ccgggaatgc tctggtactt ctatcctcta tagccgaatc acaaaagcgg     420
atcggagata tggcgatagg cccagacctg ctttactgga gtaaggtagc caagtttacg     480
cttaagctcc tgataagcca gcagttcagg ccggaggttg tcgaagtaat gagcggaaaa     540
gcatatagcc gttggagatt tgcgctcacc gatgaaactg accggaaaca ctatgcctcg     600
ctcgaaaact ccatgccgct ggcatgtatt gcggtttcag gaaaggctgg catttataat     660
cgaaaagaag ccttagattt gttcattaat accgcccttg acacatttat ccgggaccag     720
attgccctgc cgctgacag caggatgacg aacctgctat cgcaagcatg gctagattcg     780
ctcggcaccg gagagagtat ccgcctgtcg gctcctgaga tgaagaaact caaagattcg     840
gcaggccgct ggacatcccg catgaaaaca gagagcaaac aagctttaaa gacctgcttc     900
atcctggagc cgccagcccc ggatacagag tatcctgaag cgccgtggaa cctacggtac     960
tgcttgcagg catccgatga ccccagtctg gtaattccgg ctgagactgt gtggaaagag    1020
ttgaagaaga cgctgaagta cctgaataag agatacgata ccctcagga gcaattgtta    1080
caggatctcg gaaaagcgat gcagatgttt cccgaaatcg agcccagcct caacacgtca    1140
aaacctctgt ccgcaacgct gagcaccagt gaagcctaca agttcctgac agaagcggcg    1200
cctctgctgc aggacagcgg gtatagcatt atcctaccgg aatggtggcg caacagcact    1260
ggcaggctca agctcggcgc caggcttcgc ttcaagccga agccgaagg taaagcgggt    1320
aaaagccagt tcaccatgga taccctcgtc agctacgact ggcgcctggc gctgggcgat    1380
caggagatca ccgaaacaga gttcaggaag ctggcagccc tgaaagagcc gcttctgcag    1440
ataggcggga atggtttgc gctgaaaaag gaagacatag acagcatcat gaaagcattc    1500
agggcgaaga agactggaga gatggcttta tcggaggcac tgcgcctcaa cggcgggctg    1560
gaagacttca acggcatccc cgtcagcggc atgaaatcgt caggatggct ggcagaactt    1620
ttcgacaggc tggcagccgg cgaaaaaata acgagccttg ccccgccgga cggtttcaac    1680
```

-continued

```
ggggagctta gagattacca ggttaaaggc tactcctggc tggccttcat gaaaaagtat    1740
ggcctgggct ccattctggc tgacgacatg ggcctgggta agacgataca gctgctggcg    1800
ttgctcctga agagaagga aagaggcact aaaggcccta ctctgttgat ctgccccacc    1860
tcgattctcg gaaactggca gcgggaggcg aagaaatttg ccccggccct gaaagtccac    1920
atacaccatg gggcaggaag ggctgataaa gagcagttcg gaaaaatcgt caaggctcac    1980
gacctgatcc tgagcactta cgctcacgcc taccgggacg aggaactgct taagaggtg    2040 aactggaagc tggtagtgct cgacgaggct cagaatatca agaatcatca tacccggcag    2100
gccagagcta tccgggctct taaggccgat caccgaatag ccatgacggg aacgccgata    2160
gagaacagac tctcggagct gtggtcgatc gtggacttcc tgaaccccgg ctacctgggc    2220
aaggcggaga cattcaggaa acaattcgcc atacctatcg agatacga tgacgctgcc    2280 cggtcggaaa aattgaagca ggccatcaag ccctggtgc tgcgcagagt gaagacggat    2340
ccggccatca tcaaagacct gccggacaag atcgagatca aggagccctg caacctcacc    2400
aaagaacagg ccacgctcta cgaggccatc gtagagaaca tgctgaaaag tatagataag    2460
gccacggcaa tgcagagacg gggaatcgtc ttagcgtccc tgatgaagct caaacaggtc    2520
tgcgatcacc cgtcgctgta catcaaaacg ggcgctgtga ccgacgataa gacgctgatc    2580
aggtctggca agctgaagcg cctcacggag ctgctcgaag aagcgctggc cgaaggcgac    2640
agcgtgctga tcttcacca gttcgtggaa atgggggaga tgctgaaagc ctacctgcag    2700
agcacgttcg acgaagaagc cctctttttg cacggcggag taccgcagaa ggccagagac    2760
aagatggtcc tccgtttcgg ggaaaaggac gggccacgga tctttatcgt ctcgctgaaa    2820
gccggcggcg tcggcctcaa cctgacgaag gcaagccacg tgttccactt cgatcgctgg    2880
tggaacccgg cggtcgagaa ccaggcgaca gatcgagctt acaggatagg ccagagcaaa    2940
aatgtactgg tccataaatt cgtctgcgcc ggcacgctgg aagaaaagat cgacgagctg    3000
atcgagagca aaaggcgct gtcggcgaac atcctcggca cggagaaga ctggatcacg    3060 gagttgtcga ccgaacagct gagggacatg tcatgctga atgggacga ggtagccgat    3120 gatggctaa                                                           3129
```

<210> SEQ ID NO 34
<211> LENGTH: 1042
<212> TYPE: PRT
<213> ORGANISM: methanogenic archaeon
<220> FEATURE:
<223> OTHER INFORMATION: uncultured methanogenic archaeon

<400> SEQUENCE: 34

```
Met Ile Thr Leu His Gly Thr Trp Thr Thr Val Asp Pro Leu Asn Gly
  1               5                  10                  15

Thr Phe Phe Leu Trp Gly Glu Ser Asp Pro Ala Thr Gln His Lys Arg
                 20                  25                  30

Arg Gly Arg Pro Arg Lys Ser Ala Gly Glu Lys Gln His Pro Phe His
             35                  40                  45

Ala Gly Ile Lys Glu Leu Glu Ala Gly Ala Gly Ala Ile Asn Ser Ser
         50                  55                  60

Cys Ile Arg His Ile Ala Asp Ala Gly Ala Arg Ala Glu Gln Val Leu
 65                  70                  75                  80

Ile Leu Pro Ser Ala Thr Asp Arg Pro Leu Arg Ser Ala Ser Pro Ser
                 85                  90                  95

Ala Leu Glu Ser Gly Glu Glu Thr Asn Pro Asp Ser Ser Leu Gln Phe
            100                 105                 110
```

```
Leu Pro Trp Thr Val Thr Gly Ile Asn Ile Lys Pro Gly Asn Ala Leu
            115                 120                 125

Val Leu Leu Ser Ser Ile Ala Glu Ser Gln Lys Arg Ile Gly Asp Met
    130                 135                 140

Ala Ile Gly Pro Asp Leu Leu Tyr Trp Ser Lys Val Ala Lys Phe Thr
145                 150                 155                 160

Leu Lys Leu Leu Ile Ser Gln Gln Phe Arg Pro Glu Val Val Glu Val
                165                 170                 175

Met Ser Gly Lys Ala Tyr Ser Arg Trp Arg Phe Ala Leu Thr Asp Glu
            180                 185                 190

Thr Asp Arg Lys His Tyr Ala Ser Leu Glu Asn Ser Met Pro Leu Ala
            195                 200                 205

Cys Ile Ala Val Ser Gly Lys Ala Gly Ile Tyr Asn Arg Lys Glu Ala
            210                 215                 220

Leu Asp Leu Phe Ile Asn Thr Ala Leu Asp Thr Phe Ile Arg Asp Gln
225                 230                 235                 240

Ile Ala Leu Pro Ala Asp Ser Arg Met Thr Asn Leu Leu Ser Gln Ala
                245                 250                 255

Trp Leu Asp Ser Leu Gly Thr Gly Glu Ser Ile Arg Leu Ser Ala Pro
            260                 265                 270

Glu Met Lys Lys Leu Lys Asp Ser Ala Gly Arg Trp Thr Ser Arg Met
            275                 280                 285

Lys Thr Glu Ser Lys Gln Ala Leu Lys Thr Cys Phe Ile Leu Glu Pro
            290                 295                 300

Pro Ala Pro Asp Thr Glu Tyr Pro Glu Ala Pro Trp Asn Leu Arg Tyr
305                 310                 315                 320

Cys Leu Gln Ala Ser Asp Pro Ser Leu Val Ile Pro Ala Glu Thr
                325                 330                 335

Val Trp Lys Glu Leu Lys Lys Thr Leu Lys Tyr Leu Asn Lys Arg Tyr
            340                 345                 350

Asp Asn Pro Gln Glu Gln Leu Leu Gln Asp Leu Gly Lys Ala Met Gln
            355                 360                 365

Met Phe Pro Glu Ile Glu Pro Ser Leu Asn Thr Ser Lys Pro Leu Ser
            370                 375                 380

Ala Thr Leu Ser Thr Ser Glu Ala Tyr Lys Phe Leu Thr Glu Ala Ala
385                 390                 395                 400

Pro Leu Leu Gln Asp Ser Gly Tyr Ser Ile Ile Leu Pro Glu Trp Trp
                405                 410                 415

Arg Asn Ser Thr Gly Arg Leu Lys Leu Gly Ala Arg Leu Arg Phe Lys
            420                 425                 430

Pro Lys Ala Glu Gly Lys Ala Gly Lys Ser Gln Phe Thr Met Asp Thr
            435                 440                 445

Leu Val Ser Tyr Asp Trp Arg Leu Ala Leu Gly Asp Gln Glu Ile Thr
            450                 455                 460

Glu Thr Glu Phe Arg Lys Leu Ala Ala Leu Lys Glu Pro Leu Leu Gln
465                 470                 475                 480

Ile Gly Gly Lys Trp Phe Ala Leu Lys Lys Glu Asp Ile Asp Ser Ile
                485                 490                 495

Met Lys Ala Phe Arg Ala Lys Lys Thr Gly Glu Met Ala Leu Ser Glu
            500                 505                 510

Ala Leu Arg Leu Asn Gly Gly Leu Glu Asp Phe Asn Gly Ile Pro Val
            515                 520                 525

Ser Gly Met Lys Ser Ser Gly Trp Leu Ala Glu Leu Phe Asp Arg Leu
```

-continued

```
              530                 535                 540
Ala Ala Gly Glu Lys Ile Thr Ser Leu Ala Pro Pro Asp Gly Phe Asn
545                 550                 555                 560

Gly Glu Leu Arg Asp Tyr Gln Val Lys Gly Tyr Ser Trp Leu Ala Phe
                    565                 570                 575

Met Lys Lys Tyr Gly Leu Gly Ser Ile Leu Ala Asp Asp Met Gly Leu
                    580                 585                 590

Gly Lys Thr Ile Gln Leu Leu Ala Leu Leu Lys Glu Lys Glu Arg
                595                 600                 605

Gly Thr Lys Gly Pro Thr Leu Leu Ile Cys Pro Thr Ser Ile Leu Gly
                610                 615                 620

Asn Trp Gln Arg Glu Ala Lys Lys Phe Ala Pro Ala Leu Lys Val His
625                 630                 635                 640

Ile His His Gly Ala Gly Arg Ala Asp Lys Glu Gln Phe Gly Lys Ile
                    645                 650                 655

Val Lys Ala His Asp Leu Ile Leu Ser Thr Tyr Ala His Ala Tyr Arg
                660                 665                 670

Asp Glu Glu Leu Leu Lys Glu Val Asn Trp Lys Leu Val Leu Asp
                675                 680                 685

Glu Ala Gln Asn Ile Lys Asn His His Thr Arg Gln Ala Arg Ala Ile
690                 695                 700

Arg Ala Leu Lys Ala Asp His Arg Ile Ala Met Thr Gly Thr Pro Ile
705                 710                 715                 720

Glu Asn Arg Leu Ser Glu Leu Trp Ser Ile Val Asp Phe Leu Asn Pro
                    725                 730                 735

Gly Tyr Leu Gly Lys Ala Glu Thr Phe Arg Lys Gln Phe Ala Ile Pro
                740                 745                 750

Ile Glu Arg Tyr Asp Asp Ala Ala Arg Ser Glu Lys Leu Lys Gln Ala
                755                 760                 765

Ile Lys Pro Leu Val Leu Arg Arg Val Lys Thr Asp Pro Ala Ile Ile
                770                 775                 780

Lys Asp Leu Pro Asp Lys Ile Glu Ile Lys Glu Pro Cys Asn Leu Thr
785                 790                 795                 800

Lys Glu Gln Ala Thr Leu Tyr Glu Ala Ile Val Glu Asn Met Leu Lys
                    805                 810                 815

Ser Ile Asp Lys Ala Thr Ala Met Gln Arg Arg Gly Ile Val Leu Ala
                820                 825                 830

Ser Leu Met Lys Leu Lys Gln Val Cys Asp His Pro Ser Leu Tyr Ile
                835                 840                 845

Lys Thr Gly Ala Val Thr Asp Asp Lys Thr Leu Ile Arg Ser Gly Lys
                850                 855                 860

Leu Lys Arg Leu Thr Glu Leu Leu Glu Glu Ala Leu Ala Glu Gly Asp
865                 870                 875                 880

Ser Val Leu Ile Phe Thr Gln Phe Val Glu Met Gly Glu Met Leu Lys
                    885                 890                 895

Ala Tyr Leu Gln Ser Thr Phe Asp Glu Glu Ala Leu Phe Leu His Gly
                    900                 905                 910

Gly Val Pro Gln Lys Ala Arg Asp Lys Met Val Leu Arg Phe Gly Glu
                915                 920                 925

Lys Asp Gly Pro Arg Ile Phe Ile Val Ser Leu Lys Ala Gly Gly Val
                930                 935                 940

Gly Leu Asn Leu Thr Lys Ala Ser His Val Phe His Phe Asp Arg Trp
945                 950                 955                 960
```

-continued

Trp Asn Pro Ala Val Glu Asn Gln Ala Thr Asp Arg Ala Tyr Arg Ile
            965                 970                 975

Gly Gln Ser Lys Asn Val Leu Val His Lys Phe Val Cys Ala Gly Thr
            980                 985                 990

Leu Glu Glu Lys Ile Asp Glu Leu Ile Glu Ser Lys Lys Ala Leu Ser
            995                1000                1005

Ala Asn Ile Leu Gly Thr Gly Glu Asp Trp Ile Thr Glu Leu Ser
        1010            1015                1020

Thr Glu Gln Leu Arg Asp Met Val Met Leu Arg Trp Asp Glu Val
        1025            1030                1035

Ala Asp Asp Gly
        1040

<210> SEQ ID NO 35
<211> LENGTH: 2757
<212> TYPE: DNA
<213> ORGANISM: Bacillus cereus

<400> SEQUENCE: 35

| | | | | |
|---|---|---|---|---|
| atgatcaatc | aaactgaagt | aacaattagg | ctccagcacg | ttagtcacgg | ttggttcctt | 60 |
| tggggagaag | atgatagcgg | tactccatta | tccgtaacaa | gttggaaacg | aaatgcattt | 120 |
| acatggcact | ccacttcctt | ctacggcacg | tttctaaaag | aagcaagctt | tgaaggaaga | 180 |
| caaggtgtta | tgctaacaaa | cgcacaagca | tttgaataca | tcgcgaataa | accgatgaac | 240 |
| tcctttgccc | gtattcaaat | gaacggcccct | attacagcac | ttacgaaga | tgcgaacgaa | 300 |
| ttgtgggatg | ccttcacaag | cggtagcttc | gtacctgata | tggagcgttg | gcctaaacaa | 360 |
| ccatcttgga | aagttcaaaa | tactccaatc | gaagatgaaa | cattggcatc | tcttttctcg | 420 |
| gctgcagtaa | atgaaagcat | attacaagat | aaccgttcaa | atgacggatg | ggaagatgca | 480 |
| aagagacttt | atgaacatta | cgactttacg | aaaagacaat | tagacgcagc | actacatgaa | 540 |
| gaagattggc | ttcgaaaaat | tggttacatt | gaagatgacc | ttcccttac | aatcggacta | 600 |
| cgactacaag | agccgcaaga | agaatttgaa | atgtggaagc | ttgaaacaat | tgttacgcca | 660 |
| aagcgcgggg | cacatcgcat | atatgtatat | gagagtatcg | attctttacc | aaaacgatgg | 720 |
| cacgattatg | aagaacgtat | tctggaaaca | caagaaagct | tcagtaagct | cgtaccgtgg | 780 |
| ctaaaagatg | tgatacatt | ccgaagtgaa | ctctttgaaa | cagaagcgtg | gaacttctta | 840 |
| acagaagcaa | gtaacgaatt | actcgccgca | ggtattacaa | tcttattacc | atcgtggtgg | 900 |
| caaaatttaa | aagcgacaaa | accaaaatta | cgtgtgcaac | tgaagcaaaa | tgctacacaa | 960 |
| acgcaatctt | tcttcggcat | gaatacactc | gttaattttg | actggcgcat | ttcaacgaac | 1020 |
| ggcattgatt | tatcagaaag | cgaattttt | gaactcgttg | aacaaaacaa | gcggttattc | 1080 |
| aatataaatg | gtcaatggat | gcgactagat | ccagccttta | ttgaagaagt | acgaaagctc | 1140 |
| atgaatcgtg | ctgataagta | tggacttgaa | atgaaagatg | tcctgcagca | acatttatca | 1200 |
| aacacggctg | aaacagaaat | tgtagaagag | gatagtccgt | ttacagatat | tgaaattgaa | 1260 |
| ctagatggat | attatgaaga | cttattccaa | aaactattgc | acattggaga | tattccgaaa | 1320 |
| gtagatgtcc | cttcatcact | aaacgccaca | ctccgtccgt | atcaacaaca | tggcattgag | 1380 |
| tggttattat | atttaagaaa | gcttggattc | ggcgcattgt | tagctgacga | catgggactt | 1440 |
| ggaaagagta | ttcaaacgat | cacttactta | ctatatataa | aagaaaacaa | tctccaaaca | 1500 |
| ggtcctgctt | taatcgtggc | tccgacatct | gttcttggaa | attggcaaaa | agaatttgag | 1560 |
| cgtttcgcac | cgaatttacg | tgttcagtta | cattatggaa | gtaaccgagc | taaagggga | 1620 |

-continued

```
ccctttaaag atttccttca atcagcagat gttgtattaa catcttatgc attagctcag   1680
cttgatgagg aagaacttag tacgttatgc tgggatgctg ttattttgga tgaagcacaa   1740
aatattaaaa acccacatac gaaacagtct aaagcagtac gaaacttaca agcaaatcac   1800
aaaatcgcat taactgggac accgatggaa aaccgccttg ccgagctttg gtctattttc   1860
gacttcatta atcatggata tcttggcagc ttaggacaat tccagcgccg cttcgtctca   1920
ccaattgaaa aggaccgtga cgaaggaaaa atccaacaag ttcaacgttt tatctcaccg   1980
tttttactgc gtcgtacgaa gaaagatcaa acagtcgcat taaacttacc agataaacaa   2040
gaacagaaag cttactgtcc actaactggt gaacaagctt ccttatatga acaacttgtt   2100
caagatacgt tgcaaaatgt agaaggatta agcggaattg aacgacgcgg atttatatta   2160
ctcatgctga acaaacttaa acaaatttgt aatcatcccg ctctttattt aaaagaaaca   2220
gaaccgaaag acatcatcga gcgttccatg aaaacgagca cgctcatgga actcattgaa   2280
aatataaaag atcaaaatga aagttgctta atcttcacgc aatacatcgg tatggggaac   2340
atgctaaaag atgtgttaga agaacatttc ggtcagcgcg tcctcttctt aaacggtagt   2400
gtaccgaaga aagaacgtga caaaatgatc gaacagttcc aaaacggaac gtatgacatc   2460
ttcattttat cgttaaaagc aggtggtaca ggattaaact taacagctgc caaccatgtc   2520
attcactacg atcgttggtg gaatccagcg gtagaaaacc aagcaacaga ccgtgcatat   2580
cgcattggtc aaaagcgctt cgttcacgtt cataaactga ttacaacggg gacacttgaa   2640
gagaaaatcg atgaaatgtt agaaagaaaa caatcattaa acaacgccgt cattacaagc   2700
gatagttgga tgacagaact atctacagat gaactaaaag aattacttgg tgtataa      2757
```

<210> SEQ ID NO 36
<211> LENGTH: 918
<212> TYPE: PRT
<213> ORGANISM: Bacillus cereus

<400> SEQUENCE: 36

```
Met Ile Asn Gln Thr Glu Val Thr Ile Arg Leu Gln His Val Ser His
1               5                   10                  15

Gly Trp Phe Leu Trp Gly Glu Asp Asp Ser Gly Thr Pro Leu Ser Val
            20                  25                  30

Thr Ser Trp Lys Arg Asn Ala Phe Thr Trp His Ser Thr Ser Phe Tyr
        35                  40                  45

Gly Thr Phe Leu Lys Glu Ala Ser Phe Glu Gly Arg Gln Gly Val Met
    50                  55                  60

Leu Thr Asn Ala Gln Ala Phe Glu Tyr Ile Ala Asn Lys Pro Met Asn
65                  70                  75                  80

Ser Phe Ala Arg Ile Gln Met Asn Gly Pro Ile Thr Ala Leu Thr Glu
                85                  90                  95

Asp Ala Asn Glu Leu Trp Asp Ala Phe Thr Ser Gly Ser Phe Val Pro
            100                 105                 110

Asp Met Glu Arg Trp Pro Lys Gln Pro Ser Trp Lys Val Gln Asn Thr
        115                 120                 125

Pro Ile Glu Asp Glu Thr Leu Ala Ser Leu Phe Ser Ala Ala Val Asn
    130                 135                 140

Glu Ser Ile Leu Gln Asp Asn Arg Ser Asn Asp Gly Trp Glu Asp Ala
145                 150                 155                 160

Lys Arg Leu Tyr Glu His Tyr Asp Phe Thr Lys Arg Gln Leu Asp Ala
                165                 170                 175

Ala Leu His Glu Glu Asp Trp Leu Arg Lys Ile Gly Tyr Ile Glu Asp
```

```
                    180                 185                 190
Asp Leu Pro Phe Thr Ile Gly Leu Arg Leu Gln Glu Pro Gln Glu Glu
                195                 200                 205

Phe Glu Met Trp Lys Leu Glu Thr Ile Val Thr Pro Lys Arg Gly Ala
    210                 215                 220

His Arg Ile Tyr Val Tyr Glu Ser Ile Asp Ser Leu Pro Lys Arg Trp
225                 230                 235                 240

His Asp Tyr Glu Glu Arg Ile Leu Glu Thr Gln Glu Ser Phe Ser Lys
                245                 250                 255

Leu Val Pro Trp Leu Lys Asp Gly Asp Thr Phe Arg Ser Glu Leu Phe
            260                 265                 270

Glu Thr Glu Ala Trp Asn Phe Leu Thr Glu Ala Ser Asn Glu Leu Leu
        275                 280                 285

Ala Ala Gly Ile Thr Ile Leu Leu Pro Ser Trp Trp Gln Asn Leu Lys
    290                 295                 300

Ala Thr Lys Pro Lys Leu Arg Val Gln Leu Lys Gln Asn Ala Thr Gln
305                 310                 315                 320

Thr Gln Ser Phe Phe Gly Met Asn Thr Leu Val Asn Phe Asp Trp Arg
                325                 330                 335

Ile Ser Thr Asn Gly Ile Asp Leu Ser Glu Ser Glu Phe Phe Glu Leu
            340                 345                 350

Val Glu Gln Asn Lys Arg Leu Phe Asn Ile Asn Gly Gln Trp Met Arg
        355                 360                 365

Leu Asp Pro Ala Phe Ile Glu Glu Val Arg Lys Leu Met Asn Arg Ala
    370                 375                 380

Asp Lys Tyr Gly Leu Glu Met Lys Asp Val Leu Gln Gln His Leu Ser
385                 390                 395                 400

Asn Thr Ala Glu Thr Glu Ile Val Glu Glu Asp Ser Pro Phe Thr Asp
                405                 410                 415

Ile Glu Ile Glu Leu Asp Gly Tyr Tyr Glu Asp Leu Phe Gln Lys Leu
            420                 425                 430

Leu His Ile Gly Asp Ile Pro Lys Val Asp Val Pro Ser Ser Leu Asn
        435                 440                 445

Ala Thr Leu Arg Pro Tyr Gln Gln His Gly Ile Glu Trp Leu Leu Tyr
    450                 455                 460

Leu Arg Lys Leu Gly Phe Gly Ala Leu Leu Ala Asp Asp Met Gly Leu
465                 470                 475                 480

Gly Lys Ser Ile Gln Thr Ile Thr Tyr Leu Leu Tyr Ile Lys Glu Asn
                485                 490                 495

Asn Leu Gln Thr Gly Pro Ala Leu Ile Val Ala Pro Thr Ser Val Leu
            500                 505                 510

Gly Asn Trp Gln Lys Glu Phe Glu Arg Phe Ala Pro Asn Leu Arg Val
        515                 520                 525

Gln Leu His Tyr Gly Ser Asn Arg Ala Lys Gly Glu Pro Phe Lys Asp
    530                 535                 540

Phe Leu Gln Ser Ala Asp Val Val Leu Thr Ser Tyr Ala Leu Ala Gln
545                 550                 555                 560

Leu Asp Glu Glu Glu Leu Ser Thr Leu Cys Trp Asp Ala Val Ile Leu
                565                 570                 575

Asp Glu Ala Gln Asn Ile Lys Asn Pro His Thr Lys Gln Ser Lys Ala
            580                 585                 590

Val Arg Asn Leu Gln Ala Asn His Lys Ile Ala Leu Thr Gly Thr Pro
        595                 600                 605
```

```
Met Glu Asn Arg Leu Ala Glu Leu Trp Ser Ile Phe Asp Phe Ile Asn
            610                 615                 620

His Gly Tyr Leu Gly Ser Leu Gly Gln Phe Gln Arg Arg Phe Val Ser
625                 630                 635                 640

Pro Ile Glu Lys Asp Arg Asp Glu Gly Lys Ile Gln Gln Val Gln Arg
                645                 650                 655

Phe Ile Ser Pro Phe Leu Leu Arg Arg Thr Lys Lys Asp Gln Thr Val
            660                 665                 670

Ala Leu Asn Leu Pro Asp Lys Gln Glu Gln Lys Ala Tyr Cys Pro Leu
        675                 680                 685

Thr Gly Glu Gln Ala Ser Leu Tyr Glu Gln Leu Val Gly Asp Thr Leu
    690                 695                 700

Gln Asn Val Glu Gly Leu Ser Gly Ile Glu Arg Arg Gly Phe Ile Leu
705                 710                 715                 720

Leu Met Leu Asn Lys Leu Lys Gln Ile Cys Asn His Pro Ala Leu Tyr
                725                 730                 735

Leu Lys Glu Thr Glu Pro Lys Asp Ile Ile Glu Arg Ser Met Lys Thr
            740                 745                 750

Ser Thr Leu Met Glu Leu Ile Glu Asn Ile Lys Asp Gln Asn Glu Ser
        755                 760                 765

Cys Leu Ile Phe Thr Gln Tyr Ile Gly Met Gly Asn Met Leu Lys Asp
    770                 775                 780

Val Leu Glu Glu His Phe Gly Gln Arg Val Leu Phe Leu Asn Gly Ser
785                 790                 795                 800

Val Pro Lys Lys Glu Arg Asp Lys Met Ile Gln Phe Gln Asn Gly
                805                 810                 815

Thr Tyr Asp Ile Phe Ile Leu Ser Leu Lys Ala Gly Gly Thr Gly Leu
            820                 825                 830

Asn Leu Thr Ala Ala Asn His Val Ile His Tyr Asp Arg Trp Trp Asn
        835                 840                 845

Pro Ala Val Glu Asn Gln Ala Thr Asp Arg Ala Tyr Arg Ile Gly Gln
    850                 855                 860

Lys Arg Phe Val His Val His Lys Leu Ile Thr Thr Gly Thr Leu Glu
865                 870                 875                 880

Glu Lys Ile Asp Glu Met Leu Glu Arg Lys Gln Ser Leu Asn Asn Ala
                885                 890                 895

Val Ile Thr Ser Asp Ser Trp Met Thr Glu Leu Ser Thr Asp Glu Leu
            900                 905                 910

Lys Glu Leu Leu Gly Val
        915

<210> SEQ ID NO 37
<211> LENGTH: 3141
<212> TYPE: DNA
<213> ORGANISM: Crocosphaera watsonii

<400> SEQUENCE: 37
atgacaatat tacatggaac ttggattgaa aatacctctg aaaaacattt ttttatttgg       60
ggggaaactt ggcgttcttt atcctctgat atttcctcag atgattctat tttaatgtat      120 ccatttctg tagataaaca gggaattatt gaacaattaa actcgaataa gattaagatt       180
gaaaaaaaca aaaatattga atctgtttct caaatatttt atttgcctag taaatttatt      240
gctaaatcga agcaaagtat cccttttacta tcaacagaat taaagataaa agattttgaa      300
caaggggata ttcagttaat tgcttggaaa atcgaaggga taaaattaaa tgttgatgat      360
```

```
acaattaata ttttaagtca gttaccgttg ggattaacca ataatgacga aaattacata    420
ggcgataatt taaaattttg gacacatatt tatcgttgga gtctagattt attaactaga    480
ggtaaatatt taccgcaaat ggaagaacaa gataataact gttatggaca atgggaacct    540
ttactagata gtttagttga tcagcaacgg ttctctaaat ttatacaaac tatgccaaat    600
agttctcttg cttatcataa tttaatggag ggtgaattat cctcttcttt actcaaacaa    660
actactattc ttgattttt atctactatc attaatcaac aagtacgtca atttattgat    720
gttgctatta cccctagttc atttatccaa aagtggttat actctttaac acaagactta    780
tctaaatttg aagcatcaga agttgaaaga aagggattaa agaatgctat taataattgg    840
aaatcttctt taagtgaata tattataaag tctgataatc aaccattagg aattaaccag    900
tttcgtgttt gttttaaact agaaaatcca gctaaaagtg gtaagaaatt agaacaaagt    960
aattggcagt tacactacta tctccaagct ttagatgatc ctaattttct gatctctgcc   1020
aaggttattt gggaaaatcc tgttactaga ttaatctgca ataatagaac aattaatcat   1080
cctcaagaaa ccttgctaaa aggactaggt ttagcttcac gtctatatta tctaattgaa   1140
gaaagtttac aagacaataa gcctagtttt tctgagttag atcccataca agtctatgaa   1200 ttttacgtt caattgctaa tattcttaaa gataatggct taggggttat cttaccagct   1260
agtctagagc aaggagtcga agaaaaacgc ttaggaatta gtctaaccgc agaagttaag   1320
tcgaaaaaag gacaaagact tagcttacaa agtttgttaa gttataagct aaatttagca   1380
attggtgata aaacaatatc gaaaaagac tttgaaaaac tattagcgca aaagtcacct   1440
ttagttgaag taaaggaga atggatagca ttacaacctg ctgatgtcaa ggccgcacaa   1500 caaatttaa ataagtccta tgatccccta gaactttctg tagaagatgc tttacgcttc   1560
agcacaggag atatttcaac tgttgccaaa ctgccgatta ctaactttga agcaaaaggg   1620
gaattagcca atctaattaa tgctataaat aataatgaat caatccctat gatcgaaaat   1680
cccagaggat ttaaaggtca attacgtccc tatcaacagc gaggagtcgg ttggttatcg   1740
ttcttagaaa aatggggttt aggggcttgt cttgccgatg atatgggatt aggaaaaaca   1800
ccacaattaa ttgggttct cttacattta agaagcgaag gaatgttaga tcaacctacc   1860
ttagttattt gtcctacatc tgtttaaat aactgggaaa gagaagttca aaaatttgcc   1920
ccaacccttt ctactttgat tcatcatgga gataaacgta gtaaaggaa agcttttgtt   1980 aaagcagtta gtaaaaaaaa tgttatcatt actagctatt ctttaattta tcgagatatt   2040
aaaagctttg aacaggtaga atggcaaggt attgtcttag atgaagcaca aaatataaaa   2100
aatccccagg caaaacaatc ccaagcagtg cgtcaaattt ccacacagtt tcgtattgct   2160
ttaacaggaa ctcctgtaga aaatcgccta acagaattat ggtcaattct tgactttctt   2220
aacccaggat ttttagggac acagcagttt ttccgtcgtc gttttgccac tcctatcgaa   2280
aaatatgggg ataaagaatc actgcaaatt atgcgttctt tggtacgtcc tttcattctc   2340
agacgattga aaacagataa aactattatt caagatttac ccgaaaaaca agaaatgacc   2400
attttttgtg ggttatcctc agaacaagga aaactttatc aacaattagt agataattct   2460
ctggtagcaa tagaagagaa aacaggaatt gaacgcaaag gcttaatttt aagcttactg   2520
ctaaaactca aacaaatttg taaccatcct gctcattttc tcaagcaaaa gagcttaaaa   2580
acagcagaac aatctggtaa attattaaga ctagaagaaa tgctagaaga attaatcgaa   2640
gaaggagatc atgctttaat ctttacccaa ttttctgaat ggggtaaaact gctgcaacct   2700 tatttacaga aaaaatttca gcaagacgtt ctcttttgt atggtgctac tcgcagagtt   2760
```

-continued

```
caaagacaag aaatgatcga tcgctttcaa caggatccca acggacccag aattttatt      2820 ctctccttaa aagcaggggg aaccggatta aatttaaccc gcgctaacca tgtatttcat      2880
attgatcgtt ggtggaaccc agcagtagaa aatcaagcaa ccgatcgcgc gtttcgttta      2940
ggacaaaaac gcaatgttca agtacataaa tttgtctgta caggaaccct agaagaaaaa      3000
attaacgaaa tgttagaaag taaacaaaaa ttagccgaac aaaccgttga cgcagggaa       3060 caatggttga cagaattaga tacagatcaa ctgcgtaacc tcttattatt ggatcgagat      3120
accattattg acgaacaata a                                                3141
```

<210> SEQ ID NO 38
<211> LENGTH: 1046
<212> TYPE: PRT
<213> ORGANISM: Crocosphaera watsonii

<400> SEQUENCE: 38

Met Thr Ile Leu His Gly Thr Trp Ile Glu Asn Thr Ser Glu Lys His
1               5                   10                  15

Phe Phe Ile Trp Gly Glu Thr Trp Arg Ser Leu Ser Ser Asp Ile Ser
            20                  25                  30

Ser Asp Ser Ile Leu Met Tyr Pro Phe Ser Val Asp Lys Gln Gly
        35                  40                  45

Ile Ile Glu Gln Leu Asn Ser Asn Lys Ile Lys Ile Glu Lys Asn Lys
    50                  55                  60

Asn Ile Glu Ser Val Ser Gln Ile Phe Tyr Leu Pro Ser Lys Phe Ile
65                  70                  75                  80

Ala Lys Ser Lys Gln Ser Ile Pro Leu Leu Ser Thr Glu Leu Lys Asp
                85                  90                  95

Lys Asp Phe Glu Gln Gly Asp Ile Gln Leu Ile Ala Trp Lys Ile Glu
            100                 105                 110

Gly Ile Lys Leu Asn Val Asp Asp Thr Ile Asn Ile Leu Ser Gln Leu
        115                 120                 125

Pro Leu Gly Leu Thr Asn Asn Asp Glu Asn Tyr Ile Gly Asp Asn Leu
    130                 135                 140

Lys Phe Trp Thr His Ile Tyr Arg Trp Ser Leu Asp Leu Leu Thr Arg
145                 150                 155                 160

Gly Lys Tyr Leu Pro Gln Met Glu Glu Gln Asp Asn Asn Cys Tyr Gly
                165                 170                 175

Gln Trp Glu Pro Leu Leu Asp Ser Leu Val Asp Gln Gln Arg Phe Ser
            180                 185                 190

Lys Phe Ile Gln Thr Met Pro Asn Ser Ser Leu Ala Tyr His Asn Leu
        195                 200                 205

Met Glu Gly Glu Leu Ser Ser Leu Leu Lys Gln Thr Thr Ile Leu
    210                 215                 220

Asp Phe Leu Ser Thr Ile Ile Asn Gln Gln Val Arg Gln Phe Ile Asp
225                 230                 235                 240

Val Ala Ile Thr Pro Ser Ser Phe Ile Gln Lys Trp Leu Tyr Ser Leu
                245                 250                 255

Thr Gln Asp Leu Ser Lys Phe Glu Ala Ser Glu Val Glu Arg Lys Gly
            260                 265                 270

Leu Lys Asn Ala Ile Asn Asn Trp Lys Ser Ser Leu Ser Glu Tyr Ile
        275                 280                 285

Ile Lys Ser Asp Asn Gln Pro Leu Gly Ile Asn Gln Phe Arg Val Cys
    290                 295                 300

Phe Lys Leu Glu Asn Pro Ala Lys Ser Gly Lys Lys Leu Glu Gln Ser

```
                305                 310                 315                 320
Asn Trp Gln Leu His Tyr Tyr Leu Gln Ala Leu Asp Asp Pro Asn Phe
                325                 330                 335

Leu Ile Ser Ala Lys Val Ile Trp Glu Asn Pro Val Thr Arg Leu Ile
                340                 345                 350

Cys Asn Asn Arg Thr Ile Asn His Pro Gln Glu Thr Leu Leu Lys Gly
                355                 360                 365

Leu Gly Leu Ala Ser Arg Leu Tyr Tyr Leu Ile Glu Glu Ser Leu Gln
                370                 375                 380

Asp Asn Lys Pro Ser Phe Ser Glu Leu Asp Pro Ile Gln Val Tyr Glu
385                 390                 395                 400

Phe Leu Arg Ser Ile Ala Asn Ile Leu Lys Asp Asn Gly Leu Gly Val
                405                 410                 415

Ile Leu Pro Ala Ser Leu Glu Gln Gly Val Glu Lys Arg Leu Gly
                420                 425                 430

Ile Ser Leu Thr Ala Glu Val Lys Ser Lys Gly Gln Arg Leu Ser
                435                 440                 445

Leu Gln Ser Leu Leu Ser Tyr Lys Leu Asn Leu Ala Ile Gly Asp Lys
                450                 455                 460

Thr Ile Ser Lys Lys Asp Phe Glu Lys Leu Leu Ala Gln Lys Ser Pro
465                 470                 475                 480

Leu Val Glu Val Lys Gly Glu Trp Ile Ala Leu Gln Pro Ala Asp Val
                485                 490                 495

Lys Ala Ala Gln Gln Ile Leu Asn Lys Ser Tyr Asp Pro Leu Glu Leu
                500                 505                 510

Ser Val Glu Asp Ala Leu Arg Phe Ser Thr Gly Asp Ile Ser Thr Val
                515                 520                 525

Ala Lys Leu Pro Ile Thr Asn Phe Glu Ala Lys Gly Glu Leu Ala Asn
                530                 535                 540

Leu Ile Asn Ala Ile Asn Asn Glu Ser Ile Pro Met Ile Glu Asn
545                 550                 555                 560

Pro Arg Gly Phe Lys Gly Gln Leu Arg Pro Tyr Gln Arg Gly Val
                565                 570                 575

Gly Trp Leu Ser Phe Leu Glu Lys Trp Gly Leu Gly Ala Cys Leu Ala
                580                 585                 590

Asp Asp Met Gly Leu Gly Lys Thr Pro Gln Leu Ile Gly Phe Leu Leu
                595                 600                 605

His Leu Arg Ser Glu Gly Met Leu Asp Gln Pro Thr Leu Val Ile Cys
                610                 615                 620

Pro Thr Ser Val Leu Asn Asn Trp Glu Arg Glu Val Gln Lys Phe Ala
625                 630                 635                 640

Pro Thr Leu Ser Thr Leu Ile His His Gly Asp Lys Arg Ser Lys Gly
                645                 650                 655

Lys Ala Phe Val Lys Ala Val Ser Lys Asn Val Ile Ile Thr Ser
                660                 665                 670

Tyr Ser Leu Ile Tyr Arg Asp Ile Lys Ser Phe Glu Gln Val Glu Trp
                675                 680                 685

Gln Gly Ile Val Leu Asp Glu Ala Gln Asn Ile Lys Asn Pro Gln Ala
                690                 695                 700

Lys Gln Ser Gln Ala Val Arg Gln Ile Ser Thr Gln Phe Arg Ile Ala
705                 710                 715                 720

Leu Thr Gly Thr Pro Val Glu Asn Arg Leu Thr Glu Leu Trp Ser Ile
                725                 730                 735
```

-continued

```
Leu Asp Phe Leu Asn Pro Gly Phe Leu Gly Thr Gln Gln Phe Phe Arg
                740                 745                 750

Arg Arg Phe Ala Thr Pro Ile Glu Lys Tyr Gly Asp Lys Glu Ser Leu
                755                 760                 765

Gln Ile Met Arg Ser Leu Val Arg Pro Phe Ile Leu Arg Arg Leu Lys
        770                 775                 780

Thr Asp Lys Thr Ile Ile Gln Asp Leu Pro Glu Lys Gln Glu Met Thr
785                 790                 795                 800

Ile Phe Cys Gly Leu Ser Ser Glu Gln Gly Lys Leu Tyr Gln Gln Leu
                805                 810                 815

Val Asp Asn Ser Leu Val Ala Ile Glu Glu Lys Thr Gly Ile Glu Arg
                820                 825                 830

Lys Gly Leu Ile Leu Ser Leu Leu Leu Lys Leu Lys Gln Ile Cys Asn
            835                 840                 845

His Pro Ala His Phe Leu Lys Gln Lys Ser Leu Lys Thr Ala Glu Gln
        850                 855                 860

Ser Gly Lys Leu Leu Arg Leu Glu Glu Met Leu Glu Glu Leu Ile Glu
865                 870                 875                 880

Glu Gly Asp His Ala Leu Ile Phe Thr Gln Phe Ser Glu Trp Gly Lys
                885                 890                 895

Leu Leu Gln Pro Tyr Leu Gln Lys Lys Phe Gln Gln Asp Val Leu Phe
                900                 905                 910

Leu Tyr Gly Ala Thr Arg Arg Val Gln Arg Gln Glu Met Ile Asp Arg
            915                 920                 925

Phe Gln Gln Asp Pro Asn Gly Pro Arg Ile Phe Ile Leu Ser Leu Lys
        930                 935                 940

Ala Gly Gly Thr Gly Leu Asn Leu Thr Arg Ala Asn His Val Phe His
945                 950                 955                 960

Ile Asp Arg Trp Trp Asn Pro Ala Val Glu Asn Gln Ala Thr Asp Arg
                965                 970                 975

Ala Phe Arg Leu Gly Gln Lys Arg Asn Val Gln Val His Lys Phe Val
                980                 985                 990

Cys Thr Gly Thr Leu Glu Glu Lys Ile Asn Glu Met Leu Glu Ser Lys
            995                 1000                1005

Gln Lys Leu Ala Glu Gln Thr Val Asp Ala Gly Glu Gln Trp Leu
    1010                1015                1020

Thr Glu Leu Asp Thr Asp Gln Leu Arg Asn Leu Leu Leu Leu Asp
    1025                1030                1035

Arg Asp Thr Ile Ile Asp Glu Gln
    1040                1045

<210> SEQ ID NO 39
<211> LENGTH: 3027
<212> TYPE: DNA
<213> ORGANISM: Gloeobacter violaceus

<400> SEQUENCE: 39
atggctatct tgcacggtat ctgggttcac caacccccc gggccgggct tttcctttgg      60
ggagaaacct ggaggcaggt cgcaaagcgg cgcaagcgct ccgaagcacc cgctccgcat     120
ccctatgtcc agcaaccggc cgagttgtcc ccccgcctgg ctgcccagtt tccccagata     180
ccgctcagct tgctggtacc cgagacgctt gcactccagt tgcccgccac ggtcgaaaac     240
gtggtctact ccgcaagcat tgctcccgag ggcaagcttt tggagttgga accgtggctg     300
gtggaaggtt tctggctcga cggtcaccag gcttttgaac tgttgctcgg ggtaccctg      360
```

```
ggcggcgggg acgcatcgat tggcgacgac ctgcgcttct ggtcgcagtg cgcccgctgg    420
gtgcttgact tgctggtgcg cgccaagtac ctgcccgacc tggagagcgg cgacggccag    480
gaaatcccca cagcccgctg ggtgcccctg ctcgacagcg ccgtcgatca agcccgcctc    540
aaagaatttg ccgcccgttt gccgggcgcc tgccgcgccg ctaccccga  actatctccg    600
caccagattc tcaagagttt cctgagcgcc atgctcgacg cgcgggtgcg cacgctgctc    660
gcttgcgagc ctcccgatcc gcgcacgctg cctgccggag cggtgcgccc ctggcttctg    720
gccctggccc atgcccagcc ccagctcaaa tctccggacc cggagacgcc ggctctggcg    780
gaagccctgg ccacctggcg cgcccccctg agctatcagg ttcgctcgcg cacctgcttc    840
cgtctgcagc cgcccgagga gagccagggc gagtggaagc tgcactttct attgcaaaca    900
ggcgacgatc ccgattcgct gatggctgcc cagcaagtct ggagcagcgc gggtgagctg    960
caggaggtgt ttctcgcggg cttgggcctc gcctcgcgta tctttgtgcc cgtcgagcgg   1020
ggattgctcg tcccccagcc cacctgctgc accatgagca ccgtcgaggc gtttcagttt   1080
ctcaaagccg ccacctggcg gttgcgcgac agcggcttcg gggtgttgtt gcccgagagc   1140
ctcgcggacg cgggcagcct gcgcaaccgc ctgggcctca aactcgaagc gaacgcgccg   1200
gggcgcaacg gttcgggcct cggcatgcag agcttgctcg cttttaaatg ggagctgtcg   1260
ctcgcgggca agaccctgag ccgcgccgag ttcgaccgcc tcgccgctag ttctgaaccc   1320
ctggtcaaag tcaacgacaa ctgggtcgaa ttgcgccccc aggacgtgcg cgccgcccac   1380
agcttttgc  agtcgcgcaa agatcaggtc ggactctcgt tggaggatgt gctgcgcctc   1440
aacttcggcg acaccccaa  aatcgacggt ctccccatcg tcaacttcga cagctccggc   1500
cccattcagc aactgctgga gaccctcacc gatcagcgca aactcacccc catcgacgaa   1560
ccgccggggt tcaagggcac cctgcggccc tatcaaaaaa ttggcgtcgg ctggctcgcc   1620
ttttgcaga  agtgggggcct gggtgcttgc ctagccgacg acatgggact cgggaagacc   1680
gtagagttga tagcatttct tcttttttctc aaatccaaaa atgagctgga cggccctata   1740
ttgttaattt gtccgacttc agtgatggga aactgggaaa gagaaataaa gaaattttct   1800
cctagtttat ctgtacatgt ccatcatggg gcgcggcggc cgaaggggcg caattttgtc   1860
gagacggccc agaaaaagca aatcatcgtc agcagctacg ccctggtaca gcgcgacagc   1920
aaagatctca agcgcgtcga atggttgggc ctggtgctcg acgaagccca gaacatcaaa   1980
aaccccgacg ccaagcagac ccagtcgatt cgggaactga cagcgcgctt tcgcatcgcc   2040
ctcaccggca caccggtcga gaatcgcctc gcggaactgt ggtcgatcct cgatttttctc   2100
aatcccggct atctgggggc gcgcaacttc tttcagcgcc gcttcgcagt tccgatcgaa   2160
aagtacgggg atcgctcctc ggcgaacgcc ctcaaagctc tggtgcagcc gtttatcctg   2220
cggcggctca atccgaccc  gcagattatt caagatctgc ccgagaagca ggagacgaat   2280
gtcttctgtc cgctcacacc cgagcaggcg ccctctacg  agcgggtggt gaacgaatcg   2340
ctcgccaaga tcgagcagag caccggcatc cagcggcgcg ggacggtgct ggccaccttg   2400
gtcaaactca agcagatctg caaccacccg agccactacc tgggtgacga cggaccgctc   2460
gccaaccgct cgggcaaact cagccgcctg ggcgagatgc tcgaagaagt gctcgccgac   2520
gaggagcggg cgctgatttt tacccagttc gccgagtggg gccacctgct gcaggcgcac   2580
ctgagccgcc agttgggttc agaagtgttt ttcctctacg gcggcaccag caaaaaccag   2640
cgcgaggcga tgatcgagcg cttcagagc  gatccgcagg ggccgcggat ttttattctt   2700
tcgctgaagg cagggggtgt cggcctcaac ctcacccgcg ccaaccacgt cttccacttc   2760
```

```
gaccgctggt ggaacccggc ggtcgagaat caggccaccg accgcgtctt ccgcatcggc    2820
caaaccaaga acgtacaagt ctacaagtac gtgtgcaccg gcacgctcga agagcgcatc    2880
aacgccctga tcgaaagcaa aaaggccctg gctgagcagg tggtgagcgc cggtgagaac    2940
tggctgtcgg atctaaatac cgatcaactg cggcaactgt tggtactcga tcgctcggag    3000
attatcgaca cggaggacac cgcgtga                                        3027
```

<210> SEQ ID NO 40
<211> LENGTH: 1008
<212> TYPE: PRT
<213> ORGANISM: Gloeobacter violaceus

<400> SEQUENCE: 40

```
Met Ala Ile Leu His Gly Ile Trp Val His Gln Pro Pro Arg Ala Gly
1               5                   10                  15

Leu Phe Leu Trp Gly Glu Thr Trp Arg Gln Val Ala Lys Arg Arg Lys
            20                  25                  30

Arg Ser Glu Ala Pro Ala Pro His Pro Tyr Val Gln Gln Pro Ala Glu
        35                  40                  45

Leu Ser Pro Arg Leu Ala Ala Gln Phe Pro Gln Ile Pro Leu Ser Leu
    50                  55                  60

Leu Val Pro Glu Thr Leu Ala Leu Gln Leu Pro Ala Thr Val Glu Asn
65                  70                  75                  80

Val Val Tyr Ser Ala Ser Ile Ala Pro Glu Gly Lys Leu Leu Glu Leu
                85                  90                  95

Glu Pro Trp Leu Val Gly Phe Trp Leu Asp Gly His Gln Ala Phe
            100                 105                 110

Glu Leu Leu Leu Gly Val Pro Leu Gly Gly Gly Asp Ala Ser Ile Gly
        115                 120                 125

Asp Asp Leu Arg Phe Trp Ser Gln Cys Ala Arg Trp Val Leu Asp Leu
    130                 135                 140

Leu Val Arg Ala Lys Tyr Leu Pro Asp Leu Glu Ser Gly Asp Gly Gln
145                 150                 155                 160

Glu Ile Pro Thr Ala Arg Trp Val Pro Leu Leu Asp Ser Ala Val Asp
                165                 170                 175

Gln Ala Arg Leu Lys Glu Phe Ala Ala Arg Leu Pro Gly Ala Cys Arg
            180                 185                 190

Ala Ala Thr Pro Glu Leu Ser Pro His Gln Ile Leu Lys Ser Phe Leu
        195                 200                 205

Ser Ala Met Leu Asp Ala Arg Val Arg Thr Leu Leu Ala Cys Glu Pro
    210                 215                 220

Pro Asp Pro Arg Thr Leu Pro Ala Gly Ala Val Arg Pro Trp Leu Leu
225                 230                 235                 240

Ala Leu Ala His Ala Gln Pro Gln Leu Lys Ser Pro Asp Pro Glu Thr
                245                 250                 255

Pro Ala Leu Ala Glu Ala Leu Ala Thr Trp Arg Ala Pro Leu Ser Tyr
            260                 265                 270

Gln Val Arg Ser Arg Thr Cys Phe Arg Leu Gln Pro Pro Glu Glu Ser
        275                 280                 285

Gln Gly Glu Trp Lys Leu His Phe Leu Leu Gln Thr Gly Asp Asp Pro
    290                 295                 300

Asp Ser Leu Met Ala Ala Gln Gln Val Trp Ser Ser Ala Gly Glu Leu
305                 310                 315                 320

Gln Glu Val Phe Leu Ala Gly Leu Gly Leu Ala Ser Arg Ile Phe Val
                325                 330                 335
```

```
Pro Val Glu Arg Gly Leu Leu Val Pro Gln Pro Thr Cys Cys Thr Met
            340                 345                 350

Ser Thr Val Glu Ala Phe Gln Phe Leu Lys Ala Ala Thr Trp Arg Leu
            355                 360                 365

Arg Asp Ser Gly Phe Gly Val Leu Leu Pro Glu Ser Leu Ala Asp Ala
            370                 375                 380

Gly Ser Leu Arg Asn Arg Leu Gly Leu Lys Leu Glu Ala Asn Ala Pro
385                 390                 395                 400

Gly Arg Asn Gly Ser Gly Leu Gly Met Gln Ser Leu Leu Ala Phe Lys
            405                 410                 415

Trp Glu Leu Ser Leu Ala Gly Lys Thr Leu Ser Arg Ala Glu Phe Asp
            420                 425                 430

Arg Leu Ala Ala Ser Ser Glu Pro Leu Val Lys Val Asn Asp Asn Trp
            435                 440                 445

Val Glu Leu Arg Pro Gln Asp Val Arg Ala Ala His Ser Phe Leu Gln
            450                 455                 460

Ser Arg Lys Asp Gln Val Gly Leu Ser Leu Glu Asp Val Leu Arg Leu
465                 470                 475                 480

Asn Phe Gly Asp Thr Pro Lys Ile Asp Gly Leu Pro Ile Val Asn Phe
            485                 490                 495

Asp Ser Ser Gly Pro Ile Gln Gln Leu Leu Glu Thr Leu Thr Asp Gln
            500                 505                 510

Arg Lys Leu Thr Pro Ile Asp Glu Pro Pro Gly Phe Lys Gly Thr Leu
            515                 520                 525

Arg Pro Tyr Gln Lys Ile Gly Val Gly Trp Leu Ala Phe Leu Gln Lys
            530                 535                 540

Trp Gly Leu Gly Ala Cys Leu Ala Asp Asp Met Gly Leu Gly Lys Thr
545                 550                 555                 560

Val Glu Leu Ile Ala Phe Leu Leu Phe Leu Lys Ser Lys Asn Glu Leu
            565                 570                 575

Asp Gly Pro Ile Leu Leu Ile Cys Pro Thr Ser Val Met Gly Asn Trp
            580                 585                 590

Glu Arg Glu Ile Lys Lys Phe Ser Pro Ser Leu Ser Val His Val His
            595                 600                 605

His Gly Ala Arg Arg Pro Lys Gly Arg Asn Phe Val Glu Thr Ala Gln
            610                 615                 620

Lys Lys Gln Ile Ile Val Ser Ser Tyr Ala Leu Val Gln Arg Asp Ser
625                 630                 635                 640

Lys Asp Leu Lys Arg Val Glu Trp Leu Gly Leu Val Leu Asp Glu Ala
            645                 650                 655

Gln Asn Ile Lys Asn Pro Asp Ala Lys Gln Thr Gln Ser Ile Arg Glu
            660                 665                 670

Leu Thr Ala Arg Phe Arg Ile Ala Leu Thr Gly Thr Pro Val Glu Asn
            675                 680                 685

Arg Leu Ala Glu Leu Trp Ser Ile Leu Asp Phe Leu Asn Pro Gly Tyr
            690                 695                 700

Leu Gly Ala Arg Asn Phe Phe Gln Arg Arg Phe Ala Val Pro Ile Glu
705                 710                 715                 720

Lys Tyr Gly Asp Arg Ser Ser Ala Asn Ala Leu Lys Ala Leu Val Gln
            725                 730                 735

Pro Phe Ile Leu Arg Arg Leu Lys Ser Asp Pro Gln Ile Ile Gln Asp
            740                 745                 750

Leu Pro Glu Lys Gln Glu Thr Asn Val Phe Cys Pro Leu Thr Pro Glu
```

```
                    755              760              765
Gln Ala Ala Leu Tyr Glu Arg Val Val Asn Glu Ser Leu Ala Lys Ile
        770              775              780
Glu Gln Ser Thr Gly Ile Gln Arg Arg Gly Thr Val Leu Ala Thr Leu
785              790              795              800
Val Lys Leu Lys Gln Ile Cys Asn His Pro Ser His Tyr Leu Gly Asp
            805              810              815
Asp Gly Pro Leu Ala Asn Arg Ser Gly Lys Leu Ser Arg Leu Gly Glu
        820              825              830
Met Leu Glu Glu Val Leu Ala Asp Glu Glu Arg Ala Leu Ile Phe Thr
    835              840              845
Gln Phe Ala Glu Trp Gly His Leu Leu Gln Ala His Leu Ser Arg Gln
    850              855              860
Leu Gly Ser Glu Val Phe Phe Leu Tyr Gly Gly Thr Ser Lys Asn Gln
865              870              875              880
Arg Glu Ala Met Ile Glu Arg Phe Gln Ser Asp Pro Gln Gly Pro Arg
            885              890              895
Ile Phe Ile Leu Ser Leu Lys Ala Gly Gly Val Gly Leu Asn Leu Thr
            900              905              910
Arg Ala Asn His Val Phe His Phe Asp Arg Trp Trp Asn Pro Ala Val
        915              920              925
Glu Asn Gln Ala Thr Asp Arg Val Phe Arg Ile Gly Gln Thr Lys Asn
    930              935              940
Val Gln Val Tyr Lys Tyr Val Cys Thr Gly Thr Leu Glu Glu Arg Ile
945              950              955              960
Asn Ala Leu Ile Glu Ser Lys Lys Ala Leu Ala Glu Gln Val Val Ser
            965              970              975
Ala Gly Glu Asn Trp Leu Ser Asp Leu Asn Thr Asp Gln Leu Arg Gln
        980              985              990
Leu Leu Val Leu Asp Arg Ser Glu Ile Ile Asp Thr Glu Asp Thr Ala
        995              1000             1005

<210> SEQ ID NO 41
<211> LENGTH: 3186
<212> TYPE: DNA
<213> ORGANISM: Lyngbya sp.

<400> SEQUENCE: 41
atggcaattt tacacggaag ttggctccag caccccaaaa attatttgtt tatttgggga      60
gaaacctggc gtcgcattac acccaatgaa tttaatccgg ctgatggtgt tttgggttat     120
ccttttgctt taagccctgt tgaattggaa aagtggtgca gtgaaaagca gttatctata     180
gagagtaaag ttgtcgttac agaaactctc gcccttccca ctaaactctc cccaaaaata     240
ggactatatc cccttcaatc tacgcctcaa actgattctg aaactgattc tgagtcgatc     300
tgtctttatc cctggaaaat tgaaggtatt tgtctcaaca gtacagaagc ctttgacttt     360
ttacaatccc ttcctctggg aaacctgacc acagaaaact catttattgg ctcagattta     420
cagttttggt ctcatctttc ccgttggagt ttagacttac tcgcccggag taaattttta     480
cccagtctca cttttaaccc ctcaaaagat cactttatcg ctgaatggaa acctttactc     540
gatagtgcga cagatcaagc cagattaatt cgttttccta acaaatacc ctctgcttgt     600 cggatctatc aactctggtc aaaagaggct caaatcaat ttgaaaattt agccctagat     660
ttacctcaaa atccccaaaa cttaattgat gatttttaa cggcaattat tgatagtcaa     720
gtcaagaaag ttgcagaaga aagtgaaaaa aaagcgatta caaatctaac cgctattcaa     780
```

```
ccgattgttc agagttggtt acacgcttta gccagtgaat ctaatctagc aaaatccaaa    840
aaatctgaat caaaaaccct agaaaaaatt ctttccaatt ggacggctcc tcttcaacaa    900
actctcgctg aacataattt gtttagaacg ggatttcgac tctctcctcc ggaaaataat    960
caaaaaaatt ggacgctaga ttattgttta caagcaattg atgaacccga atttttagtg   1020
gatgctcaaa ctatttggac tcatccagtc gaagcctttg ttcacaatgg acgtatgatt   1080
aaacgtcctc aagaaacccct cctcaaaggt ttaggtttag cctcaaaact atatcctctc   1140
ctagaaccca gtttacaaga agcccgtcct caaacttgct tattaacgcc cctacaagcc   1200
tatgaattta ttaaaagtat taattggcgg tttacagata gcggtttagg agtgattta     1260
cccccgagtt tagtcagtca aaatggatgg gcgaaccgtt taggtttaag tgttcaagcg   1320
gcgacatcaa atccaaaca aaatgttagc ttgggattag atagtctgct gaattttaaa    1380
tgggaattgt caattggggg tcaaacctta tcaaaaacag aatttaaccg tttagtcgct   1440
caagaaagtc cgttagttga aattaatggc gaatgggtgg aattacgtcc tactgatatt   1500
aaagccgcta aagccttctt ttcgagtcgc aaagatcaac tttcacttac ccttgaagat   1560
gctttacgtt tatcgacggg tgactcgcaa atggtgaaaa agttaccgat tgttaacttt    1620
gaagcgggtg gaaaattaga agaacttctc aatactttaa cgaataaccg ttcgctcgat   1680
gagatcaaaa ctcctagtaa ttttcaagga gaactacgcc cctatcaagc ccgaggggtg   1740
agttggttag ccttttttaga agaatgggggt ttaggggctt gtttagctga tgatatgggg   1800
ctaggaaaaaa ccatagaatt aattgctttt ctcttgtatt tgcaggaaaa agaaaccttca   1860
gacgctcctg ttttactggt ttgtccgaca tcagttttag gaaactggga acgagaagtt   1920
aaacgattta gtccgagttt aaaagttact gttcatcacg gggataaacg ccagaaaggg   1980
aaaaactttg ctcaatttgc ccagaaatat aatttaatta ttaccagtta tccgttaact   2040
tttcgagatg agaagaact caaaacggta aattggaaag gattagtttt agacgaagct    2100
caaaatatta aaaatcccga ggctaaacaa tcaaaaacgg tgagaaatct acaggcgagt   2160
tttaaaattg ctctgactgg aacacctgtc gaaaaccgtc tgtctgaatt atggtcaatt   2220
atggattttc tcaacccagg ttatttagga cagcgacaat ttttttcagcg aagatttgct   2280
attccgattg aaaaatacgg cgatacagac tccttaaaaa cattgcgatc tttggttcaa   2340
ccgtttattt tacggcgctt aaaaacagat agagagatta tccaagactt acccgaaaaa   2400
caggaaaata cgatctttt gttctctgtct acagaacaag caacgcttta tcaaaagatt   2460
gttgatcagt ctttagctga catagactca gccgcaggaa ttcaacgtcg agggatgatt   2520
ttagcgttgt tagtgaaatt aaaacaggtt tgtaatcatc ccattttatt gaatggaaaa   2580
gcgacaaaaa ctggaaagaa aaaggtcgag actcagggtt taagcctgca aagttcaggg   2640
aagttacaac gcttcaaaga aatgctggaa gaattgttgt cagaaggaga tcgcgccatt   2700
gtatttaccc agtttgcaga atggggaaaa gttttacaac cttatttaga acagcaatta   2760
aaccgagagg tattatttttt gtatggcgca actcgtaaaa ataaacgaga agaaatgatt   2820
gatcgttttc aacaagatcc tcaagggcca ccgatttta ttctatcttt aaaagcggga    2880
ggtgtgggtt taaatttgac tcgtgctaat catgttttttc actttgatcg ttggtggaac   2940
cctgcggttg aaaatcaagc aacagatcgg gtgtttagaa ttggtcaaac gcgcaatgtt   3000
caggttcata gtttgtctg taccggaacg ttggaagaaa aaatccatga tttaattgaa   3060
agtaaaaaag tgtggctga acaagttgtg ggttcaggag aaaattggtt aactgaattg    3120
gatacggatc aactcagaaa cttactcatt attgaccgaa atgcggtgat tgatgaagaa   3180
``` gaataa 3186

<210> SEQ ID NO 42
<211> LENGTH: 1061
<212> TYPE: PRT
<213> ORGANISM: Lyngbya sp.

<400> SEQUENCE: 42

```
Met Ala Ile Leu His Gly Ser Trp Leu Gln His Pro Lys Asn Tyr Leu
1               5                   10                  15

Phe Ile Trp Gly Glu Thr Trp Arg Arg Ile Thr Pro Asn Glu Phe Asn
            20                  25                  30

Pro Ala Asp Gly Val Leu Gly Tyr Pro Phe Ala Leu Ser Pro Val Glu
        35                  40                  45

Leu Glu Lys Trp Cys Ser Glu Lys Gln Leu Ser Ile Glu Ser Lys Val
    50                  55                  60

Val Val Thr Glu Thr Leu Ala Leu Pro Thr Lys Leu Ser Pro Lys Ile
65                  70                  75                  80

Gly Leu Tyr Pro Leu Gln Ser Thr Pro Gln Thr Asp Ser Glu Thr Asp
                85                  90                  95

Ser Glu Ser Ile Cys Leu Tyr Pro Trp Lys Ile Glu Gly Ile Cys Leu
            100                 105                 110

Asn Ser Thr Glu Ala Phe Asp Phe Leu Gln Ser Leu Pro Leu Gly Asn
        115                 120                 125

Leu Thr Thr Glu Asn Ser Phe Ile Gly Ser Asp Leu Gln Phe Trp Ser
    130                 135                 140

His Leu Ser Arg Trp Ser Leu Asp Leu Leu Ala Arg Ser Lys Phe Leu
145                 150                 155                 160

Pro Ser Leu Thr Phe Asn Pro Ser Lys Asp His Phe Ile Ala Glu Trp
                165                 170                 175

Lys Pro Leu Leu Asp Ser Ala Thr Asp Gln Ala Arg Leu Ile Arg Phe
            180                 185                 190

Ser Lys Gln Ile Pro Ser Ala Cys Arg Ile Tyr Gln Leu Trp Ser Lys
        195                 200                 205

Glu Ala Gln Asn Gln Phe Glu Asn Leu Ala Leu Asp Leu Pro Gln Asn
    210                 215                 220

Pro Gln Asn Leu Ile Asp Asp Phe Leu Thr Ala Ile Ile Asp Ser Gln
225                 230                 235                 240

Val Lys Lys Val Ala Glu Glu Ser Glu Lys Lys Ala Ile Thr Asn Leu
                245                 250                 255

Thr Ala Ile Gln Pro Ile Val Gln Ser Trp Leu His Ala Leu Ala Ser
            260                 265                 270

Glu Ser Asn Leu Ala Lys Ser Lys Lys Ser Glu Ser Lys Thr Leu Glu
        275                 280                 285

Lys Ile Leu Ser Asn Trp Thr Ala Pro Leu Gln Gln Thr Leu Ala Glu
    290                 295                 300

His Asn Leu Phe Arg Thr Gly Phe Arg Leu Ser Pro Pro Glu Asn Asn
305                 310                 315                 320

Gln Lys Asn Trp Thr Leu Asp Tyr Cys Leu Gln Ala Ile Asp Glu Pro
                325                 330                 335

Glu Phe Leu Val Asp Ala Gln Thr Ile Trp Thr His Pro Val Glu Ala
            340                 345                 350

Phe Val His Asn Gly Arg Met Ile Lys Arg Pro Gln Glu Thr Leu Leu
        355                 360                 365
```

-continued

```
Lys Gly Leu Gly Leu Ala Ser Lys Leu Tyr Pro Leu Leu Glu Pro Ser
    370                 375                 380
Leu Gln Glu Ala Arg Pro Gln Thr Cys Leu Leu Thr Pro Leu Gln Ala
385                 390                 395                 400
Tyr Glu Phe Ile Lys Ser Ile Asn Trp Arg Phe Thr Asp Ser Gly Leu
                405                 410                 415
Gly Val Ile Leu Pro Pro Ser Leu Val Ser Gln Asn Gly Trp Ala Asn
            420                 425                 430
Arg Leu Gly Leu Ser Val Gln Ala Ala Thr Ser Lys Ser Lys Gln Asn
        435                 440                 445
Val Ser Leu Gly Leu Asp Ser Leu Leu Asn Phe Lys Trp Glu Leu Ser
    450                 455                 460
Ile Gly Gly Gln Thr Leu Ser Lys Thr Glu Phe Asn Arg Leu Val Ala
465                 470                 475                 480
Gln Glu Ser Pro Leu Val Glu Ile Asn Gly Glu Trp Val Glu Leu Arg
                485                 490                 495
Pro Thr Asp Ile Lys Ala Ala Lys Ala Phe Phe Ser Ser Arg Lys Asp
            500                 505                 510
Gln Leu Ser Leu Thr Leu Glu Asp Ala Leu Arg Leu Ser Thr Gly Asp
        515                 520                 525
Ser Gln Met Val Glu Lys Leu Pro Ile Val Asn Phe Glu Ala Gly Gly
    530                 535                 540
Lys Leu Glu Glu Leu Leu Asn Thr Leu Thr Asn Asn Arg Ser Leu Asp
545                 550                 555                 560
Glu Ile Lys Thr Pro Ser Asn Phe Gln Gly Glu Leu Arg Pro Tyr Gln
                565                 570                 575
Ala Arg Gly Val Ser Trp Leu Ala Phe Leu Glu Glu Trp Gly Leu Gly
            580                 585                 590
Ala Cys Leu Ala Asp Asp Met Gly Leu Gly Lys Thr Ile Glu Leu Ile
        595                 600                 605
Ala Phe Leu Leu Tyr Leu Gln Glu Lys Glu Thr Leu Asp Ala Pro Val
    610                 615                 620
Leu Leu Val Cys Pro Thr Ser Val Leu Gly Asn Trp Glu Arg Glu Val
625                 630                 635                 640
Lys Arg Phe Ser Pro Ser Leu Lys Val Thr Val His Gly Asp Lys
                645                 650                 655
Arg Gln Lys Gly Lys Asn Phe Ala Gln Phe Ala Gln Lys Tyr Asn Leu
            660                 665                 670
Ile Ile Thr Ser Tyr Pro Leu Thr Phe Arg Asp Glu Lys Glu Leu Lys
        675                 680                 685
Thr Val Asn Trp Lys Gly Leu Val Leu Asp Glu Ala Gln Asn Ile Lys
    690                 695                 700
Asn Pro Glu Ala Lys Gln Ser Lys Thr Val Arg Asn Leu Gln Ala Ser
705                 710                 715                 720
Phe Lys Ile Ala Leu Thr Gly Thr Pro Val Glu Asn Arg Leu Ser Glu
                725                 730                 735
Leu Trp Ser Ile Met Asp Phe Leu Asn Pro Gly Tyr Leu Gly Gln Arg
            740                 745                 750
Gln Phe Phe Gln Arg Arg Phe Ala Ile Pro Ile Glu Lys Tyr Gly Asp
        755                 760                 765
Thr Asp Ser Leu Lys Thr Leu Arg Ser Leu Val Gln Pro Phe Ile Leu
    770                 775                 780
Arg Arg Leu Lys Thr Asp Arg Glu Ile Ile Gln Asp Leu Pro Glu Lys
785                 790                 795                 800
```

```
Gln Glu Asn Thr Ile Phe Cys Ser Leu Ser Thr Glu Gln Ala Thr Leu
                805                 810                 815

Tyr Gln Lys Ile Val Asp Gln Ser Leu Ala Asp Ile Asp Ser Ala Ala
            820                 825                 830

Gly Ile Gln Arg Arg Gly Met Ile Leu Ala Leu Leu Val Lys Leu Lys
        835                 840                 845

Gln Val Cys Asn His Pro Ile Leu Leu Asn Gly Lys Ala Thr Lys Thr
    850                 855                 860

Gly Lys Lys Lys Val Glu Thr Gln Gly Leu Ser Leu Gln Ser Ser Gly
865                 870                 875                 880

Lys Leu Gln Arg Phe Lys Glu Met Leu Glu Glu Leu Leu Ser Glu Gly
            885                 890                 895

Asp Arg Ala Ile Val Phe Thr Gln Phe Ala Glu Trp Gly Lys Val Leu
        900                 905                 910

Gln Pro Tyr Leu Glu Gln Gln Leu Asn Arg Glu Val Leu Phe Leu Tyr
    915                 920                 925

Gly Ala Thr Arg Lys Asn Lys Arg Glu Glu Met Ile Asp Arg Phe Gln
930                 935                 940

Gln Asp Pro Gln Gly Pro Pro Ile Phe Ile Leu Ser Leu Lys Ala Gly
945                 950                 955                 960

Gly Val Gly Leu Asn Leu Thr Arg Ala Asn His Val Phe His Phe Asp
            965                 970                 975

Arg Trp Trp Asn Pro Ala Val Glu Asn Gln Ala Thr Asp Arg Val Phe
        980                 985                 990

Arg Ile Gly Gln Thr Arg Asn Val Gln Val His Lys Phe Val Cys Thr
    995                1000                1005

Gly Thr Leu Glu Glu Lys Ile His Asp Leu Ile Glu Ser Lys Lys
   1010                1015                1020

Val Leu Ala Glu Gln Val Val Gly Ser Gly Glu Asn Trp Leu Thr
   1025                1030                1035

Glu Leu Asp Thr Asp Gln Leu Arg Asn Leu Leu Ile Ile Asp Arg
   1040                1045                1050

Asn Ala Val Ile Asp Glu Glu Glu
   1055                1060

<210> SEQ ID NO 43
<211> LENGTH: 3237
<212> TYPE: DNA
<213> ORGANISM: Methanosarcina acetivorans

<400> SEQUENCE: 43
atgataattt tgcatgcagg aagagtcgga aaacagttct ttctgtgggg cgaaagcccg      60
gctgaaaatg aaactccgcc tgtccggcgc gggagaaagc ctaagaagcc ggttgcaaaa     120
ccttatcctt acgattcggg tgttgaaaac ctgtcttctg ctcttgagct gctgctgggc     180
agtactggcc ggaaaaaggc agaggaaatc aatgtctgga tcccgacagc aggctggaat     240
ccaatccccc tccagtcctct cgttgctgaa attccggctt cgaaagcaga actttcccta     300
gctccctgga ctgttcacgc atatcctctg gaagctgaag aagctattgt tctcctctgc     360
gcctgtatgg gaaaaaaggt tcttgctccc ggcataatct cgggaaatga tcttctctgg     420
tgggcggatg ccctgaaatt tgcaggctcg ctggtagcag acagaaaata cctgcctggc     480
gtcaggggcg gggaaggaga gtacaaggct ttcgggaaac ccgtatttc cggagaagat     540 gcggggggagc tggcaagact tgcaaagcaa atgcctccgg ctgcaaaggc tcttgctctt     600
```

```
gaaacctctt ccgtgcagcc ggaaatactt gctgctgtag cggcaaggca gtttatcgaa    660
gaggctcttg actggatagt ccggtccgag atcggggaaa aagagcttgc aaaagaggcg    720
cgtaaaagaa aatcctttga tagcgtccat gacgcctggg tttccgctct aaaagccct     780 gacgggttga tccacggaga agaaaaagaa ctcctgcagc ttgcgttccg gacccgtgaa    840
tggcagcgcc cccttactgt acttacaact tctcccttca ggttctgttt ccggcttgaa    900
gagccagctg cggaagaaga actcgaagaa accgaggaat ccgaagccgg aaaaatggat    960
actaaaaaag gcaggaaagg gatagctgac atagaagttc ccgaagaact ctggtacgtc   1020
cgctatatgc ttcagtccta cgaagaccca agccttctga ttcctgtaaa agaggcctgg   1080
aaaccaaaga agggcagccc gttgaaaaga tatgatgtaa aaaacattcg ccaatttctg   1140
ttatcttccc ttggacaggc tgctggcatc agtgcaggaa ttgcttccag ccttgaagct   1200
cccaacccgt ccggatattc ccttgatacg aaagaagctt accgcttcct gactgaaagt   1260
gcagcggatt taagccaggc gggcttcggg ttacttctcc ccggctggtg acccgtaaa    1320 ggtacaaaga cccacttaaa agcccaggct aatgttaagg gcaagaagtt gaaggccgga   1380
tacgggctta cactcgataa aatcgtcagc tttgactggg aaattgccct tggagaccgt   1440
gcactcacag tcagggaact gcaggctctt gcaaagctca agctccgct tgtgaaattc     1500 cgcgggcagt gggtcgaggt caacgatgcg gaaatccggg ctgcccttga gttctggaag   1560
aaaaaccccc acggggaagc aagtctgcgc gaagttctaa aactggctgt gggagtctcc   1620 gaaaagccg atggtgtaga cgttgaaggg cttaatgcag ccggctggat cgaagaatta     1680
atccgccgcc tgaaggacaa aaccgggttt gaagaacttc cggctcctga cggttttca    1740 ggcacccctca ggccctacca gttcagaggt tactcctggc tggctttcct gaggcagtgg   1800
ggcataggag cctgccttgc agacgacatg gggcttggta aaaccatcca gacccttgcc   1860
cttatccagc acgacctgga acaggttaaa gggcaggttg aagaaaaggt tatagaaaat   1920
gctgaagaaa aagttgaagg acttaaagct gcaaaaccgg ttcttctggt ctgtccgacc   1980
tctgtcatca caactggaaa aaagaggcg gctcgcttta ccccggaact ttcggtaatg   2040
gtccaccacg ggaccagccg gaaaaaggaa gaggaattca aaaaggaagc cacgaatcat   2100
tctattgtcg tctcaagcta cgggcttttg cagcgggatc ttaagttttt aaaaggggtt   2160
tcctgggccg gagtggtact tgacgaagcc cagaatatca aaaacccgga aaccaaacag   2220
gcaaaggcag ccagagctct tgaagccgat taccgcatag ctcttacggg gactccggtt   2280
gaaaacaacg tgggagacct ctggtctatc atggagtttt taaaccccgg cttcctaggc   2340
aaccaggcag gtttcaagcg gaatttcttt attcccattc aggccgaaag ggatcaggaa   2400
gctgcaagga ggttaaaaga aattacgggc cccttatcc tgcgccgtct gaagaccgat    2460
acttcgatta tctccgacct gccggaaaag atggaaatga aaacctattg tacgctgaca   2520
aaagaacagg cttccctcta tgccgcagtc ctcgaagaca tcgaagagac gatgaagagg   2580
gctgaagaag gcatccagag aaaaggtata atcctgtccg cccttaccag gctcaaacag   2640
gtctgcaacc atccggcgca gttttttgaag gataactctg ctgtacccgg caggtcagga   2700
aaacttgcaa ggcttaccga aatgctggat gtaatcctgg aaaatgggga aaaagccctt   2760
gtgttcaccc agtttgcgga gatgggaaaa atgctaaaag aacacctgca ggcaagtttt   2820
ggctgtgaag tccttttcct gcacggcggg gtccccagaa agcagaggga tcggatgctt   2880
gagcgtttcc aggagggaaa agaataccte cctatctttg tcctctccct taagctggaa   2940
ggcacggggc ttaaccttac aggagcgaac cacgtttttcc attttgaccg ctggtggaac   3000
```

-continued

```
cctgctgttg aaaaccaggc tacggacagg gctttccgta taggccagac gaaaaatgta    3060
gaggtgcata agttcatctg tgcgggtacg cttgaagaaa aaatcgatga gattatcgag    3120
cgcaaagtgc aggttgcaga aacgttgtc ggaacaggtg aaggttggct gacagaactt     3180
tccaacgagg aattgaagga tattcttgct ctccgagaag aagcggtagg tgaataa       3237
```

<210> SEQ ID NO 44
<211> LENGTH: 1078
<212> TYPE: PRT
<213> ORGANISM: Methanosarcina acetivorans

<400> SEQUENCE: 44

```
Met Ile Ile Leu His Ala Gly Arg Val Gly Lys Gln Phe Phe Leu Trp
1               5                   10                  15

Gly Glu Ser Pro Ala Glu Asn Glu Thr Pro Pro Val Arg Arg Gly Arg
            20                  25                  30

Lys Pro Lys Lys Pro Val Ala Lys Pro Tyr Pro Tyr Asp Ser Gly Val
        35                  40                  45

Glu Asn Leu Ser Ser Ala Leu Glu Leu Leu Gly Ser Thr Gly Arg
    50                  55                  60

Lys Lys Ala Glu Glu Ile Asn Val Trp Ile Pro Thr Ala Gly Trp Asn
65                  70                  75                  80

Pro Ile Pro Ser Ser Pro Leu Val Ala Glu Ile Pro Ala Ser Lys Ala
                85                  90                  95

Glu Leu Ser Leu Ala Pro Trp Thr Val His Ala Tyr Pro Leu Glu Ala
            100                 105                 110

Glu Glu Ala Ile Val Leu Leu Cys Ala Cys Met Gly Lys Lys Val Leu
        115                 120                 125

Ala Pro Gly Ile Ile Ser Gly Asn Asp Leu Leu Trp Trp Ala Asp Ala
    130                 135                 140

Leu Lys Phe Ala Gly Ser Leu Val Ala Gly Gln Lys Tyr Leu Pro Gly
145                 150                 155                 160

Val Arg Gly Gly Glu Gly Glu Tyr Lys Ala Phe Trp Glu Pro Val Phe
                165                 170                 175

Ser Gly Glu Asp Ala Gly Glu Leu Ala Arg Leu Ala Lys Gln Met Pro
            180                 185                 190

Pro Ala Ala Lys Ala Leu Ala Leu Glu Thr Ser Ser Val Gln Pro Glu
        195                 200                 205

Ile Leu Ala Ala Val Ala Ala Arg Gln Phe Ile Glu Glu Ala Leu Asp
    210                 215                 220

Trp Ile Val Arg Ser Glu Ile Gly Glu Lys Glu Leu Ala Lys Glu Ala
225                 230                 235                 240

Arg Lys Arg Lys Ser Phe Asp Ser Val His Asp Ala Trp Val Ser Ala
                245                 250                 255

Leu Lys Ser Pro Asp Gly Leu Ile His Gly Glu Glu Lys Glu Leu Leu
            260                 265                 270

Gln Leu Ala Phe Arg Thr Arg Glu Trp Gln Arg Pro Leu Thr Val Leu
        275                 280                 285

Thr Thr Ser Pro Phe Arg Phe Cys Phe Arg Leu Glu Glu Pro Ala Ala
    290                 295                 300

Glu Glu Glu Leu Glu Glu Thr Glu Glu Ser Glu Ala Gly Lys Met Asp
305                 310                 315                 320

Thr Lys Lys Gly Arg Lys Gly Ile Ala Asp Ile Glu Val Pro Glu Glu
                325                 330                 335

Leu Trp Tyr Val Arg Tyr Met Leu Gln Ser Tyr Glu Asp Pro Ser Leu
```

```
                340             345             350
Leu Ile Pro Val Lys Glu Ala Trp Lys Pro Lys Gly Ser Pro Leu
            355             360             365
Lys Arg Tyr Asp Val Lys Asn Ile Arg Gln Phe Leu Leu Ser Leu
            370             375             380
Gly Gln Ala Ala Gly Ile Ser Ala Gly Ile Ala Ser Ser Leu Glu Ala
385             390             395             400
Pro Asn Pro Ser Gly Tyr Ser Leu Asp Thr Lys Glu Ala Tyr Arg Phe
            405             410             415
Leu Thr Glu Ser Ala Ala Asp Leu Ser Gln Ala Gly Phe Gly Leu Leu
            420             425             430
Leu Pro Gly Trp Trp Thr Arg Lys Gly Thr Lys Thr His Leu Lys Ala
            435             440             445
Gln Ala Asn Val Lys Gly Lys Lys Leu Lys Ala Gly Tyr Gly Leu Thr
            450             455             460
Leu Asp Lys Ile Val Ser Phe Asp Trp Glu Ile Ala Leu Gly Asp Arg
465             470             475             480
Ala Leu Thr Val Arg Glu Leu Gln Ala Leu Ala Lys Leu Lys Ala Pro
            485             490             495
Leu Val Lys Phe Arg Gly Gln Trp Val Glu Val Asn Asp Ala Glu Ile
            500             505             510
Arg Ala Ala Leu Glu Phe Trp Lys Lys Asn Pro His Gly Glu Ala Ser
            515             520             525
Leu Arg Glu Val Leu Lys Leu Ala Val Gly Val Ser Glu Lys Ala Asp
            530             535             540
Gly Val Asp Val Glu Gly Leu Asn Ala Ala Gly Trp Ile Glu Glu Leu
545             550             555             560
Ile Arg Arg Leu Lys Asp Lys Thr Gly Phe Glu Leu Pro Ala Pro
            565             570             575
Asp Gly Phe Ser Gly Thr Leu Arg Pro Tyr Gln Phe Arg Gly Tyr Ser
            580             585             590
Trp Leu Ala Phe Leu Arg Gln Trp Gly Ile Gly Ala Cys Leu Ala Asp
            595             600             605
Asp Met Gly Leu Gly Lys Thr Ile Gln Thr Leu Ala Leu Ile Gln His
            610             615             620
Asp Leu Glu Gln Val Lys Gly Gln Val Glu Glu Lys Val Ile Glu Asn
625             630             635             640
Ala Glu Glu Lys Val Glu Gly Leu Lys Ala Ala Lys Pro Val Leu Leu
            645             650             655
Val Cys Pro Thr Ser Val Ile Asn Asn Trp Lys Lys Glu Ala Ala Arg
            660             665             670
Phe Thr Pro Glu Leu Ser Val Met Val His His Gly Thr Ser Arg Lys
            675             680             685
Lys Glu Glu Glu Phe Lys Lys Glu Ala Thr Asn His Ser Ile Val Val
            690             695             700
Ser Ser Tyr Gly Leu Leu Gln Arg Asp Leu Lys Phe Leu Lys Gly Val
705             710             715             720
Ser Trp Ala Gly Val Val Leu Asp Glu Ala Gln Asn Ile Lys Asn Pro
            725             730             735
Glu Thr Lys Gln Ala Lys Ala Ala Arg Ala Leu Glu Ala Asp Tyr Arg
            740             745             750
Ile Ala Leu Thr Gly Thr Pro Val Glu Asn Asn Val Gly Asp Leu Trp
            755             760             765
```

Ser Ile Met Glu Phe Leu Asn Pro Gly Phe Leu Gly Asn Gln Ala Gly
        770                 775                 780

Phe Lys Arg Asn Phe Phe Ile Pro Ile Gln Ala Glu Arg Asp Gln Glu
785                 790                 795                 800

Ala Ala Arg Arg Leu Lys Glu Ile Thr Gly Pro Phe Ile Leu Arg Arg
                805                 810                 815

Leu Lys Thr Asp Thr Ser Ile Ile Ser Asp Leu Pro Glu Lys Met Glu
                820                 825                 830

Met Lys Thr Tyr Cys Thr Leu Thr Lys Glu Gln Ala Ser Leu Tyr Ala
                835                 840                 845

Ala Val Leu Glu Asp Ile Glu Glu Thr Met Glu Ala Glu Glu Gly
        850                 855                 860

Ile Gln Arg Lys Gly Ile Ile Leu Ser Ala Leu Thr Arg Leu Lys Gln
865                 870                 875                 880

Val Cys Asn His Pro Ala Gln Phe Leu Lys Asp Asn Ser Ala Val Pro
                885                 890                 895

Gly Arg Ser Gly Lys Leu Ala Arg Leu Thr Glu Met Leu Asp Val Ile
                900                 905                 910

Leu Glu Asn Gly Glu Lys Ala Leu Val Phe Thr Gln Phe Ala Glu Met
        915                 920                 925

Gly Lys Met Leu Lys Glu His Leu Gln Ala Ser Phe Gly Cys Glu Val
        930                 935                 940

Leu Phe Leu His Gly Gly Val Pro Arg Lys Gln Arg Asp Arg Met Leu
945                 950                 955                 960

Glu Arg Phe Gln Glu Gly Lys Glu Tyr Leu Pro Ile Phe Val Leu Ser
                965                 970                 975

Leu Lys Ala Gly Gly Thr Gly Leu Asn Leu Thr Gly Ala Asn His Val
                980                 985                 990

Phe His Phe Asp Arg Trp Trp Asn Pro Ala Val Glu Asn Gln Ala Thr
        995                 1000                1005

Asp Arg Ala Phe Arg Ile Gly Gln Thr Lys Asn Val Glu Val His
    1010                1015                1020

Lys Phe Ile Cys Ala Gly Thr Leu Glu Glu Lys Ile Asp Glu Ile
    1025                1030                1035

Ile Glu Arg Lys Val Gln Val Ala Glu Asn Val Val Gly Thr Gly
    1040                1045                1050

Glu Gly Trp Leu Thr Glu Leu Ser Asn Glu Glu Leu Lys Asp Ile
    1055                1060                1065

Leu Ala Leu Arg Glu Glu Ala Val Gly Glu
    1070                1075

<210> SEQ ID NO 45
<211> LENGTH: 3147
<212> TYPE: DNA
<213> ORGANISM: Methanospirillum hungatei

<400> SEQUENCE: 45
gtgaccgcga aacgaccagc accaatccac gataaagaag aagagaccat acccgatact      60
tcgcttccgg tctttcatgc cctgatttac ccggccgttg aaggggtagc gatatgtgcc     120
gaatatataa ctgataaacc tgcaccggtc aggaaaaaag ctacgcaaa ggataaacct     180 ggcgaatatc catattccct ggatcatacc gcccttaaaa cgctcataga aactgttttt     240
ggagcatatg atgacctgaa ggctaccaga tggattatct atctccccgc tgaagaaacg     300
gttcctcctt cctctcagtt ctcatcaaaa aagaagcctt caccaaagga gaaaaactc     360

```
cccccttgttc cgatgtatat ccccgttctt ctctgcccgt atgaaaccttt ttttcaaatc      420 tggaaagccg ctcagaatac agataaaaat tatattgctg gcgattcctt ccagtacatc      480
tccattctga tggagagtac cgtccggctc atacaaaacg gacggttcaa accatctcta      540
gaacggacct ttgccggata tcatgccgta tgggtacctg ccctttctcc tcaggatatg      600
gaatgggtat cagatttttc aagccggatg ccaacggtct gcaagtacgc tatccccccgg      660 gtcgcaaaag atccctacat ttataaacct gagaccagat tagagaaatt catcgttgag      720
atgatgcggg tgatcatccg tactgccctt ggtggttata cactgaaaga agagacagat      780
cccttttatg aaccctcaga aaacgagatg cagttcatga ctgaccttct cggggtaacc      840
gacccaataa ggaacaaagg atttgagaga actttcttac gggcgatgca ggactggctg      900
accttctcaa gttcaggacg gtttgctccc tttgagttct gcatgatcat aaaagatcca      960
ccagaaggac agacagaacc atgggatttc actctcgcgg tcagatcaga ggcagaacca     1020
tctcttctca tcccggcaga aataatctgg gaattgcctg atcaccagag cgggctcttc     1080
ccccaggcag cctatctcaa acatatcctc cttgctggta tcgggctctt gacctcatca     1140
tcatcggcat tatggcgtcc cctgtccgga tcgaaaccca ccgggggaag tatgacccctg     1200 aaagaggctg caacgttctt gggttcagac ctcgcaagag ccaggaggaa gggagtaacg     1260
gtgctcctgc cagactggtg gactgatacg acctatacac cacggggtga atccatgca     1320 aggcggcggg atcccaccca tacgcagaca cggataggac tgcaggaact cctttctttt     1380
gattaccgga ttgcaatcgg tgatgagtca ttttcaccgg atgagttctg ggaaaaggta     1440
aaagaaaagg ctcccttat ctggctgggg aaccggtgga tatcctttca tccggatgcg     1500
atacaacatg ccctggattc tttcagcagg catcagagca aaggagggga tacaatagga     1560
gatctgctcc ggctctccct gaaaaaaatg gaggattccg cggtaccggt atcgattcat     1620
gcaaaagatg actgggttgc ggatcttctg gattttttca ggaccgaaac aaatcaggca     1680
gttccagtcc caaagaaatt taaagggata ctcaggccat accaggaaga ggggttctcc     1740
ttcctttgtc aatgtaccag aaggggcttt ggagcctgcc ttgcagatga catgggggctt     1800 ggaaaaactc cccagacact tgcatggctg gtctatctca aggagaaaga aaaacccacg     1860
actccgtccc tccttatatg cccgatgtcg gttgttggga actgggagcg ggagatacag     1920
cggtttgcgc catcactccg ttcatgggtg catcatggga ctgaccgatg caaaggcgat     1980
gattttgtga gacatgtcgg ttcatatgac ctggtcctga ccacctatca tctggcagca     2040
cgggacgtag accacctcaa aaccgttccc tggtctgcaa tcattcttga cgaggcacaa     2100
aatatcaaga acctccatgc aaaccagacc gtagcagtca aatctctcac cggtgagaga     2160
cgggttgctc tgaccggaac cccggtggag aaccggttac tcgaactctg gtctatcatg     2220 gacttttaa atccaggata ccttggttca cagagtgcat ttacaaaccg ctattcccgc     2280
ccgattgagc aggaaaaaaa tacgaactg atacaggaat taaggtccct catccgtccg     2340
ttcctgctca ggcggatgaa aacagacaag catgttatcg atgatcttcc ggaaaagatg     2400
gagaaccggt tatattgcac cctcacaccc gaacaggcaa ccttatatca ggctgttgtg     2460
cttgatatgg caaagaacct tgataaagtg gagggtattg ccaggaaagg ggcaatcctt     2520
gctgcgatca cacgactgaa acagatctgt aaccatccgg acgtgttgg cagggataaa     2580 acaataaagg ctgagcggtc cgggaaggtg agccggctgc ttgagatgat tgaggagatc     2640
acttccgaag gggactcagc actcatattc agtcagtatg caacatttgc tgaggaactg     2700
gcagggatga tagagaaaca gggagatacg cccgttcttc tcctgaccgg gtcaacacca     2760
```

```
cggaaaaaac gggaacagat gatagaggag tttcaggcct caaccacccc gataatcttt    2820
gttatttctc tgaaagccgg gggaacgggt ctgaacctga cgaaagcgac tcatgtgttt    2880
catgtagacc ggtggtggaa tccggcggtt gaagaccagg ctactgaccg gacgtaccgg    2940
atcggacaaa agagaaatgt ccaagttcac ctgatgataa ccgccggaac cctggaggaa    3000
cggatagatc tgataaacca ggagaaacgg acgcttgcaa aggaagtcct tgcacagagt    3060
gatgagtatc tgcaaaatct ctcaacaaaa gaacttctgg agattgtatc acttcgtgac    3120
agtctctttc gcggggagga tgcatga                                        3147

<210> SEQ ID NO 46
<211> LENGTH: 1048
<212> TYPE: PRT
<213> ORGANISM: Methanospirillum hungatei

<400> SEQUENCE: 46
```

Val Thr Ala Lys Arg Pro Ala Pro Ile His Asp Lys Glu Glu Thr
1               5                   10                  15

Ile Pro Asp Thr Ser Leu Pro Val Phe His Ala Leu Ile Tyr Pro Ala
            20                  25                  30

Val Glu Gly Val Ala Ile Cys Ala Glu Tyr Ile Thr Asp Lys Pro Ala
        35                  40                  45

Pro Val Arg Lys Lys Gly Tyr Ala Lys Asp Lys Pro Gly Glu Tyr Pro
    50                  55                  60

Tyr Ser Leu Asp His Thr Ala Leu Lys Thr Leu Ile Glu Asn Cys Phe
65                  70                  75                  80

Gly Ala Tyr Asp Asp Leu Lys Ala Thr Arg Trp Ile Ile Tyr Leu Pro
                85                  90                  95

Ala Glu Glu Thr Val Pro Pro Ser Ser Gln Phe Ser Ser Lys Lys Lys
            100                 105                 110

Pro Ser Pro Lys Glu Lys Lys Leu Pro Leu Val Pro Met Tyr Ile Pro
        115                 120                 125

Val Leu Leu Cys Pro Tyr Glu Thr Phe Phe Gln Ile Trp Lys Ala Ala
    130                 135                 140

Gln Asn Thr Asp Lys Asn Tyr Ile Ala Gly Asp Ser Phe Gln Tyr Ile
145                 150                 155                 160

Ser Ile Leu Met Glu Ser Thr Val Arg Leu Ile Gln Asn Gly Arg Phe
                165                 170                 175

Lys Pro Ser Leu Glu Arg Thr Phe Ala Gly Tyr His Ala Val Trp Val
            180                 185                 190

Pro Ala Leu Ser Pro Gln Asp Met Glu Trp Val Ser Asp Phe Ser Ser
        195                 200                 205

Arg Met Pro Thr Val Cys Lys Tyr Ala Ile Pro Arg Val Ala Lys Asp
    210                 215                 220

Pro Tyr Ile Tyr Lys Pro Glu Thr Arg Leu Glu Lys Phe Ile Val Glu
225                 230                 235                 240

Met Met Arg Val Ile Ile Arg Thr Ala Leu Gly Gly Tyr Thr Leu Lys
                245                 250                 255

Glu Glu Thr Asp Pro Phe Tyr Glu Pro Ser Glu Asn Glu Met Gln Phe
            260                 265                 270

Met Thr Asp Leu Leu Gly Val Thr Asp Pro Ile Arg Asn Lys Gly Phe
        275                 280                 285

Glu Arg Thr Phe Leu Arg Ala Met Gln Asp Trp Leu Thr Phe Ser Ser
    290                 295                 300

Ser Gly Arg Phe Ala Pro Phe Glu Phe Cys Met Ile Ile Lys Asp Pro

```
                305                 310                 315                 320

Pro Glu Gly Gln Thr Glu Pro Trp Asp Phe Thr Leu Ala Val Arg Ser
                325                 330                 335

Glu Ala Glu Pro Ser Leu Leu Ile Pro Ala Glu Ile Ile Trp Glu Leu
                340                 345                 350

Pro Asp His Gln Ser Gly Leu Phe Pro Gln Ala Ala Tyr Leu Lys His
                355                 360                 365

Ile Leu Leu Ala Gly Ile Gly Leu Leu Thr Ser Ser Ser Ala Leu
    370                 375                 380

Trp Arg Pro Leu Ser Gly Ser Lys Pro Thr Gly Gly Ser Met Thr Leu
385                 390                 395                 400

Lys Glu Ala Ala Thr Phe Leu Gly Ser Asp Leu Ala Arg Ala Arg Arg
                405                 410                 415

Lys Gly Val Thr Val Leu Leu Pro Asp Trp Trp Asp Thr Thr Tyr
                420                 425                 430

Thr Pro Arg Val Glu Ile His Ala Arg Arg Asp Pro Thr His Thr
                435                 440                 445

Gln Thr Arg Ile Gly Leu Gln Glu Leu Leu Ser Phe Asp Tyr Arg Ile
    450                 455                 460

Ala Ile Gly Asp Glu Ser Phe Ser Pro Asp Glu Phe Trp Glu Lys Val
465                 470                 475                 480

Lys Glu Lys Ala Pro Phe Ile Trp Leu Gly Asn Arg Trp Ile Ser Phe
                485                 490                 495

His Pro Asp Ala Ile Gln His Ala Leu Asp Ser Phe Ser Arg His Gln
                500                 505                 510

Ser Lys Gly Gly Asp Thr Ile Gly Asp Leu Leu Arg Leu Ser Leu Lys
                515                 520                 525

Lys Met Glu Asp Ser Ala Val Pro Val Ser Ile His Ala Lys Asp Asp
                530                 535                 540

Trp Val Ala Asp Leu Leu Asp Phe Phe Arg Thr Glu Thr Asn Gln Ala
545                 550                 555                 560

Val Pro Val Pro Lys Lys Phe Lys Gly Ile Leu Arg Pro Tyr Gln Glu
                565                 570                 575

Glu Gly Phe Ser Phe Leu Cys Gln Cys Thr Arg Arg Gly Phe Gly Ala
                580                 585                 590

Cys Leu Ala Asp Asp Met Gly Leu Gly Lys Thr Pro Gln Thr Leu Ala
                595                 600                 605

Trp Leu Val Tyr Leu Lys Glu Lys Glu Lys Pro Thr Thr Pro Ser Leu
    610                 615                 620

Leu Ile Cys Pro Met Ser Val Val Gly Asn Trp Glu Arg Glu Ile Gln
625                 630                 635                 640

Arg Phe Ala Pro Ser Leu Arg Ser Trp Val His His Gly Thr Asp Arg
                645                 650                 655

Cys Lys Gly Asp Asp Phe Val Arg His Val Gly Ser Tyr Asp Leu Val
                660                 665                 670

Leu Thr Thr Tyr His Leu Ala Ala Arg Asp Val Asp His Leu Lys Thr
                675                 680                 685

Val Pro Trp Ser Ala Ile Ile Leu Asp Glu Ala Gln Asn Ile Lys Asn
                690                 695                 700

Leu His Ala Asn Gln Thr Val Ala Val Lys Ser Leu Thr Gly Glu Arg
705                 710                 715                 720

Arg Val Ala Leu Thr Gly Thr Pro Val Glu Asn Arg Leu Leu Glu Leu
                725                 730                 735
```

```
Trp Ser Ile Met Asp Phe Leu Asn Pro Gly Tyr Leu Gly Ser Gln Ser
            740                 745                 750

Ala Phe Thr Asn Arg Tyr Ser Arg Pro Ile Glu Gln Glu Lys Asn Thr
            755                 760                 765

Glu Leu Ile Gln Glu Leu Arg Ser Leu Ile Arg Pro Phe Leu Leu Arg
            770                 775                 780

Arg Met Lys Thr Asp Lys His Val Ile Asp Asp Leu Pro Glu Lys Met
785                 790                 795                 800

Glu Asn Arg Val Tyr Cys Thr Leu Thr Pro Glu Gln Ala Thr Leu Tyr
                805                 810                 815

Gln Ala Val Val Leu Asp Met Ala Lys Asn Leu Asp Lys Val Glu Gly
            820                 825                 830

Ile Ala Arg Lys Gly Ala Ile Leu Ala Ala Ile Thr Arg Leu Lys Gln
            835                 840                 845

Ile Cys Asn His Pro Gly Arg Val Gly Arg Asp Lys Thr Ile Lys Ala
            850                 855                 860

Glu Arg Ser Gly Lys Val Ser Arg Leu Leu Glu Met Ile Glu Glu Ile
865                 870                 875                 880

Thr Ser Glu Gly Asp Ser Ala Leu Ile Phe Ser Gln Tyr Ala Thr Phe
                885                 890                 895

Ala Glu Glu Leu Ala Gly Met Ile Glu Lys Gln Gly Asp Thr Pro Val
            900                 905                 910

Leu Leu Leu Thr Gly Ser Thr Pro Arg Lys Arg Glu Gln Met Ile
            915                 920                 925

Glu Glu Phe Gln Ala Ser Thr Thr Pro Ile Ile Phe Val Ile Ser Leu
            930                 935                 940

Lys Ala Gly Gly Thr Gly Leu Asn Leu Thr Lys Ala Thr His Val Phe
945                 950                 955                 960

His Val Asp Arg Trp Trp Asn Pro Ala Val Glu Asp Gln Ala Thr Asp
                965                 970                 975

Arg Thr Tyr Arg Ile Gly Gln Lys Arg Asn Val Gln Val His Leu Met
            980                 985                 990

Ile Thr Ala Gly Thr Leu Glu Glu Arg Ile Asp Leu Ile Asn Gln Glu
            995                 1000                1005

Lys Arg Thr Leu Ala Lys Glu Val Leu Ala Gln Ser Asp Glu Tyr
            1010                1015                1020

Leu Thr Asn Leu Ser Thr Lys Glu Leu Leu Glu Ile Val Ser Leu
            1025                1030                1035

Arg Asp Ser Leu Phe Arg Gly Glu Asp Ala
            1040                1045

<210> SEQ ID NO 47
<211> LENGTH: 3270
<212> TYPE: DNA
<213> ORGANISM: Methanosarcina mazei

<400> SEQUENCE: 47
atgataattc ttcatgcagg aagagttgga aaacagttct tcttatgggg tgaaagcccg      60
gcagaaaatg aaactccggt tgttcggcgc gggagaaagc ctaaaccccc tatcgtaaaa     120
ccttaccctt acgattcggg ctttgaaaac ctgtcttctg cccttgagct gctgctgggc     180
agtactgacc ggaaaaaggc ggagaaaatc aacgtctgga ccccaactat cggagggaat     240
cctgtccctt ccagccctct tgttgctgaa atttcggatt cgaaagcaga acctgcactg     300
gctccctgta ctgttcacgc atatcctctg gaagctgaag aagctattgt tctcctctgc     360
```

```
acctgtatgg aaaaaaaggt tctggctccc ggtatcatct cgggaaatga ccttctctgg    420
tgggcagatg ccctgaaatt tgcaggctcg ctggtagcag ggcagaaata tttgcctggc    480
gtcaggggcg gggaaggaga gtacagggct ttctgggaac ccgtattttc cggcgaagat    540
gccgaaaagc tggcaaaact tgcaaagcaa atgcctcctg ctgcaagggc tcttgctcct    600
gaagcctctt ccatgccgcc ggaaatgcct gctgctttag cggcaaagca gtttattgaa    660
gactctctcg actggatagt ccggtccgag atcgggaaaa aaagcttgc aaaagagacg     720
cgcaaaagaa aatcctttga tagcgtccat gatgcctggg tttctgctct tagaagccct    780
gaagggctga tctatggaga cgaaaacgaa cttctgcagc ttgcggcccg gacccgcgaa    840
tggcagcgcc cactcaccat ccttaccact tctcctttca ggttctgttt ccgtcttgaa    900
gaaccggctt tagaagaaga gatcgaagaa actgaagaaa ccgaagaaat agaagaaat    960
gaagccggga aaagagatac taaaaaaggc agggaaggga tagctgatat agaagttccc   1020
gaagggctct ggtacgtccg ttatatgctt cagtcctacg aagacccgag ccttctgatc   1080
cctgtaaaag aagcctggaa gccaaaaaaa ggcagcccgt tgaaaaaata cgatgtgaaa   1140
aacattcgcc aattcctgtt atcttcccct ggacaggctt ccagtataag tgcaggaatt   1200
gcttcgagtc ttgaagctcc caacccatct ggatattccc ttgatactaa agaggcttac   1260
cgctttctga ctgaaagtgc agcgaattta agtcaggccg gtttcggggt acttctccct   1320
ggctggtgga cccgtaaagg tacaaagaca cacttaaaag cccaggctaa tgttaagggc   1380
aagaagaagt tgcaggccgg atacgggctt acactcgatg aaatcgtcag ctttgactgg   1440
gaaatcgccc ttggagacag ggtactgaca gtcagagaac tgcaggctct tgcaaagctt   1500
aaagctccgc ttgtgaaatt ccgcgggcag tgggttgagg taaacgatgc ggaaatcagg   1560
gctgcccttg agttctggaa gaaaaatccc aacggtgaag caagtctgcg tgaagttcta   1620
aaactggcag tgggagtttc cgaaaaagcc gatggtgtga cgttgaagg gctcaatgca    1680
accggatgga ttggagaatt aatcagccgc ttaaaagaca aaaccgggtt tgaagaactt   1740
cctgctccca acggcttttc aggcacccct cggccatatc agttcagagg ttactcctgg   1800
ctggcttttc tgaggcagtg gggtatagga gcctgccttg cagacgatat ggggcttggt   1860
aaaaccgtcc agactcttgc tcttattcag cacgatctgg aacaggctaa agagaaagct   1920
gaagaaaaga ttgaagaacc ggctgaagaa aagattgaag aaaaagttga cggacgtaag   1980
gccccaaaac ctgttcttct ggtttgtcct acctctgtta tcaacaactg gaaaaaagag   2040
gcttcccgct ttacgccaga actttcggta atggtccacc acgggaccag ccggaaaaag   2100
gaagaggaat tcaagaagga agccatgaat catgctattg tcatctcaag ctatggcctt   2160
gtgcagcgga tcttaaaatt tttaaaagag gttcattggg caggagttgt acttgacgaa   2220
gcccagaaca tcaaaaaccc ggaaaccaaa caggcaaagg cagccagggc tcttgaatcc   2280
gattaccgct tagctcttac agggactccg gttgaaaata cgtgggaga cctctggtcc    2340
ataatggagt ttttaaaccc cggcttcctc ggaagtcagg cgggtttcaa gcggaatttc   2400
tttatcccca ttcaggcaga aagggatcag gaggctgcaa ggaggctgaa agaaattaca   2460
ggtcccttca tccttcgccg tttgaagact gacacttcga ttatctccga cctgccggaa   2520
aaaatggaga tgaagaccta ttgtacgctg acaaaagaac aggcctccct ctatgctgca   2580
gtccttgaag acatcagaga agcgattgaa ggagccgaag aaggcatcca gaggaaaggt   2640
ataatcctgt ctgccctttc caggctcaag caggtctgca accacccctgc gcagttttttg   2700
aaggacaact ccactatccc cggcaggtcc ggaaaactcg caaggcttac cgaaatgctg   2760
```

```
gatgtagtcc tggaaaacgg ggaaaaagcc cttgttttta cccagtttgc ggagatgggc    2820
aaaatggtga agaacacct gcaagcaagc tttggctgtg aagtccttt cctgcacggc      2880 ggggtcccca ggaagcagag agaccggatg cttgagaggt tccaggaagg aaaagaatac    2940
ctccctattt ttgtcctctc ccttaaagcc ggcggcacgg ggcttaacct cacaggggca    3000
aaccacgttt tccactttga tcgctggtgg aacccggctg ttgaaaacca ggctacagac    3060
agggcattcc gtataggcca gaagaaaaac gttgaggtcc ataaattcat ctgcgcaggt    3120
acgcttgaag aaaaaatcga tgagattatc gaacgcaaag tgcaggtcgc agagaacgtt    3180
gttgggacag gtgaagactg gctgacagag ctttccaacg atgaactgaa ggatattctt    3240
gctcttagag aagaagcggt aggtgaataa                                      3270
```

<210> SEQ ID NO 48
<211> LENGTH: 1089
<212> TYPE: PRT
<213> ORGANISM: Methanosarcina mazei

<400> SEQUENCE: 48

```
Met Ile Ile Leu His Ala Gly Arg Val Gly Lys Gln Phe Phe Leu Trp
1               5                   10                  15

Gly Glu Ser Pro Ala Glu Asn Glu Thr Pro Val Val Arg Arg Gly Arg
            20                  25                  30

Lys Pro Lys Thr Pro Ile Val Lys Pro Tyr Pro Tyr Asp Ser Gly Phe
        35                  40                  45

Glu Asn Leu Ser Ser Ala Leu Glu Leu Leu Gly Ser Thr Asp Arg
    50                  55                  60

Lys Lys Ala Glu Lys Ile Asn Val Trp Thr Pro Thr Ile Gly Gly Asn
65                  70                  75                  80

Pro Val Pro Ser Ser Pro Leu Val Ala Glu Ile Ser Asp Ser Lys Ala
                85                  90                  95

Glu Pro Ala Leu Ala Pro Cys Thr Val His Ala Tyr Pro Leu Glu Ala
            100                 105                 110

Glu Glu Ala Ile Val Leu Leu Cys Thr Cys Met Glu Lys Lys Val Leu
        115                 120                 125

Ala Pro Gly Ile Ile Ser Gly Asn Asp Leu Leu Trp Trp Ala Asp Ala
    130                 135                 140

Leu Lys Phe Ala Gly Ser Leu Val Ala Gly Gln Lys Tyr Leu Pro Gly
145                 150                 155                 160

Val Arg Gly Gly Glu Gly Glu Tyr Arg Ala Phe Trp Glu Pro Val Phe
                165                 170                 175

Ser Gly Glu Asp Ala Gly Lys Leu Ala Lys Leu Ala Lys Gln Met Pro
            180                 185                 190

Pro Ala Ala Arg Ala Leu Ala Pro Glu Ala Ser Ser Met Pro Pro Glu
        195                 200                 205

Met Pro Ala Ala Leu Ala Ala Lys Gln Phe Ile Glu Asp Ser Leu Asp
    210                 215                 220

Trp Ile Val Arg Ser Glu Ile Gly Glu Lys Lys Leu Ala Lys Glu Thr
225                 230                 235                 240

Arg Lys Arg Lys Ser Phe Asp Ser Val His Asp Ala Trp Val Ser Ala
                245                 250                 255

Leu Arg Ser Pro Glu Gly Leu Ile Tyr Gly Asp Glu Asn Glu Leu Leu
            260                 265                 270

Gln Leu Ala Ala Arg Thr Arg Glu Trp Gln Arg Pro Leu Thr Ile Leu
        275                 280                 285
```

```
Thr Thr Ser Pro Phe Arg Phe Cys Phe Arg Leu Glu Glu Pro Ala Leu
    290                 295                 300

Glu Glu Glu Ile Glu Glu Thr Glu Glu Thr Glu Glu Ile Glu Glu Asn
305                 310                 315                 320

Glu Ala Gly Lys Arg Asp Thr Lys Lys Gly Arg Glu Gly Ile Ala Asp
                325                 330                 335

Ile Glu Val Pro Glu Gly Leu Trp Tyr Val Arg Tyr Met Leu Gln Ser
            340                 345                 350

Tyr Glu Asp Pro Ser Leu Leu Ile Pro Val Lys Glu Ala Trp Lys Pro
        355                 360                 365

Lys Lys Gly Ser Pro Leu Lys Lys Tyr Asp Val Lys Asn Ile Arg Gln
    370                 375                 380

Phe Leu Leu Ser Ser Leu Gly Gln Ala Ser Ser Ile Ser Ala Gly Ile
385                 390                 395                 400

Ala Ser Ser Leu Glu Ala Pro Asn Pro Ser Gly Tyr Ser Leu Asp Thr
                405                 410                 415

Lys Glu Ala Tyr Arg Phe Leu Thr Glu Ser Ala Ala Asn Leu Ser Gln
            420                 425                 430

Ala Gly Phe Gly Val Leu Leu Pro Gly Trp Trp Thr Arg Lys Gly Thr
        435                 440                 445

Lys Thr His Leu Lys Ala Gln Ala Asn Val Lys Gly Lys Lys Lys Leu
    450                 455                 460

Gln Ala Gly Tyr Gly Leu Thr Leu Asp Glu Ile Val Ser Phe Asp Trp
465                 470                 475                 480

Glu Ile Ala Leu Gly Asp Arg Val Leu Thr Val Arg Glu Leu Gln Ala
                485                 490                 495

Leu Ala Lys Leu Lys Ala Pro Leu Val Lys Phe Arg Gly Gln Trp Val
            500                 505                 510

Glu Val Asn Asp Ala Glu Ile Arg Ala Ala Leu Glu Phe Trp Lys Lys
        515                 520                 525

Asn Pro Asn Gly Glu Ala Ser Leu Arg Glu Val Leu Lys Leu Ala Val
    530                 535                 540

Gly Val Ser Glu Lys Ala Asp Gly Val Asn Val Glu Gly Leu Asn Ala
545                 550                 555                 560

Thr Gly Trp Ile Gly Glu Leu Ile Ser Arg Leu Lys Asp Lys Thr Gly
                565                 570                 575

Phe Glu Glu Leu Pro Ala Pro Asn Gly Phe Ser Gly Thr Leu Arg Pro
            580                 585                 590

Tyr Gln Phe Arg Gly Tyr Ser Trp Leu Ala Phe Leu Arg Gln Trp Gly
        595                 600                 605

Ile Gly Ala Cys Leu Ala Asp Asp Met Gly Leu Gly Lys Thr Val Gln
    610                 615                 620

Thr Leu Ala Leu Ile Gln His Asp Leu Glu Gln Ala Lys Glu Lys Ala
625                 630                 635                 640

Glu Glu Lys Ile Glu Glu Pro Ala Glu Glu Lys Ile Glu Glu Lys Val
                645                 650                 655

Asp Gly Arg Lys Ala Pro Lys Pro Val Leu Leu Val Cys Pro Thr Ser
            660                 665                 670

Val Ile Asn Asn Trp Lys Lys Glu Ala Ser Arg Phe Thr Pro Glu Leu
        675                 680                 685

Ser Val Met Val His His Gly Thr Ser Arg Lys Lys Glu Glu Glu Phe
    690                 695                 700

Lys Lys Glu Ala Met Asn His Ala Ile Val Ile Ser Ser Tyr Gly Leu
705                 710                 715                 720
```

Val Gln Arg Asp Leu Lys Phe Leu Lys Glu Val His Trp Ala Gly Val
            725                 730                 735

Val Leu Asp Glu Ala Gln Asn Ile Lys Asn Pro Glu Thr Lys Gln Ala
            740                 745                 750

Lys Ala Ala Arg Ala Leu Glu Ser Asp Tyr Arg Leu Ala Leu Thr Gly
            755                 760                 765

Thr Pro Val Glu Asn Asn Val Gly Asp Leu Trp Ser Ile Met Glu Phe
770                 775                 780

Leu Asn Pro Gly Phe Leu Gly Ser Gln Ala Gly Phe Lys Arg Asn Phe
785                 790                 795                 800

Phe Ile Pro Ile Gln Ala Glu Arg Asp Gln Glu Ala Ala Arg Arg Leu
                805                 810                 815

Lys Glu Ile Thr Gly Pro Phe Ile Leu Arg Arg Leu Lys Thr Asp Thr
            820                 825                 830

Ser Ile Ile Ser Asp Leu Pro Glu Lys Met Glu Met Lys Thr Tyr Cys
            835                 840                 845

Thr Leu Thr Lys Glu Gln Ala Ser Leu Tyr Ala Ala Val Leu Glu Asp
850                 855                 860

Ile Arg Glu Ala Ile Glu Gly Ala Glu Gly Ile Gln Arg Lys Gly
865                 870                 875                 880

Ile Ile Leu Ser Ala Leu Ser Arg Leu Lys Gln Val Cys Asn His Pro
                885                 890                 895

Ala Gln Phe Leu Lys Asp Asn Ser Thr Ile Pro Gly Arg Ser Gly Lys
            900                 905                 910

Leu Ala Arg Leu Thr Glu Met Leu Asp Val Val Leu Glu Asn Gly Glu
            915                 920                 925

Lys Ala Leu Val Phe Thr Gln Phe Ala Glu Met Gly Lys Met Val Lys
930                 935                 940

Glu His Leu Gln Ala Ser Phe Gly Cys Glu Val Leu Phe Leu His Gly
945                 950                 955                 960

Gly Val Pro Arg Lys Gln Arg Asp Arg Met Leu Glu Arg Phe Gln Glu
                965                 970                 975

Gly Lys Glu Tyr Leu Pro Ile Phe Val Leu Ser Leu Lys Ala Gly Gly
            980                 985                 990

Thr Gly Leu Asn Leu Thr Gly Ala Asn His Val Phe His Phe Asp Arg
            995                 1000                1005

Trp Trp Asn Pro Ala Val Glu Asn Gln Ala Thr Asp Arg Ala Phe
    1010                1015                1020

Arg Ile Gly Gln Lys Lys Asn Val Glu Val His Lys Phe Ile Cys
    1025                1030                1035

Ala Gly Thr Leu Glu Glu Lys Ile Asp Glu Ile Ile Glu Arg Lys
    1040                1045                1050

Val Gln Val Ala Glu Asn Val Val Gly Thr Gly Glu Asp Trp Leu
    1055                1060                1065

Thr Glu Leu Ser Asn Asp Glu Leu Lys Asp Ile Leu Ala Leu Arg
    1070                1075                1080

Glu Glu Ala Val Gly Glu
    1085

<210> SEQ ID NO 49
<211> LENGTH: 3042
<212> TYPE: DNA
<213> ORGANISM: Mycobacterium bovis

<400> SEQUENCE: 49

```
atgctggttt tgcacggctt ctggtccaac tccggcggga tgcggctgtg ggcggaggac    60
tccgatctgc tggtgaagag cccgagtcag gcgctgcgct ccgcgcggcc acacccgttc   120
gcggcgcccg ctgacctgat cgccggcata catccgggca aacccgcaac cgccgttttg   180
ctgttgccgt cgttgcgatc ggcgccgctg gactcgccgg agctgatccg gctcgccccg   240
cgcccggccg cgccgaaccga tccgatgctg ttggcgtgga cggtaccggt ggtggacctg   300
gaccccaccg cggcgttggc cgccttcgac cagcccgccc ccgacgtccg ctacggcgcg   360
tccgtcgact acctggccga gctggccgtt ttcgcgcgcg agttggtcga gcgtggtcgc   420
gtgctgcccc agctgcgccg cgacacccac ggcgcggccg cctgctggcg tccggtgttg   480
cagggacgcg acgtggtcgc gatgacctcg ctggtctcgg cgatgccgcc ggtctgccgc   540
gccgaagttg gtgggcacga cccgcacgaa ctggcaacct cggctctgga cgcgatggtc   600
gacgccgccg tgcgcgcggc gctgtcaccg atggacctgc tgccccgcg acggggtcgc   660
tccaaacggc atcgggccgt ggaggcttgg ctgaccgcgt tgacctgccc ggacggccgg   720
ttcgacgcgg agcccgacga actcgacgcg ctggccgagg cgttgcggcc atgggacgac   780
gtcggtatcg gcaccgtcgg cccggcgcgg gcgacgtttc ggctgtccga agtcgagacc   840
gaaaacgagg agacgcccgc gggctcgttg tggaggctgg agttcttatt gcagtcgacg   900
caggacccca gcctgctggt ccccgccgag caggcatgga cgacgacgg cagcctgcgc   960
cgctggctgg accggccgca ggagctgctg ctgaccgaac tgggccgggc ctctcggatt  1020
ttccccgagc tcgtcccggc gctgcgcacc gcgtgcccgt ccgggcttga gctcgacgcc  1080
gacggcgcct accgattcct gtcgggtacg gccgcggtgc tcgacgaggc tgggtttggc  1140
gtgctgctgc cgtcctggtg ggaccgccgc cgcaagctgg gcttggtcct gtccgcatat  1200
accccggtcg acggcgtggt gggcaaggcc agcaagttcg gccgcgagca gctcgtcgag  1260
ttccgctggg agctggccgt gggcgacgat ccgctcagcg aggaggagat cgcggcgctg  1320
accgaaaacca agtccccgct gatccggctg cgtggccagt gggtggcgct cgataccgaa  1380
cagctgcgcc gcgggctgga gttttttggag cgtaagccaa ccggccgcaa gaccaccgcc  1440
gagatcctcg cgctggccgc cagccacccc gacgacgtgg acaccccgct cgaggtcacc  1500
gccgtacgcg ccgacggctg gctcggggac ctgctcgccg gggccgccgc ggcgtcgctg  1560
cagccgttgg acccgcccga cggattcacc gcgacgctgc gtccctacca gcagcgcggt  1620
ctggcgtggc tggcgttttt gtcctcgctc ggtttgggca gctgcctggc cgacgacatg  1680
ggcctgggca agacggtgca gctattggcc ctggaaacct tggaatccgt tcagcgccac  1740
caggatcgcg gcgtcggacc cacactgcta ctgtgcccga tgtcgttggt gggcaactgg  1800
cagcaggaag cggccaggtt tgcacccaac ctgcgggtgt acgccaccca cggggcgcc  1860
cggctgcacg gcgaggcgtt gcgcgaccac ctcgagcgca ccgacctggt cgtgagcacc  1920
tataccaccg ccacccgcga catcgacgag ctgtcggaat acgaatggaa ccgggtggtg  1980
ctggacgagg cccaggcggt gaagaacagc ctgtcccggg cggccaaggc ggtgcgacgg  2040
ctacgcgcg cgcaccgggt cgcgctgacc gggacaccga tggagaaccg gctcgccgag  2100
ctgtggtcga tcatggactt cctcaacccg ggcctgctcg gatcctccga acgcttccgc  2160
acccgctacg cgatcccgat cgagcggcac gggcacaccg aaccggccga acggctgcgc  2220
gcatcgacgc ggccctacat cctgcgccgg ctcaagaccg accccggcgat catcgacgat  2280
ctgccggaga agatcgagat caagcagtac tgccaactca ccaccgagca ggcgtcgctg  2340
tatcaggccg tcgtcgccga catgatggaa aagatcgaaa acaccgaagg gatcgagcgg  2400
```

-continued

```
cgcggcaacg tgctggccgc gatggccaag ctcaaacagg tgtgcaacca ccccgcccag    2460
ctgctgcacg atcgctcccc ggtcggtcgg cggtccggga aggtgatccg gctcgaggag    2520
atcctggaag agatcctggc cgagggcgac cgggtgctgt gttttaccca gttcaccgag    2580
ttcgccgagc tgctggtgcc gcacctggcc gcacgcttcg gccgtgccgc ccgagacatt    2640
gcctacctgc acggtggcac cccgaggaag cggcgtgacg agatggtggc ccggttccag    2700
tccggtgacg gcccgcccat ttttctgctg tcgttgaagg cgggcggtac cgggctgaac    2760
ctcaccgccg ccaatcatgt tgtgcacctg gaccgctggt ggaacccggc ggtcgagaac    2820
caggcgacgg accgggcgtt tcggatcggg cagcggcgca cggtgcaggt ccgcaagttc    2880
atctgcaccg gcaccctcga ggagaagatc gacgaaatga tcgaggagaa aaaggcgctg    2940
gccgacttgg tggtcaccga cggcgaaggc tggctgaccg aactgtccac ccgcgatctg    3000
cgcgaggtgt tcgcgctgtc cgaaggcgcc gtcggtgagt ag                      3042
```

<210> SEQ ID NO 50
<211> LENGTH: 1013
<212> TYPE: PRT
<213> ORGANISM: Mycobacterium bovis

<400> SEQUENCE: 50

```
Met Leu Val Leu His Gly Phe Trp Ser Asn Ser Gly Gly Met Arg Leu
1               5                   10                  15

Trp Ala Glu Asp Ser Asp Leu Leu Val Lys Ser Pro Ser Gln Ala Leu
            20                  25                  30

Arg Ser Ala Arg Pro His Pro Phe Ala Ala Pro Ala Asp Leu Ile Ala
        35                  40                  45

Gly Ile His Pro Gly Lys Pro Ala Thr Ala Val Leu Leu Leu Pro Ser
    50                  55                  60

Leu Arg Ser Ala Pro Leu Asp Ser Pro Glu Leu Ile Arg Leu Ala Pro
65                  70                  75                  80

Arg Pro Ala Ala Arg Thr Asp Pro Met Leu Leu Ala Trp Thr Val Pro
                85                  90                  95

Val Val Asp Leu Asp Pro Thr Ala Ala Leu Ala Ala Phe Asp Gln Pro
            100                 105                 110

Ala Pro Asp Val Arg Tyr Gly Ala Ser Val Asp Tyr Leu Ala Glu Leu
        115                 120                 125

Ala Val Phe Ala Arg Glu Leu Val Glu Arg Gly Arg Val Leu Pro Gln
    130                 135                 140

Leu Arg Arg Asp Thr His Gly Ala Ala Ala Cys Trp Arg Pro Val Leu
145                 150                 155                 160

Gln Gly Arg Asp Val Val Ala Met Thr Ser Leu Val Ser Ala Met Pro
                165                 170                 175

Pro Val Cys Arg Ala Glu Val Gly Gly His Asp Pro His Glu Leu Ala
            180                 185                 190

Thr Ser Ala Leu Asp Ala Met Val Asp Ala Val Arg Ala Ala Leu
        195                 200                 205

Ser Pro Met Asp Leu Leu Pro Pro Arg Gly Arg Ser Lys Arg His
    210                 215                 220

Arg Ala Val Glu Ala Trp Leu Thr Ala Leu Thr Cys Pro Asp Gly Arg
225                 230                 235                 240

Phe Asp Ala Glu Pro Asp Glu Leu Asp Ala Leu Ala Glu Ala Leu Arg
                245                 250                 255

Pro Trp Asp Asp Val Gly Ile Gly Thr Val Gly Pro Ala Arg Ala Thr
```

-continued

```
                260                 265                 270
Phe Arg Leu Ser Glu Val Glu Thr Glu Asn Glu Thr Pro Ala Gly
            275                 280                 285
Ser Leu Trp Arg Leu Glu Phe Leu Leu Gln Ser Thr Gln Asp Pro Ser
            290                 295                 300
Leu Leu Val Pro Ala Glu Gln Ala Trp Asn Asp Asp Gly Ser Leu Arg
305                 310                 315                 320
Arg Trp Leu Asp Arg Pro Gln Glu Leu Leu Thr Glu Leu Gly Arg
            325                 330                 335
Ala Ser Arg Ile Phe Pro Glu Leu Val Pro Ala Leu Arg Thr Ala Cys
            340                 345                 350
Pro Ser Gly Leu Glu Leu Asp Ala Asp Gly Ala Tyr Arg Phe Leu Ser
            355                 360                 365
Gly Thr Ala Ala Val Leu Asp Glu Ala Gly Phe Gly Val Leu Leu Pro
            370                 375                 380
Ser Trp Trp Asp Arg Arg Arg Lys Leu Gly Leu Val Leu Ser Ala Tyr
385                 390                 395                 400
Thr Pro Val Asp Gly Val Val Gly Lys Ala Ser Lys Phe Gly Arg Glu
            405                 410                 415
Gln Leu Val Glu Phe Arg Trp Glu Leu Ala Val Gly Asp Asp Pro Leu
            420                 425                 430
Ser Glu Glu Glu Ile Ala Ala Leu Thr Glu Thr Lys Ser Pro Leu Ile
            435                 440                 445
Arg Leu Arg Gly Gln Trp Val Ala Leu Asp Thr Glu Gln Leu Arg Arg
            450                 455                 460
Gly Leu Glu Phe Leu Glu Arg Lys Pro Thr Gly Arg Lys Thr Thr Ala
465                 470                 475                 480
Glu Ile Leu Ala Leu Ala Ala Ser His Pro Asp Asp Val Asp Thr Pro
            485                 490                 495
Leu Glu Val Thr Ala Val Arg Ala Asp Gly Trp Leu Gly Asp Leu Leu
            500                 505                 510
Ala Gly Ala Ala Ala Ser Leu Gln Pro Leu Asp Pro Pro Asp Gly
            515                 520                 525
Phe Thr Ala Thr Leu Arg Pro Tyr Gln Gln Arg Gly Leu Ala Trp Leu
            530                 535                 540
Ala Phe Leu Ser Ser Leu Gly Leu Gly Ser Cys Leu Ala Asp Asp Met
545                 550                 555                 560
Gly Leu Gly Lys Thr Val Gln Leu Leu Ala Leu Glu Thr Leu Glu Ser
            565                 570                 575
Val Gln Arg His Gln Asp Arg Gly Val Gly Pro Thr Leu Leu Leu Cys
            580                 585                 590
Pro Met Ser Leu Val Gly Asn Trp Gln Gln Glu Ala Ala Arg Phe Ala
            595                 600                 605
Pro Asn Leu Arg Val Tyr Ala His His Gly Gly Ala Arg Leu His Gly
            610                 615                 620
Glu Ala Leu Arg Asp His Leu Glu Arg Thr Asp Leu Val Val Ser Thr
625                 630                 635                 640
Tyr Thr Thr Ala Thr Arg Asp Ile Asp Glu Leu Ser Glu Tyr Glu Trp
            645                 650                 655
Asn Arg Val Val Leu Asp Glu Ala Gln Ala Val Lys Asn Ser Leu Ser
            660                 665                 670
Arg Ala Ala Lys Ala Val Arg Arg Leu Arg Ala Ala His Arg Val Ala
            675                 680                 685
```

```
Leu Thr Gly Thr Pro Met Glu Asn Arg Leu Ala Glu Leu Trp Ser Ile
            690                 695                 700

Met Asp Phe Leu Asn Pro Gly Leu Leu Gly Ser Glu Arg Phe Arg
705                 710                 715                 720

Thr Arg Tyr Ala Ile Pro Ile Glu Arg His Gly His Thr Glu Pro Ala
                725                 730                 735

Glu Arg Leu Arg Ala Ser Thr Arg Pro Tyr Ile Leu Arg Arg Leu Lys
                740                 745                 750

Thr Asp Pro Ala Ile Ile Asp Asp Leu Pro Glu Lys Ile Glu Ile Lys
                755                 760                 765

Gln Tyr Cys Gln Leu Thr Thr Glu Gln Ala Ser Leu Tyr Gln Ala Val
770                 775                 780

Val Ala Asp Met Met Glu Lys Ile Glu Asn Thr Glu Gly Ile Glu Arg
785                 790                 795                 800

Arg Gly Asn Val Leu Ala Ala Met Ala Lys Leu Lys Gln Val Cys Asn
                805                 810                 815

His Pro Ala Gln Leu Leu His Asp Arg Ser Pro Val Gly Arg Arg Ser
                820                 825                 830

Gly Lys Val Ile Arg Leu Glu Glu Ile Leu Glu Glu Ile Leu Ala Glu
            835                 840                 845

Gly Asp Arg Val Leu Cys Phe Thr Gln Phe Thr Glu Phe Ala Glu Leu
850                 855                 860

Leu Val Pro His Leu Ala Ala Arg Phe Gly Arg Ala Ala Arg Asp Ile
865                 870                 875                 880

Ala Tyr Leu His Gly Gly Thr Pro Arg Lys Arg Arg Asp Glu Met Val
                885                 890                 895

Ala Arg Phe Gln Ser Gly Asp Gly Pro Pro Ile Phe Leu Leu Ser Leu
                900                 905                 910

Lys Ala Gly Gly Thr Gly Leu Asn Leu Thr Ala Ala Asn His Val Val
                915                 920                 925

His Leu Asp Arg Trp Trp Asn Pro Ala Val Glu Asn Gln Ala Thr Asp
            930                 935                 940

Arg Ala Phe Arg Ile Gly Gln Arg Arg Thr Val Gln Val Arg Lys Phe
945                 950                 955                 960

Ile Cys Thr Gly Thr Leu Glu Glu Lys Ile Asp Glu Met Ile Glu Glu
                965                 970                 975

Lys Lys Ala Leu Ala Asp Leu Val Val Thr Asp Gly Glu Gly Trp Leu
                980                 985                 990

Thr Glu Leu Ser Thr Arg Asp Leu  Arg Glu Val Phe Ala  Leu Ser Glu
                995                1000                1005

Gly Ala  Val Gly Glu
    1010

<210> SEQ ID NO 51
<211> LENGTH: 3042
<212> TYPE: DNA
<213> ORGANISM: Mycobacterium tuberculosis

<400> SEQUENCE: 51
atgctggttt tgcacggctt ctggtccaac tccggcggga tgcggctgtg ggcggaggac      60
tccgatctgc tggtgaagag cccgagtcag gcgctgcgct ccgcgcggcc acacccgttc     120
gcggcgcccg ctgacctgat cgccggcata catccgggca aacccgcaac cgccgttttg     180
ctgttgccgt cgttgcgatc ggcgccgctg actcgccgg agctgatccg gctcgccccg     240
cgcccggccg cgcgaaccga tccgatgctg ttggcgtgga cggtaccggt ggtggacctg     300
```

```
gaccccaccg cggcgttggc cgccttcgac cagcccgccc ccgacgtccg ctacggcgcg    360
tccgtcgact acctggccga gctggccgtt ttcgcgcgcg agttggtcga gcgtggtcgc    420
gtgctgcccc agctgcgccg cgacacccac ggcgcggccg cctgctggcg tccggtgttg    480
cagggacgcg acgtggtcgc gatgacctcg ctggtctcgg cgatgccgcc ggtctgccgc    540
gccgaagttg gtgggcacga cccgcacgaa ctggcaacct cggctctgga cgcgatggtc    600
gacgccgccg tgcgcgcggc gctgtcaccg atggacctgc tgccccgcg acggggtcgc     660 tccaaacggc atcgggccgt ggaggcttgg ctgaccgcgt tgacctgccc ggacggccgg    720
ttcgacgcgg agcccgacga actcgacgcg ctggccgagg cgttgcggcc atgggacgac    780
gtcggtatcg gcaccgtcgg cccggcgcgg gcgacgtttc ggctgtccga agtcgagacc    840
gaaaacgagg agacgcccgc gggctcgttg tggaggctgg agttcttatt gcagtcgacg    900 caggaccccca gcctgctggt ccccgccgag caggcatgga acgacgacgg cagcctgcgc    960
cgctggctgg accggccgca ggagctgctg ctgaccgaac tgggccgggc ctctcggatt    1020
ttccccgagc tcgtcccggc gctgcgcacc gcgtgcccgt ccgggcttga gctcgacgcc    1080
gacggcgcct accgattcct gtcgggtacg gccgcggtgc tcgacgaggc tgggtttggc    1140
gtgctgctgc cgtcctggtg ggaccgccgc cgcaagctgg gcttggtcct gtccgcatat    1200
accccggtcg acgcgtggt gggcaaggcc agcaagttcg gccgcgagca gctcgtcgag     1260
ttccgctggg agctggccgt gggcgacgat ccgctcagcg aggaggagat cgcggcgctg    1320
accgaaacca gtccccgct gatccggctg cgtggccagt gggtcgcgct cgataccgaa     1380
cagatgcgcc gcgggctgga gttttggag cgtaagccaa ccggccgcaa gaccaccgcc     1440
gagatcctcg cgctggccgc cagccacccc gacgacgtgg acaccccgct cgaggtcacc    1500
gccgtacgcg ccgacggctg gctcggggac ctgctcgccg gggccgccgc ggcgtcgctg    1560
cagccgttgg acccgcccga cggattcacc gcgacgctgc gtccctacca gcagcgcggt    1620
ctggcgtggc tggcgttttt gtcctcgctc ggtttgggca gctgcctggc cgacgacatg    1680
ggcctgggca agacggtgca gctattggcc ctggaaacct tggaatccgt tcagcgccac    1740
caggatcgcg gcgtcggacc cacactgcta ctgtgcccga tgtcgttggt gggcaactgg    1800
ccgcaggaag cggccaggtt tgcacccaac ctgcgggtgt acgcccacca cggggggcgcc    1860 cggctgcacg gcgaggcgtt gcgcgaccac ctcgagcgca ccgacctggt cgtgagcacc    1920
tataccaccg ccaccccgcga catcgacgag ctggcggaat acgaatggaa ccgggtggtg    1980
ctggacgagg cccaggcggt gaagaacagc ctgtcccggg cggccaaggc ggtgcgacgg    2040
ctacgcgcgg cgcaccgggt cgcgctgacc gggacaccga tggagaaccg gctcgccgag    2100
ctgtggtcga tcatggactt cctcaacccg ggcctgctcg gatcctccga acgcttccgc    2160
acccgctacg cgatcccgat cgagcggcac gggcacaccg aaccggccga acggctgcgc    2220
gcatcgacgc ggccctacat cctgcgccgg ctcaagaccg accggcgat catcgacgat    2280 ctgccggaga agatcgagat caagcagtac tgccaactca ccaccgagca ggcgtcgctg    2340
tatcaggccg tcgtcgccga catgatggaa aagatcgaaa acaccgaagg gatcgagcgg    2400
cgcggcaacg tgctgccgcc gatggccaag ctcaaacagg tgtgcaacca ccccgcccag    2460
ctgctgcacg atcgctcccc ggtcggtcgg cggtccggga aggtgatccg gctcgaggag    2520
atcctggaag agatcctggc cgagggcgac cgggtgctgt gttttaccca gttcaccgag    2580
ttcgccgagc tgctggtgcc gcacctggcc gcacgcttcg gccgtgccgc ccgagacatt    2640
gcctacctgc acggtggcac cccgaggaag cggcgtgacg agatggtggc ccggttccag    2700
```

-continued

```
tccggtgacg gcccgcccat ttttctgctg tcgttgaagg cgggcggtac cgggctgaac   2760
ctcaccgccg ccaatcatgt tgtgcacctg gaccgctggt ggaacccggc ggtcgagaac   2820
caggcgacgg accgggcgtt tcggatcggg cagcggcgca cggtgcaggt ccgcaagttc   2880
atctgcaccg caccctcga ggagaagatc gacgaaatga tcgaggagaa aaaggcgctg   2940
gccgacttgg tggtcaccga cggcgaaggc tggctgaccg aactgtccac ccgcgatctg   3000
cgcgaggtgt tcgcgctgtc cgaaggcgcc gtcggtgagt ag                      3042
```

<210> SEQ ID NO 52
<211> LENGTH: 1013
<212> TYPE: PRT
<213> ORGANISM: Mycobacterium tuberculosis

<400> SEQUENCE: 52

```
Met Leu Val Leu His Gly Phe Trp Ser Asn Ser Gly Gly Met Arg Leu
1               5                   10                  15

Trp Ala Glu Asp Ser Asp Leu Val Lys Ser Pro Ser Gln Ala Leu
                20                  25                  30

Arg Ser Ala Arg Pro His Pro Phe Ala Ala Pro Ala Asp Leu Ile Ala
            35                  40                  45

Gly Ile His Pro Gly Lys Pro Ala Thr Ala Val Leu Leu Pro Ser
        50                  55                  60

Leu Arg Ser Ala Pro Leu Asp Ser Pro Glu Leu Ile Arg Leu Ala Pro
65                  70                  75                  80

Arg Pro Ala Ala Arg Thr Asp Pro Met Leu Leu Ala Trp Thr Val Pro
                85                  90                  95

Val Val Asp Leu Asp Pro Thr Ala Ala Leu Ala Ala Phe Asp Gln Pro
            100                 105                 110

Ala Pro Asp Val Arg Tyr Gly Ala Ser Val Asp Tyr Leu Ala Glu Leu
        115                 120                 125

Ala Val Phe Ala Arg Glu Leu Val Glu Arg Gly Arg Val Leu Pro Gln
    130                 135                 140

Leu Arg Arg Asp Thr His Gly Ala Ala Ala Cys Trp Arg Pro Val Leu
145                 150                 155                 160

Gln Gly Arg Asp Val Val Ala Met Thr Ser Leu Val Ser Ala Met Pro
                165                 170                 175

Pro Val Cys Arg Ala Glu Val Gly Gly His Asp Pro His Glu Leu Ala
            180                 185                 190

Thr Ser Ala Leu Asp Ala Met Val Asp Ala Ala Val Arg Ala Ala Leu
        195                 200                 205

Ser Pro Met Asp Leu Leu Pro Pro Arg Gly Arg Ser Lys Arg His
    210                 215                 220

Arg Ala Val Glu Ala Trp Leu Thr Ala Leu Thr Cys Pro Asp Gly Arg
225                 230                 235                 240

Phe Asp Ala Glu Pro Asp Glu Leu Asp Ala Leu Ala Glu Ala Leu Arg
                245                 250                 255

Pro Trp Asp Asp Val Gly Ile Gly Thr Val Gly Pro Ala Arg Ala Thr
            260                 265                 270

Phe Arg Leu Ser Glu Val Glu Thr Glu Asn Glu Glu Thr Pro Ala Gly
        275                 280                 285

Ser Leu Trp Arg Leu Glu Phe Leu Leu Gln Thr Gln Asp Pro Ser
    290                 295                 300

Leu Leu Val Pro Ala Glu Gln Ala Trp Asn Asp Asp Gly Ser Leu Arg
305                 310                 315                 320
```

```
Arg Trp Leu Asp Arg Pro Gln Glu Leu Leu Thr Glu Leu Gly Arg
            325                 330                 335

Ala Ser Arg Ile Phe Pro Glu Leu Val Pro Ala Leu Arg Thr Ala Cys
            340                 345                 350

Pro Ser Gly Leu Glu Leu Asp Ala Asp Gly Ala Tyr Arg Phe Leu Ser
            355                 360                 365

Gly Thr Ala Ala Val Leu Asp Glu Ala Gly Phe Gly Val Leu Leu Pro
    370                 375                 380

Ser Trp Trp Asp Arg Arg Lys Leu Gly Leu Val Leu Ser Ala Tyr
385                 390                 395                 400

Thr Pro Val Asp Gly Val Gly Lys Ala Ser Lys Phe Gly Arg Glu
                405                 410                 415

Gln Leu Val Glu Phe Arg Trp Glu Leu Ala Val Gly Asp Pro Leu
                420                 425                 430

Ser Glu Glu Glu Ile Ala Ala Leu Thr Glu Thr Lys Ser Pro Leu Ile
            435                 440                 445

Arg Leu Arg Gly Gln Trp Val Ala Leu Asp Thr Glu Gln Met Arg Arg
    450                 455                 460

Gly Leu Glu Phe Leu Glu Arg Lys Pro Thr Gly Arg Lys Thr Thr Ala
465                 470                 475                 480

Glu Ile Leu Ala Leu Ala Ala Ser His Pro Asp Asp Val Asp Thr Pro
                485                 490                 495

Leu Glu Val Thr Ala Val Arg Ala Asp Gly Trp Leu Gly Asp Leu Leu
                500                 505                 510

Ala Gly Ala Ala Ala Ala Ser Leu Gln Pro Leu Asp Pro Pro Asp Gly
            515                 520                 525

Phe Thr Ala Thr Leu Arg Pro Tyr Gln Gln Arg Gly Leu Ala Trp Leu
    530                 535                 540

Ala Phe Leu Ser Ser Leu Gly Leu Gly Ser Cys Leu Ala Asp Asp Met
545                 550                 555                 560

Gly Leu Gly Lys Thr Val Gln Leu Leu Ala Leu Glu Thr Leu Glu Ser
                565                 570                 575

Val Gln Arg His Gln Asp Arg Gly Val Gly Pro Thr Leu Leu Leu Cys
            580                 585                 590

Pro Met Ser Leu Val Gly Asn Trp Pro Gln Glu Ala Ala Arg Phe Ala
    595                 600                 605

Pro Asn Leu Arg Val Tyr Ala His His Gly Gly Ala Arg Leu His Gly
    610                 615                 620

Glu Ala Leu Arg Asp His Leu Glu Arg Thr Asp Leu Val Val Ser Thr
625                 630                 635                 640

Tyr Thr Thr Ala Thr Arg Asp Ile Asp Glu Leu Ala Glu Tyr Glu Trp
                645                 650                 655

Asn Arg Val Val Leu Asp Glu Ala Gln Ala Val Lys Asn Ser Leu Ser
                660                 665                 670

Arg Ala Ala Lys Ala Val Arg Arg Leu Arg Ala His Arg Val Ala
            675                 680                 685

Leu Thr Gly Thr Pro Met Glu Asn Arg Leu Ala Glu Leu Trp Ser Ile
    690                 695                 700

Met Asp Phe Leu Asn Pro Gly Leu Leu Gly Ser Ser Glu Arg Phe Arg
705                 710                 715                 720

Thr Arg Tyr Ala Ile Pro Ile Glu Arg His Gly His Thr Glu Pro Ala
                725                 730                 735

Glu Arg Leu Arg Ala Ser Thr Arg Pro Tyr Ile Leu Arg Arg Leu Lys
```

```
                       740                 745                 750
Thr Asp Pro Ala Ile Ile Asp Leu Pro Glu Lys Ile Glu Ile Lys
            755                 760                 765
Gln Tyr Cys Gln Leu Thr Thr Glu Gln Ala Ser Leu Tyr Gln Ala Val
        770                 775                 780
Val Ala Asp Met Met Glu Lys Ile Glu Asn Thr Glu Gly Ile Glu Arg
785                 790                 795                 800
Arg Gly Asn Val Leu Ala Ala Met Ala Lys Leu Lys Gln Val Cys Asn
                805                 810                 815
His Pro Ala Gln Leu Leu His Asp Arg Ser Pro Val Gly Arg Arg Ser
            820                 825                 830
Gly Lys Val Ile Arg Leu Glu Glu Ile Leu Glu Glu Ile Leu Ala Glu
            835                 840                 845
Gly Asp Arg Val Leu Cys Phe Thr Gln Phe Thr Glu Phe Ala Glu Leu
        850                 855                 860
Leu Val Pro His Leu Ala Ala Arg Phe Gly Arg Ala Ala Arg Asp Ile
865                 870                 875                 880
Ala Tyr Leu His Gly Gly Thr Pro Arg Lys Arg Arg Asp Glu Met Val
                885                 890                 895
Ala Arg Phe Gln Ser Gly Asp Gly Pro Pro Ile Phe Leu Leu Ser Leu
                900                 905                 910
Lys Ala Gly Gly Thr Gly Leu Asn Leu Thr Ala Ala Asn His Val Val
            915                 920                 925
His Leu Asp Arg Trp Trp Asn Pro Ala Val Glu Asn Gln Ala Thr Asp
        930                 935                 940
Arg Ala Phe Arg Ile Gly Gln Arg Arg Thr Val Gln Val Arg Lys Phe
945                 950                 955                 960
Ile Cys Thr Gly Thr Leu Glu Glu Lys Ile Asp Glu Met Ile Glu Glu
                965                 970                 975
Lys Lys Ala Leu Ala Asp Leu Val Val Thr Asp Gly Gly Trp Leu
            980                 985                 990
Thr Glu Leu Ser Thr Arg Asp Leu  Arg Glu Val Phe Ala  Leu Ser Glu
            995                  1000               1005
Gly Ala  Val Gly Glu
    1010

<210> SEQ ID NO 53
<211> LENGTH: 3282
<212> TYPE: DNA
<213> ORGANISM: Myxococcus xanthus

<400> SEQUENCE: 53
gtgcgagcct ggaggggcgt cctccgctgg gctgccgctg gcctctccct gtccgcggct      60
cggagtccga ccggccacct cccagtgttt tcaggttttt ccgtggcgac cgatggcgtc     120
gggctgttcg cgggtctgtc tgttcgggcc cttgtccatc aagggcctgg aggaggaccg     180
ctacgagcgc ctcacggaca acccggcagg cctgcggctc acggagcggg caatcccgtg     240 cagggggcgct cgcaggcctg cttcgtgtg ccgcttgccc ggacggagtt tacattcgca     300
gcgatgcccc tcgtgttcct gcccgacgcc gagacgctgt tcctctgggg gcccgaccgg     360
ctgccacgtg agctcgccgg cctgccgag acggggggacc gcgcctccgc gctgctcgtg     420
acgcccgagg gattgcgtga atgcgagggg cacgggctgc ccctggccgc caccgtcgag     480 cggctcgcg tggtgcaaac ctccgaggcc gagtcctttc ctggctccat cgccctgtgg     540
acgctggcca gcaagctcgc gctggagttg gtggcgcgcg agcgcgtggt gcccacgctc     600
```

```
ctgcggcggg gcgagcgcat cgaggctcgc tgggcggcgg ccctctccgc caccgaggac    660
gccggccgcg tcgccgcgct cgcccggagc atgccgcccg gcgcgcacgc cgtccccgca    720
ggcgccaggc caggccgcgc cgtctgggcc ccggacgcct tgctgcgcgc cttcctcgac    780
gccaccgtcg acgccttcgt gcgcgccgcg cgcggtgcgc cttcgttgcc ggcccggcgc    840
gcggcctcgt gggacgagcg ctggcgcgag gcgctcaccg gcgcgcgacg cgacttcgcg    900
ccggagggct tcgccgagcg ctccgtcgtc gatgagctga cgcgctggag cgaacccgcg    960
ctcggcgccc gggacaagct gcgcgcctgc ttccggctgg agcccccgac ggaggagcgc   1020
gagcccttcg tgctgagctt ccacctccag tccccggacg acccaagcct gctcgtcccg   1080 gccgcgacg tctggaagac gcgcgggcgc agcctggaga agctcggccg cgccttccgt   1140
gacccgcagg agtccctgct cgaggcactc ggccgcgccg cccggctctt cccccgctg    1200 gcgctcgtgc tggagagccc acgtccccag gcgctcctgc tcgagcccga caccgcgtgg   1260
acgttcctct cggagggcgc ccgcgtgctc tcagacgccg gcttcggcgt catcgtccct   1320
ggcgagctca ccacctcggg ccgacgccgc ctgcgcctgc gcatgcgcgt gggcgcgagc   1380
acgaaggccg cggggccgt cggtggcacc gcggggctcg ggctcgacgc gctgctgcgc    1440
gtggactggg acgccgtgct gggcgaccaa cccctctccg cccaggagct ggcgctgctg   1500
gcccagcgca aggcccgct cgtgcgattc gcggcgagt gggtcgcggt ggatcccctc     1560
gaactcgacg ccatccagcg ccacctcgcc cagggccccg ccgcatggc gctgagcgag    1620 gcggtgcggg tgtccctgct aggcgaaacg cgccacggac agctccccgt caccgttctc   1680
gccaccgggg cgctggagga gcgcctgcgc ctgcttcggg agggcgggc caccgctcag    1740 gacgcccccc gcgcgctgcg cgccacgctg cggccctacc agtcgcgcgg tctgcactgg   1800
ctggacacgc tggcctcatt ggggctcggc gcctgcctcg cggacgacat gggcctgggc   1860
aagacggtgc aggtgctggc cttcctgctg cggcggctcg agcaggcgcc tgacgaggcg   1920
cgccccacgc tgctggtggc ccccacctcc gtggtgggca actgggagcg tgagctcgcc   1980
cgcttcgccc ccaccttgcg cctgacgcgg cactacggcg ccgagcgcgc ccgcgcggcg   2040
aaccgcttcc ccgcgcgcc cggcgccgtc gtgctcacca cctacggctt gctgcgccgg   2100
gacgccgcgc tgctcgcgcg cgtggactgg ggcgcggtgg tgctcgacga ggcgcagaac   2160
atcaagaacg cggcgtcggc taccgcccgc gcggcccggg cgttgcgcgc cagccagcgc   2220
ttcgcgctca cgggcacgcc ggtggagaac cgcctggcgg agctgtggtc catcctcgag   2280
ttcgccaacc cgggcctgct cgggccgctg agacgttcc ggcgggagct ggcgctgccc    2340
attgaacgcc atggcaatca ggaggcctcg gcccggctgc gccggctcgt gagcccccttc  2400 gtcctgcgcc gcctcaagag cgacccgacc atcatcacgg acctgcccgc gaagaatgag   2460
atgaaggtcg tctgcacgct cacgcgcgag caggcctcgc tctacaaggc ggtggtggac   2520
gaggagctgg ggcgcatcga ggaggccgac ggcatggagc gccggggccg cgtgctcgcg   2580
ctgctgctgt acacgaagca gatcgccaac caccccggcgc agtacctcgg ggagtccggg   2640
cccctgccgg ggcgctcggg gaagctggcg cgcgtggtgg agatgctcga ggagtccctg   2700
gccgctggcg acaaggcgct cgtcttcacg cagttccggg agatgggcga caagctggtg   2760
gcgcacctgt cggagtacct gggccacgag gtgctcttcc tccacggcgg cacgccccgc   2820
aaggcgcgcg acgagatggt gcggcgcttc caggaggacg tccacggtcc gcgtgtgttc   2880
gtgctgtccg tcaaggcggg aggcacgggg ctcaacctga cggcggcgag ccatgtgttc   2940
cattacgacc gctggtggaa cccggccgtc gaggaccagg ccaccgaccg cgcgtaccgc   3000
```

-continued

```
atcgggcaga cgcgcgcggt gcaggtccac aagctggtgt gtgcgggcac tgtcgaggag    3060
aaggtggacc ggctgctcga acagaagcgc cagctcgccg agaaggtcgt gggcgcgggc    3120
gagcactggg tgaccgagct ggacacgacg gcgctgcgcg agctgttctc gctgtccgag    3180
ggcgccgtgg cggacgatgg cgacgcggaa ggggaagacg acgcgcgggt gcgcgccccg    3240
cgacggcgcg gccgtgcgag cgcgaaggcg gtgtcgcgat ga                      3282
```

<210> SEQ ID NO 54
<211> LENGTH: 1093
<212> TYPE: PRT
<213> ORGANISM: Myxococcus xanthus

<400> SEQUENCE: 54

| | | | | | | | | | | | | | | |
|---|---|---|---|---|---|---|---|---|---|---|---|---|---|---|
| Val | Arg | Ala | Trp | Arg | Gly | Val | Leu | Arg | Trp | Ala | Ala | Gly | Leu | Ser |
| 1 | | | | 5 | | | | | 10 | | | | | 15 |

Leu Ser Ala Ala Arg Ser Pro Thr Gly His Leu Pro Val Phe Ser Gly
            20                  25                  30

Phe Ser Val Ala Thr Asp Gly Val Gly Leu Phe Ala Gly Leu Ser Val
        35                  40                  45

Arg Ala Leu Val His Gln Gly Pro Gly Gly Pro Leu Arg Ala Pro
 50                  55                  60

His Gly Gln Pro Gly Arg Pro Ala Ala His Gly Ala Gly Asn Pro Val
 65                  70                  75                  80

Gln Gly Arg Ser Gln Ala Cys Leu Arg Val Pro Leu Ala Arg Thr Glu
                85                  90                  95

Phe Thr Phe Ala Ala Met Pro Leu Val Phe Leu Pro Asp Ala Glu Thr
            100                 105                 110

Leu Phe Leu Trp Gly Pro Asp Arg Leu Pro Arg Glu Leu Ala Gly Leu
        115                 120                 125

Pro Glu Thr Gly Asp Arg Ala Ser Ala Leu Leu Val Thr Pro Glu Gly
130                 135                 140

Leu Arg Glu Cys Glu Gly His Gly Leu Pro Leu Ala Ala Thr Val Glu
145                 150                 155                 160

Arg Leu Ala Val Val Gln Thr Ser Glu Ala Glu Ser Phe Pro Gly Ser
                165                 170                 175

Ile Ala Leu Trp Thr Leu Ala Ser Lys Leu Ala Leu Glu Leu Val Ala
            180                 185                 190

Arg Glu Arg Val Val Pro Thr Leu Leu Arg Arg Gly Glu Arg Ile Glu
        195                 200                 205

Ala Arg Trp Ala Ala Ala Leu Ser Ala Thr Glu Asp Ala Gly Arg Val
210                 215                 220

Ala Ala Leu Ala Arg Ser Met Pro Pro Gly Ala His Ala Val Pro Ala
225                 230                 235                 240

Gly Ala Arg Pro Gly Arg Ala Val Trp Ala Pro Asp Ala Leu Leu Arg
                245                 250                 255

Ala Phe Leu Asp Ala Thr Val Asp Ala Phe Val Arg Ala Ala Arg Gly
            260                 265                 270

Ala Pro Ser Leu Pro Ala Arg Arg Ala Ala Ser Trp Asp Glu Arg Trp
        275                 280                 285

Arg Glu Ala Leu Thr Gly Ala Arg Arg Asp Phe Ala Pro Glu Gly Phe
    290                 295                 300

Ala Glu Arg Ser Val Val Asp Glu Leu Thr Arg Trp Ser Glu Pro Ala
305                 310                 315                 320

Leu Gly Ala Arg Asp Lys Leu Arg Ala Cys Phe Arg Leu Glu Pro Pro

```
                    325                 330                 335
Thr Glu Glu Arg Glu Pro Phe Val Leu Ser Phe His Leu Gln Ser Pro
                340                 345                 350

Asp Asp Pro Ser Leu Leu Val Pro Ala Ala Asp Val Trp Lys Thr Arg
                355                 360                 365

Gly Arg Ser Leu Glu Lys Leu Gly Arg Ala Phe Arg Asp Pro Gln Glu
                370                 375                 380

Ser Leu Leu Glu Ala Leu Gly Arg Ala Ala Arg Leu Phe Pro Pro Leu
385                 390                 395                 400

Ala Leu Val Leu Glu Ser Pro Arg Pro Gln Ala Leu Leu Leu Glu Pro
                405                 410                 415

Asp Thr Ala Trp Thr Phe Leu Ser Glu Gly Ala Arg Val Leu Ser Asp
                420                 425                 430

Ala Gly Phe Gly Val Ile Val Pro Gly Glu Leu Thr Thr Ser Gly Arg
                435                 440                 445

Arg Arg Leu Arg Leu Arg Met Arg Val Gly Ala Ser Thr Lys Ala Ala
                450                 455                 460

Gly Ala Val Gly Gly Thr Ala Gly Leu Gly Leu Asp Ala Leu Leu Arg
465                 470                 475                 480

Val Asp Trp Asp Ala Val Leu Gly Asp Gln Pro Leu Ser Ala Gln Glu
                485                 490                 495

Leu Ala Leu Leu Ala Gln Arg Lys Ala Pro Leu Val Arg Phe Arg Gly
                500                 505                 510

Glu Trp Val Ala Val Asp Pro Leu Glu Leu Asp Ala Ile Gln Arg His
                515                 520                 525

Leu Ala Gln Gly Pro Gly Arg Met Ala Leu Ser Glu Ala Val Arg Val
                530                 535                 540

Ser Leu Leu Gly Glu Thr Arg His Gly Gln Leu Pro Val Thr Val Leu
545                 550                 555                 560

Ala Thr Gly Ala Leu Glu Glu Arg Leu Arg Leu Leu Arg Glu Gly Gly
                565                 570                 575

Ala Thr Ala Gln Asp Ala Pro Arg Ala Leu Arg Ala Thr Leu Arg Pro
                580                 585                 590

Tyr Gln Ser Arg Gly Leu His Trp Leu Asp Thr Leu Ala Ser Leu Gly
                595                 600                 605

Leu Gly Ala Cys Leu Ala Asp Asp Met Gly Leu Gly Lys Thr Val Gln
                610                 615                 620

Val Leu Ala Phe Leu Leu Arg Arg Leu Glu Gln Ala Pro Asp Glu Ala
625                 630                 635                 640

Arg Pro Thr Leu Leu Val Ala Pro Thr Ser Val Val Gly Asn Trp Glu
                645                 650                 655

Arg Glu Leu Ala Arg Phe Ala Pro Thr Leu Arg Leu Thr Arg His Tyr
                660                 665                 670

Gly Ala Glu Arg Ala Arg Ala Ala Asn Arg Phe Pro Arg Ala Pro Gly
                675                 680                 685

Ala Val Val Leu Thr Thr Tyr Gly Leu Leu Arg Arg Asp Ala Ala Leu
                690                 695                 700

Leu Ala Arg Val Asp Trp Gly Ala Val Val Leu Asp Glu Ala Gln Asn
705                 710                 715                 720

Ile Lys Asn Ala Ala Ser Ala Thr Ala Arg Ala Ala Arg Ala Leu Arg
                725                 730                 735

Ala Ser Gln Arg Phe Ala Leu Thr Gly Thr Pro Val Glu Asn Arg Leu
                740                 745                 750
```

Ala Glu Leu Trp Ser Ile Leu Glu Phe Ala Asn Pro Gly Leu Leu Gly
       755                 760                 765

Pro Leu Glu Thr Phe Arg Arg Glu Leu Ala Leu Pro Ile Glu Arg His
    770                 775                 780

Gly Asn Gln Glu Ala Ser Ala Arg Leu Arg Arg Leu Val Ser Pro Phe
785                 790                 795                 800

Val Leu Arg Arg Leu Lys Ser Asp Pro Thr Ile Ile Thr Asp Leu Pro
                805                 810                 815

Ala Lys Asn Glu Met Lys Val Val Cys Thr Leu Thr Arg Glu Gln Ala
            820                 825                 830

Ser Leu Tyr Lys Ala Val Val Asp Glu Glu Leu Arg Arg Ile Glu Glu
        835                 840                 845

Ala Asp Gly Met Glu Arg Arg Gly Arg Val Leu Ala Leu Leu Leu Tyr
    850                 855                 860

Thr Lys Gln Ile Ala Asn His Pro Ala Gln Tyr Leu Gly Glu Ser Gly
865                 870                 875                 880

Pro Leu Pro Gly Arg Ser Gly Lys Leu Ala Arg Val Val Glu Met Leu
                885                 890                 895

Glu Glu Ser Leu Ala Ala Gly Asp Lys Ala Leu Val Phe Thr Gln Phe
            900                 905                 910

Arg Glu Met Gly Asp Lys Leu Val Ala His Leu Ser Glu Tyr Leu Gly
        915                 920                 925

His Glu Val Leu Phe Leu His Gly Gly Thr Pro Arg Lys Ala Arg Asp
    930                 935                 940

Glu Met Val Arg Arg Phe Gln Glu Asp Val His Gly Pro Arg Val Phe
945                 950                 955                 960

Val Leu Ser Val Lys Ala Gly Gly Thr Gly Leu Asn Leu Thr Ala Ala
                965                 970                 975

Ser His Val Phe His Tyr Asp Arg Trp Trp Asn Pro Ala Val Glu Asp
            980                 985                 990

Gln Ala Thr Asp Arg Ala Tyr Arg Ile Gly Gln Thr Arg Ala Val Gln
        995                 1000                1005

Val His Lys Leu Val Cys Ala Gly Thr Val Glu Glu Lys Val Asp
    1010                1015                1020

Arg Leu Leu Glu Gln Lys Arg Gln Leu Ala Glu Lys Val Val Gly
    1025                1030                1035

Ala Gly Glu His Trp Val Thr Glu Leu Asp Thr Thr Ala Leu Arg
    1040                1045                1050

Glu Leu Phe Ser Leu Ser Glu Gly Ala Val Ala Asp Asp Gly Asp
    1055                1060                1065

Ala Glu Gly Glu Asp Asp Ala Arg Val Arg Ala Pro Arg Arg Arg
    1070                1075                1080

Gly Arg Ala Ser Ala Lys Ala Val Ser Arg
    1085                1090

<210> SEQ ID NO 55
<211> LENGTH: 2871
<212> TYPE: DNA
<213> ORGANISM: Nocardia farcinica

<400> SEQUENCE: 55
atggtgggcg ccggcggccc gccgggtgtc ggtgccacct gcttggatgg acggatgctg    60
cacggactgt ggtcgccggg ttccggcctg gtgctgtgga ccgagggcga ggtgccgccc   120
gcgctgcccg accggccggg tgcgttgctg cgcgcatcgc ggttccggca tcgggcgcag   180

```
gtgctggtgc cgggccccgc cggcccacag ctcacgcagg tgcgcgcgca cgccctggtg      240
ccacaggccg cggtcgacgt gctgcggcag cggttacccg tcgaatcggt ggcgggtgac      300
ctgcgctttc tcgctcacgt cgccgacggg atcgatcggt gggtgcgggc cggtcgcgtg      360
gtgcccgacc tgcaccgggc cgacggacag tggtgggcgc gctggcggct ggtcggcggt      420
gcccggcagc gggcctggct ggccgaactc gcggtggcga tgcccgcggc gctgcgggtg      480
gccgggcagc ccgcggcgt gctcgacgat ctggtcaccg agctgaccga tccgatcgtg      540
cgcaccaggc tcgccgacgc gccggtgacg cacccgctgg tgcgcgcact ggtgcgggac      600
cagccgctcg agacgggtag ccaccagctg gccgaggtgc tgcggcgctg gcgcgagagc      660
ctcaccgtcg acgagccgga gctggtgttg cggctgctgg aaccggacgg ggagaccggt      720
atcgacgggg acgcggggga cgaccgggac gacaccgtgg cgctgtggcg gctggaggtc      780
tgcctccgca ccgagggcga ggccccggcc ccggtgccgg cgaccgccga cccgaacctg      840
ctgcgcatcg ccgtcgagca gctcggccgg gcgcagcggg cctaccccg gctgcgcgat      900 ctgcccggcg atccgcacag cctcgacctg ctgttgccca ccgaggtggt ggccgatctc      960
gtcgcgcacg tgcgcaggc gttgcgcgag gcggggggtgc ggctgctgct gccgcgcgcc     1020
tggaccatcg ccgaacccac cctgcggctc gcggtgagca gcgccgcgcc cgccgcggag     1080
agcaccgtgg gcatgcaggg tctgctgtcc tatcggtggg aactggccggt cggcgacaag     1140 gtgctcaccc gcgccgagat ggagcgcctg gtccgcgcca atccgacct ggtgcagttg      1200 cgcggggaat gggtgcaggc cgaccacaag gtgctcgccg ccgccgcccg ctacgtcgcc     1260
gcgcatctgg acacgtcgcc ggtcaccctc gccgacctgc tcggcgagat cgccgccacc     1320
cgcgtcgaca aggtgccgct caccgaggtc accgccaccg gctgggcggg cgagttgttc     1380
gacggcggcc gcgagccggt ggcgaccccg ggtgggctga aggcgcagct gcgcccgtat     1440
cagctgcgcg gcctgagctg gctggcgacg atgagccgga tgggctgcgg cggcatcctc     1500
gccgacgaca tgggtctcgg caagacggtg caggtgctgg ccctgctggt gcacgagcgc     1560
gagaccagca cggcaccgcc cggcccgaca ctgctggtgt gcccgatgtc ggtggtcggc     1620
aactggcagc gcgaggcgca gcggttcgcc cccgggctgc gggtgctggt gcaccacggc     1680
gccgaccgcc gtcgcgacgc cgaactcgat gccgcggtgg cggattcgga cctggtgctc     1740
accacctacg ccatcctggc cagggatgcg gccgaactgt cgcgccagtc gtgggaccgg     1800
gtggtgctcg acgaggcgca gcacatcaag aacgccgcga ccaggcaggc acgtgccgcc     1860
cgtgccctgc cggcccggca tcgcctggcg ctcaccggaa ccccggtgga gaaccggctc     1920
gaagagttgc gctcgatcat ggatttcgcg gtgcccaagc tgctcggtac cgcaccgacc     1980
ttccgcgccc ggttcgccgt ccccatcgaa cgcgggcagg atcccaacgc cctgtcccgc     2040
ctgcgcttcc tcacccaacc gttcgtgctg cgccgggtca aggccgatcc ggcggtcatc     2100
ggcgatctgc ccgacaagct cgagatgacg gtgcgggcga acctgaccgt cgagcaggcc     2160
gccctgtacc aagccgtcgt cgacgacatg ctggtgaaaac tgcgcagtgc caagggcatg     2220
gcccgcaagg gtgcggtgct cggcgcgctc accggctca gcaggtgtg caaccatccc      2280 gcgcacttcc tcggtgacgg ttccccggtg ctgcatcgcg gcaggcaccg ctccggcaag     2340
ctcgccttgg tcgaggacgt gctcgacacc gtcgtcgcgg acggggagaa ggcgttgctg     2400
ttcacccagt tccgtgagtt cggcgacctg ctcgcgccct atctgtccga gcggttcggc     2460
gcgccgatcc cgttcctgca cggcggcgtg accaagaaga accgggacac gatggtcgag     2520
cgcttccagt ccggcgacgg cccgccggtc atgctgctgt ccctcaaggc cggcggcacc     2580
```

-continued

```
gggctcaccc tcaccgccgc caatcacgtg gtgcacctgg atcgctggtg gaatccggcg    2640
gtggagaacc aggccaccga tcgcgccttc cgcatcggcc agcgccgcga cgtccaggtg    2700
cgcaagctgg tctgcgtcga caccatcgag gaacggatcg acgagatgat caccggcaag    2760
agcaggctcg cggacctggc cgtggacgcg ggggagaact ggatcaccga gctgggcacc    2820
gaggagctgc gcgagttgtt caccctcggc gccgaggcgg tgggggagtg a             2871
```

<210> SEQ ID NO 56
<211> LENGTH: 956
<212> TYPE: PRT
<213> ORGANISM: Nocardia farcinica

<400> SEQUENCE: 56

```
Met Val Gly Ala Gly Gly Pro Pro Val Gly Ala Thr Cys Leu Asp
1               5                   10                  15

Gly Arg Met Leu His Gly Leu Trp Ser Pro Gly Ser Gly Leu Val Leu
            20                  25                  30

Trp Thr Glu Gly Glu Val Pro Pro Ala Leu Pro Asp Pro Ala Gly Ala
            35                  40                  45

Leu Leu Arg Ala Ser Arg Phe Arg His Arg Ala Gln Val Leu Val Pro
50                  55                  60

Gly Pro Ala Gly Pro Gln Leu Thr Gln Val Arg Ala His Ala Leu Val
65                  70                  75                  80

Pro Gln Ala Ala Val Asp Val Leu Arg Gln Arg Leu Pro Val Glu Ser
                85                  90                  95

Val Ala Gly Asp Leu Arg Phe Leu Ala His Val Ala Asp Gly Ile Asp
            100                 105                 110

Arg Trp Val Arg Ala Gly Arg Val Val Pro Asp Leu His Arg Ala Asp
            115                 120                 125

Gly Gln Trp Trp Ala Arg Trp Arg Leu Val Gly Gly Ala Arg Gln Arg
        130                 135                 140

Ala Trp Leu Ala Glu Leu Ala Val Ala Met Pro Ala Ala Leu Arg Val
145                 150                 155                 160

Ala Gly Gln Pro Ala Ala Val Leu Asp Asp Leu Val Thr Glu Leu Thr
                165                 170                 175

Asp Pro Ile Val Arg Thr Arg Leu Ala Asp Ala Pro Val Thr His Pro
            180                 185                 190

Leu Val Arg Ala Leu Val Arg Asp Gln Pro Leu Glu Thr Gly Ser His
            195                 200                 205

Gln Leu Ala Glu Val Leu Arg Arg Trp Arg Glu Ser Leu Thr Val Asp
        210                 215                 220

Glu Pro Glu Leu Val Leu Arg Leu Leu Glu Pro Asp Gly Glu Thr Gly
225                 230                 235                 240

Ile Asp Gly Asp Gly Gly Asp Arg Asp Asp Thr Val Ala Leu Trp
            245                 250                 255

Arg Leu Glu Val Cys Leu Arg Thr Glu Gly Glu Ala Pro Ala Pro Val
                260                 265                 270

Pro Ala Thr Ala Asp Pro Asn Leu Leu Arg Ile Ala Val Glu Gln Leu
            275                 280                 285

Gly Arg Ala Gln Arg Ala Tyr Pro Arg Leu Arg Asp Leu Pro Gly Asp
        290                 295                 300

Pro His Ser Leu Asp Leu Leu Leu Pro Thr Glu Val Val Ala Asp Leu
305                 310                 315                 320

Val Ala His Gly Ala Gln Ala Leu Arg Glu Ala Gly Val Arg Leu Leu
                325                 330                 335
```

```
Leu Pro Arg Ala Trp Thr Ile Ala Glu Pro Thr Leu Arg Leu Ala Val
            340                 345                 350

Ser Ser Ala Ala Pro Ala Ala Glu Ser Thr Val Gly Met Gln Gly Leu
            355                 360                 365

Leu Ser Tyr Arg Trp Glu Leu Ala Val Gly Asp Lys Val Leu Thr Arg
            370                 375                 380

Ala Glu Met Glu Arg Leu Val Arg Ala Lys Ser Asp Leu Val Gln Leu
385                 390                 395                 400

Arg Gly Glu Trp Val Gln Ala Asp His Lys Val Leu Ala Ala Ala
                405                 410                 415

Arg Tyr Val Ala Ala His Leu Asp Thr Ser Pro Val Thr Leu Ala Asp
                420                 425                 430

Leu Leu Gly Glu Ile Ala Ala Thr Arg Val Asp Lys Val Pro Leu Thr
            435                 440                 445

Glu Val Thr Ala Thr Gly Trp Ala Gly Glu Leu Phe Asp Gly Gly Arg
        450                 455                 460

Glu Pro Val Ala Thr Pro Gly Gly Leu Lys Ala Gln Leu Arg Pro Tyr
465                 470                 475                 480

Gln Leu Arg Gly Leu Ser Trp Leu Ala Thr Met Ser Arg Met Gly Cys
                485                 490                 495

Gly Gly Ile Leu Ala Asp Asp Met Gly Leu Gly Lys Thr Val Gln Val
            500                 505                 510

Leu Ala Leu Leu Val His Glu Arg Glu Thr Ser Thr Ala Pro Pro Gly
            515                 520                 525

Pro Thr Leu Leu Val Cys Pro Met Ser Val Val Gly Asn Trp Gln Arg
            530                 535                 540

Glu Ala Gln Arg Phe Ala Pro Gly Leu Arg Val Leu Val His His Gly
545                 550                 555                 560

Ala Asp Arg Arg Arg Asp Ala Glu Leu Asp Ala Ala Val Ala Asp Ser
                565                 570                 575

Asp Leu Val Leu Thr Thr Tyr Ala Ile Leu Ala Arg Asp Ala Ala Glu
            580                 585                 590

Leu Ser Arg Gln Ser Trp Asp Arg Val Val Leu Asp Glu Ala Gln His
            595                 600                 605

Ile Lys Asn Ala Ala Thr Arg Gln Ala Arg Ala Arg Ala Leu Pro
            610                 615                 620

Ala Arg His Arg Leu Ala Leu Thr Gly Thr Pro Val Glu Asn Arg Leu
625                 630                 635                 640

Glu Glu Leu Arg Ser Ile Met Asp Phe Ala Val Pro Lys Leu Leu Gly
                645                 650                 655

Thr Ala Pro Thr Phe Arg Ala Arg Phe Ala Val Pro Ile Glu Arg Gly
            660                 665                 670

Gln Asp Pro Asn Ala Leu Ser Arg Leu Arg Phe Leu Thr Gln Pro Phe
            675                 680                 685

Val Leu Arg Arg Val Lys Ala Asp Pro Ala Val Ile Gly Asp Leu Pro
            690                 695                 700

Asp Lys Leu Glu Met Thr Val Arg Ala Asn Leu Thr Val Glu Gln Ala
705                 710                 715                 720

Ala Leu Tyr Gln Ala Val Val Asp Asp Met Leu Val Lys Leu Arg Ser
                725                 730                 735

Ala Lys Gly Met Ala Arg Lys Gly Ala Val Leu Gly Ala Leu Thr Arg
            740                 745                 750

Leu Lys Gln Val Cys Asn His Pro Ala His Phe Leu Gly Asp Gly Ser
```

|     |     |     |     |     |     |     |     |     |     |     |     |
| --- | --- | --- | --- | --- | --- | --- | --- | --- | --- | --- | --- |
|     |     |     | 755 |     |     | 760 |     |     |     | 765 |     |
| Pro | Val | Leu | His | Arg | Gly | Arg | His | Arg | Ser | Gly | Lys | Leu | Ala | Leu | Val |
| 770 |     |     |     |     | 775 |     |     |     |     | 780 |     |

Pro Val Leu His Arg Gly Arg His Arg Ser Gly Lys Leu Ala Leu Val
770                     775                     780

Glu Asp Val Leu Asp Thr Val Val Ala Asp Gly Glu Lys Ala Leu Leu
785                     790                     795                 800

Phe Thr Gln Phe Arg Glu Phe Gly Asp Leu Leu Ala Pro Tyr Leu Ser
            805                     810                     815

Glu Arg Phe Gly Ala Pro Ile Pro Phe Leu His Gly Gly Val Thr Lys
                820                     825                 830

Lys Asn Arg Asp Thr Met Val Glu Arg Phe Gln Ser Gly Asp Gly Pro
                835                 840                     845

Pro Val Met Leu Leu Ser Leu Lys Ala Gly Gly Thr Gly Leu Thr Leu
850                     855                     860

Thr Ala Ala Asn His Val His Leu Asp Arg Trp Trp Asn Pro Ala
865                 870                     875                 880

Val Glu Asn Gln Ala Thr Asp Arg Ala Phe Arg Ile Gly Gln Arg Arg
                885                     890                     895

Asp Val Gln Val Arg Lys Leu Val Cys Val Asp Thr Ile Glu Glu Arg
                900                     905                     910

Ile Asp Glu Met Ile Thr Gly Lys Ser Arg Leu Ala Asp Leu Ala Val
            915                     920                     925

Asp Ala Gly Glu Asn Trp Ile Thr Glu Leu Gly Thr Glu Glu Leu Arg
930                     935                     940

Glu Leu Phe Thr Leu Gly Ala Glu Ala Val Gly Glu
945                     950                 955

<210> SEQ ID NO 57
<211> LENGTH: 3264
<212> TYPE: DNA
<213> ORGANISM: Nodularia spumigena

<400> SEQUENCE: 57

```
atggcaattt tacacggtaa ttggttagta agaaatcaaa atggttgttt atttatttgg      60
ggtgaaactt ggcgttcatc acgagtcgat tttgctctga atgtatctca agatatacca     120
ctacatccat tggtaatgtc accaattgat ttgagtgagt tgttaagtta tcataatatc     180
aaaattccta gcttaataca gcaatcccaa gttgctttat ctggcactgg gcgaactcgt     240
aaaagtacaa gtactactaa atttagctgg acaactcact ctctaatcat tgatttacca     300
actcatatct cagaaaataa tccccaagaa atagaattta tttcccctttt gcattctgct     360
actttgggtt ctgaaataaa ttcaccccaa tatctccaac cgtggcgagt cgagggtttt     420
tgtctcaacc ccactgaagc gataaaattt ctcgctgctg ttcctttaaa tgctgctaga     480
gaagaagata ctttgttcgg tggagattta cgttttggt cacaaattgc ccgttggagt     540
ttggatttaa tctctcggtg taagttttg ccaactattc aaagacagtt tgatagttct     600
attgttgcta ggtggcaagt gcttttagac agtgcaatag atggaacacg cctggaaaaa     660
tttttctgcaa aaatgccatt agcttgtcgt acttatcgga agggaatggg gagtggggag     720
tggggagtgg ggagtgggga ggaatcttcc ccatccataa tgtatgtaga ttttccaact     780
gaaccccagg aactattatt aggatttctc aacagtacca tagatgccca agtgcgagaa     840
atgttagctt ctcaacctct actagaaact agagtgatgg catctttacc atctgcggtg     900
cgacagtggt tgcaaggttt aaccagtgca tctcacacag tgaatgcaga tgcaatggaa     960
gtagaaagat tagaagcagc cctgaaatct tggactatgc cgttgcaata tcaactggta    1020
```

```
ggaaaaccct cgtttcgcgc ctgttttcaa ctgcttcccc ctgcttctgg ggcaacagat    1080
tggatattgg catattttct ccaagctgcg gatgatgaaa atttattagt ggatgcggca    1140
actatttggc atcacccagt tgaacaatta gtttatcaaa atcgcaccat tgatcaaccc    1200
caagaaactt tattgcgggg cttgggttta gcttcgcgat tatatccagt tcttacaccg    1260
agtttagaaa cagaatatcc ccaatgttgt cgcctcaacc cattacaagc ttatgaattt    1320
atcaagtctg tagcttggcg atttgaagat agtggtttgg gggtaatttt acctcctagt    1380
ttgactaacc gcgaaggatg ggcgaaccgt ttggggttaa aaattagtgc tgaaactcaa    1440
aagaaaaaac agggacgctt gggtttacaa agtttactga attttcaatg caattggca    1500
attggtggac aaacaatttc taaaaccgag tttaataaac tggtagcttt aaatagccca    1560
ctggtagaaa ttaacggcga atgggtggaa ttgcgacccc aggatattaa aacagcacag    1620
acattttttg cttctcgtaa agacgaaatg acgctttctt tggaagatgc tttacgcctc    1680
agttctggcg atacccaagc gattgaaaag ttacctgtgg tcagttttga agcatctggg    1740
acattgcaag agttaattgg ggcgttaacc aataatcaag ccatttcacc cctcccaaca    1800
cctgcaaatt ttcaaggaca gttacgacct tatcaagaaa gagggcggc ttggctggct    1860
ttcttagaac gttgggggttt aggtgcttgt ttggctgatg atatgggct gggaaaaaca    1920
attcagttaa ttgccttttt actgcacctc aaagaacaag acgcactgga aaatcccaca    1980
ttacttgttt gtccgacttc tattttaggt aactgggaac gggaaattaa aaatttgct    2040
cctactctca aagttttaca gcaccacggc gataaacgtc tcaaaggtaa agcgtttgta    2100
gaagcagtca aaaaacacga tgtaattatt accagttact cactcgttca ccgggatatt    2160
aaatctttgc agagtgtcga ttggcaaaca gttgtattag atgaagccca gaatgtgaaa    2220
aatcctgaag ctaaacaatc gcaggctgtg aggggattaa aaactacatt tcgcatagct    2280
ttaacaggga caccagtaga aaacaaactg caagaattgt ggtctatttt agattttctt    2340
aatcctgggt atttgggaaa tcgtcaattt ttccagagac ggtttgctat gccaattgaa    2400
aagtatggtg atacagcatc tttaaatcaa ttgcggggtt tagttcaacc gtttattcta    2460
cgtcgtctga aaacagatcg tgatattatt caagatttgc cagaaaagca agaaatgacg    2520
gttttttgtg ggcttgcggc tgaacaagct gcactttatc aacaagtagt tgaagcatct    2580
ttagtagaaa ttgaatctgc tgaggttttg caacgtcgag ggatgatttt agcttactt    2640
gtgaaactta acaaatctg taatcatcca gcccaatatt tgaaagccgc gacattacaa    2700
gaacatagtt ctgctaaact gcaacggcta gatgaaatgt taacggtagc tttggaggaa    2760
ggagataggg ctttaatttt cactcaattt gctgaatggg gtaagttatt aaaagctcat    2820
ttacaacaaa cacttgggaa agaaatattc tttttatatg gtggtagcag taaaaaacaa    2880
cgcgaggaaa tgattgaccg tttccaacat gaccccaag gacctccgat tatgattctt    2940
tctttaaaag cgggtggggt aggcttgaat ttaaccaggg ctaatcatgt atttcacttt    3000
gatagatggt ggaatcccgc agtggaaaat caagcgacag atagagtatt tcgtattggt    3060
caaacccgga atgtgcaagt gcataaattt gtctgtactg gcacattaga agaaaaaatt    3120
catgacatga ttgaaagtaa aaaacaatta gcggaacaag tagttggtgc tggtgaggag    3180
tggctgactg aaatgaatac tgaccaattg cgtgatttac tcattcttga tcgcagtgcc    3240
ataattgatg aggatgaagt ttaa                                            3264
```

<210> SEQ ID NO 58
<211> LENGTH: 1087
<212> TYPE: PRT

<213> ORGANISM: Nodularia spumigena

<400> SEQUENCE: 58

```
Met Ala Ile Leu His Gly Asn Trp Leu Val Arg Asn Gln Asn Gly Cys
1               5                   10                  15

Leu Phe Ile Trp Gly Glu Thr Trp Arg Ser Ser Arg Val Asp Phe Ala
            20                  25                  30

Leu Asn Val Ser Gln Asp Ile Pro Leu His Pro Leu Val Met Ser Pro
                35                  40                  45

Ile Asp Leu Ser Glu Leu Leu Ser Tyr His Asn Ile Lys Ile Pro Ser
            50                  55                  60

Leu Ile Gln Gln Ser Gln Val Ala Leu Ser Gly Thr Gly Arg Thr Arg
65                  70                  75                  80

Lys Ser Thr Ser Thr Thr Lys Phe Ser Trp Thr Thr His Ser Leu Ile
                85                  90                  95

Ile Asp Leu Pro Thr His Ile Ser Glu Asn Asn Pro Gln Glu Ile Glu
            100                 105                 110

Phe Ile Ser Pro Leu His Ser Ala Thr Leu Gly Ser Glu Ile Asn Ser
        115                 120                 125

Pro Gln Tyr Leu Gln Pro Trp Arg Val Glu Gly Phe Cys Leu Asn Pro
130                 135                 140

Thr Glu Ala Ile Lys Phe Leu Ala Ala Val Pro Leu Asn Ala Ala Arg
145                 150                 155                 160

Glu Glu Asp Thr Leu Phe Gly Gly Asp Leu Arg Phe Trp Ser Gln Ile
                165                 170                 175

Ala Arg Trp Ser Leu Asp Leu Ile Ser Arg Cys Lys Phe Leu Pro Thr
            180                 185                 190

Ile Gln Arg Gln Phe Asp Ser Ser Ile Val Ala Arg Trp Gln Val Leu
        195                 200                 205

Leu Asp Ser Ala Ile Asp Gly Thr Arg Leu Glu Lys Phe Ser Ala Lys
210                 215                 220

Met Pro Leu Ala Cys Arg Thr Tyr Arg Lys Gly Met Gly Ser Gly Glu
225                 230                 235                 240

Trp Gly Val Gly Ser Gly Glu Ser Ser Pro Ser Ile Met Tyr Val
                245                 250                 255

Asp Phe Pro Thr Glu Pro Gln Glu Leu Leu Gly Phe Leu Asn Ser
            260                 265                 270

Thr Ile Asp Ala Gln Val Arg Glu Met Leu Ala Ser Gln Pro Leu Leu
        275                 280                 285

Glu Thr Arg Val Met Ala Ser Leu Pro Ser Ala Val Arg Gln Trp Leu
290                 295                 300

Gln Gly Leu Thr Ser Ala Ser His Thr Val Asn Ala Asp Ala Met Glu
305                 310                 315                 320

Val Glu Arg Leu Glu Ala Ala Leu Lys Ser Trp Thr Met Pro Leu Gln
                325                 330                 335

Tyr Gln Leu Val Gly Lys Pro Ser Phe Arg Ala Cys Phe Gln Leu Leu
            340                 345                 350

Pro Pro Ala Ser Gly Ala Thr Asp Trp Ile Leu Ala Tyr Phe Leu Gln
        355                 360                 365

Ala Ala Asp Asp Glu Asn Leu Leu Val Asp Ala Thr Ile Trp His
    370                 375                 380

His Pro Val Glu Gln Leu Val Tyr Gln Asn Arg Thr Ile Asp Gln Pro
385                 390                 395                 400

Gln Glu Thr Leu Leu Arg Gly Leu Gly Leu Ala Ser Arg Leu Tyr Pro
```

-continued

```
                    405                 410                 415
Val Leu Thr Pro Ser Leu Glu Thr Glu Tyr Pro Gln Cys Cys Arg Leu
                420                 425                 430

Asn Pro Leu Gln Ala Tyr Glu Phe Ile Lys Ser Val Ala Trp Arg Phe
            435                 440                 445

Glu Asp Ser Gly Leu Gly Val Ile Leu Pro Pro Ser Leu Thr Asn Arg
        450                 455                 460

Glu Gly Trp Ala Asn Arg Leu Gly Leu Lys Ile Ser Ala Glu Thr Gln
465                 470                 475                 480

Lys Lys Lys Gln Gly Arg Leu Gly Leu Gln Ser Leu Leu Asn Phe Gln
                485                 490                 495

Trp Gln Leu Ala Ile Gly Gly Gln Thr Ile Ser Lys Thr Glu Phe Asn
            500                 505                 510

Lys Leu Val Ala Leu Asn Ser Pro Leu Val Glu Ile Asn Gly Glu Trp
        515                 520                 525

Val Glu Leu Arg Pro Gln Asp Ile Lys Thr Ala Gln Thr Phe Phe Ala
    530                 535                 540

Ser Arg Lys Asp Glu Met Thr Leu Ser Leu Glu Asp Ala Leu Arg Leu
545                 550                 555                 560

Ser Ser Gly Asp Thr Gln Ala Ile Glu Lys Leu Pro Val Val Ser Phe
                565                 570                 575

Glu Ala Ser Gly Thr Leu Gln Glu Leu Ile Gly Ala Leu Thr Asn Asn
            580                 585                 590

Gln Ala Ile Ser Pro Leu Pro Thr Pro Ala Asn Phe Gln Gly Gln Leu
        595                 600                 605

Arg Pro Tyr Gln Glu Arg Gly Ala Ala Trp Leu Ala Phe Leu Glu Arg
    610                 615                 620

Trp Gly Leu Gly Ala Cys Leu Ala Asp Asp Met Gly Leu Gly Lys Thr
625                 630                 635                 640

Ile Gln Leu Ile Ala Phe Leu Leu His Leu Lys Glu Gln Asp Ala Leu
                645                 650                 655

Glu Asn Pro Thr Leu Leu Val Cys Pro Thr Ser Ile Leu Gly Asn Trp
            660                 665                 670

Glu Arg Glu Ile Lys Lys Phe Ala Pro Thr Leu Lys Val Leu Gln His
        675                 680                 685

His Gly Asp Lys Arg Leu Lys Gly Lys Ala Phe Val Glu Ala Val Lys
    690                 695                 700

Lys His Asp Val Ile Thr Ser Tyr Ser Leu Val His Arg Asp Ile
705                 710                 715                 720

Lys Ser Leu Gln Ser Val Asp Trp Gln Thr Val Val Leu Asp Glu Ala
                725                 730                 735

Gln Asn Val Lys Asn Pro Glu Ala Lys Gln Ser Gln Ala Val Arg Gly
            740                 745                 750

Leu Lys Thr Thr Phe Arg Ile Ala Leu Thr Gly Thr Pro Val Glu Asn
        755                 760                 765

Lys Leu Gln Glu Leu Trp Ser Ile Leu Asp Phe Leu Asn Pro Gly Tyr
    770                 775                 780

Leu Gly Asn Arg Gln Phe Phe Gln Arg Phe Ala Met Pro Ile Glu
785                 790                 795                 800

Lys Tyr Gly Asp Thr Ala Ser Leu Asn Gln Leu Arg Gly Leu Val Gln
                805                 810                 815

Pro Phe Ile Leu Arg Arg Leu Lys Thr Asp Arg Asp Ile Ile Gln Asp
            820                 825                 830
```

-continued

```
Leu Pro Glu Lys Gln Glu Met Thr Val Phe Cys Gly Leu Ala Ala Glu
        835                 840                 845

Gln Ala Ala Leu Tyr Gln Gln Val Val Glu Ala Ser Leu Val Glu Ile
    850                 855                 860

Glu Ser Ala Glu Gly Leu Gln Arg Arg Gly Met Ile Leu Ala Leu Leu
865                 870                 875                 880

Val Lys Leu Lys Gln Ile Cys Asn His Pro Ala Gln Tyr Leu Lys Ala
                885                 890                 895

Ala Thr Leu Gln Glu His Ser Ser Ala Lys Leu Gln Arg Leu Asp Glu
        900                 905                 910

Met Leu Thr Val Ala Leu Glu Glu Gly Asp Arg Ala Leu Ile Phe Thr
    915                 920                 925

Gln Phe Ala Glu Trp Gly Lys Leu Leu Lys Ala His Leu Gln Gln Thr
    930                 935                 940

Leu Gly Lys Glu Ile Phe Phe Leu Tyr Gly Gly Ser Ser Lys Lys Gln
945                 950                 955                 960

Arg Glu Glu Met Ile Asp Arg Phe Gln His Asp Pro Gln Gly Pro Pro
                965                 970                 975

Ile Met Ile Leu Ser Leu Lys Ala Gly Gly Val Gly Leu Asn Leu Thr
        980                 985                 990

Arg Ala Asn His Val Phe His Phe Asp Arg Trp Trp Asn Pro Ala Val
    995                 1000                1005

Glu Asn Gln Ala Thr Asp Arg Val Phe Arg Ile Gly Gln Thr Arg
    1010                1015                1020

Asn Val Gln Val His Lys Phe Val Cys Thr Gly Thr Leu Glu Glu
    1025                1030                1035

Lys Ile His Asp Met Ile Glu Ser Lys Lys Gln Leu Ala Glu Gln
    1040                1045                1050

Val Val Gly Ala Gly Glu Glu Trp Leu Thr Glu Met Asn Thr Asp
    1055                1060                1065

Gln Leu Arg Asp Leu Leu Ile Leu Asp Arg Ser Ala Ile Ile Asp
    1070                1075                1080

Glu Asp Glu Val
    1085

<210> SEQ ID NO 59
<211> LENGTH: 3228
<212> TYPE: DNA
<213> ORGANISM: Nostoc sp.

<400> SEQUENCE: 59
atggcaattc tacacggtag ttggatatta aatgagcagg agagttgttt atttatttgg      60
ggggaaactt ggcgatcgcc acaagtggat tttaattttg cggagatatc cctcaatccc     120
ttggcgctgt ctgcactgga attaagtgag tggttgcagt ctcaacatca ggcgatcgct     180
aagttgttac cgcaacaatt ggaaaaacga acctccaaag cagcaagttc tgtaaaaata     240
aatttattaa ctcattcaca ataattgcc ctgccaacgg aaatttccca acctcgtaaa     300
aaagaaacca ttttaatttc tcctgtgcat tctgccgctt tagcatctga gtcagactct     360
gaagtttatt tacaaacttg gcgtgtagaa ggttttttgtc ttcctcctag tgcagcaatt     420
aaattgctaa cttcttttacc tttaaatata actagtgggg agaatgcttt ttaggtgga      480 gatttacgtt tctggtcaca aattgcccgt tggagtttag atttaatttc taggtctaag     540
tttctcccaa ttatccaacg acaacctaat aattctgtaa gtgctaaatg caagtacttt     600
ttagatagtg ccgtagatgg aactcgttta gaaaagtttg ctgcgaagat gcccttggtt     660
```

```
tgtcggactt atcaagaaat tgggagtggg gaatctccta tatatataga ttttcctagt    720
cagccgcagg atttaatctt gggttttctc aatagtgcga tagatacgca attgcgggag    780
atggtgggga atcagcctgt ggtggaaact cggttgatgg catctttacc atcggcggtg    840
cgacagtggt tgcaagcgtt aattgctgca tctaattcaa ttgatgcaga tgctgttggt    900
ttagaaaggc tggaagcggc gctcaaggct tggacgatgc cgctacaata tcaactagca    960
agtaaaaatc aatttcgcac ttgttttgaa ttacgttctc cagaaccaga cgaaactgaa   1020
tggacgctgg cgtatttcct gcaagcagcc gatgatccag aattttttagt agatgcggcg   1080 actatttggc aaaatcctgt tgaacagcta atttatcaac agcgaacgat tgaagaaccc   1140
caggaaacgt ttttgcgagg tttggggtta gcttctcgat tgtatccggt cattgccccc   1200
actttagata cagaatcacc ccaattttgt catctcaagc ccatgcaggc ttatgaattt   1260
atcaaggctg tggcttggcg atttgaagat agcggcttag gggtgatttt acctcctagt   1320
ttggcgaatc gtgaaggctg gcaaatcgc ttgggtttga aaatctccgc cgaaacgccg   1380
aagaaaaaac caggacgctt aggattgcag agtttgctca atttccaatg cacttagcg    1440 attggtgggc aaactatttc taaagctgaa tttgacagac tggtagcttt aaaaagccca   1500
ttggtagaaa ttaacggcga gtgggtggaa ttacgtcccc aagatatcaa aacagctgaa   1560 gccttttta ctgcgcgtaa agaccaaatg gccttatctt tagaagatgc cttacgtcta    1620
agtagtggcg atacacaagt aattgagaaa ttaccagtag tcagctttga agcctctggc   1680
gcattacaag aattgattgg ggcgctgaca aataatcaag cagttgcacc attacctacg   1740
ccgaaaaact tccaaggaca gttacgtcct tatcaagaaa ggggtgcggc ttggttggcg   1800
ttcctcgaac gctgggggttt aggtgcttgt ctcgccgacg acatgggact gggaaaaacg   1860
atacagttca ttgctttcct tctccatctt aaagaacagg atgtattaga aaaaccaact   1920
ttactagtgt gtcctacttc tgttttaggt aactgggaac gagaggtgag aaaatttgca   1980
cctacactta agttctcca gtatcatggt gacaaacgtc ctaaaggtaa agcatttcaa    2040
gaagcagtaa aaaacatga tttagttatt acaagttact cattaattca tagagatatc   2100
aaatcattgc agggtattcc ttggcaaata attgttttag atgaagccca aatgtgaag   2160 aatgcggaag ccaaacaatc acaagcagtc agacaattag aaacaacatt tcgtattgct   2220
ttaacaggta caccagtaga aaatagacta caagaacttt ggtcaatttt agattttctt   2280
aatcctggtt acttaggtaa taagcaattc tttcaaagac gttttgctat gccaattgaa   2340
aagtatggtg atgcagcatc tttaaatcaa ttgcgtgctt tagtgcaacc atttattctg   2400
cgtcggctga aaacagaccg tgatattatt caagacttgc ccgataagca agaaatgaca   2460
gtattttgtg gtttgactgg agaacaagct gcactttatc aaaaagcggt agaaacatct   2520
ttagcagaaa ttgaatcagc cgaaggattg caacgccgag ggatgatttt agctttatta   2580
attaaactca aacaaatctg caatcatcca gcccaatatc tgaaaataaa tacattagaa   2640
caacacagtt ctggaaaact gcaaagatta gaagaaatgt tagaagaggt gttagcagag   2700
agtaatactt acggtgttgc cggtgcggga cgtgctttga tttttacccca atttcagaaa   2760 tggggtaagt tactcaaacc acatttagaa aaacaactag gcgggaaat attttttctta   2820 tatggtggta cgagtaaaaa gcaacgagaa gaaatgattg accgttttca acacgacccc   2880
caagggccac caattatgat tctctccctc aaagcaggtg tgtagggtt gaacttaacc    2940 agggcaaatc atgtatttca ctttgataga tggtggaatc cagccgtaga gaatcaagct   3000
acagaccgcg tatttcgcat tggtcaaact cgcaatgtac aggtgcataa atttgtttgt   3060
```

```
aatggcacct tagaagagaa aattcacgac atgattgaaa gtaaaaaaca actagcggaa    3120
caggttgttg gagcaggcga agaatggtta actgaattag atacagatca actccgcaac    3180
ttactgatac ttgatcgtag tacagtaatt gatgaagaag cagattga                 3228
```

<210> SEQ ID NO 60
<211> LENGTH: 1075
<212> TYPE: PRT
<213> ORGANISM: Nostoc sp.

<400> SEQUENCE: 60

```
Met Ala Ile Leu His Gly Ser Trp Ile Leu Asn Glu Gln Glu Ser Cys
1               5                   10                  15

Leu Phe Ile Trp Gly Glu Thr Trp Arg Ser Pro Gln Val Asp Phe Asn
            20                  25                  30

Phe Ala Glu Ile Ser Leu Asn Pro Leu Ala Leu Ser Ala Leu Glu Leu
        35                  40                  45

Ser Glu Trp Leu Gln Ser Gln His Gln Ala Ile Ala Lys Leu Leu Pro
    50                  55                  60

Gln Gln Leu Glu Lys Arg Thr Ser Lys Ala Ala Ser Val Lys Ile
65                  70                  75                  80

Asn Leu Leu Thr His Ser Gln Ile Ile Ala Leu Pro Thr Glu Ile Ser
                85                  90                  95

Gln Pro Arg Lys Lys Glu Thr Ile Leu Ile Ser Pro Val His Ser Ala
            100                 105                 110

Ala Leu Ala Ser Glu Ser Asp Ser Glu Val Tyr Leu Gln Thr Trp Arg
        115                 120                 125

Val Glu Gly Phe Cys Leu Pro Pro Ser Ala Ala Ile Lys Leu Leu Thr
    130                 135                 140

Ser Leu Pro Leu Asn Ile Thr Ser Gly Glu Asn Ala Phe Leu Gly Gly
145                 150                 155                 160

Asp Leu Arg Phe Trp Ser Gln Ile Ala Arg Trp Ser Leu Asp Leu Ile
                165                 170                 175

Ser Arg Ser Lys Phe Leu Pro Ile Ile Gln Arg Gln Pro Asn Asn Ser
            180                 185                 190

Val Ser Ala Lys Trp Gln Val Leu Leu Asp Ser Ala Val Asp Gly Thr
        195                 200                 205

Arg Leu Glu Lys Phe Ala Ala Lys Met Pro Leu Val Cys Arg Thr Tyr
    210                 215                 220

Gln Glu Ile Gly Ser Gly Ser Pro Ile Tyr Ile Asp Phe Pro Ser
225                 230                 235                 240

Gln Pro Gln Asp Leu Ile Leu Gly Phe Leu Asn Ser Ala Ile Asp Thr
                245                 250                 255

Gln Leu Arg Glu Met Val Gly Asn Gln Pro Val Val Glu Thr Arg Leu
            260                 265                 270

Met Ala Ser Leu Pro Ser Ala Val Arg Gln Trp Leu Gln Ala Leu Ile
        275                 280                 285

Ala Ala Ser Asn Ser Ile Asp Ala Asp Ala Val Gly Leu Glu Arg Leu
    290                 295                 300

Glu Ala Ala Leu Lys Ala Trp Thr Met Pro Leu Gln Tyr Gln Leu Ala
305                 310                 315                 320

Ser Lys Asn Gln Phe Arg Thr Cys Phe Glu Leu Arg Ser Pro Glu Pro
                325                 330                 335

Asp Glu Thr Glu Trp Thr Leu Ala Tyr Phe Leu Gln Ala Ala Asp Asp
            340                 345                 350
```

```
Pro Glu Phe Leu Val Asp Ala Ala Thr Ile Trp Gln Asn Pro Val Glu
            355                 360                 365
Gln Leu Ile Tyr Gln Gln Arg Thr Ile Glu Glu Pro Gln Glu Thr Phe
        370                 375                 380
Leu Arg Gly Leu Gly Leu Ala Ser Arg Leu Tyr Pro Val Ile Ala Pro
385                 390                 395                 400
Thr Leu Asp Thr Glu Ser Pro Gln Phe Cys His Leu Lys Pro Met Gln
                405                 410                 415
Ala Tyr Glu Phe Ile Lys Ala Val Ala Trp Arg Phe Glu Asp Ser Gly
            420                 425                 430
Leu Gly Val Ile Leu Pro Pro Ser Leu Ala Asn Arg Glu Gly Trp Ala
        435                 440                 445
Asn Arg Leu Gly Leu Lys Ile Ser Ala Glu Thr Pro Lys Lys Lys Pro
    450                 455                 460
Gly Arg Leu Gly Leu Gln Ser Leu Leu Asn Phe Gln Trp His Leu Ala
465                 470                 475                 480
Ile Gly Gly Gln Thr Ile Ser Lys Ala Glu Phe Asp Arg Leu Val Ala
                485                 490                 495
Leu Lys Ser Pro Leu Val Glu Ile Asn Gly Glu Trp Val Glu Leu Arg
            500                 505                 510
Pro Gln Asp Ile Lys Thr Ala Glu Ala Phe Phe Thr Ala Arg Lys Asp
        515                 520                 525
Gln Met Ala Leu Ser Leu Glu Asp Ala Leu Arg Leu Ser Ser Gly Asp
    530                 535                 540
Thr Gln Val Ile Glu Lys Leu Pro Val Val Ser Phe Glu Ala Ser Gly
545                 550                 555                 560
Ala Leu Gln Glu Leu Ile Gly Ala Leu Thr Asn Asn Gln Ala Val Ala
                565                 570                 575
Pro Leu Pro Thr Pro Lys Asn Phe Gln Gly Gln Leu Arg Pro Tyr Gln
            580                 585                 590
Glu Arg Gly Ala Ala Trp Leu Ala Phe Leu Glu Arg Trp Gly Leu Gly
        595                 600                 605
Ala Cys Leu Ala Asp Asp Met Gly Leu Gly Lys Thr Ile Gln Phe Ile
    610                 615                 620
Ala Phe Leu Leu His Leu Lys Glu Gln Asp Val Leu Glu Lys Pro Thr
625                 630                 635                 640
Leu Leu Val Cys Pro Thr Ser Val Leu Gly Asn Trp Glu Arg Glu Val
                645                 650                 655
Arg Lys Phe Ala Pro Thr Leu Lys Val Leu Gln Tyr His Gly Asp Lys
            660                 665                 670
Arg Pro Lys Gly Lys Ala Phe Gln Glu Ala Val Lys Lys His Asp Leu
        675                 680                 685
Val Ile Thr Ser Tyr Ser Leu Ile His Arg Asp Ile Lys Ser Leu Gln
    690                 695                 700
Gly Ile Pro Trp Gln Ile Ile Val Leu Asp Glu Ala Gln Asn Val Lys
705                 710                 715                 720
Asn Ala Glu Ala Lys Gln Ser Gln Ala Val Arg Gln Leu Glu Thr Thr
                725                 730                 735
Phe Arg Ile Ala Leu Thr Gly Thr Pro Val Glu Asn Arg Leu Gln Glu
            740                 745                 750
Leu Trp Ser Ile Leu Asp Phe Leu Asn Pro Gly Tyr Leu Gly Asn Lys
        755                 760                 765
Gln Phe Phe Gln Arg Arg Phe Ala Met Pro Ile Glu Lys Tyr Gly Asp
```

```
              770                 775                 780
Ala Ala Ser Leu Asn Gln Leu Arg Ala Leu Val Gln Pro Phe Ile Leu
785                 790                 795                 800

Arg Arg Leu Lys Thr Asp Arg Asp Ile Ile Gln Asp Leu Pro Asp Lys
                805                 810                 815

Gln Glu Met Thr Val Phe Cys Gly Leu Thr Gly Glu Gln Ala Ala Leu
                820                 825                 830

Tyr Gln Lys Ala Val Glu Thr Ser Leu Ala Glu Ile Ser Ala Glu
                835                 840                 845

Gly Leu Gln Arg Arg Gly Met Ile Leu Ala Leu Leu Ile Lys Leu Lys
850                 855                 860

Gln Ile Cys Asn His Pro Ala Gln Tyr Leu Lys Ile Asn Thr Leu Glu
865                 870                 875                 880

Gln His Ser Ser Gly Lys Leu Gln Arg Leu Glu Glu Met Leu Glu Glu
                885                 890                 895

Val Leu Ala Glu Ser Asn Thr Tyr Gly Val Gly Ala Gly Arg Ala
                900                 905                 910

Leu Ile Phe Thr Gln Phe Ala Glu Trp Gly Lys Leu Leu Lys Pro His
                915                 920                 925

Leu Glu Lys Gln Leu Gly Arg Glu Ile Phe Phe Leu Tyr Gly Gly Thr
930                 935                 940

Ser Lys Lys Gln Arg Glu Met Ile Asp Arg Phe Gln His Asp Pro
945                 950                 955                 960

Gln Gly Pro Pro Ile Met Ile Leu Ser Leu Lys Ala Gly Gly Val Gly
                965                 970                 975

Leu Asn Leu Thr Arg Ala Asn His Val Phe His Phe Asp Arg Trp Trp
                980                 985                 990

Asn Pro Ala Val Glu Asn Gln Ala  Thr Asp Arg Val Phe Arg Ile Gly
                995                 1000                1005

Gln Thr Arg Asn Val Gln Val  His Lys Phe Val Cys  Asn Gly Thr
                1010                1015                1020

Leu Glu Glu Lys Ile His Asp  Met Ile Glu Ser Lys  Lys Gln Leu
                1025                1030                1035

Ala Glu Gln Val Val Gly Ala  Gly Glu Glu Trp Leu  Thr Glu Leu
                1040                1045                1050

Asp Thr Asp Gln Leu Arg Asn  Leu Leu Ile Leu Asp  Arg Ser Thr
                1055                1060                1065

Val Ile Asp Glu Glu Ala Asp
                1070                1075

<210> SEQ ID NO 61
<211> LENGTH: 3168
<212> TYPE: DNA
<213> ORGANISM: Nostoc sp.

<400> SEQUENCE: 61
atgaaagtcc ttcatggctc gtggatacca aaccaatata gcgatttgt  gcagtctgga      60 gcattttatc tatgggtaga aactccgatt aataacaaaa agcgtactca tacacaagtt     120
catcccggac atctatcttc tcttgaatta ctcaattttc tgactcaaac tttggggatt     180
aaagaaactg aagcgcaatt aaaacaacgg atatgttcta atattttgc  cctaccaact     240 gctaataatg agccattacc ttcaccagag ttagtcaaat atttagaagt agaagttcct     300
gaagagtatg aaaattttca atattggcag gtaacttgtt atgaaactgt tacttctgtg     360
aaagcagtga tagcaattaa tattattaaa ttactcaaag atattcattt tttagccctg     420
```

-continued

| | |
|---|---|
| tacaatgcta gtgaatttca attagggtca gatttattat tttggtatca ttatacgcaa | 480 |
| tcatttagac aaataattac taaggatcaa tatattccat ctttaaaata tagagcgaac | 540 |
| gcagcgacta caaagaaaaa acctaaacaa ccaccccag gatttgaaat atatgctggt | 600 |
| tgggaaataa tttccgagca atacgaagcc aatattcaaa aatatattga atatatgcca | 660 |
| ttgatttgtg tagcaggtaa cagcacacaa actgataaat tagaatttttt tgctccagaa | 720 |
| actctattac gccacttcag cgagtatctg cttaataatt tagtgagtaa dacaccattg | 780 |
| accgcagcat ttgaaaaaca aattgatgat tctttaattc actattgtct ttatccccaa | 840 |
| aaacacaacc cactcaaaac ccatactgct ctccaagagt atcagcagtg gttgggatgg | 900 |
| aaaaacagga ttatccgtac tcaagctgaa tcaccatttc atctttgctt ccaattacat | 960 |
| tcacctgatg ctgaacaaat tgacaattgg cagatgcaat ttttagtatc aagtaaaaaa | 1020 |
| gatccgtctc taaaattagc tttggcagat tactggataa tgaattccaa aaccaaagct | 1080 |
| ggtgtacata aagagtttgg caaagatttc gatactaatt tactgctgaa tttaggctat | 1140 |
| gcagcaagaa tgtatcccaa actttggcaa ggtttagaaa cggactctcc cacaggaatg | 1200 |
| cagctaagtt tagatgaggc gttgatttt ctcaaagata gtgcttgggt gttggaagac | 1260 |
| tcaggattta aggtcattgt cccggcttgg tatactccgg ctggtcgtcg tcgtgcgaaa | 1320 |
| atccgcctca aagcttctag tggtcgcaag gtagctgcta cggtagggga aagcaaaagt | 1380 |
| tatttcggtt tagattcact agtgcagtat cagtatgaat tagcaattgg agagcaaact | 1440 |
| ctcacacctc aagaatggga acaattgatt aatactaaag caccactagt gcattttcgc | 1500 |
| ggtcaatgga tggaattaga ccgggataaa atgcagcagt tattagaatt ttggcagtcc | 1560 |
| cacggcgatg aacagcccca aatgagcttg ttagagttca tgcaacgcag cgcccaaggg | 1620 |
| gaagatgact gggaaattga atatgatgca gctttatcag aaataatggc aaagttacaa | 1680 |
| gataagagtc agctagagcc aatttctgaa gacttaaatt tgcaaggcaa cctgcgagaa | 1740 |
| tatcaaaagc ggggtgtagc ctggttacaa tatttagaaa aattgggatt aaatggctgt | 1800 |
| ttagccgatg atatgggact gggtaagtcc gtgcaggtaa ttgcgagatt agtacaggag | 1860 |
| aaagatagcc aaagttcccc attaccgaca ttattaattg cgccgacttc ggttgttggt | 1920 |
| aactggcaaa gagaaattgc taagtttgca ccccattaa aaactatggt gcatcatggt | 1980 |
| agcgatcgcc tgcaagatgc tgcggagttt aagtccgcct gtcaacagca tgatgtggtg | 2040 |
| ataagttcct ttactttggc tcgcttagat gaaaaactcc taaatagtgt gacatggcaa | 2100 |
| cggttagttt tagatgaagc acaaaacatt aaaaatccca aagcagcgca gactaaagct | 2160 |
| atactcaaac tcagtgctaa acaccgtcta gctttaactg gtacaccagt tgagaaccgc | 2220 |
| ttacttgatt tgtggtcaat ttttaatttt ctcaatcccg gttatttagg gaagaagca | 2280 |
| cagtttcgca aatcctttga aattcccatc cagaaggaca acgataaagt aaaatcgact | 2340 |
| accttaaaga aactggttga accgttaatt ttacgacggg tcaaaacaga ccaatcaatt | 2400 |
| attaaagact taccagataa agttgaacaa aaactctata ccaacctcac caaagaacag | 2460 |
| gcttcgctat atgaagtggt agtcagagat gtggaagaaa aattgcaaga agctgaggga | 2520 |
| atacaacgca aaggtttaat tctctcaacg ctgatgaaat taaaacagat ttgcaatcat | 2580 |
| cccagacagt tcctccaaga taatagcgaa tttttaccgg agcgctcgca caaactttcc | 2640 |
| cgcttagtcg aaatggtaga tgaagccatt tctgaaggag aaagtctttt aatatttagt | 2700 |
| caatttacag aagtctgcga acaaatagaa aaatatctca acacaacttt acattgcaat | 2760 |
| acctactacc tacatggggg tacaagtcgc caacgtcggg aacaaatgat tagtgactt | 2820 |

-continued

```
caaaatcctg atacggaagc atctgtattt gtcctttccc taaaagctgg cggcgtgggg    2880
attactttaa ctaaagccaa ccacgtcttt cattttgacc gttggtggaa tccagccgtt    2940
gaagaccaag ccacagaccg cgcttttcgc ataggtcaga aaaaaaatgt gtttgtacat    3000
aaatttgtcg cccttgggac tttagaagaa agaatcgacc aaatgattga agataagaaa    3060
aaactttctt ccgccgtagt tggtagtgat gaatcgtggc taaccgaatt agataacgaa    3120
gcctttaaga aactaattgc cttgaataaa agcacaatta tggagtag                 3168
```

<210> SEQ ID NO 62
<211> LENGTH: 1055
<212> TYPE: PRT
<213> ORGANISM: Nostoc sp.

<400> SEQUENCE: 62

```
Met Lys Val Leu His Gly Ser Trp Ile Pro Asn Gln Tyr Ser Asp Phe
 1               5                  10                  15

Val Gln Ser Gly Ala Phe Tyr Leu Trp Val Glu Thr Pro Ile Asn Asn
             20                  25                  30

Lys Lys Arg Thr His Thr Gln Val His Pro Gly His Leu Ser Ser Leu
         35                  40                  45

Glu Leu Leu Asn Phe Leu Thr Gln Thr Leu Gly Ile Lys Glu Thr Glu
     50                  55                  60

Ala Gln Leu Lys Gln Arg Ile Cys Ser Lys Tyr Phe Ala Leu Pro Thr
 65                  70                  75                  80

Ala Asn Asn Glu Pro Leu Pro Ser Pro Glu Leu Val Lys Tyr Leu Glu
                 85                  90                  95

Val Glu Val Pro Glu Glu Tyr Glu Asn Phe Gln Tyr Trp Gln Val Thr
            100                 105                 110

Cys Tyr Glu Thr Val Thr Ser Val Lys Ala Val Ile Ala Ile Asn Ile
        115                 120                 125

Ile Lys Leu Leu Lys Asp Ile His Phe Leu Ala Leu Tyr Asn Ala Ser
    130                 135                 140

Glu Phe Gln Leu Gly Ser Asp Leu Leu Phe Trp Tyr His Tyr Thr Gln
145                 150                 155                 160

Ser Phe Arg Gln Ile Ile Thr Lys Asp Gln Tyr Ile Pro Ser Leu Lys
                165                 170                 175

Tyr Arg Ala Asn Ala Ala Thr Thr Lys Lys Lys Pro Lys Gln Pro Pro
            180                 185                 190

Pro Gly Phe Glu Ile Tyr Ala Gly Trp Glu Ile Ile Ser Glu Gln Tyr
        195                 200                 205

Glu Ala Asn Ile Gln Lys Tyr Ile Glu Tyr Met Pro Leu Ile Cys Val
    210                 215                 220

Ala Gly Asn Ser Thr Gln Thr Asp Lys Leu Glu Phe Phe Ala Pro Glu
225                 230                 235                 240

Thr Leu Leu Arg His Phe Ser Glu Tyr Leu Leu Asn Asn Leu Val Ser
                245                 250                 255

Lys Thr Pro Leu Thr Ala Ala Phe Glu Lys Gln Ile Asp Asp Ser Leu
            260                 265                 270

Ile His Tyr Cys Leu Tyr Pro Gln Lys His Asn Pro Leu Lys Thr His
        275                 280                 285

Thr Ala Leu Gln Glu Tyr Gln Gln Trp Leu Gly Trp Lys Asn Arg Ile
    290                 295                 300

Ile Arg Thr Gln Ala Glu Ser Pro Phe His Leu Cys Phe Gln Leu His
305                 310                 315                 320
```

```
Ser Pro Asp Ala Glu Gln Ile Asp Asn Trp Gln Met Gln Phe Leu Val
            325                 330                 335

Ser Ser Lys Lys Asp Pro Ser Leu Lys Leu Ala Leu Ala Asp Tyr Trp
            340                 345                 350

Ile Met Asn Ser Lys Thr Lys Ala Gly Val His Lys Glu Phe Gly Lys
            355                 360                 365

Asp Phe Asp Thr Asn Leu Leu Leu Asn Leu Gly Tyr Ala Ala Arg Met
            370                 375                 380

Tyr Pro Lys Leu Trp Gln Gly Leu Glu Thr Asp Ser Pro Thr Gly Met
385                 390                 395                 400

Gln Leu Ser Leu Asp Glu Ala Phe Asp Phe Leu Lys Asp Ser Ala Trp
                405                 410                 415

Val Leu Glu Asp Ser Gly Phe Lys Val Ile Val Pro Ala Trp Tyr Thr
                420                 425                 430

Pro Ala Gly Arg Arg Ala Lys Ile Arg Leu Lys Ala Ser Ser Gly
                435                 440                 445

Arg Lys Val Ala Ala Thr Val Gly Glu Ser Lys Ser Tyr Phe Gly Leu
450                 455                 460

Asp Ser Leu Val Gln Tyr Gln Tyr Glu Leu Ala Ile Gly Glu Gln Thr
465                 470                 475                 480

Leu Thr Pro Gln Glu Trp Glu Gln Leu Ile Asn Thr Lys Ala Pro Leu
                485                 490                 495

Val His Phe Arg Gly Gln Trp Met Glu Leu Asp Arg Asp Lys Met Gln
                500                 505                 510

Gln Leu Leu Glu Phe Trp Gln Ser His Gly Asp Glu Gln Pro Gln Met
                515                 520                 525

Ser Leu Leu Glu Phe Met Gln Arg Ser Ala Gln Gly Glu Asp Asp Trp
                530                 535                 540

Glu Ile Glu Tyr Asp Ala Ala Leu Ser Glu Ile Met Ala Lys Leu Gln
545                 550                 555                 560

Asp Lys Ser Gln Leu Glu Pro Ile Ser Glu Asp Leu Asn Leu Gln Gly
                565                 570                 575

Asn Leu Arg Glu Tyr Gln Lys Arg Gly Val Ala Trp Leu Gln Tyr Leu
                580                 585                 590

Glu Lys Leu Gly Leu Asn Gly Cys Leu Ala Asp Met Gly Leu Gly
            595                 600                 605

Lys Ser Val Gln Val Ile Ala Arg Leu Val Gln Glu Lys Asp Ser Gln
            610                 615                 620

Ser Ser Pro Leu Pro Thr Leu Leu Ile Ala Pro Thr Ser Val Val Gly
625                 630                 635                 640

Asn Trp Gln Arg Glu Ile Ala Lys Phe Ala Pro His Leu Lys Thr Met
                645                 650                 655

Val His His Gly Ser Asp Arg Leu Gln Asp Ala Ala Glu Phe Lys Ser
                660                 665                 670

Ala Cys Gln Gln His Asp Val Val Ile Ser Ser Phe Thr Leu Ala Arg
            675                 680                 685

Leu Asp Glu Lys Leu Leu Asn Ser Val Thr Trp Gln Arg Leu Val Leu
            690                 695                 700

Asp Glu Ala Gln Asn Ile Lys Asn Pro Lys Ala Ala Gln Thr Lys Ala
705                 710                 715                 720

Ile Leu Lys Leu Ser Ala Lys His Arg Leu Ala Leu Thr Gly Thr Pro
                725                 730                 735

Val Glu Asn Arg Leu Leu Asp Leu Trp Ser Ile Phe Asn Phe Leu Asn
```

```
                       740               745                750
Pro Gly Tyr Leu Gly Lys Glu Ala Gln Phe Arg Lys Ser Phe Glu Ile
                755                760               765
Pro Ile Gln Lys Asp Asn Asp Lys Val Lys Ser Thr Thr Leu Lys Lys
        770               775               780
Leu Val Glu Pro Leu Ile Leu Arg Arg Val Lys Thr Asp Gln Ser Ile
785               790               795               800
Ile Lys Asp Leu Pro Asp Lys Val Glu Gln Lys Leu Tyr Thr Asn Leu
                805               810               815
Thr Lys Glu Gln Ala Ser Leu Tyr Glu Val Val Arg Asp Val Glu
        820               825               830
Glu Lys Leu Gln Glu Ala Glu Gly Ile Gln Arg Lys Gly Leu Ile Leu
        835               840               845
Ser Thr Leu Met Lys Leu Lys Gln Ile Cys Asn His Pro Arg Gln Phe
        850               855               860
Leu Gln Asp Asn Ser Glu Phe Leu Pro Glu Arg Ser His Lys Leu Ser
865               870               875               880
Arg Leu Val Glu Met Val Asp Glu Ala Ile Ser Glu Gly Glu Ser Leu
                885               890               895
Leu Ile Phe Ser Gln Phe Thr Glu Val Cys Glu Gln Ile Glu Lys Tyr
                900               905               910
Leu Lys His Asn Leu His Cys Asn Thr Tyr Tyr Leu His Gly Gly Thr
                915               920               925
Ser Arg Gln Arg Arg Glu Gln Met Ile Ser Asp Phe Gln Asn Pro Asp
        930               935               940
Thr Glu Ala Ser Val Phe Val Leu Ser Leu Lys Ala Gly Gly Val Gly
945               950               955               960
Ile Thr Leu Thr Lys Ala Asn His Val Phe His Phe Asp Arg Trp Trp
                965               970               975
Asn Pro Ala Val Glu Asp Gln Ala Thr Asp Arg Ala Phe Arg Ile Gly
                980               985               990
Gln Lys Lys Asn Val Phe Val His Lys Phe Val Ala Leu Gly Thr Leu
                995               1000              1005
Glu Glu Arg Ile Asp Gln Met Ile Glu Asp Lys Lys Leu Ser
        1010              1015              1020
Ser Ala Val Val Gly Ser Asp Glu Ser Trp Leu Thr Glu Leu Asp
        1025              1030              1035
Asn Glu Ala Phe Lys Lys Leu Ile Ala Leu Asn Lys Ser Thr Ile
        1040              1045              1050
Met Glu
    1055

<210> SEQ ID NO 63
<211> LENGTH: 2856
<212> TYPE: DNA
<213> ORGANISM: Nostoc punctiforme

<400> SEQUENCE: 63
atggcgattt tacacagtaa ttggttacta aaaagtcaaa aaggttgttt atttatttgg      60
ggagaaactt ggcgatcgcc acgagttaat ttcgagtcta atggatctgg agatatccca     120
ctaaatccat tggcaatgac atcactagag ttgagcgagt ggttggtttc ccagaagatg     180
gccattacca actttatcca gcaaccccaa attgccatcg ctactactgg gcgaacacgt     240
aaagcagcca ctgccactga gataaactta ccaacgcatt cacaaataat tgccttacca     300
```

```
acttatattc ccgaagagag tgcagaagga acatctgcaa ttttccctgt gcattctgcc       360
agcttgagac tagaaacaga ctctccgcaa tatttgcaac cgtggctagt tgagggtttt       420
tgtcttaacc ccagcgaagc agtaaaattt ctcgctgctg ttcccctgaa tgctgctaaa       480
ggggaagatg cttttttagg aggagattta cgttttggt cgcaagtttc ccgatggagt        540
ttagatttaa tctcgcggtg taagttttta ccaagaattg aacggcaatc agacggtgca       600
tttgctgcta aatggcaagt acttctagac agtgctgtag atggaactcg cctagaaaag       660
ttttctgcgg atatgccgtt ggtttgccgc acttatcagg agggagtggg gactggggac       720
tggggactga ggactgggga ggagttttcc caatccctaa tccctaattc ccaatcccta       780
ctttatgtaa acttccctac tgaacctcaa gaattgttgc tgggatttct caacagtacg       840
atagatgccc aagtgcgagg gatggtgggt tctcagcctc caatggaagc taaggcaatg       900
gcatctttac catctggggt gcggcagtgg ttgcaaggct tgactagtac atctggtaca       960
gttaacgcag atgccattga agtggaacga ctggaagcgg cactgaaggc ttggatgatg      1020
ccgctacaat accaattaac tcttaaaact ctatttcgta cctgttttca actgcgttct      1080
ccagaagctg gcgaaacaga ttggacattg gcgtattttc tgcaagcggc tgacgatcct      1140
gattttttgg tggatgcggc aactatttgg aacaatccag ttgaacgttt ggtttatgaa      1200
aatcgaacaa ttgagcaacc acaggaaaca tttttgcgag gtttaggggt agcttcccga      1260
ttatatccag cgatcgcacc cagttttgaa accgaatatc cccaatcttc tcggatcaca      1320
cccatgcaag cttatgagtt tatcaaggct gtagcttgga ggttggaaga cagtggtttg      1380
ggggtaattt tgcctcctag tttagcgaac cgcgaaggat gggcaaatcg tttgggtttg      1440
aaaattactg ctgaaacccc aagaaaaag cagggacgtt tagggttgca agtctgctg       1500 aatttccaat ggcaattggc aattggcgga cagactattt ccaaagctga gtttgataaa      1560
cttgtggctt taaatagtcc actagtgaaa attaacggtg agtgggtaga attgcggccc      1620
caagatatca agacagccca aacatttttt accactcgca aagaccaaat ggcgctttcc      1680
ttggaagatg ccttgcgttt cagtacagga gatacccagg taattgaaaa attaccagtg      1740
gtcagctttg aggcatctgg ggcattgcaa gagttgattg gggcgctaaa taataatcaa      1800
gcgatcgcac cttaccgac accagtaggc tttaaaggac agttgcgacc ttatcaagaa       1860
cgtggtgctg cttggctgtc cttcttggaa cgttggggct taggcgcgtg tctcgccgac      1920
gatatgggac tcggtaaaac tattcagttt attgcttttt tgctacatct taaagaacag      1980
gatgcactag aaaattcaac actgctagtt tgtccaactt ctgttttagg caactgggaa      2040
agggaagtca ataaatttgc accaagcctg aaaattttgc aatatcacgg tgacaaacgt      2100
ccaaaaggga agcgtttttt agaagcagtg aaaaatcacg atttaatcgt taccagctac      2160
tcactgcttc atcgggatat caagtcattg caaagtgttc cttggcagat aattgtttta      2220
gacgaagccc agaatgtgaa aaatccgag gcgaagcagt caaaagctgt gcggcaatta       2280
gaagctacat ttcgcattgc attaacgggg acaccagtag aaaatagact gcaagaacta      2340
tggtctattt tggattttct caatccaggg tatttaggta ataagcaatt tttccagcgg      2400
cggtttgcca tgccaattga aaagtatggt gatacggctt ctttgggtca attacgttca      2460
ttagttcagc catttatact gcggcgatta aaaagcgatc gcgaaattat tcaagacttg      2520
ccagataagc aagagatgac cgtatttgc ggtttaactg ccgaccaagc tgcactttat        2580
caacaagttg tagaacaatc tttagtagag atagaatctg ctgaaggatt gcaacgtcgg      2640
gggatgattt tggctttgct aatcaaactg aagcaaatct gcaatcatcc agcccaatat      2700
```

-continued

```
ttgaaacagg cgacattaga gcaacataat tcagccaaac ttctgcggct agaagaaatg   2760
ttagaagaag tttttagcaga aagtgaccgg gctttaatct ttacacaatt tgcagagtgg   2820
ggtaagttac ttaaacccaa aagtgttgaa tgttaa                              2856
```

<210> SEQ ID NO 64
<211> LENGTH: 951
<212> TYPE: PRT
<213> ORGANISM: Nostoc punctiforme

<400> SEQUENCE: 64

```
Met Ala Ile Leu His Ser Asn Trp Leu Leu Lys Ser Gln Lys Gly Cys
1               5                   10                  15

Leu Phe Ile Trp Gly Glu Thr Trp Arg Ser Pro Arg Val Asn Phe Glu
            20                  25                  30

Ser Asn Gly Ser Gly Asp Ile Pro Leu Asn Pro Leu Ala Met Thr Ser
        35                  40                  45

Leu Glu Leu Ser Glu Trp Leu Val Ser Gln Lys Met Ala Ile Thr Asn
    50                  55                  60

Phe Ile Gln Gln Pro Gln Ile Ala Ile Ala Thr Thr Gly Arg Thr Arg
65                  70                  75                  80

Lys Ala Ala Thr Ala Thr Glu Ile Asn Leu Pro Thr His Ser Gln Ile
                85                  90                  95

Ile Ala Leu Pro Thr Tyr Ile Pro Glu Glu Ser Ala Glu Gly Thr Ser
            100                 105                 110

Ala Ile Phe Pro Val His Ser Ala Ser Leu Arg Leu Glu Thr Asp Ser
        115                 120                 125

Pro Gln Tyr Leu Gln Pro Trp Leu Val Glu Gly Phe Cys Leu Asn Pro
    130                 135                 140

Ser Glu Ala Val Lys Phe Leu Ala Ala Val Pro Leu Asn Ala Ala Lys
145                 150                 155                 160

Gly Glu Asp Ala Phe Leu Gly Gly Asp Leu Arg Phe Trp Ser Gln Val
                165                 170                 175

Ser Arg Trp Ser Leu Asp Leu Ile Ser Arg Cys Lys Phe Leu Pro Arg
            180                 185                 190

Ile Glu Arg Gln Ser Asp Gly Ala Phe Ala Ala Lys Trp Gln Val Leu
        195                 200                 205

Leu Asp Ser Ala Val Asp Gly Thr Arg Leu Glu Lys Phe Ser Ala Asp
    210                 215                 220

Met Pro Leu Val Cys Arg Thr Tyr Gln Glu Gly Val Gly Thr Gly Asp
225                 230                 235                 240

Trp Gly Leu Arg Thr Gly Glu Glu Phe Ser Gln Ser Leu Ile Pro Asn
                245                 250                 255

Ser Gln Ser Leu Leu Tyr Val Asn Phe Pro Thr Glu Pro Gln Glu Leu
            260                 265                 270

Leu Leu Gly Phe Leu Asn Ser Thr Ile Asp Ala Gln Val Arg Gly Met
        275                 280                 285

Val Gly Ser Gln Pro Pro Met Glu Ala Lys Ala Met Ala Ser Leu Pro
    290                 295                 300

Ser Gly Val Arg Gln Trp Leu Gln Gly Leu Thr Ser Thr Ser Gly Thr
305                 310                 315                 320

Val Asn Ala Asp Ala Ile Glu Val Glu Arg Leu Glu Ala Ala Leu Lys
                325                 330                 335

Ala Trp Met Met Pro Leu Gln Tyr Gln Leu Thr Leu Lys Thr Leu Phe
            340                 345                 350
```

```
Arg Thr Cys Phe Gln Leu Arg Ser Pro Glu Ala Gly Glu Thr Asp Trp
        355                 360                 365

Thr Leu Ala Tyr Phe Leu Gln Ala Ala Asp Asp Pro Asp Phe Leu Val
370                 375                 380

Asp Ala Ala Thr Ile Trp Asn Asn Pro Val Glu Arg Leu Val Tyr Glu
385                 390                 395                 400

Asn Arg Thr Ile Glu Gln Pro Gln Glu Thr Phe Leu Arg Gly Leu Gly
                405                 410                 415

Val Ala Ser Arg Leu Tyr Pro Ala Ile Ala Pro Ser Phe Glu Thr Glu
                420                 425                 430

Tyr Pro Gln Ser Ser Arg Ile Thr Pro Met Gln Ala Tyr Glu Phe Ile
            435                 440                 445

Lys Ala Val Ala Trp Arg Leu Glu Asp Ser Gly Leu Gly Val Ile Leu
450                 455                 460

Pro Pro Ser Leu Ala Asn Arg Glu Gly Trp Ala Asn Arg Leu Gly Leu
465                 470                 475                 480

Lys Ile Thr Ala Glu Thr Pro Lys Lys Gln Gly Arg Leu Gly Leu
                485                 490                 495

Gln Ser Leu Leu Asn Phe Gln Trp Gln Leu Ala Ile Gly Gly Gln Thr
            500                 505                 510

Ile Ser Lys Ala Glu Phe Asp Lys Leu Val Ala Leu Asn Ser Pro Leu
    515                 520                 525

Val Glu Ile Asn Gly Glu Trp Val Glu Leu Arg Pro Gln Asp Ile Lys
530                 535                 540

Thr Ala Gln Thr Phe Phe Thr Thr Arg Lys Asp Gln Met Ala Leu Ser
545                 550                 555                 560

Leu Glu Asp Ala Leu Arg Phe Ser Thr Gly Asp Thr Gln Val Ile Glu
                565                 570                 575

Lys Leu Pro Val Val Ser Phe Glu Ala Ser Gly Ala Leu Gln Glu Leu
                580                 585                 590

Ile Gly Ala Leu Asn Asn Asn Gln Ala Ile Ala Pro Leu Pro Thr Pro
            595                 600                 605

Val Gly Phe Lys Gly Gln Leu Arg Pro Tyr Gln Glu Arg Gly Ala Ala
610                 615                 620

Trp Leu Ser Phe Leu Glu Arg Trp Gly Leu Gly Ala Cys Leu Ala Asp
625                 630                 635                 640

Asp Met Gly Leu Gly Lys Thr Ile Gln Phe Ile Ala Phe Leu Leu His
                645                 650                 655

Leu Lys Glu Gln Asp Ala Leu Glu Asn Ser Thr Leu Leu Val Cys Pro
                660                 665                 670

Thr Ser Val Leu Gly Asn Trp Glu Arg Glu Val Asn Lys Phe Ala Pro
            675                 680                 685

Ser Leu Lys Ile Leu Gln Tyr His Gly Asp Lys Arg Pro Lys Gly Lys
    690                 695                 700

Ala Phe Leu Glu Ala Val Lys Asn His Asp Leu Ile Val Thr Ser Tyr
705                 710                 715                 720

Ser Leu Leu His Arg Asp Ile Lys Ser Leu Gln Ser Val Pro Trp Gln
                725                 730                 735

Ile Ile Val Leu Asp Glu Ala Gln Asn Val Lys Asn Pro Glu Ala Lys
                740                 745                 750

Gln Ser Lys Ala Val Arg Gln Leu Glu Ala Thr Phe Arg Ile Ala Leu
            755                 760                 765

Thr Gly Thr Pro Val Glu Asn Arg Leu Gln Glu Leu Trp Ser Ile Leu
770                 775                 780
```

```
Asp Phe Leu Asn Pro Gly Tyr Leu Gly Asn Lys Gln Phe Gln Arg
785                 790                 795                 800

Arg Phe Ala Met Pro Ile Glu Lys Tyr Gly Asp Thr Ala Ser Leu Gly
                805                 810                 815

Gln Leu Arg Ser Leu Val Gln Pro Phe Ile Leu Arg Arg Leu Lys Ser
            820                 825                 830

Asp Arg Glu Ile Ile Gln Asp Leu Pro Asp Lys Gln Glu Met Thr Val
        835                 840                 845

Phe Cys Gly Leu Thr Ala Asp Gln Ala Ala Leu Tyr Gln Gln Val Val
    850                 855                 860

Glu Gln Ser Leu Val Glu Ile Glu Ser Ala Glu Gly Leu Gln Arg Arg
865                 870                 875                 880

Gly Met Ile Leu Ala Leu Leu Ile Lys Leu Lys Gln Ile Cys Asn His
                885                 890                 895

Pro Ala Gln Tyr Leu Lys Gln Ala Thr Leu Glu Gln His Asn Ser Ala
            900                 905                 910

Lys Leu Leu Arg Leu Glu Glu Met Leu Glu Glu Val Leu Ala Glu Ser
        915                 920                 925

Asp Arg Ala Leu Ile Phe Thr Gln Phe Ala Glu Trp Gly Lys Leu Leu
    930                 935                 940

Lys Pro Lys Ser Val Glu Cys
945                 950

<210> SEQ ID NO 65
<211> LENGTH: 3024
<212> TYPE: DNA
<213> ORGANISM: Pelodictyon phaeoclathratiforme

<400> SEQUENCE: 65
atgattgcgc tgcacatctc catcattgac ggagtcccgc tactctggag tgagggaaaa      60
aagatcggga tgctgaagga gttacgcctc gcaacggctg gaatcggcat gttttccctg     120
ctcgacaaca ccacaaaaga gttttgtgtc tggctgccct gccgcgagaa aaaagctgtc     180
ccatcatctc cgcttgtcgg cgccatgccc gacctgagtg atgaagagca actccatgcc     240
tttccgatta ccgcgcttcg gctgaatttc aacgctctgt cgagctttc cctgcttacg      300 gaaaagggca catccccgg cagtggcatc atcttcggaa gctctctcca ctgggcacgg      360
caggtagtaa aaattgcact gaacattgtc agaaccccagt cgctgctccc ttcgatcatc    420
aaaaacgata cattctggga ggccttgtgg ttgcccctcc ccgacagtgc cacatccctc     480
gcagttgaac agcttgccga tgccatgcct gcggtctgtc gctctctcgg ccgcaccgac     540
acgcaaccgc cggaaacacc aaaaaagtta ctgctcaaag gacttctctc tttccttgtc     600
aatacactgt cacgtacttt tgaaagagca ggggtgccaa aaatcagtga cttcgagagt     660
atccatgacg cgtggcttca tgcattatca acagtgatc cccggctgaa atggaaaaat      720
gagcaggaga ttgagcagtt tgcctgtcag ctcaacgcat ggcggcgtcc cattgacctg     780
catgagcgat cacccttcag gttttgcctg caactgacag agccaccact gaaagggcgg     840
aaaaaggagc gctggcatgt tgcctatcaa ctgcagttga agcggatcc aagcctgatt      900 cttgacgccg ggatctctg gaaccccgaa agcgaggcat cacagcacgc tttaacgtat     960
acctccgatt gtaccgaatt cctgcttact tccctgggac aagcctccgg cctctgcccc    1020
gcagtcaccc aaagcctgaa aaagaagcag ccgggtggct tgatcttga taccgaaggg   1080 gcttacagat ttttgctgga gtatgcgaa ctgttgcgaa gcgcaggatt tgtggtcaag     1140
```

```
cttccctcgt ggtggatcgg tcgcagagga gtcaaccgta tcgggatcaa gacaaaagtg    1200
aagcttccct ctatgaaagg aagcgggtcg ggtctcacgc tggatcgcat ggttgcctgc    1260
gattatgctg ctgcacttgg caatgaggag cttgacctgc aggagctgaa aacactggca    1320
aacctgaaag ttccgctggt acgggtcgcg gacagtgga cacagattga ccataaggag     1380
cttgccaatg ctctccattt tcttgaaaaa catccaactg gtgaactttc tgccagagaa    1440
ctcctctcaa cagctctcgg agcacaaaaa aaggaggatg ctctctttct tcgatcggtt    1500
gaaatcgagg ggtggcttca ggaactgctt gaaaaacttt cctctcaggg acaatttgaa    1560
ctgcttccac cacctgagca tttcgaggga acgcttcgcc tctatcagga gcgaggcttt    1620
tcatggctct catttctccg caagtgggga ctgggcgcct gtcttgccga cgacatgggc    1680
cttggcaaaa ccattcagac gcttgcactg ctgcagcggg agcgtgaact ggagaaaaa    1740 agggcggtgc tcctgatctg ccccacctct gtagtcaaca actggcgaaa ggaggcggag    1800
cggttcactc cggatttagc ggtgctggtg catcatggta tcgaccggat gaaaacagca    1860
gattttcgca aagctgcaag cgcttcagcc cttgtcattt caagctatgg attgttacag    1920
cgcgaccttg aatttctgtc gaaggttccc tgggcaggca ttattctcga tgaagcgcag    1980
aacatcaaaa accctgagac aaaacagtca aaagctgccc gaacaatccg ggctgattac    2040
cgtattgccc tgaccggcac tcccgttgaa aatcatgtcg cgacctttg ggcactcatg     2100 gattttctca atcccggttt tcttggaacc cagcactttt tcaaacagaa cttctacacg    2160
ccgattcagt ggtatggcga ccctgaggct tcagcacgac tgaagtcgct gaccggcccg    2220
tttattctgc gccgcatgaa aagcgacaag tcgattattt ccgatctgcc cgacaagatc    2280
gaaatgaaag agtattgctc gctgaccaaa gagcaggcat cgctctacaa ggctgttgtc    2340
gatgaactgc aggagaaaat tgaaagcgcc gaagggattg accggcgggg ccttgtactt    2400
gcgctgctgg tcaagctcaa gcaggtctgc aaccatccgg cacatttgct tggcgacaac    2460
tctgccattg cacatcgttc aggaaaaata aaacgcctga ccgaactgct tggcgacatc    2520
cgcgaagctg gcgaaaaaac gctgctcttt acacagttta ccatgatggg aacgatgctc    2580
cagcactatc ttcaggagtt gtacggtgaa gaggtactgt ttctgcacgg tggcgtaacc    2640
aaaaaaaggc gggatgagat ggtagagagc ttccagaagg aagagggcag ttcaccctcc    2700
atctttattc tctcactgaa agccggagga acggtctta acctgacaac agcgaaccac    2760
gttgttcact ttgaccgatg gtggaacccg gcagtagaga tcaggcaac tgaccgggct     2820 ttccgtatcg ggcagcacaa aaacgttgaa gttcataaat ttattacgac gggcacgctc    2880
gaagagcgca ttgatgagat gattgagaaa aaaacaacgg tcgccggcca ggttctcgga    2940
acgggtgagc agtggctgac cgaactgtcg aacaatgatc tgcgcaagct cattatgctc    3000
ggacaggaag caatgggaga ataa                                           3024
```

<210> SEQ ID NO 66
<211> LENGTH: 1007
<212> TYPE: PRT
<213> ORGANISM: Pelodictyon phaeoclathratiforme

<400> SEQUENCE: 66

Met Ile Ala Leu His Ile Ser Ile Ile Asp Gly Val Pro Leu Leu Trp
1               5                   10                  15

Ser Glu Gly Lys Lys Ile Gly Met Leu Lys Glu Leu Arg Leu Ala Thr
            20                  25                  30

Ala Gly Ile Gly Met Phe Ser Leu Leu Asp Asn Thr Thr Lys Glu Phe
        35                  40                  45

-continued

```
Cys Val Trp Leu Pro Cys Arg Glu Lys Lys Ala Val Pro Ser Ser Pro
     50                  55                  60
Leu Val Gly Ala Met Pro Asp Leu Ser Asp Glu Glu Gln Leu His Ala
 65                  70                  75                  80
Phe Pro Ile Thr Ala Leu Arg Leu Asn Phe Asn Ala Leu Phe Glu Leu
                 85                  90                  95
Ser Leu Leu Thr Glu Lys Gly Asn Ile Pro Gly Ser Gly Ile Ile Phe
                100                 105                 110
Gly Ser Ser Leu His Trp Ala Arg Gln Val Val Lys Ile Ala Leu Asn
            115                 120                 125
Ile Val Arg Thr Gln Ser Leu Leu Pro Ser Ile Ile Lys Asn Asp Thr
130                 135                 140
Phe Trp Glu Ala Leu Trp Leu Pro Leu Pro Asp Ser Ala Thr Ser Leu
145                 150                 155                 160
Ala Val Glu Gln Leu Ala Asp Ala Met Pro Ala Val Cys Arg Ser Leu
                165                 170                 175
Gly Arg Thr Asp Thr Gln Pro Pro Glu Thr Pro Lys Lys Leu Leu Leu
                180                 185                 190
Lys Gly Leu Leu Ser Phe Leu Val Asn Thr Leu Ser Arg Thr Phe Glu
            195                 200                 205
Arg Ala Gly Val Pro Lys Ile Ser Asp Phe Glu Ser Ile His Asp Ala
210                 215                 220
Trp Leu His Ala Leu Ser Asn Ser Asp Pro Arg Leu Lys Trp Lys Asn
225                 230                 235                 240
Glu Gln Glu Ile Glu Gln Phe Ala Cys Gln Leu Asn Ala Trp Arg Arg
                245                 250                 255
Pro Ile Asp Leu His Glu Arg Ser Pro Phe Arg Phe Cys Leu Gln Leu
                260                 265                 270
Thr Glu Pro Pro Leu Lys Gly Arg Lys Lys Glu Arg Trp His Val Ala
            275                 280                 285
Tyr Gln Leu Gln Leu Lys Ala Asp Pro Ser Leu Ile Leu Asp Ala Gly
290                 295                 300
Asp Leu Trp Asn Pro Glu Ser Glu Ala Ser Gln His Ala Leu Thr Tyr
305                 310                 315                 320
Thr Ser Asp Cys Thr Glu Phe Leu Leu Thr Ser Leu Gly Gln Ala Ser
                325                 330                 335
Gly Leu Cys Pro Ala Val Thr Gln Ser Leu Lys Lys Lys Gln Pro Gly
                340                 345                 350
Gly Phe Asp Leu Asp Thr Glu Gly Ala Tyr Arg Phe Leu Leu Glu Tyr
            355                 360                 365
Ala Glu Leu Leu Arg Ser Ala Gly Phe Val Val Lys Leu Pro Ser Trp
370                 375                 380
Trp Ile Gly Arg Arg Gly Val Asn Arg Ile Gly Ile Lys Thr Lys Val
385                 390                 395                 400
Lys Leu Pro Ser Met Lys Gly Ser Gly Ser Gly Leu Thr Leu Asp Arg
                405                 410                 415
Met Val Ala Cys Asp Tyr Ala Ala Ala Leu Gly Asn Glu Glu Leu Asp
                420                 425                 430
Leu Gln Glu Leu Lys Thr Leu Ala Asn Leu Lys Val Pro Leu Val Arg
            435                 440                 445
Val Arg Gly Gln Trp Thr Gln Ile Asp His Lys Glu Leu Ala Asn Ala
450                 455                 460
Leu His Phe Leu Glu Lys His Pro Thr Gly Glu Leu Ser Ala Arg Glu
```

-continued

```
              465                 470                 475                 480
        Leu Leu Ser Thr Ala Leu Gly Ala Gln Lys Lys Glu Asp Ala Leu Phe
                        485                 490                 495

Leu Arg Ser Val Glu Ile Glu Gly Trp Leu Gln Glu Leu Leu Glu Lys
                        500                 505                 510

Leu Ser Ser Gln Gly Gln Phe Glu Leu Leu Pro Pro Pro Glu His Phe
                        515                 520                 525

Glu Gly Thr Leu Arg Leu Tyr Gln Glu Arg Gly Phe Ser Trp Leu Ser
                        530                 535                 540

Phe Leu Arg Lys Trp Gly Leu Gly Ala Cys Leu Ala Asp Asp Met Gly
        545                 550                 555                 560

Leu Gly Lys Thr Ile Gln Thr Leu Ala Leu Leu Gln Arg Glu Arg Glu
                        565                 570                 575

Leu Gly Glu Lys Arg Ala Val Leu Leu Ile Cys Pro Thr Ser Val Val
                        580                 585                 590

Asn Asn Trp Arg Lys Glu Ala Glu Arg Phe Thr Pro Asp Leu Ala Val
                        595                 600                 605

Leu Val His His Gly Ile Asp Arg Met Lys Thr Ala Asp Phe Arg Lys
                        610                 615                 620

Ala Ala Ser Ala Ser Ala Leu Val Ile Ser Ser Tyr Gly Leu Leu Gln
        625                 630                 635                 640

Arg Asp Leu Glu Phe Leu Ser Lys Val Pro Trp Ala Gly Ile Ile Leu
                        645                 650                 655

Asp Glu Ala Gln Asn Ile Lys Asn Pro Glu Thr Lys Gln Ser Lys Ala
                        660                 665                 670

Ala Arg Thr Ile Arg Ala Asp Tyr Arg Ile Ala Leu Thr Gly Thr Pro
                        675                 680                 685

Val Glu Asn His Val Gly Asp Leu Trp Ala Leu Met Asp Phe Leu Asn
                        690                 695                 700

Pro Gly Phe Leu Gly Thr Gln His Phe Phe Lys Gln Asn Phe Tyr Thr
        705                 710                 715                 720

Pro Ile Gln Trp Tyr Gly Asp Pro Glu Ala Ser Ala Arg Leu Lys Ser
                        725                 730                 735

Leu Thr Gly Pro Phe Ile Leu Arg Arg Met Lys Ser Asp Lys Ser Ile
                        740                 745                 750

Ile Ser Asp Leu Pro Asp Lys Ile Glu Met Lys Glu Tyr Cys Ser Leu
                        755                 760                 765

Thr Lys Glu Gln Ala Ser Leu Tyr Lys Ala Val Val Asp Glu Leu Gln
                        770                 775                 780

Glu Lys Ile Glu Ser Ala Glu Gly Ile Asp Arg Arg Gly Leu Val Leu
        785                 790                 795                 800

Ala Leu Leu Val Lys Leu Lys Gln Val Cys Asn His Pro Ala His Leu
                        805                 810                 815

Leu Gly Asp Asn Ser Ala Ile Ala His Arg Ser Gly Lys Ile Lys Arg
                        820                 825                 830

Leu Thr Glu Leu Leu Gly Asp Ile Arg Glu Ala Gly Glu Lys Thr Leu
                        835                 840                 845

Leu Phe Thr Gln Phe Thr Met Met Gly Thr Met Leu Gln His Tyr Leu
                        850                 855                 860

Gln Glu Leu Tyr Gly Glu Glu Val Leu Phe Leu His Gly Gly Val Thr
        865                 870                 875                 880

Lys Lys Arg Arg Asp Glu Met Val Glu Ser Phe Gln Lys Glu Glu Gly
                        885                 890                 895
```

```
Ser Ser Pro Ser Ile Phe Ile Leu Ser Leu Lys Ala Gly Gly Thr Gly
            900                 905                 910

Leu Asn Leu Thr Thr Ala Asn His Val Val His Phe Asp Arg Trp Trp
            915                 920                 925

Asn Pro Ala Val Glu Asn Gln Ala Thr Asp Arg Ala Phe Arg Ile Gly
            930                 935                 940

Gln His Lys Asn Val Glu Val His Lys Phe Ile Thr Thr Gly Thr Leu
945                 950                 955                 960

Glu Glu Arg Ile Asp Glu Met Ile Glu Lys Lys Thr Thr Val Ala Gly
                965                 970                 975

Gln Val Leu Gly Thr Gly Glu Gln Trp Leu Thr Glu Leu Ser Asn Asn
            980                 985                 990

Asp Leu Arg Lys Leu Ile Met Leu  Gly Gln Glu Ala Met  Gly Glu
            995                 1000                 1005
```

<210> SEQ ID NO 67
<211> LENGTH: 3189
<212> TYPE: DNA
<213> ORGANISM: Prochlorococcus marinus

<400> SEQUENCE: 67

```
atgactctgc tgcacgccac ttggatttca actaattggc atccatctaa tttaggtcaa    60
tcagaattgt tcctttgggc agaccaatgg cgcgtagtaa ctccaaaaca ataatacaa    120
acaccttcac ctcacccgtt tagcctatct tcagatgaat taaaagaatg gctcaatagc   180
aaaaaattat tgcctaatga gagtattaat acatctgcat gtctcactct tcctagtaaa   240
cccattcaca aaaaaaataa ccaaaaatct aagaatcaaa aactggtat tgaatctgaa    300
tggaagggac tcccttaca agctcatgaa gaaatagcaa cacaatatga atgttggcca   360
tggaaagtag atggaatttc actcactact gtcgaagcaa cagaatggct tacaaaatta   420
cctttatcaa aaaagattc tgatcttagt gaagaattac tttggtgggc tcatttagag   480
cgttggtctc ttaatctaat tgcgagtgga ctatggctac ctcaagttaa attacacaag   540
aaagaaggaa atgaatatcg tgcatcatgg atacctctgc tgaatcaaga aaatgaaaga   600
aatcgcttag aagagtttgc aaaaaatatt cccttggtcg ctatttgtgc agtcccatgg   660
atagaagcta aaggacaaat agtcaatact gagcaagtct caattcaaa caataataca   720
ctctctttat ataggccaag acacaatcgc gtagaagtga tggatcttct cgaagaactt   780
attgatgcac aacttcgaaa agattttcaa ccaagaacta aaaacttgga tccattgtta   840
aaagcgtggc aagaagcact tggcacgaaa gatggaataa ttaacctatc gaatgaaaac   900
gctaaaagat tagaaaaagc aagtaagaat tggaaaagag ggttgtctag taatgttcaa   960
cctgcgaaaa catgtctaga gctaattgca ccgattgatg atctagattt atgggactta  1020
aacttttcat tgcaatcaga atcagatccg agtatcagac tagctgcaga tcaaatttgg  1080
gaagcaggcg tagaagtaac caaagttggc ggaataacaa ttgacaaccc aagtgaaatt  1140
cttttagaag gcctaggaag aagtcttgaa atttccctc caattgaaaa aggactagaa  1200
agcccaactc tcacacaat gaaactgtct gcatcagaag catttgtact tattagaaca   1260
gcagcagcaa aacttcgtga catgggtat tgtgtaatac tgcctaatag tttgtccaaa  1320
ggatttgcaa gtcgacttgg tcttgctatt caagccgaat taccagagtc ttcactaggc  1380
gtaatgctag agaaagttt gaactgggat tgggagttaa tgatcggagg tataaattta  1440
agcatgaaag aactagaaat gcttgcaaaa aaaatagtc ctctactcaa tcacaaaggg  1500
acatggatcg aattacgtcc taatgatctg aaaaatgctt caaaattttt tgctaatact  1560
```

```
ccagaattaa acctcgataa agcattaagg cttagtgcta ataaaggcaa cacttttatg   1620
aaacttccag tacatcattt tgaatctgga ccaagattac aaagtgtctt agagcaatat   1680
caccatcaga aagcgcctga acctttacca gcacctaatg gattccatgg gcaattaagg   1740
ccttaccaag aaagaggtct tgggtggctt gcatttcttt atcgttttaa gcaaggagca   1800
tgcttagcag atgacatggg gcttggtaaa actattcaat tattatgttt tattcagcac   1860
ctaaaagttc aaaacgagct tactaagcct gtactcctaa ttgcgcctac atctgtgctg   1920
acaaattgga aaagagaggc tgccactttt actccagaac tatgtataca tgaacactat   1980
ggtagtaaga gacattcttc aataccaaaa ttacaaaatt atctaaaaaa agttgacatt   2040
atgatcacaa gttatgggtt actttatcga gatggcgagc tgctacaaga aatcgactgg   2100
caaggaatag ttattgatga agctcaagct attaaaaatt ccaaatcaaa gcaaagtatt   2160
ataactagag cataagcaa aaatctcata agtaatccct ttagaattgc tttaacagga   2220
acgccagtag aaaatcgtat tagtgaacta tgggcactaa tggatttcct taatccaaaa   2280
gtattaggtg aagaagattt ttttaatcag cgatacaagt taccgattga gcattatggc   2340
gacatctctt cattaaaaga tctcaaaaca caggtcagtc cttttatttt aagaagattg   2400
aaaaccgatc aatctattat ttctgatttg cctcaaaaga ttgaattaaa tgagtgggtt   2460
ggactaagcc aagagcaaga gcttctatat aaacaaacgg tagagaaaag cttagatgaa   2520
ctcgcctcat tacccattgg tcaacgccag ggtaaaacat gggtctact tactcgtctt   2580 aaacaaattt gtaatcatcc agcaattgct ttaaagaaaa ctcaagtcga agaatttc    2640 ttattaagat cttcaaaatt acaaagactg gaagaaatac tacaagaagt gaaagaatct   2700
catgatagag ctctgctctt tactcaattt gctgaatggg gcatttatt gcaagcgtac    2760 ttacaaacaa aatgggaatc agaagtacct ttcctacacg gaggcactcc taagggaag    2820 cgacaagaaa tgatagatcg tttttcaagat gatcctagag gccaaatat ctttttactt    2880 tcactaaaag caggaggagt gggtcttaat ctaactcgtg cgaatcatgt ttttcatatt   2940
gatcgttggt ggaatccagc agtagaaaat caagcaacag atcgtgcata ccgaattggt   3000
caaaaaaaaa gtgttatcgt ccataagttt ataaccaccg gcacaatcga agaaaaaatc   3060
aatcaaatga ttctcgaaaa gactgaacta gcagaaaata ttgtcggatc aggagaaagc   3120
tggttagggc aattaagtct tgaaaaattg agtgaattag ttgctttaga tagcaatcca   3180
gaattctaa                                                           3189
```

<210> SEQ ID NO 68
<211> LENGTH: 1062
<212> TYPE: PRT
<213> ORGANISM: Prochlorococcus marinus

<400> SEQUENCE: 68

```
Met Thr Leu Leu His Ala Thr Trp Ile Ser Thr Asn Trp His Pro Ser
1               5                   10                  15

Asn Leu Gly Gln Ser Glu Leu Phe Leu Trp Ala Asp Gln Trp Arg Val
            20                  25                  30

Val Thr Pro Lys Gln Ile Ile Gln Thr Pro Ser Pro His Pro Phe Ser
        35                  40                  45

Leu Ser Ser Asp Glu Leu Lys Glu Trp Leu Asn Ser Lys Lys Leu Leu
    50                  55                  60

Pro Asn Glu Ser Ile Asn Thr Ser Ala Cys Leu Thr Leu Pro Ser Lys
65                  70                  75                  80
```

```
Pro Ile His Lys Lys Asn Asn Gln Lys Ser Lys Asn Gln Lys Thr Gly
                85                  90                  95
Ile Glu Ser Glu Trp Lys Gly Leu Pro Leu Gln Ala His Glu Ile
            100                 105                 110
Ala Thr Gln Tyr Glu Cys Trp Pro Trp Lys Val Asp Gly Ile Ser Leu
            115                 120                 125
Thr Thr Val Glu Ala Thr Glu Trp Leu Thr Lys Leu Pro Leu Ser Lys
130                 135                 140
Lys Asp Ser Asp Leu Ser Glu Glu Leu Leu Trp Trp Ala His Leu Glu
145                 150                 155                 160
Arg Trp Ser Leu Asn Leu Ile Ala Ser Gly Leu Trp Leu Pro Gln Val
                165                 170                 175
Lys Leu His Lys Lys Glu Gly Asn Glu Tyr Arg Ala Ser Trp Ile Pro
                180                 185                 190
Leu Leu Asn Gln Glu Asn Glu Arg Asn Arg Leu Glu Glu Phe Ala Lys
                195                 200                 205
Asn Ile Pro Leu Val Ala Ile Cys Ala Val Pro Trp Ile Glu Ala Lys
            210                 215                 220
Gly Gln Ile Val Asn Thr Glu Gln Val Ser Asn Ser Asn Asn Thr
225                 230                 235                 240
Leu Ser Leu Tyr Arg Pro Arg His Asn Arg Val Glu Val Met Asp Leu
                245                 250                 255
Leu Glu Glu Leu Ile Asp Ala Gln Leu Arg Lys Asp Phe Gln Pro Arg
            260                 265                 270
Thr Lys Asn Leu Asp Pro Leu Leu Lys Ala Trp Gln Glu Ala Leu Gly
            275                 280                 285
Thr Lys Asp Gly Ile Ile Asn Leu Ser Asn Glu Asn Ala Lys Arg Leu
            290                 295                 300
Glu Lys Ala Ser Lys Asn Trp Lys Arg Gly Leu Ser Ser Asn Val Gln
305                 310                 315                 320
Pro Ala Lys Thr Cys Leu Glu Leu Ile Ala Pro Ile Asp Asp Leu Asp
                325                 330                 335
Leu Trp Asp Leu Asn Phe Ser Leu Gln Ser Glu Ser Pro Ser Ile
            340                 345                 350
Arg Leu Ala Ala Asp Gln Ile Trp Glu Ala Gly Val Glu Val Thr Lys
            355                 360                 365
Val Gly Gly Ile Thr Ile Asp Asn Pro Ser Glu Ile Leu Leu Glu Gly
370                 375                 380
Leu Gly Arg Ser Leu Glu Ile Phe Pro Pro Ile Glu Lys Gly Leu Glu
385                 390                 395                 400
Ser Pro Thr Pro His Thr Met Lys Leu Ser Ala Ser Glu Ala Phe Val
                405                 410                 415
Leu Ile Arg Thr Ala Ala Ala Lys Leu Arg Asp Met Gly Ile Gly Val
            420                 425                 430
Ile Leu Pro Asn Ser Leu Ser Lys Gly Phe Ala Ser Arg Leu Gly Leu
            435                 440                 445
Ala Ile Gln Ala Glu Leu Pro Glu Ser Ser Leu Gly Val Met Leu Gly
            450                 455                 460
Glu Ser Leu Asn Trp Asp Trp Glu Leu Met Ile Gly Ile Asn Leu
465                 470                 475                 480
Ser Met Lys Glu Leu Glu Met Leu Ala Lys Lys Asn Ser Pro Leu Leu
                485                 490                 495
Asn His Lys Gly Thr Trp Ile Glu Leu Arg Pro Asn Asp Leu Lys Asn
                500                 505                 510
```

```
Ala Ser Lys Phe Phe Ala Asn Thr Pro Glu Leu Asn Leu Asp Lys Ala
        515                 520                 525

Leu Arg Leu Ser Ala Asn Lys Gly Asn Thr Phe Met Lys Leu Pro Val
530                 535                 540

His His Phe Glu Ser Gly Pro Arg Leu Gln Ser Val Leu Glu Gln Tyr
545                 550                 555                 560

His His Gln Lys Ala Pro Glu Pro Leu Pro Ala Pro Asn Gly Phe His
                565                 570                 575

Gly Gln Leu Arg Pro Tyr Gln Glu Arg Gly Leu Gly Trp Leu Ala Phe
            580                 585                 590

Leu Tyr Arg Phe Lys Gln Gly Ala Cys Leu Ala Asp Asp Met Gly Leu
        595                 600                 605

Gly Lys Thr Ile Gln Leu Leu Cys Phe Ile Gln His Leu Lys Val Gln
    610                 615                 620

Asn Glu Leu Thr Lys Pro Val Leu Leu Ile Ala Pro Thr Ser Val Leu
625                 630                 635                 640

Thr Asn Trp Lys Arg Glu Ala Ala Thr Phe Thr Pro Glu Leu Cys Ile
                645                 650                 655

His Glu His Tyr Gly Ser Lys Arg His Ser Ser Ile Pro Lys Leu Gln
            660                 665                 670

Asn Tyr Leu Lys Lys Val Asp Ile Met Ile Thr Ser Tyr Gly Leu Leu
        675                 680                 685

Tyr Arg Asp Gly Glu Leu Leu Gln Glu Ile Asp Trp Gln Gly Ile Val
    690                 695                 700

Ile Asp Glu Ala Gln Ala Ile Lys Asn Ser Lys Ser Lys Gln Ser Ile
705                 710                 715                 720

Ile Thr Arg Ala Ile Ser Lys Asn Leu Ile Ser Asn Pro Phe Arg Ile
                725                 730                 735

Ala Leu Thr Gly Thr Pro Val Glu Asn Arg Ile Ser Glu Leu Trp Ala
            740                 745                 750

Leu Met Asp Phe Leu Asn Pro Lys Val Leu Gly Glu Glu Asp Phe Phe
        755                 760                 765

Asn Gln Arg Tyr Lys Leu Pro Ile Glu His Tyr Gly Asp Ile Ser Ser
    770                 775                 780

Leu Lys Asp Leu Lys Thr Gln Val Ser Pro Phe Ile Leu Arg Arg Leu
785                 790                 795                 800

Lys Thr Asp Gln Ser Ile Ile Ser Asp Leu Pro Gln Lys Ile Glu Leu
                805                 810                 815

Asn Glu Trp Val Gly Leu Ser Gln Glu Gln Glu Leu Leu Tyr Lys Gln
            820                 825                 830

Thr Val Glu Lys Ser Leu Asp Glu Leu Ala Ser Leu Pro Ile Gly Gln
        835                 840                 845

Arg Gln Gly Lys Thr Leu Gly Leu Leu Thr Arg Leu Lys Gln Ile Cys
    850                 855                 860

Asn His Pro Ala Ile Ala Leu Lys Glu Thr Gln Val Glu Lys Asn Phe
865                 870                 875                 880

Leu Leu Arg Ser Ser Lys Leu Gln Arg Leu Glu Ile Leu Gln Glu
                885                 890                 895

Val Lys Glu Ser His Asp Arg Ala Leu Leu Phe Thr Gln Phe Ala Glu
            900                 905                 910

Trp Gly His Leu Leu Gln Ala Tyr Leu Gln Thr Lys Trp Glu Ser Glu
        915                 920                 925

Val Pro Phe Leu His Gly Gly Thr Pro Lys Gly Lys Arg Gln Glu Met
```

```
                930              935              940
Ile Asp Arg Phe Gln Asp Asp Pro Arg Gly Pro Asn Ile Phe Leu Leu
945                  950              955                  960

Ser Leu Lys Ala Gly Gly Val Gly Leu Asn Leu Thr Arg Ala Asn His
                965              970                  975

Val Phe His Ile Asp Arg Trp Trp Asn Pro Ala Val Glu Asn Gln Ala
            980              985              990

Thr Asp Arg Ala Tyr Arg Ile Gly Gln Lys Lys Ser Val Ile Val His
        995              1000             1005

Lys Phe Ile Thr Thr Gly Thr Ile Glu Glu Lys Ile Asn Gln Met
    1010             1015             1020

Ile Leu Glu Lys Thr Glu Leu Ala Glu Asn Ile Val Gly Ser Gly
    1025             1030             1035

Glu Ser Trp Leu Gly Gln Leu Ser Leu Glu Lys Leu Ser Glu Leu
    1040             1045             1050

Val Ala Leu Asp Ser Asn Pro Glu Phe
    1055             1060

<210> SEQ ID NO 69
<211> LENGTH: 3204
<212> TYPE: DNA
<213> ORGANISM: Prochlorococcus marinus

<400> SEQUENCE: 69
atgagtctgc tacacgctac ttggctgcca gcaatgcgaa ccggaagttc gcataatcca      60
ggactactca tctgggctga ttcatggaga gttgcaaaac caagcatagt cagcaatcag     120
cctgtaatac atccatttgc cttatcagca gcagatttac gtatttggct attgcaaaaa     180
aagcttttac ctaaagaaag tattgaatgt acagccttat taactctacc tagtaaatct     240
attaaaaact cattagacaa aaaattaaat ggagtaacgg actcacaaaa tactagcgat     300
caacctcaat ggagtggact acctttacaa gcaggagagc cagtaactaa caatgtgaa     360 tggtggccct gcaagttga aggtatagca atcaaaccca gtgaagctgc atcgtggctt     420
gcaaacttac ctctcacgaa aaaagatcct gagcttagtg aagagatcct atggtggagt     480
catttagaac gttggtctct aagtttaatt gctcgtggcc tttggttgcc acaagttgaa     540
ttaaatacaa ttgataatat tggagctaga gctaggtgga gtccctttact taataacgaa     600 aacgagcgca aaagattaga agaattctct atcaggcttc cattagtagc aacatgtgcc     660
ataaaaagag aggaaacttc tgaagaaaat caaaaccata tattaaagac tactcctagg     720
gaaacactcg atgaatacgg acttgcagta tgtcgaccaa tcaatagtcg acttcaagtg     780
gcttatctct agaagaact cgtggatgga cagctaagaa aagattttga ggaaagttct     840
gaagaccttg atccattgct gaaagcttgg caagaggcat taggatcaca taatggagtc     900
attcgtcttc cgttggaaga ttgtgaaaga ttagccaagg caagtaaaaa ttggaaagaa     960
aatttatcag gcaatgttaa aggtgcaaga gcatgccttg agctttttgc accacttgaa    1020
ggagaagatt tatgggactt acaattctct ttacaagctg aagcagatcc atcactaaag    1080
gtagcagcag aagcagtatg gaatgcagac tcagcagttc tacagattgg tgatattcaa    1140
atagcgcagc ctggagaaat tctactagaa ggtcttggca gagcactcaa tatctttcaa    1200
ccaatagaaa ggggtctgga aaatgctact ccaaataata tgcaactcac acctgcagaa    1260
gcttttgttc tagtacgtac agcctcaaag caattacgtg atattggtat tggtgtaata    1320
ctacctagaa gtttatcagg aggattagca agtcgactag gtatagctat taaagcagag    1380
```

```
ttagcgacta gtgccagagg attaacactt cgagagaatc tagaatggag ttgggagcta    1440
atgatagggg gaagcatatt aagccttaaa gatctagaac aactggcaag taaacgcagc    1500
cctctagttc gctataagga ttcatggctt gaattacgtc caaatgatct taaaatcgcc    1560
gaaaaattct gtagcaataa tcctgaatta agcctagatg acgcattaag acttaccgca    1620
actaaagggg agactctaat gaagcttcca gtacatcaat ttaatgctgg gccaaagctc    1680
caaggcgttt tagagcaata ccaccaacat acaagtcctg agcctctagc tgcaccagat    1740
ggcttctatg gacaactgag gccttatcaa gaacgtggca taggatggtt ggctttcttg    1800
catcgtttta atcaaggtgc atgtttagca gatgacatgg gcctgggcaa aacaattcaa    1860
gtgcttgctt ttattcagca cttaaaaagt aacaaggacc tcaagaaacc tgttttgcta    1920
attgcaccta cgtcagtatt aacaaactgg aaacgagaag cttattcatt tacaccagag    1980
ttatctgtat tagagcatta cggtcctaat cgttcatcta catcaacact cttgaaaaag    2040
attctcaaaa aagtagacat tcttattact agctatggcc tactacatag agataaacag    2100
cttctgaaaa caattgattg gcaaggtgta attattgatg aagcacaagc tataaaaaat    2160
ccaaattcaa aacaaagtca aacaactcgt gaaattgtta aaggcggaaa ataatccct    2220 tttcgtattg cattaactgg taccccctata gaaaatcgtg taagtgagct ttggtcatta    2280
atggattttt taaatccatc agtacttgga gaaaagaat tttttgatca acgctacaaa    2340
ttaccgattg aacgttatgg tgatatttct tcgttaaccg atctcaaagc tcgtgtcagt    2400
ccctttattc ttagaaggtt aaaaagtgat aaatcaatta tctcggatct accaagcaaa    2460
gtcgaactaa aagaatggat tactcttagt caagagcaaa gagctctta taacaaaact    2520 gtagacaata ccttcagga atcgcaaga agtcctattg gtcagcgtca tgcgaaaacc    2580
ttaggtctat taacacgtct caaacaaata tgtaatcatc ctgctcttgc cctcaaagaa    2640
aaaaacatta gcgatgattt tggaatacga tcaaccaaac ttcaaaggct ggaagaactt    2700
cttgatgtga tattcgcaac agaggacaga gctcttcttt ttacccaatt cgctgaatgg    2760
ggtcacttac tacaagctta tctagaaaaa aagtggggac atagcatact ttttctacat    2820
ggaggaactc gcaaaataga tagacaatca atggttgatc aatttcaaga agatcccaga    2880
ggcccaaaat tatttttact ttctctcaaa gcaggtggta ttggtctgaa cctgactcga    2940
gctaaccacg tgttgcatat tgatcgatgg tggaaccctg ccgtagaaaa tcaggcaaca    3000
gatcgtgctt atagaattgg tcaaaaaaat agcgtaatgg ttcacaaatt tattgctaca    3060
gggtcagtag aagaaaaaat tgatcaaatg attactgaaa agtctaagct cgcagaaaat    3120
ataattggtg caggtgaaga ttggcttggc aaacttggca tcaatgaatt acgtgaatta    3180
gtttccttag aaaaagagag ttaa                                            3204
```

<210> SEQ ID NO 70
<211> LENGTH: 1067
<212> TYPE: PRT
<213> ORGANISM: Prochlorococcus marinus

<400> SEQUENCE: 70

Met Ser Leu Leu His Ala Thr Trp Leu Pro Ala Met Arg Thr Gly Ser
1               5                   10                  15

Ser His Asn Pro Gly Leu Leu Ile Trp Ala Asp Ser Trp Arg Val Ala
            20                  25                  30

Lys Pro Ser Ile Val Ser Asn Gln Pro Val Ile His Pro Phe Ala Leu
        35                  40                  45

Ser Ala Ala Asp Leu Arg Ile Trp Leu Leu Gln Lys Lys Leu Leu Pro

```
                50                  55                  60
Lys Glu Ser Ile Glu Cys Thr Ala Leu Leu Thr Leu Pro Ser Lys Ser
 65                  70                  75                  80

Ile Lys Asn Ser Leu Asp Lys Lys Leu Asn Gly Val Thr Asp Ser Gln
                 85                  90                  95

Asn Thr Ser Asp Gln Pro Gln Trp Ser Gly Leu Pro Leu Gln Ala Gly
                100                 105                 110

Glu Pro Val Thr Lys Gln Cys Glu Trp Trp Pro Trp Gln Val Glu Gly
                115                 120                 125

Ile Ala Ile Lys Pro Ser Glu Ala Ala Ser Trp Leu Ala Asn Leu Pro
                130                 135                 140

Leu Thr Lys Lys Asp Pro Glu Leu Ser Glu Glu Ile Leu Trp Trp Ser
145                 150                 155                 160

His Leu Glu Arg Trp Ser Leu Ser Leu Ile Ala Arg Gly Leu Trp Leu
                165                 170                 175

Pro Gln Val Glu Leu Asn Thr Ile Asp Asn Ile Gly Ala Arg Ala Arg
                180                 185                 190

Trp Ser Pro Leu Leu Asn Asn Glu Asn Glu Arg Lys Arg Leu Glu Glu
                195                 200                 205

Phe Ser Ile Arg Leu Pro Leu Val Ala Thr Cys Ala Ile Lys Arg Glu
                210                 215                 220

Glu Thr Ser Glu Glu Asn Gln Asn His Ile Leu Lys Thr Thr Pro Arg
225                 230                 235                 240

Glu Thr Leu Asp Glu Tyr Gly Leu Ala Val Cys Arg Pro Ile Asn Ser
                245                 250                 255

Arg Leu Gln Val Ala Tyr Leu Leu Glu Glu Leu Val Asp Gly Gln Leu
                260                 265                 270

Arg Lys Asp Phe Glu Glu Ser Ser Glu Asp Leu Asp Pro Leu Leu Lys
                275                 280                 285

Ala Trp Gln Glu Ala Leu Gly Ser His Asn Gly Val Ile Arg Leu Pro
                290                 295                 300

Leu Glu Asp Cys Glu Arg Leu Ala Lys Ala Ser Lys Asn Trp Lys Glu
305                 310                 315                 320

Asn Leu Ser Gly Asn Val Lys Gly Ala Arg Ala Cys Leu Glu Leu Phe
                325                 330                 335

Ala Pro Leu Glu Gly Glu Asp Leu Trp Asp Leu Gln Phe Ser Leu Gln
                340                 345                 350

Ala Glu Ala Asp Pro Ser Leu Lys Val Ala Ala Glu Ala Val Trp Asn
                355                 360                 365

Ala Asp Ser Ala Val Leu Gln Ile Gly Asp Ile Gln Ile Ala Gln Pro
                370                 375                 380

Gly Glu Ile Leu Leu Glu Gly Leu Gly Arg Ala Leu Asn Ile Phe Gln
385                 390                 395                 400

Pro Ile Glu Arg Gly Leu Glu Asn Ala Thr Pro Asn Asn Met Gln Leu
                405                 410                 415

Thr Pro Ala Glu Ala Phe Val Leu Val Arg Thr Ala Ser Lys Gln Leu
                420                 425                 430

Arg Asp Ile Gly Ile Gly Val Ile Leu Pro Arg Ser Leu Ser Gly Gly
                435                 440                 445

Leu Ala Ser Arg Leu Gly Ile Ala Ile Lys Ala Glu Leu Ala Thr Ser
                450                 455                 460

Ala Arg Gly Leu Thr Leu Arg Glu Asn Leu Glu Trp Ser Trp Glu Leu
465                 470                 475                 480
```

-continued

```
Met Ile Gly Gly Ser Ile Leu Ser Leu Lys Asp Leu Glu Gln Leu Ala
                485                 490                 495

Ser Lys Arg Ser Pro Leu Val Arg Tyr Lys Asp Ser Trp Leu Glu Leu
            500                 505                 510

Arg Pro Asn Asp Leu Lys Ile Ala Glu Lys Phe Cys Ser Asn Asn Pro
        515                 520                 525

Glu Leu Ser Leu Asp Asp Ala Leu Arg Leu Thr Ala Thr Lys Gly Glu
    530                 535                 540

Thr Leu Met Lys Leu Pro Val His Gln Phe Asn Ala Gly Pro Lys Leu
545                 550                 555                 560

Gln Gly Val Leu Glu Gln Tyr His Gln His Thr Ser Pro Glu Pro Leu
                565                 570                 575

Ala Ala Pro Asp Gly Phe Tyr Gly Gln Leu Arg Pro Tyr Gln Glu Arg
            580                 585                 590

Gly Ile Gly Trp Leu Ala Phe Leu His Arg Phe Asn Gln Gly Ala Cys
        595                 600                 605

Leu Ala Asp Asp Met Gly Leu Gly Lys Thr Ile Gln Val Leu Ala Phe
    610                 615                 620

Ile Gln His Leu Lys Ser Asn Lys Asp Leu Lys Lys Pro Val Leu Leu
625                 630                 635                 640

Ile Ala Pro Thr Ser Val Leu Thr Asn Trp Lys Arg Glu Ala Tyr Ser
                645                 650                 655

Phe Thr Pro Glu Leu Ser Val Leu Glu His Tyr Gly Pro Asn Arg Ser
            660                 665                 670

Ser Thr Ser Thr Leu Leu Lys Lys Ile Leu Lys Lys Val Asp Ile Leu
        675                 680                 685

Ile Thr Ser Tyr Gly Leu Leu His Arg Asp Lys Gln Leu Leu Lys Thr
    690                 695                 700

Ile Asp Trp Gln Gly Val Ile Asp Glu Ala Gln Ala Ile Lys Asn
705                 710                 715                 720

Pro Asn Ser Lys Gln Ser Gln Thr Thr Arg Glu Ile Val Lys Gly Gly
                725                 730                 735

Lys Ile Ile Pro Phe Arg Ile Ala Leu Thr Gly Thr Pro Ile Glu Asn
            740                 745                 750

Arg Val Ser Glu Leu Trp Ser Leu Met Asp Phe Leu Asn Pro Ser Val
        755                 760                 765

Leu Gly Glu Lys Glu Phe Phe Asp Gln Arg Tyr Lys Leu Pro Ile Glu
    770                 775                 780

Arg Tyr Gly Asp Ile Ser Ser Leu Thr Asp Leu Lys Ala Arg Val Ser
785                 790                 795                 800

Pro Phe Ile Leu Arg Arg Leu Lys Ser Asp Lys Ser Ile Ile Ser Asp
                805                 810                 815

Leu Pro Ser Lys Val Glu Leu Lys Glu Trp Ile Thr Leu Ser Gln Glu
            820                 825                 830

Gln Arg Ala Leu Tyr Asn Lys Thr Val Asp Asn Thr Leu Gln Glu Ile
        835                 840                 845

Ala Arg Ser Pro Ile Gly Gln Arg His Ala Lys Thr Leu Gly Leu Leu
    850                 855                 860

Thr Arg Leu Lys Gln Ile Cys Asn His Pro Ala Leu Ala Leu Lys Glu
865                 870                 875                 880

Lys Asn Ile Ser Asp Asp Phe Gly Ile Arg Ser Thr Lys Leu Gln Arg
                885                 890                 895

Leu Glu Glu Leu Leu Asp Val Ile Phe Ala Thr Glu Asp Arg Ala Leu
            900                 905                 910
```

| | | | | | | | | | | | |
|---|---|---|---|---|---|---|---|---|---|---|---|
|Leu|Phe|Thr|Gln|Phe|Ala|Glu|Trp|Gly|His|Leu|Leu Gln Ala Tyr Leu|
| | |915| | | |920| | | |925| |

Glu Lys Lys Trp Gly His Ser Ile Leu Phe Leu His Gly Gly Thr Arg
    930                  935                  940

Lys Ile Asp Arg Gln Ser Met Val Asp Gln Phe Gln Glu Asp Pro Arg
945                  950                  955                  960

Gly Pro Lys Leu Phe Leu Leu Ser Leu Lys Ala Gly Gly Ile Gly Leu
                965                  970                  975

Asn Leu Thr Arg Ala Asn His Val Leu His Ile Asp Arg Trp Trp Asn
                980                  985                  990

Pro Ala Val Glu Asn Gln Ala Thr Asp Arg Ala Tyr Arg Ile Gly Gln
                995                  1000              1005

Lys Asn Ser Val Met Val His Lys Phe Ile Ala Thr Gly Ser Val
        1010                  1015                  1020

Glu Glu Lys Ile Asp Gln Met Ile Thr Glu Lys Ser Lys Leu Ala
        1025                  1030                  1035

Glu Asn Ile Ile Gly Ala Gly Glu Asp Trp Leu Gly Lys Leu Gly
        1040                  1045                  1050

Ile Asn Glu Leu Arg Glu Leu Val Ser Leu Glu Lys Glu Ser
        1055                  1060                  1065

```
<210> SEQ ID NO 71
<211> LENGTH: 3300
<212> TYPE: DNA
<213> ORGANISM: Prochlorococcus marinus

<400> SEQUENCE: 71
atgattggtt gtggaactcc tgcgtggatg gttgccgttg atcggcagtg cactcctgct     60
ccaagaaacc caacacatac tttttgcgtc gcggccatga gcctgctgca cgccacctgg    120
cttccagcca tccgtactcc gaccagctcc ggtcgccctg cgctccttgt gtgggcagat    180
acctggcgag tcgctacccc agcaggacca gcagcaactc ccgcactcca ccccttcaca    240
ctcaacccag acgatctacg tgcctggctg attgagcgcg atctactgcc cgatgaaatc    300
atcgacgcca cagcatgtct gaccctgcct agccgaacag tcaaaccgcg cagcaaagcc    360
aagaacgtat ccactgaatc cgacgaagac aaagaccaca aaacaagttg gacaggactg    420
cccttacaag caggcgaacc cattcccaaa cagactgaat ggtggccctg gcaggtgcaa    480
ggcctggcag tggagcctgc tgctgcaacg gcctggcttt cgaaactgcc tctttcagga    540
gatcatcctg atctcgccga tgaattgcgc tggtggagcc atctacagcg ctgggccctg    600
agcatgattg ctcgcggacg ttggctaccc caggtggaac tcagcaaggg agagggctat    660
ccccaccgag cacgctggac accgctactc aaccgtgaag atgatcgccg ccgcctcgaa    720
gaccttgccg ctcagctccc cttagtggcc acctgcgccc tccctggcg  ggagcccacc    780 ggaaggcgta gcaaccgaat gacccgccta agaccagagg cgatgcgagc cgctaaccct    840
gtggcttcat gccgaccccg cagcggtcgc cttcgcgtag ccagcctgct ggaagaactc    900
ttggatgccc aactgcgcac cggatttgaa gcgagtgagc aaggcctaga cccattgctc    960
acagcctggc aggaagcact gggtcggac agcggcgtga tcaacctccc cgatgaggaa   1020
gccgaacgtc tagcgacagc aagcaaccat tggcgagaag cgtggctgg caacgtcgca   1080 ccagccaggg cctgcttaga actcttcact cccggcgaag ggaagacct ctgggagctg    1140 cgcttcgcct acaggctga ggctgatccc acgatcaaag taccggccgc agcagcctgg   1200
gcagcgggtc caaggtcct gcaactaggc gaaatccgtg tggaacatcc aggcgaggtg   1260
```

```
ctactggaag gcatggggcg agccctcacg gtgtttgcac cgatcgaacg aggcctcgac    1320
agcgccacac cagaagcaat gcagctcacc cctgctgaag cctttgtatt ggtgcgcact    1380
gcagcggccc aactgcgtga tgttggcgtt ggcgtggaat tgcctgccag cctctcggga    1440
gggctggcca gtcgcctagg cctagcgatc aaggcggagc tatcggagag atctagaggt    1500
ttcactttgg gcgaaaccct cgactggagt tgggagctca tgatcggtgg cgtcaccctg    1560
acgcttcgcg agctggagcg actagcaagc aagcgcagcc cgcttgtcaa ccacaagggc    1620
gcctggatcg aattacgccc caacgatctc aaaaatgcgg aacacttctg cagcgtcaat    1680
ccaggcatca gcctcgacga tgccttgcgc cttaccgcaa ccgatggcga cacgctgatg    1740
agactgcccg ttcaccgctt tgaggccggt ccacgactac aggcggtgtt ggagcagtac    1800
caccagcaaa aagctcccga cccctacct gctcccgaag gcttctgcgg tcagctaagg    1860
ccttatcagg aaaggggtct gggttggctg gccttcctgc atcgcttcga tcaaggggca    1920
tgcctggcca cgacatgggc ctgggcaaa acgatccagc tactggcatt cctgcaacat    1980
ctcaaggcgg aacaggaact caaacggccg gtattgctta cgctcccac atccgtactt    2040 accaactgga gagagaggc attggccttc acaccagagt taaacgtccg agaacactat    2100
gggccgcgtc ggccctctac ccccgccgcc ttaaagaaag cactcaaagg cttagacctc    2160
gttctcacca gttacgggct cctgcagcga gatagtgagc tcctggaaac ggtcgactgg    2220
caaggagtgg tcatcgatga agcccaagcc attaagaacc ccaacgccaa acagagccaa    2280
gcagcacgcg atatgggccg cccagacaaa acaatcgct tcaggattgc tcttaccggc    2340
acacccgtcg aaaaccgagt cagtgaactt tgggcactga tggacttcct caacccaagg    2400
gttctcggtg aagaagactt cttccgccag cgctaccggc tgccaattga acgctatggc    2460
gacatgtctt ccctgcgaga cctcaaaggc cgtgttggtc ccttcatcct gagacgacta    2520
aaaaccgaca aggcaatcat ctccgaccta cctgaaaagg tagagctgag cgaatgggtg    2580
ggtctgagca agaacaggc agccctctat cgcaacacag tggatgaaac actggaggcc    2640
attgcccgcg cacccagtgg tcaacgtcat ggcaaggtgc tcggcttgct tacccgactg    2700
aagcaaatct gcaaccatcc cgccctagcc ctcaaagaaa aaccgttgc aaaaggcttc    2760 atggaccgct ccgccaagct gctgcgtttg gaagaaattc tcgaggaagt gatcgaggca    2820
ggagatcgcg ctctgttatt cacccaattc gcagaatggg gtcatctcct taaggcctac    2880
ctgcaacaac gctggcgctt tgaagttccc ttcctgcacg gcagcacaag caaaactgaa    2940
cgtcaggcca tggttgatcg cttccaggag gatccacgtg gaccccaact gttcctgctg    3000
tcactcaaag ccggtggcgt aggcctaaac ctcacgcggg ctagccatgt gtttcatgtc    3060
gatcgctggt ggaatcctgc cgtagaaaac caggccactg atcgcgctta caggatcgga    3120
caaaccaatc gggtgatggt gcacaaattc atcaccagcg gctcagttga agagaaaatt    3180
gatcgcatga ttcgcgaaaa atctcgactt gccgaagaca tcattggctc tggagaagac    3240
tggttaggtg gcttaggcgt cagtcaattg cgcgaactag tggccctaga agacagctga    3300
```

<210> SEQ ID NO 72  
<211> LENGTH: 1099  
<212> TYPE: PRT  
<213> ORGANISM: Prochlorococcus marinus

<400> SEQUENCE: 72

```
Met Ile Gly Cys Gly Thr Pro Ala Trp Met Val Ala Val Asp Arg Gln
 1               5                  10                  15
```

```
Cys Thr Pro Ala Pro Arg Asn Pro Thr His Thr Phe Cys Val Ala Ala
             20                  25                  30

Met Ser Leu Leu His Ala Thr Trp Leu Pro Ala Ile Arg Thr Pro Thr
         35                  40                  45

Ser Ser Gly Arg Pro Ala Leu Leu Val Trp Ala Asp Thr Trp Arg Val
 50                  55                  60

Ala Thr Pro Ala Gly Pro Ala Ala Thr Pro Ala Leu His Pro Phe Thr
 65                  70                  75                  80

Leu Asn Pro Asp Asp Leu Arg Ala Trp Leu Ile Glu Arg Asp Leu Leu
                 85                  90                  95

Pro Asp Glu Ile Ile Asp Ala Thr Ala Cys Leu Thr Leu Pro Ser Arg
                100                 105                 110

Thr Val Lys Pro Arg Ser Lys Ala Lys Asn Val Ser Thr Glu Ser Asp
            115                 120                 125

Glu Asp Lys Asp His Lys Thr Ser Trp Thr Gly Leu Pro Leu Gln Ala
        130                 135                 140

Gly Glu Pro Ile Pro Lys Gln Thr Glu Trp Pro Trp Gln Val Gln
145                 150                 155                 160

Gly Leu Ala Val Glu Pro Ala Ala Thr Ala Trp Leu Ser Lys Leu
                165                 170                 175

Pro Leu Ser Gly Asp His Pro Asp Leu Ala Asp Glu Leu Arg Trp Trp
            180                 185                 190

Ser His Leu Gln Arg Trp Ala Leu Ser Met Ile Ala Arg Gly Arg Trp
        195                 200                 205

Leu Pro Gln Val Glu Leu Ser Lys Gly Glu Gly Tyr Pro His Arg Ala
210                 215                 220

Arg Trp Thr Pro Leu Leu Asn Arg Glu Asp Arg Arg Arg Leu Glu
225                 230                 235                 240

Asp Leu Ala Ala Gln Leu Pro Leu Val Ala Thr Cys Ala Leu Pro Trp
                245                 250                 255

Arg Glu Pro Thr Gly Arg Arg Ser Asn Arg Met Thr Arg Leu Arg Pro
            260                 265                 270

Glu Ala Met Arg Ala Ala Asn Pro Val Ala Ser Cys Arg Pro Arg Ser
        275                 280                 285

Gly Arg Leu Arg Val Ala Ser Leu Leu Glu Glu Leu Leu Asp Ala Gln
290                 295                 300

Leu Arg Thr Gly Phe Glu Ala Ser Glu Gln Gly Leu Asp Pro Leu Leu
305                 310                 315                 320

Thr Ala Trp Gln Glu Ala Leu Gly Ser Asp Ser Gly Val Ile Asn Leu
                325                 330                 335

Pro Asp Glu Glu Ala Glu Arg Leu Ala Thr Ala Ser Asn His Trp Arg
            340                 345                 350

Glu Gly Val Ala Gly Asn Val Ala Pro Ala Arg Ala Cys Leu Glu Leu
        355                 360                 365

Phe Thr Pro Gly Glu Gly Glu Asp Leu Trp Glu Leu Arg Phe Ala Leu
370                 375                 380

Gln Ala Glu Ala Asp Pro Thr Ile Lys Val Pro Ala Ala Ala Trp
385                 390                 395                 400

Ala Ala Gly Pro Lys Val Leu Gln Leu Gly Glu Ile Arg Val Glu His
                405                 410                 415

Pro Gly Glu Val Leu Leu Glu Gly Met Gly Arg Ala Leu Thr Val Phe
            420                 425                 430

Ala Pro Ile Glu Arg Gly Leu Asp Ser Ala Thr Pro Glu Ala Met Gln
        435                 440                 445
```

```
Leu Thr Pro Ala Glu Ala Phe Val Leu Val Arg Thr Ala Ala Gln
    450                 455                 460

Leu Arg Asp Val Gly Val Gly Val Glu Leu Pro Ala Ser Leu Ser Gly
465                 470                 475                 480

Gly Leu Ala Ser Arg Leu Gly Leu Ala Ile Lys Ala Glu Leu Ser Glu
                485                 490                 495

Arg Ser Arg Gly Phe Thr Leu Gly Glu Thr Leu Asp Trp Ser Trp Glu
            500                 505                 510

Leu Met Ile Gly Gly Val Thr Leu Thr Leu Arg Glu Leu Glu Arg Leu
        515                 520                 525

Ala Ser Lys Arg Ser Pro Leu Val Asn His Lys Gly Ala Trp Ile Glu
    530                 535                 540

Leu Arg Pro Asn Asp Leu Lys Asn Ala Glu His Phe Cys Ser Val Asn
545                 550                 555                 560

Pro Gly Ile Ser Leu Asp Asp Ala Leu Arg Leu Thr Ala Thr Asp Gly
                565                 570                 575

Asp Thr Leu Met Arg Leu Pro Val His Arg Phe Glu Ala Gly Pro Arg
            580                 585                 590

Leu Gln Ala Val Leu Glu Gln Tyr His Gln Lys Ala Pro Asp Pro
        595                 600                 605

Leu Pro Ala Pro Glu Gly Phe Cys Gly Gln Leu Arg Pro Tyr Gln Glu
    610                 615                 620

Arg Gly Leu Gly Trp Leu Ala Phe Leu His Arg Phe Asp Gln Gly Ala
625                 630                 635                 640

Cys Leu Ala Asp Asp Met Gly Leu Gly Lys Thr Ile Gln Leu Leu Ala
                645                 650                 655

Phe Leu Gln His Leu Lys Ala Glu Gln Glu Leu Lys Arg Pro Val Leu
            660                 665                 670

Leu Ile Ala Pro Thr Ser Val Leu Thr Asn Trp Lys Arg Glu Ala Leu
        675                 680                 685

Ala Phe Thr Pro Glu Leu Asn Val Arg Glu His Tyr Gly Pro Arg Arg
    690                 695                 700

Pro Ser Thr Pro Ala Ala Leu Lys Lys Ala Leu Lys Gly Leu Asp Leu
705                 710                 715                 720

Val Leu Thr Ser Tyr Gly Leu Leu Gln Arg Asp Ser Glu Leu Leu Glu
                725                 730                 735

Thr Val Asp Trp Gln Gly Val Val Ile Asp Glu Ala Gln Ala Ile Lys
            740                 745                 750

Asn Pro Asn Ala Lys Gln Ser Gln Ala Ala Arg Asp Met Gly Arg Pro
        755                 760                 765

Asp Lys Asn Asn Arg Phe Arg Ile Ala Leu Thr Gly Thr Pro Val Glu
    770                 775                 780

Asn Arg Val Ser Glu Leu Trp Ala Leu Met Asp Phe Leu Asn Pro Arg
785                 790                 795                 800

Val Leu Gly Glu Glu Asp Phe Phe Arg Gln Arg Tyr Arg Leu Pro Ile
                805                 810                 815

Glu Arg Tyr Gly Asp Met Ser Ser Leu Arg Asp Leu Lys Gly Arg Val
            820                 825                 830

Gly Pro Phe Ile Leu Arg Arg Leu Lys Thr Asp Lys Ala Ile Ile Ser
        835                 840                 845

Asp Leu Pro Glu Lys Val Glu Leu Ser Glu Trp Val Gly Leu Ser Lys
    850                 855                 860

Glu Gln Ala Ala Leu Tyr Arg Asn Thr Val Asp Glu Thr Leu Glu Ala
```

```
                865                 870                 875                 880
Ile Ala Arg Ala Pro Ser Gly Gln Arg His Gly Lys Val Leu Gly Leu
                    885                 890                 895

Leu Thr Arg Leu Lys Gln Ile Cys Asn His Pro Ala Leu Ala Leu Lys
                900                 905                 910

Glu Lys Thr Val Ala Lys Gly Phe Met Asp Arg Ser Ala Lys Leu Leu
            915                 920                 925

Arg Leu Glu Glu Ile Leu Glu Glu Val Ile Glu Ala Gly Asp Arg Ala
        930                 935                 940

Leu Leu Phe Thr Gln Phe Ala Glu Trp Gly His Leu Leu Lys Ala Tyr
945                 950                 955                 960

Leu Gln Gln Arg Trp Arg Phe Glu Val Pro Phe Leu His Gly Ser Thr
                965                 970                 975

Ser Lys Thr Glu Arg Gln Ala Met Val Asp Arg Phe Gln Glu Asp Pro
            980                 985                 990

Arg Gly Pro Gln Leu Phe Leu Leu  Ser Leu Lys Ala Gly  Gly Val Gly
        995                 1000                1005

Leu Asn  Leu Thr Arg Ala Ser  His Val Phe His Val  Asp Arg Trp
    1010                1015                1020

Trp Asn  Pro Ala Val Glu Asn  Gln Ala Thr Asp Arg  Ala Tyr Arg
    1025                1030                1035

Ile Gly  Gln Thr Asn Arg Val  Met Val His Lys Phe  Ile Thr Ser
    1040                1045                1050

Gly Ser  Val Glu Glu Lys Ile  Asp Arg Met Ile Arg  Glu Lys Ser
    1055                1060                1065

Arg Leu  Ala Glu Asp Ile Ile  Gly Ser Gly Glu Asp  Trp Leu Gly
    1070                1075                1080

Gly Leu  Gly Val Ser Gln Leu  Arg Glu Leu Val Ala  Leu Glu Asp
    1085                1090                1095

Ser

<210> SEQ ID NO 73
<211> LENGTH: 3300
<212> TYPE: DNA
<213> ORGANISM: Prochlorococcus marinus

<400> SEQUENCE: 73
atgattggtt gtggaactcc tgcgtggatg gttgccgttg atcggcagtg cactcctgct      60
ccaagaaacc caacacatac tttttgcgtc gcggccatga gcctgctgca cgccaccggg     120
cttccagcca tccgtactcc gaccagctcc ggtcgccctg cgctccttgt gtgggcagat     180
acctggcgag tcgctacccc agcaggacca gcagcaactc ccgcactcca ccccttcacc     240
ctcagcccag acgatctacg tgcctggctc attgagcgcg atctactgcc tgatgaaatc     300
atcgacgcca cagcatgtct gaccctgcct agccgaacag tcaaaccgcg caacaaaacc     360
aagaacgtat ccactgaatc cgacgaagcc aaagacaaca aaacaagttg gacaggactg     420
cccttacaag caggcgaacc cattcccaaa caaacagaat ggtggccctg gcaggtgcaa     480
ggcctggcag tggaacctgc tgccgcaacg gcctggcttt cgaaactgcc tctttcagga     540
aatcatcctg atctggccga tgaattcgcc tggtggagcc atctacagcg ctgggcctg     600 agcatgattg ctcgcggacg ttggctaccc caggtggaac tcagcaaggg agagggctat     660
ccccaccgag cacgctggac accgctactc aacgtgaag atgatcgccg ccgcctcgaa     720
gaccttgccg ctcagcttcc cttagtggcc acctgcgccc tccctggcg ggagcccacc     780
```

```
ggaaggcgta gcaaccgaat gacccgccta agaccagagg cgatgcgagc cgctaaccct   840
gtggcttcat gccgacccg  cagcggtcgc cttcgcgtag ccagcttgct ggaagaactc   900
ttggatgccc aactgcgcac cggatttgaa gcgagtgagc aaggcctaga cccattgctc   960
acagcctggc aggaagcact ggggtccgac agcggcgtga tcaacctccc cgatgaggaa  1020
gccgaacgtc tagctacagc aagcaaccat tggcgtgaag gcgtggctgg caacgtcgca  1080
ccagccagag cctgcttaga actcttcact cccggagaag gggaagacct ctgggagctg  1140
cgcttctcct tacaggctga ggctgatccc acaatcaaag taccggccgc agcagcctgg  1200
gcagctggtc ccaaggtgtt gcaactaggc gaaatccgtg tggaacatcc aggcgaggtg  1260
ctactggaag gcatggggcg agccctcacg gtgtttgcac cgatcgaacg aggcctcgac  1320
agcgccacac cagaagcaat gcagctcacc cctgctgaag cctttgtatt ggtgcgcact  1380
gcagcgaccc aactgcgtga tgttggcgtt ggcgtggaat tgcctgccag cctctcggga  1440
gggctggcca gtcgcctagg cctagcgatc aaggcggagc tatcggagag atctagaggt  1500
ttcactctgg gcgaaaccct cgactggagt tgggagctca tgatcggtgg cgtcaccctg  1560
acgcttcgcg aactggagcg actagcaagc aagcgcagcc cgcttgtcaa ccacaagggc  1620
gcctggatcg aattacgccc caacgatctc aaacatgcgg aacacttctg cagcgtcaat  1680
ccaggcatca gcctcgacga tgccttgcgc cttaccgcaa cagatggcga cacgctgatg  1740
agactgcccg ttcaccgctt tgaggccggt ccacgactac aggcggtgtt ggagcagtac  1800
caccagcaaa aagcaccaga ccccctacct gctcccgaag gcttctgcgg tcagctaagg  1860
ccttatcagg aaagggtct  gggttggctg gccttcctgc atcgcttcga tcaaggggca  1920
tgcctggccg acgacatggg ccttggcaaa acgatccagc tactggcatt cctgcaacat  1980
ctcaaggcgg aacaggaact caaacggccg gtattgctta tcgctcccac gtccgtactc  2040
accaactgga gagagaggc  gttggccttc acaccagagt taaacgtccg cgaacactat  2100
gggccgcgtc ggccctctac ccccgccgcc ttaaagaaag cactcaaagg cttagacctc  2160
gttctcacca gttatgggct cctgcagcga gatagtgagc tcctggaaac ggtcgactgg  2220
caaggcgtgg tcatcgatga agcccaagcc attaagaacc ccaacgccaa acagagccaa  2280
gcagcacgcg atatgggccg cccagacaaa acaatcgct  tcaggattgc tcttaccggc  2340
acacccgtcg aaaaccgagt aagtgaactt tgggcactaa tggacttcct taacccaagg  2400
gttctcggtg aagaagactt cttccgccag cgctaccggc tgccgattga gcgctatggc  2460
gacatgtctt ccctgcgaga cctcaaggc  cgtgttggtc ccttcatcct gagacgactc  2520
aaaaccgaca aggcaatcat ctccgaccta cccgaaaaag tagagctgag cgaatgggtg  2580
gggctgagca agaacaggc  agccctctat cgcaacacag tggatgaaac actggaggcc  2640
attgcccgcg cacccagggg tcaacgccat ggcaaggtgc tcggattgct taccagactg  2700
aagcaaatct gcaaccatcc cgccctagcc ctcaaagaac aaaccgttgc aaaagggttc  2760
atggaccgct ccgccaagct gctgcgtttg aagaaattc  tcgaagaagt aatcgaggca  2820
ggagatcgcg ctctgttatt cacccaattc gcagaatggg gtcatctcct taaggcctac  2880
ctgcaacaac gctggcgctt tgaagttccc ttcctgcacg gcagcacaag caaaactgaa  2940
cgtcaggcca tggttgatcg cttccaggag gatccacgtg accccaact  gttcctgctg  3000
tcactcaaag ccggtggtgt aggcctcaac ctgacgcggg ctagccatgt gtttcatgtt  3060
gatcgctggt ggaatcctgc cgtagaaaac caggccactg atcgcgctta caggatcggg  3120
caaaccagtc gggtgatggt gcacaaattc atcaccagcg gctcagttga agagaaaatt  3180
```

```
gatcgcatga ttcgtgaaaa atctcgactt gccgaagaca tcattggctc tggagaagac    3240
tggttaggtg gcttaggcgt cagtcaattg cgcgaactag tggccctaga agacagctga    3300
```

<210> SEQ ID NO 74
<211> LENGTH: 1099
<212> TYPE: PRT
<213> ORGANISM: Prochlorococcus marinus

<400> SEQUENCE: 74

| | | | | | | | | | | | | | | |
|---|---|---|---|---|---|---|---|---|---|---|---|---|---|---|
| Met | Ile | Gly | Cys | Gly | Thr | Pro | Ala | Trp | Met | Val | Ala | Val | Asp | Arg | Gln |
| 1 | | | | 5 | | | | | 10 | | | | | 15 | |
| Cys | Thr | Pro | Ala | Pro | Arg | Asn | Pro | Thr | His | Thr | Phe | Cys | Val | Ala | Ala |
| | | | 20 | | | | | 25 | | | | | 30 | | |
| Met | Ser | Leu | Leu | His | Ala | Thr | Trp | Leu | Pro | Ala | Ile | Arg | Thr | Pro | Thr |
| | | 35 | | | | | 40 | | | | | 45 | | | |
| Ser | Ser | Gly | Arg | Pro | Ala | Leu | Leu | Val | Trp | Ala | Asp | Thr | Trp | Arg | Val |
| | 50 | | | | | 55 | | | | | 60 | | | | |
| Ala | Thr | Pro | Ala | Gly | Pro | Ala | Ala | Thr | Pro | Ala | Leu | His | Pro | Phe | Thr |
| 65 | | | | | 70 | | | | | 75 | | | | | 80 |
| Leu | Ser | Pro | Asp | Asp | Leu | Arg | Ala | Trp | Leu | Ile | Glu | Arg | Asp | Leu | Leu |
| | | | | 85 | | | | | 90 | | | | | 95 | |
| Pro | Asp | Glu | Ile | Ile | Asp | Ala | Thr | Ala | Cys | Leu | Thr | Leu | Pro | Ser | Arg |
| | | | 100 | | | | | 105 | | | | | 110 | | |
| Thr | Val | Lys | Pro | Arg | Asn | Lys | Thr | Lys | Asn | Val | Ser | Thr | Glu | Ser | Asp |
| | | 115 | | | | | 120 | | | | | 125 | | | |
| Glu | Ala | Lys | Asp | Asn | Lys | Thr | Ser | Trp | Thr | Gly | Leu | Pro | Leu | Gln | Ala |
| | 130 | | | | | 135 | | | | | 140 | | | | |
| Gly | Glu | Pro | Ile | Pro | Lys | Gln | Thr | Glu | Trp | Trp | Pro | Trp | Gln | Val | Gln |
| 145 | | | | | 150 | | | | | 155 | | | | | 160 |
| Gly | Leu | Ala | Val | Glu | Pro | Ala | Ala | Thr | Ala | Trp | Leu | Ser | Lys | Leu | |
| | | | | 165 | | | | | 170 | | | | | 175 | |
| Pro | Leu | Ser | Gly | Asn | His | Pro | Asp | Leu | Ala | Asp | Glu | Leu | Arg | Trp | Trp |
| | | | 180 | | | | | 185 | | | | | 190 | | |
| Ser | His | Leu | Gln | Arg | Trp | Ala | Leu | Ser | Met | Ile | Ala | Arg | Gly | Arg | Trp |
| | | 195 | | | | | 200 | | | | | 205 | | | |
| Leu | Pro | Gln | Val | Glu | Leu | Ser | Lys | Gly | Glu | Gly | Tyr | Pro | His | Arg | Ala |
| | 210 | | | | | 215 | | | | | 220 | | | | |
| Arg | Trp | Thr | Pro | Leu | Leu | Asn | Arg | Glu | Asp | Arg | Arg | Arg | Leu | Glu | |
| 225 | | | | | 230 | | | | | 235 | | | | | 240 |
| Asp | Leu | Ala | Ala | Gln | Leu | Pro | Leu | Val | Ala | Thr | Cys | Ala | Leu | Pro | Trp |
| | | | | 245 | | | | | 250 | | | | | 255 | |
| Arg | Glu | Pro | Thr | Gly | Arg | Arg | Ser | Asn | Arg | Met | Thr | Arg | Leu | Arg | Pro |
| | | | 260 | | | | | 265 | | | | | 270 | | |
| Glu | Ala | Met | Arg | Ala | Ala | Asn | Pro | Val | Ala | Ser | Cys | Arg | Pro | Arg | Ser |
| | | 275 | | | | | 280 | | | | | 285 | | | |
| Gly | Arg | Leu | Arg | Val | Ala | Ser | Leu | Leu | Glu | Glu | Leu | Leu | Asp | Ala | Gln |
| | 290 | | | | | 295 | | | | | 300 | | | | |
| Leu | Arg | Thr | Gly | Phe | Glu | Ala | Ser | Glu | Gln | Gly | Leu | Asp | Pro | Leu | Leu |
| 305 | | | | | 310 | | | | | 315 | | | | | 320 |
| Thr | Ala | Trp | Gln | Glu | Ala | Leu | Gly | Ser | Asp | Ser | Gly | Val | Ile | Asn | Leu |
| | | | | 325 | | | | | 330 | | | | | 335 | |
| Pro | Asp | Glu | Glu | Ala | Glu | Arg | Leu | Ala | Thr | Ala | Ser | Asn | His | Trp | Arg |
| | | | 340 | | | | | 345 | | | | | 350 | | |
| Glu | Gly | Val | Ala | Gly | Asn | Val | Ala | Pro | Ala | Arg | Ala | Cys | Leu | Glu | Leu |
| | | 355 | | | | | 360 | | | | | 365 | | | |

```
Phe Thr Pro Gly Glu Gly Glu Asp Leu Trp Glu Leu Arg Phe Ser Leu
    370                 375                 380

Gln Ala Glu Ala Asp Pro Thr Ile Lys Val Pro Ala Ala Ala Ala Trp
385                 390                 395                 400

Ala Ala Gly Pro Lys Val Leu Gln Leu Gly Glu Ile Arg Val Glu His
                405                 410                 415

Pro Gly Glu Val Leu Leu Glu Gly Met Gly Arg Ala Leu Thr Val Phe
                420                 425                 430

Ala Pro Ile Glu Arg Gly Leu Asp Ser Ala Thr Pro Glu Ala Met Gln
                435                 440                 445

Leu Thr Pro Ala Glu Ala Phe Val Leu Val Arg Thr Ala Ala Thr Gln
    450                 455                 460

Leu Arg Asp Val Gly Val Gly Val Glu Leu Pro Ala Ser Leu Ser Gly
465                 470                 475                 480

Gly Leu Ala Ser Arg Leu Gly Leu Ala Ile Lys Ala Glu Leu Ser Glu
                485                 490                 495

Arg Ser Arg Gly Phe Thr Leu Gly Glu Thr Leu Asp Trp Ser Trp Glu
                500                 505                 510

Leu Met Ile Gly Gly Val Thr Leu Thr Leu Arg Glu Leu Glu Arg Leu
    515                 520                 525

Ala Ser Lys Arg Ser Pro Leu Val Asn His Lys Gly Ala Trp Ile Glu
    530                 535                 540

Leu Arg Pro Asn Asp Leu Lys His Ala Glu His Phe Cys Ser Val Asn
545                 550                 555                 560

Pro Gly Ile Ser Leu Asp Asp Ala Leu Arg Leu Thr Ala Thr Asp Gly
                565                 570                 575

Asp Thr Leu Met Arg Leu Pro Val His Arg Phe Glu Ala Gly Pro Arg
                580                 585                 590

Leu Gln Ala Val Leu Glu Gln Tyr His Gln Lys Ala Pro Asp Pro
                595                 600                 605

Leu Pro Ala Pro Glu Gly Phe Cys Gly Gln Leu Arg Pro Tyr Gln Glu
    610                 615                 620

Arg Gly Leu Gly Trp Leu Ala Phe Leu His Arg Phe Asp Gln Gly Ala
625                 630                 635                 640

Cys Leu Ala Asp Asp Met Gly Leu Gly Lys Thr Ile Gln Leu Leu Ala
                645                 650                 655

Phe Leu Gln His Leu Lys Ala Glu Gln Glu Leu Lys Arg Pro Val Leu
                660                 665                 670

Leu Ile Ala Pro Thr Ser Val Leu Thr Asn Trp Lys Arg Glu Ala Leu
    675                 680                 685

Ala Phe Thr Pro Glu Leu Asn Val Arg Glu His Tyr Gly Pro Arg Arg
    690                 695                 700

Pro Ser Thr Pro Ala Ala Leu Lys Lys Ala Leu Lys Gly Leu Asp Leu
705                 710                 715                 720

Val Leu Thr Ser Tyr Gly Leu Leu Gln Arg Asp Ser Glu Leu Leu Glu
                725                 730                 735

Thr Val Asp Trp Gln Gly Val Val Ile Asp Glu Ala Gln Ala Ile Lys
                740                 745                 750

Asn Pro Asn Ala Lys Gln Ser Gln Ala Ala Arg Asp Met Gly Arg Pro
                755                 760                 765

Asp Lys Asn Asn Arg Phe Arg Ile Ala Leu Thr Gly Thr Pro Val Glu
                770                 775                 780

Asn Arg Val Ser Glu Leu Trp Ala Leu Met Asp Phe Leu Asn Pro Arg
```

```
                785                 790                 795                 800
Val Leu Gly Glu Glu Asp Phe Phe Arg Gln Arg Tyr Arg Leu Pro Ile
                    805                 810                 815

Glu Arg Tyr Gly Asp Met Ser Ser Leu Arg Asp Leu Lys Gly Arg Val
                820                 825                 830

Gly Pro Phe Ile Leu Arg Arg Leu Lys Thr Asp Lys Ala Ile Ile Ser
            835                 840                 845

Asp Leu Pro Glu Lys Val Glu Leu Ser Glu Trp Val Gly Leu Ser Lys
        850                 855                 860

Glu Gln Ala Ala Leu Tyr Arg Asn Thr Val Asp Glu Thr Leu Glu Ala
865                 870                 875                 880

Ile Ala Arg Ala Pro Arg Gly Gln Arg His Gly Lys Val Leu Gly Leu
                885                 890                 895

Leu Thr Arg Leu Lys Gln Ile Cys Asn His Pro Ala Leu Ala Leu Lys
                900                 905                 910

Glu Gln Thr Val Ala Lys Gly Phe Met Asp Arg Ser Ala Lys Leu Leu
            915                 920                 925

Arg Leu Glu Glu Ile Leu Glu Glu Val Ile Glu Ala Gly Asp Arg Ala
        930                 935                 940

Leu Leu Phe Thr Gln Phe Ala Glu Trp Gly His Leu Leu Lys Ala Tyr
945                 950                 955                 960

Leu Gln Gln Arg Trp Arg Phe Glu Val Pro Phe Leu His Gly Ser Thr
                965                 970                 975

Ser Lys Thr Glu Arg Gln Ala Met Val Asp Arg Phe Gln Glu Asp Pro
            980                 985                 990

Arg Gly Pro Gln Leu Phe Leu Leu  Ser Leu Lys Ala Gly  Gly Val Gly
        995                 1000                 1005

Leu Asn  Leu Thr Arg Ala Ser  His Val Phe His Val  Asp Arg Trp
    1010                1015                 1020

Trp Asn  Pro Ala Val Glu Asn  Gln Ala Thr Asp Arg  Ala Tyr Arg
    1025                1030                 1035

Ile Gly  Gln Thr Ser Arg Val  Met Val His Lys Phe  Ile Thr Ser
    1040                1045                 1050

Gly Ser  Val Glu Glu Lys Ile  Asp Arg Met Ile Arg  Glu Lys Ser
    1055                1060                 1065

Arg Leu  Ala Glu Asp Ile Ile  Gly Ser Gly Glu Asp  Trp Leu Gly
    1070                1075                 1080

Gly Leu  Gly Val Ser Gln Leu  Arg Glu Leu Val Ala  Leu Glu Asp
    1085                1090                 1095

Ser

<210> SEQ ID NO 75
<211> LENGTH: 2886
<212> TYPE: DNA
<213> ORGANISM: Rhodococcus sp.

<400> SEQUENCE: 75
atggcgcgag cagggacttc acgcgctgtc ggtcgcacct gcttggatgg gtgcatgctg      60
cacggcctct ggacaccggg ttcgggtctc atgctgtggg tggaggatcg gaatccggca     120
gctccggagc cgacggacgc ggtcgggcgg atgctggcgc ggaagttccg gcatcacgtg     180
aaggtgccga tgccgacgcc gtcggggccg agatgctcg agtgggccgc ggttgcgctc     240
gcaccaccga tgcgacgga gttcctgctg tcggtgtcgt cccgcgaccc ccggatcgcc     300
ggggatctgc gctacctcgc ccacgtcgcc cgcggtgtcg agcggtgggc acgggccggg     360
```

-continued

```
cgggtggtgc ccgaggtaca ccgggcggag ggcggctggt ggccgcgctg gcggctgctc      420
ggcggtgaac ggcagcgtgc gtggctcacg gagctggccg tggcgatgcc gccggtccag      480
cgtcacggca cgaccccccg ggccgtgctc gacgacatgg tcaccgagct gaccgacccc      540
gtcgcccgcc gtgtcctcga acgacggcac ccggacgatt ccggcggcga cgtggatcat      600
ccgctgatcg acgcgctcgt gcgggtgac cagttcgccg agggcaccgc ccagctgtcg        660
ggatcgctgg acgggtggcg cgacagcctc aaggtggacg agcccgaact ggtgctgcgg      720
ctcctcgagc cggaagacgt ggacgtggag ggggattggg accccgacac ggtgctgtgg      780
cgactggagg tctgccttcg accggaaggc gaagccccgg tgccgattcc gttgcaccgc      840
acggaggcga gtcgtctgca gatcggggtg cgcaagctga cggaggccgt ggccgcctac      900
ccgcgactgc aggacgttcc cagtgacccc gacagcctgg acctgatgtt gcccaccgcc      960
gtggtcatcg accttgtcgg gcacggtgcg gtggcgttga aggagaaggg catcagcctg     1020
ctgctgccgc gggcgtggag tgtggcgtcg ccgtcgatgc gtctgcgggt gagctcgccg     1080
agcactccgg cgagcgcgga gaaccgggcc gtcggcaaag accagttggt gcaatacaac     1140
tgggagctgc cactcggcga cacggtgctc accgccgcgg agatgaatcg actggtcaac     1200
tccaagagcg atctcgtgcg gttgcgcggt gagtgggttc gggcggatca ggaggtgctc     1260
tcccgcgccg cgcgctacgt ggcggagcgg cacgccagcg cgaccgggc catcgtggac      1320 ctgctgaagg acctgatcgc ggacgatctg tccgatcttc ccgtggagga ggtcacggcc     1380
accggctggg cggccgcgtt gctggacggc gacacgaagc gcaggacgt gccgaccccg       1440 gacgggttgg acgccacgct gcgcccgtac cagaagcggg ggctcgactg gctggtgttc     1500
atgagccgtc tcggcctcgg ggccgtcctc gccgacgaca tgggactcgg caagacgctg     1560
cagttgctgg cgctgctggc acacgagaag gcgcccacgc ccacgctgct ggtgtgcccg     1620 atgtcggtg tcggcaactg gcagcgcgag gcagcgcgct tcgtcccctc gctgcgggtg       1680
ctcgtccacc acggtccgca gcggctgagc ggcgcggagt tcaccgccgc cgtgacacag     1740
agcgatctgg tgatcaccac gtatgcgctg ctggcccgcg acgtcgcgca cctgaaggag     1800
caggactggc ggcgtgtcgt gctggacgag gcgcagcaca tcaagaacgc gaagacgtcg     1860
caggcgcggg cggcgcggag cattccggcg gcgcaccgcg tcgcgctgac cggcactccg     1920
gtcgagaacc gcctcgacga actgcgctcg atcctcgact tcgcgaactc gggcatcctg     1980
ggctcggagg tgatgttccg caagcgcttc gtggtgccga tcgagcggga gcaggacgag     2040
acagccgtcg cccggctccg cgcggtcacg tccccgttcg tgctgcgccg ggtcaagacc     2100
gatcccgcgg tcatcgccga cctcccccgac aagttcgaga tgacggtgcg cgccaacctc    2160
accgcggagc aggccgcgct gtaccgggcg gtggtcgacg acatgatggc gcagatcaag     2220
gacaagaagg ggatgaagcg caagggcgcc gtcctcgccg ccctgacgaa actcaagcag     2280
gtgtgcaacc acccggcaca cttcctgcgc gacgggtcgg cggtgatgcg gcgcggacag     2340
caccgctccg gcaagctggg gctcgtcgag gacatcctgg attccgtggt cgcggacggc     2400
gagaaggcgt tgctgttcac ccagttccgg gaattcggcg acctcgtcac cccgtacctc     2460
gcggagcgtt tcggtactcc cgtgccgttt ctgcacgggg gcgtgtccaa gcagaagcgc     2520
gacgacatgg tggcctcgtt ccagggcgac gacgggccgc cgatcatgat gctctcgctg     2580 aaggcgggg ggacgggttt gaacctcacc gcggccaatc acgtcgtcca cctcgaccgg       2640 tgtggaatc cggcggtcga gaaccaggcc acggacaggg cgttccggat cggccagcgg      2700
cgggacgtgc aggtgcgcaa gctcgtgtgc gtcggcaccc tggaggagcg gatcgacgcg     2760
```

```
atgatcgcca ccaagcagga gctggccgat ctcgccgtcg ggacgggcga gaactgggtg    2820
acggagatga gcaccgaaca actgggcgaa ctgctccgcc tcggtgacga ggcggtgggc    2880
gaatga                                                                2886
```

<210> SEQ ID NO 76
<211> LENGTH: 961
<212> TYPE: PRT
<213> ORGANISM: Rhodococcus sp.

<400> SEQUENCE: 76

```
Met Ala Arg Ala Gly Thr Ser Arg Ala Val Gly Arg Thr Cys Leu Asp
1               5                   10                  15

Gly Cys Met Leu His Gly Leu Trp Thr Pro Gly Ser Gly Leu Met Leu
            20                  25                  30

Trp Val Glu Asp Arg Asn Pro Ala Ala Pro Glu Pro Thr Asp Ala Val
        35                  40                  45

Gly Arg Met Leu Ala Arg Lys Phe Arg His His Lys Val Pro Met
    50                  55                  60

Pro Thr Pro Ser Gly Pro Glu Met Leu Glu Trp Ala Ala Val Ala Leu
65                  70                  75                  80

Ala Pro Pro Asp Ala Thr Glu Phe Leu Leu Ser Val Ser Ser Arg Asp
                85                  90                  95

Pro Arg Ile Ala Gly Asp Leu Arg Tyr Leu Ala His Val Ala Arg Gly
            100                 105                 110

Val Glu Arg Trp Ala Arg Ala Gly Arg Val Val Pro Glu Val His Arg
        115                 120                 125

Ala Glu Gly Gly Trp Trp Pro Arg Trp Arg Leu Leu Gly Gly Glu Arg
    130                 135                 140

Gln Arg Ala Trp Leu Thr Glu Leu Ala Val Ala Met Pro Pro Val Gln
145                 150                 155                 160

Arg His Gly Thr Thr Pro Arg Ala Val Leu Asp Asp Met Val Thr Glu
                165                 170                 175

Leu Thr Asp Pro Val Ala Arg Arg Val Leu Glu Arg Arg His Pro Asp
            180                 185                 190

Asp Ser Gly Gly Asp Val Asp His Pro Leu Ile Asp Ala Leu Val Arg
        195                 200                 205

Gly Asp Gln Phe Ala Glu Gly Thr Ala Gln Leu Ser Gly Ser Leu Asp
    210                 215                 220

Gly Trp Arg Asp Ser Leu Lys Val Asp Glu Pro Glu Leu Val Leu Arg
225                 230                 235                 240

Leu Leu Glu Pro Glu Asp Val Asp Val Glu Gly Asp Trp Asp Pro Asp
                245                 250                 255

Thr Val Leu Trp Arg Leu Glu Val Cys Leu Arg Pro Glu Gly Glu Ala
            260                 265                 270

Pro Val Pro Ile Pro Leu His Arg Thr Glu Ala Ser Arg Leu Gln Ile
        275                 280                 285

Gly Val Arg Lys Leu Thr Glu Ala Val Ala Ala Tyr Pro Arg Leu Gln
    290                 295                 300

Asp Val Pro Ser Asp Pro Asp Ser Leu Asp Leu Met Leu Pro Thr Ala
305                 310                 315                 320

Val Val Ile Asp Leu Gly His Gly Ala Val Ala Leu Lys Glu Lys
                325                 330                 335

Gly Ile Ser Leu Leu Leu Pro Arg Ala Trp Ser Val Ala Ser Pro Ser
            340                 345                 350
```

```
Met Arg Leu Arg Val Ser Ser Pro Ser Thr Pro Ala Ser Ala Glu Asn
            355                 360                 365

Arg Ala Val Gly Lys Asp Gln Leu Val Gln Tyr Asn Trp Glu Leu Ala
            370                 375                 380

Leu Gly Asp Thr Val Leu Thr Ala Ala Glu Met Asn Arg Leu Val Asn
385                 390                 395                 400

Ser Lys Ser Asp Leu Val Arg Leu Arg Gly Glu Trp Val Arg Ala Asp
                405                 410                 415

Gln Glu Val Leu Ser Arg Ala Ala Arg Tyr Val Ala Glu Arg His Ala
            420                 425                 430

Ser Gly Asp Arg Ala Ile Val Asp Leu Leu Lys Asp Leu Ile Ala Asp
            435                 440                 445

Asp Leu Ser Asp Leu Pro Val Glu Glu Val Thr Ala Thr Gly Trp Ala
            450                 455                 460

Ala Ala Leu Leu Asp Gly Asp Thr Lys Pro Gln Asp Val Pro Thr Pro
465                 470                 475                 480

Asp Gly Leu Asp Ala Thr Leu Arg Pro Tyr Gln Lys Arg Gly Leu Asp
                485                 490                 495

Trp Leu Val Phe Met Ser Arg Leu Gly Leu Gly Ala Val Leu Ala Asp
                500                 505                 510

Asp Met Gly Leu Gly Lys Thr Leu Gln Leu Leu Ala Leu Leu Ala His
            515                 520                 525

Glu Lys Ala Pro Thr Pro Thr Leu Leu Val Cys Pro Met Ser Val Val
            530                 535                 540

Gly Asn Trp Gln Arg Glu Ala Ala Arg Phe Val Pro Ser Leu Arg Val
545                 550                 555                 560

Leu Val His His Gly Pro Gln Arg Leu Ser Gly Ala Glu Phe Thr Ala
                565                 570                 575

Ala Val Thr Gln Ser Asp Leu Val Ile Thr Thr Tyr Ala Leu Leu Ala
            580                 585                 590

Arg Asp Val Ala His Leu Lys Glu Gln Asp Trp Arg Arg Val Val Leu
            595                 600                 605

Asp Glu Ala Gln His Ile Lys Asn Ala Lys Thr Ser Gln Ala Arg Ala
            610                 615                 620

Ala Arg Ser Ile Pro Ala Ala His Arg Val Ala Leu Thr Gly Thr Pro
625                 630                 635                 640

Val Glu Asn Arg Leu Asp Glu Leu Arg Ser Ile Leu Asp Phe Ala Asn
                645                 650                 655

Ser Gly Ile Leu Gly Ser Glu Val Met Phe Arg Lys Arg Phe Val Val
                660                 665                 670

Pro Ile Glu Arg Glu Gln Asp Glu Thr Ala Val Ala Arg Leu Arg Ala
            675                 680                 685

Val Thr Ser Pro Phe Val Leu Arg Arg Val Lys Thr Asp Pro Ala Val
            690                 695                 700

Ile Ala Asp Leu Pro Asp Lys Phe Glu Met Thr Val Arg Ala Asn Leu
705                 710                 715                 720

Thr Ala Glu Gln Ala Ala Leu Tyr Arg Ala Val Val Asp Asp Met Met
                725                 730                 735

Ala Gln Ile Lys Asp Lys Lys Gly Met Lys Arg Lys Gly Ala Val Leu
            740                 745                 750

Ala Ala Leu Thr Lys Leu Lys Gln Val Cys Asn His Pro Ala His Phe
            755                 760                 765

Leu Arg Asp Gly Ser Ala Val Met Arg Arg Gly Gln His Arg Ser Gly
```

```
                    770              775              780
Lys Leu Gly Leu Val Glu Asp Ile Leu Asp Ser Val Val Ala Asp Gly
785                 790              795                  800

Glu Lys Ala Leu Leu Phe Thr Gln Phe Arg Glu Phe Gly Asp Leu Val
                805              810              815

Thr Pro Tyr Leu Ala Glu Arg Phe Gly Thr Pro Val Pro Phe Leu His
            820              825              830

Gly Gly Val Ser Lys Gln Lys Arg Asp Asp Met Val Ala Ser Phe Gln
                835              840              845

Gly Asp Asp Gly Pro Pro Ile Met Met Leu Ser Leu Lys Ala Gly Gly
850              855              860

Thr Gly Leu Asn Leu Thr Ala Ala Asn His Val His Leu Asp Arg
865              870              875              880

Trp Trp Asn Pro Ala Val Glu Asn Gln Ala Thr Asp Arg Ala Phe Arg
                885              890              895

Ile Gly Gln Arg Arg Asp Val Gln Val Arg Lys Leu Val Cys Val Gly
                900              905              910

Thr Leu Glu Glu Arg Ile Asp Ala Met Ile Ala Thr Lys Gln Glu Leu
                915              920              925

Ala Asp Leu Ala Val Gly Thr Gly Glu Asn Trp Val Thr Glu Met Ser
930              935              940

Thr Glu Gln Leu Gly Glu Leu Leu Arg Leu Gly Asp Glu Ala Val Gly
945              950              955              960

Glu

<210> SEQ ID NO 77
<211> LENGTH: 3153
<212> TYPE: DNA
<213> ORGANISM: Salinispora tropica

<400> SEQUENCE: 77
gtgctggttg tccacgggtc gtggcggctc ggcatcgggc tcgccatctg ggccgaggac      60
agcgcgtcgc cgcctcgggc gccgcgccgg gccgggcggg cgccccgcga cgaccccac     120 ccgttcgccg ccggtcaccc cgtgcttgcg gcagctctgg ccgaggtcgc cgagccgacc    180
gagcccggca cggcactgct caccctgccc acccgagctg gttcgccgct ggactcgccg    240
gagctggtcc gcaccgcgtc ggtcgagccg ctccgtgggc cggtcacgtt ggccgggtgg    300
cgggtgcccg ccctggttta cgccccggac gccgccctgt cgctgctctc ccagatcacc    360
gcggccggcg ctctacctga cgccgtaccc ggtgccactc tgcgtcacct cgcggagctg    420
gcggccttcg ccgtggacct cgccgcccgt ggtcgggtcc tgcccggcgt ccggccaccg    480
aaggaacgtg ccagcgccgc ctgggcggtg tggcagcccc tgctcaccgg cgtggacgct    540
ggctgggccc gggccctcgc cctcgccctg ccgcccgcgg tccgtgccgc cgtcgagatc    600
gatccggctc cactcgccgt acccggcgga ccggaaacgc ccgccaacgg tggtgtgccg    660
ccgcaggctc gtacgaggcg accgaccgca gccgccgggg aaccaggtga actggtggtc    720
gaggcgctcg acgcgctcac cgacgcggcc gtacgggctg ccctcgcgga gacctccctt    780
acccggggag ccgtccgcg gggcgcggtc gcggcctggc tcgcggcgct caccggcccg    840
cgtcgtgact tcaccgccga ctcggcggag ctcgacaccc tgcgcggtga gttgacgcc    900 tggcagcgcg acgctgtggg aggttcggtc cgggccagct tccggctggt ggagccgccg    960
acggacggac tctttgaggc ggcggccggg gggctggccg cggccgaggg gtcgtggcgg   1020
gtcgagttcg gcctacagcc ggccgaccag ccgggtctgc atgttgacgc cgtgcggatc   1080
```

| | |
|---|---|
| tggcacgagt cggcggccct accgggcccg gccgctccgc aggaggccct gctgaccgag | 1140 |
| ttggggcggg ccagccgact ctggccggag ctgaactcgg ccctgcgcac cgccactcca | 1200 |
| gaggcgctgg agctggacgc cgcgggcgcg catcgctttc tacgcgacgg cgcgccggtg | 1260 |
| ctgcacgcag ccgggttcgc ggtgctgttg ccctcgtggt ggcagcgtcc gtcgtcccgg | 1320 |
| ctcggcgctc gactacaggc ccagagccgt accgccccgg gcaccgtcgc cggggctggc | 1380 |
| gacggggtgg ggttggatgc cctggtcgac taccgctggg aggtgtccct cggcgaccag | 1440 |
| ccgctgaccg ccgaggaact ggagtcgctg gccgcgctga atctccgtt ggtccgcctg | 1500 |
| cgtgggcgct gggtggagct ggacccgaaa cgtctcgccg ccggcctgcg gctgctccgt | 1560 |
| tccgccggcg agctgaccgt cggcgacctg ctgcggctcg gcctctccga ccctgctacc | 1620 |
| gacgcgctgc cggtgctcga ggtggcggcc gacggtgcgt tgggtgactt gctcgccgga | 1680 |
| gctgtggagc ggcaactcac cccggtggac gcggttccgt cgttccaggg cgttctccgc | 1740 |
| ccctaccagc ggcgagggct ggcctggctg tcctttctgc agtccctcgg cctcggcggg | 1800 |
| gtgctcgctg acgacatggg tctcggcaag acggtacagc tactcgcgtt gctcgctggt | 1860 |
| gacccgccgg gcgtcggtcc gaccctgttg gtctgtccga tgtcactggt cggtaactgg | 1920 |
| cagcgggagg cggcgacctt caccccgggc gtacgggtcc atgtgcatca cggcgccgag | 1980 |
| cgggcccgcg gggcggcgtt caccgcgcg gtggaggcag cggacctggt cctcaccacc | 2040 |
| tacacggtgg ctgcccgcga tgcggggag ctggccgggg tcgactggca tcgggtggtg | 2100 |
| gtggacgagg cacaggccat caagaacgcc tcgacgcggc aagccgaggc ggtccgggcg | 2160 |
| ttgcccgccc ggcatcggat cgcggtcacc ggcacccgg tggagaatcg gctcgccgac | 2220 |
| ctctggtcga tcatgcagtt cgccaatccc ggtctgctcg gccggccgc cgagttcaag | 2280 |
| aagcggtacg ccgaaccgat cgagcgacac ggcgacgcgg aggcggccga gcggctgcgc | 2340 |
| cggatcaccg gcccgttcgt gctgcgtcgc ctcaagaccg actcttcggt tatctccgac | 2400 |
| ctgccagaga agctggagat ggaggtggtg tgcaacctga ccgcggaaca ggctgccctc | 2460 |
| taccgtgcgg tggtggacga catgatggcc cagatcgagt ccagcgaggg catcgagcga | 2520 |
| cgtgggctcg tgctggccgc catgacccgg ctcaagcagg tctgcaacca cccggcgcac | 2580 |
| ctgctgcggg acaactcggc gctggtcggc cgctccggca gctggcccg gctgaggag | 2640 |
| atcctcgacg aggtgcttgt cgcggggag aaggccctgc tcttcaccca gtacgccgag | 2700 |
| ttcggcggca tgctgcgcgg ccacctgtcg gcccggttcg acaggagac gctgttcctg | 2760 |
| cacggcggcg tcggtaaggc cgaccgggac gcgatggtga cgcggttcca gtccccggac | 2820 |
| ggccccgcgc tcttcgtact ctcgctcaag gccggtggta ccggtctcac cctgaccgcg | 2880 |
| gccaaccatg tcgtgcacgt tgaccgctgg tggaatccgg cggtggagga ccaggccacg | 2940 |
| gaccgggcgt tccgcatcgg gcagcggcgg cgcgttcagg tccgcaagtt tgtctgcgcc | 3000 |
| ggcacggtgg aggagaaggt cgccgcgctc atcgccgaca agcgtcggct cgcctcgacg | 3060 |
| gtggtgggtg ccggtgagca gtgggttacc gagctgtcca cggcgcagct gcgggagctg | 3120 |
| ttccagctga agtccggggc ggtggccgaa tga | 3153 |

<210> SEQ ID NO 78
<211> LENGTH: 1050
<212> TYPE: PRT
<213> ORGANISM: Salinispora tropica

<400> SEQUENCE: 78

Val Leu Val Val His Gly Ser Trp Arg Leu Gly Ile Gly Leu Ala Ile

-continued

```
1               5                   10                  15
Trp Ala Glu Asp Ser Ala Ser Pro Pro Arg Pro Arg Arg Ala Gly
                20                  25                  30

Arg Ala Pro Arg Glu Arg Pro His Pro Phe Ala Gly His Pro Val
            35                  40                  45

Leu Ala Ala Ala Leu Ala Glu Val Ala Glu Pro Thr Glu Pro Gly Thr
        50                  55                  60

Ala Leu Leu Thr Leu Pro Thr Arg Ala Gly Ser Pro Leu Asp Ser Pro
65                  70                  75                  80

Glu Leu Val Arg Thr Ala Ser Val Glu Pro Leu Arg Gly Pro Val Thr
                85                  90                  95

Leu Ala Gly Trp Arg Val Pro Ala Leu Val Tyr Ala Pro Asp Ala Ala
            100                 105                 110

Leu Ser Leu Leu Ser Gln Ile Thr Ala Ala Gly Ala Leu Pro Asp Ala
        115                 120                 125

Val Pro Gly Ala Thr Leu Arg His Leu Ala Glu Leu Ala Ala Phe Ala
    130                 135                 140

Val Asp Leu Ala Ala Arg Gly Arg Val Leu Pro Gly Val Arg Pro Pro
145                 150                 155                 160

Lys Glu Arg Ala Ser Ala Ala Trp Ala Val Trp Gln Pro Leu Leu Thr
                165                 170                 175

Gly Val Asp Ala Gly Trp Ala Arg Ala Leu Ala Leu Ala Leu Pro Pro
            180                 185                 190

Ala Val Arg Ala Ala Val Glu Ile Asp Pro Ala Pro Leu Ala Val Pro
        195                 200                 205

Gly Gly Pro Glu Thr Pro Ala Asn Gly Gly Val Pro Pro Gln Ala Arg
    210                 215                 220

Thr Arg Arg Pro Thr Ala Ala Gly Glu Pro Gly Glu Leu Val Val
225                 230                 235                 240

Glu Ala Leu Asp Ala Leu Thr Asp Ala Val Arg Ala Ala Leu Ala
                245                 250                 255

Glu Thr Ser Leu Thr Arg Gly Ala Arg Pro Arg Gly Ala Val Ala Ala
            260                 265                 270

Trp Leu Ala Ala Leu Thr Gly Pro Arg Arg Asp Phe Thr Ala Asp Ser
        275                 280                 285

Ala Glu Leu Asp Thr Leu Arg Gly Glu Leu Asp Ala Trp Gln Arg Asp
    290                 295                 300

Ala Val Gly Gly Ser Val Arg Ala Ser Phe Arg Leu Val Glu Pro Pro
305                 310                 315                 320

Thr Asp Gly Leu Phe Glu Ala Ala Ala Gly Gly Leu Ala Ala Ala Glu
                325                 330                 335

Gly Ser Trp Arg Val Glu Phe Gly Leu Gln Pro Ala Asp Gln Pro Gly
            340                 345                 350

Leu His Val Asp Ala Val Arg Ile Trp His Ser Ala Ala Leu Pro
        355                 360                 365

Gly Pro Ala Ala Pro Gln Glu Ala Leu Leu Thr Glu Leu Gly Arg Ala
    370                 375                 380

Ser Arg Leu Trp Pro Glu Leu Asn Ser Ala Leu Arg Thr Ala Thr Pro
385                 390                 395                 400

Glu Ala Leu Glu Leu Asp Ala Ala Gly Ala His Arg Phe Leu Arg Asp
                405                 410                 415

Gly Ala Pro Val Leu His Ala Ala Gly Phe Ala Val Leu Leu Pro Ser
            420                 425                 430
```

-continued

```
Trp Trp Gln Arg Pro Ser Ser Arg Leu Gly Ala Arg Leu Gln Ala Gln
        435                 440                 445

Ser Arg Thr Ala Pro Gly Thr Val Ala Gly Ala Asp Gly Val Gly
    450                 455                 460

Leu Asp Ala Leu Val Asp Tyr Arg Trp Glu Val Ser Leu Gly Asp Gln
465                 470                 475                 480

Pro Leu Thr Ala Glu Glu Leu Glu Ser Leu Ala Ala Leu Lys Ser Pro
                485                 490                 495

Leu Val Arg Leu Arg Gly Arg Trp Val Glu Leu Asp Pro Lys Arg Leu
            500                 505                 510

Ala Ala Gly Leu Arg Leu Leu Arg Ser Ala Gly Glu Leu Thr Val Gly
        515                 520                 525

Asp Leu Leu Arg Leu Gly Leu Ser Asp Pro Ala Thr Asp Ala Leu Pro
530                 535                 540

Val Leu Glu Val Ala Ala Asp Gly Ala Leu Gly Asp Leu Leu Ala Gly
545                 550                 555                 560

Ala Val Glu Arg Gln Leu Thr Pro Val Asp Ala Val Pro Ser Phe Gln
                565                 570                 575

Gly Val Leu Arg Pro Tyr Gln Arg Arg Gly Leu Ala Trp Leu Ser Phe
            580                 585                 590

Leu Gln Ser Leu Gly Leu Gly Val Leu Ala Asp Asp Met Gly Leu
595                 600                 605

Gly Lys Thr Val Gln Leu Leu Ala Leu Leu Ala Gly Asp Pro Pro Gly
    610                 615                 620

Val Gly Pro Thr Leu Leu Val Cys Pro Met Ser Leu Val Gly Asn Trp
625                 630                 635                 640

Gln Arg Glu Ala Ala Thr Phe Thr Pro Gly Val Arg Val His Val His
                645                 650                 655

His Gly Ala Glu Arg Ala Arg Gly Ala Ala Phe Thr Ala Ala Val Glu
            660                 665                 670

Ala Ala Asp Leu Val Leu Thr Thr Tyr Thr Val Ala Ala Arg Asp Ala
        675                 680                 685

Gly Glu Leu Ala Gly Val Asp Trp His Arg Val Val Asp Glu Ala
    690                 695                 700

Gln Ala Ile Lys Asn Ala Ser Thr Arg Gln Ala Glu Ala Val Arg Ala
705                 710                 715                 720

Leu Pro Ala Arg His Arg Ile Ala Val Thr Gly Thr Pro Val Glu Asn
                725                 730                 735

Arg Leu Ala Asp Leu Trp Ser Ile Met Gln Phe Ala Asn Pro Gly Leu
            740                 745                 750

Leu Gly Pro Ala Ala Glu Phe Lys Lys Arg Tyr Ala Glu Pro Ile Glu
        755                 760                 765

Arg His Gly Asp Ala Glu Ala Ala Glu Arg Leu Arg Arg Ile Thr Gly
    770                 775                 780

Pro Phe Val Leu Arg Arg Leu Lys Thr Asp Ser Ser Val Ile Ser Asp
785                 790                 795                 800

Leu Pro Glu Lys Leu Glu Met Glu Val Val Cys Asn Leu Thr Ala Glu
                805                 810                 815

Gln Ala Ala Leu Tyr Arg Ala Val Val Asp Asp Met Met Ala Gln Ile
            820                 825                 830

Glu Ser Ser Glu Gly Ile Glu Arg Arg Gly Leu Val Leu Ala Ala Met
        835                 840                 845

Thr Arg Leu Lys Gln Val Cys Asn His Pro Ala His Leu Leu Arg Asp
850                 855                 860
```

```
Asn Ser Ala Leu Val Gly Arg Ser Gly Lys Leu Ala Arg Leu Glu Glu
865                 870                 875                 880

Ile Leu Asp Glu Val Leu Val Ala Gly Glu Lys Ala Leu Leu Phe Thr
            885                 890                 895

Gln Tyr Ala Glu Phe Gly Gly Met Leu Arg Gly His Leu Ser Ala Arg
        900                 905                 910

Phe Gly Gln Glu Thr Leu Phe Leu His Gly Gly Val Gly Lys Ala Asp
    915                 920                 925

Arg Asp Ala Met Val Thr Arg Phe Gln Ser Pro Asp Gly Pro Ala Leu
    930                 935                 940

Phe Val Leu Ser Leu Lys Ala Gly Gly Thr Gly Leu Thr Leu Thr Ala
945                 950                 955                 960

Ala Asn His Val Val His Val Asp Arg Trp Trp Asn Pro Ala Val Glu
                965                 970                 975

Asp Gln Ala Thr Asp Arg Ala Phe Arg Ile Gly Gln Arg Arg Val
            980                 985                 990

Gln Val Arg Lys Phe Val Cys Ala Gly Thr Val Glu Glu Lys Val Ala
        995                 1000                1005

Ala Leu Ile Ala Asp Lys Arg  Arg Leu Ala Ser Thr  Val Val Gly
    1010                1015                1020

Ala Gly Glu Gln Trp Val Thr  Glu Leu Ser Thr Ala  Gln Leu Arg
    1025                1030                1035

Glu Leu Phe Gln Leu Glu Ser  Gly Ala Val Ala Glu
    1040                1045                1050

<210> SEQ ID NO 79
<211> LENGTH: 2970
<212> TYPE: DNA
<213> ORGANISM: Symbiobacterium thermophilum

<400> SEQUENCE: 79
atgatcacgg ttcacggcag tttcgtcccc tccggcgcgt ccggcttctt cttcctgtgg      60
ggcctggacg gcgtggccgc ccgggatgcc gctcctcccg ccggcgcgcc cgcgggggtt     120
ccgcgccacc catgcgcaac cgagccggaa gcgctctacc ccgccctgag aggattgccc     180
tacctgaaca cccctgtccct ggtccagtgg cagcccggac cggacggcgt cagcccggcc    240
cgggtcccgg ggatcgccct gtccgtgccc aacgccgtgc agtggctgtt ggatctgccc     300
gaccacttcc gcggcacgcc cctcggccg gggcacagcc tgcagctctg gtgcgtcgca      360
tccaagctgc ttctggagtt cctggggcgg ggcctgatgc tgccggtgct gcaggccgag     420
gccggggtgc tgagcgcggg ctgggcgctc cacctgaccg acgccgacga cgtccgccgc     480
ctgacccggc tggccgctgg attgccggag gcctgccgcg cccttgtgcc ccccgaccga    540 accccccaaca cctaccccct gccggtcgcc gacggcctgg tccaccagtt catgcgtacg    600
gcggccgccg gcgtgatccg gctcctcctg gaggaagagc cctgccccga ggcccagtcg    660
ctacaggata ccgccctgcg ccactggctg gcggcgctga ccggggcgga ggcccgggac    720
ctgccgccgg gcctgcccgg cgcgcaggag ctgtacgccg ccctggaccg ctggagcgcc    780
cccgccaccg gcgtgctgag ccacgccagt ctgcggacgg ggtccgcct ccacctgccc     840 ggcccccgaga ccgacggcga gtgggagctg agctcacgc tccatgcgcc ggacgagggt   900 gcgctgccg tcaccgccga tgcggtctgg gccagcctgg cgccgaggt ggagatcggc     960 gggcagcggt accagggcgc cgagcagcgg ctgctggccg acctgccggc catgcccgc    1020 ctcttcccgc cactggcgcc gctgctccgg gaccccgcgc ccagccgcat gcgcattccg   1080
```

```
gcggacgacg tgctggccct gatccaggaa ggggccatgc tgctccagca ggccggccac    1140
cccgtgctgc tgccggccgc ccttgcgaag cccgccgccc tccgggtcgg aatgcgcctc    1200
agccccgccg ggggcagccc ctccatgttc gggctgcacc agatcgtgaa cgtgcgctgg    1260
gacgtggccc tgggcggcac cccgctcacg ctggacgagc tgcgccacct ggcgcggcag    1320
aagcggcccc tggtacagat gcagggccgg tgggtgcggg tggacgaacg cacccctggct   1380 gcggtcctcc gccggatcga gcagcacggc gggcagatgg agctgggcac ggcgctgcgc    1440
ctggcacccg aggcggacga ggccaccgcg accggctgga tcgccgagct gctggagcgg    1500
ctgcaggagc cagcccggat ggagccggtg ccgaccccg ggggcttcgc cggcaccctg      1560
cggccgtacc agcagcgggg cctcgcctgg ctggcgttcc tgcgccgctg gggcctgggc    1620
gcgtgcctcg ccgacgacat ggggctgggc aagaccgtgc agctcatcgc ccttctcctg    1680
cacgagcggg aggccgggtg ggccgcgggc ccgaccctgc tggtctgccc cgtctcggtc    1740
ctgggcaact ggtgccggga gctggcccgc ttcgccccgg gcctgcgggt cctggtgcac    1800
catggccccg ggaggctggg cgagccggac ttcgcccggc aggccggggc ccacgacgtg    1860
gtgctgacca cgtactccct gctggcccgg gatgccgcgc tgctgggcca ggtgacctgg    1920
aacgggatcg tcgccgacga ggcgcagaac ctgaaaaacc ccgacacaca gcacgcccgg    1980
gcgctgcgaa gccttccgg cggctaccgc atcgccctca ccgtacgcc cgtcgaaaac       2040 cacctgggcg acctgtggtc gctcttccag ttcctcaacc cggggctgct gggcagccgc    2100
gaggagttcg agcggcgcta cgccgtgccg atccagcggt accaggacga ggaggctgcg    2160
gcccggctcc gccggcaggt gggtcccttc atcctgcgcc ggcagaagaa cgaccccgcc    2220
atcgcgccgg acctgcccga caagctggag aacaccgagc tggtgaccct ctcggtggaa    2280
caggcggcgc tgtacgaggc catcgtgcag gagacgctgg agcgggccgc gcaggccgac    2340
ggcatccagc ggcaggcggc ggtcctgca ggcctcacgc ggctgaagca ggtgtgcaac      2400
catcccgcag ccgccaccgg cgacggcccc ctggtggggc ggagcggcaa gatcgaccgg    2460
ctggtgcaac tgctgcagga ggtgctgcg gcgggcgagc aggccctgct cttcacccag      2520
ttcgcccgct tcggcgggcg gctgcaggcc tacctggcgg agacgctggg ctgcgaggtg    2580
ctcttcctgc acggcggcac gccccagccc gagcgggacc ggctcgtcgc ccggttccag    2640
gccggcgagg cgcccctctt catcctctcg ctgaaagccg gcggccttgg cctcaacctc    2700
accgccgcga cccacgtctt tcacgtggac cggtggtgga atccggcggt ggaggatcag    2760
gccacagacc gggcctaccg catcggccag acgcgcaggg tgctggtgca ccggctgatc    2820
accgccggca cgctggagga gcgcatcgac cggctgctgg ccgagaagcg tgccctggcg    2880
ggccaggtga tcatcagcgg cgagtcgtgg ctcggccagc tctccaccga ggagctgcgg    2940
gccctgatcg ccctggaccg ggaggtgtag                                     2970
```

<210> SEQ ID NO 80
<211> LENGTH: 989
<212> TYPE: PRT
<213> ORGANISM: Symbiobacterium thermophilum

<400> SEQUENCE: 80

Met Ile Thr Val His Gly Ser Phe Val Pro Ser Gly Ala Ser Gly Phe
 1               5                  10                  15

Phe Phe Leu Trp Gly Leu Asp Gly Val Ala Ala Arg Asp Ala Ala Pro
            20                  25                  30

Pro Gly Arg Arg Arg Arg Gly Val Pro Arg His Pro Cys Ala Thr Glu

-continued

```
                 35                  40                  45
Pro Glu Ala Leu Tyr Pro Ala Leu Arg Gly Leu Pro Tyr Leu Asn Thr
                 50                  55                  60
Leu Ser Leu Val Gln Trp Gln Pro Gly Pro Asp Gly Val Ser Pro Ala
 65                  70                  75                  80
Arg Val Pro Gly Ile Ala Leu Ser Val Pro Asn Ala Val Gln Trp Leu
                 85                  90                  95
Leu Asp Leu Pro Asp His Phe Arg Gly Thr Pro Leu Arg Pro Gly His
                100                 105                 110
Ser Leu Gln Leu Trp Cys Val Ala Ser Lys Leu Leu Leu Glu Phe Leu
                115                 120                 125
Gly Arg Gly Leu Met Leu Pro Val Leu Gln Ala Glu Ala Gly Val Leu
                130                 135                 140
Ser Ala Gly Trp Ala Leu His Leu Thr Asp Ala Asp Asp Val Arg Arg
145                 150                 155                 160
Leu Thr Arg Leu Ala Ala Gly Leu Pro Glu Ala Cys Arg Ala Leu Val
                165                 170                 175
Pro Pro Asp Arg Thr Pro Asn Thr Tyr Pro Leu Pro Val Ala Asp Gly
                180                 185                 190
Leu Val His Gln Phe Met Arg Thr Ala Ala Gly Val Ile Arg Leu
                195                 200                 205
Leu Leu Glu Glu Glu Pro Leu Pro Glu Ala Gln Ser Leu Gln Asp Thr
                210                 215                 220
Ala Leu Arg His Trp Leu Ala Ala Leu Thr Gly Ala Glu Ala Arg Asp
225                 230                 235                 240
Leu Pro Pro Gly Leu Pro Gly Ala Gln Glu Leu Tyr Ala Ala Leu Asp
                245                 250                 255
Arg Trp Ser Ala Pro Ala Thr Gly Val Leu Ser His Ala Ser Leu Arg
                260                 265                 270
Thr Gly Val Arg Leu His Leu Pro Gly Pro Thr Asp Gly Glu Trp
                275                 280                 285
Glu Leu Glu Leu Thr Leu His Ala Pro Asp Glu Gly Ala Leu Pro Val
290                 295                 300
Thr Ala Asp Ala Val Trp Ala Ser Leu Gly Ala Glu Val Glu Ile Gly
305                 310                 315                 320
Gly Gln Arg Tyr Gln Gly Ala Glu Gln Arg Leu Leu Ala Asp Leu Pro
                325                 330                 335
Ala Met Ala Arg Leu Phe Pro Pro Leu Ala Pro Leu Leu Arg Asp Pro
                340                 345                 350
Ala Pro Ser Arg Met Arg Ile Pro Ala Asp Asp Val Leu Ala Leu Ile
                355                 360                 365
Gln Glu Gly Ala Met Leu Leu Gln Gln Ala Gly His Pro Val Leu Leu
                370                 375                 380
Pro Ala Ala Leu Ala Lys Pro Ala Leu Arg Val Gly Met Arg Leu
385                 390                 395                 400
Ser Pro Ala Gly Gly Ser Pro Ser Met Phe Gly Leu His Gln Ile Val
                405                 410                 415
Asn Val Arg Trp Asp Val Ala Leu Gly Gly Thr Pro Leu Thr Leu Asp
                420                 425                 430
Glu Leu Arg His Leu Ala Arg Gln Lys Arg Pro Leu Val Gln Met Gln
                435                 440                 445
Gly Arg Trp Val Arg Val Asp Glu Arg Thr Leu Ala Ala Val Leu Arg
                450                 455                 460
```

-continued

```
Arg Ile Glu Gln His Gly Gly Gln Met Glu Leu Gly Thr Ala Leu Arg
465                 470                 475                 480

Leu Ala Pro Glu Ala Asp Glu Ala Thr Ala Thr Gly Trp Ile Ala Glu
            485                 490                 495

Leu Leu Glu Arg Leu Gln Glu Pro Ala Arg Met Glu Pro Val Pro Thr
        500                 505                 510

Pro Gly Gly Phe Ala Gly Thr Leu Arg Pro Tyr Gln Gln Arg Gly Leu
    515                 520                 525

Ala Trp Leu Ala Phe Leu Arg Arg Trp Gly Leu Gly Ala Cys Leu Ala
530                 535                 540

Asp Asp Met Gly Leu Gly Lys Thr Val Gln Leu Ile Ala Leu Leu Leu
545                 550                 555                 560

His Glu Arg Glu Ala Gly Trp Ala Ala Gly Pro Thr Leu Leu Val Cys
            565                 570                 575

Pro Val Ser Val Leu Gly Asn Trp Cys Arg Glu Leu Ala Arg Phe Ala
        580                 585                 590

Pro Gly Leu Arg Val Leu Val His Gly Pro Gly Arg Leu Gly Glu
    595                 600                 605

Pro Asp Phe Ala Arg Gln Ala Gly Ala His Asp Val Val Leu Thr Thr
610                 615                 620

Tyr Ser Leu Leu Ala Arg Asp Ala Ala Leu Leu Gly Gln Val Thr Trp
625                 630                 635                 640

Asn Gly Ile Val Ala Asp Glu Ala Gln Asn Leu Lys Asn Pro Asp Thr
            645                 650                 655

Gln His Ala Arg Ala Leu Arg Ser Leu Ser Gly Gly Tyr Arg Ile Ala
        660                 665                 670

Leu Thr Gly Thr Pro Val Glu Asn His Leu Gly Asp Leu Trp Ser Leu
    675                 680                 685

Phe Gln Phe Leu Asn Pro Gly Leu Leu Gly Ser Arg Glu Glu Phe Glu
690                 695                 700

Arg Arg Tyr Ala Val Pro Ile Gln Arg Tyr Gln Asp Glu Glu Ala Ala
705                 710                 715                 720

Ala Arg Leu Arg Arg Gln Val Gly Pro Phe Ile Leu Arg Arg Gln Lys
            725                 730                 735

Asn Asp Pro Ala Ile Ala Pro Asp Leu Pro Asp Lys Leu Glu Asn Thr
        740                 745                 750

Glu Leu Val Thr Leu Ser Val Glu Gln Ala Ala Leu Tyr Glu Ala Ile
    755                 760                 765

Val Gln Glu Thr Leu Glu Arg Ala Ala Gln Ala Asp Gly Ile Gln Arg
770                 775                 780

Gln Ala Ala Val Leu Ala Gly Leu Thr Arg Leu Lys Gln Val Cys Asn
785                 790                 795                 800

His Pro Ala Ala Ala Thr Gly Asp Gly Pro Leu Val Gly Arg Ser Gly
            805                 810                 815

Lys Ile Asp Arg Leu Val Gln Leu Leu Gln Glu Val Leu Ala Ala Gly
        820                 825                 830

Glu Gln Ala Leu Leu Phe Thr Gln Phe Ala Arg Phe Gly Gly Arg Leu
    835                 840                 845

Gln Ala Tyr Leu Ala Glu Thr Leu Gly Cys Glu Val Leu Phe Leu His
850                 855                 860

Gly Gly Thr Pro Gln Pro Glu Arg Asp Arg Leu Val Ala Arg Phe Gln
865                 870                 875                 880

Ala Gly Glu Ala Pro Leu Phe Ile Leu Ser Leu Lys Ala Gly Gly Leu
            885                 890                 895
```

```
Gly Leu Asn Leu Thr Ala Ala Thr His Val Phe His Val Asp Arg Trp
                900                 905                 910

Trp Asn Pro Ala Val Glu Asp Gln Ala Thr Asp Arg Ala Tyr Arg Ile
            915                 920                 925

Gly Gln Thr Arg Arg Val Leu Val His Arg Leu Ile Thr Ala Gly Thr
        930                 935                 940

Leu Glu Glu Arg Ile Asp Arg Leu Leu Ala Glu Lys Arg Ala Leu Ala
945                 950                 955                 960

Gly Gln Val Ile Ile Ser Gly Glu Ser Trp Leu Gly Gln Leu Ser Thr
                965                 970                 975

Glu Glu Leu Arg Ala Leu Ile Ala Leu Asp Arg Glu Val
            980                 985
```

<210> SEQ ID NO 81
<211> LENGTH: 3114
<212> TYPE: DNA
<213> ORGANISM: Synechococcus sp.

<400> SEQUENCE: 81

```
atgagcctgc tgcacgccac ctggctgtcg gccgacaccg ccgccgtgcc cgccctggga      60
ggcggctacc ggccgggctt gctgctctgg gccgacacct ggcgggtggc ggaaccccag     120
acaccggcca gcgaggcgcc ccagcacccc ctcagcctcg accaggacga cctcggcgcc     180
tggcttgagg aggccgacct ctggacggag gatttccgcc cggccggagc caccctctgc     240
ctgcccagcc gccgccaggg ggccaggggg aaaaagaaaa gcgacaccag cagctggagc     300
ggcctgcccc tgcaggcggg cgagccgatc ccgaaatccg tggagtggtg gccctggcgg     360
gtggagggct ggtggctgga gcccggcgcc gccaccctct ggcttgggcg cctgcccctc     420
tcaggcgacc atcccgacct ggccgatgac ctgcgctggt ggagccatct gcagcgctgg     480
tcgctgagcc tgctggcccg gggccggctg ctgccccagg tggaggggg ccgcgcccgc      540 tggctgccgt tgatcaaccg cgaagacgac cggcgccgcc tggaggatct ggcctcgcgt     600
ctgccccagg tggcggtggc ggccctggag cccggccagg ggaggccgg cgtcgcgatg      660 gcgtgctggc ggccgggatc cgggcgtcgg cggctggcct cgatcctcac gcacctggtg     720
gatgcacgca tgcgtgcggg cttcaccccc agcgaagagg ggctggatcc gctgctggcg     780
gcctggcagc gggccctcgg ccccggtgac ggccgcctcg atctcgggga cgacgactgc     840
gaacgcctgc aggtggccac tcaccactgg cgcgaagcgg tggctggccg ggtcgagccg     900
gcccgggcct gtcttgagct cgacacaccc gatgaggggg aagatctctg gcccctgcgc     960
ttcagcctcc aggccgaggc cgatcccagt ctgctgctgc ccgcagccgg ggtctgggcc    1020
gccggggccg gctgcctgca gctgggtgaa accgaactcc agcaaccggt gaactgctg     1080 ctggaaggcc tcgggagagc cctgcaggtg ttcgagccga tcgagagggg tctcgacacc    1140
gccacaccgg agcggatggc tctcaccccg gccgaagcct tcgtgctggt gcgcaccgcc    1200
gcgctgaagc tgcgtgatgt gggcgtcggc gtggtcctgc ccccagcct cagcggtggc     1260 ctggccagcc ggctcggcct ctcgatcgag gccgatctgc ccgagcgctc ccgcggcttc    1320
agcctcggtg aaagcctgca gtggagctgg gagctgatga tcggcggcgt cacgctcacc    1380
ctgcgggacc tggagcggct ggcgggcaag cgcagcccgc tggtgcagca aggggggcc      1440 tggatcgagc tgcgtccggg tgatctgcgc aatgccgaga agttctgcgc cctcgatccg    1500
gtcctcagcc tcgatgacgc cctgcgcctg accggcaacg aggggagac cctgcagcgg     1560 ctgccggtgc accgcttcac agccggcccg aggctgaagg cggtgctgga gcagtaccac    1620
```

-continued

```
cagcagaagg ccccgatcc cctgccggcc cccgagggct tcgccggcca gctgcggccc    1680
taccaggagc gcggcctggg ctggctggcc ttcctgcacc gcttcgatca gggggcctgc    1740
ctggccgacg acatgggcct gggcaagaca atccagctgc tggccttcct gcagcacctc    1800
aaggcggagc aggaactgaa gcgtcccgta ctgctggtgg cccccacctc ggtgctcacc    1860
aactggctgc gggaagcgaa ggccttcacg ccggaactga cgtggtgga gcactacggc    1920 ccccggcggc cctccacccc cgccgccctg aagaagaagc tggagggat ggatctggtg    1980 ctcaccagct acggcctgct gcagcgcgac agcgagttac tgagcagcct cgactggcag    2040
ggggtggtga ttgatgaggc ccaggcgatc aagaattcct cagcgcgcca gtcgcaggca    2100
gcccgcgatc tggcacgccc gctcaagcag agccgcttcc gtatcgcact caccggcacc    2160
ccggtggaga accgggtcag tgagctctgg gccctgatgg acttcctcaa tccgaaggtg    2220
cttggggagg aggagttctt ccgccagcgc taccgcctgc cgatcgagcg ctatggcgac    2280
atggcctcgg tgcgcgacct caaggcccgc gtcggcccgt tcatcctgcg cgcctcaag    2340 actgaccgct cgatcatctc cgacctgccc gagaaggtgg aactgaagga gtgggttgga    2400
ctctcacccg agcaggtcaa gctctaccgc cgcaccgtgg aggacaccct cgatgcgatc    2460
gcgcgggcac ccgtgggcca gaagcacggc caggtgctgg ggctgctcac caagctcaag    2520
caggtctgca accacccggc cctgatgctc aaggaagggg aggtggggc cggcttcagc    2580 gcccgctcgg ccaagttgca gcggctcgag gaaatcgtcg aggaggtgat cgcggccggc    2640
gatcgggccc tcctgtttac ccagttcgcc gaatggggcc acctgctcca gacccacctg    2700
cagcagcgct tccaccagga ggtgcccttt ctctatggca gtaccagcaa ggggagcgt    2760 caggcgatgg tggatcgctt ccaggacgac cccggggac cacagctgtt cctgctctcg    2820
ctcaaggcag gcggcgtggg gctcaacctc acccgggcca gtcatgtgtt ccacatcgac    2880
cgctggtgga atccggcggt ggagaaccag gccaccgacc gggcctaccg catcggccag    2940
accaaccggg tgatggtgca aagttcatc accagcggct cggtggagga aagatcgac    3000 cgcatgatcc gcgaaaaggc ccgcctggcc gaagacatcg tcggcagcgg tgaggagtgg    3060
ctcggaggcc tcgatcccgg ccagctgcgc gacctggtgg ccctggagga gtga         3114
```

<210> SEQ ID NO 82
<211> LENGTH: 1037
<212> TYPE: PRT
<213> ORGANISM: Synechococcus sp.

<400> SEQUENCE: 82

```
Met Ser Leu Leu His Ala Thr Trp Leu Ser Ala Asp Thr Ala Ala Val
1               5                   10                  15

Pro Ala Leu Gly Gly Gly Tyr Arg Pro Gly Leu Leu Leu Trp Ala Asp
                20                  25                  30

Thr Trp Arg Val Ala Glu Pro Gln Thr Pro Ala Ser Glu Ala Pro Gln
            35                  40                  45

His Pro Leu Ser Leu Asp Gln Asp Asp Leu Gly Ala Trp Leu Glu Glu
        50                  55                  60

Ala Asp Leu Trp Thr Glu Asp Phe Arg Pro Gly Ala Thr Leu Cys
65                  70                  75                  80

Leu Pro Ser Arg Arg Gln Gly Ala Arg Gly Lys Lys Lys Ser Asp Thr
                85                  90                  95

Ser Ser Trp Ser Gly Leu Pro Leu Gln Ala Gly Glu Pro Ile Pro Lys
            100                 105                 110
```

```
Ser Val Glu Trp Trp Pro Trp Arg Val Glu Gly Trp Leu Glu Pro
        115                 120                 125

Gly Ala Ala Thr Leu Trp Leu Gly Arg Leu Pro Leu Ser Gly Asp His
    130                 135                 140

Pro Asp Leu Ala Asp Asp Leu Arg Trp Trp Ser His Leu Gln Arg Trp
145                 150                 155                 160

Ser Leu Ser Leu Leu Ala Arg Gly Arg Leu Leu Pro Gln Val Glu Gly
            165                 170                 175

Gly Arg Ala Arg Trp Leu Pro Leu Ile Asn Arg Glu Asp Asp Arg Arg
                180                 185                 190

Arg Leu Glu Asp Leu Ala Ser Arg Leu Pro Gln Val Ala Val Ala Ala
            195                 200                 205

Leu Glu Pro Gly Gln Gly Glu Ala Gly Val Ala Met Ala Cys Trp Arg
    210                 215                 220

Pro Gly Ser Gly Arg Arg Leu Ala Ser Ile Leu Thr His Leu Val
225                 230                 235                 240

Asp Ala Arg Met Arg Ala Gly Phe Thr Pro Ser Glu Glu Gly Leu Asp
                245                 250                 255

Pro Leu Leu Ala Ala Trp Gln Arg Ala Leu Gly Pro Gly Asp Gly Arg
            260                 265                 270

Leu Asp Leu Gly Asp Asp Asp Cys Glu Arg Leu Gln Val Ala Thr His
    275                 280                 285

His Trp Arg Glu Ala Val Ala Gly Arg Val Glu Pro Ala Arg Ala Cys
290                 295                 300

Leu Glu Leu Asp Thr Pro Asp Glu Gly Asp Leu Trp Pro Leu Arg
305                 310                 315                 320

Phe Ser Leu Gln Ala Glu Ala Asp Pro Ser Leu Leu Pro Ala Ala
                325                 330                 335

Gly Val Trp Ala Ala Gly Ala Gly Cys Leu Gln Leu Gly Glu Thr Glu
            340                 345                 350

Leu Gln Gln Pro Gly Glu Leu Leu Leu Glu Gly Leu Gly Arg Ala Leu
    355                 360                 365

Gln Val Phe Glu Pro Ile Glu Arg Gly Leu Asp Thr Ala Thr Pro Glu
    370                 375                 380

Arg Met Ala Leu Thr Pro Ala Glu Ala Phe Val Leu Arg Thr Ala
385                 390                 395                 400

Ala Leu Lys Leu Arg Asp Val Gly Val Gly Val Val Leu Pro Pro Ser
                405                 410                 415

Leu Ser Gly Gly Leu Ala Ser Arg Leu Gly Leu Ser Ile Glu Ala Asp
            420                 425                 430

Leu Pro Glu Arg Ser Arg Gly Phe Ser Leu Gly Glu Ser Leu Gln Trp
    435                 440                 445

Ser Trp Glu Leu Met Ile Gly Gly Val Thr Leu Thr Leu Arg Asp Leu
450                 455                 460

Glu Arg Leu Ala Gly Lys Arg Ser Pro Leu Val Gln His Lys Gly Ala
465                 470                 475                 480

Trp Ile Glu Leu Arg Pro Gly Asp Leu Arg Asn Ala Glu Lys Phe Cys
                485                 490                 495

Ala Leu Asp Pro Val Leu Ser Leu Asp Asp Ala Leu Arg Leu Thr Gly
            500                 505                 510

Asn Glu Gly Glu Thr Leu Gln Arg Leu Pro Val His Arg Phe Thr Ala
    515                 520                 525

Gly Pro Arg Leu Lys Ala Val Leu Glu Gln Tyr His Gln Gln Lys Ala
    530                 535                 540
```

```
Pro Asp Pro Leu Pro Ala Pro Glu Gly Phe Ala Gly Gln Leu Arg Pro
545                 550                 555                 560

Tyr Gln Glu Arg Gly Leu Gly Trp Leu Ala Phe Leu His Arg Phe Asp
            565                 570                 575

Gln Gly Ala Cys Leu Ala Asp Asp Met Gly Leu Gly Lys Thr Ile Gln
                580                 585                 590

Leu Leu Ala Phe Leu Gln His Leu Lys Ala Glu Gln Glu Leu Lys Arg
            595                 600                 605

Pro Val Leu Leu Val Ala Pro Thr Ser Val Leu Thr Asn Trp Leu Arg
        610                 615                 620

Glu Ala Lys Ala Phe Thr Pro Glu Leu Asn Val Val Glu His Tyr Gly
625                 630                 635                 640

Pro Arg Arg Pro Ser Thr Pro Ala Ala Leu Lys Lys Leu Glu Gly
                645                 650                 655

Met Asp Leu Val Leu Thr Ser Tyr Gly Leu Leu Gln Arg Asp Ser Glu
            660                 665                 670

Leu Leu Ser Ser Leu Asp Trp Gln Gly Val Val Ile Asp Glu Ala Gln
        675                 680                 685

Ala Ile Lys Asn Ser Ser Ala Arg Gln Ser Gln Ala Ala Arg Asp Leu
690                 695                 700

Ala Arg Pro Leu Lys Gln Ser Arg Phe Arg Ile Ala Leu Thr Gly Thr
705                 710                 715                 720

Pro Val Glu Asn Arg Val Ser Glu Leu Trp Ala Leu Met Asp Phe Leu
            725                 730                 735

Asn Pro Lys Val Leu Gly Glu Glu Phe Phe Arg Gln Arg Tyr Arg
        740                 745                 750

Leu Pro Ile Glu Arg Tyr Gly Asp Met Ala Ser Val Arg Asp Leu Lys
        755                 760                 765

Ala Arg Val Gly Pro Phe Ile Leu Arg Arg Leu Lys Thr Asp Arg Ser
770                 775                 780

Ile Ile Ser Asp Leu Pro Glu Lys Val Glu Leu Lys Glu Trp Val Gly
785                 790                 795                 800

Leu Ser Pro Glu Gln Val Lys Leu Tyr Arg Arg Thr Val Glu Asp Thr
            805                 810                 815

Leu Asp Ala Ile Ala Arg Ala Pro Val Gly Gln Lys His Gly Gln Val
        820                 825                 830

Leu Gly Leu Leu Thr Lys Leu Lys Gln Val Cys Asn His Pro Ala Leu
        835                 840                 845

Met Leu Lys Glu Gly Glu Val Gly Ala Gly Phe Ser Ala Arg Ser Ala
850                 855                 860

Lys Leu Gln Arg Leu Glu Glu Ile Val Glu Val Ile Ala Ala Gly
865                 870                 875                 880

Asp Arg Ala Leu Leu Phe Thr Gln Phe Ala Glu Trp Gly His Leu Leu
            885                 890                 895

Gln Thr His Leu Gln Gln Arg Phe His Gln Glu Val Pro Phe Leu Tyr
        900                 905                 910

Gly Ser Thr Ser Lys Gly Glu Arg Gln Ala Met Val Asp Arg Phe Gln
        915                 920                 925

Asp Asp Pro Arg Gly Pro Gln Leu Phe Leu Ser Leu Lys Ala Gly
        930                 935                 940

Gly Val Gly Leu Asn Leu Thr Arg Ala Ser His Val Phe His Ile Asp
945                 950                 955                 960

Arg Trp Trp Asn Pro Ala Val Glu Asn Gln Ala Thr Asp Arg Ala Tyr
```

```
                965                 970                 975
Arg Ile Gly Gln Thr Asn Arg Val Met Val His Lys Phe Ile Thr Ser
                    980                 985                 990
Gly Ser Val Glu Glu Lys Ile Asp  Arg Met Ile Arg Glu  Lys Ala Arg
                        995                1000               1005
Leu Ala  Glu Asp Ile Val Gly  Ser Gly Glu Glu Trp  Leu Gly Gly
    1010                1015                1020
Leu Asp  Pro Gly Gln Leu Arg  Asp Leu Val Ala Leu  Glu Glu
    1025                1030                1035

<210> SEQ ID NO 83
<211> LENGTH: 3090
<212> TYPE: DNA
<213> ORGANISM: Synechococcus sp.

<400> SEQUENCE: 83
atgagcctgc tgcacgccac ctggcttccc gccattcgta cttccagcag ttccggacaa     60
ccggcactgc tcgtttgggc tgacacctgg cgtgtcgcct accggaggg acctggactc    120 acacccgctc tgcatccctt cacccttggc tcgaacgatc tcaaggcttg gttgaccgaa    180
cgggacctga tgcctggggg cagcatcgat gccaccgcct gcctcaccct cccaagccgc    240
accgtcaaac cccgcaaaag tcgaacccaa tcgagcgaac cagatccgga ggggccagcc    300
tggaccgggt tgccaatgca agcgggagaa cccattccaa acaaatggaa atggtggcca    360
tggcaagtgc aaggcctggc ggtcgagcca tcggccgcca cggaatggct ggcccgttta    420 ccccctatcgg gccgacatcc agaccttggg gatgaactgc gctggtggag tcacctccaa    480
cgttggtccc tcagcttggt ggcccgtggt cgctggattc cccaaatgga attaagcaaa    540
ggcgaggggt accccaccg agcgcgctgg gttcccctgc tgaaccgtga ggaggatcga    600
cgccggctcg aagacctcgc cgcgacgctg ccctcgtag cgacctgtgc cctcccttgg    660
cgtgagccac tcggacgccg cagcaaccgc accaccagg ttcgaccgga agcgatgcga    720
gccgccaatc cggtcgcctg ctgtcgccca cgaagcggtc gcctcagggt ggccaccttg    780
cttgaagact tggtggatgc ggagctgcgc aagggatttg aaccaagcac ggaaggcctc    840
gaccccttac tcaccttgtg gcaagaggcc ctggcctcag aaaccggtgt tgtggaggtg    900
ggcaacgaag acgcagaacg cctcaccgcg gcaagcctgc actggcgcga gggaattgcc    960
ggaggcttcg cggccgcccg cacctgcctc gaactcaaca ccccaaacga aggcgaagaa   1020
ctctgggacc tgaagtttgg attgcaagcg gaggccgatc ccagcctcaa gctgccggcc   1080
gccgcggcct gggcctcagg agcggaaacc cttcaactgg gggaaatcca agttgaccag   1140
gcgggggaag tgctgctgga gggtcttggc cgagccctca cggtgttccc tccgatcgaa   1200
cgcggactgg aaagcgcaac accggaaacg atgcagctca ctccagcgga ggcatttgtg   1260
ttggtgcgaa cagcaacgca ccagctccgc aatgccggca tcggcgtcga actgcccccc   1320
agtctttcag ggggcctcgc cagccggctt ggcttagcga ttaaagcgga tctaccggat   1380
cgatccagcg gcttcaccct cggcgaatct cttgactgga gctgggatct catgatcggc   1440
ggcgtcacac tcaccctccg agagctcgaa cgtctcagcg gtaagcgaag tccgctggta   1500
cgccacaagg gcgcctggat cgaactacgg cccaacgatc tccgcaacgc cgaacgcttt   1560
tgtggagcca atccagaact gagcctcgac gacgcactac ggctcacggc cacagaaggg   1620
gagctcatga tgcgcctgcc ggtgcatcgc tttgatgcag ggcctcgtct tcagggagtt   1680
ctcgagcaat accaccagca aaaagcccccc gatcccctgc cagctccaga gggatttttcc    1740
```

```
ggacaactcc gtccctatca agaacgtggc ttgggctggc tggccttcct gcatcgcttc   1800
gatcagggcg cctgcctggc ggacgacatg ggcttgggca agaccatcca gttattggcg   1860
ttcctgcagc acctcaaagc ggaaaacgaa ctcaaacgcc cggtgctgtt ggtggcccca   1920
acctcggtgc tcacgaattg cgacgggaa gcggaagcct tcacccctga ctgtcggtg    1980
agagagcact acgggccacg ccggccttcc acgccggccg ccttgaaaaa agagctcaaa   2040
ggtgtggatc tggtgctcac cagttacgga ctgatgcaac gcgacagtga gctgctggac   2100
aacctcgact ggcaaggggt tgtgatcgat gaagctcagg cgatcaagaa ccctggggca   2160
aagcaaagcc aagcggcccg agacctagcg cgagccggga agagcagcag gttccgcatt   2220
gcactcacgg gcacaccggt ggaaaaccgc gtcagcgagc tgtgggcgct gatggatttc   2280
ctcaaccca aagtgttggg tgaggaagac ttttttcgtc agcgctaccg catgccaatt    2340
gagcgctacg gcgatatgtc gtcgttacgc gatctcaaag cacgggttgg tcccttcatc   2400
ctgcgccgcc tcaaaaccga caagtcgatc atttccgacc tgcctgaaaa ggtggagctc   2460
agcgaatggg tggggctcag caaagaacag aaatcgctgt acaacaaaac cgttgaagac   2520
accctcgatg ccattgccac cgcacctcga gggcaacgcc atggccaggt gctggcgctc   2580
ttgacccgtt taaaacagat ttgcaatcac ccggccttag cccaacgcga aggtgccgtt   2640
gacgccgaat tccttagccg gtccgccaag ctcatgcggc tggaagaaat ccttgaagag   2700
gtgattgaag ccggcgatcg cgctttgctg ttcacccagt tcgccgaatg gggacacctc   2760
ttgcaggcct ggatgcaaca acgctggaag tctgaggttc cctttctgca cggcggaacc   2820
cgcaaaagtg atcggcaagc gatggtggat cgattccaag aggaccccg gggacctcaa    2880
ctcttccttc tctcccctcaa ggccggtggt gttggcctaa acctcacccg gccagccac    2940
gtgttccacg ttggatcgct ggtggaatcc agcggtggaa aaccaagcca ccgaccgggc   3000
ctatcgaatt ggtcaaacca accgggtgat ggtgcacaaa ttcgtcaccc gtggctcggt   3060
ggaagaaaaa atcgaccaaa tgattcgtga                                    3090
```

<210> SEQ ID NO 84  
<211> LENGTH: 1029  
<212> TYPE: PRT  
<213> ORGANISM: Synechococcus sp.

<400> SEQUENCE: 84

```
Met Ser Leu Leu His Ala Thr Trp Leu Pro Ala Ile Arg Thr Ser Ser
1               5                   10                  15

Ser Ser Gly Gln Pro Ala Leu Leu Val Trp Ala Asp Thr Trp Arg Val
            20                  25                  30

Ala Ser Pro Glu Gly Pro Gly Leu Thr Pro Ala Leu His Pro Phe Thr
        35                  40                  45

Leu Gly Ser Asn Asp Leu Lys Ala Trp Leu Thr Glu Arg Asp Leu Met
    50                  55                  60

Pro Gly Gly Ser Ile Asp Ala Thr Ala Cys Leu Thr Leu Pro Ser Arg
65                  70                  75                  80

Thr Val Lys Pro Arg Lys Ser Arg Thr Gln Ser Ser Glu Pro Asp Pro
                85                  90                  95

Glu Gly Pro Ala Trp Thr Gly Leu Pro Met Gln Ala Gly Glu Pro Ile
            100                 105                 110

Pro Lys Gln Met Glu Trp Trp Pro Trp Gln Val Gln Gly Leu Ala Val
        115                 120                 125

Glu Pro Ser Ala Ala Thr Glu Trp Leu Ala Arg Leu Pro Leu Ser Gly
    130                 135                 140
```

Arg His Pro Asp Leu Gly Asp Glu Leu Arg Trp Trp Ser His Leu Gln
145                 150                 155                 160

Arg Trp Ser Leu Ser Leu Val Ala Arg Gly Arg Trp Ile Pro Gln Met
            165                 170                 175

Glu Leu Ser Lys Gly Glu Gly Tyr Pro His Arg Ala Arg Trp Val Pro
            180                 185                 190

Leu Leu Asn Arg Glu Glu Asp Arg Arg Leu Glu Asp Leu Ala Ala
            195                 200                 205

Thr Leu Pro Leu Val Ala Thr Cys Ala Leu Pro Trp Arg Glu Pro Leu
210                 215                 220

Gly Arg Arg Ser Asn Arg Thr Thr Arg Leu Arg Pro Glu Ala Met Arg
225                 230                 235                 240

Ala Ala Asn Pro Val Ala Cys Cys Arg Pro Arg Ser Gly Arg Leu Arg
                245                 250                 255

Val Ala Thr Leu Leu Glu Asp Leu Val Asp Ala Glu Leu Arg Lys Gly
            260                 265                 270

Phe Glu Pro Ser Thr Glu Gly Leu Asp Pro Leu Leu Thr Leu Trp Gln
            275                 280                 285

Glu Ala Leu Ala Ser Glu Thr Gly Val Val Glu Val Gly Asn Glu Asp
290                 295                 300

Ala Glu Arg Leu Thr Ala Ala Ser Leu His Trp Arg Glu Gly Ile Ala
305                 310                 315                 320

Gly Gly Phe Ala Ala Ala Arg Thr Cys Leu Glu Leu Asn Thr Pro Asn
                325                 330                 335

Glu Gly Glu Glu Leu Trp Asp Leu Lys Phe Gly Leu Gln Ala Glu Ala
            340                 345                 350

Asp Pro Ser Leu Lys Leu Pro Ala Ala Ala Trp Ala Ser Gly Ala
            355                 360                 365

Glu Thr Leu Gln Leu Gly Glu Ile Gln Val Asp Gln Ala Gly Glu Val
370                 375                 380

Leu Leu Glu Gly Leu Gly Arg Ala Leu Thr Val Phe Pro Pro Ile Glu
385                 390                 395                 400

Arg Gly Leu Glu Ser Ala Thr Pro Glu Thr Met Gln Leu Thr Pro Ala
                405                 410                 415

Glu Ala Phe Val Leu Val Arg Thr Ala Thr His Gln Leu Arg Asn Ala
            420                 425                 430

Gly Ile Gly Val Glu Leu Pro Pro Ser Leu Ser Gly Gly Leu Ala Ser
            435                 440                 445

Arg Leu Gly Leu Ala Ile Lys Ala Asp Leu Pro Asp Arg Ser Ser Gly
450                 455                 460

Phe Thr Leu Gly Glu Ser Leu Asp Trp Ser Trp Asp Leu Met Ile Gly
465                 470                 475                 480

Gly Val Thr Leu Thr Leu Arg Glu Leu Glu Arg Leu Ser Gly Lys Arg
            485                 490                 495

Ser Pro Leu Val Arg His Lys Gly Ala Trp Ile Glu Leu Arg Pro Asn
            500                 505                 510

Asp Leu Arg Asn Ala Glu Arg Phe Cys Gly Ala Asn Pro Glu Leu Ser
            515                 520                 525

Leu Asp Asp Ala Leu Arg Leu Thr Ala Thr Glu Gly Glu Leu Met Met
            530                 535                 540

Arg Leu Pro Val His Arg Phe Asp Ala Gly Pro Arg Leu Gln Gly Val
545                 550                 555                 560

Leu Glu Gln Tyr His Gln Gln Lys Ala Pro Asp Pro Leu Pro Ala Pro

-continued

```
                565                 570                 575
Glu Gly Phe Ser Gly Gln Leu Arg Pro Tyr Gln Glu Arg Gly Leu Gly
                580                 585                 590

Trp Leu Ala Phe Leu His Arg Phe Asp Gln Gly Ala Cys Leu Ala Asp
            595                 600                 605

Asp Met Gly Leu Gly Lys Thr Ile Gln Leu Leu Ala Phe Leu Gln His
        610                 615                 620

Leu Lys Ala Glu Asn Leu Lys Arg Pro Val Leu Val Ala Pro
625                 630                 635                 640

Thr Ser Val Leu Thr Asn Trp Arg Arg Glu Ala Glu Ala Phe Thr Pro
                645                 650                 655

Glu Leu Ser Val Arg Glu His Tyr Gly Pro Arg Arg Pro Ser Thr Pro
            660                 665                 670

Ala Ala Leu Lys Lys Glu Leu Lys Gly Val Asp Leu Val Leu Thr Ser
            675                 680                 685

Tyr Gly Leu Met Gln Arg Asp Ser Glu Leu Leu Asp Asn Leu Asp Trp
        690                 695                 700

Gln Gly Val Val Ile Asp Glu Ala Gln Ala Ile Lys Asn Pro Gly Ala
705                 710                 715                 720

Lys Gln Ser Gln Ala Ala Arg Asp Leu Ala Arg Ala Gly Lys Ser Ser
                725                 730                 735

Arg Phe Arg Ile Ala Leu Thr Gly Thr Pro Val Glu Asn Arg Val Ser
            740                 745                 750

Glu Leu Trp Ala Leu Met Asp Phe Leu Asn Pro Lys Val Leu Gly Glu
            755                 760                 765

Glu Asp Phe Phe Arg Gln Arg Tyr Arg Met Pro Ile Glu Arg Tyr Gly
        770                 775                 780

Asp Met Ser Ser Leu Arg Asp Leu Lys Ala Arg Val Gly Pro Phe Ile
785                 790                 795                 800

Leu Arg Arg Leu Lys Thr Asp Lys Ser Ile Ile Ser Asp Leu Pro Glu
                805                 810                 815

Lys Val Glu Leu Ser Glu Trp Val Gly Leu Ser Lys Glu Gln Lys Ser
            820                 825                 830

Leu Tyr Asn Lys Thr Val Glu Asp Thr Leu Asp Ala Ile Ala Thr Ala
            835                 840                 845

Pro Arg Gly Gln Arg His Gly Gln Val Leu Ala Leu Leu Thr Arg Leu
        850                 855                 860

Lys Gln Ile Cys Asn His Pro Ala Leu Ala Gln Arg Glu Gly Ala Val
865                 870                 875                 880

Asp Ala Glu Phe Leu Ser Arg Ser Ala Lys Leu Met Arg Leu Glu Glu
                885                 890                 895

Ile Leu Glu Glu Val Ile Glu Ala Gly Asp Arg Ala Leu Leu Phe Thr
            900                 905                 910

Gln Phe Ala Glu Trp Gly His Leu Leu Gln Ala Trp Met Gln Gln Arg
            915                 920                 925

Trp Lys Ser Glu Val Pro Phe Leu His Gly Gly Thr Arg Lys Ser Asp
        930                 935                 940

Arg Gln Ala Met Val Asp Arg Phe Gln Glu Asp Pro Arg Gly Pro Gln
945                 950                 955                 960

Leu Phe Leu Leu Ser Leu Lys Ala Gly Gly Val Gly Leu Asn Leu Thr
                965                 970                 975

Arg Ala Ser His Val Phe His Val Gly Ser Leu Val Glu Ser Ser Gly
            980                 985                 990
```

| | | | | | | | | | | |
|---|---|---|---|---|---|---|---|---|---|---|
|Gly|Lys|Pro|Ser|His|Arg|Pro|Gly|Leu|Ser|Asn|Trp|Ser|Asn|Gln|Pro|
| |995| | | |1000| | | |1005| |

| | | | | | | | | | | |
|---|---|---|---|---|---|---|---|---|---|---|
|Gly|Asp|Gly|Ala|Gln|Ile|Arg|His|Pro|Trp|Leu|Gly|Gly|Arg|Lys|
| |1010| | | |1015| | | |1020| |

Asn Arg Pro Asn Asp Ser
    1025

<210> SEQ ID NO 85
<211> LENGTH: 3195
<212> TYPE: DNA
<213> ORGANISM: Synechococcus sp.

<400> SEQUENCE: 85

```
atgagcctgc tgcacgccac ctggcttccg gccattcgta ctcctaccag ctctggacga      60
gctgcccttt tggtgtgggc cgacacctgg cgcgttgccg agcctgcagg cccaagtaca     120
accccctgcgc ttcacccgtt cacccctcagc ccagacgatc tccgggcctt gctcacggaa   180
cgggatcttt tacccgacgg catcattgat gccacggcat gcctcaccct gccgagccgc     240
agcgtgaagc cccgaaaaaa acgcgaaaca gagaccagca gcactgaaca gcccagctgg     300
acaggccttc ccttacaggc tggagaaccg atccccaaac aaacagagtg gtggccttgg     360
caggttcagg ggctcgcaat tgaccccatg gcggccaccg cctggctgtc caaactgcct     420
ctgtcaggac gacatcctga tttggctgat gagttgcgct ggtggagtca catgcagcgt     480
tggtccctca gcctcgtagc ccgaagtcgc tggctccccc aagtggagct gagcaagggc     540
gagggctatc cccatcgcgc ccgctgggta ccgcttctga tcgggaaga agacaggcgc     600
cgtctagaag acttggccgc agggctccct ctcgttgcca cctgtgccct gccttggcga     660
gaaccaacgg gcaaacgcag caaccgaatc accaggctca gaccagaagc catgcgcgcc     720
gcgaatcccg tggcttgctg caggcctcgc agcggacgac taagggttgc cacgttattg     780
gccgacctga tggacgcgca gctgcgcaag ggctttactc ctgaccctga cggcttggac     840
cccctgctac gcgcctggga ggaggccttg agctcggata caggtgaaat ccaactcagc     900
gatgaagaaa ccgaacgcct agccaccgcc agtaatcatt ggcgtgaagg ggtcgctgga     960
aatgttgctg cagcccgcgc ctgcctggag ctggcaacac cagcggacga tgaggacctt    1020
tggccactgc gcttctttct gcaggcggaa gcagatccaa ccctcaagct gcccgcagga    1080
gcggcatggg ctgcaggccc cagcggcctc caacttgggg aaatcaaggt ggagcacccc    1140
agcgaggtct gctcgaggg tatggggcga gccctgaccg tgttccaacc gatcgagcgc    1200
ggactggaca gtgccacgcc agagagcatg cagctcacac cagctgaagc gtttgttttg    1260
gtgcgcacag cagtccgaca actgcgggat gtgggcgttg cgttgaccct gccaccaagc    1320
ctgtctggag ggctggctag caggcttggc ctcgccatca aggcagaact ctccgagcgt    1380
tcgcgaggct tcacgctcgg tgaaaacctt gactggagct gggagctgat gatcggcggg    1440
gtgacgctga ccttgcgaga gcttgagcga ttggctggta gcgcagccc tctggtgcgt    1500
cacaaagggg cttggatcga actacggccc aatgacctca aaaatgccga gcgcttttgc    1560
gccgccaatc cagacctgag cctcgacgac gcgcttcggc tcaccgccac cgaaggcgac    1620
acgatgatgc gcctgccgt gcatcaattt gatgccggtc gcggctgca agccgtgctg    1680
gagcagtacc accagcagaa agcgccagac ccactcccg ctcccgaggg cttttcgggt    1740
caactcaggc cctatcaaga gagaggactc ggctggcttg ccttcctgca tcgcttcgac    1800
caaggcgcct gcttggccga tgacatgggc cttggcaaaa ccatccagct gctggctttt    1860
ctgcaacacc tcaaggcaga aaacgaactc aagcgatcag tgcttttaat tgcacccaca    1920
```

```
tctgtcctta cgaactggaa acgagaggca acagcgttta cacccgagct caaggtgcat    1980
gagcactacg gtccaaaacg cccgagcacc ccagcagcac tgaaaaaggc gctgaaagac    2040
gtggatctcg tgctcaccag ctatggcctg ttacaacgcg acagtgagct cctcgaaagt    2100
cacgattggc aaggcctcgt gatcgatgaa gcgcaggcga taaaaaaccc ctccgcgaag    2160
caaagccaag ccgcccgtga tctggcccgc ccgaaaaaga acagccgttt tcgcatcgca    2220
ctcaccggca caccagttga aaccgcgtc agcgagctct gggccctgat ggacttcctc     2280
aaccctcggg tactgggaga ggaagaattt ttccgacatc gctatcgcat gccgattgag    2340
cgttacggag acctgtcctc gctgcgcgac ctcaaagccc gagtgggacc tttcatcctc    2400
agacgactca aaacagacaa agcgatcatc tcggatctac ccgagaaggt ggaattgagc    2460 gagtggggttg ggctgagcaa agagcagaag tcgctgtatg ccaaaaccgt tgaagacacc    2520
ttggatgcca ttgcccgcgc gccacgcggc aaacgtcatg gtcaggtgtt gggtctgctc    2580
accaagctca agcagatttg caaccaccct gcgcttgccc tcaaggagca gggcgccagc    2640
gaagatttcc tcaaacggtc cgtgaagctg caacgtctcg aagaaatttt ggacgaggtt    2700
gtagaagctg gggatcgagc cttgctgttt acccagttcg cggaatgggg caagttgctc    2760
caggattatt tgcaacgacg ctggcgcagc gaagttccct tcctcagcgg cagcaccagc    2820
aaaagtgaac ggcaagccat ggtcgatcgc ttccaggagg atccgcgcgg gccccagctt    2880
ttcctgttat cactcaaagc tggcggagtc ggcctcaacc tcacgcgcgc cagtcatgtc    2940
tttcacatcg accgttggtg aaccccgcc gttgaaaatc aagccacgga ccgtgcctat     3000
cgcatcggcc aaacgaaccg ggtcatggtg cataagttca tcaccagcgg ctccgttgag    3060
gagaaaattg accgcatgat ccgcgagaag tccagactgg cggaagacat cattggctcc    3120
ggcgaagact ggcttggagg cctggaaatg ggacaactca aagagctagt gagcctggag    3180
gacaaccaag catga                                                     3195
```

<210> SEQ ID NO 86
<211> LENGTH: 1064
<212> TYPE: PRT
<213> ORGANISM: Synechococcus sp.

<400> SEQUENCE: 86

```
Met Ser Leu Leu His Ala Thr Trp Leu Pro Ala Ile Arg Thr Pro Thr
1               5                   10                  15

Ser Ser Gly Arg Ala Ala Leu Leu Val Trp Ala Asp Thr Trp Arg Val
            20                  25                  30

Ala Glu Pro Ala Gly Pro Ser Thr Thr Pro Ala Leu His Pro Phe Thr
        35                  40                  45

Leu Ser Pro Asp Asp Leu Arg Ala Leu Leu Thr Glu Arg Asp Leu Leu
    50                  55                  60

Pro Asp Gly Ile Ile Asp Ala Thr Ala Cys Leu Thr Leu Pro Ser Arg
65                  70                  75                  80

Ser Val Lys Pro Arg Lys Lys Arg Glu Thr Glu Thr Ser Ser Thr Glu
                85                  90                  95

Gln Pro Ser Trp Thr Gly Leu Pro Leu Gln Ala Gly Glu Pro Ile Pro
            100                 105                 110

Lys Gln Thr Glu Trp Trp Pro Trp Gln Val Gln Gly Leu Ala Ile Asp
        115                 120                 125

Pro Met Ala Ala Thr Ala Trp Leu Ser Lys Leu Pro Leu Ser Gly Arg
    130                 135                 140
```

His Pro Asp Leu Ala Asp Glu Leu Arg Trp Trp Ser His Met Gln Arg
145                 150                 155                 160

Trp Ser Leu Ser Leu Val Ala Arg Ser Arg Trp Leu Pro Gln Val Glu
            165                 170                 175

Leu Ser Lys Gly Glu Gly Tyr Pro His Arg Ala Arg Trp Val Pro Leu
        180                 185                 190

Leu Asn Arg Glu Glu Asp Arg Arg Leu Glu Asp Leu Ala Ala Gly
    195                 200                 205

Leu Pro Leu Val Ala Thr Cys Ala Leu Pro Trp Arg Glu Pro Thr Gly
210                 215                 220

Lys Arg Ser Asn Arg Ile Thr Arg Leu Arg Pro Glu Ala Met Arg Ala
225                 230                 235                 240

Ala Asn Pro Val Ala Cys Cys Arg Pro Arg Ser Gly Arg Leu Arg Val
                245                 250                 255

Ala Thr Leu Leu Ala Asp Leu Met Asp Ala Gln Leu Arg Lys Gly Phe
            260                 265                 270

Thr Pro Asp Pro Asp Gly Leu Asp Pro Leu Leu Arg Ala Trp Glu Glu
        275                 280                 285

Ala Leu Ser Ser Asp Thr Gly Glu Ile Gln Leu Ser Asp Glu Thr
290                 295                 300

Glu Arg Leu Ala Thr Ala Ser Asn His Trp Arg Glu Gly Val Ala Gly
305                 310                 315                 320

Asn Val Ala Ala Ala Arg Ala Cys Leu Glu Leu Ala Thr Pro Ala Asp
                325                 330                 335

Asp Glu Asp Leu Trp Pro Leu Arg Phe Phe Leu Gln Ala Glu Ala Asp
            340                 345                 350

Pro Thr Leu Lys Leu Pro Ala Gly Ala Ala Trp Ala Ala Gly Pro Ser
        355                 360                 365

Gly Leu Gln Leu Gly Glu Ile Lys Val Glu His Pro Ser Glu Val Leu
370                 375                 380

Leu Glu Gly Met Gly Arg Ala Leu Thr Val Phe Gln Pro Ile Glu Arg
385                 390                 395                 400

Gly Leu Asp Ser Ala Thr Pro Glu Ser Met Gln Leu Thr Pro Ala Glu
                405                 410                 415

Ala Phe Val Leu Val Arg Thr Ala Val Arg Gln Leu Arg Asp Val Gly
            420                 425                 430

Val Gly Val Asp Leu Pro Pro Ser Leu Ser Gly Gly Leu Ala Ser Arg
        435                 440                 445

Leu Gly Leu Ala Ile Lys Ala Glu Leu Ser Glu Arg Ser Arg Gly Phe
450                 455                 460

Thr Leu Gly Glu Asn Leu Asp Trp Ser Trp Glu Leu Met Ile Gly Gly
465                 470                 475                 480

Val Thr Leu Thr Leu Arg Glu Leu Glu Arg Leu Ala Gly Lys Arg Ser
                485                 490                 495

Pro Leu Val Arg His Lys Gly Ala Trp Ile Glu Leu Arg Pro Asn Asp
            500                 505                 510

Leu Lys Asn Ala Glu Arg Phe Cys Ala Ala Asn Pro Asp Leu Ser Leu
        515                 520                 525

Asp Asp Ala Leu Arg Leu Thr Ala Thr Glu Gly Asp Thr Met Met Arg
530                 535                 540

Leu Pro Val His Gln Phe Asp Ala Gly Pro Arg Leu Gln Ala Val Leu
545                 550                 555                 560

Glu Gln Tyr His Gln Gln Lys Ala Pro Asp Pro Leu Pro Ala Pro Glu
                565                 570                 575

```
Gly Phe Ser Gly Gln Leu Arg Pro Tyr Gln Glu Arg Gly Leu Gly Trp
            580                 585                 590

Leu Ala Phe Leu His Arg Phe Asp Gln Gly Ala Cys Leu Ala Asp Asp
            595                 600                 605

Met Gly Leu Gly Lys Thr Ile Gln Leu Leu Ala Phe Leu Gln His Leu
610                 615                 620

Lys Ala Glu Asn Glu Leu Lys Arg Ser Val Leu Leu Ile Ala Pro Thr
625                 630                 635                 640

Ser Val Leu Thr Asn Trp Lys Arg Glu Ala Thr Ala Phe Thr Pro Glu
            645                 650                 655

Leu Lys Val His Glu His Tyr Gly Pro Lys Arg Pro Ser Thr Pro Ala
            660                 665                 670

Ala Leu Lys Lys Ala Leu Lys Asp Val Asp Leu Val Leu Thr Ser Tyr
            675                 680                 685

Gly Leu Leu Gln Arg Asp Ser Glu Leu Leu Glu Ser His Asp Trp Gln
            690                 695                 700

Gly Leu Val Ile Asp Glu Ala Gln Ala Ile Lys Asn Pro Ser Ala Lys
705                 710                 715                 720

Gln Ser Gln Ala Ala Arg Asp Leu Ala Arg Pro Lys Lys Asn Ser Arg
            725                 730                 735

Phe Arg Ile Ala Leu Thr Gly Thr Pro Val Glu Asn Arg Val Ser Glu
            740                 745                 750

Leu Trp Ala Leu Met Asp Phe Leu Asn Pro Arg Val Leu Gly Glu Glu
            755                 760                 765

Glu Phe Phe Arg His Arg Tyr Arg Met Pro Ile Glu Arg Tyr Gly Asp
            770                 775                 780

Leu Ser Ser Leu Arg Asp Leu Lys Ala Arg Val Gly Pro Phe Ile Leu
785                 790                 795                 800

Arg Arg Leu Lys Thr Asp Lys Ala Ile Ile Ser Asp Leu Pro Glu Lys
            805                 810                 815

Val Glu Leu Ser Glu Trp Val Gly Leu Ser Lys Glu Gln Lys Ser Leu
            820                 825                 830

Tyr Ala Lys Thr Val Glu Asp Thr Leu Asp Ala Ile Ala Arg Ala Pro
            835                 840                 845

Arg Gly Lys Arg His Gly Gln Val Leu Gly Leu Leu Thr Lys Leu Lys
            850                 855                 860

Gln Ile Cys Asn His Pro Ala Leu Ala Leu Lys Glu Gln Gly Ala Ser
865                 870                 875                 880

Glu Asp Phe Leu Lys Arg Ser Val Lys Leu Gln Arg Leu Glu Glu Ile
            885                 890                 895

Leu Asp Glu Val Val Glu Ala Gly Asp Arg Ala Leu Leu Phe Thr Gln
            900                 905                 910

Phe Ala Glu Trp Gly Lys Leu Leu Gln Asp Tyr Leu Gln Arg Arg Trp
            915                 920                 925

Arg Ser Glu Val Pro Phe Leu Ser Gly Ser Thr Ser Lys Ser Glu Arg
            930                 935                 940

Gln Ala Met Val Asp Arg Phe Gln Glu Asp Pro Arg Gly Pro Gln Leu
945                 950                 955                 960

Phe Leu Leu Ser Leu Lys Ala Gly Gly Val Gly Leu Asn Leu Thr Arg
            965                 970                 975

Ala Ser His Val Phe His Ile Asp Arg Trp Trp Asn Pro Ala Val Glu
            980                 985                 990

Asn Gln Ala Thr Asp Arg Ala Tyr Arg Ile Gly Gln Thr Asn Arg Val
```

```
                995                 1000                1005
Met Val His Lys Phe Ile Thr Ser Gly Ser Val Glu Glu Lys Ile
          1010                1015                1020

Asp Arg Met Ile Arg Glu Lys Ser Arg Leu Ala Glu Asp Ile Ile
          1025                1030                1035

Gly Ser Gly Glu Asp Trp Leu Gly Gly Leu Glu Met Gly Gln Leu
          1040                1045                1050

Lys Glu Leu Val Ser Leu Glu Asp Asn Gln Ala
          1055                1060

<210> SEQ ID NO 87
<211> LENGTH: 3198
<212> TYPE: DNA
<213> ORGANISM: Synechococcus sp.

<400> SEQUENCE: 87
atgagcctgc tgcacgccac ctggcttccc gccatccgca cctccagcag ttccggtcaa    60
ccggcactgc tcgtttgggc tgacacctgg cgggtggcca ccggaaggg cccgggcctt   120 accccagcgc tgcaccccct cacccctaagc atgaagacc tcagggcctg ctgagcgaa   180 cgcgacctct tgcccggcgg ctgcatcgat gccacggcgt gcctcaccct gccgagccgc   240
acggtgaagc tgcgcaaaag ccgcagcaca aaagaggagc caacaccgga ccaccgggt   300 tggaccgggc taccgatgca ggccggcgaa ccgatcccca gcaaaccga atggtggccc   360 tgcaggtgc aggggctcgc ggtggaaccg tcggcagcca cggagtggct gtcccgattg   420
ccgctctccg gcaccaatcc agacctggct gatgaactgc gctggtggag ccatctgcag   480
cgctgggcct tgagtctggt ggcccggggc cgctggattc cccagatgga gttcagcaaa   540
ggggagggct atccccatcg gccccgttgg gtgccgcttc tcaaccggga agaagaccgg   600
cgccggctgg aggatctggc ggccagcctg ccgctggtgg ccacctgcgc cttgccctgg   660
cgggaacccc tggggcgccg cagcaaccgc accaccgggt tacgaccgga ggcgatgcga   720
gccgccaacc ctgtgggcag ctgccggcc cgcagcggac cctgcgggt ggcgacgctg   780 ctggaagatc tagtggacgc gcagctgcgc aaggactttg aaccctccac cgatgggctt   840
gatcccctgc tgaccctctg caggaggcc ctggggtcgg agaccggggt gatcgagatc   900
ggcgatgaag aggccgaacg cctggccacc gccagccatc actggcggga ggcatcgcc   960 ggcgattttg ctgcggcccg cacctgcctt gaactgcaca ccccaccgga tggggaggat  1020
ctctgggagc tgcgcttcgg gctgcaggcg gaagctgacc ccagcctgaa gctccggcc  1080 gccgcggcct gggcggctgg tgcggaaccg ctacagcttg gagagatccg ggtggaccaa  1140
ccgggtgaag tgctgctgga aggcatgggc gcgccctga gcgtgtttcc ggcaattgag  1200 cgggtctgg agagcgccac acctgaaacg atgcagctca ccccggccga ggccttcgtg  1260
ctggtgcgca cggccgcccg gcagctgcgg gatgccggcg tggagtgga gctgccgccc  1320 agcctctccg gtgcctggc cagccgactg ggcctgtcga tcaaagcgga actgcccgaa  1380
cgctcgagcg gttcacgtt gggtgagtgt ctggcctggg agtgggatct gatgatcggc  1440
ggggtgacgc tcaccctgcg ggaattggag cgcctgagcg gcaagcgcag cccctggtg  1500 cgccacaagg gggcctggat cgaactgcgg cccaacgacc tcaaaaatgc cgaacgcttc  1560 tgtgggcga aacctgaact gagcctcgac gacgcgctgc ggctgacggg gacggaaggg  1620
gaactgttga tgcggatgcc ggtgcaccgc ttcgacgccg gccacggct gcaatcggtg  1680 ttgcagcaat accaccagca gaaggccccc gacccccttgc cggccccgga aggattcagc  1740
```

-continued

```
gggcagctgc ggccttatca ggagcggggc ctcggctggc tcgccttcct gcaccgcttc      1800
gatcaagggg cctgtctagc tgacgacatg ggcttgggca aaaccattca gttgctagcg      1860
ttcctgcagc acctcaaagc ggagcaagaa ctgaaacgcc cggtgctgct ggtggccccc      1920
acatcggtgc tcaccaactg cgacgggag gcggaatcgt tcactccaga gttgaaggtc       1980
accgagcatt acgggcctcg ccggccctcc acacccgccg aactcaaaaa agcgttgaag      2040
gaggtggatc tggtgctcac cagctacggg ctgctgcagc gtgacagcga actgctggaa      2100
acccaggact ggcaggggt ggtgattgac gaagcccagg cgatcaagaa ccctggcgcc       2160
aaacagagcc aagccgcccg ggatctggcc cgcaccggcc gcatcaagag caaccgcttc      2220
cgcatcgcac tcaccggcac ccccgtggaa aaccgggtga gcgaactgtg ggccttgatg      2280
gacttcctca acccaaaggt gcttgggaa aagacttct tccgccagcg ctatcggatg        2340
ccgattgagc gctacggcga catgtcgtcc ctgcgggacc tgaaaggccg cgtgggtccg      2400
ttcatcctgc gccggctgaa aaccgacaag acgatcattt ccgacctgcc tgaaaaggtg     2460
gagctgagcg aatgggtggg gctgagcaag gagcagaaat ctctgtacag caagaccgtg     2520
gaagacaccc tcgatgccat tgcccggcg ccgcgcgggc agcgccacgg gcaggtgctg       2580
gccctgctca cccggctgaa acagatctgc aaccatcccg ccctggccct gagcgaaggg     2640
gccgtggacg atggcttcct gggccgttcg gccaagctgc agcggctgga ggagatcctc     2700
gatgaggtga tcgaagcggg cgatcgggcc ctgctgttca cccagttcgc cgaatggggg     2760
catttgctaa gggcctggat gcagcagcgc tggaaatcag aagtgccctt cctgcacggc     2820
ggcacccgca agaacgaacg ccaggcgatg gtggatcgct tccaggagga tccccgcggt    2880
ccacagctgt tcctgctctc gctcaaggcc ggtggtgtgg gcctcaacct cacgcgggcc    2940
agccatgtgt tccacatcga tgctggtgg aaccctgccg tggaaaacca ggccaccgac      3000
cgggcctatc ggatcggcca aacgaaccga gtgatggttc ataaattcat caccagcggt     3060
tcggtggagg aaaaaatcga tcgcatgatc cgcgagaaat cacgcctggc cgaagatgtg    3120
atcggctccg gcgaagattg gctgggaagc ctcggtggcg atcaattgcg cgatctcgtt    3180
tctttggagg acacctga                                                   3198
```

<210> SEQ ID NO 88
<211> LENGTH: 1065
<212> TYPE: PRT
<213> ORGANISM: Synechococcus sp.

<400> SEQUENCE: 88

```
Met Ser Leu Leu His Ala Thr Trp Leu Pro Ala Ile Arg Thr Ser Ser
1               5                   10                  15

Ser Ser Gly Gln Pro Ala Leu Leu Val Trp Ala Asp Thr Trp Arg Val
            20                  25                  30

Ala Thr Pro Glu Gly Pro Gly Leu Thr Pro Ala Leu His Pro Phe Thr
        35                  40                  45

Leu Ser His Glu Asp Leu Arg Ala Trp Leu Ser Glu Arg Asp Leu Leu
    50                  55                  60

Pro Gly Gly Cys Ile Asp Ala Thr Ala Cys Leu Thr Leu Pro Ser Arg
65                  70                  75                  80

Thr Val Lys Leu Arg Lys Ser Arg Ser Thr Lys Glu Glu Pro Thr Pro
                85                  90                  95

Glu Pro Pro Gly Trp Thr Gly Leu Pro Met Gln Ala Gly Glu Pro Ile
            100                 105                 110

Pro Lys Gln Thr Glu Trp Trp Pro Trp Gln Val Gln Gly Leu Ala Val
```

-continued

```
                115                 120                 125
Glu Pro Ser Ala Ala Thr Glu Trp Leu Ser Arg Leu Pro Leu Ser Gly
130                 135                 140
Thr Asn Pro Asp Leu Ala Asp Glu Leu Arg Trp Trp Ser His Leu Gln
145                 150                 155                 160
Arg Trp Ala Leu Ser Leu Val Ala Arg Gly Arg Trp Ile Pro Gln Met
                165                 170                 175
Glu Phe Ser Lys Gly Glu Gly Tyr Pro His Arg Ala Arg Trp Val Pro
                180                 185                 190
Leu Leu Asn Arg Glu Glu Asp Arg Arg Leu Glu Asp Leu Ala Ala
                195                 200                 205
Ser Leu Pro Leu Val Ala Thr Cys Ala Leu Pro Trp Arg Glu Pro Leu
210                 215                 220
Gly Arg Arg Ser Asn Arg Thr Thr Arg Leu Arg Pro Glu Ala Met Arg
225                 230                 235                 240
Ala Ala Asn Pro Val Ala Ser Cys Arg Pro Arg Ser Gly Arg Leu Arg
                245                 250                 255
Val Ala Thr Leu Leu Glu Asp Leu Val Asp Ala Gln Leu Arg Lys Asp
                260                 265                 270
Phe Glu Pro Ser Thr Asp Gly Leu Asp Pro Leu Leu Thr Leu Trp Gln
                275                 280                 285
Glu Ala Leu Gly Ser Glu Thr Gly Val Ile Glu Ile Gly Asp Glu Glu
                290                 295                 300
Ala Glu Arg Leu Ala Thr Ala Ser His His Trp Arg Glu Gly Ile Ala
305                 310                 315                 320
Gly Asp Phe Ala Ala Ala Arg Thr Cys Leu Glu Leu His Thr Pro Pro
                325                 330                 335
Asp Gly Glu Asp Leu Trp Glu Leu Arg Phe Gly Leu Gln Ala Glu Ala
                340                 345                 350
Asp Pro Ser Leu Lys Leu Pro Ala Ala Ala Trp Ala Ala Gly Ala
                355                 360                 365
Glu Pro Leu Gln Leu Gly Glu Ile Arg Val Asp Gln Pro Gly Glu Val
370                 375                 380
Leu Leu Glu Gly Met Gly Arg Ala Leu Ser Val Phe Pro Ala Ile Glu
385                 390                 395                 400
Arg Gly Leu Glu Ser Ala Thr Pro Glu Thr Met Gln Leu Thr Pro Ala
                405                 410                 415
Glu Ala Phe Val Leu Val Arg Thr Ala Ala Arg Gln Leu Arg Asp Ala
                420                 425                 430
Gly Val Gly Val Glu Leu Pro Pro Ser Leu Ser Gly Leu Ala Ser
                435                 440                 445
Arg Leu Gly Leu Ser Ile Lys Ala Glu Leu Pro Glu Arg Ser Ser Gly
450                 455                 460
Phe Thr Leu Gly Glu Cys Leu Ala Trp Glu Trp Asp Leu Met Ile Gly
465                 470                 475                 480
Gly Val Thr Leu Thr Leu Arg Glu Leu Glu Arg Leu Ser Gly Lys Arg
                485                 490                 495
Ser Pro Leu Val Arg His Lys Gly Ala Trp Ile Glu Leu Arg Pro Asn
                500                 505                 510
Asp Leu Lys Asn Ala Glu Arg Phe Cys Gly Ala Lys Pro Glu Leu Ser
                515                 520                 525
Leu Asp Asp Ala Leu Arg Leu Thr Gly Thr Glu Gly Glu Leu Leu Met
530                 535                 540
```

```
Arg Met Pro Val His Arg Phe Asp Ala Gly Pro Arg Leu Gln Ser Val
545                 550                 555                 560

Leu Gln Gln Tyr His Gln Lys Ala Pro Asp Pro Leu Pro Ala Pro
            565                 570                 575

Glu Gly Phe Ser Gly Gln Leu Arg Pro Tyr Gln Glu Arg Gly Leu Gly
            580                 585                 590

Trp Leu Ala Phe Leu His Arg Phe Asp Gln Gly Ala Cys Leu Ala Asp
            595                 600                 605

Asp Met Gly Leu Gly Lys Thr Ile Gln Leu Leu Ala Phe Leu Gln His
        610                 615                 620

Leu Lys Ala Glu Gln Glu Leu Lys Arg Pro Val Leu Leu Val Ala Pro
625                 630                 635                 640

Thr Ser Val Leu Thr Asn Trp Arg Arg Glu Ala Glu Ser Phe Thr Pro
                645                 650                 655

Glu Leu Lys Val Thr Glu His Tyr Gly Pro Arg Arg Pro Ser Thr Pro
            660                 665                 670

Ala Glu Leu Lys Lys Ala Leu Lys Glu Val Asp Leu Val Leu Thr Ser
            675                 680                 685

Tyr Gly Leu Leu Gln Arg Asp Ser Glu Leu Leu Glu Thr Gln Asp Trp
690                 695                 700

Gln Gly Val Val Ile Asp Glu Ala Gln Ala Ile Lys Asn Pro Gly Ala
705                 710                 715                 720

Lys Gln Ser Gln Ala Ala Arg Asp Leu Ala Arg Thr Gly Arg Ile Lys
                725                 730                 735

Ser Asn Arg Phe Arg Ile Ala Leu Thr Gly Thr Pro Val Glu Asn Arg
            740                 745                 750

Val Ser Glu Leu Trp Ala Leu Met Asp Phe Leu Asn Pro Lys Val Leu
            755                 760                 765

Gly Glu Glu Asp Phe Phe Arg Gln Arg Tyr Arg Met Pro Ile Glu Arg
            770                 775                 780

Tyr Gly Asp Met Ser Ser Leu Arg Asp Leu Lys Gly Arg Val Gly Pro
785                 790                 795                 800

Phe Ile Leu Arg Arg Leu Lys Thr Asp Lys Thr Ile Ile Ser Asp Leu
                805                 810                 815

Pro Glu Lys Val Glu Leu Ser Glu Trp Val Gly Leu Ser Lys Glu Gln
            820                 825                 830

Lys Ser Leu Tyr Ser Lys Thr Val Glu Asp Thr Leu Asp Ala Ile Ala
            835                 840                 845

Arg Ala Pro Arg Gly Gln Arg His Gly Gln Val Leu Ala Leu Leu Thr
850                 855                 860

Arg Leu Lys Gln Ile Cys Asn His Pro Ala Leu Ala Leu Ser Glu Gly
865                 870                 875                 880

Ala Val Asp Asp Gly Phe Leu Gly Arg Ser Ala Lys Leu Gln Arg Leu
                885                 890                 895

Glu Glu Ile Leu Asp Glu Val Ile Glu Ala Gly Asp Arg Ala Leu Leu
            900                 905                 910

Phe Thr Gln Phe Ala Glu Trp Gly His Leu Leu Arg Ala Trp Met Gln
            915                 920                 925

Gln Arg Trp Lys Ser Glu Val Pro Phe Leu His Gly Gly Thr Arg Lys
            930                 935                 940

Asn Glu Arg Gln Ala Met Val Asp Arg Phe Gln Glu Asp Pro Arg Gly
945                 950                 955                 960

Pro Gln Leu Phe Leu Leu Ser Leu Lys Ala Gly Gly Val Gly Leu Asn
                965                 970                 975
```

```
Leu Thr Arg Ala Ser His Val Phe His Ile Asp Arg Trp Trp Asn Pro
        980                 985                 990

Ala Val Glu Asn Gln Ala Thr Asp Arg Ala Tyr Arg Ile Gly Gln Thr
        995                 1000                1005

Asn Arg Val Met Val His Lys Phe Ile Thr Ser Gly Ser Val Glu
        1010                1015                1020

Glu Lys Ile Asp Arg Met Ile Arg Glu Lys Ser Arg Leu Ala Glu
        1025                1030                1035

Asp Val Ile Gly Ser Gly Glu Asp Trp Leu Gly Ser Leu Gly Gly
        1040                1045                1050

Asp Gln Leu Arg Asp Leu Val Ser Leu Glu Asp Thr
        1055                1060                1065

<210> SEQ ID NO 89
<211> LENGTH: 3192
<212> TYPE: DNA
<213> ORGANISM: Synechococcus sp.

<400> SEQUENCE: 89
atgagcctgc tgcacgccac ctggcttccc gccattcgta cttccagcag ttccggacag      60
ccggcactgc tcatttgggc tgacacctgg cgtgtcgcct caccggaggg gcccggactc     120
acacccgctc tgcatccctt cacccttggc tcggacgatc tcaaagcttg gttgaccgaa     180
cgggacctga tgcctggggg cagcatcgat gccaccgcct gcctcaccct cccaagccgc     240
agcgtcaaac cccgcaaaag tcgaacccaa ccgagcgaac cagccccaga gggaccggcc     300
tggaccggat tgccaatgca agcaggagag cccattccga agcaaatgga atggtggccc     360
tggcaggtac aaggcctcgc ggtggagcca tcggccgcaa cggaatggct cgcccgttta     420
cccctatcgg gccgacatcc agacctcgga gatgaattgc gctggtggag ccatctccaa     480
cgttggtccc tcagcttggt ggcccggggg cgctggattc cccagatgga attaagcaaa     540
ggcgagggtt accccaccg agcgcgctgg gttcccttgt gaaccgtga ggaagatcga      600 cgacggctcg aagacctcgc ggccacgctg ccctcgtgg cgacctgtgc cctcccttgg      660
cgtgagccac ttggacgccg tagcaaccgc accaccaggc ttcgaccgga agcgatgcga     720
gccgccaacc cggtggcttg ctgccgcccc cggagcggtc gcctcagggt ggccaccttg     780
cttgaagact tggtggatgc agagctgcgc aagggatttg aacccaccac agagggctc      840 gacccccta c tcaccctgtg gcaagaggcc ctggcctcag aaaccggtgt tgtgaggtg       900 ggcaacgagg atgcagaacg ccttaccgcg gcaagcctgc actggcgcga agggattgcc     960
ggaggcttcg ctgctgcccg cacctgcctc gaactaaaca ccccaaacga aggcgaagaa    1020
ctctgggacc tgaagtttgg cttgcaagcg gaggccgatc ccagcctcaa gctgccggcc    1080
gccgcggcct gggcctcagg agccgaaaca ctccagctcg gggagatcaa agttgaccag    1140 gcggggaag tgctgctgga gggtcttggc cgagccctca cggtgttccc tccgatcgaa     1200
cgcggactgg aaagcgcaac gccagaaacg atgcagctca cgccagcgga ggcgtttgtc    1260
ttggtgcgaa cagcaacgca ccagctccgc aatgccggca tcggcgtcga actgcccccc    1320
agcctttcag ggggcctcgc cagccggctt ggtttagcca tcaaggcaga tttaccagat    1380
cgatccagcg gcttcaccct cggagaatct ctggactgga gctgggatct gatgatcggc    1440
ggcgtcacac tcaccctgcg agagctcgaa cggctcagcg gtaagcgcag tccgcttgtg    1500
cgccacaagg gagcctggat cgaactgcga cccaacgatc tccgcaacgc cgaacgcttc    1560
tgtggagcca atccagaact gagcctcgac gatgccctaa ggctcacggc cacagaaggg    1620
```

```
gagctaatga tgcgcttgcc ggtgcatcgc tttgatgcgg ggcctcggct tcagggagtt   1680
ctcgagcaat atcaccagca aaagccccc gatcccttc ccgctccaga gggatttcc     1740 ggacaactgc gtccttatca agaacgtggc ttgggctggc tggccttctt acatcgcttc   1800
gatcaaggcg cctgcctggc ggacgacatg ggcttgggca agaccatcca attgttggcc   1860
ttcctgcagc acctcaaagc cgagcacgaa ctcaaacgcc cggtgctgtt ggtggcccca   1920
acctcggtgc tcacgaattg cgacgggag gcggaagcct tcaccccga gctgtcggtg     1980 aaagagcact acggcccacg ccggccttcc acgccggccg ccttgaaaaa agaactcaaa   2040
gatgtggatc tggtgctcac cagttacggc ctgatgcaac gcgacagcga gctgctggac   2100
agcgtcgact ggcaagggt tgtgatcgac gaagcgcagg cgatcaaaaa ccctggggcg    2160
aaacaaagcc aagcagcccg agacctggcc cgagctggaa agagcagcag gttccgcatc   2220
gcactcaccg gcacaccggt ggaaaaccgc gtcagcgagc tgtgggcgct gatggatttc   2280
ctcaacccaa aggtgttggg agaggaagac ttctttcgtc agcgctaccg catgccaatt   2340
gagcgctacg gcgatatgtc gtcgttacgc gatctcaaag cgcgggtcgg ccccttcatc   2400
ctgcgccgtc tcaaaaccga caagtcgatc atttccgacc tgcctgaaaa ggtggagctc   2460
agtgaatggg tgggtctcag caaagaacag aaatcgctgt acaacaaaac cgttgaagac   2520
accctcgacg ccattgccac cgcaccgcgg ggcaacgcc atggccaggt gctagccctc     2580
ttgacccggt taaagcagat ttgcaatcac ccggctttag cccaacgcga aggggccgtt   2640
gacagcgaat tccttggccg ttccgccaag ctgatgcgac tcgaagaaat cctcgaagag   2700
gtgattgaag ccggcgatcg cgctttgcta ttcacccaat cgccgaatg ggggcatctc    2760 ctgcaggcct ggatgcaaca acgctggaag tctgaggttc ccttcctgca cggcggaacc   2820
cgcaagagtg atcggcaagc gatggtggat cgattccaag aggaccccg gggacctcaa    2880 ctctttcttc tgtcccctcaa ggccggtggt gtaggcctca acctcacccg ggccagtcat  2940
gtgttccacg tcgatcgctg gtggaatcca gcggtggaaa accaagccac cgaccgggcc   3000
tatcgaattg gtcaaaccaa ccgggtaatg gtgcacaaat tcgtcacccg tggctcggtg   3060
gaagaaaaaa tcgaccaaat gattcgtgaa aaagctcgaa tggctgaaga cgtgatcggc   3120
tccggtgaag actggctcgg gagccttggc ggcgatcagc tgcgcaatct tgttgccctc   3180
gaggacacct aa                                                       3192
```

<210> SEQ ID NO 90
<211> LENGTH: 1063
<212> TYPE: PRT
<213> ORGANISM: Synechococcus sp.

<400> SEQUENCE: 90

```
Met Ser Leu Leu His Ala Thr Trp Leu Pro Ala Ile Arg Thr Ser Ser
1               5                   10                  15

Ser Ser Gly Gln Pro Ala Leu Leu Ile Trp Ala Asp Thr Trp Arg Val
            20                  25                  30

Ala Ser Pro Glu Gly Pro Gly Leu Thr Pro Ala Leu His Pro Phe Thr
        35                  40                  45

Leu Gly Ser Asp Asp Leu Lys Ala Trp Leu Thr Glu Arg Asp Leu Met
    50                  55                  60

Pro Gly Gly Ser Ile Asp Ala Thr Ala Cys Leu Thr Leu Pro Ser Arg
65                  70                  75                  80

Ser Val Lys Pro Arg Lys Ser Arg Thr Gln Pro Ser Glu Pro Ala Pro
                85                  90                  95
```

-continued

```
Glu Gly Pro Ala Trp Thr Gly Leu Pro Met Gln Ala Gly Glu Pro Ile
            100                 105                 110
Pro Lys Gln Met Glu Trp Trp Pro Trp Gln Val Gln Gly Leu Ala Val
            115                 120                 125
Glu Pro Ser Ala Ala Thr Glu Trp Leu Ala Arg Leu Pro Leu Ser Gly
            130                 135                 140
Arg His Pro Asp Leu Gly Asp Glu Leu Arg Trp Trp Ser His Leu Gln
145                 150                 155                 160
Arg Trp Ser Leu Ser Leu Val Ala Arg Gly Arg Trp Ile Pro Gln Met
                165                 170                 175
Glu Leu Ser Lys Gly Glu Gly Tyr Pro His Arg Ala Arg Trp Val Pro
            180                 185                 190
Leu Leu Asn Arg Glu Glu Asp Arg Arg Leu Glu Asp Leu Ala Ala
            195                 200                 205
Thr Leu Pro Leu Val Ala Thr Cys Ala Leu Pro Trp Arg Glu Pro Leu
            210                 215                 220
Gly Arg Arg Ser Asn Arg Thr Thr Arg Leu Arg Pro Glu Ala Met Arg
225                 230                 235                 240
Ala Ala Asn Pro Val Ala Cys Cys Arg Pro Arg Ser Gly Arg Leu Arg
                245                 250                 255
Val Ala Thr Leu Leu Glu Asp Leu Val Asp Ala Glu Leu Arg Lys Gly
            260                 265                 270
Phe Glu Pro Thr Thr Glu Gly Leu Asp Pro Leu Leu Thr Leu Trp Gln
            275                 280                 285
Glu Ala Leu Ala Ser Glu Thr Gly Val Val Glu Val Gly Asn Glu Asp
            290                 295                 300
Ala Glu Arg Leu Thr Ala Ala Ser Leu His Trp Arg Glu Gly Ile Ala
305                 310                 315                 320
Gly Gly Phe Ala Ala Arg Thr Cys Leu Glu Leu Asn Thr Pro Asn
                325                 330                 335
Glu Gly Glu Glu Leu Trp Asp Leu Lys Phe Gly Leu Gln Ala Glu Ala
            340                 345                 350
Asp Pro Ser Leu Lys Leu Pro Ala Ala Ala Trp Ala Ser Gly Ala
            355                 360                 365
Glu Thr Leu Gln Leu Gly Glu Ile Lys Val Asp Gln Ala Gly Glu Val
            370                 375                 380
Leu Leu Glu Gly Leu Gly Arg Ala Leu Thr Val Phe Pro Pro Ile Glu
385                 390                 395                 400
Arg Gly Leu Glu Ser Ala Thr Pro Glu Thr Met Gln Leu Thr Pro Ala
                405                 410                 415
Glu Ala Phe Val Leu Val Arg Thr Ala Thr His Gln Leu Arg Asn Ala
            420                 425                 430
Gly Ile Gly Val Glu Leu Pro Pro Ser Leu Ser Gly Leu Ala Ser
            435                 440                 445
Arg Leu Gly Leu Ala Ile Lys Ala Asp Leu Pro Asp Arg Ser Ser Gly
450                 455                 460
Phe Thr Leu Gly Glu Ser Leu Asp Trp Ser Trp Asp Leu Met Ile Gly
465                 470                 475                 480
Gly Val Thr Leu Thr Leu Arg Glu Leu Glu Arg Leu Ser Gly Lys Arg
                485                 490                 495
Ser Pro Leu Val Arg His Lys Gly Ala Trp Ile Glu Leu Arg Pro Asn
            500                 505                 510
Asp Leu Arg Asn Ala Glu Arg Phe Cys Gly Ala Asn Pro Glu Leu Ser
```

```
                515                 520                 525
Leu Asp Asp Ala Leu Arg Leu Thr Ala Thr Glu Gly Glu Leu Met Met
530                 535                 540

Arg Leu Pro Val His Arg Phe Asp Ala Gly Pro Arg Leu Gln Gly Val
545                 550                 555                 560

Leu Glu Gln Tyr His Gln Lys Ala Pro Asp Pro Leu Pro Ala Pro
                565                 570                 575

Glu Gly Phe Ser Gly Gln Leu Arg Pro Tyr Gln Glu Arg Gly Leu Gly
                580                 585                 590

Trp Leu Ala Phe Leu His Arg Phe Asp Gln Gly Ala Cys Leu Ala Asp
                595                 600                 605

Asp Met Gly Leu Gly Lys Thr Ile Gln Leu Leu Ala Phe Leu Gln His
                610                 615                 620

Leu Lys Ala Glu His Glu Leu Lys Arg Pro Val Leu Leu Val Ala Pro
625                 630                 635                 640

Thr Ser Val Leu Thr Asn Trp Arg Arg Glu Ala Glu Ala Phe Thr Pro
                645                 650                 655

Glu Leu Ser Val Lys Glu His Tyr Gly Pro Arg Arg Pro Ser Thr Pro
                660                 665                 670

Ala Ala Leu Lys Lys Glu Leu Lys Asp Val Asp Leu Val Leu Thr Ser
                675                 680                 685

Tyr Gly Leu Met Gln Arg Asp Ser Glu Leu Leu Asp Ser Val Asp Trp
                690                 695                 700

Gln Gly Val Val Ile Asp Glu Ala Gln Ala Ile Lys Asn Pro Gly Ala
705                 710                 715                 720

Lys Gln Ser Gln Ala Ala Arg Asp Leu Ala Arg Ala Gly Lys Ser Ser
                725                 730                 735

Arg Phe Arg Ile Ala Leu Thr Gly Thr Pro Val Glu Asn Arg Val Ser
                740                 745                 750

Glu Leu Trp Ala Leu Met Asp Phe Leu Asn Pro Lys Val Leu Gly Glu
                755                 760                 765

Glu Asp Phe Phe Arg Gln Arg Tyr Arg Met Pro Ile Glu Arg Tyr Gly
770                 775                 780

Asp Met Ser Ser Leu Arg Asp Leu Lys Ala Arg Val Gly Pro Phe Ile
785                 790                 795                 800

Leu Arg Arg Leu Lys Thr Asp Lys Ser Ile Ile Ser Asp Leu Pro Glu
                805                 810                 815

Lys Val Glu Leu Ser Glu Trp Val Gly Leu Ser Lys Glu Gln Lys Ser
                820                 825                 830

Leu Tyr Asn Lys Thr Val Glu Asp Thr Leu Asp Ala Ile Ala Thr Ala
                835                 840                 845

Pro Arg Gly Gln Arg His Gly Gln Val Leu Ala Leu Leu Thr Arg Leu
850                 855                 860

Lys Gln Ile Cys Asn His Pro Ala Leu Ala Gln Arg Glu Gly Ala Val
865                 870                 875                 880

Asp Ser Glu Phe Leu Gly Arg Ser Ala Lys Leu Met Arg Leu Glu Glu
                885                 890                 895

Ile Leu Glu Glu Val Ile Glu Ala Gly Asp Arg Ala Leu Leu Phe Thr
                900                 905                 910

Gln Phe Ala Glu Trp Gly His Leu Leu Gln Ala Trp Met Gln Gln Arg
                915                 920                 925

Trp Lys Ser Glu Val Pro Phe Leu His Gly Gly Thr Arg Lys Ser Asp
930                 935                 940
```

```
Arg Gln Ala Met Val Asp Arg Phe Gln Glu Asp Pro Arg Gly Pro Gln
945                 950                 955                 960

Leu Phe Leu Leu Ser Leu Lys Ala Gly Gly Val Gly Leu Asn Leu Thr
            965                 970                 975

Arg Ala Ser His Val Phe His Val Asp Arg Trp Trp Asn Pro Ala Val
            980                 985                 990

Glu Asn Gln Ala Thr Asp Arg Ala Tyr Arg Ile Gly Gln Thr Asn Arg
        995                 1000                1005

Val Met Val His Lys Phe Val Thr Arg Gly Ser Val Glu Glu Lys
    1010                1015                1020

Ile Asp Gln Met Ile Arg Glu Lys Ala Arg Met Ala Glu Asp Val
    1025                1030                1035

Ile Gly Ser Gly Glu Asp Trp Leu Gly Ser Leu Gly Gly Asp Gln
    1040                1045                1050

Leu Arg Asn Leu Val Ala Leu Glu Asp Thr
    1055                1060

<210> SEQ ID NO 91
<211> LENGTH: 3198
<212> TYPE: DNA
<213> ORGANISM: Synechococcus sp.

<400> SEQUENCE: 91
atgagcctgc tgcacgccac ctggctcccg gccatccgta cacccaccag ttccggcgt      60 gccgccctgc tggtgtgggc ggacacctgg cgtgtggcgg agccggcggg ccccggcgtg    120
accccggcca cccatcccctt caccctcagc gccgatgacc tgcgcgcctg gctgagcgaa    180
cgggagctgc tgcccgacgg catcatcgat gccaccgcct gcctcaccct gcccagccgc    240
acggtgaaac cgaagcggaa gcgtggcgag accgcccctg tggatgaggg ctggacgggt    300
ctgcccctgc aggcgggaga accgattccg aagcagaccg aatggtggcc ctggcaggta    360
cagggcctgg cggtcgaacc cggtgcagcc accgcctggc tggcccgctt gccctctcc     420 ggccgccacc ccgacctcgc cgatgagctg cgctggtgga ccacatgca gcgctgggcc     480 ctcagcctga ttgctcgcag tcgctggatt ccccaggtgg agctgagcaa aggggagggc    540 taccccacc gcgcccgttg ggtgcctctg ctcaatcgcg aagacgatcg ccgccgcctg     600
gaagacatgg cggccgcct gccgctggtg gccacctgcg ctctcccctg gcgcgaaccc     660
accgggaagc gcagcaaccg caccacccgg ctgcggcctg aggcgatgcg gcggccaat     720 ccggtggcct gttgtcgtcc ccgcagcggc cgactgcgcg tcgccaccct gctcgaagac    780
ctggtggatg cccagctgcg cacgggtttc acagcccaga cggacgggct cgatcccctg    840
cttgccgcct gggaggaggc cctcggcagc gacaccggcg tgatccacct gggcgatgaa    900
gacgcagagc gtctggccac cgccagccat cactggcgcg aagggtggc cggcactgtg    960 gcggcggcgc gggcctgcct ggaactggag accccgacg acggcgatga cctctggacc   1020
ctgcggttcg cactgcaggc cgaagcggat cccacgctca aggtgccggc cgccctcgcc   1080
tgggcggccg gtccgaaggg actccagctc ggcgaaatcg ccgtggagca tccgggcgaa   1140
ctgctgctgg aaggcatggg ccgggcgctc acggtgttc caccgatcga acgcggtctc   1200
gacagcgcca cgccggaagg gatgcaactc accccgccg aagccttcgt gctggtgcgc   1260
accgcagccc gcgaactccg cgatgtgggg gtgggcgtgg agcttccagc cagcctctcg   1320
ggtggcctgg cgagcaggct cggcctggcg attcaggcgg aactaccgga gaaatcccgc   1380
ggtttcacgc tgggcgaaac cctcgactgg agctgggagc tgatgatcgg cggcgtcacc   1440
```

-continued

```
ctgacgctgc gggaactgga gcgcctggcg ggcaagcgca gcccctggt gcggcacaag    1500
ggcacctgga tcgagctgcg ccccaacgat ctcaagaatg cggagcggtt tttcgccgcg    1560
aagcccgatc tcagcctcga cgatgccctg cgcctcaccg ccagcgaagg cgacacgctg    1620
atgcgcatgc cggtgcaccg cctggaagcg ggcccacggc tgcaggcggt gctcgagcag    1680
tatcaccaac agaaagctcc cgatcccctg ccggcgccgg agggcttctg cggccagctg    1740
cggccttacc aggagcgggg cctcggctgg ctggcctttc tgcaccgctt tgatcaaggc    1800
gcctgcctgg ccgacgacat gggtctgggc aagaccatcc agctgctcgc ctttctgcag    1860
cacctgaagg ccgagcagga gctgaagagg ccggtgttgc tcgtggcgcc cacctcggtg    1920
ctcaccaact ggaagcggga ggccgccgcc ttcacgccgg agctcgaggt gaaggagcac    1980
tacgggccca gcgccctgc accctgca gcactcaaga gagcctcaa ggatgtggat    2040
ctggtgctca ccagctacgg cctgctccaa cgcgacagcg aactgctcga aagtctcgat    2100
tggcaggggg tggtgatcga cgaagcgcag gcaatcaaga atccgagcgc caaacagagc    2160
atggcggccc gagacctggc ccgcgcagga cgcagcagcc gtttccgcat tgccctcacc    2220
ggcacgccgg tggagaaccg ggtgagcgag ctctgggcct tgatggattt cctcaacccg    2280
cgggtgctcg gcgaagagga cttcttccgc cagcgctacc gcatgccgat tgagcgctat    2340
ggcgacatgt cgtcgctgcg ggatctgaaa tcccgcgtgg gacctttcat tcttcgccgg    2400
ctcaaaaccg acaaagcgat catttccgac ctgcccgaaa aggtggaact gagcgaatgg    2460
gtgggattga gcagggagca gaaagcgctc tatgccaaaa ccgtcgagga caccctcgat    2520
gcgattgccc gggcgccccg cggacaacgg catggccagg tgctggggtt gctcaccaag    2580
ctgaagcaga tctgtaacca tcccgcccctg gccctgaaag aggaggcggc cggcgacgag    2640
ttcctgcagc gctccatgaa actgcagcgc ctggaggaaa tcctcgagga ggtgatcgac    2700
gccggcgacc gcgccctgct cttcacccag ttcgccgaat ggggccatct gctgcagggt    2760
tacctgcaac ggcgctggcg cagcgaagtg ccgttcctga acggcagcac cagcaagagc    2820
gaacgccagg cgatggtcga tcgcttccag gaagacccgc gggggcctca gctgttcctg    2880
ctgtcactga aagccggtgg tgtgggcctc aacctcaccc gcgccagcca tgtgtttcac    2940
atcgatcgct ggtggaatcc ggcggtggaa aaccaggcca ccgaccgcgc ctaccggatc    3000
ggccagacga accgggtgat ggtgcacaag ttcatcacca gtggatcggt cgaagaaaaa    3060
atcgaccgga tgatccgcga gaaatcacgc ctcgccgaag acatcatcgg ctcaggcgaa    3120
gattggctcg gcgggctcga catgggccag ctgaaggaac tggtgagcct cgacgacaac    3180
ggatcacttt cagcatga                                                 3198
```

<210> SEQ ID NO 92
<211> LENGTH: 1065
<212> TYPE: PRT
<213> ORGANISM: Synechococcus sp.

<400> SEQUENCE: 92

```
Met Ser Leu Leu His Ala Thr Trp Leu Pro Ala Ile Arg Thr Pro Thr
1               5                   10                  15

Ser Ser Gly Arg Ala Ala Leu Leu Val Trp Ala Asp Thr Trp Arg Val
            20                  25                  30

Ala Glu Pro Ala Gly Pro Gly Val Thr Pro Ala Thr His Pro Phe Thr
        35                  40                  45

Leu Ser Ala Asp Asp Leu Arg Ala Trp Leu Ser Glu Arg Glu Leu Leu
    50                  55                  60
```

```
Pro Asp Gly Ile Ile Asp Ala Thr Ala Cys Leu Thr Leu Pro Ser Arg
 65                  70                  75                  80

Thr Val Lys Pro Lys Arg Lys Arg Gly Glu Thr Ala Pro Val Asp Glu
             85                  90                  95

Gly Trp Thr Gly Leu Pro Leu Gln Ala Gly Glu Pro Ile Pro Lys Gln
            100                 105                 110

Thr Glu Trp Trp Pro Trp Gln Val Gln Gly Leu Ala Val Glu Pro Gly
        115                 120                 125

Ala Ala Thr Ala Trp Leu Ala Arg Leu Pro Leu Ser Gly Arg His Pro
    130                 135                 140

Asp Leu Ala Asp Glu Leu Arg Trp Trp Ser His Met Gln Arg Trp Ala
145                 150                 155                 160

Leu Ser Leu Ile Ala Arg Ser Arg Trp Ile Pro Gln Val Glu Leu Ser
                165                 170                 175

Lys Gly Glu Gly Tyr Pro His Arg Ala Arg Trp Val Pro Leu Leu Asn
            180                 185                 190

Arg Glu Asp Asp Arg Arg Leu Glu Asp Met Ala Ala Arg Leu Pro
        195                 200                 205

Leu Val Ala Thr Cys Ala Leu Pro Trp Arg Glu Pro Thr Gly Lys Arg
    210                 215                 220

Ser Asn Arg Thr Thr Arg Leu Arg Pro Glu Ala Met Arg Ala Ala Asn
225                 230                 235                 240

Pro Val Ala Cys Cys Arg Pro Arg Ser Gly Arg Leu Arg Val Ala Thr
                245                 250                 255

Leu Leu Glu Asp Leu Val Asp Ala Gln Leu Arg Thr Gly Phe Thr Ala
            260                 265                 270

Gln Thr Asp Gly Leu Asp Pro Leu Leu Ala Ala Trp Glu Glu Ala Leu
        275                 280                 285

Gly Ser Asp Thr Gly Val Ile His Leu Gly Asp Glu Asp Ala Glu Arg
    290                 295                 300

Leu Ala Thr Ala Ser His His Trp Arg Glu Gly Val Ala Gly Thr Val
305                 310                 315                 320

Ala Ala Ala Arg Ala Cys Leu Glu Leu Glu Thr Pro Asp Asp Gly Asp
                325                 330                 335

Asp Leu Trp Thr Leu Arg Phe Ala Leu Gln Ala Glu Ala Asp Pro Thr
            340                 345                 350

Leu Lys Val Pro Ala Ala Leu Ala Trp Ala Ala Gly Pro Lys Gly Leu
        355                 360                 365

Gln Leu Gly Glu Ile Ala Val Glu His Pro Gly Glu Leu Leu Leu Glu
    370                 375                 380

Gly Met Gly Arg Ala Leu Thr Val Phe Pro Pro Ile Glu Arg Gly Leu
385                 390                 395                 400

Asp Ser Ala Thr Pro Glu Gly Met Gln Leu Thr Pro Ala Glu Ala Phe
                405                 410                 415

Val Leu Val Arg Thr Ala Ala Arg Glu Leu Arg Asp Val Gly Val Gly
            420                 425                 430

Val Glu Leu Pro Ala Ser Leu Ser Gly Gly Leu Ala Ser Arg Leu Gly
        435                 440                 445

Leu Ala Ile Gln Ala Glu Leu Pro Glu Lys Ser Arg Gly Phe Thr Leu
    450                 455                 460

Gly Glu Thr Leu Asp Trp Ser Trp Glu Leu Met Ile Gly Gly Val Thr
465                 470                 475                 480

Leu Thr Leu Arg Glu Leu Glu Arg Leu Ala Gly Lys Arg Ser Pro Leu
                485                 490                 495
```

```
Val Arg His Lys Gly Thr Trp Ile Glu Leu Arg Pro Asn Asp Leu Lys
            500                 505                 510

Asn Ala Glu Arg Phe Phe Ala Ala Lys Pro Asp Leu Ser Leu Asp Asp
            515                 520                 525

Ala Leu Arg Leu Thr Ala Ser Glu Gly Asp Thr Leu Met Arg Met Pro
            530                 535                 540

Val His Arg Leu Glu Ala Gly Pro Arg Leu Gln Ala Val Leu Glu Gln
545                 550                 555                 560

Tyr His Gln Gln Lys Ala Pro Asp Pro Leu Pro Ala Pro Glu Gly Phe
            565                 570                 575

Cys Gly Gln Leu Arg Pro Tyr Gln Glu Arg Gly Leu Gly Trp Leu Ala
            580                 585                 590

Phe Leu His Arg Phe Asp Gln Gly Ala Cys Leu Ala Asp Asp Met Gly
            595                 600                 605

Leu Gly Lys Thr Ile Gln Leu Leu Ala Phe Leu Gln His Leu Lys Ala
            610                 615                 620

Glu Gln Glu Leu Lys Arg Pro Val Leu Leu Val Ala Pro Thr Ser Val
625                 630                 635                 640

Leu Thr Asn Trp Lys Arg Glu Ala Ala Ala Phe Thr Pro Glu Leu Glu
            645                 650                 655

Val Lys Glu His Tyr Gly Pro Arg Arg Pro Ala Thr Pro Ala Ala Leu
            660                 665                 670

Lys Lys Ser Leu Lys Asp Val Asp Leu Val Leu Thr Ser Tyr Gly Leu
            675                 680                 685

Leu Gln Arg Asp Ser Glu Leu Leu Glu Ser Leu Asp Trp Gln Gly Val
            690                 695                 700

Val Ile Asp Glu Ala Gln Ala Ile Lys Asn Pro Ser Ala Lys Gln Ser
705                 710                 715                 720

Met Ala Ala Arg Asp Leu Ala Arg Ala Gly Arg Ser Ser Arg Phe Arg
            725                 730                 735

Ile Ala Leu Thr Gly Thr Pro Val Glu Asn Arg Val Ser Glu Leu Trp
            740                 745                 750

Ala Leu Met Asp Phe Leu Asn Pro Arg Val Leu Gly Glu Glu Asp Phe
            755                 760                 765

Phe Arg Gln Arg Tyr Arg Met Pro Ile Glu Arg Tyr Gly Asp Met Ser
            770                 775                 780

Ser Leu Arg Asp Leu Lys Ser Arg Val Gly Pro Phe Ile Leu Arg Arg
785                 790                 795                 800

Leu Lys Thr Asp Lys Ala Ile Ile Ser Asp Leu Pro Glu Lys Val Glu
            805                 810                 815

Leu Ser Glu Trp Val Gly Leu Ser Arg Glu Gln Lys Ala Leu Tyr Ala
            820                 825                 830

Lys Thr Val Glu Asp Thr Leu Asp Ala Ile Ala Arg Ala Pro Arg Gly
            835                 840                 845

Gln Arg His Gly Gln Val Leu Gly Leu Leu Thr Lys Leu Lys Gln Ile
            850                 855                 860

Cys Asn His Pro Ala Leu Ala Leu Lys Glu Glu Ala Ala Gly Asp Glu
865                 870                 875                 880

Phe Leu Gln Arg Ser Met Lys Leu Gln Arg Leu Glu Glu Ile Leu Glu
            885                 890                 895

Glu Val Ile Asp Ala Gly Asp Arg Ala Leu Leu Phe Thr Gln Phe Ala
            900                 905                 910

Glu Trp Gly His Leu Leu Gln Gly Tyr Leu Gln Arg Arg Trp Arg Ser
```

```
                915                 920                 925
Glu Val Pro Phe Leu Asn Gly Ser Thr Ser Lys Ser Glu Arg Gln Ala
    930                 935                 940

Met Val Asp Arg Phe Gln Glu Asp Pro Arg Gly Pro Gln Leu Phe Leu
945                 950                 955                 960

Leu Ser Leu Lys Ala Gly Gly Val Gly Leu Asn Leu Thr Arg Ala Ser
                965                 970                 975

His Val Phe His Ile Asp Arg Trp Trp Asn Pro Ala Val Glu Asn Gln
            980                 985                 990

Ala Thr Asp Arg Ala Tyr Arg Ile Gly Gln Thr Asn Arg Val Met Val
            995                 1000                1005

His Lys Phe Ile Thr Ser Gly Ser Val Glu Glu Lys Ile Asp Arg
    1010                1015                1020

Met Ile Arg Glu Lys Ser Arg Leu Ala Glu Asp Ile Ile Gly Ser
    1025                1030                1035

Gly Glu Asp Trp Leu Gly Gly Leu Asp Met Gly Gln Leu Lys Glu
    1040                1045                1050

Leu Val Ser Leu Asp Asp Asn Gly Ser Leu Ser Ala
    1055                1060                1065

<210> SEQ ID NO 93
<211> LENGTH: 3213
<212> TYPE: DNA
<213> ORGANISM: Synechococcus sp.

<400> SEQUENCE: 93
atgagcctgc tgcacgccac ctggctaccc gccatccgca ctcccagcag ctccggaagg      60
gctgctttgc tggtatgggc tgacacctgg cgtgtggccg accccctcgg ccccggggcc     120
acacccgccc ttcatccgtt caccctgagc gcggaggatc tgcgcgcctg gctcacagag     180
cgcgatttgc ttccggacgg aatcatcgat gcgaccgcat gcctcaccct gccgagccgc     240
agtgtgaaac cacggcggcc ccgtggctca gctgccgcca ccccctcatc agaagagcag     300
ccccccttgg tgcgggctgc cgctgcaagc ggcgaaccga tcccgaaaac caccgagtgg     360
tggccatggc aggtgcaggg gctggcgatc gaaccgatgg ccgccacggc atggctggcc     420
aagcttccac tgtcaggcca tcaccctgat ctggccgatg agttgcgctg gtggagtcac     480
atgcagcgat gggccctcag tcttgtggct agggggcgct ggctgcccca ggtggaattg     540
agccgaggtg aggggtatcc acaccgggcc cgctgggtcc gcttctcaa tcgagaggaa      600 gaccggcgcc gcctggagga ccttgccgcc gtctgcccc tggttgccac gtgtgcgttg      660
ccctggagag agcccacagg aaagcgcagc aatcgcatca ccaggctgcg cccagaggcc     720
atgcgcgctg ccaatcccgt ggcctgctgt cgtccccgca gcggtcgatt gcgggtggcc     780
acattgctgg aggatctggt agatgcccag ctgcgcaagg gcttccatcc cgatgacgag     840
gggctcgacc ccctgctctg cgcctgggaa aacgccctga gttcggagac cggggtgatc     900
gatctgaatg atgaagatgc cgaacgcctt gccacggcga ccaccactg gcgcgaggga     960 gtggctggca atgtggcggc tgccagggcc tgccttgaac tcgccacacc gaacgagggg    1020
gaagagctct gggatctgcg cttctatctg caggccgaag ccgatccaac gctgaaggta    1080
ccggccggag cagcctgggc cgctggaccc gaaggcttc aactcgggga gattcctgtg    1140
gagcatcccg gtgaggtgct gctgaaggc atggggcgtg ctctcacggt gttcgaacca    1200
atcgaacggg gcctggatag cgccacgccg aagcgatgc agctcacccc ggcggaagcc    1260
ttcgtgctgg tgcgcaccgc cgcccgtcag ctccgggacg tgggcgttgg tgtggatctc    1320
```

-continued

| | |
|---|---|
| cctcccagcc tctcgggagg cctggccagc cgcctcggtc tggcgatcaa ggccgaacta | 1380 |
| cccaaacgct cgcggggtt caccttggg gaaaatctcg actggaactg ggagctgatg | 1440 |
| atcgggggcg tcaccctgac gctgcgggag ctggaacggc tggccggcaa cgcagcccc | 1500 |
| ttggtgcgcc acaagggggc ctggatcgaa ctcaggccca atgatctcaa aaatgcagaa | 1560 |
| cgattctgtg ccgccaatcc tgatctgagc ctggacgatg cccttcgcct gacggccagc | 1620 |
| gaagggaca cgctgatgcg cctccccgtt catgcctttg atgctggccc tcgccttcaa | 1680 |
| ggggtgttgg agcaatacca ccagcagaaa gcaccggatc cacttcctgc gcccgagggt | 1740 |
| ttctgcggtc agcttcgccc ttaccaggaa cgaggcctgg gctggctggc cttcctgcac | 1800 |
| cgcttcgatc agggagcctg cctcgccgac gacatgggcc tggcaagac gatccagctg | 1860 |
| ctggccttcc tccagcacct gaagatggaa caagaactga acggccggt gctgctggtg | 1920 |
| gctcccacct ccgtgctcac caactggaaa cgggaagccg cggccttcac ccccgagctc | 1980 |
| acagtgcatg agcactacgg ccccaaacga ccctccaccc cagcagcact gaaaaaagcc | 2040 |
| ctgaaagacg ttgacctggt gctcaccagc tacgggcttc tgcaaagaga cagtgaactg | 2100 |
| cttgaaagtt cgactggca gggaaccgtg atcgatgaag ctcaggcgat caagaaccct | 2160 |
| tcggccaagc aaagccaggc agcccgtgat ctggctcgca cccgcaaggg ctccaggttc | 2220 |
| cgcattgccc tcactggcac accggttgaa acagagtga gcgagctctg ggccctgatg | 2280 |
| gatttcctca atccgaacgt gctcggcgaa gaggaattt tccggcagcg ctaccgcatg | 2340 |
| ccgatcgaac gctatggcga tatgtcgtcg cttcgcgatc tcaagtcgcg ggtgggacca | 2400 |
| ttcattctgc ggcgcttgaa aaccgacaag gcgatcatct ccgacctccc gaaaaagtg | 2460 |
| gagctgagtg aatgggtggg gctgagcaag gaacagaagt cccttacgc gaaaaccgtg | 2520 |
| gagaacaccc tcgatgccat cgcccgagct ccccgaggca agcgtcacgg ccaggtgctg | 2580 |
| ggactgctga cgcgcctcaa acagatctgc aatcacccgg ctctggcctt aaaggaagag | 2640 |
| gtggcaggcg acgacttcct gcagcgatcg gtgaagctgc agcggctcga agagattctc | 2700 |
| gaagaggtga ttgcagcggg ggatcgagcc ctgctgttca cccagttcgc ggaatggggg | 2760 |
| catctgctgc agggctacct gcaacgccgc tggcgcagcg aggtgccgtt cctgagcggc | 2820 |
| agcactagca aggagaacg tcaggccatg gtggatcgct tccaggaaga cccgcgcggc | 2880 |
| ccccagctgt tcctgttgtc cctcaaagcc ggcggtgtgg gattgaacct gacccgggcc | 2940 |
| agccacgtgt tccacatcga ccgctggtgg aatcctgcag ttgaaaacca ggccactgac | 3000 |
| cgtgcttacc ggattggcca gaccaatcgg gtgatggtgc ataagttcat caccagtggc | 3060 |
| tcagtggaag agaagatcga ccggatgatc cgggagaagt ccagactggc ggaagacatc | 3120 |
| gtgggctccg gcgaggagtg gctcggtggc ttcgacatgg ccaactcaa ggagctggtg | 3180 |
| agcctcgagg acaacgaaac acgcaaccca tga | 3213 |

<210> SEQ ID NO 94
<211> LENGTH: 1070
<212> TYPE: PRT
<213> ORGANISM: Synechococcus sp.

<400> SEQUENCE: 94

Met Ser Leu Leu His Ala Thr Trp Leu Pro Ala Ile Arg Thr Pro Ser
1               5                   10                  15

Ser Ser Gly Arg Ala Ala Leu Leu Val Trp Ala Asp Thr Trp Arg Val
            20                  25                  30

Ala Asp Pro Leu Gly Pro Gly Ala Thr Pro Ala Leu His Pro Phe Thr

-continued

```
                35                  40                  45
Leu Ser Ala Glu Asp Leu Arg Ala Trp Leu Thr Glu Arg Asp Leu Leu
 50                  55                  60
Pro Asp Gly Ile Ile Asp Ala Thr Ala Cys Leu Thr Leu Pro Ser Arg
 65                  70                  75                  80
Ser Val Lys Pro Arg Pro Arg Gly Ser Ala Ala Thr Pro Ser
             85                  90                  95
Ser Glu Glu Gln Pro Pro Trp Cys Gly Leu Pro Leu Gln Ala Gly Glu
                100                 105                 110
Pro Ile Pro Lys Thr Thr Glu Trp Trp Pro Trp Gln Val Gln Gly Leu
            115                 120                 125
Ala Ile Glu Pro Met Ala Ala Thr Ala Trp Leu Ala Lys Leu Pro Leu
    130                 135                 140
Ser Gly His His Pro Asp Leu Ala Asp Glu Leu Arg Trp Trp Ser His
145                 150                 155                 160
Met Gln Arg Trp Ala Leu Ser Leu Val Ala Arg Gly Arg Trp Leu Pro
                165                 170                 175
Gln Val Glu Leu Ser Arg Gly Glu Gly Tyr Pro His Arg Ala Arg Trp
            180                 185                 190
Val Pro Leu Leu Asn Arg Glu Glu Asp Arg Arg Leu Glu Asp Leu
    195                 200                 205
Ala Ala Arg Leu Pro Leu Val Ala Thr Cys Ala Leu Pro Trp Arg Glu
210                 215                 220
Pro Thr Gly Lys Arg Ser Asn Arg Ile Thr Arg Leu Arg Pro Glu Ala
225                 230                 235                 240
Met Arg Ala Ala Asn Pro Val Ala Cys Cys Arg Pro Arg Ser Gly Arg
                245                 250                 255
Leu Arg Val Ala Thr Leu Leu Glu Asp Leu Val Asp Ala Gln Leu Arg
            260                 265                 270
Lys Gly Phe His Pro Asp Asp Glu Gly Leu Asp Pro Leu Leu Cys Ala
    275                 280                 285
Trp Glu Asn Ala Leu Ser Ser Glu Thr Gly Val Ile Asp Leu Asn Asp
290                 295                 300
Glu Asp Ala Glu Arg Leu Ala Thr Ala Ser His His Trp Arg Glu Gly
305                 310                 315                 320
Val Ala Gly Asn Val Ala Ala Arg Ala Cys Leu Glu Leu Ala Thr
                325                 330                 335
Pro Asn Glu Gly Glu Glu Leu Trp Asp Leu Arg Phe Tyr Leu Gln Ala
            340                 345                 350
Glu Ala Asp Pro Thr Leu Lys Val Pro Ala Gly Ala Ala Trp Ala Ala
    355                 360                 365
Gly Pro Glu Gly Leu Gln Leu Gly Glu Ile Pro Val Glu His Pro Gly
370                 375                 380
Glu Val Leu Leu Glu Gly Met Gly Arg Ala Leu Thr Val Phe Glu Pro
385                 390                 395                 400
Ile Glu Arg Gly Leu Asp Ser Ala Thr Pro Glu Ala Met Gln Leu Thr
                405                 410                 415
Pro Ala Glu Ala Phe Val Leu Val Arg Thr Ala Ala Arg Gln Leu Arg
            420                 425                 430
Asp Val Gly Val Gly Val Asp Leu Pro Pro Ser Leu Ser Gly Gly Leu
    435                 440                 445
Ala Ser Arg Leu Gly Leu Ala Ile Lys Ala Glu Leu Pro Lys Arg Ser
450                 455                 460
```

```
Arg Gly Phe Thr Leu Gly Glu Asn Leu Asp Trp Asn Trp Glu Leu Met
465                 470                 475                 480

Ile Gly Gly Val Thr Leu Thr Leu Arg Glu Leu Glu Arg Leu Ala Gly
                485                 490                 495

Lys Arg Ser Pro Leu Val Arg His Lys Gly Ala Trp Ile Glu Leu Arg
                500                 505                 510

Pro Asn Asp Leu Lys Asn Ala Glu Arg Phe Cys Ala Ala Asn Pro Asp
                515                 520                 525

Leu Ser Leu Asp Asp Ala Leu Arg Leu Thr Ala Ser Glu Gly Asp Thr
                530                 535                 540

Leu Met Arg Leu Pro Val His Ala Phe Asp Ala Gly Pro Arg Leu Gln
545                 550                 555                 560

Gly Val Leu Glu Gln Tyr His Gln Gln Lys Ala Pro Asp Pro Leu Pro
                565                 570                 575

Ala Pro Glu Gly Phe Cys Gly Gln Leu Arg Pro Tyr Gln Glu Arg Gly
                580                 585                 590

Leu Gly Trp Leu Ala Phe Leu His Arg Phe Asp Gln Gly Ala Cys Leu
                595                 600                 605

Ala Asp Asp Met Gly Leu Gly Lys Thr Ile Gln Leu Leu Ala Phe Leu
610                 615                 620

Gln His Leu Lys Met Glu Gln Glu Leu Lys Arg Pro Val Leu Leu Val
625                 630                 635                 640

Ala Pro Thr Ser Val Leu Thr Asn Trp Lys Arg Glu Ala Ala Ala Phe
                645                 650                 655

Thr Pro Glu Leu Thr Val His Glu His Tyr Gly Pro Lys Arg Pro Ser
                660                 665                 670

Thr Pro Ala Ala Leu Lys Lys Ala Leu Lys Asp Val Asp Leu Val Leu
                675                 680                 685

Thr Ser Tyr Gly Leu Leu Gln Arg Asp Ser Glu Leu Leu Glu Ser Phe
                690                 695                 700

Asp Trp Gln Gly Thr Val Ile Asp Glu Ala Gln Ala Ile Lys Asn Pro
705                 710                 715                 720

Ser Ala Lys Gln Ser Gln Ala Ala Arg Asp Leu Ala Arg Thr Arg Lys
                725                 730                 735

Gly Ser Arg Phe Arg Ile Ala Leu Thr Gly Thr Pro Val Glu Asn Arg
                740                 745                 750

Val Ser Glu Leu Trp Ala Leu Met Asp Phe Leu Asn Pro Asn Val Leu
                755                 760                 765

Gly Glu Glu Phe Phe Arg Gln Tyr Arg Met Pro Ile Glu Arg
                770                 775                 780

Tyr Gly Asp Met Ser Ser Leu Arg Asp Leu Lys Ser Arg Val Gly Pro
785                 790                 795                 800

Phe Ile Leu Arg Arg Leu Lys Thr Asp Lys Ala Ile Ile Ser Asp Leu
                805                 810                 815

Pro Glu Lys Val Glu Leu Ser Glu Trp Val Gly Leu Ser Lys Glu Gln
                820                 825                 830

Lys Ser Leu Tyr Ala Lys Thr Val Glu Asn Thr Leu Asp Ala Ile Ala
                835                 840                 845

Arg Ala Pro Arg Gly Lys Arg His Gly Gln Val Leu Gly Leu Leu Thr
                850                 855                 860

Arg Leu Lys Gln Ile Cys Asn His Pro Ala Leu Ala Leu Lys Glu Glu
865                 870                 875                 880

Val Ala Gly Asp Asp Phe Leu Gln Arg Ser Val Lys Leu Gln Arg Leu
                885                 890                 895
```

```
Glu Glu Ile Leu Glu Glu Val Ile Ala Ala Gly Asp Arg Ala Leu Leu
                900                 905                 910
Phe Thr Gln Phe Ala Glu Trp Gly His Leu Leu Gln Gly Tyr Leu Gln
        915                 920                 925
Arg Arg Trp Arg Ser Glu Val Pro Phe Leu Ser Gly Ser Thr Ser Lys
    930                 935                 940
Gly Glu Arg Gln Ala Met Val Asp Arg Phe Gln Glu Asp Pro Arg Gly
945                 950                 955                 960
Pro Gln Leu Phe Leu Leu Ser Leu Lys Ala Gly Gly Val Gly Leu Asn
                965                 970                 975
Leu Thr Arg Ala Ser His Val Phe His Ile Asp Arg Trp Trp Asn Pro
        980                 985                 990
Ala Val Glu Asn Gln Ala Thr Asp Arg Ala Tyr Arg Ile Gly Gln Thr
    995                 1000                1005
Asn Arg Val Met Val His Lys Phe Ile Thr Ser Gly Ser Val Glu
    1010                1015                1020
Glu Lys Ile Asp Arg Met Ile Arg Glu Lys Ser Arg Leu Ala Glu
    1025                1030                1035
Asp Ile Val Gly Ser Gly Glu Glu Trp Leu Gly Gly Phe Asp Met
    1040                1045                1050
Gly Gln Leu Lys Glu Leu Val Ser Leu Glu Asp Asn Glu Thr Arg
    1055                1060                1065
Asn Pro
    1070

<210> SEQ ID NO 95
<211> LENGTH: 3192
<212> TYPE: DNA
<213> ORGANISM: Synechococcus sp.

<400> SEQUENCE: 95
atgagcctgc tgcacgccac ctggcttccc gccatccgta cctctggcag ttccggccaa     60
ccggcactgc tcatttgggc tgacacctgg cgggtggcga caccagaggg ccccgggcta    120
actccggcgc tgcacccgtt caccctggaa cccgacgacc tcaaggcctg gcttcaggaa    180
cgcgacctgt tgccaggcgg cagcatcgat gccaccgcct gcctcaccct gccagtcgc    240 acggtaaaac ccgcaagag ccgcagcaaa acggccgaac cagcgcccga agagcccatc    300
tggaccggtc tgccgatgca ggccggagag ccgattccga acagacaga atggtggccg    360 tggcaagtcc agggcctcgc tgtcgagccc tctgccgcca cggagtggct ctcacgcctt    420
cccctgtcag gacggaatcc agacctggcc gatgagctgc gctggtggag ccacctgcag    480
cgctgggccc tcagccttgt ggcccggggg cgctggattc cccagatgga actgagcaaa    540
ggcgagggat atccccaccg ggcccgttgg gtgcctctgc tcaaccgcga ggaggaccgg    600
cgacgtctgg aggatctggc cgccagcctg ccgctggtgg ccacctgcgc cctgccctgg    660
cgggaaccga tgggtcggcg cagcaaccgc atgacacggc tgcgtccgga ggccatgcgt    720
gccgccaacc cggtggcctg ctgccggccc cgcagtggcc gctgcgggt ggccacgctg    780 ctggaggatc tggtcgacgc acagctgcgc aaggactttg aaccatccac cgacggcctc    840 gatccctgt tgaccctgtg caagacgcc ctgggctccg aaacaggggt gattgagatc    900
ggtgatgaac aggccgaacg gctggccagc gccagcttcc attggcgcga gggcatcgct    960
ggagatttcg ccgctgcacg cacctgcctg gaactgcaga cacctgcaga gggagaagag   1020 ctctggagc tgcggtttgg gctgcaggcg gagtcggatc cgagcctcaa gctgcccgcc   1080
```

-continued

```
gctgcggcct gggcctccgg tgccgaccaa ctccagttgg gagaagtgac agtcgagcag    1140
cccggtgaag tgctgctgga gggtctggga cgcgccctca ccgtgttccc accgatcgaa    1200
aggggcctgg agaccgctac gcctgacacg atgcagctga ccccgccga agccttcgtg     1260 ctggtgcgga ccgcagcgcg gcagctgcgg gatgccggcg tcggcgtcga ccttcccccc    1320
agcctgtcgg ggggcctggc cagccgcctg gtctggcga tcaaggcgga gctgccagag     1380
cgctccagcg gcttcagcct cggcgaatcc ctcgactgga gctgggatct gatgatcggc    1440
ggggtgacgc tcaccctgcg ggaactggag cggttgagcg gcaaacgcag ccccctcgtg    1500
cgccacaagg gggcctggat cgaattgcga ccgaacgatc tgagaaacgc cgaacgcttc    1560
tgcggtgcca accggagct cagcctggac gatgccctgc ggatcaccgc caccgaaggc     1620
gatctgctga tgcgtctgcc ggtgcatcgc tttgaggccg gccccaggct gcaggcggtg    1680
ctggagcagt accaccagca gaaggccccg gatccgttgc cagcgccgga ggggttctgc    1740
ggccagctgc ggccttacca ggagcgtggc ctgggctggc tggccttcct caaccgcttc    1800
gaccaaggcg cctgcctggc ggacgacatg ggtctgggta agaccatcca gctgctggcc    1860
ttcctgcagc acctgaaagc agagcaggaa ctgaagcgcc cggtgctgct ggtggccccc    1920
acatcggtgc tcacaaactg gcgacgggaa gcggaagcct tcacccccga actggcggtg    1980
cgcgagcact acgaccgcg gcgtccctcc actccggctg cgctgaagaa ggcgttgaag     2040
gatgtcgact tagtcctcac cagctacggc ctactgcaga gggacagtga attgctggag    2100
tctcaggatt ggcaggggt tgtgatcgat gaagcccaag cgatcaagaa tcccagtgcc    2160
aagcagagcc aggcagcccg agacctggcc agaccagcca aaggcaaccg cttccgcatc    2220
gccctcacgg gcacaccggt ggagaacagg gtcagcgagc tctgggcttt gatggatttc    2280
ctcagtccca aggtgctggg agaagaagac ttcttccgtc agcgctaccg gatgccgatc    2340
gagcgctatg cgacatggc atccctacgg gacttaaaag ccagggtcgg ccccttcatc    2400
ctgcgccggc tgaaaaccga caagacgatc atttccgatc tgcccgagaa ggtggaactc    2460
agcgaatggg tggggttgag caaggagcag aaatcgctgt acagcaaaac cgttgaagac    2520
accctggatg ccattgcccg ggcgcctcgt ggacagcgcc atggtcaggt gctgggactg    2580
ctcacccgcc tgaagcagat ctgcaaccat ccggccctgg cattgagtga aaacgctgtt    2640
gacgacggct ttctggggcg ctccgccaag ttgcaacggc ttgaggaaat cctcgatgag    2700
gtgatcgaag caggggatcg ggcgctgctg ttcacccagt tcgccgagtg gggccatctg    2760
ctgcagtcct ggatgcaaca acgttggaag gcggatgtgc ccttcctgca tggagggacg    2820
cgcaaaaacg aacggcaggc catggtggat cgttttcagg aggaccccg cggcccgcag     2880 ctgttcctgc tgtcgctcaa agccggcggg gtgggtctga acctgaccag ggccagccac    2940
gtgttccaca tcgatcgctg gtggaaccct gcggtagaga accaggccac cgaccgtgct    3000
tatcggatcg gccagaccaa ccgggtgatg gtgcacaaat tcatcacaag cggatccgta    3060
gaagaaaaaa ttgaccggat gatccgagag aagtcgcgcc tggcagagga tgtgatcggt    3120
tccggtgaag actggctcgg gtgcctggcc ggtgatcagc tgcgcaatct cgttgccctg    3180
gaggacacct ga                                                        3192
```

<210> SEQ ID NO 96
<211> LENGTH: 1063
<212> TYPE: PRT
<213> ORGANISM: Synechococcus sp.

<400> SEQUENCE: 96

```
Met Ser Leu Leu His Ala Thr Trp Leu Pro Ala Ile Arg Thr Ser Gly
1               5                   10                  15

Ser Ser Gly Gln Pro Ala Leu Leu Ile Trp Ala Asp Thr Trp Arg Val
            20                  25                  30

Ala Thr Pro Glu Gly Pro Gly Leu Thr Pro Ala Leu His Pro Phe Thr
            35                  40                  45

Leu Glu Pro Asp Asp Leu Lys Ala Trp Leu Gln Glu Arg Asp Leu Leu
50                  55                  60

Pro Gly Gly Ser Ile Asp Ala Thr Ala Cys Leu Thr Leu Pro Ser Arg
65                  70                  75                  80

Thr Val Lys Pro Arg Lys Ser Arg Ser Lys Thr Ala Glu Pro Ala Pro
                85                  90                  95

Glu Glu Pro Ile Trp Thr Gly Leu Pro Met Gln Ala Gly Glu Pro Ile
            100                 105                 110

Pro Lys Gln Thr Glu Trp Trp Pro Trp Gln Val Gln Gly Leu Ala Val
            115                 120                 125

Glu Pro Ser Ala Ala Thr Glu Trp Leu Ser Arg Leu Pro Leu Ser Gly
    130                 135                 140

Arg Asn Pro Asp Leu Ala Asp Glu Leu Arg Trp Trp Ser His Leu Gln
145                 150                 155                 160

Arg Trp Ala Leu Ser Leu Val Ala Arg Gly Arg Trp Ile Pro Gln Met
                165                 170                 175

Glu Leu Ser Lys Gly Glu Gly Tyr Pro His Arg Ala Arg Trp Val Pro
            180                 185                 190

Leu Leu Asn Arg Glu Glu Asp Arg Arg Leu Glu Asp Leu Ala Ala
            195                 200                 205

Ser Leu Pro Leu Val Ala Thr Cys Ala Leu Pro Trp Arg Glu Pro Met
    210                 215                 220

Gly Arg Arg Ser Asn Arg Met Thr Arg Leu Arg Pro Glu Ala Met Arg
225                 230                 235                 240

Ala Ala Asn Pro Val Ala Cys Cys Arg Pro Arg Ser Gly Arg Leu Arg
            245                 250                 255

Val Ala Thr Leu Leu Glu Asp Leu Val Asp Ala Gln Leu Arg Lys Asp
            260                 265                 270

Phe Glu Pro Ser Thr Asp Gly Leu Asp Pro Leu Leu Thr Leu Trp Gln
            275                 280                 285

Asp Ala Leu Gly Ser Glu Thr Gly Val Ile Glu Ile Gly Asp Glu Gln
    290                 295                 300

Ala Glu Arg Leu Ala Ser Ala Ser Phe His Trp Arg Glu Gly Ile Ala
305                 310                 315                 320

Gly Asp Phe Ala Ala Ala Arg Thr Cys Leu Glu Leu Gln Thr Pro Ala
            325                 330                 335

Glu Gly Glu Glu Leu Trp Glu Leu Arg Phe Gly Leu Gln Ala Glu Ser
            340                 345                 350

Asp Pro Ser Leu Lys Leu Pro Ala Ala Ala Trp Ala Ser Gly Ala
            355                 360                 365

Asp Gln Leu Gln Leu Gly Glu Val Thr Val Glu Gln Pro Gly Glu Val
    370                 375                 380

Leu Leu Glu Gly Leu Gly Arg Ala Leu Thr Val Phe Pro Pro Ile Glu
385                 390                 395                 400

Arg Gly Leu Glu Thr Ala Thr Pro Asp Thr Met Gln Leu Thr Pro Ala
            405                 410                 415

Glu Ala Phe Val Leu Val Arg Thr Ala Ala Arg Gln Leu Arg Asp Ala
```

```
                420             425             430
Gly Val Gly Val Asp Leu Pro Pro Ser Leu Ser Gly Gly Leu Ala Ser
        435             440             445

Arg Leu Gly Leu Ala Ile Lys Ala Glu Leu Pro Glu Arg Ser Ser Gly
        450             455             460

Phe Ser Leu Gly Glu Ser Leu Asp Trp Ser Trp Asp Leu Met Ile Gly
465             470             475             480

Gly Val Thr Leu Thr Leu Arg Glu Leu Glu Arg Leu Ser Gly Lys Arg
        485             490             495

Ser Pro Leu Val Arg His Lys Gly Ala Trp Ile Glu Leu Arg Pro Asn
        500             505             510

Asp Leu Arg Asn Ala Glu Arg Phe Cys Gly Ala Asn Pro Glu Leu Ser
        515             520             525

Leu Asp Asp Ala Leu Arg Ile Thr Ala Thr Glu Gly Asp Leu Leu Met
        530             535             540

Arg Leu Pro Val His Arg Phe Glu Ala Gly Pro Arg Leu Gln Ala Val
545             550             555             560

Leu Glu Gln Tyr His Gln Gln Lys Ala Pro Asp Pro Leu Pro Ala Pro
                565             570             575

Glu Gly Phe Cys Gly Gln Leu Arg Pro Tyr Gln Glu Arg Gly Leu Gly
        580             585             590

Trp Leu Ala Phe Leu Asn Arg Phe Asp Gln Gly Ala Cys Leu Ala Asp
        595             600             605

Asp Met Gly Leu Gly Lys Thr Ile Gln Leu Leu Ala Phe Leu Gln His
        610             615             620

Leu Lys Ala Glu Gln Glu Leu Lys Arg Pro Val Leu Leu Val Ala Pro
625             630             635             640

Thr Ser Val Leu Thr Asn Trp Arg Arg Glu Ala Glu Ala Phe Thr Pro
                645             650             655

Glu Leu Ala Val Arg Glu His Tyr Gly Pro Arg Arg Pro Ser Thr Pro
        660             665             670

Ala Ala Leu Lys Lys Ala Leu Lys Asp Val Asp Leu Val Leu Thr Ser
        675             680             685

Tyr Gly Leu Leu Gln Arg Asp Ser Glu Leu Leu Glu Ser Gln Asp Trp
        690             695             700

Gln Gly Val Val Ile Asp Glu Ala Gln Ala Ile Lys Asn Pro Ser Ala
705             710             715             720

Lys Gln Ser Gln Ala Ala Arg Asp Leu Ala Arg Pro Ala Lys Gly Asn
                725             730             735

Arg Phe Arg Ile Ala Leu Thr Gly Thr Pro Val Glu Asn Arg Val Ser
        740             745             750

Glu Leu Trp Ala Leu Met Asp Phe Leu Ser Pro Lys Val Leu Gly Glu
        755             760             765

Glu Asp Phe Phe Arg Gln Arg Tyr Arg Met Pro Ile Glu Arg Tyr Gly
        770             775             780

Asp Met Ala Ser Leu Arg Asp Leu Lys Ala Arg Val Gly Pro Phe Ile
785             790             795             800

Leu Arg Arg Leu Lys Thr Asp Lys Thr Ile Ile Ser Asp Leu Pro Glu
                805             810             815

Lys Val Glu Leu Ser Glu Trp Val Gly Leu Ser Lys Glu Gln Lys Ser
        820             825             830

Leu Tyr Ser Lys Thr Val Glu Asp Thr Leu Asp Ala Ile Ala Arg Ala
        835             840             845
```

```
Pro Arg Gly Gln Arg His Gly Gln Val Leu Gly Leu Leu Thr Arg Leu
850                 855                 860

Lys Gln Ile Cys Asn His Pro Ala Leu Ala Leu Ser Glu Asn Ala Val
865                 870                 875                 880

Asp Asp Gly Phe Leu Gly Arg Ser Ala Lys Leu Gln Arg Leu Glu Glu
                885                 890                 895

Ile Leu Asp Glu Val Ile Glu Ala Gly Asp Arg Ala Leu Leu Phe Thr
                900                 905                 910

Gln Phe Ala Glu Trp Gly His Leu Leu Gln Ser Trp Met Gln Gln Arg
            915                 920                 925

Trp Lys Ala Asp Val Pro Phe Leu His Gly Gly Thr Arg Lys Asn Glu
            930                 935                 940

Arg Gln Ala Met Val Asp Arg Phe Gln Glu Asp Pro Arg Gly Pro Gln
945                 950                 955                 960

Leu Phe Leu Leu Ser Leu Lys Ala Gly Gly Val Gly Leu Asn Leu Thr
                965                 970                 975

Arg Ala Ser His Val Phe His Ile Asp Arg Trp Trp Asn Pro Ala Val
                980                 985                 990

Glu Asn Gln Ala Thr Asp Arg Ala  Tyr Arg Ile Gly Gln  Thr Asn Arg
            995                 1000                1005

Val Met  Val His Lys Phe Ile  Thr Ser Gly Ser Val  Glu Glu Lys
1010                 1015                1020

Ile Asp  Arg Met Ile Arg Glu  Lys Ser Arg Leu Ala  Glu Asp Val
1025                 1030                1035

Ile Gly  Ser Gly Glu Asp Trp  Leu Gly Cys Leu Ala  Gly Asp Gln
1040                 1045                1050

Leu Arg  Asn Leu Val Ala Leu  Glu Asp Thr
1055                 1060

<210> SEQ ID NO 97
<211> LENGTH: 3060
<212> TYPE: DNA
<213> ORGANISM: Synechococcus elongatus

<400> SEQUENCE: 97
atggcagtgc tgcacggtgg ctggctcggc gatcgcttct gcgtttgggc cgaggcttgg      60
caggctggtg agcctcagtc ggcagcagaa attgcgattc atccctacgc gatcgcggcc     120
actgacttaa atgattggtg ccagaagtac cgtctgggat ccctgacggg gacgccaaca     180
gaagtcctgc tctctattcc cagtgacctg aagaaagagg cggttctacc gtttctgagt     240
ggtcaggaaa ttccagatgg ggcgctgctt tggtcttggc agatccccgt gctgtcgcta     300
gaagccgcga tcgccggtca atggctggcg accttgccgc tgggttcggc ggaggatcat     360
ccttggctgg ggccagatct acgcttttgg agccacatct accgctgggc acaaagtttg     420
ctggctcggg ggcgctttta tccggcgctg agtcgagcg atcgcggttt aacggcagtt     480
tggttgccac tgtttaatca agcgggcgat cgccagcgct tcgatcgcta tagtcagcag     540
ctgcccttta gtcagttttg ctatcaggca atcgaaacag cggcagcttg tccttggcag     600
cctcaaccgc aggatctgtt gctgcgagtc ctacagactt ggttgacagc acgactacaa     660
ccggcgatcg cggcgggaac tctcgtgtct gctgatctgc tggcggcttg cagcaatcg     720 ctagcgaatg gaaaaccgct aaagctagaa gacagtgaag ccagtcgctt gcaaacggcg     780
atcgatcgct ggttactacc agtgcagaat ggcgcagctc aggcttggcg gatggttttg     840
cgccttgtcc cgcctacgga gcaagagcag ccctggcaat ggagtttggg cttacaagca     900
```

-continued

| | |
|---|---|
| gcgaccgatc ccgatcgctt tcggccggcc tctctcctct ggcaggatcc gctgccacct | 960 |
| gggctaccag atcaatctca ggaattgctg ttacgcggct gggacaggc ttgtcggctc | 1020 |
| tatccccaat tgcaaaccag tctggcgaca gcctgtccag aattccatcc actgaccaca | 1080 |
| gcggaggtct atcagctgct caagcaggtg attcctcagt ggcaagagca gggcattgaa | 1140 |
| gtgcaactgc cgccgggctt gcgtggtcaa gggcgacacc ggctgggagt ggaagtcagc | 1200 |
| gccacgttgc cgagcgatcg cccgagtgtg gggctgaag cactactgca gtttcgttgg | 1260 |
| gagctgagtc tgggcggtca gcggctgacc aaagcagaag tggaacgctt ggcagccctg | 1320 |
| gaaacgccct tggtggaaat caacggcgac tggattgagg tgcggccgca ggatattgag | 1380 |
| tcggcgcgag agtttttccg taagcgcaag gatcagccaa atttgacctt ggcggatgcg | 1440 |
| atcgcgatcg ccagtggtga gtcgccgaat gttggtcgcc tgccggtggt caattttgaa | 1500 |
| gcggcgggct tactcgaaga agccttggcc gtgtttcagg ggcagcgatc gcctgcggct | 1560 |
| ttgcccgctc cgcccacctt tcagggcgag ctgcgaccct atcaagagcg ggggtgggc | 1620 |
| tggctcagct ttttgcagcg cttcgggatt ggggcttgcc tcgccgacga catgggcttg | 1680 |
| ggtaagacga ttcagctgct ggccttttta ctgcatctca aacacagcaa cgagctgacg | 1740 |
| cggccggtgc tgctagtctg tccgacttcg gtgctgggca actgggaacg ggaggtgcag | 1800 |
| aaatttgcac cggagcttcg ctggaagctg cactatggcc ccgatcgcgc tcagggtaag | 1860 |
| gctttggcga cagcgctcaa ggactgcgat ttggtgctga ccagttactc cttggtggcg | 1920 |
| cgagatcaga aagcgatcgc ggcgatcgac tggcaaggca ttgtgctgga tgaagcccag | 1980 |
| aacatcaaga atgaccaggc gaaacagacg caggcggtgc gagcgatcgc ccaaagtccg | 2040 |
| acgcaaaagc cccgctttcg gattgccctg acagggacgc cggttgagaa tcgcctcagt | 2100 |
| gagttgtggt cgattgtcga gtttttgcag ccgggacatt taggcaccaa gccattcttt | 2160 |
| caaaagcgct ttgtcacgcc gatcgagcgt tttggcgatg cggattcgct gacagcattg | 2220 |
| cggcagcgcg tgcaaccgtt aatcctacgg cgactgaaaa ccgatcgcag cattattgcc | 2280 |
| gacttgcctg agaagcaaga aatgacggtc ttttgtccgt tggtacagga gcaggccgat | 2340 |
| cgctatcagg tgctagtcaa tgaagcgcta gccaatattg aagcaagtga aggcattcag | 2400 |
| cggcgcggcc agattttggc attgctaacg cgactgaagc agctctgtaa tcatccgtcg | 2460 |
| ttgttgctcg aaaagccgaa gctcgatccg aattttggcg atcgctcagc caagttgcag | 2520 |
| cgcttactag aaatgttggc ggagctaacg gatgcgggcg atcgcgcttt ggtgtttacg | 2580 |
| cagtttgcgg gctggggtag tttgctgcag caattttttgc aggaacagct agggcgagag | 2640 |
| gtgctgtttt tgtcgggcag taccaagaag ggcgatcgcc aacagatggt tgatcgcttc | 2700 |
| caaaatgatc cgcaggcacc ggcaattttc atcctgtcat tgaaggctgg cggggtgggg | 2760 |
| ctcaacctga cgaaagccaa tcatgtctttt cattacgatc gctggtggaa tccggcagtt | 2820 |
| gaaaaccaag cgaccgatcg cgcgtttcgg attgggcaac gacgcaatgt acaggtgcac | 2880 |
| aagtttgtct gcgctggcac tctagaagaa aaaattgatc agatgatcgc tagcaagcaa | 2940 |
| gcattagcac agcagattgt cggtagtggt gaggattggc taacggaact agacaccaat | 3000 |
| caactccggc aactcttgat cctcgatcgc tcagcttggg tagaagagga agagccttag | 3060 |

<210> SEQ ID NO 98
<211> LENGTH: 1019
<212> TYPE: PRT
<213> ORGANISM: Synechococcus elongatus

<400> SEQUENCE: 98

```
Met Ala Val Leu His Gly Gly Trp Leu Gly Asp Arg Phe Cys Val Trp
1               5                   10                  15

Ala Glu Ala Trp Gln Ala Gly Glu Pro Gln Ser Ala Ala Glu Ile Ala
            20                  25                  30

Ile His Pro Tyr Ala Ile Ala Thr Asp Leu Asn Asp Trp Cys Gln
            35                  40                  45

Lys Tyr Arg Leu Gly Ser Leu Thr Gly Thr Pro Thr Glu Val Leu Leu
    50                  55                  60

Ser Ile Pro Ser Asp Leu Lys Lys Glu Ala Val Leu Pro Phe Leu Ser
65                  70                  75                  80

Gly Gln Glu Ile Pro Asp Gly Ala Leu Leu Trp Ser Trp Gln Ile Pro
                85                  90                  95

Val Leu Ser Leu Glu Ala Ala Ile Ala Gly Gln Trp Leu Ala Thr Leu
            100                 105                 110

Pro Leu Gly Ser Ala Glu Asp His Pro Trp Leu Gly Pro Asp Leu Arg
            115                 120                 125

Phe Trp Ser His Ile Tyr Arg Trp Ala Gln Ser Leu Leu Ala Arg Gly
    130                 135                 140

Arg Phe Tyr Pro Ala Leu Glu Ser Ser Asp Arg Gly Leu Thr Ala Val
145                 150                 155                 160

Trp Leu Pro Leu Phe Asn Gln Ala Gly Asp Arg Gln Arg Phe Asp Arg
                165                 170                 175

Tyr Ser Gln Gln Leu Pro Phe Ser Gln Phe Cys Tyr Gln Ala Ile Glu
            180                 185                 190

Thr Ala Ala Ala Cys Pro Trp Gln Pro Gln Pro Gln Asp Leu Leu Leu
            195                 200                 205

Arg Val Leu Gln Thr Trp Leu Thr Ala Arg Leu Gln Pro Ala Ile Ala
    210                 215                 220

Ala Gly Thr Leu Val Ser Ala Asp Leu Leu Ala Ala Trp Gln Gln Ser
225                 230                 235                 240

Leu Ala Asn Gly Lys Pro Leu Lys Leu Glu Asp Ser Glu Ala Ser Arg
                245                 250                 255

Leu Gln Thr Ala Ile Asp Arg Trp Leu Leu Pro Val Gln Asn Gly Ala
            260                 265                 270

Ala Gln Ala Trp Arg Met Val Leu Arg Leu Val Pro Pro Thr Glu Gln
    275                 280                 285

Glu Gln Pro Trp Gln Leu Glu Phe Gly Leu Gln Ala Ala Thr Asp Pro
290                 295                 300

Asp Arg Phe Arg Pro Ala Ser Leu Leu Trp Gln Asp Pro Leu Pro Pro
305                 310                 315                 320

Gly Leu Pro Asp Gln Ser Gln Glu Leu Leu Arg Gly Leu Gly Gln
            325                 330                 335

Ala Cys Arg Leu Tyr Pro Gln Leu Gln Thr Ser Leu Ala Thr Ala Cys
            340                 345                 350

Pro Glu Phe His Pro Leu Thr Thr Ala Glu Val Tyr Gln Leu Leu Lys
        355                 360                 365

Gln Val Ile Pro Gln Trp Gln Glu Gln Gly Ile Glu Val Gln Leu Pro
    370                 375                 380

Pro Gly Leu Arg Gly Gln Gly Arg His Arg Leu Gly Val Glu Val Ser
385                 390                 395                 400

Ala Thr Leu Pro Ser Asp Arg Pro Ser Val Gly Leu Glu Ala Leu Leu
            405                 410                 415

Gln Phe Arg Trp Glu Leu Ser Leu Gly Gly Gln Arg Leu Thr Lys Ala
        420                 425                 430
```

```
Glu Val Glu Arg Leu Ala Ala Leu Glu Thr Pro Leu Val Glu Ile Asn
            435                 440                 445

Gly Asp Trp Ile Glu Val Arg Pro Gln Asp Ile Glu Ser Ala Arg Glu
        450                 455                 460

Phe Phe Arg Lys Arg Lys Asp Gln Pro Asn Leu Thr Leu Ala Asp Ala
465                 470                 475                 480

Ile Ala Ile Ala Ser Gly Glu Ser Pro Asn Val Gly Arg Leu Pro Val
                485                 490                 495

Val Asn Phe Glu Ala Ala Gly Leu Leu Glu Glu Ala Leu Ala Val Phe
            500                 505                 510

Gln Gly Gln Arg Ser Pro Ala Ala Leu Pro Ala Pro Thr Phe Gln
        515                 520                 525

Gly Glu Leu Arg Pro Tyr Gln Glu Arg Gly Val Gly Trp Leu Ser Phe
        530                 535                 540

Leu Gln Arg Phe Gly Ile Gly Ala Cys Leu Ala Asp Asp Met Gly Leu
545                 550                 555                 560

Gly Lys Thr Ile Gln Leu Leu Ala Phe Leu Leu His Leu Lys His Ser
                565                 570                 575

Asn Glu Leu Thr Arg Pro Val Leu Leu Val Cys Pro Thr Ser Val Leu
            580                 585                 590

Gly Asn Trp Glu Arg Glu Val Gln Lys Phe Ala Pro Glu Leu Arg Trp
        595                 600                 605

Lys Leu His Tyr Gly Pro Asp Arg Ala Gln Gly Lys Ala Leu Ala Thr
        610                 615                 620

Ala Leu Lys Asp Cys Asp Leu Val Leu Thr Ser Tyr Ser Leu Val Ala
625                 630                 635                 640

Arg Asp Gln Lys Ala Ile Ala Ile Asp Trp Gln Gly Ile Val Leu
                645                 650                 655

Asp Glu Ala Gln Asn Ile Lys Asn Asp Gln Ala Lys Gln Thr Gln Ala
            660                 665                 670

Val Arg Ala Ile Ala Gln Ser Pro Thr Gln Lys Pro Arg Phe Arg Ile
        675                 680                 685

Ala Leu Thr Gly Thr Pro Val Glu Asn Arg Leu Ser Glu Leu Trp Ser
        690                 695                 700

Ile Val Glu Phe Leu Gln Pro Gly His Leu Gly Thr Lys Pro Phe Phe
705                 710                 715                 720

Gln Lys Arg Phe Val Thr Pro Ile Glu Arg Phe Gly Asp Ala Asp Ser
                725                 730                 735

Leu Thr Ala Leu Arg Gln Arg Val Gln Pro Leu Ile Leu Arg Arg Leu
            740                 745                 750

Lys Thr Asp Arg Ser Ile Ile Ala Asp Leu Pro Glu Lys Gln Glu Met
        755                 760                 765

Thr Val Phe Cys Pro Leu Val Gln Glu Gln Ala Asp Arg Tyr Gln Val
        770                 775                 780

Leu Val Asn Glu Ala Leu Ala Asn Ile Glu Ala Ser Glu Gly Ile Gln
785                 790                 795                 800

Arg Arg Gly Gln Ile Leu Ala Leu Leu Thr Arg Leu Lys Gln Leu Cys
                805                 810                 815

Asn His Pro Ser Leu Leu Leu Glu Lys Pro Lys Leu Asp Pro Asn Phe
            820                 825                 830

Gly Asp Arg Ser Ala Lys Leu Gln Arg Leu Leu Glu Met Leu Ala Glu
        835                 840                 845

Leu Thr Asp Ala Gly Asp Arg Ala Leu Val Phe Thr Gln Phe Ala Gly
```

```
                   850              855              860
Trp Gly Ser Leu Leu Gln Gln Phe Leu Gln Glu Gln Leu Gly Arg Glu
865                 870              875                  880

Val Leu Phe Leu Ser Gly Ser Thr Lys Lys Gly Asp Arg Gln Gln Met
                885                  890                  895

Val Asp Arg Phe Gln Asn Asp Pro Gln Ala Pro Ala Ile Phe Ile Leu
                900                  905                  910

Ser Leu Lys Ala Gly Gly Val Gly Leu Asn Leu Thr Lys Ala Asn His
                915                  920              925

Val Phe His Tyr Asp Arg Trp Trp Asn Pro Ala Val Glu Asn Gln Ala
            930                  935              940

Thr Asp Arg Ala Phe Arg Ile Gly Gln Arg Arg Asn Val Gln Val His
945                 950                  955                  960

Lys Phe Val Cys Ala Gly Thr Leu Glu Glu Lys Ile Asp Gln Met Ile
                965                  970                  975

Ala Ser Lys Gln Ala Leu Ala Gln Gln Ile Val Gly Ser Gly Glu Asp
                980                  985                  990

Trp Leu Thr Glu Leu Asp Thr Asn  Gln Leu Arg Gln Leu  Leu Ile Leu
                995                 1000                 1005

Asp Arg  Ser Ala Trp Val Glu  Glu Glu Glu Pro
    1010                 1015

<210> SEQ ID NO 99
<211> LENGTH: 3060
<212> TYPE: DNA
<213> ORGANISM: Synechococcus elongatus

<400> SEQUENCE: 99
atggcagtgc tgcacggtgg ctggctcggc gatcgcttct gcgtttgggc cgaggcttgg      60
caggctggtg agcctcagtc ggcagcagaa attgcgattc atccctacgc gatcgcggcc     120
actgacttaa atgattggtg ccagaagtac cgtctgggat ccctgacggg gacgccaaca     180
gaagtcctgc tctctattcc cagtgacctg aagaaagagg cggttctacc gtttctgagt     240
ggtcaggaaa ttccagatgg ggcgctgctt tggtcttggc agatccccgt gctgtcacta     300
gaagccgcga tcgccggtca atggctggcg accttgccgc tgggttcggc ggaggatcat     360
ccttggctgg ggccagatct acgcttttgg agccacatct accgctgggc acaaagtttg     420
ctggctcggg gcgcttttta tccggcgctg gagtcgagcg atcgcggttt aacggcagtt     480
tggttgccac tgtttaatca gcgggcgat cgccagcgct tcgatcgcta tagtcagcag     540 ctgccctta gtcagttttg ctatcaggca atcgaaacag cggcagcttg tccttggcag     600
cctcaaccgc aggatctgtt gctgcgagtc ctacagactt ggttgacagc acgactacaa     660
ccggcgatcg cggcgggaac tctcgtgtct gctgatctgc tggcggcttg cagcaatcg     720 ctagcgaatg aaaaaccgct aaagctagaa gacagtgaag ccagtcgctt gcaaacggcg     780
atcgatcgct ggttactacc agtgcagaat ggcgcagctc aggcttggcg gatggttttg     840
cgccttgtcc cgcctacgga gcaagagcag ccctggcaat ggagtttggg cttacaagca     900
gcgaccgatc ccgatcgctt ttggccggcc tctctcctct ggcaggatcc gctgccacct     960
gggctaccag atcaatctca ggaattgctg ttacgcggct tgggacaggc ttgtcggctc    1020
tatccccaat tgcaaaccag tctggcgaca gcctgtccag aattccatcc actgaccaca    1080
gcggaggtct atcagctgct caagcaggtg attcctcagt ggcaagagca gggcattgaa    1140
gtgcaactgc cgccgggctt gcgtggtcaa gggcgacacc ggctgggagt ggaagtcagc    1200
```

```
gccacgttgc cgagcgatcg cccgagtgtg gggctggaag cactactgca gtttcgttgg    1260
gagctgagtc tgggcggtca gcggctgacc aaagcagaag tggaacgctt ggcagccctg    1320
gaaacgccct tggtggaaat caacggcgac tggattgagg tgcggccgca ggatattgag    1380
tcggcgcgag agtttttccg taagcgcaag gatcagccaa atttgacctt gcggatgcg     1440 atcgcgatcg ccagtggtga gtcgccgaat gttggtcgcc tgccggtggt caattttgaa    1500
gcggcgggct tactcgaaga agccttggcc gtgtttcagg gcagcgatc gcctgcggct     1560 ttgcccgctc cgcccacctt tcagggcgag ctgcgaccct atcaagagcg gggggtgggc    1620
tggctcagct ttttgcagcg cttcgggatt gggcttgcc tcgccgacga catgggcttg     1680
ggtaagacga ttcagctgct ggccttttta ctgcatctca acacagcaa cgagctgacg     1740 cggccggtgc tgctagtctg tccgacttcg gtgctgggca actgggaacg ggaggtgcag    1800
aaatttgcac cggagcttcg ctggaagctg cactatggcc ccgatcgcgc tcagggtaag    1860
gctttggcga cagcgctcaa ggactgcgat tggtgctga ccagttactc cttggtggcg     1920
cgagatcaga aagcgatcgc ggcgatcgac tggcaaggca ttgtgctgga tgaagcccag    1980
aacatcaaga atgaccaggc gaaacagacg caggcggtgc gagcgatcgc ccaaagtccg    2040
acgcaaaagc cccgctttcg gattgccctg acagggacgc cggttgagaa tcgcctcagt    2100
gagttgtggt cgattgtcga gttttgcag ccgggacatt taggcaccaa gccattcttt     2160
caaaagcgct tgtcacgcc gatcgagcgt tttggcgatg cggattcgct gacagcattg      2220
cggcagcgcg tgcaaccgtt aatcctacgc gactgaaaa ccgatcgcag cattattgcc     2280
gacttgcctg agaagcaaga aatgacggtc ttttgtccgt tggtacagga gcaggccgat    2340
cgctatcagg tgctagtcaa tgaagcgcta gccaatattg aagcaagtga aggcattcag    2400
cggcgcggcc agattttggc attgctaacg cgactgaagc agctctgtaa tcatccgtcg    2460
ttgttgctcg aaaagccgaa gctcgatccg aattttggcg atcgctcagc caagttgcag    2520
cgcttactag aaatgttggc ggagctaacg gatgcgggcg atcgcgcttt ggtgtttacg    2580
cagtttgcgg gctggggtag tttgctgcag caattttgc aggaacagct agggcgagag     2640 gtgctgttt tgtcgggcag taccaagaag ggcgatcgcc aacagatggt tgatcgcttc    2700
caaaatgatc cgcaggcacc ggcaattttc atcctgtcat tgaaggctgg cggggtgggg   2760
ctcaacctga cgaaagccaa tcatgtcttt cattacgatc gctggtggaa tccggcagtt    2820
gaaaaccaag cgaccgatcg cgcgtttcgg attgggcaac gacgcaatgt acaggtgcac    2880
aagtttgtct gcgctggcac tctagaagaa aaaattgatc agatgatcgc tagcaagcaa    2940
gcattagcac agcagattgt cggtagtggt gaggattggc taacggaact agacaccaat    3000
caactccggc aactcttgat cctcgatcgc tcagcttggg tagaagagga agagccttag   3060
```

<210> SEQ ID NO 100
<211> LENGTH: 1019
<212> TYPE: PRT
<213> ORGANISM: Synechococcus elongatus

<400> SEQUENCE: 100

Met Ala Val Leu His Gly Gly Trp Leu Gly Asp Arg Phe Cys Val Trp
1               5                   10                  15

Ala Glu Ala Trp Gln Ala Gly Glu Pro Gln Ser Ala Ala Glu Ile Ala
            20                  25                  30

Ile His Pro Tyr Ala Ile Ala Ala Thr Asp Leu Asn Asp Trp Cys Gln
        35                  40                  45

Lys Tyr Arg Leu Gly Ser Leu Thr Gly Thr Pro Thr Glu Val Leu Leu

-continued

```
            50                  55                  60
Ser Ile Pro Ser Asp Leu Lys Lys Glu Ala Val Leu Pro Phe Leu Ser
 65                  70                  75                  80

Gly Gln Glu Ile Pro Asp Gly Ala Leu Leu Trp Ser Trp Gln Ile Pro
                 85                  90                  95

Val Leu Ser Leu Glu Ala Ala Ile Ala Gly Gln Trp Leu Ala Thr Leu
            100                 105                 110

Pro Leu Gly Ser Ala Glu Asp His Pro Trp Leu Gly Pro Asp Leu Arg
            115                 120                 125

Phe Trp Ser His Ile Tyr Arg Trp Ala Gln Ser Leu Leu Ala Arg Gly
        130                 135                 140

Arg Phe Tyr Pro Ala Leu Glu Ser Ser Asp Arg Gly Leu Thr Ala Val
145                 150                 155                 160

Trp Leu Pro Leu Phe Asn Gln Ala Gly Asp Arg Gln Arg Phe Asp Arg
                165                 170                 175

Tyr Ser Gln Gln Leu Pro Phe Ser Gln Phe Cys Tyr Gln Ala Ile Glu
            180                 185                 190

Thr Ala Ala Ala Cys Pro Trp Gln Pro Gln Pro Gln Asp Leu Leu Leu
            195                 200                 205

Arg Val Leu Gln Thr Trp Leu Thr Ala Arg Leu Gln Pro Ala Ile Ala
        210                 215                 220

Ala Gly Thr Leu Val Ser Ala Asp Leu Leu Ala Trp Gln Gln Ser
225                 230                 235                 240

Leu Ala Asn Gly Lys Pro Leu Lys Leu Glu Asp Ser Glu Ala Ser Arg
                245                 250                 255

Leu Gln Thr Ala Ile Asp Arg Trp Leu Leu Pro Val Gln Asn Gly Ala
            260                 265                 270

Ala Gln Ala Trp Arg Met Val Leu Arg Leu Pro Pro Thr Glu Gln
            275                 280                 285

Glu Gln Pro Trp Gln Leu Glu Phe Gly Leu Gln Ala Ala Thr Asp Pro
        290                 295                 300

Asp Arg Phe Trp Pro Ala Ser Leu Leu Trp Gln Asp Pro Leu Pro Pro
305                 310                 315                 320

Gly Leu Pro Asp Gln Ser Gln Glu Leu Leu Leu Arg Gly Leu Gly Gln
                325                 330                 335

Ala Cys Arg Leu Tyr Pro Gln Leu Gln Thr Ser Leu Ala Thr Ala Cys
            340                 345                 350

Pro Glu Phe His Pro Leu Thr Thr Ala Glu Val Tyr Gln Leu Leu Lys
            355                 360                 365

Gln Val Ile Pro Gln Trp Gln Glu Gln Gly Ile Glu Val Gln Leu Pro
        370                 375                 380

Pro Gly Leu Arg Gly Gln Gly Arg His Arg Leu Gly Val Glu Val Ser
385                 390                 395                 400

Ala Thr Leu Pro Ser Asp Arg Pro Ser Val Gly Leu Glu Ala Leu Leu
                405                 410                 415

Gln Phe Arg Trp Glu Leu Ser Leu Gly Gly Gln Arg Leu Thr Lys Ala
            420                 425                 430

Glu Val Glu Arg Leu Ala Ala Leu Glu Thr Pro Leu Val Glu Ile Asn
            435                 440                 445

Gly Asp Trp Ile Glu Val Arg Pro Gln Asp Ile Glu Ser Ala Arg Glu
        450                 455                 460

Phe Phe Arg Lys Arg Lys Asp Gln Pro Asn Leu Thr Leu Ala Asp Ala
465                 470                 475                 480
```

-continued

Ile Ala Ile Ala Ser Gly Glu Ser Pro Asn Val Gly Arg Leu Pro Val
            485                 490                 495

Val Asn Phe Glu Ala Ala Gly Leu Leu Glu Ala Leu Ala Val Phe
        500                 505                 510

Gln Gly Gln Arg Ser Pro Ala Ala Leu Pro Ala Pro Pro Thr Phe Gln
            515                 520                 525

Gly Glu Leu Arg Pro Tyr Gln Glu Arg Gly Val Gly Trp Leu Ser Phe
        530                 535                 540

Leu Gln Arg Phe Gly Ile Gly Ala Cys Leu Ala Asp Asp Met Gly Leu
545                 550                 555                 560

Gly Lys Thr Ile Gln Leu Leu Ala Phe Leu Leu His Leu Lys His Ser
                565                 570                 575

Asn Glu Leu Thr Arg Pro Val Leu Leu Val Cys Pro Thr Ser Val Leu
            580                 585                 590

Gly Asn Trp Glu Arg Glu Val Gln Lys Phe Ala Pro Glu Leu Arg Trp
        595                 600                 605

Lys Leu His Tyr Gly Pro Asp Arg Ala Gln Gly Lys Ala Leu Ala Thr
            610                 615                 620

Ala Leu Lys Asp Cys Asp Leu Val Leu Thr Ser Tyr Ser Leu Val Ala
625                 630                 635                 640

Arg Asp Gln Lys Ala Ile Ala Ala Ile Asp Trp Gln Gly Ile Val Leu
                645                 650                 655

Asp Glu Ala Gln Asn Ile Lys Asn Asp Gln Ala Lys Gln Thr Gln Ala
            660                 665                 670

Val Arg Ala Ile Ala Gln Ser Pro Thr Gln Lys Pro Arg Phe Arg Ile
        675                 680                 685

Ala Leu Thr Gly Thr Pro Val Glu Asn Arg Leu Ser Glu Leu Trp Ser
        690                 695                 700

Ile Val Glu Phe Leu Gln Pro Gly His Leu Gly Thr Lys Pro Phe Phe
705                 710                 715                 720

Gln Lys Arg Phe Val Thr Pro Ile Glu Arg Phe Gly Asp Ala Asp Ser
                725                 730                 735

Leu Thr Ala Leu Arg Gln Arg Val Gln Pro Leu Ile Leu Arg Arg Leu
            740                 745                 750

Lys Thr Asp Arg Ser Ile Ile Ala Asp Leu Pro Glu Lys Gln Glu Met
        755                 760                 765

Thr Val Phe Cys Pro Leu Val Gln Glu Gln Ala Asp Arg Tyr Gln Val
        770                 775                 780

Leu Val Asn Glu Ala Leu Ala Asn Ile Glu Ala Ser Glu Gly Ile Gln
785                 790                 795                 800

Arg Arg Gly Gln Ile Leu Ala Leu Leu Thr Arg Leu Lys Gln Leu Cys
                805                 810                 815

Asn His Pro Ser Leu Leu Leu Glu Lys Pro Lys Leu Asp Pro Asn Phe
            820                 825                 830

Gly Asp Arg Ser Ala Lys Leu Gln Arg Leu Leu Glu Met Leu Ala Glu
        835                 840                 845

Leu Thr Asp Ala Gly Asp Arg Ala Leu Val Phe Thr Gln Phe Ala Gly
        850                 855                 860

Trp Gly Ser Leu Leu Gln Gln Phe Leu Gln Glu Gln Leu Gly Arg Glu
865                 870                 875                 880

Val Leu Phe Leu Ser Gly Ser Thr Lys Lys Gly Asp Arg Gln Gln Met
                885                 890                 895

Val Asp Arg Phe Gln Asn Asp Pro Gln Ala Pro Ala Ile Phe Ile Leu
            900                 905                 910

```
Ser Leu Lys Ala Gly Gly Val Gly Leu Asn Leu Thr Lys Ala Asn His
        915                 920                 925

Val Phe His Tyr Asp Arg Trp Trp Asn Pro Ala Val Glu Asn Gln Ala
        930                 935                 940

Thr Asp Arg Ala Phe Arg Ile Gly Gln Arg Arg Asn Val Gln Val His
945                 950                 955                 960

Lys Phe Val Cys Ala Gly Thr Leu Glu Glu Lys Ile Asp Gln Met Ile
            965                 970                 975

Ala Ser Lys Gln Ala Leu Ala Gln Gln Ile Val Gly Ser Gly Glu Asp
            980                 985                 990

Trp Leu Thr Glu Leu Asp Thr Asn Gln Leu Arg Gln Leu Leu Ile Leu
        995                1000                1005

Asp Arg Ser Ala Trp Val Glu Glu Glu Glu Pro
    1010                1015

<210> SEQ ID NO 101
<211> LENGTH: 3000
<212> TYPE: DNA
<213> ORGANISM: Thermosynechococcus elongatus

<400> SEQUENCE: 101
atggctattt ccatggcac atggctccca gagccggcgc cacagttttt catttgggcg     60
gaagaatggc gatcgctggc tcaggcaatc acgccttggg ctcccccggc gattccggtt    120
tatccctacg ccacccagag aaaaacacct cttaggaaga cagcccgccc aagtgccacc    180
tacgttgctt taccggccca gattcagggg catcaactgt taccaccacc gctggcggaa    240
gtgcaggggg aactcctatt tttgtggcag gtgcccggct ggtcaattcc cgcttcagaa    300
gttttagaac aactgcatca actgagtctt cacggccaag acagtggcag tattggcgat    360
gatttgcgct attggctgca cgtgagtcgc tggttgctgg atttaattgt gcgtggccaa    420
tacctgccaa caccagaggg ctggcggatt ctgctgaccc acggggcga tcgcgatcgc    480 ctgcgccact tcagccaatt gatgccggat ctgtgtcgct gttatcaagc cgatggcaca    540
gcgttgcagt tgccaccca tgctgcagat ctcctggcgg atttctaca gcacacccta    600 cagggttatc tccacactgc ccttgctgac ctcgaattgc caaagtagg cttagccaaa    660 gaacatggcc actggctagc cttcctgaaa acgggtcaaa ccccggaact gccacctccc    720
ctcattgaac gcctgcaccg ctggcaagaa ccctaccgcg agcagttgca tctgcgtccc    780
caatggcgac tggctctgca attggttccc ccagatactg ccgatggtga ctggcacttg    840
gcctttgggc tgcaaacgga aggggaaacg gacaccatgc taagggccgc cgagatttgg    900
caatgcaccc aagaggccct cctctatcaa gggcaggtgc tctggcagcc caagaaaacc    960
ctgttgcggg gactgggctt ggcctcccgc atctatcgtc ccctcgatcg cagtcttcaa   1020
gaacgctccc ccgtgctct gactttgcac accacggaag tttatgcctt cttgcaaagt   1080
gcaattgcgc cccttgagca gcaggggtt gcgatcattt tgccaccgag tctgcgccgc   1140
aatagcgccc aacatcgctt gggtctgaaa ataattgcca cattgccgcc gccgccact   1200 aacggcttga cgattgacag cttgatgcag tttcagtggc agttgcagtt ggggcagcat   1260
cccctctcgg aggcggattt tgatcaactg cgccgccaag ggacgcccct ggtttatctc   1320
aatggtgagt gggtcttgct gcgccccaa gaggtcaagg ccgctcaaga gtttctccag   1380
tctcccccaa agacccaact ctccttgca gagacactgc gcattgctac gggggatacg   1440
gtaacggtgg ccaagttgcc gattcttggc ttagacacca tgatgcact ccagaccctc   1500
```

-continued

```
ttggatggcc tcacgggcaa acaaagcctt gatccagtgc aacaccgca ggagttttgc    1560
ggtgaactgc gccctacca ggcacggggg gtggcgtggc tgagtttctt ggaacgctgg    1620
cggctggggg cttgcttggc ggacgatatg ggcttgggga aaaccattca actgttggcc    1680
tttttgctcc acctcaagga aacgggacgg gcctaccgac cgacactgtt gatctgtcct    1740
acctcggtgc tggggaactg gctgcgggag tgccaaaagt ttgccccaac cttgcgggcc    1800
tatgtccacc atgggagcga tcgccccaag ggcaaggcat ttctgaaaaa ggttgaaact    1860
cacgatctaa ttttgaccag ttatgccctc ctccagcgcg atcgcaccac cttgcagcag    1920
gttctgtggc agcatttggt actggatgaa gcccaaaaca tcaagaatgc caacacccag    1980
cagtcccaag cagcgcggga actttccgcc cagtttcgca ttgccctgac gggaaccccc    2040
ctagaaaacc gcctcctcga actttggtcc attatggact tcctccatcc ggggtacttg    2100
ggccatcgca cctactttca acaccgctat gtccgtccca ttgaacgcta tggcgacacc    2160
acctccctca tgctctgcg cacctatgtc cagcccttta ttctgcggcg cctgaaaacc    2220
gaccgcagta ttattcaaga cctgccggaa aaacaggaga tgctggtgta ttgtggcctc    2280
accctagagc agatgcagct ttacactgct gtggtggaag actcccttgc tgctatcgaa    2340
aatagtcaag gcattcagcg gcggggcaat atcttggcca ccctgaccaa gttgaagcaa    2400
atctgtaacc atcccgccca gtatctcaag caagaagact atgcccccga tcgctcaggt    2460
aaattgcaac ggcttataga aatgctgcaa gcgcttcagg aagtgggcga tcgcgccctt    2520
gtctttaccc aatttgccga gtttggcacc cacctgaaaa cctatctgga aaaggcgctc    2580
cagcaggagg tgttttttcct ctcaggacgc accccaaag cccagcggga actcatggtg    2640
gaacgctttc aacacgatcc cgaggccccc agggtcttta ttctttccct caaggcaggg    2700
ggcgtcggtc tcaatttgac tcgcgctaac catgtcttc actacgatcg ctggtggaac    2760
ccagcggtag aaaatcaggc cagcgatcgc gtcttccgca ttggtcaggc ccgcaatgtc    2820
caaatccata aatttatctg cacgggtacc ctcgaagaaa agatccacga gcaaatcgaa    2880
cagaaaaaag cccttgcgga aatgattgtg ggtagtggcg aacactggct gactgaactc    2940
aacctcgacc agttgcggca actgctcacc ttagacaaag agcggctgat cacctctag    3000
```

<210> SEQ ID NO 102
<211> LENGTH: 999
<212> TYPE: PRT
<213> ORGANISM: Thermosynechococcus elongatus

<400> SEQUENCE: 102

```
Met Ala Ile Phe His Gly Thr Trp Leu Pro Glu Pro Ala Pro Gln Phe
1               5                   10                  15

Phe Ile Trp Ala Glu Glu Trp Arg Ser Leu Ala Gln Ala Ile Thr Pro
            20                  25                  30

Trp Ala Pro Pro Ala Ile Pro Val Tyr Pro Tyr Ala Thr Gln Arg Lys
        35                  40                  45

Thr Pro Leu Arg Lys Thr Ala Arg Pro Ser Ala Thr Tyr Val Ala Leu
    50                  55                  60

Pro Ala Gln Ile Gln Gly His Gln Leu Leu Pro Pro Leu Ala Glu
65                  70                  75                  80

Val Gln Gly Glu Leu Leu Phe Leu Trp Gln Val Pro Gly Trp Ser Ile
                85                  90                  95

Pro Ala Ser Glu Val Leu Glu Gln Leu His Gln Leu Ser Leu His Gly
            100                 105                 110

Gln Asp Ser Gly Ser Ile Gly Asp Asp Leu Arg Tyr Trp Leu His Val
```

```
            115                 120                 125
Ser Arg Trp Leu Leu Asp Leu Ile Val Arg Gly Gln Tyr Leu Pro Thr
130                 135                 140
Pro Glu Gly Trp Arg Ile Leu Leu Thr His Gly Gly Asp Arg Asp Arg
145                 150                 155                 160
Leu Arg His Phe Ser Gln Leu Met Pro Asp Leu Cys Arg Cys Tyr Gln
                165                 170                 175
Ala Asp Gly Thr Ala Leu Gln Leu Pro Pro His Ala Ala Asp Leu Leu
                180                 185                 190
Ala Asp Phe Leu Gln His Thr Leu Gln Gly Tyr Leu His Thr Ala Leu
                195                 200                 205
Ala Asp Leu Glu Leu Pro Lys Val Gly Leu Ala Lys Glu His Gly His
                210                 215                 220
Trp Leu Ala Phe Leu Lys Thr Gly Gln Thr Pro Glu Leu Pro Pro Pro
225                 230                 235                 240
Leu Ile Glu Arg Leu His Arg Trp Gln Glu Pro Tyr Arg Glu Gln Leu
                245                 250                 255
His Leu Arg Pro Gln Trp Arg Leu Ala Leu Gln Leu Val Pro Pro Asp
                260                 265                 270
Thr Ala Asp Gly Asp Trp His Leu Ala Phe Gly Leu Gln Thr Glu Gly
                275                 280                 285
Glu Thr Asp Thr Met Leu Arg Ala Ala Glu Ile Trp Gln Cys Thr Gln
                290                 295                 300
Glu Ala Leu Leu Tyr Gln Gly Gln Val Leu Trp Gln Pro Gln Glu Thr
305                 310                 315                 320
Leu Leu Arg Gly Leu Gly Leu Ala Ser Arg Ile Tyr Arg Pro Leu Asp
                325                 330                 335
Arg Ser Leu Gln Glu Arg Ser Pro Val Ala Leu Thr Leu His Thr Thr
                340                 345                 350
Glu Val Tyr Ala Phe Leu Gln Ser Ala Ile Ala Pro Leu Glu Gln Gln
                355                 360                 365
Gly Val Ala Ile Ile Leu Pro Pro Ser Leu Arg Arg Asn Ser Ala Gln
370                 375                 380
His Arg Leu Gly Leu Lys Ile Ile Ala Thr Leu Pro Pro Pro Ala Thr
385                 390                 395                 400
Asn Gly Leu Thr Ile Asp Ser Leu Met Gln Phe Gln Trp Gln Leu Gln
                405                 410                 415
Leu Gly Gln His Pro Leu Ser Glu Ala Asp Phe Asp Gln Leu Arg Arg
                420                 425                 430
Gln Gly Thr Pro Leu Val Tyr Leu Asn Gly Glu Trp Val Leu Leu Arg
                435                 440                 445
Pro Gln Glu Val Lys Ala Ala Gln Glu Phe Leu Gln Ser Pro Pro Lys
450                 455                 460
Thr Gln Leu Ser Leu Ala Glu Thr Leu Arg Ile Ala Thr Gly Asp Thr
465                 470                 475                 480
Val Thr Val Ala Lys Leu Pro Ile Leu Gly Leu Asp Thr Asn Asp Ala
                485                 490                 495
Leu Gln Thr Leu Leu Asp Gly Leu Thr Gly Lys Gln Ser Leu Asp Pro
                500                 505                 510
Val Pro Thr Pro Gln Glu Phe Cys Gly Glu Leu Arg Pro Tyr Gln Ala
                515                 520                 525
Arg Gly Val Ala Trp Leu Ser Phe Leu Glu Arg Trp Arg Leu Gly Ala
530                 535                 540
```

```
Cys Leu Ala Asp Asp Met Gly Leu Gly Lys Thr Ile Gln Leu Leu Ala
545                 550                 555                 560

Phe Leu Leu His Leu Lys Glu Thr Gly Arg Ala Tyr Arg Pro Thr Leu
            565                 570                 575

Leu Ile Cys Pro Thr Ser Val Leu Gly Asn Trp Leu Arg Glu Cys Gln
            580                 585                 590

Lys Phe Ala Pro Thr Leu Arg Ala Tyr Val His His Gly Ser Asp Arg
        595                 600                 605

Pro Lys Gly Lys Ala Phe Leu Lys Lys Val Glu Thr His Asp Leu Ile
        610                 615                 620

Leu Thr Ser Tyr Ala Leu Leu Gln Arg Asp Arg Thr Thr Leu Gln Gln
625                 630                 635                 640

Val Leu Trp Gln His Leu Val Leu Asp Glu Ala Gln Asn Ile Lys Asn
                645                 650                 655

Ala Asn Thr Gln Gln Ser Gln Ala Ala Arg Glu Leu Ser Ala Gln Phe
            660                 665                 670

Arg Ile Ala Leu Thr Gly Thr Pro Leu Glu Asn Arg Leu Leu Glu Leu
        675                 680                 685

Trp Ser Ile Met Asp Phe Leu His Pro Gly Tyr Leu Gly His Arg Thr
690                 695                 700

Tyr Phe Gln His Arg Tyr Val Arg Pro Ile Glu Arg Tyr Gly Asp Thr
705                 710                 715                 720

Thr Ser Leu Asn Ala Leu Arg Thr Tyr Val Gln Pro Phe Ile Leu Arg
                725                 730                 735

Arg Leu Lys Thr Asp Arg Ser Ile Ile Gln Asp Leu Pro Glu Lys Gln
            740                 745                 750

Glu Met Leu Val Tyr Cys Gly Leu Thr Leu Glu Gln Met Gln Leu Tyr
        755                 760                 765

Thr Ala Val Val Glu Asp Ser Leu Ala Ala Ile Glu Asn Ser Gln Gly
        770                 775                 780

Ile Gln Arg Arg Gly Asn Ile Leu Ala Thr Leu Thr Lys Leu Lys Gln
785                 790                 795                 800

Ile Cys Asn His Pro Ala Gln Tyr Leu Lys Gln Glu Asp Tyr Ala Pro
                805                 810                 815

Asp Arg Ser Gly Lys Leu Gln Arg Leu Ile Glu Met Leu Gln Ala Leu
            820                 825                 830

Gln Glu Val Gly Asp Arg Ala Leu Val Phe Thr Gln Phe Ala Glu Phe
        835                 840                 845

Gly Thr His Leu Lys Thr Tyr Leu Glu Lys Ala Leu Gln Gln Glu Val
        850                 855                 860

Phe Phe Leu Ser Gly Arg Thr Pro Lys Ala Gln Arg Glu Leu Met Val
865                 870                 875                 880

Glu Arg Phe Gln His Asp Pro Glu Ala Pro Arg Val Phe Ile Leu Ser
                885                 890                 895

Leu Lys Ala Gly Gly Val Gly Leu Asn Leu Thr Arg Ala Asn His Val
            900                 905                 910

Phe His Tyr Asp Arg Trp Trp Asn Pro Ala Val Glu Asn Gln Ala Ser
        915                 920                 925

Asp Arg Val Phe Arg Ile Gly Gln Ala Arg Asn Val Gln Ile His Lys
        930                 935                 940

Phe Ile Cys Thr Gly Thr Leu Glu Glu Lys Ile His Glu Gln Ile Glu
945                 950                 955                 960

Gln Lys Lys Ala Leu Ala Glu Met Ile Val Gly Ser Gly Glu His Trp
                965                 970                 975
```

```
Leu Thr Glu Leu Asn Leu Asp Gln Leu Arg Gln Leu Leu Thr Leu Asp
            980                 985                 990

Lys Glu Arg Leu Ile Thr Leu
        995

<210> SEQ ID NO 103
<211> LENGTH: 10
<212> TYPE: PRT
<213> ORGANISM: Artificial sequence
<220> FEATURE:
<223> OTHER INFORMATION: motif 1 of SWI2/SNF2 polypeptides
<220> FEATURE:
<221> NAME/KEY: VARIANT
<222> LOCATION: (10)..(10)
<223> OTHER INFORMATION: Xaa is Ser or Thr

<400> SEQUENCE: 103

Leu Ala Asp Asp Met Gly Leu Gly Lys Xaa
1               5                   10

<210> SEQ ID NO 104
<211> LENGTH: 12
<212> TYPE: PRT
<213> ORGANISM: Artificial sequence
<220> FEATURE:
<223> OTHER INFORMATION: motif 1a of SWI2/SNF2 polypeptides
<220> FEATURE:
<221> NAME/KEY: VARIANT
<222> LOCATION: (2)..(2)
<223> OTHER INFORMATION: Xaa is Val, Ile or Leu
<220> FEATURE:
<221> NAME/KEY: VARIANT
<222> LOCATION: (3)..(3)
<223> OTHER INFORMATION: Xaa is Ile, Leu or Val
<220> FEATURE:
<221> NAME/KEY: VARIANT
<222> LOCATION: (4)..(4)
<223> OTHER INFORMATION: Xaa is Cys or Ala
<220> FEATURE:
<221> NAME/KEY: VARIANT
<222> LOCATION: (6)..(6)
<223> OTHER INFORMATION: Xaa is Met, Val or Thr
<220> FEATURE:
<221> NAME/KEY: VARIANT
<222> LOCATION: (8)..(8)
<223> OTHER INFORMATION: Xaa is Ile, Leu or Val
<220> FEATURE:
<221> NAME/KEY: VARIANT
<222> LOCATION: (9)..(9)
<223> OTHER INFORMATION: Xaa is Ile, Leu or Val
<220> FEATURE:
<221> NAME/KEY: UNSURE
<222> LOCATION: (10)..(10)
<223> OTHER INFORMATION: Xaa can be any naturally occurring amino acid

<400> SEQUENCE: 104

Leu Xaa Xaa Xaa Pro Xaa Ser Xaa Xaa Xaa Asn Trp
1               5                   10

<210> SEQ ID NO 105
<211> LENGTH: 8
<212> TYPE: PRT
<213> ORGANISM: Artificial sequence
<220> FEATURE:
<223> OTHER INFORMATION: motif 2 of SWI2/SNF2 polypeptides
<220> FEATURE:
<221> NAME/KEY: VARIANT
<222> LOCATION: (5)..(5)
<223> OTHER INFORMATION: Xaa is Ala, His or Asn
<220> FEATURE:
<221> NAME/KEY: VARIANT
<222> LOCATION: (6)..(6)
<223> OTHER INFORMATION: Xaa is Ile, Leu or Val
```

<400> SEQUENCE: 105

Asp Glu Ala Gln Xaa Xaa Lys Asn
1               5

<210> SEQ ID NO 106
<211> LENGTH: 9
<212> TYPE: PRT
<213> ORGANISM: Artificial sequence
<220> FEATURE:
<223> OTHER INFORMATION: motif 3 of SWI2/SNF2 polypeptides
<220> FEATURE:
<221> NAME/KEY: VARIANT
<222> LOCATION: (2)..(2)
<223> OTHER INFORMATION: Xaa is Met or Leu
<220> FEATURE:
<221> NAME/KEY: UNSURE
<222> LOCATION: (7)..(7)
<223> OTHER INFORMATION: Xaa can be any naturally occurring amino acid

<400> SEQUENCE: 106

Ala Xaa Thr Gly Thr Pro Xaa Glu Asn
1               5

<210> SEQ ID NO 107
<211> LENGTH: 6
<212> TYPE: PRT
<213> ORGANISM: Artificial sequence
<220> FEATURE:
<223> OTHER INFORMATION: motif 4 of SWI2/SNF2 polypeptides
<220> FEATURE:
<221> NAME/KEY: VARIANT
<222> LOCATION: (1)..(1)
<223> OTHER INFORMATION: Xaa is Ile or Leu
<220> FEATURE:
<221> NAME/KEY: UNSURE
<222> LOCATION: (2)..(2)
<223> OTHER INFORMATION: Xaa can be any naturally occurring amino acid
<220> FEATURE:
<221> NAME/KEY: VARIANT
<222> LOCATION: (4)..(4)
<223> OTHER INFORMATION: Xaa is Ser or Thr
<220> FEATURE:
<221> NAME/KEY: VARIANT
<222> LOCATION: (6)..(6)
<223> OTHER INFORMATION: Xaa is Tyr or Phe

<400> SEQUENCE: 107

Xaa Xaa Phe Xaa Gln Xaa
1               5

<210> SEQ ID NO 108
<211> LENGTH: 17
<212> TYPE: PRT
<213> ORGANISM: Artificial sequence
<220> FEATURE:
<223> OTHER INFORMATION: motif 5 of SWI2/SNF2 polypeptides
<220> FEATURE:
<221> NAME/KEY: VARIANT
<222> LOCATION: (2)..(2)
<223> OTHER INFORMATION: Xaa is Val or Leu
<220> FEATURE:
<221> NAME/KEY: VARIANT
<222> LOCATION: (7)..(7)
<223> OTHER INFORMATION: Xaa is Thr, Leu or Val
<220> FEATURE:
<221> NAME/KEY: VARIANT
<222> LOCATION: (9)..(9)
<223> OTHER INFORMATION: Xaa is Ile or Leu
<220> FEATURE:
<221> NAME/KEY: VARIANT
<222> LOCATION: (10)..(10)
<223> OTHER INFORMATION: Xaa is Ile or Asn
<220> FEATURE:

```
<221> NAME/KEY: UNSURE
<222> LOCATION: (13)..(13)
<223> OTHER INFORMATION: Xaa can be any naturally occurring amino acid

<400> SEQUENCE: 108

Ser Xaa Lys Ala Gly Gly Xaa Gly Xaa Xaa Leu Thr Xaa Ala Asn His
1               5                   10                  15

Val

<210> SEQ ID NO 109
<211> LENGTH: 9
<212> TYPE: PRT
<213> ORGANISM: Artificial sequence
<220> FEATURE:
<223> OTHER INFORMATION: motif 5a of SWI2/SNF2 polypeptides

<400> SEQUENCE: 109

Asp Arg Trp Trp Asn Pro Ala Val Glu
1               5

<210> SEQ ID NO 110
<211> LENGTH: 11
<212> TYPE: PRT
<213> ORGANISM: Artificial sequence
<220> FEATURE:
<223> OTHER INFORMATION: motif 6 of SWI2/SNF2 polypeptides
<220> FEATURE:
<221> NAME/KEY: VARIANT
<222> LOCATION: (3)..(3)
<223> OTHER INFORMATION: Xaa is Ser or Thr
<220> FEATURE:
<221> NAME/KEY: VARIANT
<222> LOCATION: (6)..(6)
<223> OTHER INFORMATION: Xaa is Thr, Val or Ala
<220> FEATURE:
<221> NAME/KEY: VARIANT
<222> LOCATION: (7)..(7)
<223> OTHER INFORMATION: Xaa is Tyr or Phe
<220> FEATURE:
<221> NAME/KEY: VARIANT
<222> LOCATION: (9)..(9)
<223> OTHER INFORMATION: Xaa is Leu or Ile

<400> SEQUENCE: 110

Gln Ala Xaa Asp Arg Xaa Xaa Arg Xaa Gly Gln
1               5                   10

<210> SEQ ID NO 111
<211> LENGTH: 460
<212> TYPE: PRT
<213> ORGANISM: Artificial sequence
<220> FEATURE:
<223> OTHER INFORMATION: ATPase domain of SEQ ID NO: 2

<400> SEQUENCE: 111

Leu Ala Asp Asp Met Gly Leu Gly Lys Thr Pro Gln Leu Leu Ala Phe
1               5                   10                  15

Leu Leu His Leu Ala Ala Glu Asp Met Leu Val Lys Pro Val Leu Ile
                20                  25                  30

Val Cys Pro Thr Ser Val Leu Ser Asn Trp Gly His Glu Ile Asn Lys
            35                  40                  45

Phe Ala Pro Gln Leu Lys Thr Leu His His Gly Asp Arg Arg Lys
        50                  55                  60

Lys Gly Gln Pro Leu Val Lys Gln Val Lys Asp Gln Ile Val Leu
65                  70                  75                  80

Thr Ser Tyr Ala Leu Leu Gln Arg Asp Phe Ser Ser Leu Lys Leu Val
                85                  90                  95
```

Asp Trp Gln Gly Ile Val Leu Asp Glu Ala Gln Asn Ile Lys Asn Pro
            100                 105                 110

Gln Ala Lys Gln Ser Gln Ala Ala Arg Gln Leu Pro Ala Gly Phe Arg
        115                 120                 125

Ile Ala Leu Thr Gly Thr Pro Val Glu Asn Arg Leu Thr Glu Leu Trp
    130                 135                 140

Ser Ile Leu Glu Phe Leu Asn Pro Gly Phe Leu Gly Asn Gln Ser Phe
145                 150                 155                 160

Phe Gln Arg Arg Phe Ala Asn Pro Ile Glu Lys Phe Gly Asp Arg Gln
                165                 170                 175

Ser Leu Leu Ile Leu Arg Asn Leu Val Arg Pro Phe Ile Leu Arg Arg
            180                 185                 190

Leu Lys Thr Asp Gln Thr Ile Ile Gln Asp Leu Pro Glu Lys Gln Glu
        195                 200                 205

Met Thr Val Phe Cys Asp Leu Ser Gln Glu Gln Ala Gly Leu Tyr Gln
    210                 215                 220

Gln Leu Val Glu Glu Ser Leu Gln Ala Ile Ala Asp Ser Glu Gly Ile
225                 230                 235                 240

Gln Arg His Gly Leu Val Leu Thr Leu Leu Thr Lys Leu Lys Gln Val
                245                 250                 255

Cys Asn His Pro Asp Leu Leu Leu Lys Lys Pro Ala Ile Thr His Gly
            260                 265                 270

His Gln Ser Gly Lys Leu Ile Arg Leu Ala Glu Met Leu Glu Glu Ile
        275                 280                 285

Ile Ser Glu Gly Asp Arg Val Leu Ile Phe Thr Gln Phe Ala Ser Trp
    290                 295                 300

Gly His Leu Leu Lys Pro Tyr Leu Glu Lys Tyr Phe Asn Gln Glu Val
305                 310                 315                 320

Leu Tyr Leu His Gly Gly Thr Pro Ala Glu Gln Arg Gln Ala Leu Val
                325                 330                 335

Glu Arg Phe Gln Gln Asp Pro Asn Ser Pro Tyr Leu Phe Ile Leu Ser
            340                 345                 350

Leu Lys Ala Gly Gly Thr Gly Leu Asn Leu Thr Arg Ala Asn His Val
        355                 360                 365

Phe His Val Asp Arg Trp Trp Asn Pro Ala Val Glu Asn Gln Ala Thr
    370                 375                 380

Asp Arg Ala Phe Arg Ile Gly Gln Thr Arg Asn Val Gln Val His Lys
385                 390                 395                 400

Phe Val Cys Thr Gly Thr Leu Glu Glu Lys Ile Asn Ala Met Met Ala
                405                 410                 415

Asp Lys Gln Gln Leu Ala Glu Gln Thr Val Asp Ala Gly Glu Asn Trp
            420                 425                 430

Leu Thr Arg Leu Asp Thr Asp Lys Leu Arg Gln Leu Leu Thr Leu Ser
        435                 440                 445

Ala Thr Pro Val Asp Tyr Gln Ala Glu Ala Ser Asp
    450                 455                 460

<210> SEQ ID NO 112
<211> LENGTH: 1244
<212> TYPE: DNA
<213> ORGANISM: Oryza sativa

<400> SEQUENCE: 112
aaaaccaccg agggacctga tctgcaccgg ttttgatagt tgagggaccc gttgtgtctg    60

-continued

```
gttttccgat cgagggacga aaatcggatt cggtgtaaag ttaagggacc tcagatgaac    120
ttattccgga gcatgattgg gaagggagga cataaggccc atgtcgcatg tgtttggacg    180
gtccagatct ccagatcact cagcaggatc ggccgcgttc gcgtagcacc cgcggtttga    240
ttcggcttcc cgcaaggcgg cggccggtgg ccgtgccgcc gtagcttccg ccggaagcga    300
gcacgccgcc gccgccgacc cggctctgcg tttgcaccgc cttgcacgcg atacatcggg    360
atagatagct actactctct ccgtttcaca atgtaaatca ttctactatt ttccacattc    420
atattgatgt taatgaatat agacatatat atctatttag attcattaac atcaatatga    480
atgtaggaaa tgctagaatg acttacattg tgaattgtga aatggacgaa gtacctacga    540
tggatggatg caggatcatg aaagaattaa tgcaagatcg tatctgccgc atgcaaaatc    600
ttactaattg cgctgcatat atgcatgaca gcctgcatgc gggcgtgtaa gcgtgttcat    660
ccattaggaa gtaaccttgt cattacttat accagtacta catactatat agtattgatt    720
tcatgagcaa atctacaaaa ctggaaagca ataagaaata cgggactgga aaagactcaa    780
cattaatcac caaatatttc gccttctcca gcagaatata tatctctcca tcttgatcac    840
tgtacacact gacagtgtac gcataaacgc agcagccagc ttaactgtcg tctcaccgtc    900
gcacactggc cttccatctc aggctagctt tctcagccac ccatcgtaca tgtcaactcg    960
gcgcgcgcac aggcacaaat tacgtacaaa acgcatgacc aaatcaaaac caccggagaa   1020
gaatcgctcc cgcgcgcggc ggcgacgcgc acgtacgaac gcacgcacgc acgcccaacc   1080
ccacgacacg atcgcgcgcg acgccggcga caccggccgt ccacccgcgc cctcacctcg   1140
ccgactataa atacgtaggc atctgcttga tcttgtcatc catctcacca ccaaaaaaaa   1200
aaggaaaaaa aaacaaaaca caccaagcca aataaaagcg acaa                    1244
```

<210> SEQ ID NO 113
<211> LENGTH: 59
<212> TYPE: DNA
<213> ORGANISM: Artificial sequence
<220> FEATURE:
<223> OTHER INFORMATION: primer: prm08774

<400> SEQUENCE: 113

```
ggggacaagt ttgtacaaaa aagcaggctt aaacaatggc gactatccac ggtaattgg      59
```

<210> SEQ ID NO 114
<211> LENGTH: 49
<212> TYPE: DNA
<213> ORGANISM: Artificial sequence
<220> FEATURE:
<223> OTHER INFORMATION: primer: prm08779

<400> SEQUENCE: 114

```
ggggaccact ttgtacaaga aagctgggtt caatcggacg cttcggctt                 49
```

PLANTS HAVING ENHANCED YIELD-RELATED TRAITS AND A METHOD FOR MAKING THE SAME

RELATED APPLICATIONS

This application is a national stage application (under 35 U.S.C. §371) of PCT/EP2008/052450, filed Feb. 28, 2008, which claims benefit of European Application 07103271.8, filed Feb. 28, 2007, European Application 07104197.4 filed on Mar. 15, 2007, U.S. Provisional Application 60/896,050 filed on Mar. 21, 2007 and U.S. Provisional Application 60/909,510 filed on Apr. 2, 2007.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sequence_Listing__14546 __00051_US. The size of the text file is 509 KB, and the text file was created on Aug. 26, 2009.

The present invention relates generally to the field of molecular biology and concerns a method for enhancing various economically important yield-related traits in plants. More specifically, the present invention concerns a method for enhancing yield-related traits in plants by modulating expression in a plant of a nucleic acid encoding a Harpin-associated Factor G polypeptide (hereinafter termed "HpaG"). The present invention also concerns plants having modulated expression of a nucleic acid encoding an HpaG polypeptide, which plants have enhanced yield-related traits relative to control plants. The invention also provides constructs comprising HpaG-encoding nucleic acids, useful in performing the methods of the invention. The present invention also provides a method for enhancing yield-related traits in plants relative to control plants, by modulating (preferably increasing) expression in a plant of a nucleic acid sequence encoding a SWITCH 2/SUCROSE NON-FERMENTING 2 (SWI2/SNF2) polypeptide. The present invention also concerns plants having modulated expression of a nucleic acid sequence encoding a SWI2/SNF2 polypeptide, which plants have enhanced yield-related traits relative to control plants. The invention also provides constructs useful in performing the methods of the invention.

The ever-increasing world population and the dwindling supply of arable land available for agriculture fuels research towards increasing the efficiency of agriculture. Conventional means for crop and horticultural improvements utilise selective breeding techniques to identify plants having desirable characteristics. However, such selective breeding techniques have several drawbacks, namely that these techniques are typically labour intensive and result in plants that often contain heterogeneous genetic components that may not always result in the desirable trait being passed on from parent plants. Advances in molecular biology have allowed mankind to modify the germplasm of animals and plants. Genetic engineering of plants entails the isolation and manipulation of genetic material (typically in the form of DNA or RNA) and the subsequent introduction of that genetic material into a plant. Such technology has the capacity to deliver crops or plants having various improved economic, agronomic or horticultural traits.

A trait of particular economic interest is increased yield. Yield is normally defined as the measurable produce of economic value from a crop. This may be defined in terms of quantity and/or quality. Yield is directly dependent on several factors, for example, the number and size of the organs, plant architecture (for example, the number of branches), seed production, leaf senescence and more. Root development, nutrient uptake, stress tolerance and early vigour may also be important factors in determining yield. Optimizing the above-mentioned factors may therefore contribute to increasing crop yield.

Seed yield is a particularly important trait, since the seeds of many plants are important for human and animal nutrition. Crops such as, corn, rice, wheat, canola and soybean account for over half the total human caloric intake, whether through direct consumption of the seeds themselves or through consumption of meat products raised on processed seeds. They are also a source of sugars, oils and many kinds of metabolites used in industrial processes. Seeds contain an embryo (the source of new shoots and roots) and an endosperm (the source of nutrients for embryo growth during germination and during early growth of seedlings). The development of a seed involves many genes, and requires the transfer of metabolites from the roots, leaves and stems into the growing seed. The endosperm, in particular, assimilates the metabolic precursors of carbohydrates, oils and proteins and synthesizes them into storage macromolecules to fill out the grain.

Harvest index, the ratio of seed yield to aboveground dry weight, is relatively stable under many environmental conditions and so a robust correlation between plant size and grain yield can often be obtained (e.g. Rebetzke et al. (2002) Crop Science 42:739). These processes are intrinsically linked because the majority of grain biomass is dependent on current or stored photosynthetic productivity by the leaves and stem of the plant (Gardener et al. (1985) Physiology of Crop Plants. Iowa State University Press, pp 68-73). Therefore, selecting for plant size, even at early stages of development, has been used as an indicator for future potential yield (e.g. Tittonell et al. (2005) Agric Ecosys & Environ 105: 213). When testing for the impact of genetic differences on stress tolerance, the ability to standardize soil properties, temperature, water and nutrient availability and light intensity is an intrinsic advantage of greenhouse or plant growth chamber environments compared to the field. However, artificial limitations on yield due to poor pollination due to the absence of wind or insects, or insufficient space for mature root or canopy growth, can restrict the use of these controlled environments for testing yield differences. Therefore, measurements of plant size in early development, under standardized conditions in a growth chamber or greenhouse, are standard practices to provide indication of potential genetic yield advantages.

Another trait of particular economic interest is that of enhanced yield-related traits of plants grown under abiotic stress conditions. Abiotic stress is a primary cause of crop loss worldwide, reducing average yields for most major crop plants by more than 50% (Wang et al., Planta (2003) 218: 1-14). Abiotic stresses may be caused by drought, salinity, temperature extremes, chemical toxicity and oxidative stress. The ability to enhance yield-related traits in plants grown under abiotic stress conditions would be of great economic advantage to farmers worldwide and would allow for the cultivation of crops during adverse conditions and in territories where cultivation of crops may not otherwise be possible.

The ability to increase plant yield would have many applications in areas such as agriculture, including in the production of ornamental plants, arboriculture, horticulture and forestry. Increasing yield may also find use in the production of algae for use in bioreactors (for the biotechnological production of substances such as pharmaceuticals, antibodies or vaccines, or for the bioconversion of organic waste) and other such areas.

BACKGROUND

I. Harpin

The Type III Secretion System (TTSS) is an exporting machinery specific for Gram-negative bacteria and is found among plant and animal pathogens, but also in endosymbiotic *Rhizobia*. TTSS is postulated to deliver proteins into the host cell to which the bacterium is associated. In plant pathogenic bacteria, the TTSS is a cluster of hypersensitive response and pathogenicity genes comprising about 20 genes, the Hrp cluster. Nine of these genes (the harpin conserved or hrc) are conserved among both plant and animal pathogens, eight of them share homology with genes encoding the flagella apparatus (Bogdanove et al., Mol. Microbiol. 20, 681-683, 1996), the ninth, hrcC, is homologous to the GSP outer membrane secretins (Deng and Huang, J. Bacteriol. 180, 4523-4531, 1999). The hpa (hrp-associated) genes contribute to pathogenicity and to the induction of the hypersensitive response (HR) in nonhost plants, but are not essential for the pathogenic interactions of bacteria with plants. The flagella apparatus and the TTSS are postulated to be evolved from a common origin (Gophna et al., Gene 312, 151-163, 2003); the TTSS has furthermore spread among evolutionary distant bacterial species via multiple horizontal-transfer events (Nguyen et al., J. Mol. Microbiol. Biotechnol. 2, 125-144, 2000).

Many gram-negative plant-pathogenic bacteria possess two sets of genes that modulate their interactions with plants. The avirulence genes determine host specificity based on gene—for gene interactions, and the hrp (hypersensitive reaction and pathogenicity) genes are involved in pathogenicity and the induction of hypersensitive responses (HR) in non-host plants. The HR is a highly localized plant cell death that occurs when non-host plants or resistant cultivars of host plants are infiltrated with the plant pathogen or HR elicitor molecules, such as Avr proteins and harpins. The HR is thought be a resistance reaction of plants to microbial pathogens.

Harpins are a group of HR elicitors that are secreted by the type III secretion pathway (TTSS) and elicit HR when infiltrated into the apoplast of leaves of non-host plants. Unlike Avr proteins, which must be delivered inside the cell to exert their functions, harpins can elicit HR when delivered to the intercellular space of plant cells. Since the first harpin, HrpN, was identified from *Erwinia amylovora*, many harpins have been reported from various species, including *Pseudomonas, Ralstonia*, and *Xanthomonas*. Harpins are glycine-rich, heat stable proteins, lacking cysteine, and are postulated to be present in all plant pathogenic bacteria having a TTSS (Alfano and Colmer, Annu. Rev. Phytopathol. 42, 385-414, 2004). The biochemical mechanism of HR elicitation by harpins in non-host plants remains unclear. HrpZ of *Pseudomonas syringae* pv. syringae associates with the cell walls rather than the membranes of plant cells, and the protein elicits no response from protoplasts, which lack walls (Hoyos et al. Mol. Plant-Microbe Interact. 9, 608-616, 1996). However, HrpZ of *P. syringae* pv. phaseolicola binds to lipid bilayers and forms an ion-conducting pore (Lee et al., Proc. Natl. Acad. Sci. USA 98, 289-294, 2001). The N-terminal 109 amino acids and the C-terminal 216 amino acids of HrpZ are able to elicit HR to a level similar to full-length HrpZ (Alfano et al., Mol. Microbiol. 19, 715-728, 1996). Kim et al. and Charkowski et al. showed that the HrpW harpins of *E. amylovora* and *P. syringae* pv. tomato are composed of two domains—the N-terminal harpin domain and C-terminal Pel (pectate lyase) domain—and proposed that HrpW acts in the cell wall (Charkowski et al., J. Bacteriol. 180, 5211-5217, 1998; Kim and Beer, J. Bacteriol. 180, 5203-5210, 1998).

Besides harpins, the TTSS cluster in bacteria may also include genes encoding Harpin associated Factors. HpaG polypeptides are smaller than harpins, and they share little sequence homology. These sequence differences with harpins are postulated to contribute to the difference in the ability to elicit HR in plants between HpaG polypeptides and harpins (Kim et al., J. Bacteriol. 186, 6239-6247, 2004)

Korean patent application KR20030068302 discloses the *Xanthomonas* HpaG protein, which, when applied to plants or plant seeds, confers disease resistance, in particular resistance to *Xanthomonas axonopodis* infection. Harpin associated Factors have been used to confer disease resistance in plants; and as a result of this biotic stress resistance, plants had better yield compared to the control plants under biotic stress conditions.

Surprisingly it has now been found that modulating expression in a plant of a nucleic acid encoding a Harpin-associated Factor G polypeptide (HpaG) give plants enhanced yield-related traits relative to control plant. These enhanced yield-related traits were obtained in plants that were not exposed to stress.

II. SNF2

The present invention concerns a method for enhancing yield-related traits in plants relative to control plants by increasing expression in a plant of a nucleic acid sequence encoding a SWITCH 2/SUCROSE NON-FERMENTING 2 (SWI2/SNF2) polypeptide.

Many chromosome-associated cellular processes, such as replication, transcription, DNA repair, or recombination, require accessible DNA. To deal with these events, cells possess activities that can remodel chromatin in eukaryotes or disrupt other DNA:protein complexes in both pro- and eukaryotes, using ATP hydrolysis. One of the best-studied examples of these activities is carried out by the SWI2/SNF2 family of ATPases, a large group of proteins implicated in many different remodeling-like processes.

SWI2/SNF2 family proteins are ubiquitous, as they are found in bacteria, archaea and eukaryotes. They have recently been classified into 24 distinct subfamilies, after multiple sequence alignment of the SWI2/SNF2 ATPase domain comprising the seven conserved sequence motifs (I, Ia, II, III, IV, V, and VI) (Flaus et al. (2006) Nucleic Acids Res. 2006; 34(10): 2887-2905). These subfamilies have traditionally taken the name of the archetypal member. One subfamily is named SSO1653, after the sole SWI2/SNF2 family member in archaeal *Sulfolobus solfataricus* (Flaus et al., supra; Duur et al. (2005) Cell 121(3): 363-373), the uniquely archaeal and eubacterial subfamily most similar to the eukaryotic SWI2/SNF2 proteins. The SSO1653 subfamily carries all the SWI2/SNF2 family sequence and structural hallmarks.

US patent application US2003/233670 describes polynucleotides and proteins encoded by the polynucleotides. SEQ ID NO: 125 is a polynucleotide sequence encoding a SWI2/SNF2 polypeptide of the SSO1653 subfamily from *Synechocystis* sp. PCC 6803. US patent application US2005/108791 describes 24149 nucleic acid and polypeptide sequences, among which a nucleic acid sequence represented by SEQ ID NO: 57 encoding a SWI2/SNF2 polypeptide of the SSO1653 subfamily from *Synechocystis* sp. PCC 6803, as represented by SEQ ID NO: 396.

Surprisingly, it has now been found that increasing expression in a plant of a nucleic acid sequence encoding a SWI2/

SNF2 polypeptide gives plants having enhanced yield-related traits relative to control plants.

DEFINITIONS

Polypeptide(s)/Protein(s)

The terms "polypeptide" and "protein" are used interchangeably herein and refer to amino acids in a polymeric form of any length.

Polynucleotide(s)/Nucleic acid(s)/Nucleic acid sequence(s)/nucleotide sequence(s)

The terms "polynucleotide(s)", "nucleic acid sequence(s)", "nucleotide sequence(s)" are used interchangeably herein and refer to nucleotides, either ribonucleotides or deoxyribonucleotides or a combination of both, in a polymeric form of any length.

Control Plant(s)

The choice of suitable control plants is a routine part of an experimental setup and may include corresponding wild type plants or corresponding plants without the gene of interest. The control plant is typically of the same plant species or even of the same variety as the plant to be assessed. The control plant may also be a nullizygote of the plant to be assessed. A "control plant" as used herein refers not only to whole plants, but also to plant parts, including seeds and seed parts.

Homologue(s)

"Homologues" of a protein encompass peptides, oligopeptides, polypeptides, proteins and enzymes having amino acid substitutions, deletions and/or insertions relative to the unmodified protein in question and having similar biological and functional activity as the unmodified protein from which they are derived.

A deletion refers to removal of one or more amino acids from a protein.

An insertion refers to one or more amino acid residues being introduced into a predetermined site in a protein. Insertions may comprise N-terminal and/or C-terminal fusions as well as intra-sequence insertions of single or multiple amino acids. Generally, insertions within the amino acid sequence will be smaller than N- or C-terminal fusions, of the order of about 1 to 10 residues. Examples of N- or C-terminal fusion proteins or peptides include the binding domain or activation domain of a transcriptional activator as used in the yeast two-hybrid system, phage coat proteins, (histidine)-6-tag, glutathione S-transferase-tag, protein A, maltose-binding protein, dihydrofolate reductase, Tag•100 epitope, c-myc epitope, FLAG®-epitope, lacZ, CMP (calmodulin-binding peptide), HA epitope, protein C epitope and VSV epitope.

A substitution refers to replacement of amino acids of the protein with other amino acids having similar properties (such as similar hydrophobicity, hydrophilicity, antigenicity, propensity to form or break α-helical structures or β-sheet structures). Amino acid substitutions are typically of single residues, but may be clustered depending upon functional constraints placed upon the polypeptide; insertions will usually be of the order of about 1 to 10 amino acid residues. The amino acid substitutions are preferably conservative amino acid substitutions. Conservative substitution tables are well known in the art (see for example Creighton (1984) Proteins. W. H. Freeman and Company and Table 1 below).

TABLE 1

Examples of conserved amino acid substitutions

| Residue | Conservative Substitutions |
|---|---|
| Ala | Ser |
| Arg | Lys |
| Asn | Gln; His |
| Asp | Glu |
| Gln | Asn |
| Cys | Ser |
| Glu | Asp |
| Gly | Pro |
| His | Asn; Gln |
| Ile | Leu, Val |
| Leu | Ile; Val |
| Lys | Arg; Gln |
| Met | Leu; Ile |
| Phe | Met; Leu; Tyr |
| Ser | Thr; Gly |
| Thr | Ser; Val |
| Trp | Tyr |
| Tyr | Trp; Phe |
| Val | Ile; Leu |

Amino acid substitutions, deletions and/or insertions may readily be made using peptide synthetic techniques well known in the art, such as solid phase peptide synthesis and the like, or by recombinant DNA manipulation. Methods for the manipulation of DNA sequences to produce substitution, insertion or deletion variants of a protein are well known in the art. For example, techniques for making substitution mutations at predetermined sites in DNA are well known to those skilled in the art and include M13 mutagenesis, T7-Gen in vitro mutagenesis (USB, Cleveland, Ohio), QuickChange Site Directed mutagenesis (Stratagene, San Diego, Calif.), PCR-mediated site-directed mutagenesis or other site-directed mutagenesis protocols.

Derivatives

"Derivatives" include peptides, oligopeptides, polypeptides which may, compared to the amino acid sequence of the naturally-occurring form of the protein, such as the one presented in SEQ ID NO: 2, comprise substitutions of amino acids with non-naturally occurring amino acid residues, or additions of non-naturally occurring amino acid residues. "Derivatives" of a protein also encompass peptides, oligopeptides, polypeptides which comprise naturally occurring altered (glycosylated, acylated, prenylated, phosphorylated, myristoylated, sulphated etc.) or non-naturally altered amino acid residues compared to the amino acid sequence of a naturally-occurring form of the polypeptide. A derivative may also comprise one or more non-amino acid substituents or additions compared to the amino acid sequence from which it is derived, for example a reporter molecule or other ligand, covalently or non-covalently bound to the amino acid sequence, such as a reporter molecule which is bound to facilitate its detection, and non-naturally occurring amino acid residues relative to the amino acid sequence of a naturally-occurring protein.

Orthologue(s)/Paralogue(s)

Orthologues and paralogues encompass evolutionary concepts used to describe the ancestral relationships of genes. Paralogues are genes within the same species that have originated through duplication of an ancestral gene and orthologues are genes from different organisms that have originated through speciation.

Domain

The term "domain" refers to a set of amino acids conserved at specific positions along an alignment of sequences of evolutionarily related proteins. While amino acids at other positions can vary between homologues, amino acids that are highly conserved at specific positions indicate amino acids that are likely essential in the structure, stability or activity of a protein. Identified by their high degree of conservation in aligned sequences of a family of protein homologues, they can be used as identifiers to determine if any polypeptide in question belongs to a previously identified polypeptide family.

Motif/Consensus Sequence/Signature

The term "motif" or "consensus sequence" or "signature" refers to a short conserved region in the sequence of evolutionarily related proteins. Motifs are frequently highly conserved parts of domains, but may also include only part of the domain, or be located outside of conserved domain (if all of the amino acids of the motif fall outside of a defined domain).

Hybridisation

The term "hybridisation" as defined herein is a process wherein substantially homologous complementary nucleotide sequences anneal to each other. The hybridisation process can occur entirely in solution, i.e. both complementary nucleic acids are in solution. The hybridisation process can also occur with one of the complementary nucleic acids immobilised to a matrix such as magnetic beads, Sepharose beads or any other resin. The hybridisation process can furthermore occur with one of the complementary nucleic acids immobilised to a solid support such as a nitro-cellulose or nylon membrane or immobilised by e.g. photolithography to, for example, a siliceous glass support (the latter known as nucleic acid arrays or microarrays or as nucleic acid chips). In order to allow hybridisation to occur, the nucleic acid molecules are generally thermally or chemically denatured to melt a double strand into two single strands and/or to remove hairpins or other secondary structures from single stranded nucleic acids.

The term "stringency" refers to the conditions under which a hybridisation takes place. The stringency of hybridisation is influenced by conditions such as temperature, salt concentration, ionic strength and hybridisation buffer composition. Generally, low stringency conditions are selected to be about 30° C. lower than the thermal melting point (Tm) for the specific sequence at a defined ionic strength and pH. Medium stringency conditions are when the temperature is 20° C. below Tm, and high stringency conditions are when the temperature is 10° C. below Tm. High stringency hybridisation conditions are typically used for isolating hybridising sequences that have high sequence similarity to the target nucleic acid sequence. However, nucleic acids may deviate in sequence and still encode a substantially identical polypeptide, due to the degeneracy of the genetic code. Therefore medium stringency hybridisation conditions may sometimes be needed to identify such nucleic acid molecules.

The Tm is the temperature under defined ionic strength and pH, at which 50% of the target sequence hybridises to a perfectly matched probe. The Tm is dependent upon the solution conditions and the base composition and length of the probe. For example, longer sequences hybridise specifically at higher temperatures. The maximum rate of hybridisation is obtained from about 16° C. up to 32° C. below Tm. The presence of monovalent cations in the hybridisation solution reduce the electrostatic repulsion between the two nucleic acid strands thereby promoting hybrid formation; this effect is visible for sodium concentrations of up to 0.4M (for higher concentrations, this effect may be ignored). Formamide reduces the melting temperature of DNA-DNA and DNA-RNA duplexes with 0.6 to 0.7° C. for each percent formamide, and addition of 50% formamide allows hybridisation to be performed at 30 to 45° C., though the rate of hybridisation will be lowered. Base pair mismatches reduce the hybridisation rate and the thermal stability of the duplexes. On average and for large probes, the Tm decreases about 1° C. per % base mismatch. The Tm may be calculated using the following equations, depending on the types of hybrids:

1) DNA-DNA hybrids (Meinkoth and Wahl, Anal. Biochem., 138: 267-284, 1984):
Tm=81.5° C.+16.6×log 10[Na$^+$]$^a$+0.41×%[G/C$^b$]−500×[L$^c$]−1−0.61×% formamide 2) DNA-RNA or RNA-RNA hybrids:
Tm=79.8+18.5(log$_{10}$ [Na$^+$]$^a$)+0.58(% G/C$^b$)+11.8(% G/C$^b$) 2−820/L$^c$ 3) oligo-DNA or oligo-RNA$^d$ hybrids:
For <20 nucleotides: Tm=2 (ln)
For 20-35 nucleotides: Tm=22+1.46 (ln)

$^a$ or for other monovalent cation, but only accurate in the 0.01-0.4 M range.
$^b$ only accurate for % GC in the 30% to 75% range.
$^c$ L=length of duplex in base pairs.
$^d$ Oligo, oligonucleotide; ln, effective length of primer=2×(no. of G/C)+(no. of A/T).

Non-specific binding may be controlled using any one of a number of known techniques such as, for example, blocking the membrane with protein containing solutions, additions of heterologous RNA, DNA, and SDS to the hybridisation buffer, and treatment with Rnase. For non-homologous probes, a series of hybridizations may be performed by varying one of (i) progressively lowering the annealing temperature (for example from 68° C. to 42° C.) or (ii) progressively lowering the formamide concentration (for example from 50% to 0%). The skilled artisan is aware of various parameters which may be altered during hybridisation and which will either maintain or change the stringency conditions.

Besides the hybridisation conditions, specificity of hybridisation typically also depends on the function of post-hybridisation washes. To remove background resulting from non-specific hybridisation, samples are washed with dilute salt solutions. Critical factors of such washes include the ionic strength and temperature of the final wash solution: the lower the salt concentration and the higher the wash temperature, the higher the stringency of the wash. Wash conditions are typically performed at or below hybridisation stringency. A positive hybridisation gives a signal that is at least twice of that of the background. Generally, suitable stringent conditions for nucleic acid hybridisation assays or gene amplification detection procedures are as set forth above. More or less stringent conditions may also be selected. The skilled artisan is aware of various parameters which may be altered during washing and which will either maintain or change the stringency conditions.

For example, typical high stringency hybridisation conditions for DNA hybrids longer than 50 nucleotides encompass hybridisation at 65° C. in 1×SSC or at 42° C. in 1×SSC and 50% formamide, followed by washing at 65° C. in 0.3×SSC. Examples of medium stringency hybridisation conditions for DNA hybrids longer than 50 nucleotides encompass hybridisation at 50° C. in 4×SSC or at 40° C. in 6×SSC and 50% formamide, followed by washing at 50° C. in 2×SSC. The length of the hybrid is the anticipated length for the hybridising nucleic acid. When nucleic acids of known sequence are hybridised, the hybrid length may be determined by aligning the sequences and identifying the conserved regions described herein. 1×SSC is 0.15M NaCl and 15 mM sodium citrate; the hybridisation solution and wash solutions may additionally include 5×Denhardt's reagent, 0.5-1.0% SDS, 100 μg/ml denatured, fragmented salmon sperm DNA, 0.5% sodium pyrophosphate.

For the purposes of defining the level of stringency, reference can be made to Sambrook et al. (2001) Molecular Cloning: a laboratory manual, 3rd Edition Cold Spring Harbor Laboratory Press, CSH, New York or to Current Protocols in Molecular Biology, John Wiley & Sons, N.Y. (1989 and yearly updates).

Gene Shuffling/Directed Evolution

Gene shuffling or directed evolution consists of iterations of DNA shuffling followed by appropriate screening and/or selection to generate variants of nucleic acids or portions thereof encoding proteins having a modified biological activity (Castle et al., (2004) Science 304(5674): 1151-4; U.S. Pat. Nos. 5,811,238 and 6,395,547).

Regulatory Element/Control Sequence/Promoter

The terms "regulatory element", "control sequence" and "promoter" are all used interchangeably herein and are to be taken in a broad context to refer to regulatory nucleic acid sequences capable of effecting expression of the sequences to which they are ligated. The term "promoter" typically refers to a nucleic acid control sequence located upstream from the transcriptional start of a gene and which is involved in recognising and binding of RNA polymerase and other proteins, thereby directing transcription of an operably linked nucleic acid. Encompassed by the aforementioned terms are transcriptional regulatory sequences derived from a classical eukaryotic genomic gene (including the TATA box which is required for accurate transcription initiation, with or without a CCAAT box sequence) and additional regulatory elements (i.e. upstream activating sequences, enhancers and silencers) which alter gene expression in response to developmental and/or external stimuli, or in a tissue-specific manner. Also included within the term is a transcriptional regulatory sequence of a classical prokaryotic gene, in which case it may include a −35 box sequence and/or −10 box transcriptional regulatory sequences. The term "regulatory element" also encompasses a synthetic fusion molecule or derivative that confers, activates or enhances expression of a nucleic acid molecule in a cell, tissue or organ.

A "plant promoter" comprises regulatory elements, which mediate the expression of a coding sequence segment in plant cells. Accordingly, a plant promoter need not be of plant origin, but may originate from viruses or micro-organisms, for example from viruses which attack plant cells. The "plant promoter" can also originate from a plant cell, e.g. from the plant which is transformed with the nucleic acid sequence to be expressed in the inventive process and described herein. This also applies to other "plant" regulatory signals, such as "plant" terminators. The promoters upstream of the nucleotide sequences useful in the methods of the present invention can be modified by one or more nucleotide substitution(s), insertion(s) and/or deletion(s) without interfering with the functionality or activity of either the promoters, the open reading frame (ORF) or the 3'-regulatory region such as terminators or other 3' regulatory regions which are located away from the ORF. It is furthermore possible that the activity of the promoters is increased by modification of their sequence, or that they are replaced completely by more active promoters, even promoters from heterologous organisms. For expression in plants, the nucleic acid molecule must, as described above, be linked operably to or comprise a suitable promoter which expresses the gene at the right point in time and with the required spatial expression pattern.

Operably Linked

The term "operably linked" as used herein refers to a functional linkage between the promoter sequence and the gene of interest, such that the promoter sequence is able to initiate transcription of the gene of interest.

Constitutive Promoter

A "constitutive promoter" refers to a promoter that is transcriptionally active during most, but not necessarily all, phases of growth and development and under most environmental conditions, in at least one cell, tissue or organ. Table 2a below gives examples of constitutive promoters.

TABLE 2a

Examples of constitutive promoters

| Gene Source | Reference |
|---|---|
| Actin | McElroy et al, Plant Cell, 2: 163-171, 1990 |
| HMGP | WO 2004/070039 |
| CAMV 35S | Odell et al, Nature, 313: 810-812, 1985 |
| CaMV 19S | Nilsson et al., Physiol. Plant. 100: 456-462, 1997 |
| GOS2 | de Pater et al, Plant J Nov; 2(6): 837-44, 1992, WO 2004/065596 |
| Ubiquitin | Christensen et al, Plant Mol. Biol. 18: 675-689, 1992 |
| Rice cyclophilin | Buchholz et al, Plant Mol Biol. 25(5): 837-43, 1994 |
| Maize H3 histone | Lepetit et al, Mol. Gen. Genet. 231: 276-285, 1992 |
| Alfalfa H3 histone | Wu et al. Plant Mol. Biol. 11: 641-649, 1988 |
| Actin 2 | An et al, Plant J. 10(1); 107-121, 1996 |
| 34S FMV | Sanger et al., Plant. Mol. Biol., 14, 1990: 433-443 |
| Rubisco small subunit | U.S. Pat. No. 4,962,028 |
| OCS | Leisner (1988) Proc Natl Acad Sci USA 85(5): 2553 |
| SAD1 | Jain et al., Crop Science, 39 (6), 1999: 1696 |
| SAD2 | Jain et al., Crop Science, 39 (6), 1999: 1696 |
| Nos | Shaw et al. (1984) Nucleic Acids Res. 12(20): 7831-7846 |
| V-ATPase | WO 01/14572 |
| Super promoter | WO 95/14098 |
| G-box proteins | WO 94/12015 |

Ubiquitous Promoter

A ubiquitous promoter is active in substantially all tissues or cells of an organism.

Developmentally-Regulated Promoter

A developmentally-regulated promoter is active during certain developmental stages or in parts of the plant that undergo developmental changes.

Inducible Promoter

An inducible promoter has induced or increased transcription initiation in response to a chemical (for a review see Gatz 1997, Annu. Rev. Plant Physiol. Plant Mol. Biol., 48:89-108), environmental or physical stimulus, or may be "stress-inducible", i.e. activated when a plant is exposed to various stress conditions, or a "pathogen-inducible" i.e. activated when a plant is exposed to exposure to various pathogens.

Organ-Specific/Tissue-Specific Promoter

An organ-specific or tissue-specific promoter is one that is capable of preferentially initiating transcription in certain organs or tissues, such as the leaves, roots, seed tissue etc. For example, a "root-specific promoter" is a promoter that is transcriptionally active predominantly in plant roots, substantially to the exclusion of any other parts of a plant, whilst still allowing for any leaky expression in these other plant parts. Promoters able to initiate transcription in certain cells only are referred to herein as "cell-specific".

Examples of root-specific promoters are listed in Table 2b below:

TABLE 2b

Examples of root-specific promoters

| Gene Source | Reference |
|---|---|
| RCc3 | Plant Mol Biol. 1995 January; 27(2): 237-48 |
| Arabidopsis PHT1 | Kovama et al., 2005; Mudge et al. (2002, Plant J. 31: 341) |
| Medicago phosphate transporter | Xiao et al., 2006 |
| Arabidopsis Pyk10 | Nitz et al. (2001) Plant Sci 161(2): 337-346 |
| root-expressible genes | Tingey et al., EMBO J. 6: 1, 1987. |
| tobacco auxin-inducible gene | Van der Zaal et al., Plant Mol. Biol. 16, 983, 1991. |
| β-tubulin | Oppenheimer, et al., Gene 63: 87, 1988. |
| tobacco root-specific genes | Conkling, et al., Plant Physiol. 93: 1203, 1990. |
| B. napus G1-3b gene | U.S. Pat. No. 5,401,836 |
| SbPRP1 | Suzuki et al., Plant Mol. Biol. 21: 109-119, 1993. |
| LRX1 | Baumberger et al. 2001, Genes & Dev. 15: 1128 |
| BTG-26 Brassica napus | US 20050044585 |
| LeAMT1 (tomato) | Lauter et al. (1996, PNAS 3: 8139) |
| The LeNRT1-1 (tomato) | Lauter et al. (1996, PNAS 3: 8139) |
| class I patatin gene (potato) | Liu et al., Plant Mol. Biol. 153: 386-395, 1991. |
| KDC1 (Daucus carota) | Downey et al. (2000, J. Biol. Chem. 275: 39420) |
| TobRB7 gene | W Song (1997) PhD Thesis, North Carolina State University, Raleigh, NC USA |
| OsRAB5a (rice) | Wang et al. 2002, Plant Sci. 163: 273 |
| ALF5 (Arabidopsis) | Diener et al. (2001, Plant Cell 13: 1625) |
| NRT2;1Np (N. plumbaginifolia) | Quesada et al. (1997, Plant Mol. Biol. 34: 265) |

A seed-specific promoter is transcriptionally active predominantly in seed tissue, but not necessarily exclusively in seed tissue (in cases of leaky expression). The seed-specific promoter may be active during seed development and/or during germination. The seed specific promoter may be endosperm and/or aleurone and/or embryo specific. Examples of seed-specific promoters (endosperm/aleurone/embryo specific) are shown in Table 2c, d, e, f below. Further examples of seed-specific promoters are given in Qing Qu and Takaiwa (Plant Biotechnol. J. 2, 113-125, 2004), which disclosure is incorporated by reference herein as if fully set forth.

TABLE 2c

Examples of seed-specific promoters

| Gene source | Reference |
|---|---|
| seed-specific genes | Simon et al., Plant Mol. Biol. 5: 191, 1985; Scofield et al., J. Biol. Chem. 262: 12202, 1987.; Baszczynski et al., Plant Mol. Biol. 14: 633, 1990. |
| Brazil Nut albumin | Pearson et al., Plant Mol. Biol. 18: 235-245, 1992. |
| Legumin | Ellis et al., Plant Mol. Biol. 10: 203-214, 1988. |
| glutelin (rice) | Takaiwa et al., Mol. Gen. Genet. 208: 15-32 1986; Takaiwa et al., FEBS Letts. 221: 43-47, 1987. |
| Zein | Matzke et al Plant Mol Biol, 14(3): 323-32 1990 |
| napA | Stalberg et al, Planta 199: 515-519, 1996. |
| wheat LMW and HMW glutenin-1 | Mol Gen Genet 216: 81-90, 1989; NAR 17: 461-2, 1989 |
| wheat SPA | Albani et al, Plant Cell, 9: 171-184, 1997 |
| wheat α, β, γ-gliadins | EMBO J. 3: 1409-15, 1984 |
| barley Itr1 promoter | Diaz et al. (1995) Mol Gen Genet 248(5): 592-8 |
| barley B1, C, D, hordein | Theor Appl Gen 98: 1253-62, 1999; Plant J 4: 343-55, 1993; Mol Gen Genet 250: 750-60, 1996 |
| barley DOF | Mena et al, The Plant Journal, 116(1): 53-62, 1998 |
| blz2 | EP99106056.7 |
| synthetic promoter | Vicente-Carbajosa et al., Plant J. 13: 629-640, 1998. |
| rice prolamin NRP33 | Wu et al, Plant Cell Physiology 39(8) 885-889, 1998 |
| rice a-globulin Glb-1 | Wu et al, Plant Cell Physiology 39(8) 885-889, 1998 |
| rice OSH1 | Sato et al, Proc. Natl. Acad. Sci. USA, 93: 8117-8122, 1996 |
| rice α-globulin REB/OHP-1 | Nakase et al. Plant Mol. Biol. 33: 513-522, 1997 |
| rice ADP-glucose pyrophosphorylase | Trans Res 6: 157-68, 1997 |
| maize ESR gene family | Plant J 12: 235-46, 1997 |
| sorghum α-kafirin | DeRose et al., Plant Mol. Biol 32: 1029-35, 1996 |
| KNOX | Postma-Haarsma et al, Plant Mol. Biol. 39: 257-71, 1999 |
| rice oleosin | Wu et al, J. Biochem. 123: 386, 1998 |
| sunflower oleosin | Cummins et al., Plant Mol. Biol. 19: 873-876, 1992 |

TABLE 2c-continued

Examples of seed-specific promoters

| Gene source | Reference |
| --- | --- |
| PRO0117, putative rice 40S ribosomal protein | WO 2004/070039 |
| PRO0136, rice alanine aminotransferase | unpublished |
| PRO0147, trypsin inhibitor ITR1 (barley) | unpublished |
| PRO0151, rice WSI18 | WO 2004/070039 |
| PRO0175, rice RAB21 | WO 2004/070039 |
| PRO005 | WO 2004/070039 |
| PRO0095 | WO 2004/070039 |
| α-amylase (Amy32b) | Lanahan et al, Plant Cell 4: 203-211, 1992; Skriver et al, Proc Natl Acad Sci USA 88: 7266-7270, 1991 |
| cathepsin β-like gene | Cejudo et al, Plant Mol Biol 20: 849-856, 1992 |
| Barley Ltp2 | Kalla et al., Plant J. 6: 849-60, 1994 |
| Chi26 | Leah et al., Plant J. 4: 579-89, 1994 |
| Maize B-Peru | Selinger et al., Genetics 149; 1125-38,1998 |

TABLE 2d examples of endosperm-specific promoters

| Gene source | Reference |
| --- | --- |
| glutelin (rice) | Takaiwa et al. (1986) Mol Gen Genet 208: 15-22; Takaiwa et al. (1987) FEBS Letts. 221: 43-47 |
| Zein | Matzke et al., (1990) Plant Mol Biol 14(3): 323-32 |
| wheat LMW and HMW glutenin-1 | Colot et al. (1989) Mol Gen Genet 216: 81-90, Anderson et al. (1989) NAR 17: 461-2 |
| wheat SPA | Albani et al. (1997) Plant Cell 9: 171-184 |
| wheat gliadins | Rafalski et al. (1984) EMBO 3: 1409-15 |
| barley Itr1 promoter | Diaz et al. (1995) Mol Gen Genet 248(5): 592-8 |
| barley B1, C, D, hordein | Cho et al. (1999) Theor Appl Genet 98: 1253-62; Muller et al. (1993) Plant J 4: 343-55; Sorenson et al. (1996) Mol Gen Genet 250: 750-60 |
| barley DOF | Mena et al, (1998) Plant J 116(1): 53-62 |
| blz2 | Onate et al. (1999) J Biol Chem 274(14): 9175-82 |
| Synthetic promoter | Vicente-Carbajosa et al. (1998) Plant J 13: 629-640 |
| rice prolamin NRP33 | Wu et al, (1998) Plant Cell Physiol 39(8) 885-889 |
| rice globulin Glb-1 | Wu et al. (1998) Plant Cell Physiol 39(8) 885-889 |
| rice globulin REB/OHP-1 | Nakase et al. (1997) Plant Molec Biol 33: 513-522 |
| rice ADP-glucose pyrophosphorylase | Russell et al. (1997) Trans Res 6: 157-68 |
| maize ESR gene family | Opsahl-Ferstad et al. (1997) Plant J 12: 235-46 |
| *Sorghum* kafirin | DeRose et al. (1996) Plant Mol Biol 32: 1029-35 |

TABLE 2e

Examples of embryo specific promoters:

| Gene source | Reference |
| --- | --- |
| rice OSH1 | Sato et al, Proc. Natl. Acad. Sci. USA, 93: 8117-8122, 1996 |
| KNOX | Postma-Haarsma et al, Plant Mol. Biol. 39: 257-71, 1999 |
| PRO0151 | WO 2004/070039 |
| PRO0175 | WO 2004/070039 |
| PRO005 | WO 2004/070039 |
| PRO0095 | WO 2004/070039 |

TABLE 2f

Examples of aleurone-specific promoters:

| Gene source | Reference |
| --- | --- |
| α-amylase (Amy32b) | Lanahan et al, Plant Cell 4: 203-211, 1992; Skriver et al, Proc Natl Acad Sci USA 88: 7266-7270, 1991 |
| Cathepsin β-like gene | Cejudo et al, Plant Mol Biol 20: 849-856, 1992 |
| Barley Ltp2 | Kalla et al., Plant J. 6: 849-60, 1994 |

TABLE 2f-continued

Examples of aleurone-specific promoters:

| Gene source | Reference |
| --- | --- |
| Chi26 | Leah et al., Plant J. 4: 579-89, 1994 |
| Maize B-Peru | Selinger et al., Genetics 149; 1125-38, 1998 |

A green tissue-specific promoter as defined herein is a promoter that is transcriptionally active predominantly in green tissue, substantially to the exclusion of any other parts of a plant, whilst still allowing for any leaky expression in these other plant parts.

Examples of green tissue-specific promoters which may be used to perform the methods of the invention are shown in Table 2g below.

TABLE 2g

Examples of green tissue-specific promoters

| Gene | Expression | Reference |
|---|---|---|
| Maize Orthophosphate dikinase | Leaf specific | Fukayama et al., 2001 |
| Maize Phosphoenolpyruvate carboxylase | Leaf specific | Kausch et al., 2001 |
| Rice Phosphoenolpyruvate carboxylase | Leaf specific | Liu et al., 2003 |
| Rice small subunit Rubisco | Leaf specific | Nomura et al., 2000 |
| rice beta expansin EXBP9 | Shoot specific | WO 2004/070039 |
| Pigeonpea small subunit Rubisco | Leaf specific | Panguluri et al., 2005 |
| Pea RBCS3A | Leaf specific | |

Another example of a tissue-specific promoter is a meristem-specific promoter, which is transcriptionally active predominantly in meristematic tissue, substantially to the exclusion of any other parts of a plant, whilst still allowing for any leaky expression in these other plant parts. Examples of green meristem-specific promoters which may be used to perform the methods of the invention are shown in Table 2h below.

TABLE 2h

Examples of meristem-specific promoters

| Gene source | Expression pattern | Reference |
|---|---|---|
| rice OSH1 | Shoot apical meristem, from embryo globular stage to seedling stage | Sato et al. (1996) Proc. Natl. Acad. Sci. USA, 93: 8117-8122 |
| Rice metallothionein | Meristem specific | BAD87835.1 |
| WAK1 & WAK2 | Shoot and root apical meristems, and in expanding leaves and sepals | Wagner & Kohorn (2001) Plant Cell 13(2): 303-318 |

Terminator

The term "terminator" encompasses a control sequence which is a DNA sequence at the end of a transcriptional unit which signals 3' processing and polyadenylation of a primary transcript and termination of transcription. The terminator can be derived from the natural gene, from a variety of other plant genes, or from T-DNA. The terminator to be added may be derived from, for example, the nopaline synthase or octopine synthase genes, or alternatively from another plant gene, or less preferably from any other eukaryotic gene.

Selectable Marker (Gene)/Reporter Gene

"Selectable marker", "selectable marker gene" or "reporter gene" includes any gene that confers a phenotype on a cell in which it is expressed to facilitate the identification and/or selection of cells that are transfected or transformed with a nucleic acid construct of the invention. These marker genes enable the identification of a successful transfer of the nucleic acid molecules via a series of different principles. Suitable markers may be selected from markers that confer antibiotic or herbicide resistance, that introduce a new metabolic trait or that allow visual selection. Examples of selectable marker genes include genes conferring resistance to antibiotics (such as nptII that phosphorylates neomycin and kanamycin, or hpt, phosphorylating hygromycin, or genes conferring resistance to, for example, bleomycin, streptomycin, tetracyclin, chloramphenicol, ampicillin, gentamycin, geneticin (G418), spectinomycin or blasticidin), to herbicides (for example bar which provides resistance to Basta®; aroA or gox providing resistance against glyphosate, or the genes conferring resistance to, for example, imidazolinone, phosphinothricin or sulfonylurea), or genes that provide a metabolic trait (such as manA that allows plants to use mannose as sole carbon source or xylose isomerase for the utilisation of xylose, or antinutritive markers such as the resistance to 2-deoxyglucose). Expression of visual marker genes results in the formation of colour (for example β-glucuronidase, GUS or β-galactosidase with its coloured substrates, for example X-Gal), luminescence (such as the luciferin/luciferase system) or fluorescence (Green Fluorescent Protein, GFP, and derivatives thereof). This list represents only a small number of possible markers. The skilled worker is familiar with such markers. Different markers are preferred, depending on the organism and the selection method.

Transgenic/Transgene/Recombinant

For the purposes of the invention, "transgenic", "transgene" or "recombinant" means with regard to, for example, a nucleic acid sequence, an expression cassette, gene construct or a vector comprising the nucleic acid sequence or an organism transformed with the nucleic acid sequences, expression cassettes or vectors according to the invention, all those constructions brought about by recombinant methods in which either (a) the nucleic acid sequences encoding proteins useful in the methods of the invention, or (b) genetic control sequence(s) which is operably linked with the nucleic acid sequence according to the invention, for example a promoter, or (c) a) and b)

are not located in their natural genetic environment or have been modified by recombinant methods, it being possible for the modification to take the form of, for example, a substitution, addition, deletion, inversion or insertion of one or more nucleotide residues. The natural genetic environment is understood as meaning the natural genomic or chromosomal locus in the original plant or the presence in a genomic library. In the case of a genomic library, the natural genetic environment of the nucleic acid sequence is preferably retained, at least in part. The environment flanks the nucleic acid sequence at least on one side and has a sequence length of at least 50 bp, preferably at least 500 bp, especially preferably at least 1000 bp, most preferably at least 5000 bp. A naturally occurring expression cassette—for example the naturally occurring combination of the natural promoter of the nucleic acid sequences with the corresponding nucleic acid sequence encoding a polypeptide useful in the methods of the present invention, as defined above—becomes a transgenic expression cassette when this expression cassette is modified by non-natural, synthetic ("artificial") methods such as, for example, mutagenic treatment. Suitable methods are described, for example, in U.S. Pat. No. 5,565,350 or WO 00/15815.

A transgenic plant for the purposes of the invention is thus understood as meaning, as above, that the nucleic acids used in the method of the invention are not at their natural locus in the genome of said plant, it being possible for the nucleic acids to be expressed homologously or heterologously. However, as mentioned, transgenic also means that, while the nucleic acids according to the invention or used in the inventive method are at their natural position in the genome of a plant, the sequence has been modified with regard to the natural sequence, and/or that the regulatory sequences of the natural sequences have been modified. Transgenic is preferably understood as meaning the expression of the nucleic acids according to the invention at an unnatural locus in the genome, i.e. homologous or, preferably, heterologous expression of the nucleic acids takes place. Preferred transgenic plants are mentioned herein.

Transformation

The term "introduction" or "transformation" as referred to herein encompasses the transfer of an exogenous polynucleotide into a host cell, irrespective of the method used for transfer. Plant tissue capable of subsequent clonal propagation, whether by organogenesis or embryogenesis, may be transformed with a genetic construct of the present invention and a whole plant regenerated there from. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a host cell and may be maintained non-integrated, for example, as a plasmid. Alternatively, it may be integrated into the host genome. The resulting transformed plant cell may then be used to regenerate a transformed plant in a manner known to persons skilled in the art.

The transfer of foreign genes into the genome of a plant is called transformation. Transformation of plant species is now a fairly routine technique. Advantageously, any of several transformation methods may be used to introduce the gene of interest into a suitable ancestor cell. The methods described for the transformation and regeneration of plants from plant tissues or plant cells may be utilized for transient or for stable transformation. Transformation methods include the use of liposomes, electroporation, chemicals that increase free DNA uptake, injection of the DNA directly into the plant, particle gun bombardment, transformation using viruses or pollen and microprojection. Methods may be selected from the calcium/polyethylene glycol method for protoplasts (Krens, F. A. et al., (1982) Nature 296, 72-74; Negrutiu I et al. (1987) Plant Mol Biol 8: 363-373); electroporation of protoplasts (Shillito R. D. et al. (1985) Bio/Technol 3, 1099-1102); microinjection into plant material (Crossway A et al., (1986) Mol. Gen Genet 202: 179-185); DNA or RNA-coated particle bombardment (Klein T M et al., (1987) Nature 327: 70) infection with (non-integrative) viruses and the like. Transgenic plants, including transgenic crop plants, are preferably produced via Agrobacterium-mediated transformation. An advantageous transformation method is the transformation in planta. To this end, it is possible, for example, to allow the agrobacteria to act on plant seeds or to inoculate the plant meristem with agrobacteria. It has proved particularly expedient in accordance with the invention to allow a suspension of transformed agrobacteria to act on the intact plant or at least on the flower primordia. The plant is subsequently grown on until the seeds of the treated plant are obtained (Clough and Bent, Plant J. (1998) 16, 735-743). Methods for Agrobacterium-mediated transformation of rice include well known methods for rice transformation, such as those described in any of the following: European patent application EP 1198985 A1, Aldemita and Hodges (Planta 199: 612-617, 1996); Chan et al. (Plant Mol Biol 22 (3): 491-506, 1993), Hiei et al. (Plant J 6 (2): 271-282, 1994), which disclosures are incorporated by reference herein as if fully set forth. In the case of corn transformation, the preferred method is as described in either Ishida et al. (Nat. Biotechnol 14(6): 745-50, 1996) or Frame et al. (Plant Physiol 129(1): 13-22, 2002), which disclosures are incorporated by reference herein as if fully set forth. Said methods are further described by way of example in B. Jenes et al., Techniques for Gene Transfer, in: Transgenic Plants, Vol. 1, Engineering and Utilization, eds. S. D. Kung and R. Wu, Academic Press (1993) 128-143 and in Potrykus Annu. Rev. Plant Physiol. Plant Molec. Biol. 42 (1991) 205-225). The nucleic acids or the construct to be expressed is preferably cloned into a vector, which is suitable for transforming Agrobacterium tumefaciens, for example pBin19 (Bevan et al., Nucl. Acids Res. 12 (1984) 8711). Agrobacteria transformed by such a vector can then be used in known manner for the transformation of plants, such as plants used as a model, like Arabidopsis (Arabidopsis thaliana is within the scope of the present invention not considered as a crop plant), or crop plants such as, by way of example, tobacco plants, for example by immersing bruised leaves or chopped leaves in an agrobacterial solution and then culturing them in suitable media. The transformation of plants by means of Agrobacterium tumefaciens is described, for example, by Höfgen and Willmitzer in Nucl. Acid Res. (1988) 16, 9877 or is known inter alia from F. F. White, Vectors for Gene Transfer in Higher Plants; in Transgenic Plants, Vol. 1, Engineering and Utilization, eds. S. D. Kung and R. Wu, Academic Press, 1993, pp. 15-38.

In addition to the transformation of somatic cells, which then have to be regenerated into intact plants, it is also possible to transform the cells of plant meristems and in particular those cells which develop into gametes. In this case, the transformed gametes follow the natural plant development, giving rise to transgenic plants. Thus, for example, seeds of Arabidopsis are treated with agrobacteria and seeds are obtained from the developing plants of which a certain proportion is transformed and thus transgenic [Feldman, K A and Marks M D (1987). Mol Gen Genet 208:274-289; Feldmann K (1992). In: C Koncz, N-H Chua and J Shell, eds, Methods in Arabidopsis Research. Word Scientific, Singapore, pp. 274-289]. Alternative methods are based on the repeated removal of the inflorescences and incubation of the excision site in the center of the rosette with transformed agrobacteria, whereby transformed seeds can likewise be obtained at a later point in time (Chang (1994). Plant J. 5: 551-558; Katavic (1994). Mol Gen Genet, 245: 363-370). However, an especially effective method is the vacuum infiltration method with its modifications such as the "floral dip" method. In the case of vacuum infiltration of Arabidopsis, intact plants under reduced pressure are treated with an agrobacterial suspension [Bechthold, N (1993). C R Acad Sci Paris Life Sci, 316: 1194-1199], while in the case of the "floral dip" method the developing floral tissue is incubated briefly with a surfactant-treated agrobacterial suspension [Clough, S J and Bent, A F (1998). The Plant J. 16, 735-743]. A certain proportion of transgenic seeds are harvested in both cases, and these seeds can be distinguished from non-transgenic seeds by growing under the above-described selective conditions. In addition the stable transformation of plastids is of advantages because plastids are inherited maternally is most crops reducing or eliminating the risk of transgene flow through pollen. The transformation of the chloroplast genome is generally achieved by a process which has been schematically displayed in Klaus et al., 2004 [Nature Biotechnology 22 (2), 225-229]. Briefly the sequences to be transformed are cloned together with a selectable marker gene between flanking sequences homologous to the chloroplast genome. These homologous flanking sequences direct site specific integration into the plastome. Plastidal transformation has been described for many different plant species and an overview is given in Bock (2001) Transgenic plastids in basic research and plant biotechnology. J Mol Biol. 2001 Sep. 21; 312 (3): 425-38 or Maliga, P (2003) Progress towards commercialization of plastid transformation technology. Trends Biotechnol. 21, 20-28. Further biotechnological progress has recently been reported in form of marker free plastid transformants, which can be produced by a transient co-integrated maker gene (Klaus et al., 2004, Nature Biotechnology 22(2), 225-229).

TILLING

TILLING (Targeted Induced Local Lesions In Genomes) is a mutagenesis technology useful to generate and/or identify nucleic acids encoding proteins with modified expression and/or activity. TILLING also allows selection of plants carrying such mutant variants. These mutant variants may exhibit modified expression, either in strength or in location or in timing (if the mutations affect the promoter for example). These mutant variants may exhibit higher activity than that exhibited by the gene in its natural form. TILLING combines high-density mutagenesis with high-throughput screening methods. The steps typically followed in TILLING are: (a) EMS mutagenesis (Redei GP and Koncz C (1992) In Methods in Arabidopsis Research, Koncz C, Chua N H, Schell J, eds. Singapore, World Scientific Publishing Co, pp. 16-82; Feldmann et al., (1994) In Meyerowitz E M, Somerville C R, eds, Arabidopsis. Cold Spring Harbor Laboratory Press, Cold Spring Harbor, N.Y., pp 137-172; Lightner J and Caspar T (1998) In J Martinez-Zapater, J Salinas, eds, Methods on Molecular Biology, Vol. 82. Humana Press, Totowa, N.J., pp 91-104); (b) DNA preparation and pooling of individuals; (c) PCR amplification of a region of interest; (d) denaturation and annealing to allow formation of heteroduplexes; (e) DHPLC, where the presence of a heteroduplex in a pool is detected as an extra peak in the chromatogram; (f) identification of the mutant individual; and (g) sequencing of the mutant PCR product. Methods for TILLING are well known in the art (McCallum et al., (2000) Nat Biotechnol 18: 455-457; reviewed by Stemple (2004) Nat Rev Genet 5(2): 145-50).

Yield

The term "yield" in general means a measurable produce of economic value, typically related to a specified crop, to an area, and to a period of time. Individual plant parts directly contribute to yield based on their number, size and/or weight, or the actual yield is the yield per acre for a crop and year, which is determined by dividing total production (includes both harvested and appraised production) by planted acres.

Increase/Improve/Enhance

The terms "increase", "improve" or "enhance" are interchangeable and shall mean in the sense of the application at least a 5%, 6%, 7%, 8%, 9% or 10%, preferably at least 15% or 20%, more preferably 25%, 30%, 35% or 40% more yield and/or growth in comparison to control plants as defined herein.

Seed Yield

Increased seed yield may manifest itself as one or more of the following: a) an increase in seed biomass (total seed weight) which may be on an individual seed basis and/or per plant and/or per hectare or acre; b) increased number of flowers per plant; c) increased number of (filled) seeds; d) increased seed filling rate (which is expressed as the ratio between the number of filled seeds divided by the total number of seeds); e) increased harvest index, which is expressed as a ratio of the yield of harvestable parts, such as seeds, divided by the total biomass; and f) increased thousand kernel weight (TKW), which is extrapolated from the number of filled seeds counted and their total weight. An increased TKW may result from an increased seed size and/or seed weight, and may also result from an increase in embryo and/or endosperm size.

An increase in seed yield may also be manifested as an increase in seed size and/or seed volume. Furthermore, an increase in seed yield may also manifest itself as an increase in seed area and/or seed length and/or seed width and/or seed perimeter. Increased yield may also result in modified architecture, or may occur because of modified architecture.

Plant

The term "plant" as used herein encompasses whole plants, ancestors and progeny of the plants and plant parts, including seeds, shoots, stems, leaves, roots (including tubers), flowers, and tissues and organs, wherein each of the aforementioned comprise the gene/nucleic acid of interest. The term "plant" also encompasses plant cells, suspension cultures, callus tissue, embryos, meristematic regions, gametophytes, sporophytes, pollen and microspores, again wherein each of the aforementioned comprises the gene/nucleic acid of interest.

Plants that are particularly useful in the methods of the invention include all plants which belong to the superfamily Viridiplantae, in particular monocotyledonous and dicotyledonous plants including fodder or forage legumes, ornamental plants, food crops, trees or shrubs selected from the list comprising *Acer* spp., *Actinidia* spp., *Abelmoschus* spp., *Agave sisalana*, *Agropyron* spp., *Agrostis stolonifera*, *Allium* spp., *Amaranthus* spp., *Ammophila arenaria*, *Ananas comosus*, *Annona* spp., *Apium graveolens*, *Arachis* spp, *Artocarpus* spp., *Asparagus officinalis*, *Avena* spp. (e.g. *Avena sativa*, *Avena fatua*, *Avena byzantina*, *Avena fatua* var. *sativa*, *Avena hybrida*), *Averrhoa carambola*, *Bambusa* sp., *Benincasa hispida*, *Bertholletia excelsea*, *Beta vulgaris*, *Brassica* spp. (e.g. *Brassica napus*, *Brassica rapa* ssp. [canola, oilseed rape, turnip rape]), *Cadaba farinosa*, *Camellia sinensis*, *Canna indica*, *Cannabis sativa*, *Capsicum* spp., *Carex elata*, *Carica papaya*, *Carissa macrocarpa*, *Carya* spp., *Carthamus tinctorius*, *Castanea* spp., *Ceiba pentandra*, *Cichorium endivia*, *Cinnamomum* spp., *Citrullus lanatus*, *Citrus* spp., *Cocos* spp., *Coffea* spp., *Colocasia esculenta*, *Cola* spp., *Corchorus* sp., *Coriandrum sativum*, *Corylus* spp., *Crataegus* spp., *Crocus sativus*, *Cucurbita* spp., *Cucumis* spp., *Cynara* spp., *Daucus carota*, *Desmodium* spp., *Dimocarpus longan*, *Dioscorea* spp., *Diospyros* spp., *Echinochloa* spp., *Elaeis* (e.g. *Elaeis guineensis*, *Elaeis oleifera*), *Eleusine coracana*, *Erianthus* sp., *Eriobotrya japonica*, *Eucalyptus* sp., *Eugenia uniflora*, *Fagopyrum* spp., *Fagus* spp., *Festuca arundinacea*, *Ficus carica*, *Fortunella* spp., *Fragaria* spp., *Ginkgo biloba*, *Glycine* spp. (e.g. *Glycine max*, *Soja hispida* or *Soja max*), *Gossypium hirsutum*, *Helianthus* spp. (e.g. *Helianthus annuus*), *Hemerocallis fulva*, *Hibiscus* spp., *Hordeum* spp. (e.g. *Hordeum vulgare*), *Ipomoea batatas*, *Juglans* spp., *Lactuca sativa*, *Lathyrus* spp., *Lens culinaris*, *Linum usitatissimum*, *Litchi chinensis*, *Lotus* spp., *Luffa acutangula*, *Lupinus* spp., *Luzula sylvatica*, *Lycopersicon* spp. (e.g. *Lycopersicon esculentum*, *Lycopersicon lycopersicum*, *Lycopersicon pyriforme*), *Macrotyloma* spp., *Malus* spp., *Malpighia emarginata*, *Mammea americana*, *Mangifera indica*, *Manihot* spp., *Manilkara zapota*, *Medicago sativa*, *Melilotus* spp., *Mentha* spp., *Miscanthus sinensis*, *Momordica* spp., *Morus nigra*, *Musa* spp., *Nicotiana* spp., *Olea* spp., *Opuntia* spp., *Ornitho*- pus spp., *Oryza* spp. (e.g. *Oryza sativa, Oryza latifolia*), *Panicum miliaceum, Panicum virgatum, Passiflora edulis, Pastinaca sativa, Pennisetum* sp., *Persea* spp., *Petroselinum crispum, Phalaris arundinacea, Phaseolus* spp., *Phleum pratense, Phoenix* spp., *Phragmites australis, Physalis* spp., *Pinus* spp., *Pistacia vera, Pisum* spp., *Poa* spp., *Populus* spp., *Prosopis* spp., *Prunus* spp., *Psidium* spp., *Punica granatum, Pyrus communis, Quercus* spp., *Raphanus sativus, Rheum rhabarbarum, Ribes* spp., *Ricinus communis, Rubus* spp., *Saccharum* spp., *Salix* sp., *Sambucus* spp., *Secale cereale, Sesamum* spp., *Sinapis* sp., *Solanum* spp. (e.g. *Solanum tuberosum, Solanum integrifolium* or *Solanum lycopersicum*), *Sorghum bicolor, Spinacia* spp., *Syzygium* spp., *Tagetes* spp., *Tamarindus indica, Theobroma cacao, Trifolium* spp., *Triticosecale rimpaui, Triticum* spp. (e.g. *Triticum aestivum, Triticum durum, Triticum turgidum, Triticum hybernum, Triticum macha, Triticum sativum* or *Triticum vulgare*), *Tropaeolum minus, Tropaeolum majus, Vaccinium* spp., *Vicia* spp., *Vigna* spp., *Viola odorata, Vitis* spp., *Zea mays, Zizania palustris, Ziziphus* spp., amongst others.

DETAILED DESCRIPTION OF THE INVENTION

I. Harpin

According to a first embodiment, the present invention provides a method for enhancing yield-related traits in plants, comprising modulating expression in a plant of a nucleic acid encoding a Harpin-associated Factor G (hereinafter termed "HpaG") polypeptide.

A preferred method for modulating (preferably, increasing) expression of a nucleic acid encoding an HpaG polypeptide is by introducing and expressing in a plant a nucleic acid encoding an HpaG polypeptide.

Any reference hereinafter to a "protein useful in the methods of the invention" is taken to mean an HpaG polypeptide as defined herein. Any reference hereinafter to a "nucleic acid useful in the methods of the invention" is taken to mean a nucleic acid capable of encoding such an HpaG polypeptide. The nucleic acid to be introduced into a plant (and therefore useful in performing the methods of the invention) is any nucleic acid encoding the type of protein which will now be described, hereafter also named "HpaG nucleic acid" or "HpaG gene".

An HpaG polypeptide as defined herein comprises any polypeptide having the following features:

(i) in increasing order of preference, at least 35%, 40%, 45%, 50%, 55%, 60%, 65%, 70%, 75%, 80%, 85%, 90%, 95% or more sequence identity to the HpaG polypeptide sequence represented by SEQ ID NO: 2; and (ii) an amino acid composition wherein the glycine content ranges from between about 13% and about 25%, the glutamine content ranges from between about 13% and about 20%, the cysteine content ranges from between about 0% and about 1%, the histidine content ranges from between about 0% and about 1%, and wherein tryptophan is absent.

Preferably, the length of the HpaG polypeptide ranges between about 121 and about 143 amino acids.

Preferably, the HpaG protein also comprises the conserved motif 1 (SEQ ID NO: 3)

```
G(G/E/D)(N/E)X(Q/R/P)Q(A/S)GX(N/D)G
``` wherein X on position 4 may be any amino acid, preferably one of S, N, P, R, or Q, and wherein X on position 9 may be any amino acid, preferably one of Q, E, S, or P; and/or the conserved motif 2 (SEQ ID NO: 4)

```
(P/A/V)S(P/Q/A)(F/L/Y)TQ(M/A)LM(H/N/Q)IV(G/M)
(E/D/Q)
```

Optionally, the HpaG protein also has the conserved motif 3:

```
QGISEKQLDQLL
(found within SEQ ID NO: 2)
```

And/or the conserved motif 4:

```
ILQAQN
(found within SEQ ID NO: 2)
```

Furthermore, HpaG polypeptides (at least in their native form) elicit a hypersensitive response in *Arabidopsis thaliana* ecotype Cvi-0 (Kim et al., J. Bacteriol. 185, 3155-3166, 2003).

Alternatively, the homologue of a HpaG protein has in increasing order of preference at least 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% overall sequence identity to the amino acid represented by SEQ ID NO: 2, provided that the homologous protein comprises the conserved motifs as outlined above. The overall sequence identity is determined using a global alignment algorithm, such as the Needleman Wunsch algorithm in the program GAP (GCG Wisconsin Package, Accelrys), preferably with default parameters. Compared to overall sequence identity, the sequence identity will generally be higher when only conserved domains or motifs are considered.

The term "domain" and "motif" is as defined in the "definitions" section herein. Specialist databases exist for the identification of domains, for example, SMART (Schultz et al. (1998) Proc. Natl. Acad. Sci. USA 95, 5857-5864; Letunic et al. (2002) Nucleic Acids Res 30, 242-244, InterPro (Mulder et al., (2003) Nucl. Acids. Res. 31, 315-318, Prosite (Bucher and Bairoch (1994), A generalized profile syntax for biomolecular sequences motifs and its function in automatic sequence interpretation. (In) ISMB-94; Proceedings 2nd International Conference on Intelligent Systems for Molecular Biology. Altman R., Brutlag D., Karp P., Lathrop R., Searls D., Eds., pp 53-61, AAAIPress, Menlo Park; Hulo et al., Nucl. Acids. Res. 32:D134-D137, (2004), or Pfam (Bateman et al., Nucleic Acids Research 30(1): 276-280 (2002). A set of tools for in silico analysis of protein sequences is available on the ExPASY proteomics server (hosted by the Swiss Institute of Bioinformatics (Gasteiger et al., ExPASy: the proteomics server for in-depth protein knowledge and analysis, Nucleic Acids Res. 31:3784-3788 (2003)). Domains may also be identified using routine techniques, such as by sequence alignment.

Methods for the alignment of sequences for comparison are well known in the art, such methods include GAP, BESTFIT, BLAST, FASTA and TFASTA. GAP uses the algorithm of Needleman and Wunsch ((1970) J Mol Biol 48: 443-453) to find the global (i.e. spanning the complete sequences) alignment of two sequences that maximizes the number of matches and minimizes the number of gaps. The BLAST algorithm (Altschul et al. (1990) J Mol Biol 215: 403-10) calculates percent sequence identity and performs a statistical analysis of the similarity between the two sequences. The software for performing BLAST analysis is publicly available through the National Centre for Biotechnology Information (NCBI). Homologues may readily be identified using, for example, the ClustalW multiple sequence alignment algorithm (version 1.83), with the default pairwise alignment parameters, and a scoring method in percentage. Global percentages of similarity and identity may also be determined using one of the methods available in the MatGAT software package (Campanella et al., BMC Bioinformatics. 2003 Jul. 10; 4:29. MatGAT: an application that generates similarity/identity matrices using protein or DNA sequences.). Minor manual editing may be performed to optimise alignment between conserved motifs, as would be apparent to a person skilled in the art. Furthermore, instead of using full-length sequences for the identification of homologues, specific domains may also be used. The sequence identity values may be determined over the entire nucleic acid or amino acid sequence or over selected domains or conserved motif(s), using the programs mentioned above using the default parameters.

The present invention is illustrated by transforming plants with the nucleic acid sequence represented by SEQ ID NO: 1, encoding the polypeptide sequence of SEQ ID NO: 2. However, performance of the invention is not restricted to these sequences; the methods of the invention may advantageously be performed using any HpaG-encoding nucleic acid or HpaG-like polypeptide as defined herein.

Examples of nucleic acids encoding HpaG polypeptides are given in Table A of Example 1 herein. Such nucleic acids are useful in performing the methods of the invention. The amino acid sequences given in Table A of Example 1 are example sequences of orthologues and paralogues of the HpaG polypeptide represented by SEQ ID NO: 2, the terms "orthologues" and "paralogues" being as defined herein. Further orthologues and paralogues may readily be identified by performing a so-called reciprocal blast search. Typically, this involves a first BLAST involving BLASTing a query sequence (for example using any of the sequences listed in Table A of Example 1) against any sequence database, such as the publicly available NCBI database. BLASTN or TBLASTX (using standard default values) are generally used when starting from a nucleotide sequence, and BLASTP or TBLASTN (using standard default values) when starting from a protein sequence. The BLAST results may optionally be filtered. The full-length sequences of either the filtered results or non-filtered results are then BLASTed back (second BLAST) against sequences from the organism from which the query sequence is derived (where the query sequence is SEQ ID NO: 1 or SEQ ID NO: 2, the second BLAST would therefore be against Xanthomonas sequences). The results of the first and second BLASTs are then compared. A paralogue is identified if a high-ranking hit from the first blast is from the same species as from which the query sequence is derived, a BLAST back then ideally results in the query sequence amongst the highest hits; an orthologue is identified if a high-ranking hit in the first BLAST is not from the same species as from which the query sequence is derived, and preferably results upon BLAST back in the query sequence being among the highest hits.

High-ranking hits are those having a low E-value. The lower the E-value, the more significant the score (or in other words the lower the chance that the hit was found by chance). Computation of the E-value is well known in the art. In addition to E-values, comparisons are also scored by percentage identity. Percentage identity refers to the number of identical nucleotides (or amino acids) between the two compared nucleic acid (or polypeptide) sequences over a particular length. In the case of large families, ClustalW may be used, followed by a neighbour joining tree, to help visualize clustering of related genes and to identify orthologues and paralogues.

Nucleic acid variants may also be useful in practising the methods of the invention. Examples of such variants include nucleic acids encoding homologues and derivatives of any one of the amino acid sequences given in Table A of Example 1, the terms "homologue" and "derivative" being as defined herein. Also useful in the methods of the invention are nucleic acids encoding homologues and derivatives of orthologues or paralogues of any one of the amino acid sequences given in Table A of Example 1. Homologues and derivatives useful in the methods of the present invention have substantially the same biological and functional activity as the unmodified protein from which they are derived.

Further nucleic acid variants useful in practising the methods of the invention include portions of nucleic acids encoding HpaG polypeptides, nucleic acids hybridising to nucleic acids encoding HpaG polypeptides, and variants of nucleic acids encoding HpaG polypeptides obtained by gene shuffling. The terms hybridising sequence, and gene shuffling are as described herein.

Nucleic acids encoding HpaG polypeptides need not be full-length nucleic acids, since performance of the methods of the invention does not rely on the use of full-length nucleic acid sequences. According to the present invention, there is provided a method for enhancing yield-related traits in plants, comprising introducing and expressing in a plant a portion of any one of the nucleic acid sequences given in Table A of Example 1, or a portion of a nucleic acid encoding an orthologue, paralogue or homologue of any of the amino acid sequences given in Table A of Example 1.

A portion of a nucleic acid may be prepared, for example, by making one or more deletions to the nucleic acid. The portions may be used in isolated form or they may be fused to other coding (or non-coding) sequences in order to, for example, produce a protein that combines several activities. When fused to other coding sequences, the resultant polypeptide produced upon translation may be bigger than that predicted for the protein portion.

Portions useful in the methods of the invention, encode an HpaG polypeptide as defined herein, and have substantially the same biological activity as the amino acid sequences given in Table A of Example 1. Preferably, the portion is a portion of any one of the nucleic acids given in Table A of Example 1, or is a portion of a nucleic acid encoding an orthologue or paralogue of any one of the amino acid sequences given in Table A of Example 1. Preferably the portion is, in increasing order of preference at least 70, 90, 110, 130 consecutive nucleotides in length, the consecutive nucleotides being of any one of the nucleic acid sequences given in Table A of Example 1, or of a nucleic acid encoding an orthologue or paralogue of any one of the amino acid sequences given in Table A of Example 1. Most preferably the portion is a portion of the nucleic acid of SEQ ID NO: 1. Preferably, the portion encodes an amino acid sequence which when used in the construction of a phylogenetic tree, such as the one depicted in FIG. 2, tends to cluster with the group of HpaG polypeptides comprising the amino acid sequence represented by SEQ ID NO: 2 rather than with any other group.

Another nucleic acid variant useful in the methods of the invention is a nucleic acid capable of hybridising, under reduced stringency conditions, preferably under stringent conditions, with a nucleic acid encoding an HpaG polypeptide as defined herein, or with a portion as defined herein.

According to the present invention, there is provided a method for enhancing yield-related traits in plants, comprising introducing and expressing in a plant a nucleic acid capable of hybridizing to any one of the nucleic acids given in Table A of Example 1, or comprising introducing and expressing in a plant a nucleic acid capable of hybridising to a nucleic acid encoding an orthologue, paralogue or homologue of any of the nucleic acid sequences given in Table A of Example 1.

Hybridising sequences useful in the methods of the invention encode an HpaG polypeptide as defined herein, and have substantially the same biological activity as the amino acid sequences given in Table A of Example 1. Preferably, the hybridising sequence is capable of hybridising to any one of the nucleic acids given in Table A of Example 1, or to a portion of any of these sequences, a portion being as defined above, or wherein the hybridising sequence is capable of hybridising to a nucleic acid encoding an orthologue or paralogue of any one of the amino acid sequences given in Table A of Example 1. Most preferably, the hybridising sequence is capable of hybridising to a nucleic acid as represented by SEQ ID NO: 1 or to a portion thereof.

Preferably, the hybridising sequence encodes an amino acid sequence which when used in the construction of a phylogenetic tree, such as the one depicted in FIG. 2, tends to cluster with the group of HpaG polypeptides comprising the amino acid sequence represented by SEQ ID NO: 2 rather than with any other group.

Gene shuffling or directed evolution may also be used to generate variants of nucleic acids encoding HpaG polypeptides as defined above; the term "gene shuffling" being as defined herein.

According to the present invention, there is provided a method for enhancing yield-related traits in plants, comprising introducing and expressing in a plant a variant of any one of the nucleic acid sequences given in Table A of Example 1, or comprising introducing and expressing in a plant a variant of a nucleic acid encoding an orthologue, paralogue or homologue of any of the amino acid sequences given in Table A of Example 1, which variant nucleic acid is obtained by gene shuffling.

Preferably, the amino acid sequence encoded by the variant nucleic acid obtained by gene shuffling, when used in the construction of a phylogenetic tree such as the one depicted in FIG. 2, tends to cluster with the group of HpaG polypeptides comprising the amino acid sequence represented by SEQ ID NO: 2 rather than with any other group.

Furthermore, nucleic acid variants may also be obtained by site-directed mutagenesis. Several methods are available to achieve site-directed mutagenesis, the most common being PCR based methods (Current Protocols in Molecular Biology. Wiley Eds.).

Nucleic acids encoding HpaG polypeptides may be derived from any natural or artificial source. The nucleic acid may be modified from its native form in composition and/or genomic environment through deliberate human manipulation. Preferably the HpaG polypeptide-encoding nucleic acid is of prokaryotic origin, preferably from a Gram-negative bacterium possessing a TTSS, further preferably from a plant pathogenic bacterium possessing a TTSS, more preferably from the family of Pseudomonaceae, furthermore preferably from the genus *Xanthomonas*, most preferably the nucleic acid is from *Xanthomonas axonopodis*.

Performance of the methods of the invention gives plants having enhanced yield-related traits. In particular performance of the methods of the invention gives plants having increased yield, especially increased biomass and/or increased seed yield relative to control plants. The terms "yield" and "seed yield" are described in more detail in the "definitions" section herein.

Reference herein to enhanced yield-related traits is taken to mean an increase in biomass (weight) of one or more parts of a plant, which may include aboveground (harvestable) parts and/or (harvestable) parts below ground. In particular, such harvestable parts are seeds, and performance of the methods of the invention results in plants having increased seed yield relative to the seed yield of suitable control plants.

Taking corn as an example, a yield increase may be manifested as one or more of the following: increase in the number of plants established per hectare or acre, an increase in the number of ears per plant, an increase in the number of rows, number of kernels per row, kernel weight, thousand kernel weight, ear length/diameter, increase in the seed filling rate (which is the number of filled seeds divided by the total number of seeds and multiplied by 100), among others. Taking rice as an example, a yield increase may manifest itself as an increase in one or more of the following: number of plants per hectare or acre, number of panicles per plant, number of spikelets per panicle, number of flowers (florets) per panicle (which is expressed as a ratio of the number of filled seeds over the number of primary panicles), increase in the seed filling rate (which is the number of filled seeds divided by the total number of seeds and multiplied by 100), increase in thousand kernel weight, among others.

The present invention provides a method for increasing yield, especially biomass and/or seed yield of plants, relative to control plants, which method comprises modulating expression, preferably increasing expression, in a plant of a nucleic acid encoding an HpaG polypeptide as defined herein. It should be noted that the observed yield increase is not the result of increased biotic stress resistance.

Since the transgenic plants according to the present invention have increased yield, it is likely that these plants exhibit an increased growth rate (during at least part of their life cycle), relative to the growth rate of control plants at a corresponding stage in their life cycle. Besides the increased yield capacity, an increased efficiency of nutrient uptake may also contribute to the increase in yield. It is observed that the plants according to the present invention show a higher efficiency in nutrient uptake. Increased efficiency of nutrient uptake allows better growth of the plant.

The increased growth rate may be specific to one or more parts of a plant (including seeds), or may be throughout substantially the whole plant. Plants having an increased growth rate may have a shorter life cycle. The life cycle of a plant may be taken to mean the time needed to grow from a mature seed up to the stage where the plant has produced mature seeds, similar to the starting material. This life cycle may be influenced by factors such as early vigour, growth rate, greenness index, flowering time and speed of seed maturation. The increase in growth rate may take place at one or more stages in the life cycle of a plant or during substantially the whole plant life cycle. Increased growth rate during the early stages in the life cycle of a plant may reflect enhanced vigour. The increase in growth rate may alter the harvest cycle of a plant allowing plants to be sown later and/or harvested sooner than would otherwise be possible (a similar effect may be obtained with earlier flowering time). If the growth rate is sufficiently increased, it may allow for the further sowing of seeds of the same plant species (for example sowing and harvesting of rice plants followed by sowing and harvesting of further rice plants all within one conventional growing period). Similarly, if the growth rate is sufficiently increased, it may allow for the further sowing of seeds of different plants species (for example the sowing and harvesting of corn plants followed by, for example, the sowing and optional harvesting of soybean, potato or any other suitable plant). Harvesting additional times from the same rootstock in the case of some crop plants may also be possible. Altering the harvest cycle of a plant may lead to an increase in annual biomass production per acre (due to an increase in the number of times (say in a year) that any particular plant may be grown and harvested). An increase in growth rate may also allow for the cultivation of transgenic plants in a wider geographical area than their wild-type counterparts, since the territorial limitations for growing a crop are often determined by adverse environmental conditions either at the time of planting (early season) or at the time of harvesting (late season). Such adverse conditions may be avoided if the harvest cycle is shortened. The growth rate may be determined by deriving various parameters from growth curves, such parameters may be: T-Mid (the time taken for plants to reach 50% of their maximal size) and T-90 (time taken for plants to reach 90% of their maximal size), amongst others.

According to a preferred feature of the present invention, performance of the methods of the invention gives plants having an increased growth rate relative to control plants. Therefore, according to the present invention, there is provided a method for increasing the growth rate of plants, which method comprises modulating expression, preferably increasing expression, in a plant of a nucleic acid encoding an HpaG polypeptide as defined herein. It should be noted that the observed increase in growth rate is not the result of biotic stress resistance.

An increase in yield and/or growth rate occurs whether the plant is under non-stress conditions or whether the plant is exposed to various abiotic stresses compared to control plants. Plants typically respond to exposure to abiotic stress by growing more slowly. In conditions of severe stress, the plant may even stop growing altogether. Mild stress on the other hand is defined herein as being any stress to which a plant is exposed which does not result in the plant ceasing to grow altogether without the capacity to resume growth. Mild stress in the sense of the invention leads to a reduction in the growth of the stressed plants of less than 40%, 35% or 30%, preferably less than 25%, 20% or 15%, more preferably less than 14%, 13%, 12%, 11% or 10% or less in comparison to the control plant under non-stress conditions. Due to advances in agricultural practices (irrigation, fertilization, pesticide treatments) severe stresses are not often encountered in cultivated crop plants. As a consequence, the compromised growth induced by mild stress is often an undesirable feature for agriculture. The term "mild stresses" are the everyday abiotic (environmental) stresses to which a plant is exposed. Abiotic stresses may be due to drought or excess water, anaerobic stress, salt stress, chemical toxicity, oxidative stress and hot, cold or freezing temperatures. The abiotic stress may be an osmotic stress caused by a water stress (particularly due to drought), salt stress, oxidative stress or an ionic stress.

The term "abiotic stress" as defined herein is taken to mean any one or more of: water stress (due to drought or excess water), anaerobic stress, salt stress, temperature stress (due to hot, cold or freezing temperatures), chemical toxicity stress and oxidative stress. According to one aspect of the invention, the abiotic stress is an osmotic stress, selected from water stress, salt stress, oxidative stress and ionic stress. Preferably, the water stress is drought stress. The term salt stress is not restricted to common salt (NaCl), but may be any one or more of: NaCl, KCl, LiCl, $MgCl_2$, $CaCl_2$, amongst others.

Another example of abiotic environmental stress is the reduced availability of one or more nutrients that need to be assimilated by the plants for growth and development. Because of the strong influence of nutrition utilization efficiency on plant yield and product quality, a huge amount of fertilizer is poured onto fields to optimize plant growth and quality. Productivity of plants ordinarily is limited by three primary nutrients, phosphorous, potassium and nitrogen, which is usually the rate-limiting element in plant growth of these three. Therefore the major nutritional element required for plant growth is nitrogen (N). It is a constituent of numerous important compounds found in living cells, including amino acids, proteins (enzymes), nucleic acids, and chlorophyll. 1.5% to 2% of plant dry matter is nitrogen and approximately 16% of total plant protein. Thus, nitrogen availability is a major limiting factor for crop plant growth and production (Frink et al. (1999) Proc Natl Acad Sci USA 96(4): 1175-1180), and has as well a major impact on protein accumulation and amino acid composition. Therefore, of great interest are crop plants with an increased yield when grown under nitrogen-limiting conditions.

Biotic stresses are typically those stresses caused by pathogens, such as bacteria, viruses, fungi, nematodes and insects.

In particular, the methods of the present invention may be performed under non-stress conditions or under conditions of drought to give plants having increased yield relative to control plants. As reported in Wang et al. (Planta (2003) 218: 1-14), abiotic stress leads to a series of morphological, physiological, biochemical and molecular changes that adversely affect plant growth and productivity. Drought, salinity, extreme temperatures and oxidative stress are known to be interconnected and may induce growth and cellular damage through similar mechanisms. Rabbani et al. (Plant Physiol (2003) 133: 1755-1767) describes a particularly high degree of "cross talk" between drought stress and high-salinity stress. For example, drought and/or salinisation are manifested primarily as osmotic stress, resulting in the disruption of homeostasis and ion distribution in the cell. Oxidative stress, which frequently accompanies high or low temperature, salinity or drought stress, may cause denaturing of functional and structural proteins. As a consequence, these diverse environmental stresses often activate similar cell signalling pathways and cellular responses, such as the production of stress proteins, up-regulation of anti-oxidants, accumulation of compatible solutes and growth arrest.

The term "non-stress" conditions as used herein are those environmental conditions that allow optimal growth of plants. Persons skilled in the art are aware of normal soil conditions and climatic conditions for any given location.

Performance of the methods of the invention gives plants, grown under non-stress conditions or under drought stress conditions, increased yield relative to suitable control plants grown under comparable conditions. Therefore, according to the present invention, there is provided a method for increasing yield in plants grown under non-stress conditions or under drought conditions, which method comprises increasing expression in a plant of a nucleic acid encoding an HpaG polypeptide.

Furthermore, performance of the methods of the invention gives plants grown under conditions of nutrient deficiency, particularly under conditions of nitrogen deficiency, increased yield relative to control plants grown under comparable conditions. Therefore, according to the present invention, there is also provided a method for increasing yield in plants grown under conditions of nutrient deficiency, which method comprises increasing expression in a plant of a nucleic acid encoding an HpaG polypeptide.

Performance of the methods of the invention also gives plants having increased plant vigour relative to control plants, particularly during the early stages of plant development (typically three, four weeks post germination in the case of rice and maize, but this will vary from species to species) leading to early vigour. Therefore, according to the present invention, there is provided a method for increasing the plant early vigour, which method comprises modulating, preferably increasing, expression in a plant of a nucleic acid encoding a HpaG polypeptide. Preferably the increase in seedling vigour is achieved by expressing the nucleic acid encoding the HpaG polypeptide under the control of a shoot specific promoter. There is also provided a method for producing plants having early vigour relative to control plants, which method comprises modulating, preferably increasing, expression in a plant of a nucleic acid encoding a HpaG polypeptide.

Early vigour may also result from increased plant fitness due to, for example, the plants being better adapted to their environment (i.e. optimizing the use of energy resources and partitioning between shoot and root). Plants having early vigour also show increase seedling survival and a better establishment of the crop, which often results in highly uniform fields (with the crop growing in uniform manner, i.e. with the majority of plants reaching the various stages of development at substantially the same time), and often better and higher yield. Therefore, early vigour may be determined by measuring various factors, such as thousand kernel weight, percentage germination, percentage emergence, seedling growth, seedling height, root length, root and shoot biomass and many more.

The present invention encompasses plants or parts thereof (including seeds) obtainable by the methods according to the present invention. The plants or parts thereof comprise a nucleic acid transgene encoding an HpaG polypeptide as defined above.

The invention also provides genetic constructs and vectors to facilitate introduction and/or expression in plants of nucleic acids encoding HpaG polypeptides. The gene constructs may be inserted into vectors, which may be commercially available, suitable for transforming into plants and suitable for expression of the gene of interest in the transformed cells. The invention also provides use of a gene construct as defined herein in the methods of the invention.

More specifically, the present invention provides a construct comprising:

(a) a nucleic acid encoding an HpaG polypeptide as defined above;

(b) one or more control sequences capable of driving expression of the nucleic acid sequence of (a); and optionally (c) a transcription termination sequence.

Preferably, the HpaG encoding nucleic acid is (i) a nucleic acid as presented by SEQ ID NO: 1 or the complement thereof, (ii) a nucleic acid encoding an HpaG polypeptide as defined above.

The term "control sequence" and "termination sequence" are as defined herein.

Plants are transformed with a vector comprising any of the nucleic acids described above. The skilled artisan is well aware of the genetic elements that must be present on the vector in order to successfully transform, select and propagate host cells containing the sequence of interest. The sequence of interest is operably linked to one or more control sequences (at least to a promoter).

Advantageously, any type of promoter, whether natural or synthetic, may be used to drive expression of the nucleic acid sequence. A constitutive promoter or a green tissue specific promoter is particularly useful in the methods. See the "Definitions" section herein for definitions of the various promoter types.

Preferably, the HpaG nucleic acid or variant thereof is operably linked to a constitutive promoter. A preferred constitutive promoter is one that is also substantially ubiquitously expressed. Further preferably the promoter is derived from a plant, more preferably a monocotyledonous plant. Most preferred is use of a GOS2 promoter (from rice) (SEQ ID NO: 5). It should be clear that the applicability of the present invention is not restricted to the HpaG nucleic acid represented by SEQ ID NO: 1, nor is the applicability of the invention restricted to expression of a HpaG nucleic acid when driven by a GOS2 promoter. Examples of other constitutive promoters which may also be used to drive expression of an HpaG nucleic acid are shown in Table 2a in the Definitions section herein.

Preferably, the consecutive promoter is of medium strength and has weaker activity than the CaMV 35S promoter.

Alternatively, the HpaG nucleic acid or variant thereof is operably linked to a green tissue-specific promoter. A green tissue-specific promoter as defined herein is a promoter that is transcriptionally active predominantly in green tissue, substantially to the exclusion of any other parts of a plant, whilst still allowing for any leaky expression in these other plant parts. The green tissue-specific promoter is preferably a protochlorophylid reductase promoter, more preferably the protochlorophylid reductase promoter represented by a nucleic acid sequence substantially similar to SEQ ID NO: 6, most preferably the promoter is as represented by SEQ ID NO: 6. It should be clear that the applicability of the present invention is not restricted to the HpaG encoding nucleic acid represented by SEQ ID NO: 1, nor is the applicability of the invention restricted to expression of such a HpaG encoding nucleic acid when driven by a protochlorophylid reductase promoter. Examples of other green tissue-specific promoters which may also be used to perform the methods of the invention are shown in the definitions section herein.

For the identification of functionally equivalent promoters, the promoter strength and/or expression pattern of a candidate promoter may be analysed for example by operably linking the promoter to a reporter gene and assaying the expression level and pattern of the reporter gene in various tissues of the plant. Suitable well-known reporter genes include for example beta-glucuronidase or beta galactosidase. The promoter activity is assayed by measuring the enzymatic activity of the beta-glucuronidase or beta-galactosidase. The promoter strength and/or expression pattern may then be compared to that of a reference promoter (such as the one used in the methods of the present invention). Alternatively, promoter strength may be assayed by quantifying mRNA levels or by comparing mRNA levels of the nucleic acid used in the methods of the present invention, with mRNA levels of housekeeping genes such as 18S rRNA, using methods known in the art, such as Northern blotting with densitometric analysis of autoradiograms, quantitative real-time PCR or RT-PCR (Heid et al., 1996 Genome Methods 6: 986-994). Generally a "weak promoter" refers to a promoter that drives expression of a coding sequence at a low level. By "low level" is intended at levels of about 1/10,000 transcripts to about 1/100,000 transcripts, to about 1/500,0000 transcripts per cell. Conversely, a "strong promoter" drives expression of a coding sequence at high level, or at about 1/10 transcripts to about 1/100 transcripts to about 1/1,000 transcripts per cell.

Optionally, one or more terminator sequences may be used in the construct introduced into a plant. Additional regulatory elements may include transcriptional as well as translational enhancers. Those skilled in the art will be aware of terminator and enhancer sequences that may be suitable for use in performing the invention. Such sequences would be known or may readily be obtained by a person skilled in the art.

An intron sequence may also be added to the 5' untranslated region (UTR) or in the coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg, Mol. Cell Biol. 8:4395-4405 (1988); Callis et al., Genes Dev. 1:1183-1200 (1987)). Such intron enhancement of gene expression is typically greatest when placed near the 5' end of the transcription unit. Use of the maize introns Adh1-S intron 1, 2, and 6, the Bronze-1 intron are known in the art. For general information, see The Maize Handbook, Chapter 116, Freeling and Walbot, Eds., Springer, N.Y. (1994).

Other control sequences (besides promoter, enhancer, silencer, intron sequences, 3'UTR and/or 5'UTR regions) may be protein and/or RNA stabilizing elements. Such sequences would be known or may readily be obtained by a person skilled in the art. Furthermore, the codon usage of the coding sequence to be inserted on the construct may be optimised with reference to the host cell into which the construct will be introduced. While the genetic code is degenerated, organisms tend to use a particular codon for an amino acid more than other codons for that same amino acid. Tables with preferred codon usage for various organisms are known in the art.

The genetic constructs of the invention may further include an origin of replication sequence that is required for maintenance and/or replication in a specific cell type. One example is when a genetic construct is required to be maintained in a bacterial cell as an episomal genetic element (e.g. plasmid or cosmid molecule). Preferred origins of replication include, but are not limited to, the f1-ori and colE1.

For the detection of the successful transfer of the nucleic acid sequences as used in the methods of the invention and/or selection of transgenic plants comprising these nucleic acids, it is advantageous to use marker genes (or reporter genes). Therefore, the genetic construct may optionally comprise a selectable marker gene. Selectable markers are described in more detail in the "definitions" section herein.

It is known that upon stable or transient integration of nucleic acids into plant cells, only a minority of the cells takes up the foreign DNA and, if desired, integrates it into its genome, depending on the expression vector used and the transfection technique used. To identify and select these integrants, a gene coding for a selectable marker (such as the ones described above) is usually introduced into the host cells together with the gene of interest. These markers can for example be used in mutants in which these genes are not functional by, for example, deletion by conventional methods. Furthermore, nucleic acid molecules encoding a selectable marker can be introduced into a host cell on the same vector that comprises the sequence encoding the polypeptides of the invention or used in the methods of the invention, or else in a separate vector. Cells which have been stably transfected with the introduced nucleic acid can be identified for example by selection (for example, cells which have integrated the selectable marker survive whereas the other cells die).

Since the marker genes, particularly genes for resistance to antibiotics and herbicides, are no longer required or are undesired in the transgenic host cell once the nucleic acids have been introduced successfully, the process according to the invention for introducing the nucleic acids advantageously employs techniques which enable the removal or excision of these marker genes. One such a method is what is known as co-transformation. The co-transformation method employs two vectors simultaneously for the transformation, one vector bearing the nucleic acid according to the invention and a second bearing the marker gene(s). A large proportion of transformants receives or, in the case of plants, comprises (up to 40% or more of the transformants), both vectors. In case of transformation with Agrobacteria, the transformants usually receive only a part of the vector, i.e. the sequence flanked by the T-DNA, which usually represents the expression cassette. The marker genes can subsequently be removed from the transformed plant by performing crosses. In another method, marker genes integrated into a transposon are used for the transformation together with desired nucleic acid (known as the Ac/Ds technology). The transformants can be crossed with a transposase source or the transformants are transformed with a nucleic acid construct conferring expression of a transposase, transiently or stable. In some cases (approx. 10%), the transposon jumps out of the genome of the host cell once transformation has taken place successfully and is lost. In a further number of cases, the transposon jumps to a different location. In these cases the marker gene must be eliminated by performing crosses. In microbiology, techniques were developed which make possible, or facilitate, the detection of such events. A further advantageous method relies on what is known as recombination systems; whose advantage is that elimination by crossing can be dispensed with. The best-known system of this type is what is known as the Cre/lox system. Cre1 is a recombinase that removes the sequences located between the loxP sequences. If the marker gene is integrated between the loxP sequences, it is removed once transformation has taken place successfully, by expression of the recombinase. Further recombination systems are the HIN/HIX, FLP/FRT and REP/STB system (Tribble et al., J. Biol. Chem., 275, 2000: 22255-22267; Velmurugan et al., J. Cell Biol., 149, 2000: 553-566). A site-specific integration into the plant genome of the nucleic acid sequences according to the invention is possible. Naturally, these methods can also be applied to microorganisms such as yeast, fungi or bacteria.

The invention also provides a method for the production of transgenic plants having enhanced yield-related traits relative to control plants, comprising introduction and expression in a plant of any nucleic acid encoding an HpaG polypeptide as defined hereinabove.

More specifically, the present invention provides a method for the production of transgenic plants having increased enhanced yield-related traits, particularly increased biomass and/or seed yield, which method comprises:

(i) introducing and expressing in a plant or plant cell an HpaG polypeptide-encoding nucleic acid; and (ii) cultivating the plant cell under conditions promoting plant growth and development.

The nucleic acid of (i) may be any of the nucleic acids capable of encoding an HpaG polypeptide as defined herein.

The nucleic acid may be introduced directly into a plant cell or into the plant itself (including introduction into a tissue, organ or any other part of a plant). According to a preferred feature of the present invention, the nucleic acid is preferably introduced into a plant by transformation. The term "transformation" is described in more detail in the "definitions" section herein.

The genetically modified plant cells can be regenerated via all methods with which the skilled worker is familiar. Suitable methods can be found in the abovementioned publications by S. D. Kung and R. Wu, Potrykus or Hofgen and Willmitzer.

Generally after transformation, plant cells or cell groupings are selected for the presence of one or more markers which are encoded by plant-expressible genes co-transferred with the gene of interest, following which the transformed material is regenerated into a whole plant. To select transformed plants, the plant material obtained in the transformation is, as a rule, subjected to selective conditions so that transformed plants can be distinguished from untransformed plants. For example, the seeds obtained in the above-described manner can be planted and, after an initial growing period, subjected to a suitable selection by spraying. A further possibility consists in growing the seeds, if appropriate after sterilization, on agar plates using a suitable selection agent so that only the transformed seeds can grow into plants. Alternatively, the transformed plants are screened for the presence of a selectable marker such as the ones described above.

Following DNA transfer and regeneration, putatively transformed plants may also be evaluated, for instance using Southern analysis, for the presence of the gene of interest, copy number and/or genomic organisation. Alternatively or additionally, expression levels of the newly introduced DNA may be monitored using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed and homozygous second-generation (or T2) transformants selected, and the T2 plants may then further be propagated through classical breeding techniques.

The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

The present invention clearly extends to any plant cell or plant produced by any of the methods described herein, and to all plant parts and propagules thereof. The present invention extends further to encompass the progeny of a primary transformed or transfected cell, tissue, organ or whole plant that has been produced by any of the aforementioned methods, the only requirement being that progeny exhibit the same genotypic and/or phenotypic characteristic(s) as those produced by the parent in the methods according to the invention.

The invention also includes host cells containing an isolated nucleic acid encoding an HpaG polypeptide as defined hereinabove. Preferred host cells according to the invention are plant cells. Host plants for the nucleic acids or the vector used in the method according to the invention, the expression cassette or construct or vector are, in principle, advantageously all plants, which are capable of synthesizing the polypeptides used in the inventive method.

The methods of the invention are advantageously applicable to any plant.

Plants that are particularly useful in the methods of the invention include all plants which belong to the superfamily Viridiplantae, in particular monocotyledonous and dicotyledonous plants including fodder or forage legumes, ornamental plants, food crops, trees or shrubs. According to a preferred embodiment of the present invention, the plant is a crop plant. Examples of crop plants include soybean, sunflower, canola, alfalfa, rapeseed, cotton, tomato, potato and tobacco. Further preferably, the plant is a monocotyledonous plant. Examples of monocotyledonous plants include sugarcane. More preferably the plant is a cereal. Examples of cereals include rice, maize, wheat, barley, millet, triticale, rye, sorghum and oats.

The invention also extends to harvestable parts of a plant such as, but not limited to seeds, leaves, fruits, flowers, stems, rhizomes, tubers and bulbs. The invention furthermore relates to products derived, preferably directly derived, from a harvestable part of such a plant, such as dry pellets or powders, oil, fat and fatty acids, starch or proteins.

According to a preferred feature of the invention, the modulated expression is increased expression. Methods for increasing expression of nucleic acids or genes, or gene products, are well documented in the art and include, for example, overexpression driven by appropriate promoters, the use of transcription enhancers or translation enhancers. Isolated nucleic acids which serve as promoter or enhancer elements may be introduced in an appropriate position (typically upstream) of a non-heterologous form of a polynucleotide so as to upregulate expression. For example, endogenous promoters may be altered in vivo by mutation, deletion, and/or substitution (see, Kmiec, U.S. Pat. No. 5,565,350; Zarling et al., PCT/US93/03868), or isolated promoters may be introduced into a plant cell in the proper orientation and distance from a gene of the present invention so as to control the expression of the gene.

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added may be derived from, for example, the nopaline synthase or octopine synthase genes, or alternatively from another plant gene, or less preferably from any other eukaryotic gene.

The present invention also encompasses use of nucleic acids encoding HpaG polypeptides as described herein and use of these HpaG polypeptide in enhancing any of the aforementioned yield-related traits in plants.

The methods according to the present invention result in plants having enhanced yield-related traits, as described hereinbefore. These traits may also be combined with other economically advantageous traits, such as further yield-enhancing traits, tolerance to other abiotic and biotic stresses, traits modifying various architectural features and/or biochemical and/or physiological features.

II. SNF2

According to a first embodiment, the present invention provides a method for enhancing yield-related traits in plants relative to control plants, comprising increasing expression in a plant of a nucleic acid sequence encoding an SWI2/SNF2 polypeptide.

A preferred method for increasing expression of a nucleic acid sequence encoding an SWI2/SNF2 polypeptide is by introducing and expressing in a plant a nucleic acid sequence encoding a SWI2/SNF2 polypeptide.

Any reference hereinafter to a "protein useful in the methods of the invention" is taken to mean an SWI2/SNF2 polypeptide as defined herein. Any reference hereinafter to a "nucleic acid sequence useful in the methods of the invention" is taken to mean a nucleic acid sequence capable of encoding such an SWI2/SNF2 polypeptide. The nucleic acid sequence to be introduced into a plant (and therefore useful in performing the methods of the invention) is any nucleic acid sequence encoding the type of protein, which will now be described, hereafter also named "SWI2/SNF2 nucleic acid sequence" or "SWI2/SNF2 gene".

An "SWI2/SNF2 polypeptide" as defined herein refers to any polypeptide which comprises an ATPase domain comprising from N-terminus to C-terminus at least five, preferably six, more preferably seven, most preferably eight of the following motifs:

(i) Motif I LADDMGLGK(T/S), as represented by SEQ ID NO: 103 or a motif having in increasing order of preference at least 50%, 55%, 60%, 65%, 70%, 75%, 80%, 85%, 90%, 95%, 98%, 99% or more sequence identity to the sequence of Motif I;

(ii) Motif Ia L(L/V/I)(V/I/L)(A/C)P(T/M/V)S(V/I/L)(V/I/L)XNW, as represented by SEQ ID NO: 104 or a motif having in increasing order of preference at least 50%, 55%, 60%, 65%, 70%, 75%, 80%, 85%, 90%, 95%, 98%, 99% or more sequence identity to the sequence of Motif Ia;

(iii) Motif II DEAQ(N/A/H)(V/I/L)KN, as represented by SEQ ID NO: 105 or a motif having in increasing order of preference at least 50%, 55%, 60%, 65%, 70%, 75%, 80%, 85%, 90%, 95%, 98%, 99% or more sequence identity to the sequence of Motif II;

(iv) Motif III A(L/M)TGTPXEN, as represented by SEQ ID NO: 106 or a motif having in increasing order of preference at least 50%, 55%, 60%, 65%, 70%, 75%, 80%, 85%, 90%, 95%, 98%, 99% or more sequence identity to the sequence of Motif III;

(v) Motif IV (L/I)XF(T/S)Q(F/Y), as represented by SEQ ID NO: 107 or a motif having in increasing order of preference at least 50%, 55%, 60%, 65%, 70%, 75%, 80%, 85%, 90%, 95%, 98%, 99% or more sequence identity to the sequence of Motif IV;

(vi) Motif V S(L/V)KAGG(V/T/L)G(L/I)(N/T)LTXA(N/S/T)HV, as represented by SEQ ID NO: 108 or a motif having in increasing order of preference at least 50%, 55%, 60%, 65%, 70%, 75%, 80%, 85%, 90%, 95%, 98%, 99% or more sequence identity to the sequence of Motif V;

(vii) Motif Va DRWWNPAVE, as represented by SEQ ID NO: 109 or a motif having in increasing order of preference at least 50%, 55%, 60%, 65%, 70%, 75%, 80%, 85%, 90%, 95%, 98%, 99% or more sequence identity to the sequence of Motif Va; and (viii) Motif VI QA(T/S)DR(A/TN)(F/Y)R(I/L)GQ, as represented by SEQ ID NO: 110 or a motif having in increasing order of preference at least 50%, 55%, 60%, 65%, 70%, 75%, 80%, 85%, 90%, 95%, 98%, 99% or more sequence identity to the sequence of Motif VI, where X in Motif Ia, Motif III, Motif IV, and Motif V, is any amino acid.

Alternatively or additionally, an "SWI2/SNF2 polypeptide" as defined herein refers to any polypeptide sequence which when used in the construction of a phylogenetic tree, such as the one depicted in FIG. 7 (described in Flaus et al. (2006), supra), tends to cluster with the SSO1653 Glade of SWI2/SNF2 polypeptides comprising the polypeptide sequence as represented by SEQ ID NO: 30, rather than with any other SWI2/SNF2 Glade.

Alternatively or additionally, an "SWI2/SNF2 polypeptide" as defined herein refers to any polypeptide sequence comprising an ATPase domain having in increasing order of preference at least 45%, 50%, 55%, 60%, 65%, 70%, 75%, 80%, 85%, 90%, 95%, 98%, 99% or more sequence identity to the ATPase domain as represented by SEQ ID NO: 111, comprised in SEQ ID NO: 30.

Alternatively or additionally, an "SWI2/SNF2 polypeptide" as defined herein refers to any polypeptide having in increasing order of preference at least 30%, 35%, 40%, 45%, 50%, 55%, 60%, 65%, 70%, 75%, 80%, 85%, 90%, 95%, 98%, 99% or more sequence identity to the SWI2/SNF2 polypeptide as represented by SEQ ID NO: 30 or to any of the polypeptide sequences given in Table E herein.

The terms "domain" and "motif" are defined in the "definitions" section herein. Specialist databases exist for the identification of domains, for example, SMART (Schultz et al. (1998) Proc. Natl. Acad. Sci. USA 95, 5857-5864; Letunic et al. (2002) Nucleic Acids Res 30, 242-244), InterPro (Mulder et al., (2003) Nucl. Acids. Res. 31, 315-318, Prosite (Bucher and Bairoch (1994), A generalized profile syntax for biomolecular sequences motifs and its function in automatic sequence interpretation. (In) ISMB-94; Proceedings 2nd International Conference on Intelligent Systems for Molecular Biology. Altman R., Brutlag D., Karp P., Lathrop R., Searls D., Eds., pp 53-61, AAAI Press, Menlo Park; Hulo et al., (2004) Nucl. Acids. Res. 32: D134-D137), or Pfam (Bateman et al., (2002) Nucleic Acids Research 30(1): 276-280). A set of tools for in silico analysis of protein sequences is available on the ExPASY proteomics server (hosted by the Swiss Institute of Bioinformatics (Gasteiger et al., (2003) ExPASy: the proteomics server for in-depth protein knowledge and analysis, Nucleic Acids Res 31: 3784-3788). Domains may also be identified using routine techniques, such as by sequence alignment. Analysis of the polypeptide sequence of SEQ ID NO: 30 is presented below in Examples 9 and 11.

Methods for the alignment of sequences for comparison are well known in the art, such methods include GAP, BESTFIT, BLAST, FASTA and TFASTA. GAP uses the algorithm of Needleman and Wunsch ((1970) J Mol Biol 48: 443-453) to find the global (i.e. spanning the complete sequences) alignment of two sequences that maximizes the number of matches and minimizes the number of gaps. The BLAST algorithm (Altschul et al. (1990) J Mol Biol 215: 403-10) calculates percent sequence identity and performs a statistical analysis of the similarity between the two sequences. The software for performing BLAST analysis is publicly available through the National Centre for Biotechnology Information (NCBI). Homologues may readily be identified using, for example, the ClustalW multiple sequence alignment algorithm (version 1.83), with the default pairwise alignment parameters, and a scoring method in percentage. Global percentages of similarity and identity may also be determined using one of the methods available in the MatGAT software package (Campanella et al., BMC Bioinformatics. 2003 Jul. 10; 4:29. MatGAT: an application that generates similarity/identity matrices using protein or DNA sequences.). Minor manual editing may be performed to optimise alignment between conserved motifs, as would be apparent to a person skilled in the art. Furthermore, instead of using full-length sequences for the identification of homologues, specific domains may also be used. The sequence identity values, which are indicated below in Example 3 as a percentage were determined over the entire nucleic acid or polypeptide sequence (Table F herein), and/or over selected domains (such as the ATPase domain as represented by SEQ ID NO: 111, comprised in SEQ ID NO: 30; Table F1 herein) or conserved motif(s), using the programs mentioned above using the default parameters.

The present invention is illustrated by transforming plants with the nucleic acid sequence represented by SEQ ID NO:

29, encoding the polypeptide sequence of SEQ ID NO: 30. However, performance of the invention is not restricted to these sequences; the methods of the invention may advantageously be performed using any SWI2/SNF2-encoding nucleic acid sequence or SWI2/SNF2 polypeptides as defined herein.

Examples of nucleic acid sequences encoding plant SWI2/SNF2 polypeptides are given in Table E of Example 8 herein. Such nucleic acid sequences are useful in performing the methods of the invention. The polypeptide sequences given in Table E of Example 8 are example sequences of orthologues and paralogues of the SWI2/SNF2 polypeptides represented by SEQ ID NO: 30, the terms "orthologues" and "paralogues" being as defined herein. Further orthologues and paralogues may readily be identified by performing a so-called reciprocal blast search. Typically, this involves a first BLAST involving BLASTing a query sequence (for example using any of the sequences listed in Table E of Example 8) against any sequence database, such as the publicly available NCBI database. BLASTN or TBLASTX (using standard default values) are generally used when starting from a nucleotide sequence, and BLASTP or TBLASTN (using standard default values) when starting from a protein sequence. The BLAST results may optionally be filtered. The full-length sequences of either the filtered results or non-filtered results are then BLASTed back (second BLAST) against sequences from the organism from which the query sequence is derived (where the query sequence is SEQ ID NO: 29 or SEQ ID NO: 30, the second BLAST would therefore be against *Synechocystis* sequences). The results of the first and second BLASTs are then compared. A paralogue is identified if a high-ranking hit from the first blast is from the same species as from which the query sequence is derived, a BLAST back then ideally results in the query sequence amongst the highest hits; an orthologue is identified if a high-ranking hit in the first BLAST is not from the same species as from which the query sequence is derived, and preferably results upon BLAST back in the query sequence being among the highest hits.

High-ranking hits are those having a low E-value. The lower the E-value, the more significant the score (or in other words the lower the chance that the hit was found by chance). Computation of the E-value is well known in the art. In addition to E-values, comparisons are also scored by percentage identity. Percentage identity refers to the number of identical nucleotides (or amino acids) between the two compared nucleic acid (or polypeptide) sequences over a particular length. In the case of large families, ClustalW may be used, followed by a neighbour joining tree, to help visualize clustering of related genes and to identify orthologues and paralogues (see FIG. 7).

Nucleic acid variants may also be useful in practising the methods of the invention. Examples of such variants include nucleic acid sequences encoding homologues and derivatives of any one of the polypeptide sequences given in Table E of Example 8, the terms "homologue" and "derivative" being as defined herein. Also useful in the methods of the invention are nucleic acid sequences encoding homologues and derivatives of orthologues or paralogues of any one of the polypeptide sequences given in Table E of Example 8. Homologues and derivatives useful in the methods of the present invention have substantially the same biological and functional activity as the unmodified protein from which they are derived.

Further nucleic acid variants useful in practising the methods of the invention include portions of nucleic acid sequences encoding SWI2/SNF2 polypeptides, nucleic acid sequences hybridising to nucleic acid sequences encoding SWI2/SNF2 polypeptides, splice variants of nucleic acid sequences encoding SWI2/SNF2 polypeptides, allelic variants of nucleic acid sequences encoding SWI2/SNF2 polypeptides, and variants of nucleic acid sequences encoding SWI2/SNF2 polypeptides obtained by gene shuffling. The terms hybridising sequence, splice variant, allelic variant and gene shuffling are as described herein.

Nucleic acid sequences encoding SWI2/SNF2 polypeptides need not be full-length nucleic acid sequences, since performance of the methods of the invention does not rely on the use of full-length nucleic acid sequences. According to the present invention, there is provided a method for enhancing yield-related traits in plants, comprising introducing and expressing in a plant a portion of any one of the nucleic acid sequences given in Table E of Example 8, or a portion of a nucleic acid sequence encoding an orthologue, paralogue or homologue of any of the polypeptide sequences given in Table E of Example 8.

A portion of a nucleic acid sequence may be prepared, for example, by making one or more deletions to the nucleic acid sequence. The portions may be used in isolated form or they may be fused to other coding (or non-coding) sequences in order to, for example, produce a protein that combines several activities. When fused to other coding sequences, the resultant polypeptide produced upon translation may be bigger than that predicted for the protein portion.

Portions useful in the methods of the invention, encode SWI2/SNF2 polypeptides as defined herein, and have substantially the same biological activity (i.e., enhancing yield-related traits) as the polypeptide sequences given in Table E of Example 8. Preferably, the portion is a portion of any one of the nucleic acid sequences given in Table E of Example 8, or is a portion of a nucleic acid sequence encoding an orthologue or paralogue of any one of the polypeptide sequences given in Table E of Example 8. Preferably the portion is, in increasing order of preference at least 1000, 1100, 1200, 1300 or 1400 consecutive nucleotides in length, the consecutive nucleotides being of any one of the nucleic acid sequences given in Table E of Example 8, or of a nucleic acid sequence encoding an orthologue or paralogue of any one of the polypeptide sequences given in Table E of Example 8. Most preferably the portion is a portion of the nucleic acid sequence of SEQ ID NO: 29. Preferably, the portion encodes a polypeptide sequence comprising any one or more of the domains or motifs defined herein. Preferably, the portion encodes a polypeptide sequence which when used in the construction of a phylogenetic tree, such as the one depicted in FIG. 7, tends to cluster with the SSO1653 Glade of SWI2/SNF2 polypeptides comprising the polypeptide sequence as represented by SEQ ID NO: 30 rather than with any other SWI2/SNF2 Glade.

Another nucleic acid variant useful in the methods of the invention is a nucleic acid sequence capable of hybridising, under reduced stringency conditions, preferably under stringent conditions, with a nucleic acid sequence encoding an SWI2/SNF2 polypeptide as defined herein, or with a portion as defined herein.

According to the present invention, there is provided a method for enhancing yield-related traits in plants, comprising introducing and expressing in a plant a nucleic acid sequence capable of hybridizing to any one of the nucleic acid sequences given in Table E of Example 8, or comprising introducing and expressing in a plant a nucleic acid sequence capable of hybridising to a nucleic acid sequence encoding an orthologue, paralogue or homologue of any of the nucleic acid sequences given in Table E of Example 8.

Hybridising sequences useful in the methods of the invention encode a SWI2/SNF2 polypeptide as defined herein, and have substantially the same biological activity (i.e., enhancing yield-related traits) as the polypeptide sequences given in Table E of Example 8. Preferably, the hybridising sequence is capable of hybridising to any one of the nucleic acid sequences given in Table E of Example 8, or to a portion of any of these sequences, a portion being as defined above, or wherein the hybridising sequence is capable of hybridising to a nucleic acid sequence encoding an orthologue or paralogue of any one of the polypeptide sequences given in Table E of Example 8. Most preferably, the hybridising sequence is capable of hybridising to a nucleic acid sequence as represented by SEQ ID NO: 29 or to a portion thereof. Preferably, the hybridising sequence encodes a polypeptide sequence comprising any one or more of the motifs or domains as defined herein. Preferably, the hybridising sequence encodes a polypeptide sequence which when used in the construction of a phylogenetic tree, such as the one depicted in FIG. 7, tends to cluster with the SSO1653 Glade of SWI2/SNF2 polypeptides comprising the polypeptide sequence as represented by SEQ ID NO: 30 rather than with any other SWI2/SNF2 Glade.

Another nucleic acid variant useful in the methods of the invention is a splice variant encoding a SWI2/SNF2 polypeptide as defined hereinabove, a splice variant being as defined herein.

According to the present invention, there is provided a method for enhancing yield related traits in plants, comprising introducing and expressing in a plant a splice variant of any one of the nucleic acid sequences given in Table E of Example 8, or a splice variant of a nucleic acid sequence encoding an orthologue, paralogue or homologue of any of the polypeptide sequences given in Table E of Example 8.

The splice variants useful in the methods of the present invention have substantially the same biological activity (i.e., enhancing yield-related traits) as the SWI2/SNF2 polypeptide of SEQ ID NO: 30 and any of the polypeptide sequences depicted in Table E of Example 8. Preferably, the polypeptide sequence encoded by the splice variant comprises any one or more of the motifs or domains as defined herein. Preferably, the polypeptide sequence encoded by the splice variant, when used in the construction of a phylogenetic tree, such as the one depicted in FIG. 7, tends to cluster with the SSO1653 Glade of SWI2/SNF2 polypeptides comprising the polypeptide sequence as represented by SEQ ID NO: 30 rather than with any other SWI2/SNF2 Glade.

Another nucleic acid variant useful in performing the methods of the invention is an allelic variant of a nucleic acid sequence encoding an SWI2/SNF2 polypeptide as defined hereinabove, an allelic variant being as defined herein.

According to the present invention, there is provided a method for enhancing yield-related traits in plants, comprising introducing and expressing in a plant an allelic variant of any one of the nucleic acid sequences given in Table E of Example 8, or comprising introducing and expressing in a plant an allelic variant of a nucleic acid sequence encoding an orthologue, paralogue or homologue of any of the polypeptide sequences given in Table E of Example 8.

The allelic variants useful in the methods of the present invention have substantially the same biological activity (i.e., enhancing yield-related traits) as the SWI2/SNF2 polypeptide of SEQ ID NO: 30 and any of the polypeptide sequences depicted in Table E of Example 8. Allelic variants exist in nature, and encompassed within the methods of the present invention is the use of these natural alleles. Preferably, the allelic variant is an allelic variant of SEQ ID NO: 29 or an allelic variant of a nucleic acid sequence encoding an orthologue or paralogue of SEQ ID NO: 30. Preferably, the polypeptide sequence encoded by the allelic variant comprises any one or more of the motifs or domains as defined herein. Preferably, the polypeptide sequence encoded by the allelic variant, when used in the construction of a phylogenetic tree, such as the one depicted in FIG. 7, tends to cluster with the SSO1653 Glade of SWI2/SNF2 polypeptides comprising the polypeptide sequence as represented by SEQ ID NO: 30 rather than with any other SWI2/SNF2 Glade.

Gene shuffling or directed evolution may also be used to generate variants of nucleic acid sequences encoding SWI2/SNF2 polypeptides as defined above; the term "gene shuffling" being as defined herein.

According to the present invention, there is provided a method for enhancing yield-related traits in plants, comprising introducing and expressing in a plant a variant of any one of the nucleic acid sequences given in Table E of Example 8, or comprising introducing and expressing in a plant a variant of a nucleic acid sequence encoding an orthologue, paralogue or homologue of any of the polypeptide sequences given in Table E of Example 8, which variant nucleic acid sequence is obtained by gene shuffling.

The variant nucleic acid sequences obtained by gene shuffling useful in the methods of the present invention have substantially the same biological activity as the SWI2/SNF2 polypeptide of SEQ ID NO: 30 and any of the polypeptide sequences depicted in Table E of Example 8. Preferably, the variant nucleic acid sequence obtained by gene shuffling encodes a polypeptide sequence comprising any one or more of the motifs or domains as defined herein. Preferably, the polypeptide sequence encoded by the variant nucleic acid sequence obtained by gene shuffling, when used in the construction of a phylogenetic tree, such as the one depicted in FIG. 7, tends to cluster with the SSO1653 Glade of SWI2/SNF2 polypeptides comprising the polypeptide sequence as represented by SEQ ID NO: 30 rather than with any other SWI2/SNF2 Glade.

Furthermore, nucleic acid variants may also be obtained by site-directed mutagenesis. Several methods are available to achieve site-directed mutagenesis, the most common being PCR based methods (Current Protocols in Molecular Biology, Wiley Eds.).

Nucleic acid sequences encoding SWI2/SNF2 polypeptides may be derived from any natural or artificial source. The nucleic acid sequence may be modified from its native form in composition and/or genomic environment through deliberate human manipulation. Preferably the SWI2/SNF2 polypeptide-encoding nucleic acid sequence is from a microbial genome, further preferably from archea (such from as the following phyla: Crenarcheaota, Euryarchaeota (comprising Halobacteria, Methanobacteria, Methanococci, Methanopyri, Archaeoglobi, Thermoplasmata, and Thermococci classes), Korarchaeota, or Nanoarchaeota) or bacteria (such from as the following phyla: Actinobacteria, Aquificae, Bacteroidetes/Chlorobi, Chlamydiae, Chloroflexi, Chrysiogenetes, Cyanobacteria, Deferribacteres, Deinococcus-Thermus, Dictyoglomi, Fibrobacteres/Acidobacteria, Firmicutes, Fusobacteria, Gemmatimonadetes, Lentisphaerae, Nitrospirae, Planctomycetes, Proteobacteria, Spirochaetes, Thermodesulfobacteria, Thermomicrobia, Thermotogae, Verrucomicrobia), more preferably from cyanobacteria, such as *Synechocystis* sp., *Nostoc* sp., *Synechococcus* sp., *Prochlorococcus* sp., *Anaebena* sp., *Gloeobacter* sp., or *Thermosynechococcus* sp., more preferably from *Synechocystis* sp., most preferably from *Synechocystis* sp. PCC6803.

Performance of the methods of the invention gives plants having enhanced yield-related traits relative to control plants.

Reference herein to "enhanced yield-related traits" is taken to mean an increase in biomass (weight) of one or more parts of a plant, which may include aboveground (harvestable) parts and/or (harvestable) parts below ground. In particular, such harvestable parts are seeds, and performance of the methods of the invention results in plants having enhanced seed yield relative to control plants.

Taking corn as an example, a yield increase may be manifested as one or more of the following: increase in the number of plants established per hectare or acre, an increase in the number of ears per plant, an increase in the number of rows, number of kernels per row, kernel weight, thousand kernel weight, ear length/diameter, increase in the seed filling rate (which is the number of filled seeds divided by the total number of seeds and multiplied by 100), among others. Taking rice as an example, a yield increase may manifest itself as an increase in one or more of the following: number of plants per hectare or acre, number of panicles per plant, number of spikelets per panicle, number of flowers (florets) per panicle (which is expressed as a ratio of the number of filled seeds over the number of primary panicles), increase in the seed filling rate (which is the number of filled seeds divided by the total number of seeds and multiplied by 100), increase in thousand kernel weight, among others.

The present invention provides a method for enhancing yield-related traits of plants relative to control plants, which method comprises increasing expression in a plant of a nucleic acid sequence encoding an SWI2/SNF2 polypeptide as defined herein. Preferably, enhanced yield-related traits is one or more of: (i) increased number of flowers per panicle; (ii) increased total seed weight per plant; (iii) increased number of (filled) seeds; or (iv) increased harvest index.

Since the transgenic plants according to the present invention have enhanced yield-related traits, it is likely that these plants exhibit an increased growth rate (during at least part of their life cycle), relative to the growth rate of control plants at a corresponding stage in their life cycle. Besides the increased yield capacity, an increased efficiency of nutrient uptake may also contribute to the increase in yield. It is observed that the plants according to the present invention show a higher efficiency in nutrient uptake. Increased efficiency of nutrient uptake allows better growth of the plant, whether the plant is grown under stress or non-stress conditions.

The increased growth rate may be specific to one or more parts of a plant (including seeds), or may be throughout substantially the whole plant. Plants having an increased growth rate may have a shorter life cycle. The life cycle of a plant may be taken to mean the time needed to grow from a dry mature seed up to the stage where the plant has produced dry mature seeds, similar to the starting material. This life cycle may be influenced by factors such as early vigour, growth rate, greenness index, flowering time and speed of seed maturation. The increase in growth rate may take place at one or more stages in the life cycle of a plant or during substantially the whole plant life cycle. Increased growth rate during the early stages in the life cycle of a plant may reflect enhanced vigour. The increase in growth rate may alter the harvest cycle of a plant allowing plants to be sown later and/or harvested sooner than would otherwise be possible (a similar effect may be obtained with earlier flowering time). If the growth rate is sufficiently increased, it may allow for the further sowing of seeds of the same plant species (for example sowing and harvesting of rice plants followed by sowing and harvesting of further rice plants all within one conventional growing period). Similarly, if the growth rate is sufficiently increased, it may allow for the further sowing of seeds of different plants species (for example the sowing and harvesting of corn plants followed by, for example, the sowing and optional harvesting of soybean, potato or any other suitable plant). Harvesting additional times from the same rootstock in the case of some crop plants may also be possible. Altering the harvest cycle of a plant may lead to an increase in annual biomass production per acre (due to an increase in the number of times (say in a year) that any particular plant may be grown and harvested). An increase in growth rate may also allow for the cultivation of transgenic plants in a wider geographical area than their wild-type counterparts, since the territorial limitations for growing a crop are often determined by adverse environmental conditions either at the time of planting (early season) or at the time of harvesting (late season). Such adverse conditions may be avoided if the harvest cycle is shortened. The growth rate may be determined by deriving various parameters from growth curves, such parameters may be: T-Mid (the time taken for plants to reach 50% of their maximal size) and T-90 (time taken for plants to reach 90% of their maximal size), amongst others.

According to a preferred feature of the present invention, performance of the methods of the invention gives plants having an increased growth rate relative to control plants. Therefore, according to the present invention, there is provided a method for increasing the growth rate of plants, which method comprises increasing expression in a plant of a nucleic acid sequence encoding an SWI2/SNF2 polypeptide as defined herein.

An increase in yield and/or growth occurs whether the plant is grown under non-stress conditions or whether the plant is exposed to various stresses compared to control plants. Plants typically respond to exposure to stress by growing more slowly. In conditions of severe stress, the plant may even stop growing altogether. Mild stress on the other hand is defined herein as being any stress to which a plant is exposed which does not result in the plant ceasing to grow altogether without the capacity to resume growth. Mild stress in the sense of the invention leads to a reduction in the growth of the stressed plants of less than 40%, 35% or 30%, preferably less than 25%, 20% or 15%, more preferably less than 14%, 13%, 12%, 11% or 10% or less in comparison to the control plant grown under non-stress conditions. Due to advances in agricultural practices (irrigation, fertilization, pesticide treatments) severe stresses are not often encountered in cultivated crop plants. As a consequence, the compromised growth induced by mild stress is often an undesirable feature for agriculture. Mild stresses are the everyday biotic and/or abiotic (environmental) stresses to which a plant is exposed. Abiotic stresses may be due to drought or excess water, anaerobic stress, salt stress, chemical toxicity, oxidative stress and hot, cold or freezing temperatures. The abiotic stress may be an osmotic stress caused by a water stress (particularly due to drought), salt stress, oxidative stress or an ionic stress. Biotic stresses are typically those stresses caused by pathogens, such as bacteria, viruses, fungi, nematodes, and insects. The term "non-stress" conditions as used herein are preferably those environmental conditions that do not significantly go beyond the everyday climatic and other abiotic conditions that plants may encounter most preferably those conditions that allow optimal growth of plants. Persons skilled in the art are aware of normal soil conditions and climatic conditions for a given location.

Performance of the methods of the invention gives plants grown under non-stress conditions or under mild drought conditions having enhanced yield-related traits relative to control plants grown under comparable stress conditions. Therefore, according to the present invention, there is provided a method for enhancing yield-related traits in plants grown under non-stress conditions or under mild drought conditions, which method comprises increasing expression in a plant of a nucleic acid sequence encoding an SWI2/SNF2 polypeptide as defined above.

Performance of the methods according to the present invention results in plants grown under abiotic stress conditions having enhanced yield-related traits relative to control plants grown under comparable stress conditions. As reported in Wang et al. (Planta (2003) 218: 1-14), abiotic stress leads to a series of morphological, physiological, biochemical and molecular changes that adversely affect plant growth and productivity. Drought, salinity, extreme temperatures and oxidative stress are known to be interconnected and may induce growth and cellular damage through similar mechanisms. For example, drought and/or salinisation are manifested primarily as osmotic stress, resulting in the disruption of homeostasis and ion distribution in the cell. Oxidative stress, which frequently accompanies high or low temperature, salinity or drought stress may cause denaturation of functional and structural proteins. As a consequence, these diverse environmental stresses often activate similar cell signaling pathways and cellular responses, such as the production of stress proteins, up-regulation of anti-oxidants, accumulation of compatible solutes and growth arrest. Since diverse environmental stresses activate similar pathways, the exemplification of the present invention with drought stress should not be seen as a limitation to drought stress, but more as a screen to indicate the involvement of SWI2/SNF2 polypeptides as defined above, in enhancing yield-related traits relative to control plants grown in comparable stress conditions, in abiotic stresses in general.

A particularly high degree of "cross talk" is reported between drought stress and high-salinity stress (Rabbani et al. (2003) Plant Physiol 133: 1755-1767). Therefore, it would be apparent that an SWI2/SNF2 polypeptides would, along with their usefulness in enhancing yield-related traits in plants relative to control plants grown under drought stress conditions, also find use in enhancing yield-related traits in plants, relative to control plants grown under various other abiotic stress conditions.

The term "abiotic stress" as defined herein is taken to mean any one or more of: water stress (due to drought or excess water), anaerobic stress, salt stress, temperature stress (due to hot, cold or freezing temperatures), chemical toxicity stress and oxidative stress. According to one aspect of the invention, the abiotic stress is an osmotic stress, selected from water stress, salt stress, oxidative stress and ionic stress. Preferably, the water stress is drought stress. The term salt stress is not restricted to common salt (NaCl), but may be any one or more of: NaCl, KCl, LiCl, $MgCl_2$, $CaCl_2$, amongst others.

In particular, the enhanced yield-related traits in plants grown under abiotic stress conditions (preferably under drought stress conditions) relative to control plants grown in comparable stress conditions, may include one or more of the following: (i) increased aboveground area; (ii) increased total root biomass; (iii) increased thick root biomass; (iv) increased thin root biomass; (v) increased number of flowers per panicle; (vi) increased seed fill rate; (vii) increased total seed weight per plant; (viii) increased number of (filled) seeds; or (ix) increased harvest index.

Performance of the methods of the invention gives plants having enhanced yield-related traits under abiotic stress conditions relative to control plants grown in comparable stress conditions. Therefore, according to the present invention, there is provided a method for enhanced yield-related traits in plants grown under abiotic stress conditions, which method comprises increasing expression in a plant of a nucleic acid sequence encoding a SWI2/SNF2 polypeptide. According to one aspect of the invention, the abiotic stress is an osmotic stress, selected from one or more of the following: water stress, salt stress, oxidative stress and ionic stress. Preferably, the water stress is drought stress.

Another example of abiotic environmental stress is the reduced availability of one or more nutrients that need to be assimilated by the plants for growth and development. Because of the strong influence of nutrition utilization efficiency on plant yield and product quality, a huge amount of fertilizer is poured onto fields to optimize plant growth and quality. Productivity of plants ordinarily is limited by three primary nutrients, phosphorous, potassium and nitrogen, which is usually the rate-limiting element in plant growth of these three. Therefore the major nutritional element required for plant growth is nitrogen (N). It is a constituent of numerous important compounds found in living cells, including amino acids, proteins (enzymes), nucleic acids, and chlorophyll. 1.5% to 2% of plant dry matter is nitrogen and approximately 16% of total plant protein. Thus, nitrogen availability is a major limiting factor for crop plant growth and production (Frink et al. (1999) Proc Natl Acad Sci USA 96(4): 1175-1180), and has as well a major impact on protein accumulation and amino acid composition. Therefore, of great interest are crop plants with an increased yield when grown under nitrogen-limiting conditions.

The present invention encompasses plants, parts thereof (including seeds), or plant cells obtainable by the methods according to the present invention. The plants, plant parts or plant cells comprise an isolated nucleic acid transgene encoding an SWI2/SNF2 polypeptide as defined above.

The invention also provides genetic constructs and vectors to facilitate introduction and/or expression in plants of nucleic acid sequences encoding SWI2/SNF2 polypeptides. The gene constructs may be inserted into vectors, which may be commercially available, suitable for transforming into plants and suitable for expression of the gene of interest in the transformed cells. The invention also provides use of a gene construct as defined herein in the methods of the invention.

More specifically, the present invention provides a construct comprising:
 (d) a nucleic acid sequence encoding an SWI2/SNF2 polypeptide as defined above;
 (e) one or more control sequences capable of driving expression of the nucleic acid sequence of (a); and optionally
 (f) a transcription termination sequence.

The term "control sequence" and "termination sequence" are as defined herein.

In one embodiment, one of the control sequences of a construct is a tissue-specific promoter, preferably a promoter for expression in young expanding tissues. An example of a tissue-specific promoter for expression in young expanding tissues is a beta-expansin promoter, for example a rice beta-expansin promoter as represented by SEQ ID NO: 112.

Plants are transformed with a vector comprising any of the nucleic acid sequences described above. The skilled artisan is well aware of the genetic elements that must be present on the vector in order to successfully transform, select and propagate host cells containing the sequence of interest. The sequence of interest is operably linked to one or more control sequences (at least to a promoter).

Advantageously, any type of promoter may be used to drive expression of the nucleic acid sequence. The promoter may be a constitutive promoter, which refers to a promoter that is transcriptionally active during most, but not necessarily all, phases of its growth and development and under most environmental conditions, in at least one cell, tissue or organ. Alternatively, the promoter may be an inducible promoter, i.e. having induced or increased transcription initiation in response to a chemical (for a review see Gatz 1997, Annu. Rev. Plant Physiol. Plant Mol. Biol., 48:89-108), environmental or physical stimulus. Another example of an inducible promoter is a stress-inducible promoter, i.e. a promoter activated when a plant is exposed to various stress conditions, or a pathogen-induced promoter.

Additionally or alternatively, the promoter may be an organ-specific or tissue-specific promoter, i.e. one that is capable of preferentially initiating transcription in certain organs or tissues, such as the leaves, roots, seed tissue etc; or the promoter may be a ubiquitous promoter, which is active in substantially all tissues or cells of an organism, or the promoter may be developmentally regulated, thereby being active during certain developmental stages or in parts of the plant that undergo developmental changes. Promoters able to initiate transcription in certain organs or tissues only are referred to herein as "organ-specific" or "tissue-specific" respectively, similarly, promoters able to initiate transcription in certain cells only are referred to herein as "cell-specific".

In one embodiment, a nucleic acid sequence encoding SWI2/SNF2 polypeptide as defined above, such as the nucleic acid sequence as represented by SEQ ID NO: 29, is operably linked to a tissue-specific promoter, preferably to a promoter capable of preferentially expressing the nucleic acid sequence in young expanding tissues, or in the apical meristem.

Preferably, the promoter capable of preferentially expressing the nucleic acid sequence in young expanding tissues has a comparable expression profile to a beta-expansin promoter. More specifically, the promoter capable of preferentially expressing the nucleic acid sequence in young expanding tissues is a promoter capable of driving expression in the cell expansion zone of a shoot or root. Most preferably, the promoter capable of preferentially expressing the nucleic acid sequence in young expanding tissues is a beta-expansin promoter, for example a rice beta-expansin promoter as represented by SEQ ID NO: 112.

For the identification of functionally equivalent promoters, the promoter strength and/or expression pattern of a candidate promoter may be analysed for example by operably linking the promoter to a reporter gene and assaying the expression level and pattern of the reporter gene in various tissues of the plant. Suitable well-known reporter genes include for example beta-glucuronidase or beta galactosidase. The promoter activity is assayed by measuring the enzymatic activity of the beta-glucuronidase or beta-galactosidase. The promoter strength and/or expression pattern may then be compared to that of a reference promoter (such as the one used in the methods of the present invention). Alternatively, promoter strength may be assayed by quantifying mRNA levels or by comparing mRNA levels of the nucleic acid sequence used in the methods of the present invention, with mRNA levels of housekeeping genes such as 18S rRNA, using methods known in the art, such as Northern blotting with densitometric analysis of autoradiograms, quantitative real-time PCR or RT-PCR (Heid et al., 1996 Genome Methods 6: 986-994). Generally by "weak promoter" is intended a promoter that drives expression of a coding sequence at a low level. By "low level" is intended at levels of about 1/10,000 transcripts to about 1/100,000 transcripts, to about 1/500,0000 transcripts per cell. Conversely, a "strong promoter" drives expression of a coding sequence at high level, or at about 1/10 transcripts to about 1/100 transcripts to about 1/1,000 transcripts per cell.

Optionally, one or more terminator sequences may be used in the construct introduced into a plant. Additional regulatory elements may include transcriptional as well as translational enhancers. Those skilled in the art will be aware of terminator and enhancer sequences that may be suitable for use in performing the invention. Such sequences would be known or may readily be obtained by a person skilled in the art.

An intron sequence may also be added to the 5' untranslated region (UTR) or in the coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg, Mol. Cell Biol. 8:4395-4405 (1988); Callis et al., Genes Dev. 1:1183-1200 (1987)). Such intron enhancement of gene expression is typically greatest when placed near the 5' end of the transcription unit. Use of the maize introns Adh1-S intron 1, 2, and 6, the Bronze-1 intron are known in the art. For general information, see The Maize Handbook, Chapter 116, Freeling and Walbot, Eds., Springer, N.Y. (1994).

Other control sequences (besides promoter, enhancer, silencer, intron sequences, 3'UTR and/or 5'UTR regions) may be protein and/or RNA stabilizing elements. Such sequences would be known or may readily be obtained by a person skilled in the art.

The genetic constructs of the invention may further include an origin of replication sequence that is required for maintenance and/or replication in a specific cell type. One example is when a genetic construct is required to be maintained in a bacterial cell as an episomal genetic element (e.g. plasmid or cosmid molecule). Preferred origins of replication include, but are not limited to, the f1-ori and colE1.

For the detection of the successful transfer of the nucleic acid sequences as used in the methods of the invention and/or selection of transgenic plants comprising these nucleic acid sequences, it is advantageous to use marker genes (or reporter genes). Therefore, the genetic construct may optionally comprise a selectable marker gene. Selectable markers are described in more detail in the "definitions" section herein.

It is known that upon stable or transient integration of nucleic acid sequences into plant cells, only a minority of the cells takes up the foreign DNA and, if desired, integrates it into its genome, depending on the expression vector used and the transfection technique used. To identify and select these integrants, a gene coding for a selectable marker (such as the ones described above) is usually introduced into the host cells together with the gene of interest. These markers can for example be used in mutants in which these genes are not functional by, for example, deletion by conventional methods. Furthermore, nucleic acid sequences encoding a selectable marker can be introduced into a host cell on the same vector that comprises the sequence encoding the polypeptides of the invention or used in the methods of the invention, or else in a separate vector. Cells which have been stably transfected with the introduced nucleic acid sequence can be identified for example by selection (for example, cells which have integrated the selectable marker survive whereas the other cells die).

Since the marker genes, particularly genes for resistance to antibiotics and herbicides, are no longer required or are undesired in the transgenic host cell once the nucleic acid sequences have been introduced successfully, the process according to the invention for introducing the nucleic acid sequences advantageously employs techniques, which enable the removal or excision of these marker genes. One such a method is what is known as co-transformation. The co-transformation method employs two vectors simultaneously for the transformation, one vector bearing the nucleic acid sequence according to the invention and a second bearing the marker gene(s). A large proportion of transformants receives or, in the case of plants, comprises (up to 40% or more of the transformants), both vectors. In case of transformation with Agrobacteria, the transformants usually receive only a part of the vector, i.e. the sequence flanked by the T-DNA, which usually represents the expression cassette. The marker genes can subsequently be removed from the transformed plant by performing crosses. In another method, marker genes integrated into a transposon are used for the transformation together with desired nucleic acid sequence (known as the Ac/Ds technology). The transformants can be crossed with a transposase source or the transformants are transformed with a nucleic acid construct conferring expression of a transposase, transiently or stable. In some cases (approx. 10%), the transposon jumps out of the genome of the host cell once transformation has taken place successfully and is lost. In a further number of cases, the transposon jumps to a different location. In these cases the marker gene must be eliminated by performing crosses. In microbiology, techniques were developed which make possible, or facilitate, the detection of such events. A further advantageous method relies on what is known as recombination systems; whose advantage is that elimination by crossing can be dispensed with. The best-known system of this type is what is known as the Cre/lox system. Cre1 is a recombinase that removes the sequences located between the loxP sequences. If the marker gene is integrated between the loxP sequences, it is removed once transformation has taken place successfully, by expression of the recombinase. Further recombination systems are the HIN/HIX, FLP/FRT and REP/STB system (Tribble et al., J. Biol. Chem., 275, 2000: 22255-22267; Velmurugan et al., J. Cell Biol., 149, 2000: 553-566). A site-specific integration into the plant genome of the nucleic acid sequences according to the invention is possible. Naturally, these methods can also be applied to microorganisms such as yeast, fungi or bacteria.

The invention also provides a method for the production of transgenic plants having enhanced yield-related traits relative to control plants, comprising introduction and expression in a plant of any nucleic acid sequence encoding an SWI2/SNF2 polypeptide as defined hereinabove.

More specifically, the present invention provides a method for the production of transgenic plants having enhanced yield-related traits relative to control plants, which method comprises:
(i) introducing and expressing in a plant or plant cell a nucleic acid sequence encoding an SWI2/SNF2 polypeptide; and
(ii) cultivating the plant cell under conditions promoting plant growth and development.

The nucleic acid sequence may be introduced directly into a plant cell or into the plant itself (including introduction into a tissue, organ or any other part of a plant). According to a preferred feature of the present invention, the nucleic acid sequence is preferably introduced into a plant by transformation. The term "transformation" is described in more detail in the "definitions" section herein.

The genetically modified plant cells can be regenerated via all methods with which the skilled worker is familiar. Suitable methods can be found in the abovementioned publications by S. D. Kung and R. Wu, Potrykus or Höfgen and Willmitzer.

Generally after transformation, plant cells or cell groupings are selected for the presence of one or more markers which are encoded by plant-expressible genes co-transferred with the gene of interest, following which the transformed material is regenerated into a whole plant. To select transformed plants, the plant material obtained in the transformation is, as a rule, subjected to selective conditions so that transformed plants can be distinguished from untransformed plants. For example, the seeds obtained in the above-described manner can be planted and, after an initial growing period, subjected to a suitable selection by spraying. A further possibility consists in growing the seeds, if appropriate after sterilization, on agar plates using a suitable selection agent so that only the transformed seeds can grow into plants. Alternatively, the transformed plants are screened for the presence of a selectable marker such as the ones described above.

Following DNA transfer and regeneration, putatively transformed plants may also be evaluated, for instance using Southern analysis or quantitative PCR, for the presence of the gene of interest, copy number and/or genomic organisation. Alternatively or additionally, expression levels of the newly introduced DNA may be monitored using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed and homozygous second-generation (or T2) transformants selected, and the T2 plants may then further be propagated through classical breeding techniques.

The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

The present invention clearly extends to any plant cell or plant produced by any of the methods described herein, and to all plant parts and propagules thereof. The present invention extends further to encompass the progeny of a primary transformed or transfected cell, tissue, organ or whole plant that has been produced by any of the aforementioned methods, the only requirement being that progeny exhibit the same genotypic and/or phenotypic characteristic(s) as those produced by the parent in the methods according to the invention.

The invention also includes host cells containing an isolated nucleic acid sequence encoding an SWI2/SNF2 polypeptide as defined hereinabove. Preferred host cells according to the invention are plant cells. Host plants for the nucleic acid sequences or the vector used in the method according to the invention, the expression cassette or construct or vector are, in principle, advantageously all plants, which are capable of synthesizing the polypeptides used in the inventive method.

The methods of the invention are advantageously applicable to any plant. Plants that are particularly useful in the methods of the invention include all plants which belong to the superfamily Viridiplantae, in particular monocotyledonous and dicotyledonous plants including fodder or forage legumes, ornamental plants, food crops, trees or shrubs. According to a preferred embodiment of the present invention, the plant is a crop plant. Examples of crop plants include soybean, sunflower, canola, alfalfa, rapeseed, cotton, tomato, potato and tobacco. Further preferably, the plant is a monocotyledonous plant. Examples of monocotyledonous plants include sugarcane. More preferably the plant is a cereal. Examples of cereals include rice, maize, wheat, barley, millet, rye, triticale, sorghum and oats.

The invention also extends to harvestable parts of a plant such as, but not limited to seeds, leaves, fruits, flowers, stems, rhizomes, tubers and bulbs. The invention furthermore relates to products derived, preferably directly derived, from a harvestable part of such a plant, such as dry pellets or powders, oil, fat and fatty acids, starch or proteins.

Methods for increasing expression of nucleic acid sequences or genes, or gene products, are well documented in the art and include, for example, overexpression driven by appropriate promoters, the use of transcription enhancers or translation enhancers. Isolated nucleic acid sequences which serve as promoter or enhancer elements may be introduced in an appropriate position (typically upstream) of a non-heterologous form of a polynucleotide so as to upregulate expression. For example, endogenous promoters may be altered in vivo by mutation, deletion, and/or substitution (see, Kmiec, U.S. Pat. No. 5,565,350; Zarling et al., PCT/US93/03868), or isolated promoters may be introduced into a plant cell in the proper orientation and distance from a gene of the present invention so as to control the expression of the gene.

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added may be derived from, for example, the nopaline synthase or octopine synthase genes, or alternatively from another plant gene, or less preferably from any other eukaryotic gene.

As mentioned above, a preferred method for increasing expression of a nucleic acid sequence encoding an SWI2/SNF2 polypeptide is by introducing and expressing in a plant a nucleic acid sequence encoding an SWI2/SNF2 polypeptide; however the effects of performing the method, i.e. enhancing yield-related traits, may also be achieved using other well known techniques. A description of some of these techniques will now follow.

One such technique is T-DNA activation tagging (Hayashi et al. Science (1992) 1350-1353), which involves insertion of T-DNA, usually containing a promoter (may also be a translation enhancer or an intron), in the genomic region of the gene of interest or 10 kb up- or downstream of the coding region of a gene in a configuration such that the promoter directs expression of the targeted gene. Typically, regulation of expression of the targeted gene by its natural promoter is disrupted and the gene falls under the control of the newly introduced promoter. The promoter is typically embedded in a T-DNA. This T-DNA is randomly inserted into the plant genome, for example, through Agrobacterium infection and leads to modified expression of genes near the inserted T-DNA. The resulting transgenic plants show dominant phenotypes due to modified expression of genes close to the introduced promoter.

The effects of the invention may also be reproduced using the technique of TILLING (Targeted Induced Local Lesions In Genomes); for a description of the same see the "definitions" section.

The effects of the invention may also be reproduced using homologous recombination; for a description of the same see the "definitions" section.

The present invention also encompasses use of nucleic acid sequences encoding SWI2/SNF2 polypeptides as described herein and use of these SWI2/SNF2 polypeptides in enhancing yield-related traits in plants relative to control plants. Preferably, enhanced yield-related traits is one or more of: (i) increased number of flowers per panicle; (ii) increased total seed weight per plant; (iii) increased number of (filled) seeds; or (iv) increased harvest index.

The present invention further encompasses use of nucleic acid sequences encoding SWI2/SNF2 polypeptides as described herein and use of these SWI2/SNF2 polypeptides in enhancing yield-related traits in plants grown under abiotic stress conditions (preferably under drought stress conditions), relative to control plants grown under comparable stress conditions. Preferably, enhanced yield-related traits are one or more of: (i) increased aboveground area; (ii) increased total root biomass; (iii) increased thick root biomass; (iv) increased thin root biomass; (v) increased number of flowers per panicle; (vi) increased seed fill rate; (vii) increased total seed weight per plant; (viii) increased number of (filled) seeds; or (ix) increased harvest index.

Nucleic acid sequences encoding SWI2/SNF2 polypeptides described herein, or the SWI2/SNF2 polypeptides themselves, may find use in breeding programmes in which a DNA marker is identified, which may be genetically linked to a gene encoding an SWI2/SNF2 polypeptide. The genes/nucleic acid sequences or the SWI2/SNF2 polypeptides themselves may be used to define a molecular marker. This DNA or protein marker may then be used in breeding programmes to select plants having enhanced yield-related traits as defined hereinabove in the methods of the invention.

Allelic variants of a gene/nucleic acid sequence encoding an SWI2/SNF2 polypeptide may also find use in marker-assisted breeding programmes. Such breeding programmes sometimes require introduction of allelic variation by mutagenic treatment of the plants, using for example EMS mutagenesis; alternatively, the programme may start with a collection of allelic variants of so called "natural" origin caused unintentionally. Identification of allelic variants then takes place, for example, by PCR. This is followed by a step for selection of superior allelic variants of the sequence in question and which give enhanced yield-related traits. Selection is typically carried out by monitoring growth performance of plants containing different allelic variants of the sequence in question. Growth performance may be monitored in a greenhouse or in the field. Further optional steps include crossing plants in which the superior allelic variant was identified with another plant. This could be used, for example, to make a combination of interesting phenotypic features.

Nucleic acid sequences encoding SWI2/SNF2 polypeptides may also be used as probes for genetically and physically mapping the genes that they are a part of, and as markers for traits linked to those genes. Such information may be useful in plant breeding in order to develop lines with desired phenotypes. Such use of nucleic acid sequences encoding an SWI2/SNF2 polypeptide requires only a nucleic acid sequence of at least 15 nucleotides in length. The nucleic acid sequences encoding an SWI2/SNF2 polypeptide may be used as restriction fragment length polymorphism (RFLP) markers. Southern blots (Sambrook J, Fritsch E F and Maniatis T (1989) Molecular Cloning, A Laboratory Manual) of restriction-digested plant genomic DNA may be probed with nucleic acid sequences encoding the SWI2/SNF2 polypeptide. The resulting banding patterns may then be subjected to genetic analyses using computer programs such as MapMaker (Lander et al. (1987) Genomics 1: 174-181) in order to construct a genetic map. In addition, the nucleic acid sequences may be used to probe Southern blots containing restriction endonuclease-treated genomic DNAs of a set of individuals representing parent and progeny of a defined genetic cross. Segregation of the DNA polymorphisms is noted and used to calculate the position of the nucleic acid sequence encoding the SWI2/SNF2 polypeptide in the genetic map previously obtained using this population (Botstein et al. (1980) Am. J. Hum. Genet. 32:314-331).

The production and use of plant gene-derived probes for use in genetic mapping is described in Bernatzky and Tanksley (1986) Plant Mol. Biol. Reporter 4: 37-41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

The nucleic acid probes may also be used for physical mapping (i.e., placement of sequences on physical maps; see Hoheisel et al. In: Non-mammalian Genomic Analysis: A Practical Guide, Academic press 1996, pp. 319-346, and references cited therein).

In another embodiment, the nucleic acid probes may be used in direct fluorescence in situ hybridisation (FISH) mapping (Trask (1991) Trends Genet. 7:149-154). Although current methods of FISH mapping favour use of large clones (several kb to several hundred kb; see Laan et al. (1995) Genome Res. 5:13-20), improvements in sensitivity may allow performance of FISH mapping using shorter probes.

A variety of nucleic acid amplification-based methods for genetic and physical mapping may be carried out using the nucleic acid sequences. Examples include allele-specific amplification (Kazazian (1989) J. Lab. Clin. Med 11:95-96), polymorphism of PCR-amplified fragments (CAPS; Sheffield et al. (1993) Genomics 16:325-332), allele-specific ligation (Landegren et al. (1988) Science 241:1077-1080), nucleotide extension reactions (Sokolov (1990) Nucleic Acid Res. 18:3671), Radiation Hybrid Mapping (Walter et al. (1997) Nat. Genet. 7:22-28) and Happy Mapping (Dear and Cook (1989) Nucleic Acid Res. 17:6795-6807). For these methods, the sequence of a nucleic acid is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

The methods according to the present invention result in plants having enhanced yield-related traits relative to control plants, as described hereinbefore. This trait may also be combined with other economically advantageous traits, such as further yield-enhancing traits (under normal or stress growth conditions), tolerance to other abiotic and biotic stresses, traits modifying various architectural features and/or biochemical and/or physiological features.

DESCRIPTION OF FIGURES

The present invention will now be described with reference to the following figures in which:

FIG. 1 shows an alignment of HpaG polypeptides with motifs 1 and 2 indicated in bold and underlined for SEQ ID NO: 2. The sequences shown are: ABJ97680 (SEQ IDNO: 20); AAC95121 (SED IDNO: 22): BAD29979 (SEO IDNO: 24): ABB72197 (SEO IDNO: 26): ABK51590 (SEQ IDNO: 14); ABK51589 (SEQ IDNO: 8); ABK51587 (SEQ IDNO: 10); ABK51588 (SEQ IDNO: 16) AAM35307 (SEQ IDNO: 12); ABG36696 (SEQ IDNO: 18); AAM40538 (SEQ IDNO: 28).

FIG. 4 details examples of Harpin sequences useful in performing the methods according to the present invention.

FIG. 10 details examples of SNF2 sequences useful in performing the methods according to the present invention.

EXAMPLES

The present invention will now be described with reference to the following examples, which are by way of illustration alone. The following examples are not intended to completely define or otherwise limit the scope of the invention.

Example 1

Identification of HpaG Sequences

Sequences (full length cDNA, ESTs or genomic) related to SEQ ID NO: 1 and/or protein sequences related to SEQ ID NO: 2 were identified amongst those maintained in the Entrez Nucleotides database at the National Center for Biotechnology Information (NCBI) using database sequence search tools, such as the Basic Local Alignment Tool (BLAST) (Altschul et al. (1990) J. Mol. Biol. 215:403-410; and Altschul et al. (1997) Nucleic Acids Res. 25:3389-3402). The program was used to find regions of local similarity between sequences by comparing nucleic acid or polypeptide sequences to sequence databases and by calculating the statistical significance of matches. The polypeptide encoded by SEQ ID NO: 1 was used for the TBLASTN algorithm, with default settings and the filter to ignore low complexity sequences set off. The output of the analysis was viewed by pairwise comparison, and ranked according to the probability score (E-value), where the score reflects the probability that a particular alignment occurs by chance (the lower the E-value, the more significant the hit). In addition to E-values, comparisons were also scored by percentage identity. Percentage identity refers to the number of identical nucleotides (or amino acids) between the two compared nucleic acid (or polypeptide) sequences over a particular length. In some instances, the default parameters may be adjusted to modify the stringency of the search.

Table A provides a list of nucleic acid and protein sequences related to the nucleic acid sequence as represented by SEQ ID NO: 1 and the protein sequence represented by SEQ ID NO: 2.

Example 2

Alignment of HpaG Polypeptide Sequences

Alignment of polypeptide sequences (FIG. 1) was performed using the ClustalW programme which is based on the popular Clustal algorithm of progressive alignment (Thompson et al. (1997) Nucleic Acids Res 25:4876-4882; Chenna et al. (2003). Nucleic Acids Res 31:3497-3500). Default values are for the gap open penalty of 10, for the gap extension penalty of 0.1 and the selected weight matrix is Blosum 62 (if polypeptides are aligned). Minor manual editing was done to further optimise the alignment.

Figure 2:
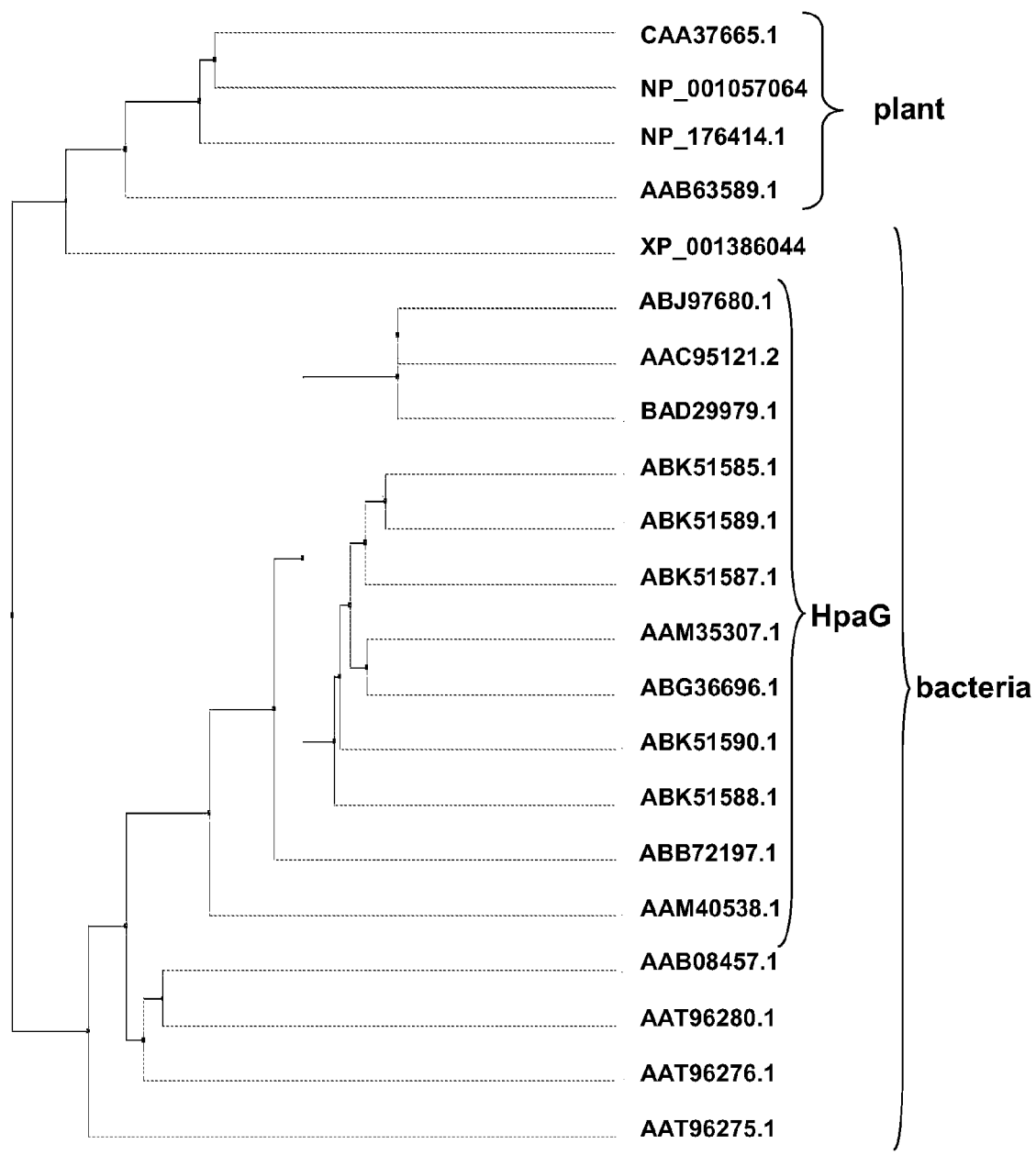
FIG. 2 shows a phylogenetic tree with the group of HpaG polypeptides delineated from other bacterial and from plant proteins (the various sequences are indicated by their GenBank accession numbers and/or gi numbers).
Figure 3:
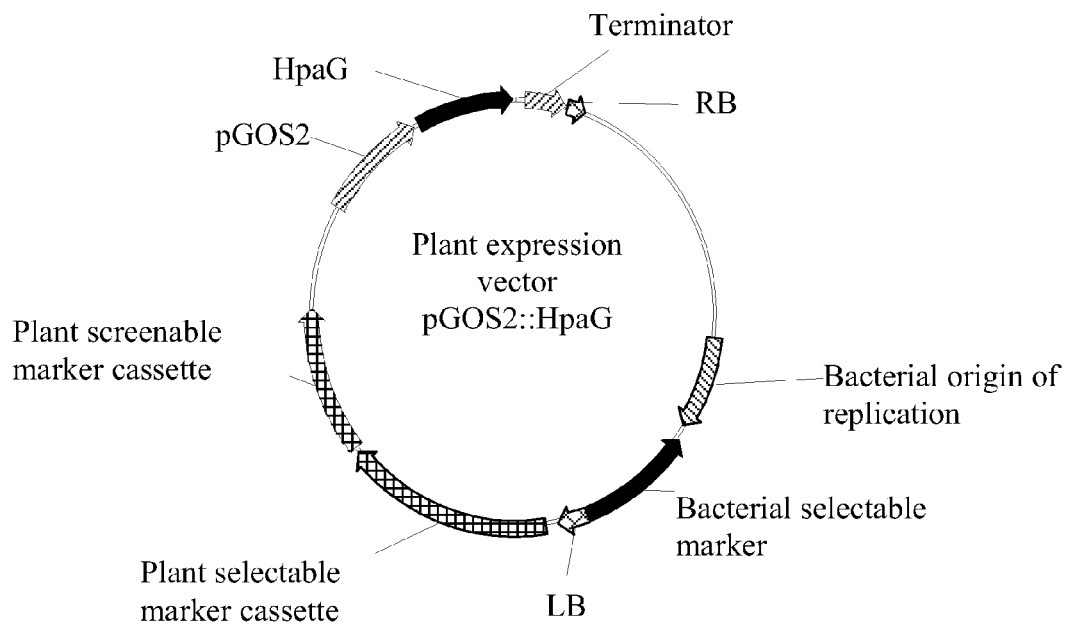
FIG. 3 shows the binary vector for increased expression in Oryza sativa of an HpaG protein-encoding nucleic acid from Xanthomonas under the control of a rice GOS2 promoter (pGOS2).
Figure 5:
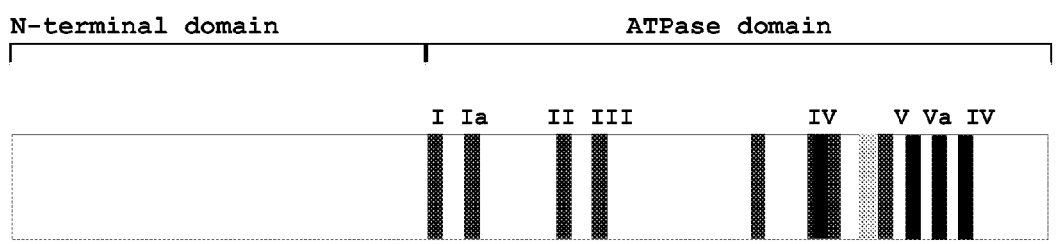
FIG. 5 shows a scheme of the structure of SWI2/SNF2 polypeptides useful in performing the methods of the invention. The SWI2/SNF2 polypeptides useful in performing the methods of the invention comprise an N-terminal domain and an ATPase domain, both marked as an open box. The typical 8 motifs I, Ia, II, III, IV, V, Va and VI comprised in the ATPase domain of the SWI2/SNF2 polypeptides useful in performing the methods of the invention are marked as black vertical lines.

A phylogenetic tree of HpaG polypeptides (FIG. 2) was constructed using a neighbour-joining clustering algorithm as provided in the AlignX programme from the Vector NTI (Invitrogen).

Example 3

Calculation of Global Percentage Identity Between Polypeptide Sequences Useful in Performing the Methods of the Invention Global percentages of similarity and identity between full length polypeptide sequences useful in performing the methods of the invention were determined using one of the methods available in the art, the MatGAT (Matrix Global Alignment Tool) software (Campanella et al., BMC Bioinformatics. 2003 4:29. MatGAT: an application that generates similarity/identity matrices using protein or DNA sequences). MatGAT software generates similarity/identity matrices for DNA or protein sequences without needing pre-alignment of the data. The program performs a series of pair-wise alignments using the Myers and Miller global alignment algorithm (with a gap opening penalty of 12, and a gap extension penalty of 2), calculates similarity and identity using for example Blosum 62 (for polypeptides), and then places the results in a distance matrix. Sequence similarity is shown in the bottom half of the dividing line and sequence identity is shown in the top half of the diagonal dividing line.

Parameters used in the comparison were:
Scoring matrix: Blosum62
First Gap: 12
Extending gap: 2

TABLE A

HpaG-encoding nucleic acid sequences and HpaG polypeptides useful in the methods of the present invention.

| Name | Source organism | Nucleic acid SEQ ID NO: | Polypeptide SEQ ID NO: | Status |
| --- | --- | --- | --- | --- |
| HpaG | *Xanthomonas axonopodis* | 1 | 2 | Full length |
| HpaG_T44C | Synthetic construct | 7 | 8 | Full length |
| HpaG-T | Synthetic construct | 9 | 10 | Full length |
| Hpa1 | *Xanthomonas axonopodis* pv. citri str. 306 | 11 | 12 | Full length |
| HpaG-N | Synthetic construct | 13 | 14 | Full length |
| HpaG_G | *Xanthomonas axonopodis* | 15 | 16 | Full length |
| Hrp | *Xanthomonas smithii* subsp. *smithii* | 17 | 18 | Full length |
| hypersensitive response-functioning factor A | *Xanthomonas oryzae* pv. *oryzae* strain JXOIII | 19 | 20 | Full length |
| Hpa1 | *Xanthomonas oryzae* pv. *oryzae* | 21 | 22 | Full length |
| Hpa1 | *Xanthomonas oryzae* pv. *oryzae* | 23 | 24 | Full length |
| hpaGXooc | *Xanthomonas oryzae* pv. oryzicola | 25 | 26 | Full length |
| Hpa1 | *Xanthomonas campestris* pv. *campestris* str. ATCC 33913 | 27 | 28 | Full length |

Results of the software analysis are shown in Table B for the global similarity and identity over the full length of the polypeptide sequences (excluding the partial polypeptide sequences).

Percentage identity is given above the diagonal in bold and percentage similarity is given below the diagonal (normal face).

The percentage identity between the HpaG polypeptide sequences useful in performing the methods of the invention can be as low as 37% amino acid identity compared to SEQ ID NO: 9.

Example 5

Plant Transformation

Rice Transformation

The *Agrobacterium* containing the expression vector was used to transform *Oryza sativa* plants. Mature dry seeds of the rice japonica cultivar Nipponbare were dehusked. Sterilization was carried out by incubating for one minute in 70% ethanol, followed by 30 minutes in 0.2% $HgCl_2$, followed by a 6 times 15 minutes wash with sterile distilled water. The

TABLE B

MatGAT results for global similarity and identity over the full length of the polypeptide sequences.

|  | 1 | 2 | 3 | 4 | 5 | 6 | 7 | 8 | 9 | 10 | 11 | 12 |
|---|---|---|---|---|---|---|---|---|---|---|---|---|
| 1. SEQ ID NO: 2 |  | 99.2 | 94.0 | 91.2 | 91.0 | 90.2 | 85.4 | 66.7 | 66.7 | 66.7 | 59.6 | 37.7 |
| 2. ABK51589 | 99.2 |  | 93.2 | 90.5 | 90.2 | 89.5 | 84.7 | 67.4 | 67.4 | 67.4 | 60.3 | 37.7 |
| 3. ABK51587 | 94.0 | 93.2 |  | 85.4 | 85.0 | 92.0 | 79.6 | 60.3 | 60.3 | 60.3 | 56.4 | 33.3 |
| 4. AAM35307 | 92.0 | 91.2 | 86.1 |  | 82.5 | 81.8 | 89.8 | 70.9 | 70.9 | 70.9 | 61.4 | 36.6 |
| 5. ABK51590 | 91.0 | 90.2 | 90.4 | 83.2 |  | 81.2 | 76.6 | 57.4 | 57.4 | 57.4 | 50.7 | 32.8 |
| 6. ABK51588 | 90.2 | 89.5 | 92.0 | 82.5 | 89.3 |  | 75.2 | 58.2 | 58.2 | 58.2 | 56.4 | 33.8 |
| 7. ABG36696 | 89.5 | 88.7 | 83.5 | 92.7 | 80.5 | 79.7 |  | 70.7 | 70.7 | 70.7 | 58.8 | 37.0 |
| 8. ABJ97680 | 77.0 | 77.7 | 70.5 | 80.6 | 67.6 | 68.3 | 81.3 |  | 100.0 | 100.0 | 64.5 | 35.0 |
| 9. AAC95121 | 77.0 | 77.7 | 70.5 | 80.6 | 67.6 | 68.3 | 81.3 | 100.0 |  | 100.0 | 64.5 | 35.0 |
| 10. BAD29979 | 77.0 | 77.7 | 70.5 | 80.6 | 67.6 | 68.3 | 81.3 | 100.0 | 100.0 |  | 64.5 | 35.0 |
| 11. ABB72197 | 72.9 | 73.7 | 72.8 | 73.7 | 68.0 | 72.8 | 72.9 | 72.7 | 72.7 | 72.7 |  | 34.6 |
| 12. AAM40538 | 51.9 | 51.9 | 48.0 | 49.6 | 46.3 | 50.4 | 50.4 | 45.3 | 45.3 | 45.3 | 53.6 |  |

Example 4

Cloning and Vector Construction

Unless otherwise stated, recombinant DNA techniques are performed according to standard protocols described in (Sambrook (2001) Molecular Cloning: a laboratory manual, 3rd Edition Cold Spring Harbor Laboratory Press, CSH, New York) or in Volumes 1 and 2 of Ausubel et al. (1994), Current Protocols in Molecular Biology, Current Protocols. Standard materials and methods for plant molecular work are described in Plant Molecular Biology Labfax (1993) by R. D. D. Croy, published by BIOS Scientific Publications Ltd (UK) and Blackwell Scientific Publications (UK).

The *Xanthomonas* HpaG coding sequence was amplified by PCR from a *Xanthomonas axonopodis* DNA library. The PCR fragment of the expected length was purified and subsequently cloned in a Gateway® vector using standard technology. The entry clone comprising SEQ ID NO: 1 was then used in an LR reaction with a destination vector used for Oryza sativa transformation. This vector contained as functional elements within the T-DNA borders: a plant selectable marker; a screenable marker expression cassette; and a Gateway cassette intended for LR in vivo recombination with the nucleic acid sequence of interest already cloned in the entry clone. A rice GOS2 promoter (SEQ ID NO: 5) for constitutive expression was located upstream of this Gateway cassette. Alternatively, a green tissue specific promoter, such as the protochlorophyllide reductase promoter (SEQ ID NO: 6), was shown to be equally useful.

After the LR recombination step, the resulting expression vector pGOS2::HpaG was transformed into *Agrobacterium* strain LBA4044 according to methods well known in the art.

sterile seeds were then germinated on a medium containing 2,4-D (callus induction medium). After incubation in the dark for four weeks, embryogenic, scutellum-derived calli were excised and propagated on the same medium. After two weeks, the calli were multiplied or propagated by subculture on the same medium for another 2 weeks. Embryogenic callus pieces were sub-cultured on fresh medium 3 days before co-cultivation (to boost cell division activity).

*Agrobacterium* strain LBA4404 containing the expression vector was used for co-cultivation. *Agrobacterium* was inoculated on AB medium with the appropriate antibiotics and cultured for 3 days at 28° C. The bacteria were then collected and suspended in liquid co-cultivation medium to a density ($OD_{600}$) of about 1. The suspension was then transferred to a Petri dish and the calli immersed in the suspension for 15 minutes. The callus tissues were then blotted dry on a filter paper and transferred to solidified, co-cultivation medium and incubated for 3 days in the dark at 25° C. Co-cultivated calli were grown on 2,4-D-containing medium for 4 weeks in the dark at 28° C. in the presence of a selection agent. During this period, rapidly growing resistant callus islands developed. After transfer of this material to a regeneration medium and incubation in the light, the embryogenic potential was released and shoots developed in the next four to five weeks. Shoots were excised from the calli and incubated for 2 to 3 weeks on an auxin-containing medium from which they were transferred to soil. Hardened shoots were grown under high humidity and short days in a greenhouse.

Approximately 35 independent T0 rice transformants were generated for one construct. The primary transformants were transferred from a tissue culture chamber to a greenhouse. After a quantitative PCR analysis to verify copy number of the T-DNA insert, only single copy transgenic plants that exhibit tolerance to the selection agent were kept for harvest of T1 seed. Seeds were then harvested three to five months after transplanting. The method yielded single locus transformants at a rate of over 50% (Aldemita and Hodges 1996, Chan et al. 1993, Hiei et al. 1994).

Corn Transformation

Transformation of maize (*Zea mays*) is performed with a modification of the method described by Ishida et al. (1996) Nature Biotech 14(6): 745-50. Transformation is genotype-dependent in corn and only specific genotypes are amenable to transformation and regeneration. The inbred line A188 (University of Minnesota) or hybrids with A188 as a parent are good sources of donor material for transformation, but other genotypes can be used successfully as well. Ears are harvested from corn plant approximately 11 days after pollination (DAP) when the length of the immature embryo is about 1 to 1.2 mm. Immature embryos are cocultivated with *Agrobacterium tumefaciens* containing the expression vector, and transgenic plants are recovered through organogenesis. Excised embryos are grown on callus induction medium, then maize regeneration medium, containing the selection agent (for example imidazolinone but various selection markers can be used). The Petri plates are incubated in the light at 25° C. for 2-3 weeks, or until shoots develop. The green shoots are transferred from each embryo to maize rooting medium and incubated at 25° C. for 2-3 weeks, until roots develop. The rooted shoots are transplanted to soil in the greenhouse. T1 seeds are produced from plants that exhibit tolerance to the selection agent and that contain a single copy of the T-DNA insert.

Wheat Transformation

Transformation of wheat is performed with the method described by Ishida et al. (1996) Nature Biotech 14(6): 745-50. The cultivar Bobwhite (available from CIMMYT, Mexico) is commonly used in transformation. Immature embryos are co-cultivated with *Agrobacterium tumefaciens* containing the expression vector, and transgenic plants are recovered through organogenesis. After incubation with *Agrobacterium*, the embryos are grown in vitro on callus induction medium, then regeneration medium, containing the selection agent (for example imidazolinone but various selection markers can be used). The Petri plates are incubated in the light at 25° C. for 2-3 weeks, or until shoots develop. The green shoots are transferred from each embryo to rooting medium and incubated at 25° C. for 2-3 weeks, until roots develop. The rooted shoots are transplanted to soil in the greenhouse. T1 seeds are produced from plants that exhibit tolerance to the selection agent and that contain a single copy of the T-DNA insert.

Soybean Transformation

Soybean is transformed according to a modification of the method described in the Texas A&M U.S. Pat. No. 5,164,310. Several commercial soybean varieties are amenable to transformation by this method. The cultivar Jack (available from the Illinois Seed foundation) is commonly used for transformation. Soybean seeds are sterilised for in vitro sowing. The hypocotyl, the radicle and one cotyledon are excised from seven-day old young seedlings. The epicotyl and the remaining cotyledon are further grown to develop axillary nodes. These axillary nodes are excised and incubated with *Agrobacterium tumefaciens* containing the expression vector. After the cocultivation treatment, the explants are washed and transferred to selection media. Regenerated shoots are excised and placed on a shoot elongation medium. Shoots no longer than 1 cm are placed on rooting medium until roots develop. The rooted shoots are transplanted to soil in the greenhouse. T1 seeds are produced from plants that exhibit tolerance to the selection agent and that contain a single copy of the T-DNA insert.

Rapeseed/Canola Transformation

Cotyledonary petioles and hypocotyls of 5-6 day old young seedling are used as explants for tissue culture and transformed according to Babic et al. (1998, Plant Cell Rep 17: 183-188). The commercial cultivar Westar (Agriculture Canada) is the standard variety used for transformation, but other varieties can also be used. Canola seeds are surface-sterilized for in vitro sowing. The cotyledon petiole explants with the cotyledon attached are excised from the in vitro seedlings, and inoculated with *Agrobacterium* (containing the expression vector) by dipping the cut end of the petiole explant into the bacterial suspension. The explants are then cultured for 2 days on MSBAP-3 medium containing 3 mg/l BAP, 3% sucrose, 0.7% Phytagar at 23° C., 16 hr light. After two days of co-cultivation with *Agrobacterium*, the petiole explants are transferred to MSBAP-3 medium containing 3 mg/l BAP, cefotaxime, carbenicillin, or timentin (300 mg/l) for 7 days, and then cultured on MSBAP-3 medium with cefotaxime, carbenicillin, or timentin and selection agent until shoot regeneration. When the shoots are 5-10 mm in length, they are cut and transferred to shoot elongation medium (MSBAP-0.5, containing 0.5 mg/l BAP). Shoots of about 2 cm in length are transferred to the rooting medium (MS0) for root induction. The rooted shoots are transplanted to soil in the greenhouse. T1 seeds are produced from plants that exhibit tolerance to the selection agent and that contain a single copy of the T-DNA insert.

Alfalfa Transformation

A regenerating clone of alfalfa (Medicago sativa) is transformed using the method of (McKersie et al., 1999 Plant Physiol 119: 839-847). Regeneration and transformation of alfalfa is genotype dependent and therefore a regenerating plant is required. Methods to obtain regenerating plants have been described. For example, these can be selected from the cultivar Rangelander (Agriculture Canada) or any other commercial alfalfa variety as described by Brown DCW and A Atanassov (1985. Plant Cell Tissue Organ Culture 4: 111-112). Alternatively, the RA3 variety (University of Wisconsin) has been selected for use in tissue culture (Walker et al., 1978 Am J Bot 65:654-659). Petiole explants are cocultivated with an overnight culture of *Agrobacterium tumefaciens* C58C1 pMP90 (McKersie et al., 1999 Plant Physiol 119: 839-847) or LBA4404 containing the expression vector. The explants are cocultivated for 3 d in the dark on SH induction medium containing 288 mg/L Pro, 53 mg/L thioproline, 4.35 g/L K2SO4, and 100 μm acetosyringinone. The explants are washed in half-strength Murashige-Skoog medium (Murashige and Skoog, 1962) and plated on the same SH induction medium without acetosyringinone but with a suitable selection agent and suitable antibiotic to inhibit Agrobacterium growth. After several weeks, somatic embryos are transferred to BOi2Y development medium containing no growth regulators, no antibiotics, and 50 g/L sucrose. Somatic embryos are subsequently germinated on half-strength Murashige-Skoog medium. Rooted seedlings were transplanted into pots and grown in a greenhouse. T1 seeds are produced from plants that exhibit tolerance to the selection agent and that contain a single copy of the T-DNA insert.

Cotton Transformation

Cotton is transformed using Agrobacterium tumefaciens according to the method described in U.S. Pat. No. 5,159,135. Cotton seeds are surface sterilised in 3% sodium hypochlorite solution during 20 minutes and washed in distilled water with 500 μg/ml cefotaxime. The seeds are then transferred to SH-medium with 50 μg/ml benomyl for germination. Hypocotyls of 4 to 6 days old seedlings are removed, cut into 0.5 cm pieces and are placed on 0.8% agar. An *Agrobacterium* suspension (approx. 108 cells per ml, diluted from an overnight culture transformed with the gene of interest and suitable selection markers) is used for inoculation of the hypocotyl explants. After 3 days at room temperature and lighting, the tissues are transferred to a solid medium (1.6 g/l Gelrite) with Murashige and Skoog salts with B5 vitamins (Gamborg et al., Exp. Cell Res. 50:151-158 (1968)), 0.1 mg/l 2,4-D, 0.1 mg/l 6-furfurylaminopurine and 750 μg/ml MgCL2, and with 50 to 100 μg/ml cefotaxime and 400-500 μg/ml carbenicillin to kill residual bacteria. Individual cell lines are isolated after two to three months (with subcultures every four to six weeks) and are further cultivated on selective medium for tissue amplification (30° C., 16 hr photoperiod). Transformed tissues are subsequently further cultivated on non-selective medium during 2 to 3 months to give rise to somatic embryos. Healthy looking embryos of at least 4 mm length are transferred to tubes with SH medium in fine vermiculite, supplemented with 0.1 mg/l indole acetic acid, 6 furfurylaminopurine and gibberellic acid. The embryos are cultivated at 30° C. with a photoperiod of 16 hrs, and plantlets at the 2 to 3 leaf stage are transferred to pots with vermiculite and nutrients. The plants are hardened and subsequently moved to the greenhouse for further cultivation.

Example 6

Phenotypic Evaluation Procedure 6.1 Evaluation Setup

Approximately 35 independent TO rice transformants were generated. The primary transformants were transferred from a tissue culture chamber to a greenhouse for growing and harvest of T1 seed. Six events, of which the T1 progeny segregated 3:1 for presence/absence of the transgene, were retained. For each of these events, approximately 10 T1 seedlings containing the transgene (hetero- and homo-zygotes) and approximately 10 T1 seedlings lacking the transgene (nullizygotes) were selected by monitoring visual marker expression. The transgenic plants and the corresponding nullizygotes were grown side-by-side at random positions. Greenhouse conditions were of shorts days (12 hours light), 28° C. in the light and 22° C. in the dark, and a relative humidity of 70%.

Four T1 events were further evaluated in the T2 generation following the same evaluation procedure as for the T1 generation but with more individuals per event. From the stage of sowing until the stage of maturity the plants were passed several times through a digital imaging cabinet. At each time point digital images (2048×1536 pixels, 16 million colours) were taken of each plant from at least 6 different angles.

Drought Screen

Plants from six events (T2 seeds) were grown in potting soil under normal conditions until they approached the heading stage. They were then transferred to a "dry" section where irrigation was withheld. Humidity probes were inserted in randomly chosen pots to monitor the soil water content (SWC). When SWC went below certain thresholds, the plants were automatically re-watered continuously until a normal level was reached again. The plants were then re-transferred again to normal conditions. The rest of the cultivation (plant maturation, seed harvest) was the same as for plants not grown under abiotic stress conditions. Growth and yield parameters are recorded as detailed for growth under normal conditions.

Nitrogen Use Efficiency Screen

Rice plants from T2 seeds are grown in potting soil under normal conditions except for the nutrient solution. The pots are watered from transplantation to maturation with a specific nutrient solution containing reduced N nitrogen (N) content, usually between 7 to 8 times less.

The rest of the cultivation (plant maturation, seed harvest) is the same as for plants not grown under abiotic stress. Growth and yield parameters are recorded as detailed for growth under normal conditions.

Salt Stress Screen

Plants are grown on a substrate made of coco fibers and argex (3 to 1 ratio). A normal nutrient solution is used during the first two weeks after transplanting the plantlets in the greenhouse. After the first two weeks, 25 mM of salt (NaCl) is added to the nutrient solution, until the plants are harvested. Seed-related parameters were then measured.

6.2 Statistical Analysis: F-Test

A two factor ANOVA (analysis of variants) was used as a statistical model for the overall evaluation of plant phenotypic characteristics. An F-test was carried out on all the parameters measured of all the plants of all the events transformed with the gene of the present invention. The F-test was carried out to check for an effect of the gene over all the transformation events and to verify for an overall effect of the gene, also known as a global gene effect. The threshold for significance for a true global gene effect was set at a 5% probability level for the F-test. A significant F-test value points to a gene effect, meaning that it is not only the mere presence or position of the gene that is causing the differences in phenotype.

Because two experiments with overlapping events were carried out, a combined analysis was performed. This is useful to check consistency of the effects over the two experiments, and if this is the case, to accumulate evidence from both experiments in order to increase confidence in the conclusion. The method used was a mixed-model approach that takes into account the multilevel structure of the data (i.e. experiment-event-segregants). P-values were obtained by comparing likelihood ratio test to chi square distributions.

6.3 Parameters Measured

Biomass-Related Parameter Measurement

From the stage of sowing until the stage of maturity the plants were passed several times through a digital imaging cabinet. At each time point digital images (2048×1536 pixels, 16 million colours) were taken of each plant from at least 6 different angles.

The plant aboveground area (or leafy biomass) was determined by counting the total number of pixels on the digital images from aboveground plant parts discriminated from the background. This value was averaged for the pictures taken on the same time point from the different angles and was converted to a physical surface value expressed in square mm by calibration. Experiments show that the aboveground plant area measured this way correlates with the biomass of plant parts above ground. The above ground area is the area measured at the time point at which the plant had reached its maximal leafy biomass. The early vigour is the plant (seedling) aboveground area three weeks post-germination. Increase in root biomass is expressed as an increase in total root biomass (measured as maximum biomass of roots observed during the lifespan of a plant); or as an increase in the root/shoot index (measured as the ratio between root mass and shoot mass in the period of active growth of root and shoot).

Early vigour was determined by counting the total number of pixels from aboveground plant parts discriminated from the background. This value was averaged for the pictures taken on the same time point from different angles and was converted to a physical surface value expressed in square mm by calibration. The results described below are for plants three weeks post-germination.

Seed-Related Parameter Measurements

The mature primary panicles were harvested, counted, bagged, barcode-labelled and then dried for three days in an oven at 37° C. The panicles were then threshed and all the seeds were collected and counted. The filled husks were separated from the empty ones using an air-blowing device. The empty husks were discarded and the remaining fraction was counted again. The filled husks were weighed on an analytical balance. The number of filled seeds was determined by counting the number of filled husks that remained after the separation step. The total seed yield was measured by weighing all filled husks harvested from a plant. Total seed number per plant was measured by counting the number of husks harvested from a plant. Thousand Kernel Weight (TKW) is extrapolated from the number of filled seeds counted and their total weight. The Harvest Index (HI) in the present invention is defined as the ratio between the total seed yield and the above ground area (mm$^2$), multiplied by a factor $10^6$. The total number of flowers per panicle as defined in the present invention is the ratio between the total number of seeds and the number of mature primary panicles. The seed fill rate as defined in the present invention is the proportion (expressed as a %) of the number of filled seeds over the total number of seeds (or florets).

Example 7

Results of the Phenotypic Evaluation of the Transgenic Plants

The results of the evaluation of transgenic rice plants expressing an HpaG nucleic acid under non-stress conditions are presented below. An increase was observed for above-ground biomass (AreaMax), emergence vigour (early vigour), total seed yield, number of filled seeds, fill rate, number of flowers per panicle, harvest index, and thousand kernel weight (see table C)

TABLE C

Results of the measurements for yield increase under non-stress conditions

| Parameter | Overall increase (in %) | p-value of F-test |
| --- | --- | --- |
| AreaMax | 13 | 0.0000 |
| Early vigour | 25 | 0.0041 |
| Total weight of seeds | 30 | 0.0000 |
| Nr of filled seeds | 26 | 0.0000 |
| Fill rate | 9 | 0.0000 |
| Flowers per panicle | 12 | 0.0371 |
| Harvest Index | 18 | 0.0000 |
| Thousand Kernel Weight | 4 | 0.0000 |

The results of the evaluation of transgenic rice plants expressing an HpaG nucleic acid under drought-stress conditions are presented hereunder. An increase was observed for total seed weight, number of filled seeds, fill rate, harvest index and thousand-kernel weight (Table D).

TABLE D

Results of the measurements for yield increase under drought stress conditions

| Parameter | Overall increase (in %) | p-value of F-test |
| --- | --- | --- |
| Total weight of seeds | 40 | 0.0000 |
| Nr of filled seeds | 37 | 0.0000 |
| Fill rate | 30 | 0.0000 |
| Harvest Index | 37 | 0.0000 |
| Thousand Kernel Weight | 3 | 0.0001 |

Example 8

Identification of Sequences Related to SEQ ID NO: 29 and SEQ ID NO: 30

Sequences (full length cDNA, ESTs or genomic) related to SEQ ID NO: 29 and/or protein sequences related to SEQ ID NO: 30 were identified amongst those maintained in the Entrez Nucleotides database at the National Center for Biotechnology Information (NCBI) using database sequence search tools, such as the Basic Local Alignment Tool (BLAST) (Altschul et al. (1990) J. Mol. Biol. 215:403-410; and Altschul et al. (1997) Nucleic Acids Res. 25:3389-3402). The program was used to find regions of local similarity between sequences by comparing nucleic acid or polypeptide sequences to sequence databases and by calculating the statistical significance of matches. The polypeptide encoded by SEQ ID NO: 29 was used for the TBLASTN algorithm, with default settings and the filter to ignore low complexity sequences set off. The output of the analysis was viewed by pairwise comparison, and ranked according to the probability score (E-value), where the score reflects the probability that a particular alignment occurs by chance (the lower the E-value, the more significant the hit). In addition to E-values, comparisons were also scored by percentage identity. Percentage identity refers to the number of identical nucleotides (or amino acids) between the two compared nucleic acid (or polypeptide) sequences over a particular length. In some instances, the default parameters may be adjusted to modify the stringency of the search.

Table E provides a list of nucleic acid and polypeptide sequences related to the nucleic acid sequence as represented by SEQ ID NO: 29 and the polypeptide sequence represented by SEQ ID NO: 30.

| Name | Source organism | NCBI polypeptide accession number | NA SEQ ID NO | AA SEQ ID NO |
| --- | --- | --- | --- | --- |
| Synecho_PCC6803_SNF2 | Synechocystis sp. PCC 6803 BA000022 | NP_442847.1 | 29 | 30 |
| Anava_SNF2 | Anaebena variabilis ATCC 29413 | YP_323780.1 | 31 | 32 |
| Archaeon RC-I_SNF2 | Uncultured methanogenic archaeon RC-I_SNF2 | CAJ35100.1 | 33 | 34 |

-continued

| Name | Source organism | NCBI polypeptide accession number | NA SEQ ID NO | AA SEQ ID NO |
|---|---|---|---|---|
| Bacce__ATCC10987__SNF2 | *Bacillus cereus* ATCC 10987 | AAS44264.1 | 35 | 36 |
| Crowa__SNF2 | *Crocosphaera watsonii* WH 8501 ctg336 | ZP__00516613.1 | 37 | 38 |
| Glovi__SNF2 | *Gloeobacter violaceus* PCC 7421 | NP__925212 | 39 | 40 |
| Lyn__sp__SNF2 | *Lyngbya* sp. PCC 8106 | ZP__01622333.1 | 41 | 42 |
| Metac__C2A__SNF2 | *Methanosarcina acetivorans* C2A | NP__615162.1 | 43 | 44 |
| Methu__JF-1__SNF2 | *Methanospirillum hungatei* JF-1 | ABD41401.1 | 45 | 46 |
| Metma__Go1__SNF2 | *Methanosarcina mazei* Goe1 | NP__633503.1 | 47 | 48 |
| Mycbo__SNF2 | *Mycobacterium bovis* BCG Pasteur 1173P2 | CAL72108.1 | 49 | 50 |
| Myctu__SNF2 | *Mycobacterium tuberculosis* H37Rv | BX842578.1 | 51 | 52 |
| Myxxa__DK__SNF2 | *Myxococcus xanthus* DK 1622 | YP__635387.1 | 53 | 54 |
| Nocfa__IFM 10152__SNF2 | *Nocardia farcinica* IFM 10152 | BAD55876.1 | 55 | 56 |
| Nodsp__SNF2 | *Nodularia spumigena* | ZP__01629192.1 | 57 | 58 |
| Nos__sp__PCC7120__SNF2 | *Nostoc* sp. PCC7120 | BAB78256.1 | 59 | 60 |
| Nos__sp__PCC7120__SNF2 II | *Nostoc* sp. PCC7120 | ZP__00106150.1 | 61 | 62 |
| Nospu__PCC 73102__SNF2 | *Nostoc punctiforme* PCC 73102 | NP__488438 | 63 | 64 |
| Pelph__BU-1__SNF2 | *Pelodictyon phaeoclathratiforme* BU-1 | ZP__00589405.1 | 65 | 66 |
| Proma__CCMP1375__SNF2 | *Prochlorococcus marinus* str. CCMP1375 | NP__874441.1 | 67 | 68 |
| Proma__MIT 9211__SNF2 | *Prochlorococcus marinus* str. MIT 9211 | ZP__01006255.1 | 69 | 70 |
| Proma__MIT 9303__SNF2 | *Prochlorococcus marinus* str. MIT 9303 | YP__001018833.1 | 71 | 72 |
| Proma__MIT9313__SNF2 | *Prochlorococcus marinus* str. MIT 9313 | NP__895982.1 | 73 | 74 |
| Rho__sp__RHA1__SNF2 | *Rhodococcus* sp. RHA1 | ABG93371.1 | 75 | 76 |
| Saltr__CNB-440__SNF2 | *Salinispora tropica* CNB-440 | ZP__01431310 | 77 | 78 |
| Symth__IAM14863__SNF2 | *Symbiobacterium thermophilum* IAM 14863 | BAD39642 | 79 | 80 |
| Syn__sp__WH5701__SNF2 | *Synechococcus* sp. WH 5701 | ZP__01083591.1 | 81 | 82 |
| Syn__sp__BL107__SNF2 | *Synechococcus* sp. BL107 | ZP__01469219.1 | 83 | 84 |
| Syn__sp__CC9311__SNF2 | *Synechococcus* sp. CC9311 | YP__731958.1 | 85 | 86 |
| Syn__sp__CC9605__SNF2 | *Synechococcus* sp. CC9605 | YP__382805.1 | 87 | 88 |
| Syn__sp__CC9902__SNF2 | *Synechococcus* sp. CC9902 | YP__378176.1 | 89 | 90 |
| Syn__sp__RS9916__SNF2 | *Synechococcus* sp. RS9916 | ZP__01471362 | 91 | 92 |
| Syn__sp__WH 7805__SNF2 | *Synechococcus* sp. WH 7805 | ZP__01125039.1 | 93 | 94 |
| Syn__sp__WH 8102__SNF2 | *Synechococcus* sp. WH 8102 | NP__898451.1 | 95 | 96 |
| Synel__PCC6301__SNF2 | *Synechococcus elongatus* PCC 6301 | YP__171376 | 97 | 98 |
| Synel__PCC7942__SNF2 | *Synechococcus elongatus* PCC 7942 | YP__399891.1 | 99 | 100 |
| Theel__BP-1__SNF2 | *Thermosynechococcus elongatus* BP-1 | NP__682403.1 | 101 | 102 |

Additional sources of SWI2/SNF2 polypeptides useful in performing the methods of the invention can be found in the supplementary table S1C provided by Flaus et al. (2006). The authors scanned 24 complete archeal and 269 bacterial genomes, and identified 149 SWI2/SNF2 of the SSO1653 subfamily type.

Example 9

Alignment of SWI2/SNF2 Polypeptide Sequences

Figure 8:
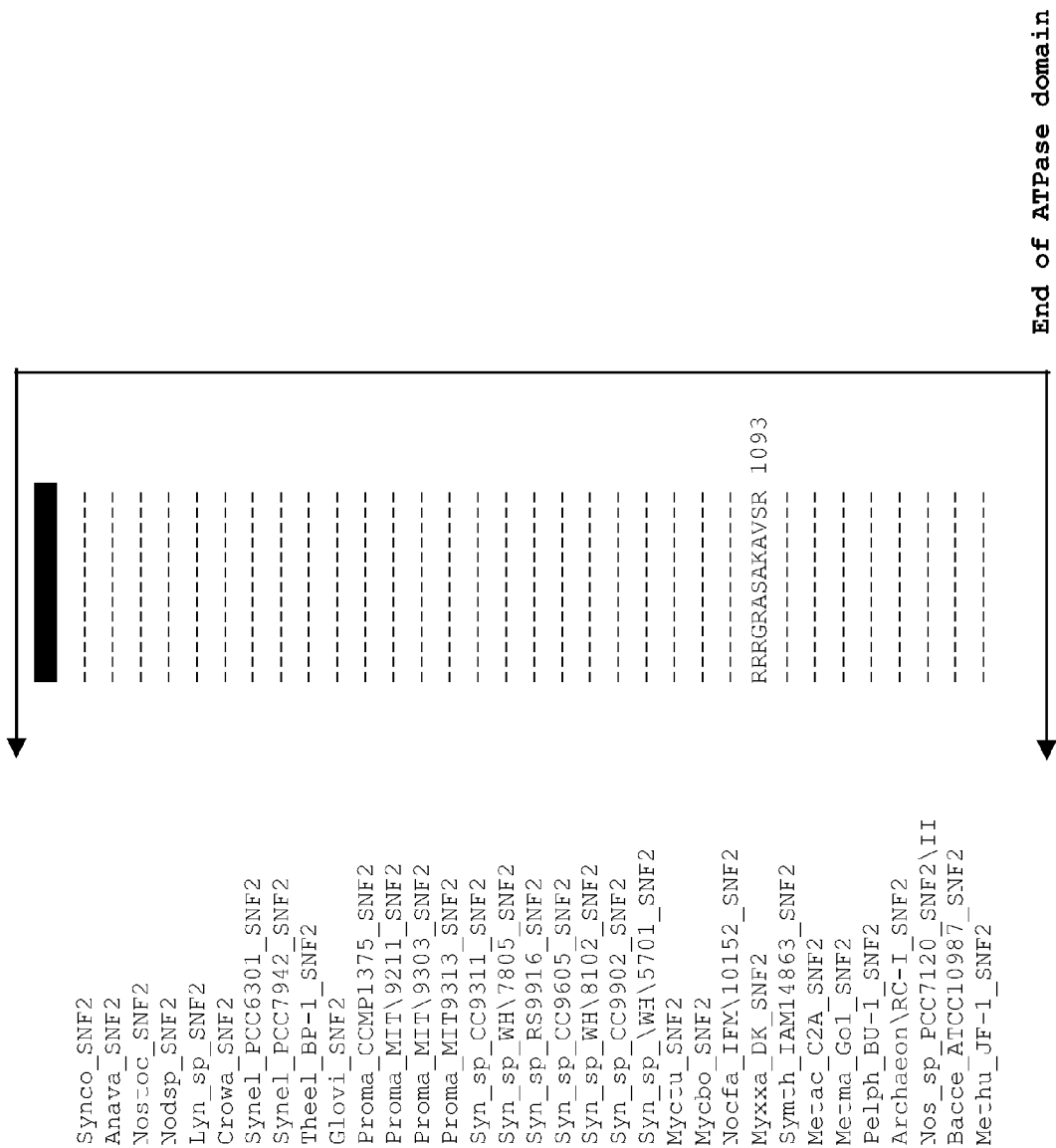
FIG. 8 shows a CLUSTAL W (1,83) multiple sequence alignment of SWI2/SNF2 polypeptides from various microbes, using default values. SWI2/SNF2 polypeptides share sequence conservation essentially in Motifs I, Ia, II, III, IV, V, Va and VI, comprised in the ATPase domain. These are boxed and identified as such. Another feature that is highlighted is the ATPase domain, for example as represented by SEQ ID NO: 111, comprised in SEQ ID NO: 30. The ATPase domain is comprised (from N to C-terminus) between the first amino acid residue of Motif 1 and the last amino acid residue at the C-terminus of the SWI2/SNF2polypeptide. The beginning and the end of the ATPase domain are marked, and the ATPase domain itself is identified using a black block above the aligned polypeptides. The sequences shown are: Synco SNF2 (SEQ ID NO: 30); Anava SNF2 (SEQ ID NO: 32); Nostoc $_{13}$ SNF2(SEQ ID NO: 60); Nodsp$_{13}$ SNF2 (SEQ ID NO: 58); Lyn$_{13}$ sp_SNF2 (SEQ ID NO: 42); Crowa$_{13}$ SNF2 (SEQ ID NO: 38); Synel PCC6301_SNF2 (SEQ ID NO: 98); Synel$_{13}$ PCC7942_SNF2(SEQ ID NO: 100); Theel_BP-1 $_{13}$ SNF2 (SEQ ID NO: 102); Glovi$_{13}$ SNF2 (SEQ ID NO: 40); Proma CCMP1375 SNF2 (SEQ ID NO: 68); Proma$_{13}$ MIT\9211$_{13}$ SNF2 (SEQ ID NO: 70); Proma$_{13}$ MIT\9303 $_{13}$ SNF2 (SEQ ID NO: 72); Proma$_{13}$ MIT9313_SNF2 (SEQ ID NO: 74): Syn_sp_CC9311_SNF2 (SEQ ID NO: 86); Syn_sp_WH\7805 SNF2 (SEQ ID NO: 94); Syn_sp_RS9916 SNF2 (SEQ ID NO: 92); Syn_sp_CC9605_SNF2 (SEQ ID NO: 88); Syn_sp_WH\8102_SNF2 (SEQ ID NO: 96); Syn_sp_CC9902_SNF2 (SEQ ID NO: 90); Syn_sp_\WH\5701_SNF2 (SEQ ID NO: 82); Myctu_SNF2 (SEQ ID NO: 52); Mycbo_SNF2 (SEQ ID NO: 50); Nocfa_IFM\10152_SNF2 (SEQ ID NO: 56); Myxxa_DK_SNF2 (SEQ ID NO: 54); Symth_IAM14863_SNF2 (SEQ ID NO: 80); Metac_C2A_SNF2 (SEQ ID NO: 44); Metma_Go1_SNF2 (SEQ ID NO: 48); Pelph_BU-1 $_{13}$ SNF2 (SEQ ID NO: 66); Archaeon\RC-I_SNF2 (SEQ ID NO: 34); Nos_sp_PCC7120_SNF2\II (SEQ ID NO: 62); Bacce_ATCC10987_SNF2 (SEQ ID NO: 36); Methu_JF-1_SNF2 (SEQ ID NO: 46).
Figure 9:
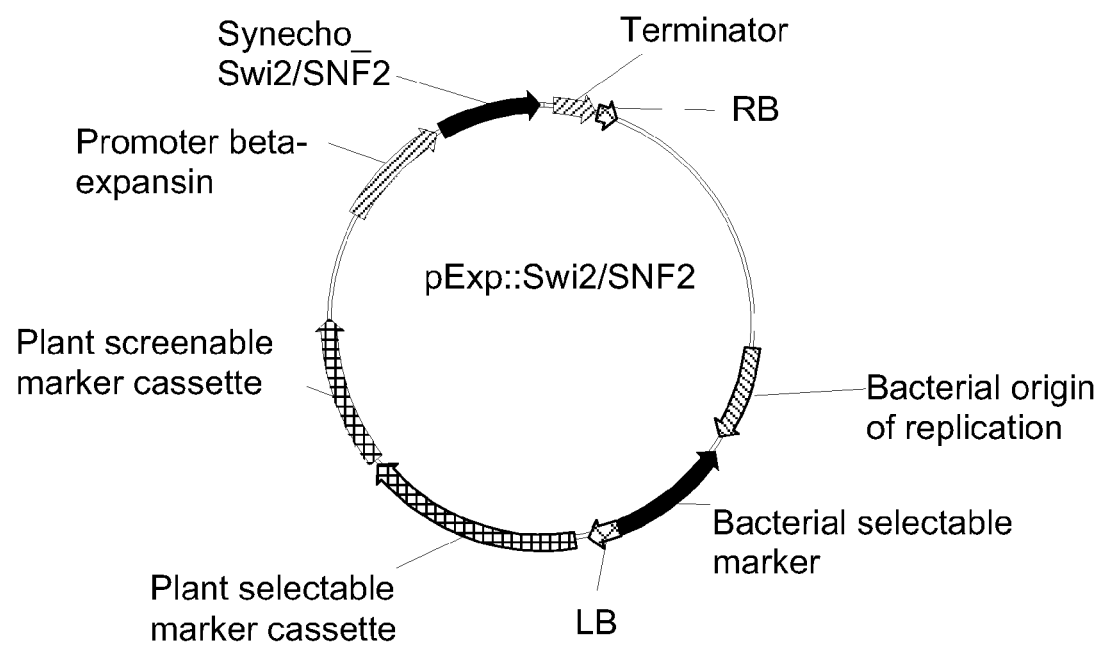
FIG. 9 shows the binary vector for increased expression in Oryza sativa of a *Synechocystis* sp. PCC6803 nucleic acid sequence encoding a SWI2/SNF2 polypeptide under the control of a beta-expansin promoter.

Alignment of polypeptide sequences was performed the Clustal algorithm (1.83) of progressive alignment, using default values (Thompson et al. (1997) Nucleic Acids Res 25:4876-4882; Chenna et al. (2003). Nucleic Acids Res 31:3497-3500). Results in FIG. 8 show that SWI2/SNF2 polypeptides share sequence conservation essentially in Motifs I, Ia, II, III, IV, V, Va and VI (which are boxed), represented as follows:

(i) Motif I LADDMGLGK(T/S), as represented by SEQ ID N0: 103 or a motif having in increasing order of preference at least 50%, 55%, 60%, 65%, 70%, 75%, 80%, 85%, 90%, 95%, 98%, 99% or more sequence identity to the sequence of Motif I;

(ii) Motif Ia L(L/V/I)(V/I/L)(A/C)P(T/M/V)S(V/I/L)(V/I/L)XNW, as represented by SEQ ID N0: 104 or a motif having in increasing order of preference at least 50%, 55%, 60%, 65%, 70%, 75%, 80%, 85%, 90%, 95%, 98%, 99% or more sequence identity to the sequence of Motif Ia;

(iii) Motif II DEAQ(N/A/H)(V/I/L)KN, as represented by SEQ ID N0: 105 or a motif having in increasing order of preference at least 50%, 55%, 60%, 65%, 70%, 75%, 80%, 85%, 90%, 95%, 98%, 99% or more sequence identity to the sequence of Motif II;

(iv) Motif III A(L/M)TGTPXEN, as represented by SEQ ID N0: 106 or a motif having in increasing order of preference at least 50%, 55%, 60%, 65%, 70%, 75%, 80%, 85%, 90%, 95%, 98%, 99% or more sequence identity to the sequence of Motif III;

(v) Motif IV (L/I)XF(T/S)Q(F/Y), as represented by SEQ ID N0: 107 or a motif having in increasing order of preference at least 50%, 55%, 60%, 65%, 70%, 75%, 80%, 85%, 90%, 95%, 98%, 99% or more sequence identity to the sequence of Motif IV;

(vi) Motif V S(L/V)KAGG(V/T/L)G(L/I)(N/T)LTXA(N/S/T)HV, as represented by SEQ ID N0: 108 or a motif having in increasing order of preference at least 50%, 55%, 60%, 65%, 70%, 75%, 80%, 85%, 90%, 95%, 98%, 99% or more sequence identity to the sequence of Motif V;

(vii) Motif Va DRWWNPAVE, as represented by SEQ ID N0: 109 or a motif having in increasing order of preference at least 50%, 55%, 60%, 65%, 70%, 75%, 80%, 85%, 90%, 95%, 98%, 99% or more sequence identity to the sequence of Motif Va; and (viii) Motif VI QA(T/S)DR(A/TN)(F/Y)R(I/L)GQ, as represented by SEQ ID N0: 110 or a motif having in increasing order of preference at least 50%, 55%, 60%, 65%, 70%, 75%, 80%, 85%, 90%, 95%, 98%, 99% or more sequence identity to the sequence of Motif VI, where X in Motif Ia, Motif III, Motif IV, and Motif V, is any amino acid.

These eight motifs are comprised within the ATPase domain. The ATPase domain is comprised (from N-terminus to C-terminus) between the first amino acid residue of Motif 1 and the last amino acid residue at the C-terminus of the SWI2/SNF2 polypeptide. The beginning and the end of the ATPase domain are marked in FIG. 8, and the ATPase domain itself is identified using a black block above the aligned polypeptides. An example of an ATPase domain is the ATPase domain of SEQ ID NO: 30, represented by SEQ ID NO: 111.

Figure 6:
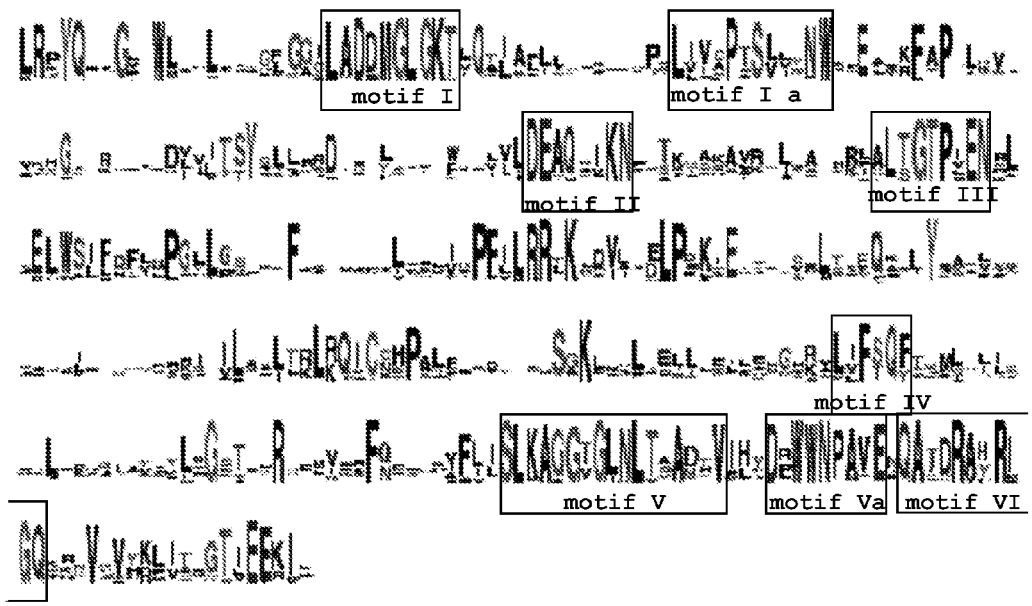
FIG. 6 shows the sequence logo of the ATPase domain of the 149 SWI2/SNF2 SSO1653 subfamily members as in Flaus et al., (2006). The ATPase domain as represented by SEQ ID NO: 111, and comprised in SEQ ID NO: 30, is in accordance with this sequence logo.

The sequence logo of the ATPase domain of the 149 SWI2/SNF2 SSO1653 subfamily members is presented in Flaus et al., (2006), and shown in FIG. 6. Sequence logos are a graphical representation of an amino acid or nucleic acid multiple sequence alignment. Each logo consists of stacks of symbols, one stack for each position in the sequence. The overall height of the stack indicates the sequence conservation at that position, while the height of symbols within the stack indicates the relative frequency of each amino or nucleic acid at that position. In general, a sequence logo provides a richer and more precise description of, for example, a binding site, than would a consensus sequence. The algorithm (WebLogo) to produce such logos is available at the server of the University of California, Berkeley. The ATPase domain as represented by SEQ ID NO: 111, and comprised in SEQ ID NO: 30, is in accordance with the sequence logo as represented in FIG. 6.

Figure 7:
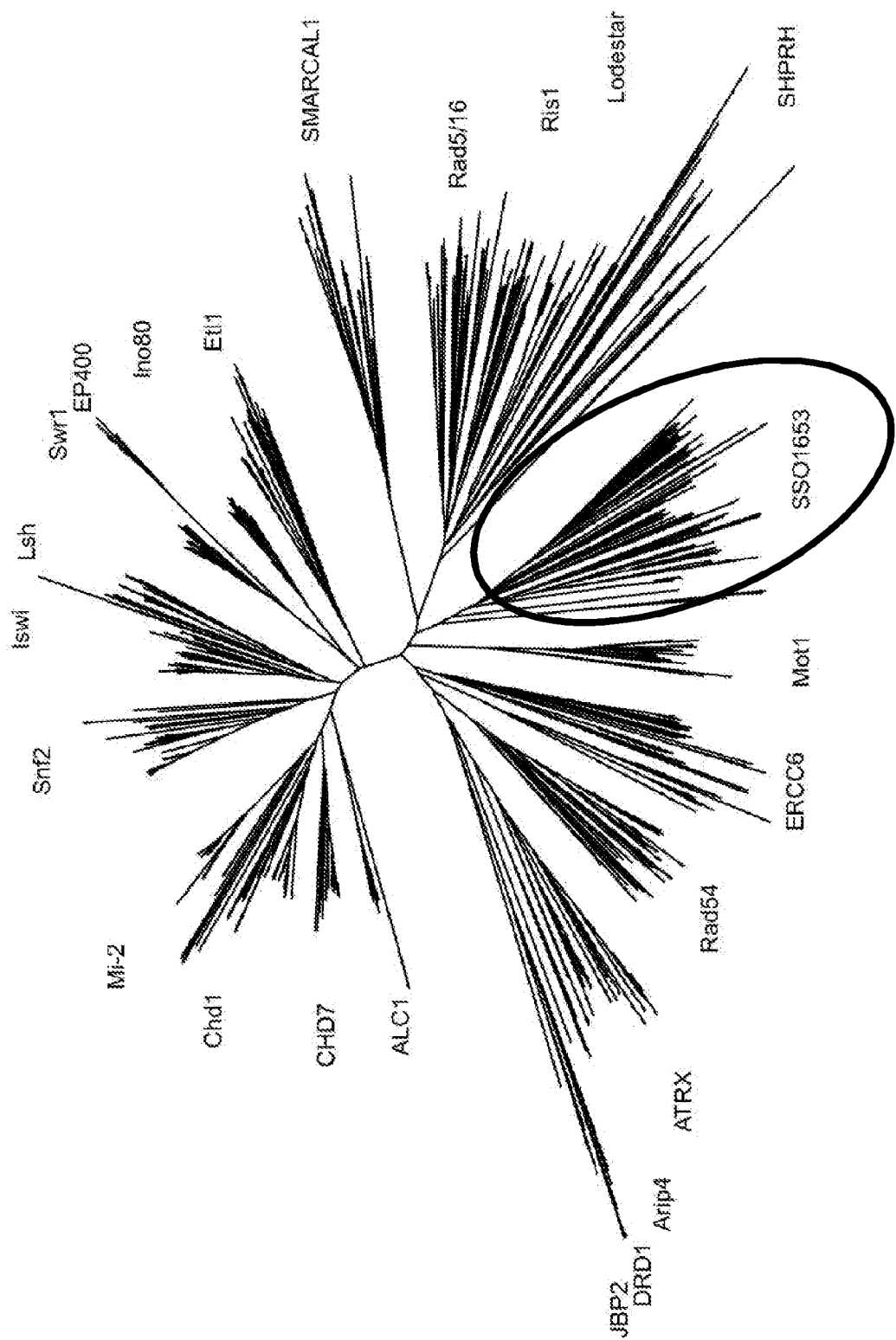
FIG. 7 shows an unrooted radial neighbor-joining tree of SWI2/SNF2 polypeptides from numerous SWI2/SNF2 subfamilies (including the 149 SWI2/SNF2 SSO1653 subfamily members) constructed by Flaus et al., (2006). The polypeptide as represented by SEQ ID NO: 30 is comprised within the SSO1653 cluster (circled in the Figure), together with all the archeal and bacterial (collectively called microbial) SWI2/SNF2 polypeptides.

An unrooted radial neighbor-joining tree of SWI2/SNF2 polypeptides from numerous SWI2/SNF2 subfamilies (including SSO1653) was constructed by Flaus et al., (2006), as shown in FIG. 7. The polypeptide as represented by SEQ ID NO: 30 is comprised within the SSO1653 cluster (circled in the Figure), together with all the archeal and bacterial (collectively called microbial) SWI2/SNF2 polypeptides.

Example 10

Calculation of Global Percentage Identity Between Polypeptide Sequences Useful in Performing the Methods of the Invention Global percentages of similarity and identity between full length polypeptide sequences useful in performing the methods of the invention were determined using one of the methods available in the art, the MatGAT (Matrix Global Alignment Tool) software (BMC Bioinformatics. 2003 4:29. MatGAT: an application that generates similarity/identity matrices using protein or DNA sequences. Campanella J J, Bitincka L, Smalley J; software hosted by Ledion Bitincka). MatGAT software generates similarity/identity matrices for DNA or protein sequences without needing pre-alignment of the data. The program performs a series of pair-wise alignments using the Myers and Miller global alignment algorithm (with a gap opening penalty of 12, and a gap extension penalty of 2), calculates similarity and identity using for example Blosum 62 (for polypeptides), and then places the results in a distance matrix. Sequence similarity is shown in the bottom half of the dividing line and sequence identity is shown in the top half of the diagonal dividing line.

Parameters used in the comparison were:

Scoring matrix: Blosum62

First Gap: 12

Extending gap: 2

Results of the software analysis are shown in Table F for the global similarity and identity over the full length of the polypeptide sequences (excluding the partial polypeptide sequences). Percentage identity is given above the diagonal and percentage similarity is given below the diagonal.

The percentage identity between the full length SWI2/SNF2 polypeptide sequences of the SSO1653 subfamily, useful in performing the methods of the invention, ranges between 33 and 52% amino acid identity compared to SEQ ID NO: 30 (Table F).

The percentage identity between the ATPase domain of the SWI2/SNF2 polypeptide sequences of the SSO1653 subfamily, useful in performing the methods of the invention, ranges between 45 and 70% amino acid identity compared to the ATPase domain as represented by SEQ ID NO: 111, comprised in SEQ ID NO: 30 (Table F1).

TABLE F

MatGAT results for global similarity and identity over the full length of the SWI2/SNF2 polypeptide sequences.

| | 1 | 2 | 3 | 4 | 5 | 6 | 7 | 8 | 9 | 10 | 11 | 12 | 13 | 14 | 15 | 16 | 17 | 18 | 19 |
|---|---|---|---|---|---|---|---|---|---|---|---|---|---|---|---|---|---|---|---|
| 1. Synco_SNF2 | | 48 | 38 | 33 | 52 | 46 | 48 | 38 | 33 | 37 | 37 | 37 | 38 | 36 | 47 | 34 | 40 | 49 | 37 |
| 2. Anava_SNF2 | 64 | | 40 | 32 | 53 | 52 | 60 | 38 | 34 | 37 | 38 | 38 | 38 | 35 | 76 | 36 | 66 | 94 | 38 |
| 3. Archaeon_RC-I_SNF2 | 57 | 60 | | 34 | 39 | 40 | 40 | 41 | 34 | 40 | 42 | 42 | 39 | 36 | 41 | 36 | 32 | 41 | 38 |
| 4. Bacce_ATCC10987_SNF2 | 49 | 48 | 52 | | 33 | 34 | 33 | 33 | 33 | 32 | 34 | 34 | 31 | 34 | 32 | 32 | 26 | 32 | 34 |
| 5. Crowa_SNF2 | 68 | 70 | 60 | 51 | | 47 | 53 | 36 | 34 | 36 | 36 | 36 | 35 | 32 | 52 | 35 | 43 | 53 | 38 |
| 6. Glovi_SNF2\ | 62 | 67 | 59 | 51 | 65 | | 53 | 38 | 34 | 39 | 40 | 40 | 38 | 37 | 52 | 37 | 41 | 52 | 39 |
| 7. Lyn_sp_SNF2 | 64 | 75 | 60 | 51 | 71 | 68 | | 37 | 34 | 37 | 37 | 37 | 36 | 33 | 59 | 35 | 47 | 60 | 38 |
| 8. Metac_C2A_SNF2 | 55 | 56 | 60 | 50 | 56 | 56 | 57 | | 34 | 90 | 42 | 42 | 38 | 36 | 38 | 36 | 30 | 38 | 47 |
| 9. Methu_JF-1_SNF2 | 53 | 53 | 55 | 48 | 56 | 52 | 53 | 52 | | 34 | 35 | 35 | 32 | 33 | 33 | 31 | 27 | 34 | 33 |
| 10. Metma_Goe1_SNF2 | 55 | 56 | 60 | 48 | 55 | 56 | 57 | 95 | 52 | | 41 | 41 | 38 | 35 | 38 | 36 | 29 | 38 | 47 |
| 11. Mycbo_SNF2 | 53 | 54 | 58 | 50 | 56 | 57 | 53 | 57 | 52 | 57 | | 99 | 41 | 43 | 39 | 35 | 31 | 38 | 40 |
| 12. Myctu_SNF2 | 53 | 54 | 58 | 50 | 56 | 57 | 53 | 57 | 52 | 57 | 99 | | 41 | 42 | 39 | 35 | 31 | 38 | 40 |
| 13. Myxxa_DK1622_SNF2 | 53 | 55 | 56 | 46 | 53 | 54 | 54 | 55 | 49 | 56 | 54 | 54 | | 38 | 39 | 33 | 30 | 38 | 37 |
| 14. Nocfa_IFM10152_SNF2 | 51 | 51 | 52 | 51 | 51 | 55 | 51 | 50 | 48 | 51 | 55 | 55 | 50 | | 35 | 33 | 27 | 35 | 37 |
| 15. Nodsp_SNF2 | 64 | 87 | 60 | 49 | 68 | 67 | 73 | 56 | 52 | 56 | 55 | 55 | 55 | 50 | | 36 | 68 | 76 | 37 |
| 16. Nos_sp_PCC7120_SNF2 II | 53 | 56 | 58 | 51 | 56 | 55 | 55 | 56 | 51 | 56 | 54 | 54 | 52 | 51 | 55 | | 29 | 37 | 37 |
| 17. Nospu_PCC73102_SNF2 | 56 | 75 | 51 | 47 | 60 | 60 | 63 | 47 | 44 | 46 | 48 | 48 | 44 | 47 | 76 | 48 | | 67 | 30 |
| 18. Nostoc_SNF2 | 64 | 97 | 60 | 48 | 70 | 67 | 76 | 57 | 53 | 56 | 54 | 54 | 55 | 51 | 86 | 58 | 76 | | 38 |
| 19. Pelph_BU-1_SNF2 | 55 | 55 | 57 | 51 | 56 | 57 | 56 | 63 | 52 | 62 | 58 | 58 | 53 | 53 | 54 | 54 | 48 | 54 | |
| 20. Proma_CCMP1375_SNF2 | 58 | 60 | 56 | 47 | 60 | 58 | 62 | 56 | 51 | 55 | 52 | 52 | 50 | 48 | 59 | 52 | 51 | 59 | 52 |
| 21. Proma_MIT9211_SNF2 | 58 | 58 | 55 | 46 | 60 | 58 | 61 | 55 | 50 | 54 | 53 | 53 | 50 | 50 | 59 | 52 | 51 | 59 | 54 |
| 22. Proma_MIT9303_SNF2 | 58 | 59 | 54 | 45 | 59 | 57 | 59 | 54 | 50 | 54 | 51 | 50 | 52 | 49 | 58 | 49 | 50 | 58 | 51 |
| 23. Proma_MIT9313_SNF2 | 58 | 58 | 54 | 43 | 58 | 57 | 59 | 54 | 50 | 54 | 51 | 51 | 52 | 49 | 58 | 49 | 50 | 58 | 51 |
| 24. Rho_sp_RHA1_SNF2 | 51 | 51 | 51 | 52 | 52 | 54 | 51 | 52 | 49 | 52 | 55 | 55 | 49 | 75 | 50 | 50 | 48 | 51 | 54 |
| 25. Saltr_CNB-440_SNF2 | 55 | 56 | 58 | 49 | 56 | 56 | 55 | 58 | 49 | 57 | 65 | 65 | 55 | 56 | 56 | 54 | 48 | 55 | 58 |
| 26. Symth_IAM14863_SNF2 | 53 | 53 | 56 | 51 | 53 | 58 | 52 | 53 | 50 | 53 | 55 | 55 | 53 | 54 | 53 | 52 | 47 | 53 | 55 |

TABLE F-continued

MatGAT results for global similarity and identity over the full length of the SWI2/SNF2 polypeptide sequences.

| | | | | | | | | | | | | | | | | | | |
|---|---|---|---|---|---|---|---|---|---|---|---|---|---|---|---|---|---|---|
| 27. Syn_sp_WH5701_SNF2 | 60 | 59 | 57 | 46 | 61 | 60 | 60 | 54 | 51 | 54 | 53 | 53 | 52 | 50 | 58 | 50 | 51 | 60 | 52 |
| 28. Syn_sp_BL107_SNF2 | 56 | 56 | 53 | 44 | 57 | 57 | 57 | 50 | 47 | 50 | 49 | 49 | 48 | 47 | 55 | 48 | 53 | 56 | 51 |
| 29. Syn_sp_CC9311_SNF2 | 59 | 60 | 56 | 44 | 60 | 60 | 61 | 55 | 51 | 54 | 52 | 52 | 51 | 49 | 59 | 52 | 51 | 60 | 52 |
| 30. Syn_sp_CC9605_SNF2 | 59 | 60 | 57 | 46 | 60 | 59 | 61 | 55 | 52 | 55 | 52 | 52 | 52 | 50 | 59 | 52 | 51 | 60 | 54 |
| 31. Syn_sp_CC9902_SNF2 | 59 | 59 | 56 | 46 | 61 | 59 | 61 | 55 | 51 | 54 | 52 | 52 | 51 | 50 | 59 | 52 | 52 | 60 | 54 |
| 32. Syn_sp_RS9916_SNF2 | 59 | 60 | 56 | 45 | 59 | 59 | 60 | 56 | 50 | 55 | 53 | 53 | 52 | 50 | 58 | 52 | 51 | 60 | 53 |
| 33. Syn_sp_WH7805_SNF2 | 58 | 60 | 55 | 45 | 60 | 58 | 61 | 55 | 52 | 55 | 52 | 52 | 51 | 49 | 59 | 51 | 51 | 60 | 52 |
| 34. Syn_sp_WH8102_SNF2 | 60 | 60 | 56 | 45 | 62 | 59 | 61 | 54 | 51 | 55 | 53 | 53 | 51 | 50 | 59 | 51 | 51 | 60 | 54 |
| 35. Synel_PCC6301_SNF2 | 63 | 65 | 58 | 50 | 63 | 64 | 66 | 53 | 52 | 53 | 54 | 54 | 51 | 52 | 65 | 54 | 57 | 66 | 56 |
| 36. Synel_PCC7942_SNF2 | 63 | 65 | 58 | 51 | 63 | 64 | 66 | 53 | 52 | 53 | 54 | 54 | 51 | 52 | 65 | 53 | 57 | 66 | 56 |
| 37. Theel_BP-1_SNF2 | 60 | 62 | 56 | 51 | 63 | 65 | 63 | 55 | 51 | 53 | 55 | 55 | 51 | 52 | 61 | 54 | 55 | 63 | 54 |

| | 20 | 21 | 22 | 23 | 24 | 25 | 26 | 27 | 28 | 29 | 30 | 31 | 32 | 33 | 34 | 35 | 36 | 37 |
|---|---|---|---|---|---|---|---|---|---|---|---|---|---|---|---|---|---|---|
| 1. Synco_SNF2 | 41 | 41 | 41 | 41 | 36 | 38 | 37 | 42 | 40 | 42 | 43 | 43 | 43 | 42 | 43 | 47 | 47 | 46 |
| 2. Anava_SNF2 | 42 | 40 | 41 | 41 | 36 | 40 | 37 | 43 | 38 | 43 | 42 | 42 | 43 | 43 | 42 | 48 | 48 | 48 |
| 3. Archaeon_RC-I_SNF2 | 36 | 36 | 37 | 37 | 36 | 39 | 38 | 38 | 33 | 37 | 37 | 36 | 37 | 37 | 37 | 39 | 39 | 39 |
| 4. Bacce_ATCC10987_SNF2 | 30 | 30 | 28 | 28 | 33 | 32 | 35 | 29 | 27 | 29 | 30 | 30 | 30 | 29 | 29 | 33 | 33 | 34 |
| 5. Crowa_SNF2 | 41 | 40 | 38 | 38 | 33 | 36 | 34 | 39 | 34 | 39 | 38 | 38 | 38 | 39 | 39 | 44 | 44 | 45 |
| 6. Glovi_SNF2\ | 41 | 40 | 40 | 40 | 37 | 40 | 40 | 43 | 39 | 43 | 41 | 42 | 42 | 42 | 42 | 46 | 46 | 49 |
| 7. Lyn_sp_SNF2 | 41 | 40 | 39 | 39 | 34 | 38 | 37 | 41 | 36 | 40 | 41 | 40 | 41 | 40 | 40 | 48 | 48 | 47 |
| 8. Metac_C2A_SNF2 | 36 | 35 | 35 | 35 | 36 | 41 | 38 | 37 | 33 | 36 | 36 | 36 | 36 | 37 | 36 | 36 | 36 | 38 |
| 9. Methu_JF-1_SNF2 | 30 | 31 | 31 | 31 | 33 | 33 | 32 | 30 | 29 | 31 | 32 | 32 | 31 | 32 | 31 | 33 | 33 | 34 |
| 10. Metma_Goe1_SNF2 | 35 | 34 | 35 | 35 | 36 | 41 | 37 | 36 | 33 | 36 | 36 | 36 | 35 | 36 | 36 | 35 | 35 | 37 |
| 11. Mycbo_SNF2 | 35 | 35 | 35 | 35 | 41 | 52 | 39 | 38 | 33 | 36 | 36 | 36 | 37 | 37 | 37 | 39 | 39 | 39 |
| 12. Myctu_SNF2 | 35 | 35 | 35 | 35 | 41 | 52 | 39 | 38 | 33 | 36 | 36 | 36 | 37 | 37 | 37 | 39 | 39 | 39 |
| 13. Myxxa_DK1622_SNF2 | 33 | 33 | 36 | 36 | 37 | 43 | 41 | 37 | 34 | 36 | 37 | 36 | 37 | 37 | 36 | 37 | 37 | 37 |
| 14. Nocfa_IFM10152_SNF2 | 31 | 33 | 35 | 35 | 64 | 43 | 40 | 35 | 32 | 35 | 36 | 35 | 36 | 36 | 36 | 37 | 37 | 37 |
| 15. Nodsp_SNF2 | 41 | 41 | 41 | 41 | 34 | 39 | 37 | 41 | 38 | 42 | 42 | 41 | 41 | 42 | 42 | 46 | 46 | 48 |
| 16. Nos_sp_PCC7120_SNF2 II | 33 | 31 | 30 | 30 | 32 | 35 | 32 | 32 | 29 | 32 | 32 | 32 | 32 | 31 | 31 | 34 | 34 | 35 |
| 17. Nospu_PCC73102_SNF2 | 34 | 34 | 34 | 34 | 27 | 30 | 29 | 33 | 35 | 34 | 35 | 34 | 34 | 35 | 35 | 36 | 36 | 39 |
| 18. Nostoc_SNF2 | 43 | 41 | 41 | 41 | 36 | 39 | 37 | 42 | 38 | 42 | 42 | 42 | 42 | 43 | 43 | 48 | 48 | 48 |
| 19. Pelph_BU-1_SNF2 | 35 | 36 | 37 | 36 | 37 | 40 | 39 | 36 | 35 | 37 | 38 | 38 | 37 | 36 | 38 | 37 | 37 | 38 |
| 20. Proma_CCMP1375_SNF2 | | 63 | 60 | 60 | 32 | 34 | 36 | 58 | 57 | 61 | 62 | 61 | 62 | 61 | 61 | 41 | 41 | 40 |
| 21. Proma_MIT9211_SNF2 | 78 | | 66 | 66 | 32 | 35 | 35 | 61 | 61 | 66 | 66 | 65 | 66 | 66 | 65 | 42 | 42 | 40 |
| 22. Proma_MIT9303_SNF2 | 76 | 80 | | 99 | 35 | 38 | 37 | 73 | 75 | 83 | 82 | 80 | 84 | 83 | 82 | 44 | 44 | 40 |
| 23. Proma_MIT9313_SNF2 | 76 | 80 | 99 | | 35 | 38 | 37 | 72 | 75 | 84 | 82 | 79 | 84 | 83 | 82 | 44 | 44 | 39 |
| 24. Rho_sp_RHA1_SNF2 | 49 | 51 | 49 | 49 | | 43 | 40 | 36 | 31 | 35 | 35 | 35 | 35 | 35 | 35 | 37 | 37 | 38 |
| 25. Saltr_CNB-440_SNF2 | 52 | 53 | 52 | 52 | 55 | | 42 | 39 | 35 | 39 | 39 | 39 | 39 | 39 | 39 | 40 | 40 | 39 |
| 26. Symth_IAM14863_SNF2 | 52 | 52 | 51 | 51 | 55 | 56 | | 38 | 35 | 37 | 38 | 38 | 37 | 37 | 38 | 37 | 37 | 39 |
| 27. Syn_sp_WH5701_SNF2 | 73 | 77 | 81 | 81 | 51 | 54 | 53 | | 68 | 74 | 73 | 73 | 75 | 75 | 74 | 47 | 47 | 42 |
| 28. Syn_sp_BL107_SNF2 | 73 | 75 | 83 | 83 | 48 | 50 | 51 | 79 | | 78 | 85 | 93 | 78 | 79 | 85 | 42 | 42 | 38 |
| 29. Syn_sp_CC9311_SNF2 | 77 | 81 | 89 | 89 | 49 | 54 | 51 | 83 | 86 | | 84 | 83 | 89 | 91 | 85 | 45 | 45 | 41 |
| 30. Syn_sp_CC9605_SNF2 | 78 | 81 | 88 | 88 | 51 | 54 | 53 | 82 | 90 | 91 | | 90 | 85 | 85 | 92 | 45 | 45 | 41 |
| 31. Syn_sp_CC9902_SNF2 | 77 | 80 | 88 | 88 | 50 | 54 | 54 | 82 | 94 | 91 | 95 | | 83 | 84 | 91 | 46 | 46 | 41 |
| 32. Syn_sp_RS9916_SNF2 | 79 | 81 | 90 | 90 | 49 | 55 | 51 | 83 | 87 | 94 | 92 | 92 | | 89 | 85 | 46 | 46 | 41 |
| 33. Syn_sp_WH7805_SNF2 | 77 | 81 | 89 | 89 | 49 | 54 | 51 | 83 | 85 | 94 | 91 | 90 | 94 | | 85 | 46 | 46 | 41 |
| 34. Syn_sp_WH8102_SNF2 | 78 | 81 | 89 | 89 | 51 | 54 | 53 | 83 | 91 | 92 | 96 | 96 | 92 | 92 | | 46 | 46 | 41 |
| 35. Synel_PCC6301_SNF2 | 59 | 59 | 59 | 59 | 53 | 56 | 53 | 62 | 58 | 60 | 61 | 61 | 60 | 60 | 61 | | 99 | 48 |
| 36. Synel_PCC7942_SNF2 | 59 | 59 | 59 | 59 | 53 | 56 | 53 | 62 | 58 | 60 | 61 | 61 | 60 | 60 | 61 | 99 | | 48 |
| 37. Theel_BP-1_SNF2 | 57 | 55 | 54 | 54 | 53 | 54 | 56 | 58 | 55 | 56 | 56 | 57 | 56 | 56 | 56 | 64 | 64 | |

TABLE F1

MatGAT results for global similarity and identity between the ATPase domain of the SWI2/SNF2 polypeptide sequences.

| | 1 | 2 | 3 | 4 | 5 | 6 | 7 | 8 | 9 | 10 | 11 | 12 | 13 | 14 | 15 | 16 | 17 | 18 | 19 |
|---|---|---|---|---|---|---|---|---|---|---|---|---|---|---|---|---|---|---|---|
| 1. ATPase_Synec_SNF2 | | 65 | 52 | 50 | 70 | 63 | 63 | 63 | 54 | 50 | 52 | 52 | 52 | 52 | 51 | 65 | 48 | 45 | 65 |
| 2. ATPase_Anava_SNF2 | 77 | | 55 | 50 | 70 | 69 | 69 | 72 | 54 | 50 | 53 | 54 | 54 | 54 | 52 | 85 | 51 | 60 | 97 |
| 3. ATPase_Archaeon\RC-I_SNF2 | 70 | 74 | | 51 | 53 | 56 | 56 | 56 | 54 | 50 | 53 | 56 | 55 | 53 | 54 | 56 | 52 | 37 | 54 |
| 4. ATPase_Bacce_ATCC10987_SNF2 | 67 | 67 | 72 | | 50 | 49 | 49 | 50 | 49 | 51 | 49 | 49 | 49 | 46 | 48 | 50 | 49 | 35 | 50 |
| 5. ATPase_Crowa_SNF2 | 82 | 84 | 74 | 68 | | 64 | 64 | 68 | 52 | 51 | 52 | 52 | 52 | 51 | 50 | 71 | 51 | 48 | 70 |
| 6. ATPase_Glovi_SNF2 | 77 | 82 | 74 | 69 | 81 | | 99 | 68 | 52 | 50 | 53 | 52 | 52 | 53 | 51 | 70 | 52 | 44 | 68 |
| 7. ATPase_Glovi_SNF2\ | 77 | 82 | 74 | 69 | 81 | 99 | | 68 | 52 | 50 | 53 | 52 | 52 | 53 | 51 | 70 | 52 | 44 | 68 |
| 8. ATPase_Lyn_sp_SNF2 | 77 | 86 | 75 | 69 | 83 | 82 | 82 | | 53 | 51 | 52 | 51 | 51 | 51 | 49 | 72 | 49 | 47 | 72 |
| 9. ATPase_Metac_C2A_SNF2 | 70 | 71 | 74 | 67 | 71 | 71 | 71 | 72 | | 49 | 92 | 55 | 55 | 51 | 52 | 55 | 53 | 36 | 53 |
| 10. ATPase_Methu_JF-1_SNF2 | 69 | 70 | 71 | 69 | 73 | 70 | 70 | 70 | 67 | | 48 | 51 | 51 | 47 | 48 | 49 | 49 | 35 | 50 |
| 11. ATPase_Metma_Goe1_SNF2 | 70 | 70 | 74 | 67 | 70 | 70 | 70 | 71 | 96 | 67 | | 54 | 54 | 51 | 51 | 54 | 52 | 34 | 52 |
| 12. ATPase_Mycbo_SNF2 | 68 | 70 | 73 | 67 | 70 | 71 | 71 | 69 | 69 | 69 | 69 | | 99 | 54 | 60 | 54 | 50 | 36 | 54 |
| 13. ATPase_Myctu_SNF2 | 68 | 70 | 73 | 67 | 70 | 71 | 71 | 69 | 69 | 69 | 69 | 99 | | 54 | 60 | 54 | 49 | 36 | 54 |
| 14. ATPase_Myxxa_DK1622_SNF2 | 67 | 69 | 70 | 63 | 67 | 70 | 70 | 69 | 69 | 63 | 69 | 68 | 68 | | 55 | 53 | 46 | 35 | 53 |
| 15. ATPase_Nocfa_IFM\10152_SNF2 | 68 | 69 | 69 | 65 | 69 | 70 | 70 | 66 | 68 | 65 | 68 | 73 | 73 | 67 | | 51 | 49 | 35 | 52 |
| 16. ATPase_Nodsp_SNF2 | 77 | 91 | 76 | 69 | 85 | 82 | 82 | 85 | 71 | 70 | 71 | 71 | 71 | 69 | 70 | | 52 | 58 | 86 |
| 17. ATPase_Nos_sp_PCC7120_SNF2\II | 68 | 71 | 74 | 70 | 70 | 71 | 71 | 70 | 70 | 68 | 70 | 68 | 68 | 66 | 67 | 72 | | 35 | 51 |

TABLE F1-continued

MatGAT results for global similarity and identity between the ATPase domain of the SWI2/SNF2 polypeptide sequences.

| | | | | | | | | | | | | | | | | | | |
|---|---|---|---|---|---|---|---|---|---|---|---|---|---|---|---|---|---|---|
| 18. ATPase_Nospu_PCC\73102_SNF2 | 55 | 63 | 51 | 50 | 58 | 55 | 55 | 57 | 48 | 50 | 48 | 49 | 49 | 45 | 48 | 64 | 49 | 60 |
| 19. ATPase_Nostoc_SNF2 | 77 | 99 | 74 | 67 | 84 | 82 | 82 | 85 | 71 | 69 | 70 | 70 | 70 | 69 | 69 | 92 | 71 | 63 |
| 20. ATPase_Pelph_BU-1_SNF2 | 70 | 71 | 72 | 70 | 73 | 73 | 73 | 71 | 79 | 68 | 79 | 72 | 72 | 68 | 71 | 72 | 70 | 49 | 71 |
| 21. ATPase_Proma_CCMP1375_SNF2 | 71 | 71 | 69 | 66 | 73 | 72 | 72 | 71 | 67 | 64 | 67 | 66 | 66 | 64 | 63 | 73 | 64 | 49 | 72 |
| 22. ATPase_Proma_MIT\9211_SNF2 | 72 | 70 | 69 | 63 | 73 | 72 | 72 | 72 | 67 | 63 | 67 | 67 | 66 | 63 | 65 | 72 | 65 | 48 | 71 |
| 23. ATPase_Proma_MIT\9303_SNF2 | 74 | 73 | 70 | 64 | 75 | 75 | 75 | 72 | 69 | 65 | 69 | 66 | 66 | 64 | 65 | 74 | 64 | 51 | 72 |
| 24. ATPase_Proma_MIT9313_SNF2 | 74 | 73 | 69 | 64 | 75 | 75 | 75 | 72 | 69 | 65 | 69 | 66 | 66 | 64 | 65 | 74 | 64 | 51 | 72 |
| 25. ATPase_Rho_sp_RHA1_SNF2 | 69 | 71 | 70 | 66 | 72 | 70 | 70 | 69 | 71 | 67 | 71 | 74 | 74 | 67 | 83 | 73 | 68 | 50 | 71 |
| 26. ATPase_Symth_IAM14863_SNF2 | 67 | 67 | 71 | 68 | 67 | 71 | 71 | 68 | 70 | 67 | 68 | 68 | 68 | 69 | 69 | 69 | 68 | 47 | 67 |
| 27. ATPase_Syn_sp_WH5701_SNF2 | 74 | 73 | 69 | 64 | 75 | 73 | 73 | 73 | 68 | 65 | 68 | 67 | 67 | 65 | 65 | 73 | 64 | 51 | 73 |
| 28. ATPase_Syn_sp_BL107_SNF2 | 64 | 62 | 60 | 57 | 66 | 65 | 65 | 63 | 58 | 54 | 58 | 56 | 55 | 55 | 57 | 63 | 55 | 54 | 62 |
| 29. ATPase_Syn_sp_CC9311_SNF2 | 74 | 73 | 69 | 63 | 74 | 74 | 74 | 73 | 68 | 65 | 68 | 65 | 65 | 64 | 65 | 73 | 64 | 51 | 73 |
| 30. ATPase_Syn_sp_CC9605_SNF2 | 74 | 72 | 71 | 64 | 74 | 75 | 75 | 73 | 69 | 64 | 69 | 65 | 65 | 64 | 66 | 74 | 64 | 50 | 72 |
| 31. ATPase_Syn_sp_CC9902_SNF2 | 74 | 71 | 70 | 64 | 75 | 74 | 74 | 72 | 69 | 64 | 69 | 65 | 64 | 64 | 66 | 73 | 65 | 51 | 71 |
| 32. ATPase_Syn_sp_RS9916_SNF2 | 74 | 73 | 69 | 62 | 74 | 74 | 74 | 72 | 69 | 64 | 69 | 66 | 65 | 65 | 64 | 72 | 65 | 50 | 72 |
| 33. ATPase_Syn_sp_WH\7805_SNF2 | 72 | 72 | 68 | 62 | 73 | 73 | 73 | 72 | 68 | 64 | 68 | 65 | 65 | 64 | 63 | 72 | 64 | 50 | 72 |
| 34. ATPase_Syn_sp_WH\8102_SNF2 | 74 | 72 | 70 | 63 | 75 | 75 | 75 | 73 | 69 | 64 | 69 | 66 | 65 | 64 | 65 | 73 | 64 | 50 | 72 |
| 35. ATPase_Synel_PCC6301_SNF2 | 75 | 79 | 70 | 70 | 78 | 76 | 76 | 79 | 67 | 68 | 67 | 66 | 66 | 66 | 67 | 79 | 69 | 52 | 78 |
| 36. ATPase_Synel_PCC7942_SNF2 | 75 | 79 | 70 | 70 | 78 | 76 | 76 | 79 | 67 | 68 | 67 | 66 | 66 | 66 | 67 | 79 | 69 | 52 | 78 |
| 37. ATPase_Theel_BP-1_SNF2 | 75 | 78 | 72 | 69 | 79 | 79 | 79 | 76 | 69 | 71 | 69 | 68 | 68 | 66 | 67 | 79 | 70 | 54 | 78 |

| | 20 | 21 | 22 | 23 | 24 | 25 | 26 | 27 | 28 | 29 | 30 | 31 | 32 | 33 | 34 | 35 | 36 | 37 |
|---|---|---|---|---|---|---|---|---|---|---|---|---|---|---|---|---|---|---|
| 1. ATPase_Synec_SNF2 | 53 | 54 | 55 | 57 | 57 | 52 | 52 | 57 | 49 | 56 | 57 | 58 | 58 | 56 | 57 | 63 | 63 | 62 |
| 2. ATPase_Anava_SNF2 | 53 | 55 | 52 | 55 | 55 | 54 | 51 | 56 | 47 | 56 | 56 | 55 | 56 | 56 | 56 | 65 | 65 | 67 |
| 3. ATPase_Archaeon\RC-I_SNF2 | 55 | 49 | 49 | 52 | 52 | 53 | 54 | 52 | 44 | 51 | 52 | 52 | 52 | 51 | 51 | 53 | 53 | 55 |
| 4. ATPase_Bacce_ATCC10987_SNF2 | 50 | 46 | 46 | 46 | 46 | 49 | 50 | 46 | 38 | 45 | 46 | 44 | 47 | 45 | 45 | 49 | 49 | 50 |
| 5. ATPase_Crowa_SNF2 | 55 | 56 | 54 | 56 | 56 | 51 | 50 | 55 | 47 | 55 | 55 | 55 | 55 | 56 | 56 | 63 | 63 | 63 |
| 6. ATPase_Glovi_SNF2 | 54 | 53 | 52 | 55 | 55 | 52 | 54 | 54 | 47 | 54 | 55 | 56 | 54 | 54 | 55 | 61 | 61 | 64 |
| 7. ATPase_Glovi_SNF2\ | 54 | 53 | 52 | 55 | 55 | 52 | 54 | 54 | 47 | 54 | 55 | 56 | 54 | 54 | 55 | 61 | 61 | 64 |
| 8. ATPase_Lyn_sp_SNF2 | 53 | 53 | 51 | 54 | 54 | 51 | 51 | 55 | 46 | 54 | 55 | 55 | 55 | 55 | 55 | 64 | 64 | 62 |
| 9. ATPase_Metac_C2A_SNF2 | 65 | 49 | 49 | 51 | 51 | 53 | 53 | 51 | 43 | 51 | 51 | 52 | 51 | 51 | 51 | 50 | 50 | 54 |
| 10. ATPase_Methu_JF-1_SNF2 | 49 | 43 | 43 | 45 | 45 | 50 | 50 | 43 | 38 | 43 | 44 | 44 | 44 | 44 | 43 | 50 | 50 | 52 |
| 11. ATPase_Metma_Goe1_SNF2 | 64 | 48 | 48 | 50 | 50 | 52 | 51 | 50 | 43 | 50 | 51 | 51 | 49 | 49 | 50 | 50 | 50 | 53 |
| 12. ATPase_Mycbo_SNF2 | 55 | 47 | 46 | 48 | 48 | 59 | 52 | 50 | 40 | 48 | 48 | 48 | 48 | 48 | 49 | 51 | 51 | 54 |
| 13. ATPase_Myctu_SNF2 | 55 | 47 | 46 | 48 | 48 | 59 | 52 | 50 | 40 | 48 | 48 | 48 | 48 | 48 | 49 | 51 | 51 | 54 |
| 14. ATPase_Myxxa_DK1622_SNF2 | 50 | 45 | 47 | 49 | 49 | 52 | 56 | 49 | 41 | 48 | 49 | 49 | 49 | 49 | 48 | 51 | 51 | 52 |
| 15. ATPase_Nocfa_IFM\10152_SNF2 | 55 | 46 | 47 | 49 | 49 | 75 | 55 | 49 | 41 | 49 | 49 | 48 | 48 | 49 | 50 | 50 | 50 | 52 |
| 16. ATPase_Nodsp_SNF2 | 53 | 55 | 53 | 57 | 57 | 53 | 52 | 56 | 47 | 56 | 57 | 56 | 56 | 56 | 56 | 65 | 65 | 68 |
| 17. ATPase_Nos_sp_PCC7120_SNF2\II | 52 | 46 | 44 | 46 | 46 | 49 | 48 | 46 | 38 | 46 | 46 | 46 | 46 | 46 | 46 | 49 | 49 | 51 |
| 18. ATPase_Nospu_PCC\73102_SNF2 | 36 | 37 | 36 | 39 | 39 | 35 | 36 | 38 | 41 | 39 | 39 | 39 | 38 | 39 | 39 | 41 | 41 | 45 |
| 19. ATPase_Nostoc_SNF2 | 53 | 55 | 53 | 55 | 55 | 53 | 51 | 55 | 46 | 56 | 56 | 55 | 55 | 56 | 56 | 65 | 65 | 66 |
| 20. ATPase_Pelph_BU-1_SNF2 | | 51 | 52 | 55 | 55 | 55 | 56 | 52 | 45 | 54 | 54 | 54 | 53 | 53 | 54 | 52 | 52 | 54 |
| 21. ATPase_Proma_CCMP1375_SNF2 | 68 | | 71 | 71 | 71 | 48 | 50 | 69 | 61 | 70 | 70 | 70 | 70 | 71 | 70 | 57 | 57 | 56 |
| 22. ATPase_Proma_MIT\9211_SNF2 | 69 | 83 | | 74 | 73 | 47 | 49 | 69 | 61 | 72 | 73 | 72 | 71 | 72 | 72 | 56 | 56 | 54 |
| 23. ATPase_Proma_MIT\9303_SNF2 | 69 | 84 | 87 | | 99 | 50 | 53 | 85 | 75 | 87 | 88 | 86 | 87 | 86 | 88 | 59 | 59 | 57 |
| 24. ATPase_Proma_MIT9313_SNF2 | 69 | 84 | 87 | 99 | | 50 | 53 | 85 | 75 | 87 | 88 | 86 | 87 | 86 | 88 | 59 | 59 | 57 |
| 25. ATPase_Rho_sp_RHA1_SNF2 | 73 | 66 | 65 | 66 | 66 | | 55 | 50 | 42 | 50 | 50 | 50 | 50 | 50 | 52 | 52 | 52 | 52 |
| 26. ATPase_Symth_IAM14863_SNF2 | 70 | 65 | 66 | 68 | 68 | 69 | | 51 | 44 | 51 | 53 | 53 | 52 | 52 | 52 | 51 | 51 | 53 |
| 27. ATPase_Syn_sp_WH5701_SNF2 | 70 | 83 | 85 | 93 | 93 | 66 | 67 | | 73 | 84 | 84 | 84 | 85 | 85 | 86 | 59 | 59 | 57 |
| 28. ATPase_Syn_sp_BL107_SNF2 | 60 | 73 | 74 | 81 | 82 | 59 | 58 | 80 | | 74 | 79 | 84 | 75 | 74 | 79 | 51 | 51 | 49 |
| 29. ATPase_Syn_sp_CC9311_SNF2 | 68 | 84 | 85 | 94 | 94 | 65 | 66 | 91 | 81 | | 87 | 85 | 91 | 92 | 88 | 59 | 59 | 58 |
| 30. ATPase_Syn_sp_CC9605_SNF2 | 69 | 85 | 87 | 93 | 93 | 67 | 68 | 91 | 83 | 93 | | 92 | 88 | 87 | 95 | 59 | 59 | 57 |
| 31. ATPase_Syn_sp_CC9902_SNF2 | 69 | 84 | 86 | 93 | 94 | 66 | 68 | 91 | 87 | 92 | 96 | | 87 | 85 | 92 | 60 | 60 | 57 |
| 32. ATPase_Syn_sp_RS9916_SNF2 | 69 | 84 | 86 | 94 | 94 | 66 | 66 | 91 | 81 | 96 | 94 | 93 | | 92 | 88 | 60 | 60 | 57 |
| 33. ATPase_Syn_sp_WH\7805_SNF2 | 67 | 83 | 85 | 92 | 92 | 65 | 66 | 91 | 79 | 95 | 92 | 91 | 96 | | 88 | 60 | 60 | 57 |
| 34. ATPase_Syn_sp_WH\8102_SNF2 | 69 | 84 | 87 | 94 | 94 | 66 | 68 | 92 | 84 | 93 | 97 | 96 | 94 | 92 | | 59 | 59 | 56 |
| 35. ATPase_Synel_PCC6301_SNF2 | 70 | 73 | 72 | 74 | 74 | 66 | 68 | 74 | 63 | 74 | 73 | 73 | 74 | 73 | 74 | | 99 | 63 |
| 36. ATPase_Synel_PCC7942_SNF2 | 70 | 73 | 72 | 74 | 74 | 66 | 68 | 74 | 63 | 74 | 73 | 73 | 74 | 73 | 74 | 99 | | 63 |
| 37. ATPase_Theel_BP-1_SNF2 | 71 | 71 | 70 | 71 | 71 | 69 | 69 | 72 | 63 | 72 | 71 | 71 | 72 | 71 | 71 | 76 | 76 | |

Example 11

Identification of Domains Comprised in Polypeptide Sequences Useful in Performing the Methods of the Invention The Integrated Resource of Protein Families, Domains and Sites (InterPro) database is an integrated interface for the commonly used signature databases for text- and sequence-based searches. The InterPro database combines these databases, which use different methodologies and varying degrees of biological information about well-characterized proteins to derive protein signatures. Collaborating databases include SWISS-PROT, PROSITE, TrEMBL, PRINTS, ProDom and Pfam, Smart and TIGRFAMs. Interpro is hosted at the European Bioinformatics Institute in the United Kingdom.

The relevant results of the InterPro scan of the polypeptide sequence as represented by SEQ ID NO: 30 are presented in Table G. SWI2/SNF2 polypeptides (or remodeling enzymes) share sequence similarity with helicases (particularly SF2 helicases), which are enzymes capable of catalyzing the separation of DNA strands using ATP hydrolysis. The sequence similarity is limited to the ATPase domain of both types of enzymes.

TABLE G

InterPro scan results (major accession numbers) of the polypeptide sequence as represented by SEQ ID NO: 2.

| InterPro accession number | InterPro decription | Originating database | Original accession number | Accession name |
|---|---|---|---|---|
| IPR000330 | SNF2 related | Pfam | PF00176 | SNF2_N |
| IPR001650 | Helicase, C-terminal | Pfam | PF00271 | Helicase_C |
| | | SMART | SM00490 | HELICc |
| | | Profile | PS51194 | Helicase_CTER |
| IPR014001 | DEAD-like helicases, N-terminal | SMART | SM00487 | DEXDc |
| IPR014021 | Helicase superfamily a and 2 ATP binding | PROFILE | PS51192 | Helicase_ATP_BIND_1 |

Example 12

Cloning of Nucleic Acid Sequence as Represented by SEQ ID NO: 29

Unless otherwise stated, recombinant DNA techniques are performed according to standard protocols described in (Sambrook (2001) Molecular Cloning: a laboratory manual, 3rd Edition Cold Spring Harbor Laboratory Press, CSH, New York) or in Volumes 1 and 2 of Ausubel et al. (1994), Current Protocols in Molecular Biology, Current Protocols. Standard materials and methods for plant molecular work are described in Plant Molecular Biology Labfax (1993) by R. D. D. Croy, published by BIOS Scientific Publications Ltd (UK) and Blackwell Scientific Publications (UK).

The *Synechocystis* sp. PCC6803 SWI2/SNF2 gene was amplified by PCR using as template *Synechocystis* sp. PCC6803 genomic DNA. Primers prm08774 (SEQ ID NO: 113; sense: 5'-ggggacaagtttgtacaaaaaagcag-gcttaaacaatggcgactatccacggtaattgg-3') and prm08779 (SEQ ID NO: 114; reverse, complementary: 5'-ggggaccactttgtacaa-gaaagctgggttcaatcggacgcttcggctt-3'), which include the AttB sites for Gateway recombination, were used for PCR amplification. PCR was performed using Hifi Taq DNA polymerase in standard conditions. A PCR fragment of the expected length (including attB sites) was amplified and purified also using standard methods. The first step of the Gateway procedure, the BP reaction, was then performed, during which the PCR fragment recombined in vivo with the pDONR201 plasmid to produce, according to the Gateway terminology, an "entry clone". Plasmid pDONR201 was purchased from Invitrogen, as part of the Gateway® technology.

Example 13

Expression Vector Construction Using the Nucleic Acid Sequence as Represented by SEQ ID NO: 29

The entry clone comprising SEQ ID NO: 29 was subsequently used in an LR reaction with a destination vector used for *Oryza sativa* transformation. This vector contained as functional elements within the T-DNA borders: a plant selectable marker; a screenable marker expression cassette; and a Gateway cassette intended for LR in vivo recombination with the nucleic acid sequence of interest already cloned in the entry clone. A rice beta-expansin promoter (SEQ ID NO: 112) for expression in young expanding tissues was located upstream of this Gateway cassette.

After the LR recombination step, the resulting expression vector pExp::SWI2/SNF2 (FIG. 8) was transformed into Agrobacterium strain LBA4044 according to methods well known in the art.

Example 14

Plant Transformation

See Example 5 above for rice transformation

Example 15

Phenotypic Evaluation Procedure 15.1 Evaluation Setup

Approximately 35 independent T0 rice transformants were generated. The primary transformants were transferred from a tissue culture chamber to a greenhouse for growing and harvest of T1 seed. Six events, of which the T1 progeny segregated 3:1 for presence/absence of the transgene, were retained. For each of these events, approximately 10 T1 seedlings containing the transgene (hetero- and homo-zygotes) and approximately 10 T1 seedlings lacking the transgene (nullizygotes) were selected by monitoring visual marker expression. The transgenic plants and the corresponding nullizygotes were grown side-by-side at random positions. Greenhouse conditions were of shorts days (12 hours light), 28° C. in the light and 22° C. in the dark, and a relative humidity of 70%.

Five T1 events were further evaluated in the T2 generation following the same evaluation procedure as for the T1 generation but with more individuals per event. From the stage of sowing until the stage of maturity the plants were passed several times through a digital imaging cabinet. At each time point digital images (2048×1536 pixels, 16 million colours) were taken of each plant from at least 6 different angles.

Drought Screen

Plants from five events (T2 seeds) were grown in potting soil under normal conditions until they approached the heading stage. They were then transferred to a "dry" section where irrigation was withheld. Humidity probes were inserted in randomly chosen pots to monitor the soil water content (SWC). When SWC went below certain thresholds, the plants were automatically re-watered continuously until a normal level was reached again. The plants were then re-transferred again to normal conditions. The rest of the cultivation (plant maturation, seed harvest) was the same as for plants not grown under abiotic stress conditions. Growth and yield parameters are recorded as detailed for growth under normal conditions.

Salt Stress Screen

The rice plants are grown on a substrate made of coco fibers and argex (3 to 1 ratio). A normal nutrient solution is used during the first two weeks after transplanting the plantlets in the greenhouse. After the first two weeks, 25 mM of salt (NaCl) is added to the nutrient solution comprising the components listed below.

NPK Nutrient mix, 20-20-20 Peters professional (Scotts, Marysville, Ohio, USA) at a concentration of 1 kg/m$^3$.
Magnesium chelate, Chelal Mg (BMS, Bornem, Belgium) at 333.33 ml/m$^3$
Iron chelate, Libfer (CIBA, Bradford, UK) at 21.67 g/m$^3$
NaCl 1.425 kg/m3

Salt concentration is monitored on a weekly basis and additions are made where necessary. Plants are grown under these conditions until the start of grain filling. They are then transferred to a different compartment of the greenhouse where they are irrigated daily with fresh water until seed harvest. Growth and yield parameters are recorded as for growth under normal conditions.

Reduced Nutrient (Nitrogen) Availability Screen

The rice plants are grown in potting soil under normal conditions except for the nutrient solution. The pots are watered from transplantation to maturation with a specific nutrient solution containing reduced N nitrogen (N) content, usually between 7 to 8 times less. The rest of the cultivation (plant maturation, seed harvest) is the same as for plants not grown under abiotic stress. Growth and yield parameters are recorded as for growth under normal conditions.

15.2 Statistical Analysis: F-Test

A two factor ANOVA (analysis of variants) was used as a statistical model for the overall evaluation of plant phenotypic characteristics. An F-test was carried out on all the parameters measured of all the plants of all the events transformed with the gene of the present invention.

The F-test was carried out to check for an effect of the gene over all the transformation events and to verify for an overall effect of the gene, also known as a global gene effect. The threshold for significance for a true global gene effect was set at a 5% probability level for the F-test. A significant F-test value points to a gene effect, meaning that it is not only the mere presence or position of the gene that is causing the differences in phenotype.

15.3 Parameters Measured

Biomass-Related Parameter Measurement

From the stage of sowing until the stage of maturity the plants were passed several times through a digital imaging cabinet. At each time point digital images (2048×1536 pixels, 16 million colours) were taken of each plant from at least 6 different angles.

The plant aboveground area (or leafy biomass) was determined by counting the total number of pixels on the digital images from aboveground plant parts discriminated from the background. This value was averaged for the pictures taken on the same time point from the different angles and was converted to a physical surface value expressed in square mm by calibration. Experiments show that the aboveground plant area measured this way correlates with the biomass of plant parts above ground. The above ground area is the area measured at the time point at which the plant had reached its maximal leafy biomass. The early vigor is the plant (seedling) aboveground area three weeks post-germination.

To measure root-related parameters, plants were grown in specially designed pots with transparent bottoms to allow visualization of the roots. A digital camera recorded images through the bottom of the pot during plant growth. Increase in root biomass is expressed as an increase in total root biomass (measured as maximum biomass of roots observed during the lifespan of a plant); or as an increase in the root/shoot index (measured as the ratio between root mass and shoot mass in the period of active growth of root and shoot). Furthermore, the maximum biomass of roots above a certain thickness threshold observed during the lifespan of a plant is calculated (thick roots), as well as maximum biomass of roots below a certain thickness threshold (thin roots).

Seed-Related Parameter Measurements

The mature primary panicles were harvested, counted, bagged, barcode-labelled and then dried for three days in an oven at 37° C. The panicles were then threshed and all the seeds were collected and counted. The filled husks were separated from the empty ones using an air-blowing device. The empty husks were discarded and the remaining fraction was counted again. The filled husks were weighed on an analytical balance. The number of filled seeds was determined by counting the number of filled husks that remained after the separation step. The total seed weight per plant was measured by weighing all filled husks harvested from one plant. Total seed number per plant was measured by counting the number of husks harvested from a plant. Thousand Kernel Weight (TKW) is extrapolated from the number of filled seeds counted and their total weight. The Harvest Index (HI) in the present invention is defined as the ratio between the total seed weight per plant and the above ground area (mm$^2$), multiplied by a factor $10^6$. The total number of flowers per panicle as defined in the present invention is the ratio between the total number of seeds and the number of mature primary panicles. The seed fill rate as defined in the present invention is the proportion (expressed as a %) of the number of filled seeds over the total number of seeds (or florets).

Example 16

Results of the Phenotypic Evaluation of the Transgenic Rice Plants Expressing the SWI2/SNF2 Nucleic Acid Sequence, Grown Under Normal Conditions The results of the evaluation of transgenic rice plants expressing the SWI2/SNF2 nucleic acid sequence, under normal growth conditions, are shown in Table H below.

There was an increase in the number of flowers per panicle, the total seed weight per plant, the total number of seeds, the number of filled seeds, and the harvest index of the transgenics compared to corresponding nullizygotes (controls).

TABLE H

Results of the evaluation of transgenic rice plants expressing the SWI2/SNF2 nucleic acid sequence, under normal growth conditions.

| | Average % increase of best performing events in T1 generation | Average % increase of best performing events in T2 generation |
|---|---|---|
| Number of flowers per panicle | 11% | 3% |
| Total seed weight per plant | 13% | 28% |
| Total number of seeds | 14% | 6% |
| Number of filled seeds | 14% | 25% |
| Harvest index | 10% | 25% |

Example 17

Results of the Phenotypic Evaluation of the Transgenic Rice Plants, Grown Under Drought Stress Conditions The results of the evaluation of transgenic rice plants expressing SWI2/SNF2 nucleic acid sequence, under drought stress growth conditions are presented in Table I.

There was an increase in the aboveground area, the total root biomass, the number of flowers per panicle, the seed fill rate, the total seed weight per plant, the total number of seeds, the number of filled seeds, and the harvest index of the transgenics compared to corresponding nullizygotes (controls).

TABLE I

Results of the evaluation of transgenic rice plants expressing the SWI2/SNF2 nucleic acid sequence, under drought stress growth conditions.

| | Average % increase of best performing events in T2 generation |
|---|---|
| Aboveground area | 16% |
| Total root biomass | 13% |
| Biomass thick roots | 10% |
| Biomass thin roots | 13% |
| Number of flowers per panicle | 7% |
| Seed fill rate | 28% |
| Total seed weight per plant | 57% |
| Total number of seeds | 44% |
| Number of filled seeds | 54% |
| Harvest index | 31% |

Example 18

Examples of Transformation of Corn, Alfalfa, Cotton, Soyabean, Rapeseed/Canola, Wheat See Example 5 above.

The invention claimed is:

1. A method for the production of a transgenic plant having increased yield, biomass, and/or seed yield relative to a control plant, comprising:
   1) introducing and expressing in a plant or plant cell a nucleic acid sequence encoding a SWITCH 2/SUCROSE NON-FERMENTING 2 (SWI2/SNF2) polypeptide having at least 95% sequence identity to the SWI2/SNF2 polypeptide as shown in SEQ ID NO: 30; and
   2) selecting a plant having increased yield, biomass, and/or seed yield relative to a corresponding control plant on the basis of said plant showing increased yield, biomass, and/or seed yield relative to said control plant.

2. The method of claim 1, wherein said SWI2/SNF2 polypeptide comprises an ATPase domain comprising from N-terminus to C-terminus at least five of the following motifs:
   (i) Motif I LADDMGLGK(T/S), as shown in SEQ ID NO: 103;
   (ii) Motif Ia L(L/V/I)(V/I/L)(A/C)P(T/M/V)S(V/I/L)(V/I/L)XNW, as shown in SEQ ID NO: 104;
   (iii) Motif II DEAQ(N/A/H)(V/I/L)KN, as shown in SEQ ID NO: 105;
   (iv) Motif III A(L/M)TGTPXEN, as shown in SEQ ID NO: 106;

(v) Motif IV (L/I)XF(T/S)Q(F/Y), as shown in SEQ ID NO: 107;
(vi) Motif V S(L/V)KAGG(V/T/L)G(L/I)(N/T)LTXA(N/S/T)HV, as shown in SEQ ID NO: 108;
(vii) Motif Va DRWWNPAVE, as shown in SEQ ID NO: 109; and
(viii) Motif VI QA(T/S)DR(A/T/V)(F/Y)R(I/L)GQ, as shown in SEQ ID NO: 110, where X in Motif Ia, Motif III, Motif IV, and Motif V, is any amino acid.

3. A transgenic plant or progeny thereof having increased yield, biomass, and/or seed yield relative to a control plant, produced by the method of claim 1 and resulting from increased expression of the nucleic acid, or a transgenic plant cell derived from said transgenic plant, wherein the transgenic plant comprises the nucleic acid and one or more control sequences capable of driving expression of the nucleic acid and wherein said one or more control sequences comprises a beta-expansin promoter.

4. A method for increasing yield, biomass, and/or seed yield in a plant relative to a control plant, comprising:
1) increasing expression in a plant of a nucleic acid sequence encoding a SWITCH 2/SUCROSE NON-FERMENTING 2(SWI2/SNF2) polypeptide having at least 95% sequence identity to the SWI2/SNF2 polypeptide as shown in SEQ ID NO: 30; and
2) selecting a plant having increased yield, biomass, and/or seed yield relative to a corresponding control plant on the basis of said plant showing increased yield, biomass, and/or seed yield relative to a corresponding control plant.

5. The method of claim 4, wherein said SWI2/SNF2 polypeptide comprises an ATPase domain comprising from N-terminus to C-terminus at least five of the following motifs:
(i) Motif I LADDMGLGK(T/S), as shown in SEQ ID NO: 103;
(ii) Motif Ia L(LN/I)(V/I/L)(A/C)P(T/MN)S(V/I/L)(V/I/L)XNW, as shown in SEQ ID NO: 104;
(iii) Motif II DEAQ(N/A/H)(V/I/L)KN, as shown in SEQ ID NO: 105;
(iv) Motif III A(L/M)TGTPXEN, as shown in SEQ ID NO: 106;
(v) Motif IV (L/I)XF(T/S)Q(F/Y), as shown in SEQ ID NO: 107;
(vi) Motif V S(L/V)KAGG(V/T/L)G(L/I)(N/T)LTXA(N/S/T)HV, as shown in SEQ ID NO: 108;
(vii) Motif Va DRWWNPAVE, as shown in SEQ ID NO: 109; and
(viii) Motif VI QA(T/S)DR(A/T/V)(F/Y)R(I/L)GQ, as shown in SEQ ID NO: 110, where X in Motif Ia, Motif III, Motif IV, and Motif V, is any amino acid.

6. The method of claim 4, wherein said SWI2/SNF2 polypeptide comprises an ATPase domain having at least 95% or more sequence identity to the ATPase domain as shown in SEQ ID NO: 111, comprised in SEQ ID NO: 30.

7. The method of claim 4, wherein said SWI2/SNF2 polypeptide comprises the amino acid sequence of the SWI2/SNF2 polypeptide as shown in SEQ ID NO: 30.

8. The method of claim 4, wherein said nucleic acid sequence encoding the SWI2/SNF2 polypeptide comprises a sequence capable of hybridizing with the full length of SEQ ID NO: 29 under high stringency hybridization conditions, wherein said conditions comprise hybridizing at 1×SSC at 65° C. or 1×SSC and 50% formamide at 45° C., followed by washing at 65° in 0.3×SSC.

9. The method of claim 4, wherein said increased expression is effected by introducing and expressing in a plant a nucleic acid sequence encoding the SWI2/SNF2 polypeptide.

10. The method of claim 4, wherein said increased yield, biomass, and/or seed yield are one or more of: (i) increased number of flowers per panicle; (ii) increased total seed weight per plant; (iii) increased number of (filled) seeds; or (iv) increased harvest index.

11. The method of claim 4, wherein said yield, biomass, and/or seed yield are increased in plants grown under abiotic stress conditions relative to control plants grown under corresponding stress conditions.

12. The method of claim 11, wherein said increased yield, biomass, and/or seed yield are one or more of: (i) increased aboveground area; (ii) increased total root biomass; (iii) increased thick root biomass; (iv) increased thin root biomass; (v) increased number of flowers per panicle; (vi) increased seed fill rate; (vii) increased total seed weight per plant; (viii) increased number of (filled) seeds; or (ix) increased harvest index.

13. The method of claim 9, wherein said nucleic acid sequence is operably linked to a tissue-specific promoter.

14. The method of claim 4, wherein said nucleic acid sequence is from a microbial genome.

15. A plant, part thereof, including seed, or a plant cell obtained by the method of claim 4, wherein said plant, part or cell thereof comprises an isolated nucleic acid transgene encoding the SWI2/SNF2 polypeptide and one or more control sequences capable of driving expression of the nucleic acid, wherein the one or more control sequences comprises a beta-expansin promoter.

16. The transgenic plant of claim 3, wherein said plant is a crop plant, a monocot, a cereal, rice, maize, wheat, barley, millet, rye, triticale, sorghum, or oats, or a transgenic plant cell derived from said transgenic plant.

17. Harvestable parts of the plant of claim 16, wherein said harvestable parts are transgenic seeds.

* * * * *

UNITED STATES PATENT AND TRADEMARK OFFICE
CERTIFICATE OF CORRECTION

PATENT NO. : 8,440,881 B2  Page 1 of 1
APPLICATION NO. : 12/528809
DATED : May 14, 2013
INVENTOR(S) : Park et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 447 days.

Signed and Sealed this
Eighth Day of September, 2015

Michelle K. Lee
*Director of the United States Patent and Trademark Office*